(12) United States Patent
Yamamoto et al.

(10) Patent No.: US 9,981,960 B2
(45) Date of Patent: May 29, 2018

(54) PYRROLIDINE COMPOUND AND APPLICATION AS MELANOCORTIN RECEPTOR AGONIST

(71) Applicant: MITSUBISHI TANABE PHARMA CORPORATION, Osaka-shi, Osaka (JP)

(72) Inventors: Yasuo Yamamoto, Osaka (JP); Atsushi Sato, Osaka (JP); Kenji Morokuma, Osaka (JP); Hiroaki Shitama, Osaka (JP); Takashi Adachi, Osaka (JP); Masahiko Miyashiro, Osaka (JP)

(73) Assignee: MITSUBISHI TANABE PHARMA CORPORATION, Osaka-Shi (JP)

( * ) Notice: Subject to any disclaimer, the term of this patent is extended or adjusted under 35 U.S.C. 154(b) by 0 days. days.

(21) Appl. No.: 15/313,407

(22) PCT Filed: May 28, 2015

(86) PCT No.: PCT/JP2015/065469
§ 371 (c)(1),
(2) Date: Nov. 22, 2016

(87) PCT Pub. No.: WO2015/182723
PCT Pub. Date: Dec. 3, 2015

(65) Prior Publication Data
US 2017/0190697 A1    Jul. 6, 2017

(30) Foreign Application Priority Data

May 29, 2014 (JP) ................. 2014-111378

(51) Int. Cl.
| | | |
|---|---|---|
| C07D 417/14 | (2006.01) | |
| C07D 405/14 | (2006.01) | |
| C07D 401/14 | (2006.01) | |
| C07D 207/16 | (2006.01) | |
| C07D 401/12 | (2006.01) | |
| C07D 401/06 | (2006.01) | |
| C07D 413/14 | (2006.01) | |
| C07D 403/06 | (2006.01) | |

(52) U.S. Cl.
CPC ......... *C07D 417/14* (2013.01); *C07D 207/16* (2013.01); *C07D 401/06* (2013.01); *C07D 401/12* (2013.01); *C07D 401/14* (2013.01); *C07D 403/06* (2013.01); *C07D 405/14* (2013.01); *C07D 413/14* (2013.01)

(58) Field of Classification Search
CPC .................................................. C07D 417/14
See application file for complete search history.

(56) References Cited

U.S. PATENT DOCUMENTS 6,423,710 B1 * 7/2002 Martins ............... C07D 403/12
                                                              514/231.5
6,716,871 B2     4/2004 Martins et al.

FOREIGN PATENT DOCUMENTS

| | | |
|---|---|---|
| JP | 2003-519135 A | 6/2003 |
| JP | 2003-519139 A | 6/2003 |
| JP | 2009-543774 A | 12/2009 |
| JP | 2010-512304 A | 4/2010 |
| WO | WO 01/47879 A1 | 7/2001 |
| WO | WO 01/47905 A1 | 7/2001 |
| WO | WO 01/47914 A1 | 7/2001 |
| WO | WO 01/47915 A1 | 7/2001 |
| WO | WO 02/068388 A2 | 9/2002 |
| WO | WO 2004/078717 A1 | 9/2004 |
| WO | WO 2005/040109 A1 | 5/2005 |
| WO | WO 2005/077935 A1 | 8/2005 |

(Continued)

OTHER PUBLICATIONS

Lupus [online] retrieved from the internet on May 14, 2017. URL http://www.mayoclinic.org/diseases-conditions/lupus/basics/definition/CON-20019676.*
Catania et al., "Targeting Melanocortin Receptors as a Novel Strategy to Control Inflammation," Pharmacological Reviews, Mar. 2004, vol. 56, No. 1, pp. 1-29.
Ceriani et al., "The Neuropeptide Alpha-Melanocyte-Stimulating Hormone Inhibits Experimental Arthritis in Rats," Neuroimmunomodulation, 1994, vol. 1, No. 1, pp. 28-32.
Hadley et al., "The Proopiomelanocortin System," Annals of the New York Academy of Sciences, Oct. 1999, vol. 885, pp. 1-21.
Herpin et al., "Discovery of Tyrosine-Based Potent and Selective Melanocortin-1 Receptor Small-Molecule Agonists with Anti-inflammatory Properties," Journal of Medicinal Chemistry, 2003 (published on web Feb. 20, 2003), vol. 46, No. 7, pp. 1123-1126.

(Continued)

*Primary Examiner* — Shawquia Jackson
(74) *Attorney, Agent, or Firm* — Birch, Stewart, Kolasch & Birch, LLP

(57) ABSTRACT

The present invention relates to a novel pyrrolidine compound having melanocortin receptor agonist activity or a pharmaceutically acceptable salt thereof, and to pharmaceutical applications thereof. The present invention relates to a pyrrolidine derivative represented by formula [I], wherein ring A represents an optionally substituted aryl group or the like; $R^1$ represents an optionally substituted alkyl group or the like; $R^2$ represents a halogen atom or the like; and $R^3$ is an alkyl group substituted with an optionally substituted aryl group or the like, and $R^4$ is a hydrogen atom or the like; or $R^3$ and $R^4$ are terminally attached to each other, and together with the nitrogen atom to which they are attached, form an optionally substituted nitrogen-containing aliphatic heterocyclic ring that may partially contain a double bond; or to a pharmaceutically acceptable salt thereof.

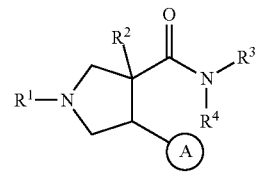

[I]

33 Claims, No Drawings

(56) References Cited

FOREIGN PATENT DOCUMENTS

| WO | WO 2008/007930 A1 | 1/2008 |
|---|---|---|
| WO | WO 2008/039418 A2 | 4/2008 |
| WO | WO 2010/028862 A1 | 3/2010 |

OTHER PUBLICATIONS

International Preliminary Report on Patentability and English translation of the Written Opinion of the International Searching Authority (Forms PCT/IB/373 and PCT/ISA/237), dated Nov. 29, 2016, for International Application No. PCT/JP2015/065469.

International Search Report (Form PCT/ISA/210), dated Aug. 18, 2015, for International Application No. PCT/JP2015/065469.

Slominski et al., "Corticotropin Releasing Hormone and Proopiomelanocortin Involvement in the Cutaneous Response to Stress," Physiological Reviews, Jul. 2000, vol. 80, No. 3, pp. 979-1020.

Suzuki et al., "Binding of melanotropic hormones to the melanocortin receptor MC1R on human melanocytes stimulates proliferation and melanogenesis," Endocrinology, 1996, vol. 137, No. 5, pp. 1627-1633.

Tian et al., "Design, Synthesis, and Evaluation of Proline and Pyrrolidine Based Melanocortin Receptor Agonists. A Conformationally Restricted Dipeptide Mimic Approach," Journal of Medicinal Chemistry, 2006 (published on web Jun. 24, 2006), vol. 49, No. 15, pp. 4745-4761.

Australian Office Action dated Jun. 19, 2017 in Australian Patent Application No. AU2015268505.

Extended European Search Report, dated Nov. 7, 2017, for European Application No. 15799731.3.

Nichols et al., "Preparation of Pyrrolidine-Based PDE4 Inhibitors via Enantioselective Conjugate Addition of α-Substituted Malonates to Aromatic Nitroalkenes," Organic Letters, vol. 8, No. 7, 2006 (Published on Web Mar. 4, 2006), pp. 1495-1498, XP002747953.

\* cited by examiner

PYRROLIDINE COMPOUND AND APPLICATION AS MELANOCORTIN RECEPTOR AGONIST

TECHNICAL FIELD

The present invention relates to a novel pyrrolidine compound having melanocortin receptor (MCR) agonistic activity (agonist activity).

BACKGROUND ART

α-Melanocyte-stimulating hormone (α-MSH) is a hormone derived from pro-opiomelanocortin (POMC) (Non-Patent Literature 1), and is referred to as a melanocortin peptide, along with α-MSH, γ-MSH, and adrenocorticotropic hormone (ACTH). α-MSH is known to exhibit inhibitory action on the production of inflammation- and fibrosis-associated mediators involved in the occurrence of various pathological conditions, and shows efficacy in autoimmune disease models such as colitis, uveoretinitis, and arthritis (Non-Patent Literature 2). α-MSH analogs have also been developed for use in the treatment of protoporphyria, acute renal failure, or postoperative pain.

Melanocortin receptors (MCRs), which are receptors for α-MSH, are seven-transmembrane G-protein-coupled receptors (GPCRs), and increase intracellular cyclic AMP (cAMP) through their activation (Non-Patent Literature 3). There are five sub-types of MCRs, i.e., from MC1R to MC5R.

MC1R is a receptor that is mainly activated by α-MSH, and is expressed in melanocytes, immune and inflammatory cells, fibroblasts, keratinocytes, endothelial cells, glia cells, and the like. Thus, the activation of MC1R is known to increase the cAMP level in cells in which MC1R are expressed, leading to effects such as homeostasis in the skin against melanogenesis and external stimuli (Non-Patent Literature 4), anti-inflammatory action, and inhibitory action on fibrosis of tissue (Non-Patent Literature 5). MC2R is a receptor that has a low response to α-MSH, and is mainly activated by ACTH. MC2R is mostly expressed in the adrenal cortex. The activation of MC2R is known to have a steroidogenic effect. MC3R is a receptor that is mainly activated by γ-MSH and ACTH, and is expressed in central nerves, macrophages, and the like. The activation of MC3R is known to produce effects such as regulation of autonomic function and anti-inflammatory action. MC4R is a receptor that is mainly activated by α-MSH and ACTH, and is expressed in central nerves and the like. Thus, the activation of MC4R is known to produce effects such as suppression of food intake and erectile function improvement. MC5R is a receptor that is mainly activated by α-MSH, and is expressed in exocrine glands, lymphocytes, and the like. The activation of MC5R is known to produce effects such as regulation of exocrine fluids and regulation of immune function. Therefore, the activation of these melanocortin receptors (MCRs) is expected to provide effects such as immune regulation, anti-inflammation, and suppression of tissue fibrosis, through cAMP formation.

Patent Literatures 1 and 2, for example, are known as documents which disclose pyrrolidine compounds having a carbamoyl group in the 3-position of pyrrolidine. The compounds disclosed in Patent Literature 1, however, are compounds that bind to HDM2 to exhibit anticancer action, which also have an alkyl, aryl, or heteroaryl group as a substituent in the 2-position of pyrrolidine. Thus, Patent Literature 1 does not disclose pyrrolidine compounds having substituents in the 1-, 3-, and 4-positions, like the compounds of the present invention.

The compounds described in Patent Literature 2 are compounds substituted with only a carbamoyl group in the 3-position of pyrrolidine. Thus, Patent Literature 2 does not disclose 3,3-di-substituted pyrrolidine compounds having two substituents in the 3-position of pyrrolidine, like the compounds of the present invention.

CITATION LIST

Patent Literature

Patent Literature 1: WO 2010/028862
Patent Literature 2: WO 2008/007930

Non Patent Literature

Non Patent Literature 1: *Annals of the New York Academy of Science*, 1999; 885: p. 1-21
Non Patent Literature 2: *Pharmacological Review*, 2004; 56: p. 1-29
Non Patent Literature 3: *Endocrinology*, 1996; 137: p. 1627-1633
Non Patent Literature 4: *Physiological Reviews*, 2000; 80: p. 979-1020
Non Patent Literature 5: *Neuroimmunomodulation*, 1994; 1: p. 28-32

SUMMARY OF INVENTION

Problems to be Solved by Invention

The present invention relates to a novel pyrrolidine compound having melanocortin receptor (NCR) agonistic activity (agonist activity), in particular, melanocortin 1 receptor (MC1R) agonistic activity (agonist activity), or a pharmaceutically acceptable salt thereof. The compound of the present invention is therefore useful for preventing or treating various diseases or symptoms in which activation of MCRs, in particular, MC1R, is involved.

Means to Solve Problems

The present invention relates to a pyrrolidine derivative represented by formula [I]:

[Formula 1]

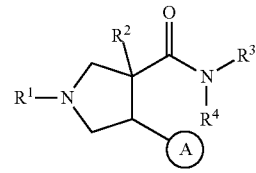

wherein ring A represents an optionally substituted aryl group or an optionally substituted heteroaryl group;
R¹ represents an optionally substituted alkyl group, an optionally substituted cycloalkyl group, an optionally substituted aliphatic heterocyclic group, an optionally substituted aryl group that may be partially hydrogenated, an optionally substituted heteroaryl group, or an optionally substituted carbamoyl group;

$R^2$ represents a halogen atom, an alkyl group, or an optionally substituted alkoxy group;

$R^3$ is an alkyl group substituted with an optionally substituted aryl group, or an alkyl group substituted with an optionally substituted heteroaryl group; and $R^4$ is a hydrogen atom or an alkyl group; or $R^3$ and $R^4$ are terminally attached to each other, and together with the nitrogen atom to which they are attached, form an optionally substituted nitrogen-containing aliphatic heterocyclic ring that may partially contain a double bond;

or a pharmaceutically acceptable salt thereof, provided that compounds represented by formulas (a), (b), (c), (d), and (e) are excluded:

[Formula 2]

(a)
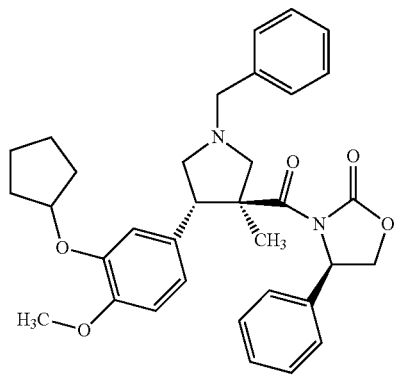

(b)
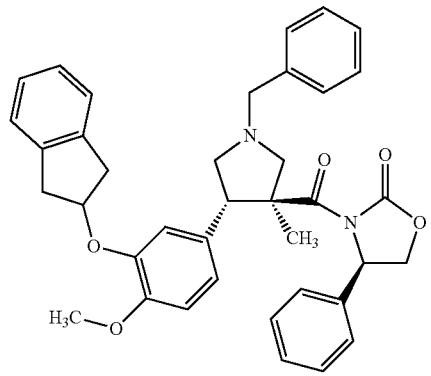

(c)
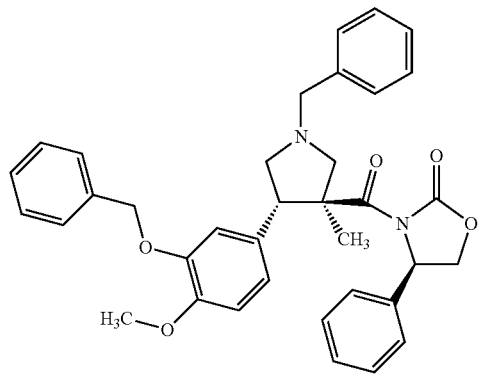

(d)
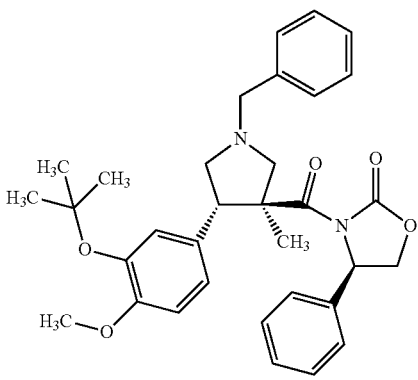

(e)
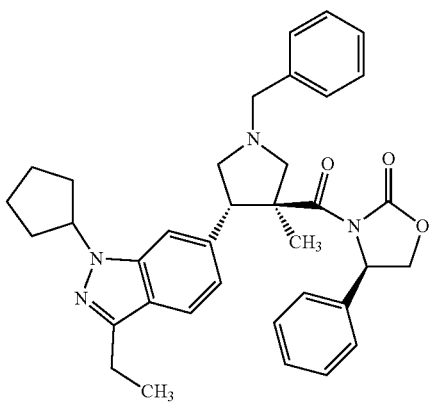

The present invention also relates to a method for preventing or treating various diseases and/or symptoms in which activation of MCRs (in particular, MC1R) is involved, which includes administering to a patient an effective amount of the compound represented by general formula [I] above or a pharmaceutically acceptable salt thereof. The present invention also relates to a pharmaceutical composition comprising as an active ingredient the above-described compound [I] or a pharmaceutically acceptable salt thereof, as well as use of the compound [I] for the manufacture of the pharmaceutical composition. The present invention also relates to the compound [I] or a pharmaceutically acceptable salt thereof for use in preventing or treating various diseases or symptoms in which MCRs (in particular, MC1R) are involved, or a pharmaceutical composition comprising the same as an active ingredient. The present invention also relates to a method of producing the above-described compound [I] or a pharmaceutically acceptable salt thereof.

Effect of Invention

The compound of the present invention exhibits melanocortin receptor (MCR) agonistic activity (agonist activity), in particular, MC1R agonistic activity (agonist activity). The compound of the present invention is therefore useful in preventing or treating various diseases or symptoms in which activation of MCRs, in particular, MC1R, is involved.

MODE FOR CARRYING OUT THE INVENTION

The definitions of the groups as used herein can be combined as desired, unless otherwise specified.

As used herein, the "alkyl" refers to a straight or branched saturated hydrocarbon chain group having one to six carbon atom(s) ($C_{1-6}$). Alkyl group having one to four carbon atom(s) ($C_{1-4}$), in particular, is preferable. Specific examples include methyl, ethyl, n-propyl, i-propyl, n-butyl, t-butyl, 2-methyl-n-butyl, i-amyl (3-methyl-n-butyl), and 2-methyl-n-pentyl. In particular, methyl, ethyl, i-propyl, or t-butyl is preferable.

The "alkenyl" refers to a straight or branched hydrocarbon chain group having two to six carbon atom(s) ($C_{2-6}$) having at least one double bond. In particular, the "alkenyl" may be alkenyl groups having two to four carbon atoms ($C_{2-4}$). Specific examples include vinyl, propenyl, and butenyl.

The "cycloalkyl" refers to a monocyclic saturated hydrocarbon group having three to seven carbon atoms ($C_{3-7}$) and adamantyl, and specific examples include cyclopropyl, cyclobutyl, cyclopentyl, cyclohexyl, cycloheptyl, and adamantyl.

The "cycloalkenyl" refers to a cyclic group having three to seven carbon atoms ($C_{3-7}$) having at least one double bond. Specific examples include cyclopropenyl, cyclobutenyl, cyclopentenyl, and cyclohexenyl.

The "alkoxy" refers to a monovalent group in which the above-described alkyl is attached to an oxygen atom, for example, a straight or branched alky-O— having one to six carbon atom(s) ($C_{1-6}$). Alkyl-O— having one to four carbon atom(s) ($C_{1-4}$) is preferable. Specific examples include methoxy, ethoxy, n-propoxy, i-propoxy, n-butoxy, t-butoxy, 2-methyl-n-propoxy, and 3-methyl-n-butoxy.

The "alkanoyl" refers to a group in which carbonyl (C=O) is attached to the above-described alkyl, for example, a straight or branched alkyl-C(=O)— having one to six carbon atom(s) ($C_{1-6}$). Alkyl-C(=O)— having one to four carbon atom(s) ($C_{1-4}$) is preferable. Specific examples include acetyl, propionyl, and butyryl.

The "alkylene" refers to a straight or branched divalent saturated hydrocarbon group having one to six carbon atom(s) ($C_{1-6}$), with alkylene group having one to four carbon atom(s) ($C_{1-4}$) being preferable. Specific examples include methylene, ethylene, trimethylene (propylene), and tetramethylene (n-butylene).

The "alkyleneoxy" refers to a divalent group in which an oxygen atom is attached to the above-described alkylene. The "alkyleneoxy" may specifically be alkylene-O— having one to six carbon atom(s) ($C_{1-6}$), and is preferably alkylene-O— having one to four carbon atom(s) ($C_{1-4}$). An alkyleneoxy group may be attached as a substituent to two different atoms (e.g., carbon atoms), or may be attached as a substituent to the same atom (e.g., carbon atom) to form a spiro ring.

Examples of halogen or halo include fluorine, chlorine, bromine, and iodine atoms. In particular, halogen or halo may be a fluorine or chlorine atom.

The "haloalkyl" refers to an alkyl substituted with one to three halogen atom(s), and specific examples include difluoromethyl, trifluoromethyl, 1-fluoromethyl, and 2-fluoroethyl.

The "haloalkoxy" refers to an alkyl-O— substituted with one to three halogen atom(s), and a specific example may be trifluoromethoxy.

The "hydroxyalkyl" refers to an alkyl substituted with one hydroxy group, and specific examples include hydroxymethyl, hydroxyethyl, 2-hydroxy-1,1-dimethylethyl, and 4-hydroxy-4-methyl-n-pentyl.

The "cyanoalkyl" refers to an alkyl substituted with one cyano group, and a specific example may be cyanomethyl.

The "alkoxyalkyl" refers to an alkyl substituted with one alkoxy group, and specific examples include methoxymethyl, methoxyethyl, 2-methoxy-1,1-dimethylethyl, and 4-methoxy-4-methyl-n-pentyl.

The "aryl" may be a 6- to 10-membered aromatic hydrocarbon cyclic group, for example. Monocyclic or bicyclic aryl is preferable, and specific examples include phenyl and naphthyl, with phenyl, in particular, being preferable.

The "aryl that may be partially hydrogenated" includes both the above-described aryl and the above-described aryl that is partially hydrogenated, and includes, for example, a cyclic group formed by the condensation of a phenyl group and a cycloalkyl group, and a cyclic group formed by the condensation of a phenyl group and a cycloalkenyl group. Specific examples include phenyl, naphthyl, dihydrophenyl, indanyl, dihydronaphthyl, and tetrahydronaphthyl.

The "heteroaryl" refers to a 5- to 10-membered monocyclic or bicyclic group containing one to four heteroatom(s) independently selected from the group consisting of sulfur, oxygen, and nitrogen atoms. A preferable example may be 5- or 6-membered monocyclic heteroaryl containing at least one nitrogen atom, and optionally further containing a heteroatom independently selected from the group consisting of sulfur, oxygen, and nitrogen atoms. Another preferable example is a 5- or 6-membered monocyclic heteroaryl group containing one to four heteroatom(s) independently selected from the group consisting of oxygen, sulfur, and nitrogen atoms. Specific examples include pyrrolyl, furanyl, thienyl, imidazolyl, pyrazolyl, oxazolyl, isoxazolyl, thiazolyl, tetrazolyl, oxadiazolyl, pyridinyl, pyrazinyl, pyrimidinyl, pyridazinyl, thiazinyl, triazinyl, indolyl, isoindolyl, and benzoimidazolyl.

The "aliphatic heterocyclic ring" refers to a 4- to 8-membered saturated cyclic group containing one to three heteroatom(s) independently selected from the group consisting of oxygen, sulfur, and nitrogen atoms. The aliphatic heterocyclic ring may also be a group in which two carbon atoms forming the ring are bridged by an alkylene group to form a bicyclic or tricyclic group, and may contain a double bond in the ring. Preferable is a 4- to 7-membered monocyclic aliphatic heterocyclic ring containing at least one nitrogen atom, and optionally further containing one heteroatom selected from the group consisting of oxygen, sulfur, and nitrogen atoms. Another preferable example is a 5- or 6-membered monocyclic aliphatic heterocyclic ring containing one or two heteroatom(s) independently selected from the group consisting of oxygen, sulfur, and nitrogen atoms. Specific examples include azetidinyl, pyrrolidinyl, tetrahydrofuranyl, imidazolinyl, thiazolidinyl, isothiazolidinyl, piperidinyl, piperazinyl, morpholinyl, thiomorpholinyl, tetrahydropyranyl, dihydropyridinyl, homopiperazinyl, homomorpholinyl, 3-azabicyclo[3.1.0]hexyl, and octahydropyrrolo[3,4-c]pyrrolyl. Azetidinyl, pyrrolidinyl, piperidinyl, morpholinyl, thiomorpholinyl, piperazinyl, 3-azabicyclo[3.1.0]hexyl, and the like are preferable. Moreover, pyrrolidinyl, piperidinyl, piperazinyl, morpholinyl, and the like are preferable, and pyrrolidinyl, piperidinyl, and morpholinyl are particularly preferable. Tetrahydrofuranyl, tetrahydropyranyl, piperidinyl, and the like are also preferable.

The "aliphatic heterocyclic carbonyl" refers to a group in which carbonyl group is attached to the above-described aliphatic heterocyclic ring. Preferable is 4- to 7-membered monocyclic aliphatic heterocyclic ring-C(=O)— containing one to three heteroatom(s) independently selected from the group consisting of sulfur, oxygen, and nitrogen atoms. More preferable is 4- to 7-membered monocyclic aliphatic heterocyclic carbonyl containing at least one nitrogen atom, and optionally further containing one heteroatom selected from the group consisting of sulfur, oxygen, and nitrogen atoms. Particularly preferable is 5- or 6-membered monocyclic aliphatic heterocyclic carbonyl containing at least one nitrogen atom, in which a carbonyl group is attached to the nitrogen atom in the ring.

The "aliphatic heterocyclic sulfonyl" refers to a group in which sulfonyl group is attached to the above-described aliphatic heterocyclic rings, and may, for example, be 4- to 7-membered monocyclic aliphatic heterocyclic ring-(SO$_2$)— containing one to three heteroatom(s) independently selected from the group consisting of sulfur, oxygen, and nitrogen atoms. In particular, 4- to 7-membered monocyclic aliphatic heterocyclic ring-(SO$_2$)— containing at least one nitrogen atom, and optionally further containing one heteroatom selected from the group consisting of sulfur, oxygen, and nitrogen atoms is preferable. In particular, 5- or 6-membered monocyclic aliphatic heterocyclic ring-(SO$_2$)— containing at least one nitrogen atom, in which a sulfonyl group is attached to the nitrogen atom, is preferable.

Each of the symbols used in the compound [I] of the present invention is hereinafter described.

The aryl moiety of the "optionally substituted aryl group" represented by ring A may be a 6- to 10-membered monocyclic or bicyclic aryl, for example, and may specifically be phenyl, naphthyl, or the like. A phenyl group, in particular, is preferable.

The heteroaryl moiety of the "optionally substituted heteroaryl group" represented by ring A is preferably a 5- or 6-membered monocyclic heteroaryl containing at least one nitrogen atom, and optionally further containing one to three heteroatom(s) independently selected from the group consisting of oxygen, sulfur, and nitrogen atoms. Specific examples include pyrrolyl, furanyl, thienyl, pyridinyl, pyrimidinyl, and pyridazinyl groups. A pyridinyl group is particularly preferable.

Substituents on each of the "optionally substituted aryl group" and "optionally substituted heteroaryl group" represented by ring A may be one to three group(s) that are each independently selected, and examples include a halogen atom, alkyl group, haloalkyl group, cycloalkyl group, alkoxy group, haloalkoxy group, and alkyleneoxy group. Specific examples include a fluorine atom, chlorine atom, methyl group, ethyl group, i-propyl group, trifluoromethyl group, cyclopropyl group, methoxy group, ethoxy group, trifluoromethoxy group, and ethyleneoxy group.

Examples of ring A include an aryl group optionally substituted with one or two group(s) independently selected from the group consisting of a halogen atom, alkyl group, haloalkyl group, cycloalkyl group, alkoxy group, haloalkoxy group, and alkyleneoxy group; and a heteroaryl group optionally substituted with one or two group(s) independently selected from the group consisting of a halogen atom and alkoxy group. Preferable are an aryl group optionally substituted with one or two group(s) independently selected from the group consisting of a halogen atom, alkyl group, haloalkyl group, cycloalkyl group, alkoxy group, haloalkoxy group, and alkyleneoxy group; and a heteroaryl group optionally substituted with a halogen atom or alkoxy group. More preferable is an aryl group optionally substituted with one or two groups independently selected from the group consisting of a halogen atom, alkyl group, haloalkyl group, cycloalkyl group, alkoxy group, haloalkoxy group, and alkyleneoxy group; and particularly preferable is an aryl group optionally substituted with an alkoxy group.

Herein, among the "aryl groups optionally substituted with an alkyleneoxy group", "phenyl substituted with an alkyleneoxy group" includes, for example, structures of the following formulas:

[Formula 3]

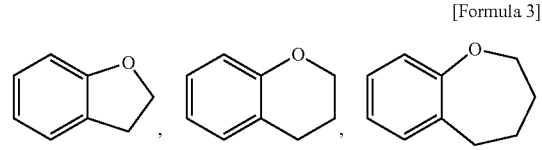

Examples of ring A also include an aryl group optionally substituted with one or two group(s) independently selected from the group consisting of a halogen atom, alkyl group, haloalkyl group, cycloalkyl group, alkoxy group, haloalkoxy group, and alkyleneoxy group; and a heteroaryl group optionally substituted with one or two groups independently selected from the group consisting of a halogen atom and alkoxy group. More specifically, examples of ring A include a phenyl group optionally substituted with one or two groups independently selected from the group consisting of a fluorine atom, chlorine atom, methyl group, ethyl group, i-propyl group, trifluoromethyl group, cyclopropyl group, methoxy group, ethoxy group, and trifluoromethoxy group; a dihydrobenzofuranyl group; a pyridinyl group optionally substituted with a fluorine atom; and a pyridinyl group optionally substituted with a methoxy group. Preferable is a phenyl group optionally substituted with one or two group(s) independently selected from the group consisting of a fluorine atom, chlorine atom, methyl group, ethyl group, i-propyl group, trifluoromethyl group, cyclopropyl group, methoxy group, ethoxy group, and trifluoromethoxy group; and more preferable is a phenyl group optionally substituted with a methoxy group.

The alkyl of the "optionally substituted alkyl group" represented by R$^1$ is preferably t-butyl, in particular.

The cycloalkyl of the "optionally substituted cycloalkyl group" represented by R$^1$ is preferably cyclopentyl or cyclohexyl, in particular.

The aliphatic heterocyclic ring of the "optionally substituted aliphatic heterocyclic group" represented by R$^1$ is preferably a 5- or 6-membered monocyclic aliphatic heterocyclic group containing one or two heteroatom(s) independently selected from the group consisting of oxygen, sulfur, and nitrogen atoms. Specifically, tetrahydrofuranyl, tetrahydropyranyl, or piperidinyl is preferable.

The aryl that may be partially hydrogenated of the "optionally substituted aryl group that may be partially hydrogenated" represented by R$^1$ may be phenyl, naphthyl, or indanyl, for example. Indanyl, in particular, is preferable.

The heteroaryl of the "optionally substituted heteroaryl group" represented by R$^1$ is preferably a 5- or 6-membered monocyclic heteroaryl group containing one to four heteroatom(s) independently selected from the group consisting of oxygen, sulfur, and nitrogen atoms. In particular, a 5- or 6-membered monocyclic nitrogen-containing heteroaryl containing at least one nitrogen atom, and optionally further containing one heteroatom selected from the group consisting of oxygen, sulfur, and nitrogen atoms is preferable. Specific examples include pyrrolyl, imidazolyl, pyrazolyl, oxazolyl, isoxazolyl, thiazolyl, oxadiazolyl, pyridinyl, pyrazinyl, pyrimidinyl, pyridazinyl, thiazinyl, and triazinyl. Particularly preferable are pyridinyl, pyridazinyl, pyrimidinyl, and the like.

Substituents on each of the "optionally substituted alkyl group", "optionally substituted cycloalkyl group", "optionally substituted aliphatic heterocyclic group", "optionally substituted aryl group that may be partially hydrogenated", "optionally substituted heteroaryl group", and "optionally substituted carbamoyl group" represented by $R^1$ may be one to three group(s), and preferably one or two group(s), which are the same or different. Examples include a halogen atom; a hydroxy group; an oxo group; a cyano group; an alkyl group; a hydroxyalkyl group; an alkoxyalkyl group; a haloalkyl group; a cycloalkyl group; an alkoxy group; an alkanoyl group; an alkylsulfonyl group; an aliphatic heterocyclic group; an aliphatic heterocyclic carbonyl group optionally substituted with one or two group(s) independently selected from the group consisting of a halogen atom, alkyl group, haloalkyl group, and alkoxyalkyl group; an aliphatic heterocyclic sulfonyl group; a carbamoyl group optionally substituted with one or two alkyl group(s); and an alkyleneoxy group.

More particularly, examples of the substituent(s) include a halogen atom; a hydroxy group; an oxo group; a cyano group; an alkyl group; a hydroxyalkyl group; an alkoxyalkyl group; a haloalkyl group; a cycloalkyl group; an alkoxy group; an alkanoyl group; an alkylsulfonyl group; an aliphatic heterocyclic group (wherein the aliphatic heterocyclic group is a 4- to 7-membered monocyclic aliphatic heterocyclic group containing one or two heteroatom(s) independently selected from the group consisting of oxygen, sulfur, and nitrogen atoms); an aliphatic heterocyclic carbonyl group optionally substituted with one or two group(s) independently selected from the group consisting of a halogen atom, alkyl group, haloalkyl group, and alkoxyalkyl group (wherein the aliphatic heterocyclic ring is a 4- to 7-membered monocyclic aliphatic heterocyclic ring containing at least one nitrogen atom, and optionally further containing one heteroatom selected from the group consisting of oxygen, sulfur, and nitrogen atoms); an aliphatic heterocyclic sulfonyl group (wherein the aliphatic heterocyclic ring is a 4- to 7-membered monocyclic aliphatic heterocyclic ring containing at least one nitrogen atom, and optionally further containing one heteroatom selected from the group consisting of oxygen, sulfur, and nitrogen atoms); a carbamoyl group optionally substituted with one or two alkyl group(s); and an alkyleneoxy group.

Herein, the "cycloalkyl group substituted with an alkyleneoxy group" includes a group in which an alkyleneoxy group is attached to any common carbon atom on the cycloalkyl group (namely, a spiro ring). For example, a cyclohexyl group substituted with a trimethyleneoxy (propyleneoxy) group includes a group of the following formula:

[Formula 4]

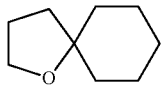

Substituent(s) on the "optionally substituted alkyl group" represented by $R^1$ may be one to three group(s), and preferably one or two group(s), which are the same or different. Examples of the substituent(s) include a halogen atom; a hydroxy group; a cycloalkyl group; an alkoxy group; an aliphatic heterocyclic group; an aliphatic heterocyclic carbonyl group optionally substituted with one or two group(s) independently selected from the group consisting of a halogen atom, alkyl group, haloalkyl group, and alkoxyalkyl group; an aliphatic heterocyclic sulfonyl group; and a carbamoyl group optionally substituted with one or two alkyl group(s).

More particularly, the substituent(s) may be one or two group(s) independently selected from the group consisting of a halogen atom; a hydroxy group; a cycloalkyl group; an alkoxy group; an aliphatic heterocyclic group (wherein the aliphatic heterocyclic group is a 4- to 7-membered monocyclic aliphatic heterocyclic group containing at least one oxygen atom, and optionally further containing one heteroatom selected from the group consisting of oxygen, sulfur, and nitrogen atoms); an aliphatic heterocyclic carbonyl group optionally substituted with one or two group(s) independently selected from the group consisting of a halogen atom, alkyl group, haloalkyl group, and alkoxyalkyl group; (wherein the aliphatic heterocyclic ring is a 4- to 7-membered monocyclic aliphatic heterocyclic ring containing at least one nitrogen atom, and optionally further containing one heteroatom selected from the group consisting of oxygen, sulfur, and nitrogen atoms); an aliphatic heterocyclic sulfonyl group (wherein the aliphatic heterocyclic ring is a 4- to 7-membered monocyclic aliphatic heterocyclic group containing at least one nitrogen atom, and optionally further containing one heteroatom selected from the group consisting of oxygen, sulfur, and nitrogen atoms); and a carbamoyl group optionally substituted with one or two alkyl group(s).

More specifically, examples of the substituent(s) include a fluorine atom; a hydroxy group; a cyclopropyl group; a cyclobutyl group; a methoxy group; a tetrahydropyranyl group; a pyrrolidinylcarbonyl group optionally substituted with a group selected from the group consisting of a fluorine atom, methyl group, trifluoromethyl group, and methoxymethyl group; a piperidinylcarbonyl group optionally substituted with one or two fluorine atom(s); a morpholinylcarbonyl group; a pyrrolidinylsulfonyl group; and a dimethylcarbamoyl group.

Examples of the "optionally substituted alkyl group" represented by $R^1$ include methyl, ethyl, i-propyl, i-amyl (3-methyl-n-butyl), 3-methyl-n-butyl, 1-fluoromethyl-2-fluoroethyl, t-butyl, cyclopropylmethyl, cyclobutylmethyl, 2-hydroxyethyl, 1,1-dimethyl-2-N,N-dimethylcarbamoylethyl, 4-hydroxy-4-methyl-n-pentyl, 1,1-dimethyl-2-methoxyethyl, 4-methoxy-4-methyl-n-pentyl, N,N-dimethylaminocarbonylmethyl, 2-N,N-dimethylaminocarbonylethyl, 1,1-dimethyl-2-N,N-dimethyiaminocarbonyl-ethyl, 3-N,N-dimethylaminocarbonyl-n-propyl, tetrahydropyranylmethyl, piperazinylcarbonylmethyl, pyrrolidinylcarbonyl, 2-methylpyrrolidinylcarbonylmethyl, 2-trifluoromethyl-pyrrolidinyl-carbonylmethyl, 2-methoxymethyl-pyrrolidinylcarbonyl, 3-fluoro-pyrrolidinylcarbonylmethyl, morpholinylcarbonylmethyl, 4,4-difluoro-piperidinylcarbonylmethyl, and 3-pyrrolidinylsulfonylpropyl groups. A t-butyl group, in particular, is preferable.

Substituents on the "optionally substituted cycloalkyl group" represented by $R^1$ may be one to three group(s), which are the same or different, and examples include a halogen atom, hydroxy group, oxo group, cyano group, alkyl group, alkoxy group, alkoxyalkyl group, and alkyleneoxy group. Herein, the alkyleneoxy group may be a substituent on common carbon on the cycloalkyl.

More particularly, the substituent(s) may be one or two group(s) independently selected from the group consisting of a halogen atom, hydroxy group, oxo group, cyano group, alkyl group, alkoxy group, alkoxyalkyl group, and alkyleneoxy group, for example. More specifically, the substituents are one or two group(s) independently selected from the group consisting of a fluorine atom, hydroxy group, oxo group, cyano group, methyl group, methoxy group, ethoxy group, isopropoxy group, methoxymethyl group, and trimethyleneoxy group (propyleneoxy group), for example. In particular, methoxy, ethoxy, and cyano groups are preferable.

The "optionally substituted cycloalkyl group" represented by $R^1$ may be a cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group, for example.

More particularly, examples include a 3- to 7-membered monocyclic cycloalkyl group optionally substituted with one to three group(s) independently selected from the group consisting of a halogen atom, hydroxy group, oxo group, cyano group, alkyl group, alkoxy group, alkoxyalkyl group, and alkyleneoxy group; and an adamantyl group optionally substituted with a hydroxy group.

More specifically, examples include a cyclopropyl group; a cyclobutyl group; a cyclopentyl group optionally substituted with one to three group(s) independently selected from the group consisting of a fluorine atom, hydroxy group, oxo group, cyano group, methyl group, methoxy group, ethoxy group, i-propoxy group, and methoxymethyl group; a cyclohexyl group optionally substituted with one to three group(s) independently selected from the group consisting of a fluorine atom, hydroxy group, oxo group, cyano group, methyl group, methoxy group, ethoxy group, i-propoxy group, and trimethyleneoxy group (propyleneoxy group); and a cycloheptyl group.

In particular, a cyclopentyl group optionally substituted with one group selected from the group consisting of methoxy, ethoxy, and cyano groups; a cyclohexyl group optionally substituted with one group selected from the group consisting of methoxy, ethoxy, and cyano groups; and the like are preferable.

Examples of substituents on the "optionally substituted aliphatic heterocyclic group" represented by $R^1$ include alkyl, hydroxyalkyl, haloalkyl, alkanoyl, and alkylsulfonyl groups. More specifically, examples include methyl, hydroxymethyl, 2-fluoro-1-fluoromethyl-ethyl, acetyl, ethylcarbonyl, and ethylsulfonyl groups.

Examples of the "optionally substituted aliphatic heterocyclic group" represented by $R^1$ include a tetrahydrofuranyl group optionally substituted with an alkyl, hydroxy, or hydroxyalkyl group; a tetrahydropyranyl group optionally substituted with a hydroxy, alkyl, or hydroxyalkyl group; and a piperidinyl group optionally substituted with a group selected from the group consisting of haloalkyl, alkanoyl and alkylsulfonyl group.

More specifically, examples include a tetrahydrofuranyl group; a tetrahydropyranyl group optionally substituted with a methyl or hydroxymethyl group; and a piperidinyl group optionally substituted with a group selected from the group consisting of 1-fluoromethyl-2-fluoroethyl, acetyl, ethylcarbonyl, and ethylsulfonyl groups; with a tetrahydropyranyl group being preferable.

The "optionally substituted aryl group that may be partially hydrogenated" represented by $R^1$ is preferably an indanyl group (in particular, a 1-indanyl group, a 2-indanyl group, or the like).

Substituent(s) on the "optionally substituted heteroaryl group" represented by $R^1$ may be one to three group(s), which are the same or different, and examples include cyano, alkyl, alkoxy, and carbamoyl groups. More specifically, examples include cyano, methyl, methoxy, and carbamoyl groups. A methyl group, in particular, is preferable.

Examples of the "optionally substituted heteroaryl group" represented by $R^1$ include a pyridazinyl group optionally substituted with one group selected from the group consisting of cyano, alkyl, alkoxy, and carbamoyl groups; a pyridinyl group optionally substituted with one or two group(s) independently selected from the group consisting of cyano, alkyl, and alkoxy groups; and a pyrimidinyl group optionally substituted with an alkyl group.

More specifically, examples include a pyridazinyl group optionally substituted with one group selected from the group consisting of cyano, methyl, methoxy, and carbamoyl groups; a pyridinyl group optionally substituted with one or two group(s) independently selected from the group consisting of cyano, methyl, and methoxy groups; and a pyrimidinyl group optionally substituted with a methyl group. In particular, a pyrimidinyl group optionally substituted with a methyl group and a pyridinyl group substituted with a methyl group are preferable.

A substituent on the "optionally substituted carbamoyl group" represented by $R^1$ may be an alkyl group, for example. More specifically, examples include methyl, ethyl, and i-propyl groups, with a methyl group, in particular, being preferable.

Examples of the "optionally substituted carbamoyl group" represented by $R^1$ include carbamoyl, monomethylcarbamoyl, and dimethylcarbamoyl groups, with carbamoyl and monomethylcarbamoyl groups being preferable.

$R^1$ is preferably an alkyl group, an optionally substituted cycloalkyl group, an aliphatic heterocyclic group, or an optionally substituted heteroaryl group. More particularly, $R^1$ is preferably an alkyl group; a cycloalkyl group optionally substituted with a cyano or alkoxy group; a 5- or 6-membered monocyclic aliphatic heterocyclic group containing one or two heteroatom(s) independently selected from the group consisting of oxygen, sulfur, and nitrogen atoms; or a heteroaryl group optionally substituted with an alkyl group (wherein the heteroaryl group is a 5- or 6-membered monocyclic heteroaryl group containing one to four heteroatom(s) independently selected from the group consisting of oxygen, sulfur, and nitrogen atoms). Specifically, $R^1$ is preferably a t-butyl group; a cyclopentyl group; a cyclohexyl group optionally substituted with a methoxy, ethoxy, or cyano group; a tetrahydropyranyl group; or a pyridinyl group optionally substituted with a methyl group.

$R^1$ is preferably an optionally substituted cycloalkyl group or an optionally substituted aliphatic heterocyclic group. More particularly, $R^1$ is preferably a 3- to 7-membered monocyclic cycloalkyl group optionally substituted with a cyano or alkoxy group; or an aliphatic heterocyclic group optionally substituted with an alkyl, haloalkyl, or hydroxyalkyl group (wherein the aliphatic heterocyclic group is a group selected from the group consisting of tetrahydrofuranyl, tetrahydropyranyl, pyrrolidinyl, and piperidinyl groups). Specifically, $R^1$ is preferably a cyclopentyl group; a cyclohexyl group optionally substituted with a methoxy, ethoxy, or cyano group; a piperidinyl group optionally substituted with a haloalkyl group; or a tetrahydropyranyl group optionally substituted with an alkyl or hydroxyalkyl group.

$R^1$ is particularly preferably an optionally substituted cycloalkyl group. More particularly, $R^1$ is preferably a cycloalkyl group optionally substituted with a cyano or alkoxy group. Specifically, $R^1$ is preferably a cyclopentyl group; or a cyclohexyl group optionally substituted with a group selected from the group consisting of methoxy, ethoxy, and cyano groups.

The alkyl of the "alkyl group" represented by $R^2$ is preferably $C_{1-3}$ alkyl, and specifically, the alkyl is preferably methyl, ethyl, i-propyl, or the like.

The alkoxy of the "optionally substituted alkoxy group" represented by $R^2$ is preferably $C_{1-4}$ alkoxy, and is specifically methoxy, ethoxy, i-propoxy, n-butoxy, or the like.

Examples of substituent(s) on the "optionally substituted alkoxy group" represented by $R^2$ include a halogen atom, hydroxy group, and alkoxy group. More specifically, examples include a fluorine atom, chlorine atom, hydroxy group, and methoxy group.

Examples of the "optionally substituted alkoxy group" represented by $R^2$ include methoxy, ethoxy, trifluoromethoxy, and difluoromethoxy groups, with a methoxy group being preferable.

Suitable examples of $R^2$ include a halogen atom, an alkyl group, and an alkoxy group, with a halogen atom and an alkoxy group being more preferable. In particular, a fluorine atom or methoxy group is preferable.

The alkyl of the "alkyl group substituted with an optionally substituted aryl group, or the alkyl group substituted with an optionally substituted heteroaryl group" represented by $R^3$ is preferably a $C_{1-4}$ straight or branched alkyl.

The aryl moiety may be a monocyclic or bicyclic aryl, and may specifically be phenyl, naphthyl, or the like. A phenyl group, in particular, is preferable.

The heteroaryl moiety may be, for example, a 5- to 10-membered monocyclic or bicyclic heteroaryl group containing one to four heteroatom(s) independently selected from the group consisting of oxygen, sulfur, and nitrogen atoms. In particular, the heteroaryl moiety may be, for example, a 5- or 6-membered monocyclic nitrogen-containing heteroaryl containing at least one nitrogen atom, and optionally further containing one heteroatom selected from the group consisting of oxygen, sulfur, and nitrogen atoms. Specifically, pyrrolyl, imidazolyl, pyrazolyl, oxazolyl, isoxazolyl, thiazolyl, tetrazolyl, oxadiazolyl, pyridinyl, pyrazinyl, pyrimidinyl, pyridazinyl, thiazinyl, triazinyl, and the like are preferable. A particularly suitable example is a pyridinyl group.

Examples of substituent(s) on each of the "optionally substituted aryl group" and "optionally substituted heteroaryl group" in $R^3$ include (1) an optionally substituted aliphatic heterocyclic group; and (2) an optionally substituted alkyl group.

The aliphatic heterocyclic ring of the "optionally substituted aliphatic heterocyclic group" in (1) above may be, for example, a 4- to 8-membered monocyclic or bicyclic aliphatic heterocyclic ring containing one or two heteroatom(s) independently selected from the group consisting of oxygen, sulfur, and nitrogen atoms. Preferable is a 4- to 8-membered monocyclic or bicyclic aliphatic heterocyclic ring containing at least one nitrogen atom, and optionally further containing one heteroatom selected from the group consisting of oxygen, sulfur, and nitrogen atoms. Specifically, azetidinyl, pyrrolidinyl, piperidinyl, morpholinyl, thiomorpholinyl, piperazinyl, 3-azabicyclo[3.1.0]hexyl, and the like are preferable. A particularly suitable example is piperidinyl. Herein, substituent(s) on the aliphatic heterocyclic group may be one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonylaminocarbonyl group; an aliphatic heterocyclic carbonyl group optionally substituted with a carboxyl group (wherein the aliphatic heterocyclic ring is a 4- to 7-membered monocyclic group containing at least one nitrogen atom, and optionally further containing one heteroatom independently selected from the group consisting of oxygen, sulfur, and nitrogen atoms); an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic ring is a 4- to 7-membered monocyclic group containing one or two heteroatom(s) independently selected from the group consisting of oxygen, sulfur, and nitrogen atoms); an alkylsulfonyl group; a heteroaryl group (wherein the heteroaryl group is a 5- or 6-membered monocyclic group containing one to four heteroatom(s) independently selected from the group consisting of oxygen, sulfur, and nitrogen atoms); and an aminosulfonyl group optionally substituted with one or two alkyl group(s). Carboxyl and carbamoyl groups are preferable, and in particular, a carboxyl group is preferable.

The "optionally substituted alkyl group" in (2) above is preferably a haloalkyl group. In particular, suitable examples include trifluoromethyl and difluoromethyl groups.

The "alkyl group substituted with an optionally substituted aryl group, or the alkyl group substituted with an optionally substituted heteroaryl group" represented by $R^3$ may be a methyl group substituted with a substituted phenyl group, for example (wherein the phenyl group is substituted with a piperidinyl group substituted with a carboxyl group, and a trifluoromethyl group).

The "alkyl group" represented by $R^4$ is preferably a $C_{1-4}$ straight or branched alkyl.

$R^4$ is preferably a hydrogen atom, methyl group, ethyl group, i-propyl group, or the like.

Preferably, $R^3$ and $R^4$ are terminally attached to each other, and together with the nitrogen atom to which they are attached, form an optionally substituted aliphatic heterocyclic ring that may contain a double bond.

Specifically, $R^3$ and $R^4$ are terminally attached to each other, and together with the nitrogen atom to which they are attached, form a group, which is preferably a group represented by formula [II]:

[Formula 5]

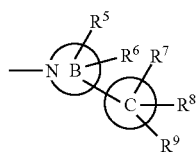

[II]

wherein ring B represents a nitrogen-containing aliphatic heterocyclic group that may partially contain a double bond,
ring C represents an aryl or heteroaryl group,
$R^5$ and $R^6$ each independently represent a group selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and an alkoxy group;

$R^7$ represents an optionally substituted alkyl group, an optionally substituted alkenyl group, an optionally substituted cycloalkyl group, an optionally substituted cycloalkenyl group, an optionally substituted aryl group, an optionally substituted heteroaryl group, an optionally substituted aliphatic heterocyclic group, an optionally substituted alkoxy group, an amino group optionally substituted with one or two alkyl group(s) optionally substituted with a carboxyl group, or a carbamoyl group optionally substituted with one or two alkyl group(s) optionally substituted with a carboxyl group; and $R^8$ and $R^9$ each independently represent a group selected from the group consisting of a hydrogen atom, halogen atom, cyano group, alkyl group, haloalkyl group, and haloalkoxy group.

More preferably, the group represented by general formula [II] above may be a group wherein $R^7$ represents an optionally substituted alkyl group, an optionally substituted alkenyl group, an optionally substituted cycloalkyl group, an optionally substituted cycloalkenyl group, an optionally substituted aryl group, an optionally substituted heteroaryl group, an optionally substituted aliphatic heterocyclic group, an optionally substituted alkoxy group, an amino group optionally substituted with one or two alkyl group(s) optionally substituted with a carboxyl group, or a carbamoyl group which is optionally substituted with one or two alkyl group(s) optionally substituted with a carboxyl group, wherein substituent(s) on the optionally substituted alkyl group is/are one or two groups independently selected from the group consisting of a hydroxy group; an oxo group; a cyano group; an alkoxy group; an alkanoyl group; a carboxyl group; an alkoxycarbonyl group; an aliphatic heterocyclic carbonyl group optionally substituted with a carboxyl group; a heteroaryl group optionally substituted with a hydroxy or oxo group; an aliphatic heterocyclic group optionally substituted with one or two oxo group(s); a carbamoyl group optionally substituted with one or two group(s) independently selected from the group consisting of an alkyl group (the alkyl moiety is optionally substituted with a hydroxy, alkoxy, or carboxyl group) and a hydroxy group; an alkylsulfonyl group; an aminosulfonyl group optionally substituted with one or two alkyl group(s); an aminosulfonylaminocarbonyl group optionally substituted with one or two alkyl group(s); an alkylsulfonylaminocarbonyl group; and an amino group optionally substituted with one or two group(s) independently selected from the group consisting of alkyl, alkanoyl, and alkylsulfonyl groups, and substituent(s) on each of the optionally substituted alkenyl group, the optionally substituted cycloalkyl group, the optionally substituted cycloalkenyl group, the optionally substituted aryl group, the optionally substituted heteroaryl group, the optionally substituted aliphatic heterocyclic group, and the optionally substituted alkoxy group are one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; an aliphatic heterocyclic carbonyl group optionally substituted with a carboxyl group; a heteroaryl group optionally substituted with a hydroxy or oxo group; an aliphatic heterocyclic group optionally substituted with one or two oxo group(s); a carbamoyl group optionally substituted with one or two group(s) independently selected from the group consisting of an alkyl group (the alkyl moiety is optionally substituted with a hydroxy, alkoxy, or carboxyl group) and a hydroxy group; an alkylsulfonyl group; an aminosulfonyl group optionally substituted with one or two alkyl group(s); an aminosulfonylaminocarbonyl group optionally substituted with one or two alkyl group(s); an alkylsulfonylaminocarbonyl group; and an amino group optionally substituted with one or two group(s) independently selected from the group consisting of alkyl, alkanoyl, and alkylsulfonyl groups.

The "nitrogen-containing aliphatic heterocyclic group that may partially contain a double bond" represented by ring B is preferably a 4- to 8-membered monocyclic or bicyclic aliphatic heterocyclic ring that may further contain, in addition to the nitrogen atom shown in formula [II], one heteroatom selected from the group consisting of oxygen, sulfur, and nitrogen atom. Specifically, examples include azetidinyl, pyrrolidinyl, imidazolinyl, thiazolidinyl, isothiazolidinyl, piperidinyl, piperazinyl, morpholinyl, thiomorpholinyl, tetrahydropyridinyl, homopiperazinyl, homomorpholinyl, 3-azabicyclo[3.1.0]hexyl, and octahydropyrrolo[3,4-c]pyrrolyl groups. Preferable examples include azetidinyl, pyrrolidinyl, piperidinyl, tetrahydropyridinyl, piperazinyl, homopiperazinyl, and octahydropyrrolo[3,4-c]pyrrolyl groups. More suitable examples include pyrrolidinyl and piperidinyl groups, and in particular, a pyrrolidinyl group is preferable.

The "aryl group" represented by ring C may be monocyclic or bicyclic aryl, and may specifically be phenyl or naphthyl, and is preferably phenyl.

The "heteroaryl group" represented by ring C may be, for example, a 5- or 6-membered monocyclic heteroaryl containing one to four heteroatom(s) independently selected from the group consisting of oxygen, sulfur, and nitrogen atoms. More specifically, a pyridinyl group is preferable.

$R^5$ and $R^6$ may each be a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group, for example. More specifically, $R^5$ and $R^6$ may each be a group independently selected from the group consisting of a hydrogen atom, fluorine atom, cyano group, methyl group, fluoromethyl group, cyanomethyl group, hydroxymethyl group, 1-hydroxy-1-methylethyl group, methoxymethyl group, ethoxymethyl group, carboxyl group, dimethylcarbamoyl group, and methoxy group, for example.

Suitable examples include those in which $R^5$ is a group selected from the group consisting of a halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group; and $R^6$ is a hydrogen atom; $R^5$ is an alkoxyalkyl group, and $R^6$ is a halogen atom, alkyl group, or alkoxy group; both $R^5$ and $R^6$ are halogen atoms; both $R^5$ and $R^6$ are alkyl groups; and both $R^5$ and $R^6$ are hydrogen atoms. More specifically, examples include those in which $R^5$ is a group selected from the group consisting of a fluorine atom, cyano group, methyl group, fluoromethyl group, cyanomethyl group, hydroxymethyl group, 1-hydroxy-1-methylethyl group, methoxymethyl group, ethoxymethyl group, carboxyl group, dimethylcarbamoyl group, and methoxy group, and $R^6$ is a hydrogen atom; $R^5$ is a methoxymethyl group, and $R^6$ is a fluorine atom, methyl group, or methoxy group; both $R^5$ and $R^6$ are fluorine atoms; both $R^5$ and $R^6$ are methyl groups; and both $R^5$ and $R^6$ are hydrogen atoms.

The alkyl of the "optionally substituted alkyl group" represented by $R^7$ is preferably ethyl, n-butyl, or the like.

The alkenyl of the "optionally substituted alkenyl group" represented by $R^7$ is preferably n-butenyl or the like.

The cycloalkyl of the "optionally substituted cycloalkyl group" represented by $R^7$ is preferably cyclohexyl.

The cycloalkenyl of the "optionally substituted cycloalkenyl group" represented by $R^7$ is preferably cyclohexenyl, in particular.

The aryl moiety of the "optionally substituted aryl group" represented by $R^7$ may be phenyl, naphthyl, or the like, and is preferably phenyl, in particular.

The heteroaryl moiety of the "optionally substituted heteroaryl group" represented by $R^7$ is preferably a 5- or 6-membered monocyclic heteroaryl containing at least one nitrogen atom, and optionally further containing one heteroatom selected from oxygen, sulfur, and nitrogen atoms. Specifically, pyrrolyl, imidazolyl, pyrazolyl, oxazolyl, isoxazolyl, thiazolyl, tetrazolyl, oxadiazolyl, pyridinyl, pyrazinyl, pyrimidinyl, pyridazinyl, thiazinyl, and triazinyl are preferable. In particular, pyrazolyl and oxazolyl groups are preferable.

The aliphatic heterocyclic ring of the "optionally substituted aliphatic heterocyclic group" represented by $R^7$ is preferably a 4- to 8-membered monocyclic or bicyclic aliphatic heterocyclic ring containing at least one nitrogen atom, and optionally further containing one heteroatom selected from the group consisting of oxygen, sulfur, and nitrogen atoms. Specifically, azetidinyl, pyrrolidinyl, piperidinyl, piperazinyl, morpholinyl, thiomorpholinyl, and 3-azabicyclo[3.1.0]hexyl groups, for example, are preferable. A particularly suitable example is a piperidinyl group.

The alkoxy of the "optionally substituted alkoxy group" represented by $R^7$ is preferably methoxy, n-propoxy, 2-methyl-n-propoxy, 3-methyl-n-butoxy, or the like.

The "amino group optionally substituted with one or two alkyl group(s) optionally substituted with a carboxyl group" represented by $R^7$ may specifically be a N-methyl-N-3-carboxyl-n-propylamino group or the like.

The "carbamoyl group optionally substituted with one or two alkyl group(s) optionally substituted with a carboxyl group" represented by $R^7$ is preferably a carbamoyl group, for example.

Substituent(s) on each of the "optionally substituted alkyl group", the "optionally substituted alkenyl group", the "optionally substituted cycloalkyl group", the "optionally substituted cycloalkenyl group", the "optionally substituted aryl group", the "optionally substituted heteroaryl group", the "optionally substituted aliphatic heterocyclic group", and the "optionally substituted alkoxy group" represented by $R^7$ may be one or two groups, which are the same or different, and may be one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; an aliphatic heterocyclic carbonyl group optionally substituted with a carboxyl group (wherein the aliphatic heterocyclic ring is preferably a 4- to 7-membered monocyclic aliphatic heterocyclic ring, and more preferably a 5- or 6-membered monocyclic aliphatic heterocyclic ring, containing at least one nitrogen atom, and optionally further containing one heteroatom selected from the group consisting of oxygen, sulfur, and nitrogen atoms); a heteroaryl group optionally substituted with a hydroxy or oxo group (wherein the heteroaryl group is preferably a 5- or 6-membered monocyclic heteroaryl group containing one to four heteroatom(s) independently selected from the group consisting of oxygen, sulfur, and nitrogen atoms); an aliphatic heterocyclic group optionally substituted with one or two oxo group(s) (wherein the aliphatic heterocyclic group is preferably a 4- to 7-membered monocyclic aliphatic heterocyclic group, and more preferably a 5- or 6-membered monocyclic aliphatic heterocyclic group, containing one or two heteroatom(s) independently selected from the group consisting of oxygen, sulfur, and nitrogen atoms); a carbamoyl group optionally substituted with one or two group(s) independently selected from the group consisting of alkyl and hydroxy groups (wherein the alkyl group is optionally substituted with a hydroxy, alkoxy, or carboxyl group); an alkylsulfonyl group; an aminosulfonyl group optionally substituted with one or two alkyl group(s); an alkylsulfonylaminocarbonyl group; an aminosulfonylaminocarbonyl group optionally substituted with one or two alkyl group(s); and an amino group optionally substituted with one or two group(s) independently selected from the group consisting of alkyl, alkanoyl, and alkylsulfonyl groups.

More specifically, examples of the substituent(s) include hydroxy, oxo, cyano, methyl, carboxymethyl, methoxy, carboxyl, carbamoyl, N-methylcarbamoyl, N-ethylcarbamoyl, N-1-carboxymethylcarbamoyl, N-2-hydroxyethylcarbamoyl, N-2-methoxyethylcarbamoyl, N-hydroxycarbamoyl, N-methyl-N-1-carboxymethylcarbamoyl, N-methyl-N-2-hydroxyethylcarbamoyl, N-methyl-N-2-methoxyethylcarbamoyl, N,N-dimethylcarbamoyl, t-butoxycarbonyl, acetyl, N,N-dimethylaminosulfonylaminocarbonyl, methylsulfonyl, methylsulfonylaminocarbonyl, aminosulfonyl, N,N-dimethylaminosulfonyl, N,N-dimethylamino, N-methyl-N-acetylamino, N-methyl-N-methylsulfonylamino, tetrazolyl, 4H-[1,2,4]oxadiazol-5-one-2-yl, 5-hydroxyisoxazolyl, pyrrolidinecarbonyl, 2-carboxylpyrrolidinecarbonyl, 2-oxopyrrolidinyl, and 1,1'-dioxoisothiazolidin-2-yl groups. In particular, carbamoyl and carboxyl groups are preferable, and a carboxyl group is particularly preferable.

$R^7$ may be (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group, (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of alkyl and hydroxy groups (wherein the alkyl group is optionally substituted with a hydroxy, alkoxy, or carboxyl group); an alkylsulfonylaminocarbonyl group; an aliphatic heterocyclic carbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s);

an alkylsulfonyl group; a tetrazolyl group; and an aminosulfonyl group optionally substituted with one or two alkyl group(s), (8) an alkoxy group optionally substituted with a group selected from the group consisting of a cyano group; a carboxyl group; a heteroaryl group optionally substituted with a hydroxy or oxo group; an aminosulfonylaminocarbonyl group optionally substituted with one or two alkyl group(s); and an alkylsulfonylaminocarbonyl group, (9) an amino group which is optionally substituted with one or two alkyl group(s) optionally substituted with a carboxyl group, or

(10) a carbamoyl group, for example.

Specifically, the heteroaryl group of the "(6) heteroaryl group optionally substituted with a carboxyl group or an alkyl group optionally substituted with a carboxyl group" is a 5- or 6-membered monocyclic heteroaryl group containing one to four heteroatom(s) independently selected from the group consisting of oxygen, sulfur, and nitrogen atoms. The heteroaryl group is, for example, a pyrrolyl, imidazolyl, pyrazolyl, oxazolyl, isoxazolyl, thiazolyl, tetrazolyl, oxadiazolyl, pyridyl, pyrazinyl, pyrimidinyl, pyridazinyl, thiazinyl, or triazinyl group; preferably a pyrrolyl, pyrazolyl, oxazolyl, pyridyl, or pyrimidinyl group; and more preferably an oxazolyl or pyrazolyl group.

The aliphatic heterocyclic moiety of the "(7) aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group and a hydroxy group (wherein the alkyl group is optionally substituted with a hydroxy, alkoxy, or carboxyl group); an alkylsulfonylaminocarbonyl group; an aliphatic heterocyclic carbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s); an alkylsulfonyl group; and an aminosulfonyl group optionally substituted with one or two alkyl group(s)" is preferably a 4- to 7-membered monocyclic aliphatic heterocyclic group containing one or two heteroatom(s) independently selected from the group consisting of oxygen, sulfur, and nitrogen atoms. Specific examples include azetidinyl, pyrrolidinyl, tetrahydrofuranyl, imidazolinyl, thiazolidinyl, isothiazolidinyl, piperidinyl, piperazinyl, morpholinyl, thiomorpholinyl, tetrahydropyranyl, homopiperazinyl, homomorpholinyl, 3-azabicyclo[3.1.0]hexyl, and octahydropyrrolo[3,4-c]pyrrolyl groups. Azetidinyl, pyrrolidinyl, piperidinyl, piperazinyl, morpholinyl, thiomorpholinyl, and 3-azabicyclo[3.1.0]hexyl groups are more preferable.

Herein, the aliphatic heterocyclic ring of the "aliphatic heterocyclic carbonyl group optionally substituted with a carboxyl group" is preferably a 4- to 7-membered monocyclic aliphatic heterocyclic ring containing at least one nitrogen atom, and optionally further containing one heteroatom selected from the group consisting of oxygen, sulfur, and nitrogen atoms. Examples include azetidinyl, pyrrolidinyl, imidazolinyl, thiazolidinyl, isothiazolidinyl, piperidinyl, piperazinyl, morpholinyl, thiomorpholinyl, homopiperazinyl, and homomorpholinyl groups. A pyrrolidinyl group is particularly preferable. The aliphatic heterocyclic group of the "aliphatic heterocyclic group optionally substituted with one or two oxo group(s)" is preferably a 4- to 7-membered monocyclic aliphatic heterocyclic group containing one or two heteroatom(s) independently selected from the group consisting of oxygen, sulfur, and nitrogen atoms, and may specifically be an azetidinyl, pyrrolidinyl, tetrahydrofuranyl, imidazolinyl, thiazolidinyl, isothiazolidinyl, piperidinyl, piperazinyl, morpholinyl, thiomorpholinyl, tetrahydropyranyl, homopiperazinyl, or homomorpholinyl group. A pyrrolidinyl or isothiazolidinyl group is particularly preferable.

The heteroaryl group of the "(8) alkoxy group optionally substituted with a group selected from the group consisting of a cyano group; a carboxyl group; a heteroaryl group optionally substituted with a hydroxy or oxo group; an aminosulfonylaminocarbonyl group optionally substituted with one or two alkyl group(s); and an alkylsulfonylaminocarbonyl group" is preferably a 5- or 6-membered monocyclic heteroaryl group containing one to four heteroatom(s) independently selected from the group consisting of oxygen, sulfur, and nitrogen atoms. Specific examples include pyrrolyl, imidazolyl, pyrazolyl, oxazolyl, isoxazolyl, thiazolyl, tetrazolyl, oxadiazolyl, pyridinyl, pyrazinyl, pyrimidinyl, pyridazinyl, thiazinyl, and triazinyl groups. Tetrazolyl, oxadiazolyl, and isoxazolyl groups are particularly preferable.

Particularly suitable examples of $R^7$ include an alkyl group substituted with a carboxyl group, an alkenyl group substituted with a carboxyl group, a cycloalkyl group substituted with a carboxyl group, a cycloalkenyl group substituted with a carboxyl group, an aryl group substituted with a carboxyl group, a heteroaryl group substituted with a carboxyl group, an aliphatic heterocyclic group substituted with a carboxyl group, an alkoxy group substituted with a carboxyl group, an amino group which is optionally substituted with one or two alkyl group(s) substituted with a carboxyl group, and a carbamoyl group. In particular, an aliphatic heterocyclic group substituted with a carboxyl group is preferable, and a piperidinyl group substituted with a carboxyl group is particularly preferable.

The halogen atom of the "hydrogen atom, halogen atom, cyano group, alkyl group, haloalkyl group, and haloalkoxy group" represented by $R^8$ or $R^9$ is preferably a fluorine or chlorine atom. Suitable examples of the "alkyl group" include methyl, ethyl, and i-propyl groups. The "haloalkyl group" is preferably a trifluoromethyl or difluoromethyl group, for example. The "haloalkoxy group" is preferably a trifluoromethoxy group, for example.

Preferable examples of $R^8$ and $R^9$ include a hydrogen atom, fluorine atom, chlorine atom, methyl group, ethyl group, i-propyl group, trifluromethyl group, difluoromethyl group, and trifluoromethoxy group.

Particularly preferably, $R^8$ is a fluorine atom, chlorine atom, methyl group, i-propyl group, trifluoromethyl group, difluoromethyl group, or trifluoromethoxy group, and $R^9$ is a hydrogen atom. In particular, preferably, $R^8$ is a fluorine atom, chlorine atom, methyl group, or trifluoromethyl group, and $R^9$ is a hydrogen atom. Moreover, preferably, both $R^8$ and $R^9$ are fluorine atoms.

In a preferred embodiment, the present invention encompasses a compound represented by general formula [I] above, wherein ring A is an optionally substituted aryl group or an optionally substituted heteroaryl group;

wherein substituent(s) on each of the optionally substituted aryl group and the optionally substituted heteroaryl group is/are one to three group(s) independently selected from the group consisting of a halogen atom, alkyl group, haloalkyl group, cycloalkyl group, alkoxy group, haloalkoxy group, and alkyleneoxy group;

$R^1$ is an optionally substituted alkyl group, an optionally substituted cycloalkyl group, an optionally substituted aliphatic heterocyclic group, an optionally substituted aryl group that may be partially hydrogenated, an optionally substituted heteroaryl group, or a carbamoyl group optionally substituted with one or two alkyl group(s), wherein substituent(s) on the optionally substituted alkyl group is/are one to three group(s) independently selected from the group consisting of a halogen atom; a hydroxy group; an oxo group; a cyano group; a cycloalkyl group; an alkoxy group; an alkanoyl group; a carbamoyl group optionally substituted with one or two alkyl group(s); an aliphatic heterocyclic group; an aliphatic heterocyclic carbonyl group optionally substituted with one or two group(s) independently selected from the group consisting of a halogen atom, alkyl group, haloalkyl group, and alkoxyalkyl group; an alkylsulfonyl group; an aliphatic heterocyclic sulfonyl group; and an alkyleneoxy group, and substituent(s) on each of the optionally substituted cycloalkyl group, the optionally substituted aliphatic heterocyclic group, the optionally substituted aryl group that may be partially hydrogenated, and the optionally substituted heteroaryl group are one to three group(s) independently selected from the group consisting of a halogen atom; a hydroxy group; an oxo group; a cyano group; an alkyl group; a haloalkyl group; a cycloalkyl group; an alkoxy group; a hydroxyalkyl group; an alkoxyalkyl group; an alkanoyl group; a carbamoyl group optionally substituted with one or two alkyl group(s); an aliphatic heterocyclic group; an aliphatic heterocyclic carbonyl group optionally substituted with one or two group(s) independently selected from the group consisting of a halogen atom, alkyl group, haloalkyl group, and alkoxyalkyl group; an alkylsulfonyl group; an aliphatic heterocyclic sulfonyl group; and an alkyleneoxy group;

$R^2$ is a halogen atom, alkyl group, or alkoxy group;

$R^3$ is an alkyl group substituted with a substituted aryl group, or an alkyl group substituted with a substituted heteroaryl group, wherein a substituent on each of the substituted aryl group and substituted heteroaryl group is an aliphatic heterocyclic group optionally substituted with a carboxyl group, and the aryl group and heteroaryl group are each optionally further substituted with a haloalkyl group; and $R^4$ is a hydrogen atom or alkyl group; or $R^3$ and $R^4$ are terminally attached to each other, and together with the nitrogen atom to which they are attached, form a group represented by formula [II]:

[Formula 6]

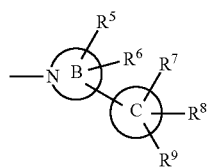

[II]

wherein ring B represents a nitrogen-containing aliphatic heterocyclic group that may partially contain a double bond;

ring C represents an aryl or heteroaryl group;

$R^5$ and $R^6$ each independently represent a group selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

$R^7$ represents an optionally substituted alkyl group, an optionally substituted alkenyl group, an optionally substituted cycloalkyl group, an optionally substituted cycloalkenyl group, an optionally substituted aryl group, an optionally substituted heteroaryl group, an optionally substituted aliphatic heterocyclic group, an optionally substituted alkoxy group, an amino group optionally substituted with one or two alkyl group(s) optionally substituted with a carboxyl group, or a carbamoyl group optionally substituted with one or two alkyl group(s) optionally substituted with a carboxyl group, wherein substituent(s) on the optionally substituted alkyl group is/are one or two group(s) independently selected from the group consisting of a hydroxy group; an oxo group; a cyano group; an alkoxy group; an alkanoyl group; a carboxyl group; an alkoxycarbonyl group; an aliphatic heterocyclic carbonyl group optionally substituted with a carboxyl group; a heteroaryl group optionally substituted with a hydroxy or oxo group; an aliphatic heterocyclic group optionally substituted with one or two oxo groups; a carbamoyl group optionally substituted with one or two group(s) independently selected from the group consisting of an alkyl group (the alkyl moiety is optionally substituted with a hydroxy, alkoxy, or carboxyl group) and a hydroxy group; an alkylsulfonyl group; an aminosulfonyl group optionally substituted with one or two alkyl group(s); an aminosulfonylaminocarbonyl group optionally substituted with one or two alkyl group(s); an alkylsulfonylaminocarbonyl group; and an amino group optionally substituted with one or two group(s) independently selected from the group consisting of alkyl, alkanoyl, and alkylsulfonyl groups, and substituent(s) on each of the optionally substituted alkenyl group, the optionally substituted cycloalkyl group, the optionally substituted cycloalkenyl group, the optionally substituted aryl group, the optionally substituted heteroaryl group, the optionally substituted aliphatic heterocyclic group, and the optionally substituted alkoxy group is/are one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; an aliphatic heterocyclic carbonyl group optionally substituted with a carboxyl group; a heteroaryl group optionally substituted with a hydroxy or oxo group; an aliphatic heterocyclic group optionally substituted with one or two oxo group(s); a carbamoyl group optionally substituted with one or two group(s) independently selected from the group consisting of an alkyl group (the alkyl moiety is optionally substituted with a hydroxy, alkoxy, or carboxyl group) and a hydroxy group; an alkylsulfonyl group; an aminosulfonyl group optionally substituted with one or two alkyl group(s); an aminosulfonylaminocarbonyl group optionally substituted with one or two alkyl group(s); an alkylsulfonylaminocarbonyl group; and an amino group optionally substituted with one or two group(s) independently selected from the group consisting of alkyl, alkanoyl, and alkylsulfonyl groups; and $R^8$ and $R^9$ each independently represent a group selected from the group consisting of a hydrogen atom, halogen atom, cyano group, alkyl group, haloalkyl group, and haloalkoxy group;

or a pharmaceutically acceptable salt thereof.

In another preferred embodiment, the present invention encompasses a compound represented by general formula [I]

above, wherein ring A is an optionally substituted aryl group or an optionally substituted heteroaryl group, wherein substituent(s) on each of the optionally substituted aryl group and the optionally substituted heteroaryl group is/are one to three group(s) independently selected from the group consisting of a halogen atom, alkyl group, haloalkyl group, cycloalkyl group, alkoxy group, haloalkoxy group, and alkyleneoxy group;

the aryl moiety of the optionally substituted aryl group represented by ring A is a monocyclic or bicyclic aryl, and the heteroaryl moiety of the optionally substituted heteroaryl group represented by ring A is a 5- to 10-membered monocyclic or bicyclic heteroaryl containing one to four heteroatom(s) independently selected from the group consisting of oxygen, sulfur, and nitrogen atoms;

$R^1$ is an optionally substituted alkyl group, an optionally substituted cycloalkyl group, an optionally substituted aliphatic heterocyclic group, an optionally substituted aryl group that may be partially hydrogenated, an optionally substituted heteroaryl group, or a carbamoyl group optionally substituted with one or two alkyl group(s), wherein substituent(s) on the optionally substituted alkyl group are one to three group(s) independently selected from the group consisting of a halogen atom; a hydroxy group; an oxo group; a cyano group; a cycloalkyl group; an alkoxy group; an alkanoyl group; a carbamoyl group optionally substituted with one or two alkyl group(s); a 4- to 7-membered monocyclic aliphatic heterocyclic group containing one or two heteroatom(s) independently selected from the group consisting of oxygen, sulfur, and nitrogen atoms; an aliphatic heterocyclic carbonyl group optionally substituted with one or two group(s) independently selected from the group consisting of a halogen atom, alkyl group, haloalkyl group, and alkoxyalkyl group; an alkylsulfonyl group; an aliphatic heterocyclic sulfonyl group; and an alkyleneoxy group, substituent(s) on each of the optionally substituted cycloalkyl group, the optionally substituted aliphatic heterocyclic group, the optionally substituted aryl group that may be partially hydrogenated, and the optionally substituted heteroaryl group are one to three group(s) independently selected from the group consisting of a halogen atom; a hydroxy group; an oxo group; a cyano group; an alkyl group; a haloalkyl group; a cycloalkyl group; an alkoxy group; a hydroxyalkyl group; an alkoxyalkyl group; an alkanoyl group; a carbamoyl group optionally substituted with one or two alkyl group(s); a 4- to 7-membered monocyclic aliphatic heterocyclic group containing one or two heteroatom(s) independently selected from the group consisting of oxygen, sulfur, and nitrogen atoms; an aliphatic heterocyclic carbonyl group optionally substituted with one or two group(s) independently selected from the group consisting of a halogen atom, alkyl group, haloalkyl group, and alkoxyalkyl group; an alkylsulfonyl group; an aliphatic heterocyclic sulfonyl group; and an alkyleneoxy group, the aliphatic heterocyclic moiety of each of the aliphatic heterocyclic carbonyl group and aliphatic heterocyclic sulfonyl group with which $R^1$ is substituted is a 4- to 7-membered monocyclic aliphatic heterocyclic ring containing at least one nitrogen atom, and optionally further containing one heteroatom selected from the group consisting of oxygen, sulfur, and nitrogen atoms, the aliphatic heterocyclic moiety of the optionally substituted aliphatic heterocyclic group represented by $R^1$ is a 4- to 7-membered monocyclic aliphatic heterocyclic ring containing one or two heteroatom(s) independently selected from the group consisting of oxygen, sulfur, and nitrogen atoms, and the heteroaryl moiety of the optionally substituted heteroaryl group represented by $R^1$ is 5- or 6-membered monocyclic heteroaryl containing one to four heteroatom(s) independently selected from the group consisting of oxygen, sulfur, and nitrogen atoms;

$R^2$ is a halogen atom, alkyl group, or alkoxy group;

$R^3$ is an alkyl group substituted with a substituted aryl group, wherein substituent(s) on the substituted aryl group is/are an aliphatic heterocyclic group optionally substituted with a carboxyl group (wherein the aliphatic heterocyclic group is a 4- to 8-membered monocyclic or bicyclic aliphatic heterocyclic group containing one or two heteroatom(s) independently selected from the group consisting of oxygen, sulfur, and nitrogen atoms) and a haloalkyl group; and $R^4$ is a hydrogen atom or alkyl group; or $R^3$ and $R^4$ are terminally attached to each other, and together with the nitrogen atom to which they are attached, form a group represented by formula [II], wherein ring B is a 4- to 8-membered monocyclic or bicyclic aliphatic heterocyclic group that may further contain, in addition to the nitrogen atom shown in formula [II], one heteroatom selected from the group consisting of oxygen, sulfur, and nitrogen atoms, and may partially contain a double bond;

ring C is a monocyclic aryl group, or a 5- or 6-membered monocyclic heteroaryl group containing one to four heteroatom(s) independently selected from the group consisting of oxygen, sulfur, and nitrogen atoms;

$R^5$ and $R^6$ are each independently a group selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

$R^7$ is an optionally substituted alkyl group, an optionally substituted alkenyl group, an optionally substituted cycloalkyl group, an optionally substituted cycloalkenyl group, an optionally substituted aryl group, an optionally substituted heteroaryl group, an optionally substituted aliphatic heterocyclic group, an optionally substituted alkoxy group, an amino group optionally substituted with one or two alkyl group(s) optionally substituted with a carboxyl group, or a carbamoyl group which is optionally substituted with one or two alkyl group(s) optionally substituted with a carboxyl group, wherein substituent(s) on the optionally substituted alkyl group are one or two group(s) independently selected from the group consisting of a hydroxy group; an oxo group; a cyano group; an alkoxy group; an alkanoyl group; a carboxyl group; an alkoxycarbonyl group; an aliphatic heterocyclic carbonyl group optionally substituted with a carboxyl group; a heteroaryl group optionally substituted with a hydroxy or oxo group; a 4- to 7-membered monocyclic aliphatic heterocyclic group optionally substituted with one or two oxo group(s), and containing one or two heteroatom(s) independently selected from the group consisting of oxygen, sulfur, and nitrogen atoms; a carbamoyl group optionally substituted with one or two groups independently selected from the group consisting of an alkyl group (the alkyl group is optionally substituted with a hydroxy, alkoxy, or carboxyl group) and a hydroxy group; an alkylsulfonyl group; an aminosulfonyl group optionally substituted with one or two alkyl group(s); an aminosulfonylaminocarbonyl group optionally substituted with one or two alkyl group(s); an alkylsulfonylaminocarbonyl group; and an amino group optionally substituted with one or two group(s) independently selected from the group consisting of alkyl, alkanoyl, and alkylsulfonyl groups, substituent(s) on each of the optionally substituted alkenyl group, the optionally substituted cycloalkyl group, the optionally substituted cycloalkenyl group, the optionally substituted aryl group, the optionally substituted heteroaryl group, the optionally substituted aliphatic heterocyclic group, and the optionally substituted alkoxy group are one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; an aliphatic heterocyclic carbonyl group optionally substituted with a carboxyl group; a heteroaryl group optionally substituted with a hydroxy or oxo group; a 4- to 7-membered monocyclic aliphatic heterocyclic group optionally substituted with one or two oxo group(s), and containing one or two heteroatom(s) independently selected from the group consisting of oxygen, sulfur, and nitrogen atoms; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonyl group; an aminosulfonyl group optionally substituted with one or two alkyl group(s); an aminosulfonylaminocarbonyl group optionally substituted with one or two alkyl group(s); an alkylsulfonylaminocarbonyl group; and an amino group optionally substituted with one or two group(s) independently selected from the group consisting of alkyl, alkanoyl, and alkylsulfonyl groups, the aliphatic heterocyclic moiety of the aliphatic heterocyclic carbonyl group with which $R^7$ is substituted is a 4- to 7-membered monocyclic aliphatic heterocyclic ring containing at least one nitrogen atom, and optionally further containing one heteroatom selected from the group consisting of oxygen, sulfur, and nitrogen atoms, the heteroaryl group with which $R^7$ is substituted is a 5- or 6-membered monocyclic heteroaryl group containing one to four heteroatom(s) independently selected from the group consisting of oxygen, sulfur, and nitrogen atoms, the heteroaryl moiety of the optionally substituted heteroaryl group represented by $R^7$ is 5- or 6-membered monocyclic heteroaryl containing one to four heteroatom(s) independently selected from the group consisting of oxygen, sulfur, and nitrogen atoms, and the aliphatic heterocyclic moiety of the optionally substituted aliphatic heterocyclic group represented by $R^7$ is a 4- to 8-membered monocyclic or bicyclic aliphatic heterocyclic ring containing one or two heteroatom(s) independently selected from the group consisting of oxygen, sulfur, and nitrogen atoms; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In still another preferred embodiment, the present invention encompasses a compound represented by general formula [I] above, wherein ring A is an optionally substituted aryl group or an optionally substituted heteroaryl group, wherein substituents on each of the optionally substituted aryl and heteroaryl groups are one or two group(s) independently selected from the group consisting of a halogen atom, alkyl group, haloalkyl group, cycloalkyl group, alkoxy group, haloalkoxy group, and alkyleneoxy group;

the aryl moiety of the optionally substituted aryl group represented by ring A is a group selected from the group consisting of phenyl and naphthyl, and the heteroaryl moiety of the optionally substituted heteroaryl group represented by ring A is a group selected from the group consisting of pyrrolyl, furanyl, thienyl, imidazolyl, pyrazolyl, oxazolyl, isoxazolyl, thiazolyl, tetrazolyl, oxadiazolyl, pyridinyl, pyrazinyl, pyrimidinyl, pyridazinyl, thiazinyl, triazinyl, indolyl, isoindolyl, and benzoimidazolyl;

$R^1$ is an optionally substituted alkyl group, an optionally substituted cycloalkyl group, an optionally substituted aliphatic heterocyclic group, an optionally substituted aryl group that may be partially hydrogenated, an optionally substituted heteroaryl group, or a carbamoyl group optionally substituted with one or two alkyl groups, wherein substituent(s) on the optionally substituted alkyl group is/are one or two group(s) independently selected from the group consisting of a halogen atom; a hydroxy group; an oxo group; a cyano group; a cycloalkyl group; an alkoxy group; an alkanoyl group; a carbamoyl group optionally substituted with one or two alkyl group(s); an aliphatic heterocyclic group; an aliphatic heterocyclic carbonyl group optionally substituted with one or two group(s) independently selected from the group consisting of a halogen atom, alkyl group, haloalkyl group, and alkoxyalkyl group; an alkylsulfonyl group; an aliphatic heterocyclic sulfonyl group; and an alkyleneoxy group, substituent(s) on each of the optionally substituted cycloalkyl group, the optionally substituted aliphatic heterocyclic group, the optionally substituted aryl group that may be partially hydrogenated, and the optionally substituted heteroaryl group is/are one or two group(s) independently selected from the group consisting of a halogen atom; a hydroxy group; an oxo group; a cyano group; an alkyl group; a haloalkyl group; a cycloalkyl group; an alkoxy group; a hydroxyalkyl group; an alkoxyalkyl group; an alkanoyl group; a carbamoyl group optionally substituted with one or two alkyl group(s); an aliphatic heterocyclic group; an aliphatic heterocyclic carbonyl group optionally substituted with one or two group(s) independently selected from the group consisting of a halogen atom, alkyl group, haloalkyl group, and alkoxyalkyl group; an alkylsulfonyl group; an aliphatic heterocyclic sulfonyl group; and an alkyleneoxy group, the aliphatic heterocyclic group with which $R^1$ is substituted is a group selected from the group consisting of an azetidinyl group, pyrrolidinyl group, tetrahydrofuranyl group, imidazolinyl group, thiazolidinyl group, isothiazolidinyl group, piperidinyl group, piperazinyl group, morpholinyl group, thiomorpholinyl group, tetrahydropyranyl group, homopiperazinyl group, and homomorpholinyl group, the aliphatic heterocyclic moiety of each of the aliphatic heterocyclic carbonyl group and the aliphatic heterocyclic sulfonyl group with which $R^1$ is substituted is a group selected from the group consisting of azetidinyl, pyrrolidinyl, imidazolinyl, thiazolidinyl, isothiazolidinyl, piperidinyl, piperazinyl, morpholinyl, thiomorpholinyl, homopiperazinyl, and homomorpholinyl, the aryl moiety of the optionally substituted aryl group that may be partially hydrogenated represented by $R^1$ is a group selected from the group consisting of phenyl, naphthyl, dihydrophenyl, indanyl, and tetrahydronaphthyl, the aliphatic heterocyclic moiety of the optionally substituted aliphatic heterocyclic group represented by $R^1$ is a group selected from the group consisting of azetidinyl, pyrrolidinyl, tetrahydrofuranyl, imidazolinyl, thiazolidinyl, isothiazolidinyl, piperidinyl, piperazinyl, morpholinyl, thiomorpholinyl, tetrahydropyranyl, homopiperazinyl, and homomorpholinyl, and the heteroaryl moiety of the optionally substituted heteroaryl group represented by $R^1$ is a group selected from the group consisting of pyrrolyl, furanyl, thienyl, imidazolyl, pyrazolyl, oxazolyl, isoxazolyl, thiazolyl, tetrazolyl, oxadiazolyl, pyridinyl, pyrazinyl, pyrimidinyl, pyridazinyl, thiazinyl, and triazinyl;

$R^2$ is a halogen atom, alkyl group, or alkoxy group;

$R^3$ is an alkyl group substituted with a substituted aryl group, wherein substituent(s) on the substituted aryl group are an aliphatic heterocyclic group optionally substituted with a carboxyl group (wherein the aliphatic heterocyclic group is a group selected from the group consisting of an azetidinyl group, pyrrolidinyl group, tetrahydrofuranyl group, imidazolinyl group, thiazolidinyl group, isothiazolidinyl group, piperidinyl group, piperazinyl group, morpholinyl group, thiomorpholinyl group, tetrahydropyranyl group, homopiperazinyl group, homomorpholinyl group, 3-azabicyclo[3.1.0]hexyl group, and octahydropyrrolo[3,4-c]pyrrolyl group) and a haloalkyl group; and $R^4$ is a hydrogen atom or alkyl group; or $R^3$ and $R^4$ are terminally attached to each other, and together with the nitrogen atom to which they are attached, form a group represented by formula [II], wherein ring B is a group selected from the group consisting of an azetidinyl group, pyrrolidinyl group, imidazolinyl group, thiazolidinyl group, isothiazolidinyl group, piperidinyl group, piperazinyl group, morpholinyl group, thiomorpholinyl group, tetrahydropyridinyl group, homopiperazinyl group, homomorpholinyl group, 3-azabicyclo[3.1.0]hexyl group, and octahydropyrrolo[3,4-c]pyrrolyl group;

ring C is a group selected from the group consisting of a phenyl group, pyrrolyl group, furanyl group, thienyl group, imidazolyl group, pyrazolyl group, oxazolyl group, isoxazolyl group, thiazolyl group, tetrazolyl group, oxadiazolyl group, pyridinyl group, pyrazinyl group, pyrimidinyl group, pyridazinyl group, thiazinyl group, and triazinyl group;

$R^5$ and $R^6$ are each independently a group selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

$R^7$ is an optionally substituted alkyl group, an optionally substituted alkenyl group, an optionally substituted cycloalkyl group, an optionally substituted cycloalkenyl group, an optionally substituted aryl group, an optionally substituted heteroaryl group, an optionally substituted aliphatic heterocyclic group, an optionally substituted alkoxy group, an amino group optionally substituted with one or two alkyl group(s) optionally substituted with a carboxyl group, or a carbamoyl group optionally which is substituted with one or two alkyl group(s) optionally substituted with a carboxyl group, wherein substituent(s) on the optionally substituted alkyl group is/are one or two group(s) independently selected from the group consisting of a hydroxy group; an oxo group; a cyano group; an alkoxy group; an alkanoyl group; a carboxyl group; an alkoxycarbonyl group; an aliphatic heterocyclic carbonyl group optionally substituted with a carboxyl group; a heteroaryl group optionally substituted with a hydroxy or oxo group; an aliphatic heterocyclic group optionally substituted with one or two oxo group(s); a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonyl group; an aminosulfonyl group optionally substituted with one or two alkyl group(s); an aminosulfonylaminocarbonyl group optionally substituted with one or two alkyl group(s); an alkylsulfonylaminocarbonyl group; and an amino group optionally substituted with one or two group(s) independently selected from the group consisting of alkyl, alkanoyl, and alkylsulfonyl groups, substituent(s) on each of the optionally substituted alkenyl group, the optionally substituted cycloalkyl group, the optionally substituted cycloalkenyl group, the optionally substituted aryl group, the optionally substituted heteroaryl group, the optionally substituted aliphatic heterocyclic group, and the optionally substituted alkoxy group are one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; an aliphatic heterocyclic carbonyl group optionally substituted with a carboxyl group; a heteroaryl group optionally substituted with a hydroxy or oxo group; an aliphatic heterocyclic group optionally substituted with one or two oxo group(s); a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonyl group; an aminosulfonyl group optionally substituted with one or two alkyl group(s); an aminosulfonylaminocarbonyl group optionally substituted with one or two alkyl group(s); an alkylsulfonylaminocarbonyl group; and an amino group optionally substituted with one or two group(s) independently selected from the group consisting of alkyl, alkanoyl, and alkylsulfonyl groups, the aliphatic heterocyclic moiety of the aliphatic heterocyclic carbonyl group with which $R^7$ is substituted is a group selected from the group consisting of azetidinyl, pyrrolidinyl, imidazolinyl, thiazolidinyl, isothiazolidinyl, piperidinyl, piperazinyl, morpholinyl, thiomorpholinyl, homopiperazinyl, and homomorpholinyl, the heteroaryl group with which $R^7$ is substituted is a group selected from the group consisting of a pyrrolyl group, furanyl group, thienyl group, imidazolyl group, pyrazolyl group, oxazolyl group, isoxazolyl group, thiazolyl group, tetrazolyl group, oxadiazolyl group, pyridinyl group, pyrazinyl group, pyrimidinyl group, pyridazinyl group, thiazinyl group, and triazinyl group;

the aliphatic heterocyclic group with which $R^7$ is substituted is a group selected from the group consisting of an azetidinyl group, pyrrolidinyl group, tetrahydrofuranyl group, imidazolinyl group, thiazolidinyl group, isothiazolidinyl group, piperidinyl group, piperazinyl group, morpholinyl group, thiomorpholinyl group, tetrahydropyranyl group, homopiperazinyl group, and homomorpholinyl group, the heteroaryl moiety of the optionally substituted heteroaryl group represented by $R^7$ is a group selected from the group consisting of pyrrolyl, furanyl, thienyl, imidazolyl, pyrazolyl, oxazolyl, isoxazolyl, thiazolyl, tetrazolyl, oxadiazolyl, pyridinyl, pyrazinyl, pyrimidinyl, pyridazinyl, thiazinyl, and triazinyl, and the aliphatic heterocyclic moiety of the optionally substituted aliphatic heterocyclic group represented by $R^7$ is a group selected from the group consisting of azetidinyl, pyrrolidinyl, tetrahydrofuranyl, imidazolinyl, thiazolidinyl, isothiazolidinyl, piperidinyl, piperazinyl, morpholinyl, thiomorpholinyl, tetrahydropyranyl, homopiperazinyl, homomorpholinyl, 3-azabicyclo[3.1.0]hexyl, and octahydropyrrolo[3,4-c]pyrrolyl; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In yet another preferred embodiment, the present invention encompasses a compound represented by general formula [I] above, wherein ring A is a phenyl or naphthyl group optionally substituted with one or two group(s) independently selected from the group consisting of a halogen atom, alkyl group, haloalkyl group, cycloalkyl group, alkoxy group, haloalkoxy group, and alkyleneoxy group, or a heteroaryl group optionally substituted with one or two group (s) independently selected from the group consisting of a halogen atom and alkoxy group, wherein the heteroaryl group is a group selected from the group consisting of a pyrrolyl group, furanyl group, thienyl group, imidazolyl group, pyrazolyl group, oxazolyl group, isoxazolyl group, thiazolyl group, tetrazolyl group, oxadiazolyl group, pyridinyl group, pyrazinyl group, pyrimidinyl group, pyridazinyl group, thiazinyl group, triazinyl group, indolyl group, isoindolyl group, and benzoimidazolyl group;

$R^1$ is (1) an alkyl group optionally substituted with one or two group(s) independently selected from the group consisting of a halogen atom; a hydroxy group; a cycloalkyl group; an alkoxy group; an aliphatic heterocyclic group; an aliphatic heterocyclic carbonyl group optionally substituted with one or two group(s) independently selected from the group consisting of a halogen atom, alkyl group, haloalkyl group, and alkoxyalkyl group; an aliphatic heterocyclic sulfonyl group; and a carbamoyl group optionally substituted with one or two alkyl group(s)

(wherein the aliphatic heterocyclic group is a group selected from the group consisting of an azetidinyl group, pyrrolidinyl group, tetrahydrofuranyl group, imidazolinyl group, thiazolidinyl group, isothiazolidinyl group, piperidinyl group, piperazinyl group, morpholinyl group, thiomorpholinyl group, tetrahydropyranyl group, homopiperazinyl group, and homomorpholinyl group, and the aliphatic heterocyclic moiety of each of the aliphatic heterocyclic carbonyl group and aliphatic heterocyclic sulfonyl group is a group selected from the group consisting of azetidinyl, pyrrolidinyl, imidazolinyl, thiazolidinyl, isothiazolidinyl, piperidinyl, piperazinyl, morpholinyl, thiomorpholinyl, homopiperazinyl, and homomorpholinyl), (2) a monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group, (3) an adamantyl group optionally substituted with a hydroxy group, (4) an aliphatic heterocyclic group optionally substituted with a group selected from the group consisting of an alkyl group, hydroxyalkyl group, haloalkyl group, alkanoyl group, and alkylsulfonyl group (wherein the aliphatic heterocyclic group is a group selected from the group consisting of an azetidinyl group, pyrrolidinyl group, tetrahydrofuranyl group, imidazolinyl group, thiazolidinyl group, isothiazolidinyl group, piperidinyl group, piperazinyl group, morpholinyl group, thiomorpholinyl group, tetrahydropyranyl group, homopiperazinyl group, and homomorpholinyl group), (5) a group selected from the group consisting of a phenyl group, naphthyl group, dihydrophenyl group, indanyl group, and tetrahydronaphthyl group, (6) a heteroaryl group which is optionally substituted with a group selected from the group consisting of a cyano group, alkyl group, alkoxy group, and carbamoyl group (wherein the heteroaryl group is a group selected from the group consisting of a pyrrolyl group, furanyl group, thienyl group, imidazolyl group, pyrazolyl group, oxazolyl group, isoxazolyl group, thiazolyl group, tetrazolyl group, oxadiazolyl group, pyridinyl group, pyrazinyl group, pyrimidinyl group, pyridazinyl group, thiazinyl group, and triazinyl group), (7) a carbamoyl group, or (8) a mono-alkylcarbamoyl group;

$R^2$ is a halogen atom, alkyl group, or alkoxy group;

$R^3$ is an alkyl group substituted with a substituted phenyl group, wherein substituent(s) on the substituted phenyl group is/are an aliphatic heterocyclic group substituted with a carboxyl group (wherein the aliphatic heterocyclic group is a group selected from the group consisting of an azetidinyl group, pyrrolidinyl group, tetrahydrofuranyl group, imidazolinyl group, thiazolidinyl group, isothiazolidinyl group, piperidinyl group, piperazinyl group, morpholinyl group, thiomorpholinyl group, tetrahydropyranyl group, homopiperazinyl group, homomorpholinyl group, 3-azabicyclo[3.1.0]hexyl group, and octahydropyrrolo[3,4-c]pyrrolyl group) and a haloalkyl group; and $R^4$ is an alkyl group; or $R^3$ and $R^4$ are terminally attached to each other, and together with the nitrogen atom to which they are attached, form a group represented by formula [II], wherein ring B is a group selected from the group consisting of an azetidinyl group, imidazolinyl group, thiazolidinyl group, isothiazolidinyl group, piperazinyl group, morpholinyl group, thiomorpholinyl group, tetrahydropyridinyl group, homopiperazinyl group, homomorpholinyl group, 3-azabicyclo[3.1.0]hexyl group, and octahydropyrrolo[3,4-c]pyrrolyl group, and both $R^5$ and $R^6$ represent hydrogen atoms, or ring B is a piperidinyl group, and $R^5$ and $R^6$ are each a group independently selected from the group consisting of a hydrogen atom, cyano group, and alkoxyalkyl group, or ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a group selected from the group consisting of a phenyl group, pyrrolyl group, furanyl group, thienyl group, imidazolyl group, pyrazolyl group, oxazolyl group, isoxazolyl group, thiazolyl group, tetrazolyl group, oxadiazolyl group, pyridinyl group, pyrazinyl group, pyrimidinyl group, pyridazinyl group, thiazinyl group, and triazinyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group (wherein the heteroaryl group is a group selected from the group consisting of a pyrrolyl group, furanyl group, thienyl group, imidazolyl group, pyrazolyl group, oxazolyl group, isoxazolyl group, thiazolyl group, tetrazolyl group, oxadiazolyl group, pyridinyl group, pyrazinyl group, pyrimidinyl group, pyridazinyl group, thiazinyl group, and triazinyl group), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonylaminocarbonyl group; an aliphatic heterocyclic carbonyl group optionally substituted with a carboxyl group (wherein the aliphatic heterocyclic ring is a group selected from the group consisting of azetidinyl, pyrrolidinyl, imidazolinyl, thiazolidinyl, isothiazolidinyl, piperidinyl, piperazinyl, morpholinyl, thiomorpholinyl, homopiperazinyl, and homomorpholinyl); an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic group is a group selected from the group consisting of an azetidinyl group, pyrrolidinyl group, tetrahydrofuranyl group, imidazolinyl group, thiazolidinyl group, isothiazolidinyl group, piperidinyl group, piperazinyl group, morpholinyl group, thiomorpholinyl group, tetrahydropyranyl group, homopiperazinyl group, and homomorpholinyl group); an alkylsulfonyl group; a heteroaryl group (wherein the heteroaryl group is a group selected from the group consisting of a pyrrolyl group, furanyl group, thienyl group, imidazolyl group, pyrazolyl group, oxazolyl group, isoxazolyl group, thiazolyl group, tetrazolyl group, oxadiazolyl group, pyridinyl group, pyrazinyl group, pyrimidinyl group, pyridazinyl group, thiazinyl group, and triazinyl group); and an aminosulfonyl group optionally substituted with one or two alkyl group(s)

(wherein the aliphatic heterocyclic group is a group selected from the group consisting of an azetidinyl group, pyrrolidinyl group, tetrahydrofuranyl group, imidazolinyl group, thiazolidinyl group, isothiazolidinyl group, piperidinyl group, piperazinyl group, morpholinyl group, thiomorpholinyl group, tetrahydropyranyl group, homopiperazinyl group, homomorpholinyl group, 3-azabicyclo[3.1.0]hexyl group, and octahydropyrrolo[3,4-c]pyrrolyl group), (8) an alkoxy group optionally substituted with a group selected from the group consisting of a cyano group; a carboxyl group; a heteroaryl group optionally substituted with a hydroxy or oxo group (wherein the heteroaryl group is a group selected from the group consisting of a pyrrolyl group, furanyl group, thienyl group, imidazolyl group, pyrazolyl group, oxazolyl group, isoxazolyl group, thiazolyl group, tetrazoyl group, oxadiazolyl group, pyridinyl group, pyrazinyl group, pyrimidinyl group, pyridazinyl group, thiazinyl group, and triazinyl group); an aminosulfonylaminocarbonyl group optionally substituted with one or two alkyl group(s); and an alkylsulfonylaminocarbonyl group, (9) an amino group which is optionally substituted with one or two alkyl group(s) optionally substituted with a carboxyl group, or

(10) a carbamoyl group; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

A more preferable example may be a compound represented by general formula [I] above, wherein $R^3$ and $R^4$ are terminally attached to each other, and together with the nitrogen atom to which they are attached, form a group represented by formula [II]; or a pharmaceutically acceptable salt thereof.

A still more preferable example may be a compound represented by general formula [I] above, wherein $R^3$ and $R^4$ are terminally attached to each other, and together with the nitrogen atom to which they are attached, form a group represented by formula [II], wherein ring B is a pyrrolidinyl group; or a pharmaceutically acceptable salt thereof.

An even more preferable example may be a compound represented by general formula [I] above, wherein $R^3$ and $R^4$ are terminally attached to each other, and together with the nitrogen atom to which they are attached, form a group represented by formula [II], wherein ring B is a pyrrolidinyl group, and ring C is a phenyl group; or a pharmaceutically acceptable salt thereof.

Still another preferable example may be a compound represented by general formula [I] above, wherein $R^1$ is (1) a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group;

(2) an adamantyl group optionally substituted with a hydroxy group; or (3) an aliphatic heterocyclic group optionally substituted with a group selected from the group consisting of an alkyl group, hydroxyalkyl group, haloalkyl group, alkanoyl group, and alkylsulfonyl group (wherein the aliphatic heterocyclic group is a group selected from the group consisting of tetrahydrofuranyl, tetrahydropyranyl, and piperidinyl groups);

or a pharmaceutically acceptable salt thereof.

A still more preferable example may be a compound represented by general formula [I] above, wherein $R^1$ is a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group; or a pharmaceutically acceptable salt thereof.

Yet another preferable example may be a compound represented by general formula [I] above, wherein $R^1$ is a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group, and $R^3$ and $R^4$ are terminally attached to each other, and together with the nitrogen atom to which they are attached, form a group represented by formula [II], wherein ring B is a pyrrolidinyl group, and ring C is a phenyl group;

or a pharmaceutically acceptable salt thereof.

In still another preferred embodiment, the present invention encompasses a compound represented by general formula [I] above, wherein ring A is a phenyl group optionally substituted with one or two group(s) independently selected from the group consisting of a halogen atom, alkyl group, haloalkyl group, cycloalkyl group, alkoxy group, haloalkoxy group, and alkyleneoxy group, or a pyridinyl group optionally substituted with a group selected from the group consisting of a halogen atom and alkoxy group;

$R^1$ is (1) an alkyl group optionally substituted with one or two group(s) independently selected from the group consisting of a halogen atom; a hydroxy group; a 3- to 7-membered monocyclic cycloalkyl group; an alkoxy group; a tetrahydropyranyl group; an aliphatic heterocyclic carbonyl group optionally substituted with one or two group(s) independently selected from the group consisting of a halogen atom, alkyl group, haloalkyl group, and alkoxyalkyl group (wherein the aliphatic heterocyclic ring is a group selected from the group consisting of pyrrolidinyl, piperidinyl, and morpholinyl); a pyrrolidinylsulfonyl group; and a carbamoyl group optionally substituted with one or two alkyl group(s), (2) a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group, (3) an adamantyl group optionally substituted with a hydroxy group, (4) an aliphatic heterocyclic group optionally substituted with a group selected from the group consisting of an alkyl group, hydroxyalkyl group, haloalkyl group, alkanoyl group, and alkylsulfonyl group (wherein the aliphatic heterocyclic group is a group selected from the group consisting of tetrahydrofuranyl, tetrahydropyranyl, and piperidinyl groups), (5) an indanyl group, (6) a heteroaryl group which is optionally substituted with a group selected from the group consisting of a cyano group, alkyl group, alkoxy group, and carbamoyl group (wherein the heteroaryl group is a group selected from the group consisting of pyridazinyl, pyridinyl, and pyrimidinyl groups), (7) a carbamoyl group, or (8) a mono-alkylcarbamoyl group;

$R^2$ is a halogen atom, $C_{1-3}$ alkyl group, or alkoxy group;

$R^3$ is an alkyl group substituted with a substituted phenyl group, wherein substituent(s) on the substituted phenyl group is/are a piperidinyl group substituted with a carboxyl group, and a haloalkyl group; and $R^4$ is an alkyl group; or $R^3$ and $R^4$ are terminally attached to each other, and together with the nitrogen atom to which they are attached, form a group represented by formula [II], wherein ring B is a group selected from the group consisting of an azetidinyl group, tetrahydropyridinyl group, piperazinyl group, homopiperazinyl group, and octahydropyrrolo[3,4-c]pyrrolyl group, and both $R^5$ and $R^6$ represent hydrogen atoms, or ring B is a piperidinyl group, and $R^5$ and $R^6$ are each a group independently selected from the group consisting of a hydrogen atom, cyano group, and alkoxyalkyl group, or ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a phenyl or pyridinyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group (wherein the heteroaryl group is a group selected from the group consisting of oxazolyl and pyrazolyl groups), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic group is a group selected from the group consisting of pyrrolidinyl and isothiazolidinyl groups); an alkylsulfonyl group; a tetrazolyl group; and an aminosulfonyl group optionally substituted with one or two alkyl group(s)

(wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo [3.1.0]hexyl group), (8) an alkoxy group optionally substituted with a group selected from the group consisting of a cyano group; a carboxyl group; a heteroaryl group optionally substituted with a hydroxy or oxo group (wherein the heteroaryl group is a group selected from the group consisting of isoxazolyl, oxadiazolyl, and tetrazolyl groups); an aminosulfonylaminocarbonyl group optionally substituted with one or two alkyl group(s); and an alkylsulfonylaminocarbonyl group, (9) an amino group which is optionally substituted with one or two alkyl group(s) optionally substituted with a carboxyl group, or

(10) a carbamoyl group; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In yet another preferred embodiment, the present invention encompasses a compound represented by general formula [I] above, wherein ring A is a phenyl group optionally substituted with one or two group(s) independently selected from the group consisting of a halogen atom, alkyl group, haloalkyl group, cycloalkyl group, alkoxy group, haloalkoxy group, and alkyleneoxy group, or a pyridinyl group optionally substituted with a group selected from the group consisting of a halogen atom and alkoxy group;

$R^1$ is (1) an alkyl group optionally substituted with one or two group(s) independently selected from the group consisting of a halogen atom; a hydroxy group; a 3- to 7-membered monocyclic cycloalkyl group; an alkoxy group; a tetrahydropyranyl group; an aliphatic heterocyclic carbonyl group optionally substituted with one or two group(s) independently selected from the group consisting of a halogen atom, alkyl group, haloalkyl group, and alkoxyalkyl group (wherein the aliphatic heterocyclic ring is a group selected from the group consisting of pyrrolidinyl, piperidinyl, and morpholinyl); a pyrrolidinylsulfonyl group; and a carbamoyl group optionally substituted with one or two alkyl group(s), (2) a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group, (3) an adamantyl group optionally substituted with a hydroxy group, (4) an aliphatic heterocyclic group optionally substituted with a group selected from the group consisting of an alkyl group, hydroxyalkyl group, haloalkyl group, alkanoyl group, and alkylsulfonyl group
(wherein the aliphatic heterocyclic group is a group selected from the group consisting of tetrahydrofuranyl, tetrahydropyranyl, and piperidinyl groups), (5) an indanyl group, (6) a heteroaryl group which is optionally substituted with a group selected from the group consisting of a cyano group, alkyl group, alkoxy group, and carbamoyl group
(wherein the heteroaryl group is a group selected from the group consisting of pyridazinyl, pyridinyl, and pyrimidinyl groups), (7) a carbamoyl group, or (8) a mono-alkylcarbamoyl group;

$R^2$ is a halogen atom, $C_{1-3}$ alkyl group, or alkoxy group;

$R^3$ is an alkyl group substituted with a substituted phenyl group, wherein substituent(s) on the substituted phenyl group is/are (1) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic group is a group selected from the group consisting of pyrrolidinyl and isothiazolidinyl groups); an alkylsulfonyl group; a tetrazolyl group; and an aminosulfonyl group optionally substituted with one or two alkyl group(s) (wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo[3.1.0]hexyl group), and (2) a haloalkyl group; and $R^4$ is an alkyl group; or $R^3$ and $R^4$ are terminally attached to each other, and together with the nitrogen atom to which they are attached, form a group represented by formula [II], wherein ring B is a group selected from the group consisting of an azetidinyl group, tetrahydropyridinyl group, piperazinyl group, homopiperazinyl group, and octahydropyrrolo[3,4-c]pyrrolyl group, and both $R^5$ and $R^6$ represent hydrogen atoms, or ring B is a piperidinyl group, and $R^5$ and $R^6$ are each a group independently selected from the group consisting of a hydrogen atom, cyano group, and alkoxyalkyl group, or ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a phenyl or pyridinyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group
(wherein the heteroaryl group is a group selected from the group consisting of oxazolyl and pyrazolyl groups), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic group is a group selected from the group consisting of pyrrolidinyl and isothiazolidinyl groups); an alkylsulfonyl group; a tetrazolyl group; and an aminosulfonyl group optionally substituted with one or two alkyl group(s)
(wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo[3.1.0]hexyl group), (8) an alkoxy group optionally substituted with a group selected from the group consisting of a cyano group; a carboxyl group; a heteroaryl group optionally substituted with a hydroxy or oxo group (wherein the heteroaryl group is a group selected from the group consisting of isoxazolyl, oxadiazolyl, and tetrazolyl groups); an aminosulfonylaminocarbonyl group optionally substituted with one or two alkyl group(s); and an alkylsulfonylaminocarbonyl group, (9) an amino group which is optionally substituted with one or two alkyl group(s) optionally substituted with a carboxyl group, or

(10) a carbamoyl group; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In yet another preferred embodiment, the present invention encompasses a compound represented by general formula [I] above, wherein ring A is a phenyl group optionally substituted with one or two group(s) independently selected from the group consisting of a halogen atom, alkyl group, haloalkyl group, cycloalkyl group, alkoxy group, haloalkoxy group, and alkyleneoxy group, or a pyridinyl group optionally substituted with a group selected from the group consisting of a halogen atom and alkoxy group;

$R^1$ is (1) an alkyl group optionally substituted with one or two group(s) independently selected from the group consisting of a halogen atom; a hydroxy group; a 3- to 7-membered monocyclic cycloalkyl group; an alkoxy group; a tetrahydropyranyl group; an aliphatic heterocyclic carbonyl group optionally substituted with one or two group(s) independently selected from the group consisting of a halogen atom, alkyl group, haloalkyl group, and alkoxyalkyl group (wherein the aliphatic heterocyclic ring is a group selected from the group consisting of pyrrolidinyl, piperidinyl, and morpholinyl); a pyrrolidinylsulfonyl group; and a carbamoyl group optionally substituted with one or two alkyl group(s), (2) a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group, (3) an adamantyl group optionally substituted with a hydroxy group, (4) an aliphatic heterocyclic group optionally substituted with a group selected from the group consisting of an alkyl group, hydroxyalkyl group, haloalkyl group, alkanoyl group, and alkylsulfonyl group (wherein the aliphatic heterocyclic group is a group selected from the group consisting of tetrahydrofuranyl, tetrahydropyranyl, and piperidinyl groups), (5) an indanyl group, (6) a heteroaryl group which is optionally substituted with a group selected from the group consisting of a cyano group, alkyl group, alkoxy group, and carbamoyl group (wherein the heteroaryl group is a group selected from the group consisting of pyridazinyl, pyridinyl, and pyrimidinyl groups), (7) a carbamoyl group, or (8) a mono-alkylcarbamoyl group;

$R^2$ is a halogen atom, $C_{1-3}$ alkyl group, or alkoxy group;

$R^3$ and $R^4$ are terminally attached to each other, and together with the nitrogen atom to which they are attached, form a group represented by formula [II], wherein ring B is a group selected from the group consisting of an azetidinyl group, tetrahydropyridinyl group, piperazinyl group, homopiperazinyl group, and octahydropyrrolo[3,4-c]pyrrolyl group, and both $R^5$ and $R^6$ represent hydrogen atoms, or ring B is a piperidinyl group, and $R^5$ and $R^6$ are each a group independently selected from the group consisting of a hydrogen atom, cyano group, and alkoxyalkyl group, or ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a phenyl or pyridinyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group (wherein the heteroaryl group is a group selected from the group consisting of oxazolyl and pyrazolyl groups), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic group is a group selected from the group consisting of pyrrolidinyl and isothiazolidinyl groups); an alkylsulfonyl group; a tetrazolyl group; and an aminosulfonyl group optionally substituted with one or two alkyl group(s)

(wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo[3.1.0]hexyl group), (8) an alkoxy group optionally substituted with a group selected from the group consisting of a cyano group; a carboxyl group; a heteroaryl group optionally substituted with a hydroxy or oxo group (wherein the heteroaryl group is a group selected from the group consisting of isoxazolyl, oxadiazolyl, and tetrazolyl groups); an aminosulfonylaminocarbonyl group optionally substituted with one or two alkyl group(s); and an alkylsulfonylaminocarbonyl group, (9) an amino group which is optionally substituted with one or two alkyl group(s) optionally substituted with a carboxyl group, or

(10) a carbamoyl group; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In still another preferred embodiment, the present invention encompasses a compound represented by general formula [I] above, wherein ring A is a phenyl group optionally substituted with one or two group(s) independently selected from the group consisting of a halogen atom, alkyl group, haloalkyl group, cycloalkyl group, alkoxy group, haloalkoxy group, and alkyleneoxy group, or a pyridinyl group optionally substituted with a group selected from the group consisting of a halogen atom and alkoxy group;

$R^1$ is (1) a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group, (2) an adamantyl group optionally substituted with a hydroxy group; or (3) an aliphatic heterocyclic group optionally substituted with a group selected from the group consisting of an alkyl group, hydroxyalkyl group, haloalkyl group, alkanoyl group, and alkylsulfonyl group (wherein the aliphatic heterocyclic group is a group selected from the group consisting of tetrahydrofuranyl, tetrahydropyranyl, and piperidinyl groups);

$R^2$ is a halogen atom, $C_{1-3}$ alkyl group, or alkoxy group;

$R^3$ is an alkyl group substituted with a substituted phenyl group, wherein substituents on the substituted phenyl group are a piperidinyl group substituted with a carboxyl group, and a haloalkyl group; and $R^4$ is an alkyl group; or $R^3$ and $R^4$ are terminally attached to each other, and together with the nitrogen atom to which they are attached, form a group represented by formula [II], wherein ring B is a group selected from the group consisting of an azetidinyl group, tetrahydropyridinyl group, piperazinyl group, homopiperazinyl group, and octahydropyrrolo[3,4-c]pyrrolyl group, and both $R^5$ and $R^6$ represent hydrogen atoms, or ring B is a piperidinyl group, and $R^5$ and $R^6$ are each a group independently selected from the group consisting of a hydrogen atom, cyano group, and alkoxyalkyl group, or ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a phenyl or pyridinyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group (wherein the heteroaryl group is a group selected from the group consisting of oxazolyl and pyrazolyl groups), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic group is a group selected from the group consisting of pyrrolidinyl and isothiazolidinyl groups); an alkylsulfonyl group; a tetrazolyl group; and an aminosulfonyl group optionally substituted with one or two alkyl group(s)

(wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo[3.1.0]hexyl group), (8) an alkoxy group optionally substituted with a group selected from the group consisting of a cyano group; a carboxyl group; a heteroaryl group optionally substituted with a hydroxy or oxo group (wherein the heteroaryl group is a group selected from the group consisting of isoxazolyl, oxadiazolyl, and tetrazolyl groups); an aminosulfonylaminocarbonyl group optionally substituted with one or two alkyl group(s); and an alkylsulfonylaminocarbonyl group, (9) an amino group which is optionally substituted with one or two alkyl group(s) optionally substituted with a carboxyl group, or

(10) a carbamoyl group; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In still another preferred embodiment, the present invention encompasses a compound represented by general formula [I] above, wherein ring A is a phenyl group optionally substituted with one or two group(s) independently selected from the group consisting of a halogen atom, alkyl group, haloalkyl group, cycloalkyl group, alkoxy group, haloalkoxy group, and alkyleneoxy group, or a pyridinyl group optionally substituted with a group selected from the group consisting of a halogen atom and alkoxy group;

$R^1$ is a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group;

$R^2$ is a halogen atom, $C_{1-3}$ alkyl group, or alkoxy group;

$R^3$ is an alkyl group substituted with a substituted phenyl group, wherein substituent(s) on the substituted phenyl group is/are a piperidinyl group substituted with a carboxyl group, and a haloalkyl group; and $R^4$ is an alkyl group; or $R^3$ and $R^4$ are terminally attached to each other, and together with the nitrogen atom to which they are attached, form a group represented by formula [II], wherein ring B is a group selected from the group consisting of an azetidinyl group, tetrahydropyridinyl group, piperazinyl group, homopiperazinyl group, and octahydropyrrolo[3,4-c]pyrrolyl group, and both $R^5$ and $R^6$ represent hydrogen atoms, or ring B is a piperidinyl group, and $R^5$ and $R^6$ are each a group independently selected from the group consisting of a hydrogen atom, cyano group, and alkoxyalkyl group, or ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a phenyl or pyridinyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group (wherein the heteroaryl group is a group selected from the group consisting of oxazolyl and pyrazolyl groups), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic group is a group selected from the group consisting of pyrrolidinyl and isothiazolidinyl groups); an alkylsulfonyl group; a tetrazolyl group; and an aminosulfonyl group optionally substituted with one or two alkyl group(s)

(wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo [3.1.0]hexyl group), (8) an alkoxy group optionally substituted with a group selected from the group consisting of a cyano group; a carboxyl group; a heteroaryl group optionally substituted with a hydroxy or oxo group (wherein the heteroaryl group is a group selected from the group consisting of isoxazolyl, oxadiazolyl, and tetrazolyl groups); an aminosulfonylaminocarbonyl group optionally substituted with one or two alkyl group(s); and an alkylsulfonylaminocarbonyl group, (9) an amino group which is optionally substituted with one or two alkyl group(s) optionally substituted with a carboxyl group, or

(10) a carbamoyl group; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In still another preferred embodiment, the present invention encompasses a compound represented by general formula [I] above, wherein ring A is a phenyl group optionally substituted with one or two group(s) independently selected from the group consisting of a halogen atom, alkyl group, haloalkyl group, cycloalkyl group, alkoxy group, haloalkoxy group, and alkyleneoxy group, or a pyridinyl group optionally substituted with a group selected from the group consisting of a halogen atom and alkoxy group;

$R^1$ is (1) a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group, (2) an adamantyl group optionally substituted with a hydroxy group; or (3) an aliphatic heterocyclic group optionally substituted with a group selected from the group consisting of an alkyl group, hydroxyalkyl group, haloalkyl group, alkanoyl group, and alkylsulfonyl group (wherein the aliphatic heterocyclic group is a group selected from the group consisting of tetrahydrofuranyl, tetrahydropyranyl, and piperidinyl groups);

$R^2$ is a halogen atom, $C_{1-3}$ alkyl group, or alkoxy group;

$R^3$ and $R^4$ are terminally attached to each other, and together with the nitrogen atom to which they are attached, form a group represented by formula [II], wherein ring B is a group selected from the group consisting of an azetidinyl group, tetrahydropyridinyl group, piperazinyl group, homopiperazinyl group, and octahydropyrrolo[3,4-c]pyrrolyl group, and both $R^5$ and $R^6$ represent hydrogen atoms, or ring B is a piperidinyl group, and $R^5$ and $R^6$ are each a group independently selected from the group consisting of a hydrogen atom, cyano group, and alkoxyalkyl group, or ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a phenyl or pyridinyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group (wherein the heteroaryl group is a group selected from the group consisting of oxazolyl and pyrazolyl groups), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic group is a group selected from the group consisting of pyrrolidinyl and isothiazolidinyl groups); an alkylsulfonyl group; a tetrazolyl group; and an aminosulfonyl group optionally substituted with one or two alkyl group(s)

(wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo [3.1.0]hexyl group), (8) an alkoxy group optionally substituted with a group selected from the group consisting of a cyano group; a carboxyl group; a heteroaryl group optionally substituted with a hydroxy or oxo group (wherein the heteroaryl group is a group selected from the group consisting of isoxazolyl, oxadiazolyl, and tetrazolyl groups); an aminosulfonylaminocarbonyl group optionally substituted with one or two alkyl group(s); and an alkylsulfonylaminocarbonyl group, (9) an amino group which is optionally substituted with one or two alkyl group(s) optionally substituted with a carboxyl group, or

(10) a carbamoyl group; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In yet another preferred embodiment, the present invention encompasses a compound represented by general formula [I] above, wherein ring A is a phenyl group optionally substituted with one or two group(s) independently selected from the group consisting of a halogen atom, alkyl group, haloalkyl group, cycloalkyl group, alkoxy group, haloalkoxy group, and alkyleneoxy group, or a pyridinyl group optionally substituted with a group selected from the group consisting of a halogen atom and alkoxy group;

$R^1$ is a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group;

$R^2$ is a halogen atom, $C_{1-3}$ alkyl group, or alkoxy group;

$R^3$ and $R^4$ are terminally attached to each other, and together with the nitrogen atom to which they are attached, form a group represented by formula [II], wherein ring B is a group selected from the group consisting of an azetidinyl group, tetrahydropyridinyl group, piperazinyl group, homopiperazinyl group, and octahydropyrrolo[3,4-c]pyrrolyl group, and both $R^5$ and $R^6$ represent hydrogen atoms, or ring B is a piperidinyl group, and $R^3$ and $R^6$ are each a group independently selected from the group consisting of a hydrogen atom, cyano group, and alkoxyalkyl group, or ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a phenyl or pyridinyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group (wherein the heteroaryl group is a group selected from the group consisting of oxazolyl and pyrazolyl groups), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic group is a group selected from the group consisting of pyrrolidinyl and isothiazolidinyl groups); an alkylsulfonyl group; a tetrazolyl group; and an aminosulfonyl group optionally substituted with one or two alkyl group(s)

(wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo [3.1.0]hexyl group), (8) an alkoxy group optionally substituted with a group selected from the group consisting of a cyano group; a carboxyl group; a heteroaryl group optionally substituted with a hydroxy or oxo group (wherein the heteroaryl group is a group selected from the group consisting of isoxazolyl, oxadiazolyl, and tetrazolyl groups); an aminosulfonylaminocarbonyl group optionally substituted with one or two alkyl group(s); and an alkylsulfonylaminocarbonyl group, (9) an amino group which is optionally substituted with one or two alkyl group(s) optionally substituted with a carboxyl group, or

(10) a carbamoyl group; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In still another preferred embodiment, the present invention encompasses a compound represented by general formula [I] above, wherein ring A is a phenyl group optionally substituted with one or two group(s) independently selected from the group consisting of a halogen atom, alkyl group, haloalkyl group, cycloalkyl group, alkoxy group, haloalkoxy group, and alkyleneoxy group, or a pyridinyl group optionally substituted with a group selected from the group consisting of a halogen atom and alkoxy group;

$R^1$ is (1) an alkyl group optionally substituted with one or two group(s) independently selected from the group consisting of a halogen atom; a hydroxy group; a 3- to 7-membered monocyclic cycloalkyl group; an alkoxy group; a tetrahydropyranyl group; an aliphatic heterocyclic carbonyl group optionally substituted with one or two group(s) independently selected from the group consisting of a halogen atom, alkyl group, haloalkyl group, and alkoxyalkyl group (wherein the aliphatic heterocyclic ring is a group selected from the group consisting of pyrrolidinyl, piperidinyl, and morpholinyl); a pyrrolidinylsulfonyl group; and a carbamoyl group optionally substituted with one or two alkyl group(s), (2) a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group, (3) an adamantyl group optionally substituted with a hydroxy group, (4) an aliphatic heterocyclic group optionally substituted with a group selected from the group consisting of an alkyl group, hydroxyalkyl group, haloalkyl group, alkanoyl group, and alkylsulfonyl group (wherein the aliphatic heterocyclic group is a group selected from the group consisting of tetrahydrofuranyl, tetrahydropyranyl, and piperidinyl groups), (5) an indanyl group, (6) a heteroaryl group which is optionally substituted with a group selected from the group consisting of a cyano group, alkyl group, alkoxy group, and carbamoyl group (wherein the heteroaryl group is a group selected from the group consisting of pyridazinyl, pyridinyl, and pyrimidinyl groups), (7) a carbamoyl group, or (8) a mono-alkylcarbamoyl group;

$R^2$ is a halogen atom, $C_{1-3}$ alkyl group, or alkoxy group;

$R^3$ and $R^4$ are terminally attached to each other, and together with the nitrogen atom to which they are attached, form a group represented by formula [II], wherein ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a phenyl or pyridinyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group (wherein the heteroaryl group is a group selected from the group consisting of oxazolyl and pyrazolyl groups), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic group is a group selected from the group consisting of pyrrolidinyl and isothiazolidinyl groups); an alkylsulfonyl group; a tetrazolyl group; and an aminosulfonyl group optionally substituted with one or two alkyl group(s)

(wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo[3.1.0]hexyl group), (8) an alkoxy group optionally substituted with a group selected from the group consisting of a cyano group; a carboxyl group; a heteroaryl group optionally substituted with a hydroxy or oxo group (wherein the heteroaryl group is a group selected from the group consisting of isoxazolyl, oxadiazolyl, and tetrazolyl groups); an aminosulfonylaminocarbonyl group optionally substituted with one or two alkyl group(s); and an alkylsulfonylaminocarbonyl group, (9) an amino group which is optionally substituted with one or two alkyl group(s) optionally substituted with a carboxyl group, or

(10) a carbamoyl group; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In still another preferred embodiment, the present invention encompasses a compound represented by general formula [I] above, wherein ring A is a phenyl group optionally substituted with one or two group(s) independently selected from the group consisting of a halogen atom, alkyl group, haloalkyl group, cycloalkyl group, alkoxy group, haloalkoxy group, and alkyleneoxy group, or a pyridinyl group optionally substituted with a group selected from the group consisting of a halogen atom and alkoxy group;

$R^1$ is (1) a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group, (2) an adamantyl group optionally substituted with a hydroxy group, or (3) an aliphatic heterocyclic group optionally substituted with a group selected from the group consisting of an alkyl group, hydroxyalkyl group, haloalkyl group, alkanoyl group, and alkylsulfonyl group (wherein the aliphatic heterocyclic group is a group selected from the group consisting of tetrahydrofuranyl, tetrahydropyranyl, and piperidinyl groups);

$R^2$ is a halogen atom, $C_{1-3}$ alkyl group, or alkoxy group;

$R^3$ and $R^4$ are terminally attached to each other, and together with the nitrogen atom to which they are attached, form a group represented by formula [II], wherein ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a phenyl or pyridinyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group (wherein the heteroaryl group is a group selected from the group consisting of oxazolyl and pyrazolyl groups), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic group is a group selected from the group consisting of pyrrolidinyl and isothiazolidinyl groups); an alkylsulfonyl group; a tetrazolyl group; and an aminosulfonyl group optionally substituted with one or two alkyl group(s)

(wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo [3.1.0]hexyl group), (8) an alkoxy group optionally substituted with a group selected from the group consisting of a cyano group; a carboxyl group; a heteroaryl group optionally substituted with a hydroxy or oxo group (wherein the heteroaryl group is a group selected from the group consisting of isoxazolyl, oxadiazolyl, and tetrazolyl groups); an aminosulfonylaminocarbonyl group optionally substituted with one or two alkyl groups; and an alkylsulfonylaminocarbonyl group, (9) an amino group which is optionally substituted with one or two alkyl group(s) optionally substituted with a carboxyl group, or

(10) a carbamoyl group; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In still another preferred embodiment, the present invention encompasses a compound represented by general formula [I] above, wherein ring A is a phenyl group optionally substituted with one or two group(s) independently selected from the group consisting of a halogen atom, alkyl group, haloalkyl group, cycloalkyl group, alkoxy group, haloalkoxy group, and alkyleneoxy group, or a pyridinyl group optionally substituted with a group selected from the group consisting of a halogen atom and alkoxy group;

$R^1$ is a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group;

$R^2$ is a halogen atom, $C_{1-3}$ alkyl group, or alkoxy group;

$R^3$ and $R^4$ are terminally attached to each other, and together with the nitrogen atom to which they are attached, form a group represented by formula [II], wherein ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a phenyl or pyridinyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group (wherein the heteroaryl group is a group selected from the group consisting of oxazolyl and pyrazolyl groups), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic group is a group selected from the group consisting of pyrrolidinyl and isothiazolidinyl groups); an alkylsulfonyl group; a tetrazolyl group; and an aminosulfonyl group optionally substituted with one or two alkyl group(s)

(wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo [3.1.0]hexyl group), (8) an alkoxy group optionally substituted with a group selected from the group consisting of a cyano group; a carboxyl group; a heteroaryl group optionally substituted with a hydroxy or oxo group (wherein the heteroaryl group is a group selected from the group consisting of isoxazolyl, oxadiazolyl, and tetrazolyl groups); an aminosulfonylaminocarbonyl group optionally substituted with one or two alkyl group(s); and an alkylsulfonylaminocarbonyl group, (9) an amino group which is optionally substituted with one or two alkyl group(s) optionally substituted with a carboxyl group, or

(10) a carbamoyl group; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In yet another preferred embodiment, the present invention encompasses a compound represented by general formula [I] above, wherein ring A is a phenyl group optionally substituted with one or two group(s) independently selected from the group consisting of a halogen atom, alkyl group, haloalkyl group, cycloalkyl group, alkoxy group, haloalkoxy group, and alkyleneoxy group;

$R^1$ is (1) an alkyl group optionally substituted with one or two group(s) independently selected from the group consisting of a halogen atom; a hydroxy group; a 3- to 7-membered monocyclic cycloalkyl group; an alkoxy group; a tetrahydropyranyl group; an aliphatic heterocyclic carbonyl group optionally substituted with one or two group(s) independently selected from the group consisting of a halogen atom, alkyl group, haloalkyl group, and alkoxyalkyl group (wherein the aliphatic heterocyclic ring is a group selected from the group consisting of pyrrolidinyl, piperidinyl, and morpholinyl); a pyrrolidinylsulfonyl group; and a carbamoyl group optionally substituted with one or two alkyl group(s), (2) a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group, (3) an adamantyl group optionally substituted with a hydroxy group, (4) an aliphatic heterocyclic group optionally substituted with a group selected from the group consisting of an alkyl group, hydroxyalkyl group, haloalkyl group, alkanoyl group, and alkylsulfonyl group (wherein the aliphatic heterocyclic group is a group selected from the group consisting of tetrahydrofuranyl, tetrahydropyranyl, and piperidinyl groups), (5) an indanyl group, (6) a heteroaryl group which is optionally substituted with a group selected from the group consisting of a cyano group, alkyl group, alkoxy group, and carbamoyl group (wherein the heteroaryl group is a group selected from the group consisting of pyridazinyl, pyridinyl, and pyrimidinyl groups), (7) a carbamoyl group, or (8) a mono-alkylcarbamoyl group;

$R^2$ is a halogen atom or alkoxy group;

$R^3$ and $R^4$ are terminally attached to each other, and together with the nitrogen atom to which they are attached, form a group represented by formula [II], wherein ring B is a group selected from the group consisting of an azetidinyl group, tetrahydropyridinyl group, piperazinyl group, homopiperazinyl group, and octahydropyrrolo[3,4-c]pyrrolyl group, and both $R^5$ and $R^6$ represent hydrogen atoms, or ring B is a piperidinyl group, and $R^5$ and $R^6$ are each a group independently selected from the group consisting of a hydrogen atom, cyano group, and alkoxyalkyl group, or ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a phenyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group (wherein the heteroaryl group is a group selected from the group consisting of oxazolyl and pyrazolyl groups), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic group is a group selected from the group consisting of pyrrolidinyl and isothiazolidinyl groups); an alkylsulfonyl group; a tetrazolyl group; and an aminosulfonyl group optionally substituted with one or two alkyl group(s)

(wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo[3.1.0]hexyl group), (8) an alkoxy group optionally substituted with a group selected from the group consisting of a cyano group; a carboxyl group; a heteroaryl group optionally substituted with a hydroxy or oxo group (wherein the heteroaryl group is a group selected from the group consisting of isoxazolyl, oxadiazolyl, and tetrazolyl groups); an aminosulfonylaminocarbonyl group optionally substituted with one or two alkyl group(s); and an alkylsulfonylaminocarbonyl group, (9) an amino group which is optionally substituted with one or two alkyl group(s) optionally substituted with a carboxyl group, or

(10) a carbamoyl group; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In yet another preferred embodiment, the present invention encompasses a compound represented by general formula [I] above, wherein ring A is a phenyl group optionally substituted with one or two group(s) independently selected from the group consisting of a halogen atom, alkyl group, haloalkyl group, cycloalkyl group, alkoxy group, haloalkoxy group, and alkyleneoxy group;

$R^1$ is (1) a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group, (2) an adamantyl group optionally substituted with a hydroxy group, or (3) an aliphatic heterocyclic group optionally substituted with a group selected from the group consisting of an alkyl group, hydroxyalkyl group, haloalkyl group, alkanoyl group, and alkylsulfonyl group (wherein the aliphatic heterocyclic group is a group selected from the group consisting of tetrahydrofuranyl, tetrahydropyranyl, and piperidinyl groups);

$R^2$ is a halogen atom or alkoxy group;

$R^3$ and $R^4$ are terminally attached to each other, and together with the nitrogen atom to which they are attached, form a group represented by formula [II], wherein ring B is a group selected from the group consisting of an azetidinyl group, tetrahydropyridinyl group, piperazinyl group, homopiperazinyl group, and octahydropyrrolo[3,4-c]pyrrolyl group, and both $R^5$ and $R^6$ represent hydrogen atoms, or ring B is a piperidinyl group, and $R^5$ and $R^6$ are each a group independently selected from the group consisting of a hydrogen atom, cyano group, and alkoxyalkyl group, or ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a phenyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group (wherein the heteroaryl group is a group selected from the group consisting of oxazolyl and pyrazolyl groups), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic group is a group selected from the group consisting of pyrrolidinyl and isothiazolidinyl groups); an alkylsulfonyl group; a tetrazolyl group; and an aminosulfonyl group optionally substituted with one or two alkyl group(s)

(wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo[3.1.0]hexyl group), (8) an alkoxy group optionally substituted with a group selected from the group consisting of a cyano group; a carboxyl group; a heteroaryl group optionally substituted with a hydroxy or oxo group (wherein the heteroaryl group is a group selected from the group consisting of isoxazolyl, oxadiazolyl, and tetrazolyl groups); an aminosulfonylaminocarbonyl group optionally substituted with one or two alkyl group(s); and an alkylsulfonylaminocarbonyl group, (9) an amino group which is optionally substituted with one or two alkyl group(s) optionally substituted with a carboxyl group, or

(10) a carbamoyl group; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In still another preferred embodiment, the present invention encompasses a compound represented by general formula [I] above, wherein ring A is a phenyl group optionally substituted with one or two group(s) independently selected from the group consisting of a halogen atom, alkyl group, haloalkyl group, cycloalkyl group, alkoxy group, haloalkoxy group, and alkyleneoxy group;

$R^1$ is (1) a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group, (2) an adamantyl group optionally substituted with a hydroxy group; or (3) an aliphatic heterocyclic group optionally substituted with a group selected from the group consisting of an alkyl group, hydroxyalkyl group, haloalkyl group, alkanoyl group, and alkylsulfonyl group (wherein the aliphatic heterocyclic group is a group selected from the group consisting of tetrahydrofuranyl, tetrahydropyranyl, and piperidinyl groups);

$R^2$ is a halogen atom or alkoxy group;

$R^3$ and $R^4$ are terminally attached to each other, and together with the nitrogen atom to which they are attached, form a group represented by formula [II], wherein ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a phenyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group (wherein the heteroaryl group is a group selected from the group consisting of oxazolyl and pyrazolyl groups), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic group is a group selected from the group consisting of pyrrolidinyl and isothiazolidinyl groups); an alkylsulfonyl group; a tetrazolyl group; and an aminosulfonyl group optionally substituted with one or two alkyl group(s)

(wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo [3.1.0]hexyl group), (8) an alkoxy group optionally substituted with a group selected from the group consisting of a cyano group; a carboxyl group; a heteroaryl group optionally substituted with a hydroxy or oxo group (wherein the heteroaryl group is a group selected from the group consisting of isoxazolyl, oxadiazolyl, and tetrazolyl groups); an aminosulfonylaminocarbonyl group optionally substituted with one or two alkyl group(s); and an alkylsulfonylaminocarbonyl group, (9) an amino group which is optionally substituted with one or two alkyl group(s) optionally substituted with a carboxyl group, or

(10) a carbamoyl group; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In still another preferred embodiment, the present invention encompasses a compound represented by general formula [I] above, wherein ring A is a phenyl group optionally substituted with one or two group(s) independently selected from the group consisting of a halogen atom, alkyl group, haloalkyl group, cycloalkyl group, alkoxy group, haloalkoxy group, and alkyleneoxy group;

$R^1$ is a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group;

$R^2$ is a halogen atom or alkoxy group;

$R^3$ and $R^4$ are terminally attached to each other, and together with the nitrogen atom to which they are attached, form a group represented by formula [II], wherein ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a phenyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group (wherein the heteroaryl group is a group selected from the group consisting of oxazolyl and pyrazolyl groups), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two groups independently selected from the group consisting of an alkyl group (the alkyl group is optionally substituted with a hydroxy, alkoxy, or carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic group is a group selected from the group consisting of pyrrolidinyl and isothiazolidinyl groups); an alkylsulfonyl group; a tetrazolyl group; and an aminosulfonyl group optionally substituted with one or two alkyl group(s)

(wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo[3.1.0]hexyl group), (8) an alkoxy group optionally substituted with a group selected from the group consisting of a cyano group; a carboxyl group; a heteroaryl group optionally substituted with a hydroxy or oxo group (wherein the heteroaryl group is a group selected from the group consisting of isoxazolyl, oxadiazolyl, and tetrazolyl groups); an aminosulfonylaminocarbonyl group optionally substituted with one or two alkyl group(s); and an alkylsulfonylaminocarbonyl group, (9) an amino group which is optionally substituted with one or two alkyl group(s) optionally substituted with a carboxyl group, or

(10) a carbamoyl group; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In yet another preferred embodiment, the present invention encompasses a compound represented by general formula [I] above, wherein ring A is a phenyl group optionally substituted with one or two group(s) independently selected from the group consisting of a halogen atom, alkyl group, haloalkyl group, cycloalkyl group, alkoxy group, haloalkoxy group, and alkyleneoxy group;

$R^1$ is a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group;

$R^2$ is a halogen atom or alkoxy group;

$R^3$ and $R^4$ are terminally attached to each other, and together with the nitrogen atom to which they are attached, form a group represented by formula [II], wherein ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a phenyl group;

$R^7$ is an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy, alkoxy, or carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of alkyl, alkanoyl, and alkylsulfonyl groups; an aliphatic heterocyclic group optionally substituted with one or two oxo group(s) (wherein the aliphatic heterocyclic group is a group selected from the group consisting of pyrrolidinyl and isothiazolidinyl groups); an alkylsulfonyl group; a tetrazolyl group; and an aminosulfonyl group optionally substituted with one or two alkyl group(s)

(wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo[3.1.0]hexyl group); and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In still another preferred embodiment, the present invention encompasses a compound represented by general formula [I] above, wherein ring A is a phenyl group optionally substituted with one or two group(s) independently selected from the group consisting of a halogen atom, alkyl group, haloalkyl group, cycloalkyl group, alkoxy group, haloalkoxy group, and alkyleneoxy group, or a pyridinyl group optionally substituted with one or two group(s) independently selected from the group consisting of a halogen atom and alkoxy group;

$R^1$ is (1) an alkyl group optionally substituted with one or two group(s) independently selected from the group consisting of a halogen atom; a hydroxy group; a 3- to 7-membered monocyclic cycloalkyl group; an alkoxy group; a tetrahydropyranyl group; an aliphatic heterocyclic carbonyl group optionally substituted with one or two group(s) independently selected from the group consisting of a halogen atom, alkyl group, haloalkyl group, and alkoxyalkyl group (wherein the aliphatic heterocyclic ring is a group selected from the group consisting of pyrrolidinyl, piperidinyl, and morpholinyl); a pyrrolidinylsulfonyl group; and a carbamoyl group optionally substituted with one or two alkyl group(s), (2) a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group, (3) an adamantyl group optionally substituted with a hydroxy group, (4) an aliphatic heterocyclic group optionally substituted with a group selected from the group consisting of an alkyl group, hydroxyalkyl group, haloalkyl group, alkanoyl group, and alkylsulfonyl group (wherein the aliphatic heterocyclic group is a group selected from the group consisting of tetrahydrofuranyl, tetrahydropyranyl, and piperidinyl groups), (5) an indanyl group, (6) a heteroaryl group which is optionally substituted with a group selected from the group consisting of a cyano group, alkyl group, alkoxy group, and carbamoyl group (wherein the heteroaryl group is a group selected from the group consisting of pyridazinyl, pyridinyl, and pyrimidinyl groups), (7) a carbamoyl group, or (8) a mono-alkylcarbamoyl group;

$R^2$ is a halogen atom, $C_{1-3}$ alkyl group, or alkoxy group;

$R^3$ and $R^4$ are terminally attached to each other, and together with the nitrogen atom to which they are attached, form a group represented by formula [II], wherein ring B is a group selected from the group consisting of an azetidinyl group, tetrahydropyridinyl group, piperazinyl group, homopiperazinyl group, and octahydropyrrolo[3,4-c]pyrrolyl group, and both $R^5$ and $R^6$ represent hydrogen atoms, or ring B is a piperidinyl group, and $R^5$ and $R^6$ are each a group independently selected from the group consisting of a hydrogen atom, cyano group, and alkoxyalkyl group, or ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a phenyl or pyridinyl group;

$R^7$ is (1) an alkyl group substituted with a carboxyl group, (2) an alkenyl group substituted with a carboxyl group, (3) a 3- to 7-membered monocyclic cycloalkyl group substituted with a carboxyl group, (4) a 3- to 7-membered monocyclic cycloalkenyl group substituted with a carboxyl group, (5) a phenyl group substituted with a carboxyl group, (6) a heteroaryl group which is substituted with a carboxyl group or an alkyl group substituted with a carboxyl group (wherein the heteroaryl group is a group selected from the group consisting of oxazolyl and pyrazolyl groups), (7) an aliphatic heterocyclic group substituted with one or two group(s) independently selected from the group consisting of an alkyl group substituted with a carboxyl group, and a carboxyl group (wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo [3.1.0]hexyl group), or (8) an alkoxy group substituted with a carboxyl group; and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In yet another preferred embodiment, the present invention encompasses a compound represented by general formula [I] above, wherein ring A is a phenyl group optionally substituted with one or two group(s) independently selected from the group consisting of a halogen atom, alkyl group, haloalkyl group, cycloalkyl group, alkoxy group, haloalkoxy group, and alkyleneoxy group;

$R^1$ is a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group;

$R^2$ is a halogen atom or alkoxy group;

$R^3$ and $R^4$ are terminally attached to each other, and together with the nitrogen atom to which they are attached, form a group represented by formula [II], wherein ring B is a pyrrolidinyl group, and $R^5$ and $R^6$ are each a group independently selected from the group consisting of a hydrogen atom, halogen atom, cyano group, alkyl group, haloalkyl group, cyanoalkyl group, hydroxyalkyl group, alkoxyalkyl group, carboxyl group, carbamoyl group optionally substituted with one or two alkyl group(s), and alkoxy group;

ring C is a phenyl group;

$R^7$ is an aliphatic heterocyclic group optionally substituted with a carboxyl group (wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo [3.1.0]hexyl group); and $R^8$ and $R^9$ are each independently a group selected from the group consisting of a hydrogen atom, halogen atom, cyano group, alkyl group, haloalkyl group, and haloalkoxy group;

or a pharmaceutically acceptable salt thereof.

In still another preferred embodiment, the present invention encompasses a compound represented by general formula [I] above, wherein ring A is a phenyl group optionally substituted with an alkoxy group;

$R^1$ is an alkyl group; an aliphatic heterocyclic group (wherein the aliphatic heterocyclic group is a group selected from the group consisting of tetrahydrofuranyl, tetrahydropyranyl, and piperidinyl groups); a 3- to 7-membered monocyclic cycloalkyl group optionally substituted with a group selected from the group consisting of alkoxy and cyano groups; or a heteroaryl group optionally substituted with an alkyl group (wherein the heteroaryl group is a group selected from the group consisting of pyridazinyl, pyridinyl, and pyrimidinyl groups);

$R^2$ is a halogen atom or alkoxy group;

$R^3$ and $R^4$ are terminally attached to each other, and together with the nitrogen atom to which they are attached, form a group represented by formula [II]:

[Formula 7]

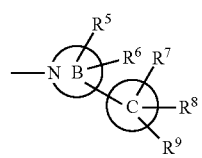

[II]

wherein ring B is selected from the group consisting of an azetidinyl group, pyrrolidinyl group, piperidinyl group, tetrahydropyridinyl group, and piperazinyl group, and $R^5$ and $R^6$ are hydrogen atoms, or ring B is a pyrrolidinyl group, $R^5$ is an alkoxyalkyl group, and $R^6$ is a hydrogen or halogen atom;

ring C is a phenyl group;
R⁷ is an aliphatic heterocyclic group substituted with a carboxyl group (wherein the aliphatic heterocyclic group is a group selected from the group consisting of an azetidinyl group, pyrrolidinyl group, piperidinyl group, morpholinyl group, thiomorpholinyl group, piperazinyl group, and 3-azabicyclo[3.1.0]hexyl group);
R⁸ is a halogen atom or haloalkyl group; and
R⁹ is a hydrogen atom;
or a pharmaceutically acceptable salt thereof.

In yet another preferred embodiment, the present invention encompasses a compound represented by general formula [I] above, wherein ring A is a phenyl group optionally substituted with an alkoxy group;
R¹ is a tetrahydropyranyl group; or a 5- or 6-membered monocyclic cycloalkyl group optionally substituted with a group selected from the group consisting of alkoxy and cyano groups;
R² is a halogen atom or alkoxy group;
R³ and R⁴ are terminally attached to each other, and together with the nitrogen atom to which they are attached, form a group represented by formula [II]:

[Formula 8]

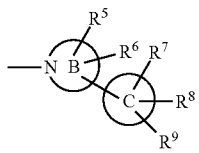

wherein ring B is a pyrrolidinyl group, R⁵ is an alkoxyalkyl group, and R⁶ is a hydrogen or halogen atom;
ring C is a phenyl group;
R⁷ is a piperidinyl group substituted with a carboxyl group;
R⁸ is a halogen atom or haloalkyl group; and
R⁹ is a hydrogen atom;
or a pharmaceutically acceptable salt thereof.

In still another preferred embodiment, the present invention encompasses a compound represented by general formula [I] above, wherein ring A is a phenyl group optionally substituted with an alkoxy group;
R¹ is a 5- or 6-membered monocyclic cycloalkyl group optionally substituted with a group selected from the group consisting of alkoxy and cyano groups;
R² is a halogen atom or alkoxy group;
R³ and R⁴ are terminally attached to each other, and together with the nitrogen atom to which they are attached, form a group represented by formula [II]:

[Formula 9]

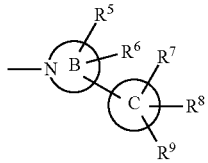

wherein ring B is a pyrrolidinyl group, R⁵ is an alkoxyalkyl group, and R⁶ is a hydrogen or halogen atom;
ring C is a phenyl group;
R⁷ is a piperidinyl group substituted with a carboxyl group;
R⁸ is a halogen atom or haloalkyl group; and
R⁹ is a hydrogen atom;
or a pharmaceutically acceptable salt thereof.

Among the compounds [I] of the present invention, a compound is preferable wherein R³ and R⁴ are terminally attached to each other, and together with the nitrogen atom to which they are attached, form a group represented by formula [II]. Herein, the definitions of the other substituents in the compounds [I] are the same as the definitions used in any of the embodiments of the present invention described in this specification.

Moreover, among the compounds [I] of the present invention, a compound is preferable wherein R¹ is a 3- to 7-membered monocyclic cycloalkyl group optionally substituted with one or two group(s) independently selected from the group consisting of a halogen atom, hydroxy group, oxo group, cyano group, alkyl group, alkoxy group, alkoxyalkyl group, and alkyleneoxy group.

Furthermore, a compound is more preferable wherein R³ and R⁴ are terminally attached to each other, and together with the nitrogen atom to which they are attached, form a group represented by formula [II], wherein ring B is a pyrrolidinyl group, and ring C is a phenyl group.

In still another preferred embodiment, the present invention may provide a compound selected from the group consisting of:
1-{2-[(3S,5S)-1-{[(3R,4R)-1-(trans-4-ethoxycyclohexyl)-3-methoxy-4-(4-methoxyphenyl)pyrrolidin-3-yl]carbonyl}-5-(ethoxymethyl)pyrrolidin-3-yl]-5-(trifluoromethyl)phenyl}piperidine-4-carboxylic acid;
1-{2-[(3S,5S)-1-{[(3R,4R)-3-fluoro-4-(4-methoxyphenyl)-1-(2-methylpyridin-4-yl) pyrrolidin-3-yl]carbonyl}-5-(methoxymethyl)pyrrolidin-3-yl]-5-(trifluoromethyl)phenyl}piperidine-4-carboxylic acid;
1-{2-[(3S,5S)-1-{[(3R,4R)-3-fluoro-4-(4-methoxyphenyl)-1-(2-methylpyrimidin-4-yl)pyrrolidin-3-yl]carbonyl}-5-(methoxymethyl)pyrrolidin-3-yl]-5-(trifluoromethyl)phenyl}piperidine-4-carboxylic acid;
1-{5-fluoro-2-[(3S,5S)-1-{[(3R,4R)-3-fluoro-1-(trans-4-methoxycyclohexyl)-4-(4-methoxyphenyl)pyrrolidin-3-yl]carbonyl}-5-(methoxymethyl)pyrrolidin-3-yl]phenyl}piperidine-4-carboxylic acid;
1-{2-[(3S,5S)-1-{[(3R,4R)-1-(trans-4-ethoxycyclohexyl)-3-methoxy-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,5S)-1-{[(3R,4R)-1-(trans-4-cyanocyclohexyl)-3-fluoro-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,4S)-1-{[(3R,4R)-1-(trans-4-ethoxycyclohexyl)-3-methoxy-4-(4-methoxyphenyl)pyrrolidin-3-yl]carbonyl}-4-fluoro-4-(methoxymethyl)pyrrolidin-3-yl]-5-(trifluoromethyl)phenyl}piperidine-4-carboxylic acid;
1-{2-[(3S,4R)-1-{[(3R,4R)-1-(trans-4-ethoxycyclohexyl)-3-methoxy-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid;
1-{2-[(3S,5S)-1-{[(3R,4R)-1-cyclohexyl-3-fluoro-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,5S)-1-{[(3R,4R)-3-fluoro-4-(4-methoxyphenyl)-1-(tetrahydro-2H-pyran-4-yl)pyrrolidin-3-yl]carbonyl}-

5-(methoxymethyl)pyrrolidin-3-yl]-5-(trifluoromethyl)phenyl}piperidine-4-carboxylic acid;

1-{2-[(3S,5S)-1-{[(3R,4R)-3-fluoro-1-(trans-4-methoxycyclohexyl)-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;

1-{2-[(3S,5S)-1-{[3R,4R)-1-cyclopentyl-3-fluoro-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;

1-{2-[(3S,4R)-1-{[(3R,4R)-3-fluoro-4-(4-methoxyphenyl)-1-(2-methylpyridin-4-yl)pyrrolidin-3-yl]carbonyl}-4-(methoxymethyl)pyrrolidin-3-yl]-5-(trifluoromethyl)phenyl}piperidine-4-carboxylic acid;

1-{2-[((3S,4S)-4-fluoro-1-{[(3R,4R)-3-fluoro-1-(trans-4-methoxycyclohexyl)-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid;

1-{5-chloro-2-[(3S,4R)-1-{[(3R,4R)-3-fluoro-1-(trans-4-methoxycyclohexyl)-4-(4-methoxyphenyl)pyrrolidin-3-yl]carbonyl}-4-(methoxymethyl)pyrrolidin-3-yl]phenyl}piperidine-4-carboxylic acid;

1-{2-[(3S,4R)-4-(cyanomethyl)-1-{[(3R,4R)-1-cyclopentyl-3-fluoro-4-(4-methoxyphenyl)pyrrolidin-3-yl]carbonyl}pyrrolidin-3-yl]-5-(trifluoromethyl)phenyl}piperidine-4-carboxylic acid;

1-{2-[(3S,4R)-1-{[(3R,4R)-3-fluoro-1-(trans-4-methoxycyclohexyl)-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid;

1-[2-(1-{[(3R,4R)-3-fluoro-1-(trans-4-methoxycyclohexyl)-4-(4-methoxyphenyl)pyrrolidin-3-yl]carbonyl}piperidin-4-yl)-5-(trifluoromethyl)phenyl]piperidine-4-carboxylic acid;

1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid; and 1-{2-[(3S)-1-{[(3R,4R)-3-fluoro-1-(trans-4-methoxycyclohexyl)-4-(4-methoxyphenyl)pyrrolidin-3-yl]carbonyl}pyrrolidin-3-yl]-5-(trifluoromethyl)phenyl}piperidine-4-carboxylic acid;

or a pharmaceutically acceptable salt thereof.

In yet another preferred embodiment, the present invention may provide a compound selected from the group consisting of:

1-{2-[(3S,5S)-1-{[(3R,4R)-1-(trans-4-ethoxycyclohexyl)-3-methoxy-4-(4-methoxyphenyl)pyrrolidin-3-yl]carbonyl}-5-(ethoxymethyl)pyrrolidin-3-yl]-5-(trifluoromethyl)phenyl}piperidine-4-carboxylic acid;

1-{5-fluoro-2-[(3S,5S)-1-{[(3R,4R)-3-fluoro-1-(trans-4-methoxycyclohexyl)-4-(4-methoxyphenyl)pyrrolidin-3-yl]carbonyl}-5-(methoxymethyl)pyrrolidin-3-yl]phenyl}piperidine-4-carboxylic acid;

1-{2-[(3S,5S)-1-{[(3R,4R)-1-(trans-4-ethoxycyclohexyl)-3-methoxy-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;

1-{2-[(3S,5S)-1-{[(3R,4R)-1-(trans-4-cyanocyclohexyl)-3-fluoro-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;

1-{2-[(3S,4S)-1-{[(3R,4R)-1-(trans-4-ethoxycyclohexyl)-3-methoxy-4-(4-methoxyphenyl)pyrrolidin-3-yl]carbonyl}-4-fluoro-4-(methoxymethyl)pyrrolidin-3-yl]-5-(trifluoromethyl)phenyl}piperidine-4-carboxylic acid;

1-{2-[(3S,4R)-1-{[(3R,4R)-1-(trans-4-ethoxycyclohexyl)-3-methoxy-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid;

1-{2-[(3S,5S)-1-{[(3R,4R)-1-cyclohexyl-3-fluoro-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;

1-{2-[(3S,5S)-1-{[(3R,4R)-3-fluoro-1-(trans-4-methoxycyclohexyl)-4-(4-methoxyphenyl) pyrrolidin-3-yl]carbonyl}-5-(methoxymethyl)pyrrolidin-3-yl]-5-(trifluoromethyl)phenyl}piperidine-4-carboxylic acid;

1-{2-[(3S,5S)-1-{[(3R,4R)-1-cyclopentyl-3-fluoro-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;

1-{2-[(3S,4S)-4-fluoro-1-{[(3R,4R)-3-fluoro-1-(trans-4-methoxycyclohexyl)-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid;

1-{5-chloro-2-[(3S,4R)-1-{[(3R,4R)-3-fluoro-1-(trans-4-methoxycyclohexyl)-4-(4-methoxyphenyl)pyrrolidin-3-yl]carbonyl}-4-(methoxymethyl)pyrrolidin-3-yl]phenyl}piperidine-4-carboxylic acid;

1-{2-[(3S,4R)-4-(cyanomethyl)-1-{[(3R,4R)-1-cyclopentyl-3-fluoro-4-(4-methoxyphenyl)pyrrolidin-3-yl]carbonyl}pyrrolidin-3-yl]-5-(trifluoromethyl)phenyl}piperidine-4-carboxylic acid;

1-{2-[(3S,4R)-1-{[(3R,4R)-3-fluoro-1-(trans-4-methoxycyclohexyl)-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid;

1-[2-(1-{[(3R,4R)-3-fluoro-1-(trans-4-methoxycyclohexyl)-4-(4-methoxyphenyl)pyrrolidin-3-yl]carbonyl}piperidin-4-yl)-5-(trifluoromethyl)phenyl]piperidine-4-carboxylic acid;

1-{2-[(3S,4R)-1{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid; and 1-{2-[(3S)-1-{[(3R,4R)-3-fluoro-1-(trans-4-methoxycyclohexyl)-4-(4-methoxyphenyl)pyrrolidin-3-yl]carbonyl}pyrrolidin-3-yl]-5-(trifluoromethyl)phenyl}piperidine-4-carboxylic acid;

or a pharmaceutically acceptable salt thereof.

In still another preferred embodiment, the present invention may provide a compound selected from the group consisting of:

1-{5-fluoro-2-[(3S,5S)-1-{[(3R,4R)-3-fluoro-1-(trans-4-methoxycyclohexyl)-4-(4-methoxyphenyl)pyrrolidin-3-yl]carbonyl}-5-(methoxymethyl)pyrrolidin-3-yl]phenyl}piperidine-4-carboxylic acid;

1-{2-[(3S,5S)-1-{[(3R,4R)-1-(trans-4-ethoxycyclohexyl)-3-methoxy-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;

1-{2-[(3S,5S)-1-{[(3R,4R)-3-fluoro-1-(trans-4-methoxycyclohexyl)-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;

1-{2-[(3S,5S)-1-{[(3R,4R)-1-cyclopentyl-3-fluoro-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;

1-{2-[(3S,4S)-4-fluoro-1-{[(3R,4R)-3-fluoro-1-(trans-4-methoxycyclohexyl)-4-(4-methoxyphenyl)pyrrolidin-3- yl]carbonyl}-4-(methoxymethyl)pyrrolidin-3-yl]-5-(trifluoromethyl)phenyl}piperidine-4-carboxylic acid;
1-{5-chloro-2-[(3S,4R)-1-{[(3R,4R)-3-fluoro-1-(trans-4-methoxycyclohexyl)-4-(4-methoxyphenyl)pyrrolidin-3-yl]carbonyl}-4-(methoxymethyl)pyrrolidin-3-yl]phenyl}piperidine-4-carboxylic acid;
1-{2-[(3S,4R)-1-{[(3R,4R)-3-fluoro-1-(trans-4-methoxycyclohexyl)-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid; and
1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid;
or a pharmaceutically acceptable salt thereof.

When the compound [I] of the present invention has an asymmetric carbon atom in the molecule, it may exist as a plurality of stereoisomers (i.e., diastereoisomers or optical isomers) based on the asymmetric carbon atom. The present invention encompasses both any one of these stereoisomers and a mixture thereof. To indicate that the compound [I] of the present invention is a mixture of a plurality of stereoisomers, the compound [I] may be represented using a bond shown by the following wavy line:

[Formula 10]

The compound [I] of the present invention may also contain cis- and trans-isomers as geometrical isomers. Further, when the compound [I] of the present invention has axial chirality in the molecule, it may contain isomers based on the axial chirality. The present invention encompasses both any one of these isomers and a mixture thereof.

The compound [I] of the present invention encompasses compounds labeled with isotopes (e.g., $^3$H, $^{13}$C, $^{14}$C, $^{15}$N, $^{18}$F, $^{32}$P, $^{35}$S, and $^{125}$I) or the like, and deuterated products.

The compound [I] of the present invention or a pharmaceutically acceptable salt thereof has outstanding MC1R agonist activity. The target compound of the present invention and a pharmaceutical composition comprising the same as an active ingredient are useful for treating or preventing various autoimmune diseases, inflammation-related diseases, and fibrosis-related diseases of which pathological conditions are expected to be improved through the agonist activity of MC1R. Examples of such diseases include rheumatoid arthritis, gouty arthritis, osteoarthrosis, inflammatory bowel disease, systemic sclerosis, psoriasis, fibrosis, protoporphyria (e.g., erythropoietic protoporphyria), systemic lupus erythematosus, melanoma, skin cancer, vitiligo, hair loss, pain, ischemia/reperfusion damage, cerebral inflammatory disease, hepatitis, septicemia/septic shock, nephritis, transplantation, HIV disease exacerbation, vasculitis, uveitis, retinitis pigmentosa, age-related macular degeneration, microbial infection, celiac disease, nephrotic syndrome, and melanoma invasion.

In particular, the target compound of the present invention and a pharmaceutical composition comprising the same as an active ingredient are useful for treating or preventing systemic sclerosis, psoriasis, protoporphyria, melanoma, skin cancer, vitiligo, hair loss, retinitis pigmentosa, age-related macular degeneration, nephrotic syndrome, and the like. The target compound of the present invention and a pharmaceutical composition comprising the same as an active ingredient are particularly useful for treating or preventing systemic sclerosis, protoporphyria, melanoma, vitiligo, retinitis pigmentosa, age-related macular degeneration, nephrotic syndrome, and the like.

As described above, the compound [I] of the present invention or a pharmaceutically acceptable salt thereof has excellent agonist activity for MC1R, and as a result of examination of the agonist activity for human MC1R in accordance with the assay method described in Experimental Example 1 described below, all the compounds described in the present Examples had an $EC_{50}$ value of 1000 nM or less. The compound [I] of the present invention or a pharmaceutically acceptable salt thereof was also found to have drug efficacy in bleomycin-induced inflammation models (in accordance with the method described in *Arthritis and Rheumatology*, 2009; 60: p. 592-603). Additionally, the compound [I] of the present invention encompasses compounds having high selectivity for MC1R. For example, the compound described in present Example 147 (chemical name: 1-{5-fluoro-2-[(3S,5S)-1-{[(3R,4R)-3-fluoro-1-(trans-4-methoxycyclohexyl)-4-(4-methoxyphenyl) pyrrolidin-3-yl]carbonyl}-5-(methoxymethyl)pyrrolidin-3-yl]phenyl}piperidine-4-carboxylic acid dihydrochloride) shows the ratio of the $EC_{50}$ value for human MC1R agonist activity (1.7 nM) to the $EC_{50}$ value for human MC4R agonist activity (341 nM) is approximately 1:200, and is thus one of the compounds having high selectivity for MC1R.

The compound [I] of the present invention can be used for pharmaceutical purposes either in free form or in the form of a pharmaceutically acceptable salt thereof. Examples of pharmaceutically acceptable salts include inorganic acid salts such as hydrochloride, sulfate, phosphate, and hydrobromate; and organic acid salts such as acetate, fumarate, oxalate, citrate, methanesulfonate, benzenesulfonate, tosylate, and maleate.

The compound [I] of the present invention or a pharmaceutically acceptable salt thereof includes all of an inner salt or addition product thereof, a solvate or hydrate thereof, a cocrystal thereof, and the like.

One or more of the compounds of formula [I] of the present invention or pharmaceutically acceptable salts thereof may be directly administered to a patient; preferably, however, the compound of formula [I] of the present invention or a pharmaceutically acceptable salt thereof may be mixed with pharmaceutically and pharmaceutically acceptable additives, and be provided as a pharmaceutical preparation in a form well known to those skilled in the art.

As pharmaceutically and pharmaceutically acceptable additives, appropriate additives that are generally used in the manufacture of pharmaceuticals can be used, such as excipients, disintegrators, binders, lubricants, coating agents, colorants, diluents, bases, and isotonic agents.

Then, the compound of the present invention, together with the above-described additives, can be prepared into an appropriate dosage form (e.g., a powder, injection, tablet, capsule, or topical preparation), and then administered to a patient (a human or animal) using an appropriate method of administration in accordance with the dosage form (e.g., intravenously, orally, percutaneously, or topically).

The dose may be determined depending on the age, body weight, general health condition, sex, diet, time of administration, method of administration, excretion rate, combination of drugs, and the severity of the condition of the disease of the patient under treatment during application, in consideration of these or other factors. The compound of the present invention or a pharmaceutically acceptable salt thereof has low toxicity and can be safely used. The daily dose thereof may vary depending on the condition or body weight of the patient, the type of the compound, or the administration route. For example, in the case of parenteral administration, the compound of the present invention is desirably administered subcutaneously, intravenously, intramuscularly, or intrarectally at a dose of approximately 0.0001 to 1000 mg/person/day, preferably approximately 0.001 to 1000 mg/person/day, and particularly preferably 0.01 to 500 mg/person/day, and in the case of oral administration, the compound of the present invention is desirably administered at a dose of approximately 0.0001 to 1000 mg/person/day, and more preferably approximately 0.01 to 500 mg/person/day.

The compound of the present invention or a pharmaceutically acceptable salt thereof can be produced as follows, for example. Note that each of the abbreviations used in this specification means the following:

Me: Methyl
Et: Ethyl
Synthesis Method A-1

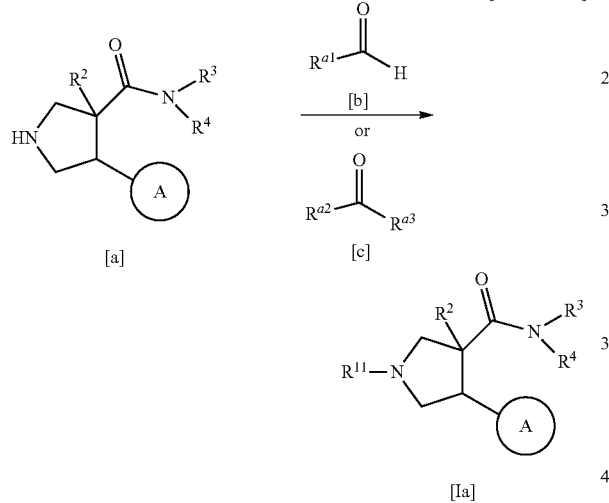

[Formula 11]

Among the target compounds [I] of the present invention, a compound wherein $R^1$ is an optionally substituted alkyl, cycloalkyl, or aliphatic heterocyclic group, which is represented by general formula [Ia](wherein $R^{11}$ represents an optionally substituted alkyl, cycloalkyl, or aliphatic heterocyclic group, and the other symbols have the same meanings as those described above), can be produced as follows, for example.

The target compound [Ia] or a pharmaceutically acceptable salt thereof can be obtained by subjecting a compound represented by general formula [a] (wherein the symbols have the same meanings as those described above) or a salt thereof to a reductive amination reaction with a compound represented by general formula [b] (wherein $R^{a1}$ represents an optionally substituted alkyl group) or a carbonyl equivalent thereof, or with a compound represented by general formula [c] (wherein $R^{a2}$ and $R^{a3}$ each independently represent an optionally substituted alkyl group, or $R^{a2}$ and $R^{a3}$ are terminally attached to each other, and together with the carbon atom to which they are attached, form an optionally substituted cycloalkyl or aliphatic heterocyclic group) or a carbonyl equivalent thereof, and, as desired, by converting the resulting product into a pharmaceutically acceptable salt thereof.

The carbonyl equivalent may be a ketal, for example, and may specifically be alkoxy-trialkylsilyloxy-ketal or the like. The carbonyl equivalent of the compound [c]may preferably be 1-ethyloxy-1-(trimethylsilyloxy)cyclopropane, for example.

As the salt of the compound [a], a salt with an inorganic acid such as hydrochloric acid or a carboxylic acid such as acetic acid can be used.

The reductive amination reaction of the compound [a] or a salt thereof with the compound [b] or [c], or a carbonyl equivalent thereof can be performed in accordance with a conventional method, in an appropriate solvent in the presence of a reducing agent and an acid, for example. The solvent may be any that does not hinder the reaction, and examples of such solvents include a halogenated aliphatic hydrocarbon such as methylene chloride, an alcohol such as methanol, an ether such as tetrahydrofuran, an aromatic hydrocarbon such as toluene, and mixtures thereof. Examples of reducing agents include hydrogenated sodium triacetoxyborohydride, sodium borohydride, as well as hydrogen and palladium catalysts (e.g., a palladium catalyst supported on activated carbon). The acid may be acetic acid, for example. The amount of the compound [b], compound [c], or a carbonyl equivalent thereof used may be 0.1 to 10 equivalents, preferably 1 to 5 equivalents, relative to the compound [a]. The amount of the reducing agent used may be 1 to 10 equivalents, preferably 1 to 3 equivalents, relative to the compound [a]. The amount of the acid used may be 1 to 10 equivalents, preferably 1 to 3 equivalents, relative to the compound [a]. This reaction can be performed at −10 to 100° C., preferably 10 to 50° C.

Synthesis Method A-2

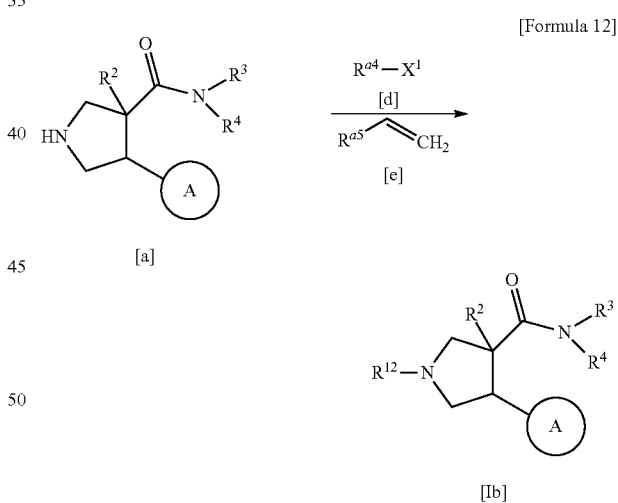

[Formula 12]

Among the target compounds [I], a compound wherein $R^1$ is an optionally substituted alkyl group, which is represented by general formula [Ib] (wherein $R^{12}$ represents an optionally substituted alkyl group, and the other symbols have the same meanings as those described above), can be produced as follows, for example.

The target compound [Ib] can be obtained by reacting the compound [a] or a salt thereof with a compound represented by general formula [d] (wherein $R^{a4}$ represents an optionally substituted alkyl group, and $X^1$ represents a leaving group), and, as desired, by converting the resulting product into a pharmaceutically acceptable salt thereof.

Alternatively, the target compound [Ib] or a pharmaceutically acceptable salt thereof can be obtained by subjecting the compound [a] or a salt thereof to a Michael addition reaction with a compound represented by general formula [e] (wherein $R^{a5}$ represents an electron-withdrawing group (e.g., an alkoxycarbonyl, cyano, or sulfonyl group)), and as desired, by converting the resulting product into a pharmaceutically acceptable salt thereof.

Examples of the leaving group represented by $X^1$ include halogen atoms (e.g., fluorine, chlorine, bromine, and iodine atoms), a methylsulfonyloxy group, and a p-toluenesulfonyloxy group. In particular, a halogen atom is suitable.

The reaction of the compound [a] or a salt thereof with the compound [d] can be performed in an appropriate solvent in the presence of a base, for example. The solvent may be any that does not hinder the reaction, and examples of such solvents include a nitrile such as acetonitrile, a halogenated aliphatic hydrocarbon such as methylene chloride, an ether such as tetrahydrofuran, an aromatic hydrocarbon such as toluene, an amide such as N,N-dimethylformamide, dimethylsulfoxide, and mixtures thereof. Examples of bases include an amine such as diisopropylethylamine and an alkali metal carbonate such as potassium carbonate. In this reaction, a reaction adjuvant may be added to accelerate the reaction. Examples of reaction adjuvants include inorganic salts such as sodium iodide and potassium iodide. The amount of the compound [d] used may be 0.1 to 10 equivalents, preferably 0.8 to 2 equivalents, relative to the compound [a]. The amount of the base used may be 1 to 10 equivalents, preferably 1 to 3 equivalents, relative to the compound [a]. The amount of the reaction adjuvant used may be 0.01 to 10 equivalents, preferably 0.1 to 1 equivalent, relative to the compound [a]. This reaction can be performed at 0 to 150° C., preferably 20 to 100° C.

The Michael addition reaction of the compound [a] or a salt thereof with the compound [e] can be performed in accordance with a conventional method, in an appropriate solvent in the presence of a base, for example. The solvent may be any that does not hinder the reaction, and examples of such solvents include an alcohol such as ethanol, an aromatic hydrocarbon such as toluene, an ether such as tetrahydrofuran, a halogenated aliphatic hydrocarbon such as methylene chloride, an amide such as N,N-dimethylformamide, dimethylsulfoxide, a nitrile such as acetonitrile, and mixtures thereof. Examples of bases include an amine such as triethylamine and an alkali metal carbonate such as potassium carbonate. The amount of the compound [e] used may be 1 to 10 equivalents, preferably 1 to 3 equivalents, relative to the compound [a]. The amount of the base used may be 1 to 10 equivalents, preferably 1 to 3 equivalents, relative to the compound [a]. This reaction can be performed at 0 to 150° C., preferably 20 to 100° C.

Synthesis Method A-3

[Formula 13]

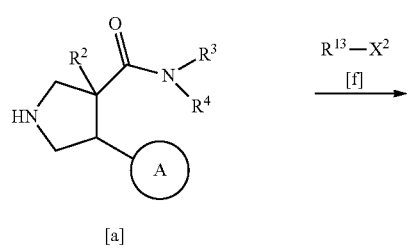

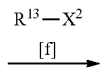

-continued

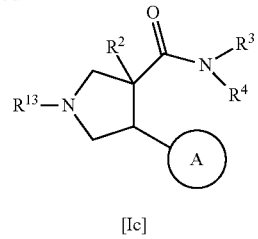

Among the target compounds [I], a compound wherein $R^1$ is an optionally substituted aryl group or an optionally substituted heteroaryl group, which is represented by general formula [Ic] (wherein $R^{13}$ represents an optionally substituted aryl group or an optionally substituted heteroaryl group, and the other symbols have the same meanings as those described above), can be produced as follows, for example.

The target compound [Ic] or a pharmaceutically acceptable salt thereof can be obtained by subjecting the compound [a] or a salt thereof to a coupling reaction with a compound represented by general formula [f](wherein $X^2$ represents a leaving group, and the other symbol has the same meaning as that described above), and, as desired, by converting the resulting product into a pharmaceutically acceptable salt thereof.

Examples of the leaving group represented by $X^2$ include halogen atoms (e.g., fluorine, chlorine, and bromine atoms) and a trifluoromethylsulfonyloxy group. In particular, a halogen atom is suitable.

The coupling reaction of the compound [a] or a salt thereof with the compound [f] can be performed in accordance with a conventional method, in an appropriate solvent in the presence of a base, for example, and additionally in the presence of a palladium catalyst, as desired. The solvent may be any that does not hinder the reaction, and examples of such solvents include ethers such as 1,4-dioxane and tetrahydrofuran, an amide such as N,N-dimethylformamide, an aromatic hydrocarbon such as toluene, an alcohol such as t-butanol, and mixtures thereof. Examples of palladium catalysts include tris(dibenzylideneacetone)dipalladium, palladium acetate, tetrakis(triphenylphosphine)palladium, palladium chloride, and dichloro[1,1'-bis(diphenylphosphino)ferrocene]palladium (II) dichloromethane adduct. Examples of bases include t-butoxysodium, t-butoxypotassium, cesium carbonate, tripotassium phosphate, and diisopropylethylamine. In this reaction, a ligand may be added to accelerate the reaction. Examples of ligands include 2,2'-bis(diphenylphosphino)-1,1'-binaphthyl, 2-di-t-butylphosphino-2',4',6'-triisopropylbiphenyl, 2-dicyclohexyl-phosphino-2',6'-dimethoxybiphenyl, 2-di-t-butylphosphino-3,4,5,6-tetramethyl-2',4',6'-triisopropyl-1,1'-biphenyl, and 1,1'-bis(diphenylphosphino)ferrocene. The amount of the compound [f] used may be 1 to 10 equivalents, preferably 1 to 3 equivalents, relative to the compound [a]. The amount of the palladium catalyst used may be 0.001 to 0.5 equivalent, preferably 0.01 to 0.3 equivalent, relative to the compound [a]. The amount of the base used may be 1 to 10 equivalents, preferably 1 to 3 equivalents, relative to the compound [a]. The amount of the ligand used may be 0.001 to 0.5 equivalent, preferably 0.01 to 0.3 equivalent, relative to the compound [a]. This reaction can be performed at 0 to 200° C., preferably 50 to 150° C.

Synthesis Method A-4

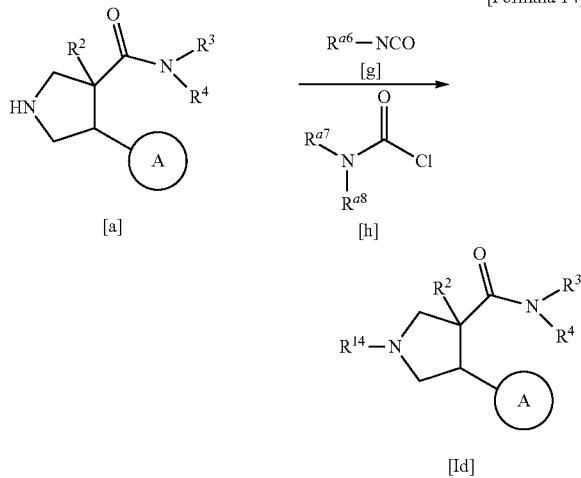

[Formula 14]

Among the target compounds [I], a compound wherein $R^1$ is a carbamoyl group optionally substituted with one or two alkyl groups, which is represented by general formula [Id] (wherein $R^{14}$ represents a carbamoyl group optionally substituted with one or two alkyl groups, and the other symbols have the same meanings as those described above), can be produced as follows, for example.

The target compound [Id] or a pharmaceutically acceptable salt thereof can be obtained by reacting the compound [a] or a salt thereof with a compound represented by general formula [g] (wherein $R^{a6}$ represents an alkyl or trialkylsilyl group) or with a compound represented by general formula [h] (wherein $R^{a7}$ and $R^{a8}$ are each independently an alkyl group, or one of them represents an alkyl group and the other represents a hydrogen atom), and, as desired, by converting the resulting product into a pharmaceutically acceptable salt thereof.

The reaction of the compound [a] or a salt thereof with the compound [g] or [h] can be performed in accordance with a conventional method, in an appropriate solvent in the presence of a base. The solvent may be any that does not hinder the reaction, and examples of such solvents include a halogenated aliphatic hydrocarbon such as methylene chloride, an ether such as tetrahydrofuran, an aromatic hydrocarbon such as toluene, and mixtures thereof. Examples of bases include amines such as triethylamine and diisopropylethylamine, and an alkali metal carbonate such as potassium carbonate. The amount of the compound [g] or [h] used may be 0.5 to 30 equivalents, preferably 1 to 20 equivalents, relative to the compound [a]. The amount of the base used may be 1 to 10 equivalents, preferably 1 to 5 equivalents, relative to the compound [a]. This reaction can be performed at −20 to 100° C., preferably 10 to 50° C.

Synthesis Method B

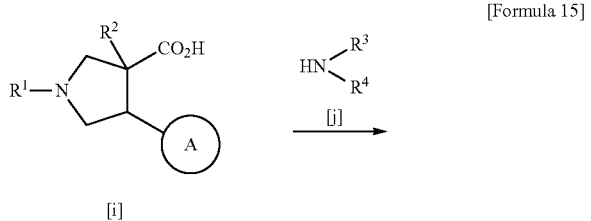

[Formula 15]

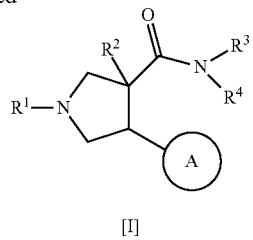

[I]

The target compound [I] (wherein the symbols have the same meanings as those described above) of the present invention can also be produced as follows, for example.

The target compound [I] or a pharmaceutically acceptable salt thereof can be produced by condensing a compound represented by general formula [i] (wherein the symbols have the same meanings as those described above), a salt thereof, or an acid chloride thereof, with a compound represented by general formula [j] (wherein the symbols have the same meanings as those described above) or a salt thereof, and, as desired, by converting the resulting product into a pharmaceutically acceptable salt thereof.

The condensation reaction of the compound [i] or a salt thereof with the compound [j] or a salt thereof can be performed in accordance with a conventional method, in an appropriate solvent in the presence of a condensing agent, for example. As the salt of the compound [i], a salt with sodium or potassium is usable, for example. As the salt of the compound [j], a salt with an inorganic acid such as hydrochloride or sulfate is usable, for example. The solvent may be any that does not hinder the reaction, and examples of such solvents include an amide such as N,N-dimethylformamide, a halogenated aliphatic hydrocarbon such as methylene chloride, an ether such as tetrahydrofuran, water, and mixtures thereof. Examples of condensing agents include 1-ethyl-3-(3-dimethylaminopropyl)carbodiimide hydrochloride (EDAC); o-(7-azabenzotriazol-1-yl)-N,N,N′,N′-tetramethyluronium hexafluorophosphate (HATU); and 4-(4,6-dimethoxy-1,3,5-triazin-2-yl)-4-methylmorpholinium chloride (DMT-MM). In this reaction, a base may be added to accelerate the reaction. Examples of bases include amines such as triethylamine and diisopropylethylamine, and an alkali metal carbonate such as potassium carbonate. A reaction adjuvant may also be added to accelerate the reaction. Examples of such reaction adjuvants include 1-hydroxy-7-azabenzotriazole (HOAt), 1-hydroxybenzotriazole (HOBt), and 4-dimethylaminopyridine. The amount of the compound [j] used may be 0.1 to 10 equivalents, preferably 0.5 to 5 equivalents, relative to the compound [i]. The amount of the condensing agent used may be 0.5 to 10 equivalents, preferably 1 to 3 equivalents, relative to the compound [i]. The amount of the base used may be 0 to 10 equivalents, preferably 1 to 5 equivalents, relative to the compound [i]. The amount of the reaction adjuvant used may be 0.5 to 10 equivalents, preferably 1 to 3 equivalents, relative to the compound [i]. This reaction can be performed at −10 to 100° C., preferably 10 to 80° C. The condensation reaction of an acid chloride of the compound [i] with the compound [j] or a salt thereof can be performed in accordance with a conventional method, in an appropriate solvent in the presence of a base.

An acid chloride of the compound [i] can be produced by treating the compound [i] with a conventional reagent such as thionyl chloride or oxalyl chloride, in accordance with a conventional method. As the solvent and the base, those mentioned for the condensation reaction of the compound [i] or a salt thereof with the compound [j] or a salt thereof can be suitably used.

Intermediate Production Method a

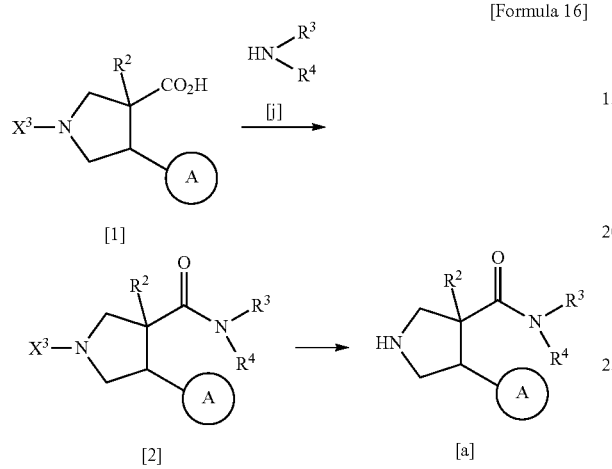

The above-described compound [a] used in Synthesis Methods A-1 to A-4 can be produced as follows, for example.

A compound represented by general formula [1](wherein $X^3$ represents an amino-protecting group, and the other symbols have the same meanings as those described above) is subjected to a condensation reaction with the compound [j] to obtain a compound represented by general formula [2] (wherein the symbols have the same meanings as those described above).

The compound [a] can be obtained by removing the amino-protecting group of the obtained compound [2].

Examples of the amino-protecting group represented by $X^3$ include benzyl and t-butoxycarbonyl groups.

The condensation reaction of the compound [1] with the compound [j] can be performed as in the condensation reaction of the compound [i] with the compound [j] described in Synthesis Method B above.

The reaction of removing the amino-protecting group of the compound [2] can be performed in accordance with a conventional method. Where $X^3$ is a benzyl group, for example, the removal reaction can be performed in an appropriate solvent in the presence of hydrogen and a palladium catalyst. The solvent may be any that does not hinder the reaction, and examples of such solvents include an ether such as tetrahydrofuran, an alcohol such as methanol, an ester such as ethyl acetate, and mixtures thereof. The palladium catalyst may be a palladium catalyst supported on activated carbon, for example. Where $X^3$ is a t-butoxycarbonyl group, for example, the removal reaction can be performed in an appropriate solvent in the presence of an acid. The solvent may be any that does not hinder the reaction, and examples of such solvents include a halogenated aliphatic hydrocarbon such as methylene chloride, an ether such as 1,4-dioxane, and mixtures thereof. Examples of acids include hydrochloric acid and trifluoroacetic acid.

Intermediate Production Method b-1

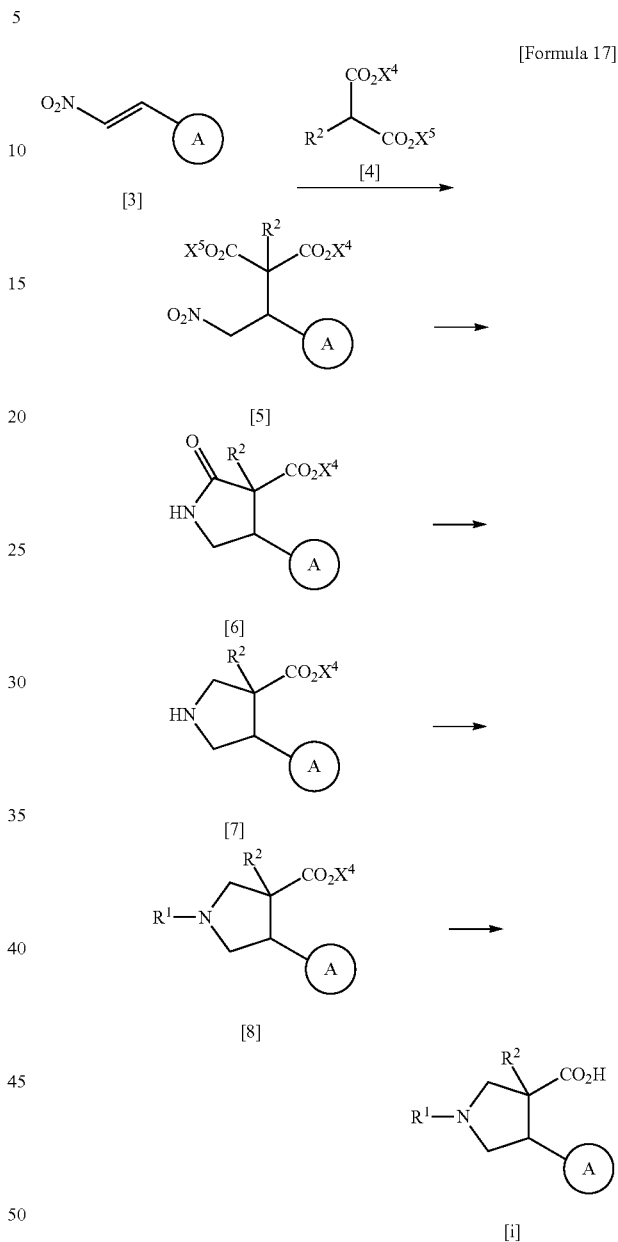

The above-described compound [i] used in Synthesis Method B can be produced as follows, for example.

A compound represented by general formula [3](wherein the symbol has the same meaning as that described above) is subjected to an addition reaction with a compound represented by general formula [4](wherein $X^4$ and $X^5$ represent carboxyl-protecting groups, and the other symbol has the same meanings as that described above) to obtain a compound represented by general formula [5] (wherein the symbols have the same meanings as those described above).

The compound [5] is subjected to a reduction reaction and a ring closure reaction to obtain a compound represented by general formula [6] (wherein the symbols have the same meanings as those described above).

The compound [6] is subjected to a reduction reaction to obtain a compound represented by general formula [7] (wherein the symbols have the same meanings as those described above).

The substituent $R^1$ is introduced into the amino group of the compound [7] to obtain a compound represented by general formula [8] (wherein the symbols have the same meanings as those described above).

The compound [i] can be obtained by removing the carboxyl-protecting group of the obtained compound [8].

The carboxyl-protecting groups represented by $X^4$ and $X^5$ may be alkyl groups, for example.

The addition reaction of the compound [3] with the compound [4] can be performed in an appropriate solvent in accordance with a conventional method. The solvent may be any that does not hinder the reaction, and examples of such solvents include an aromatic hydrocarbon such as toluene, a halogenated aliphatic hydrocarbon such as methylene chloride, a nitrile such as acetonitrile, and mixtures thereof. In this reaction, the addition reaction can be stereoselectively performed by adding a chiral catalyst into the reaction system. Examples of chiral catalysts include 1-[3,5-bis(trifluoromethyl)phenyl]-3-[(1R,2R)-(−)-2-(dimethylamino)cyclohexyl]thiourea; and 6'-hydroxycinchonine.

The reduction reaction and ring closure reaction of the compound [5] can be performed in an appropriate solvent in accordance with a conventional method, by performing treatment with a reducing agent, followed by treatment with a base, as desired. Examples of solvents include an alcohol such as methanol, a halogenated aliphatic hydrocarbon such as methylene chloride, an ether such as tetrahydrofuran, an aromatic hydrocarbon such as toluene, and mixtures thereof. As the reducing agents, hydrogen and a palladium catalyst (e.g., a palladium catalyst supported on activated carbon), or sodium borohydride and nickel chloride are usable, for example. In this reaction, an acid may be added to accelerate the reduction reaction. Examples of acids include hydrochloric acid and acetic acid. Next, as desired, the ring closure reaction can be performed by the action of a base. The base may be 1,8-diazabicyclo[5.4.0]-7-undecene, for example.

The reduction reaction of the compound [6] can be performed, by treating the compound [6] with an alkylating agent, as desired, and subsequently by treating the resulting product with a reducing agent in an appropriate solvent, together with an acid, as required. The solvent may be any that does not hinder the reaction, and examples of such solvents include a halogenated aliphatic hydrocarbon such as methylene chloride, an alcohol such as methanol, an ether such as tetrahydrofuran, an aromatic hydrocarbon such as toluene, and mixtures thereof. Examples of reducing agents include cyano sodium borohydride, sodium borohydride, and a borane-pyridine complex. Examples of acids include acetic acid and trifluoroacetic acid. Examples of alkylating agents include trimethyloxonium tetrafluoroborate and methyl trifluoromethanesulfonate.

The reaction of introducing the substituent ($R^1$) into the amino group of the compound [7] can be performed, for example, as in the reactions of converting the compound [a] into the compound [Ia], compound [Ib], compound [Ic], and compound [Id] shown in Synthesis Methods A-1 to A-4 above.

The reaction of removing the carboxyl-protecting group from the compound [8] to produce the compound [i] can be performed in accordance with a conventional method, in an appropriate solvent, together with a base, for example. The solvent may be any that does not hinder the reaction, and examples of such solvents include an alcohol such as methanol, water, and mixtures thereof. The base may be sodium hydroxide, for example.

Alternatively, this reaction can be performed in an appropriate solvent in the presence of an acid. The solvent may be any that does not hinder the reaction, and examples of such solvents include a halogenated aliphatic hydrocarbon such as methylene chloride, an ether such as 1,4-dioxane, and mixtures thereof. Examples of acids include trifluoroacetic acid and hydrochloric acid.

Intermediate Production Method b-2

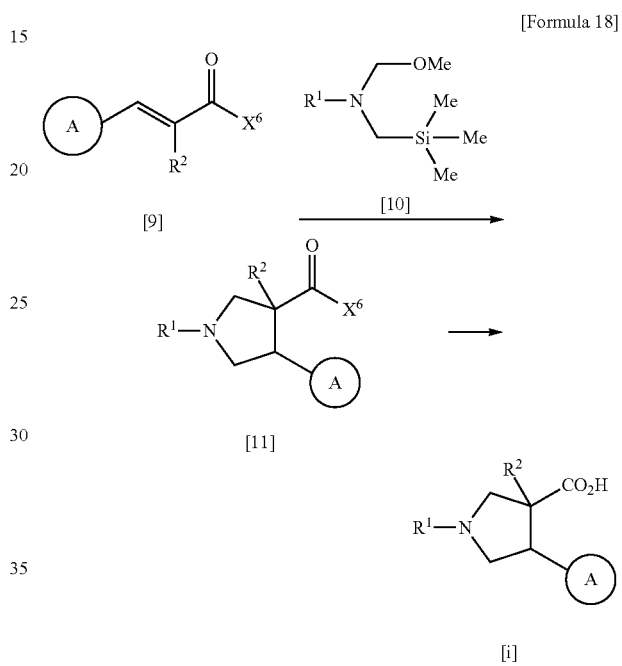

[Formula 18]

Where an optically active compound is required for the compound [i] used in Synthesis Method B described above, such an optically active compound can be produced as follows, for example.

First, a compound represented by general formula [9] (wherein $X^6$ represents an asymmetric auxiliary group, and the other symbols have the same meanings as those described above) is reacted with a compound represented by general formula [10] (wherein the symbol has the same meaning as that described above) to obtain a compound represented by general formula [11] (wherein the symbols have the same meanings as those described above).

The compound [i] can be obtained by removing the asymmetric auxiliary group of the compound [11].

Examples of the asymmetric auxiliary group represented by $X^6$ include chiral 4-benzyl-2-oxazolidinone, chiral 4-phenyl-2-oxazolidinone, and chiral 10,2-camphorsultam.

The reaction of the compound [9] with the compound [10] can be performed in an appropriate solvent in the presence of an acid. The solvent may be any that does not hinder the reaction, and examples of such solvents include a halogenated aliphatic hydrocarbon such as methylene chloride, an aromatic hydrocarbon such as toluene, a nitrile such as acetonitrile, an ether such as tetrahydrofuran, and mixtures thereof. The acid may be trifluoroacetic acid, for example.

The reaction of removing the asymmetric auxiliary group of the compound [11] can be performed in accordance with a conventional method, in an appropriate solvent, in the presence of water together with a base, for example. The solvent may be any that does not hinder the reaction, and examples of such solvents include an ether such as tetrahydrofuran, an alcohol such as methanol, and mixtures thereof. Examples of bases include sodium hydroxide and lithium hydroxide.

Intermediate Production Method b-3

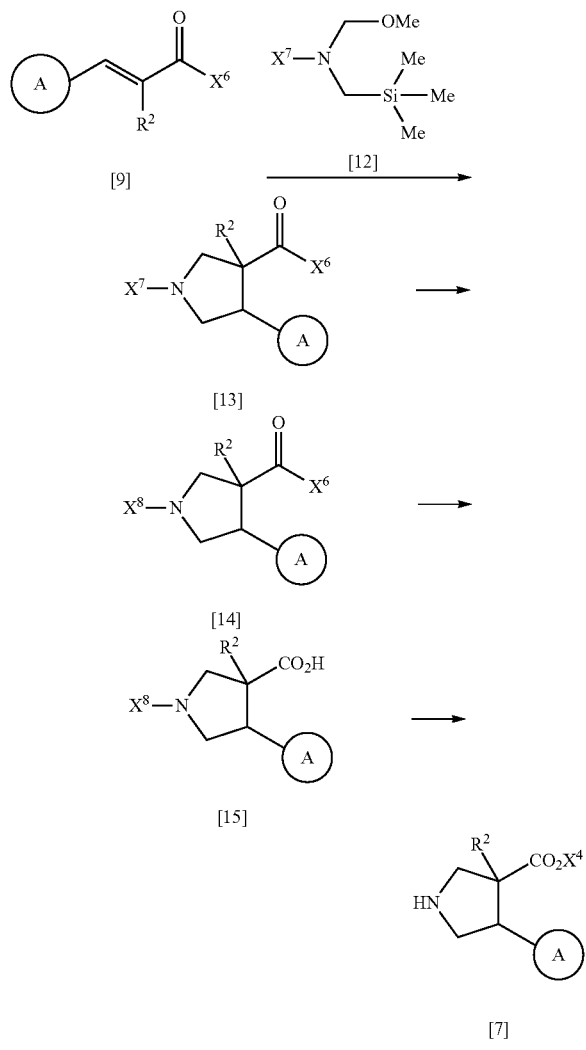

[Formula 19]

Where an optically active compound is required for the compound [7] used in Intermediate Production Method b-1 described above, such an optically active compound can also be produced as follows, for example.

The compound [9] is reacted with a compound represented by general formula [12] (wherein $X^7$ represents an amino-protecting group) to obtain a compound represented by general formula [13] (wherein the symbols have the same meanings as those described above).

The compound [13] is converted into a compound represented by general formula [14] (wherein $X^8$ represents an amino-protecting group different from $X^7$, and the other symbols have the same meanings as those described above), by exchanging the amino-protecting group of the compound [13] with another amino-protecting group.

The asymmetric auxiliary group of the compound [14] is removed to obtain a compound represented by general formula [15] (wherein the symbols have the same meanings as those described above).

The amino-protecting group is removed from the obtained compound [15] to obtain the compound [7] with the carboxyl group being protected.

The amino-protecting group represented by $X^7$ is preferably an amino-protecting group that is not removed under acidic conditions, for example, a benzyl group.

The amino-protecting group represented by $X^8$ may be an amino-protecting group different from $X^7$ described above, and in particular, is preferably a group capable of being removed with an acid. A specific example may be a t-butoxycarbonyl group.

The reaction of the compound [9] with the compound [12] can be performed as in the reaction of the compound [9] with the compound [10] in Intermediate Production Method b-2 described above.

The substitution reaction of the amino-protecting group from the compound [13] into the compound [14] can be performed in accordance with a conventional method. Where $X^7$ is a benzyl group, for example, the substitution reaction can be performed in an appropriate solvent in the presence of hydrogen, a palladium catalyst, and a donor of the amino-protecting group. The solvent may be any that does not hinder the reaction, and examples of such solvents include an ether such as tetrahydrofuran, an alcohol such as ethanol, and mixtures thereof. The palladium catalyst may be a palladium catalyst supported on activated carbon, for example. Where $X^8$ is a t-butoxycarbonyl group, for example, the donor of the amino-protecting group may be di-t-butyl dicarbonate, for example.

The reaction of removing the asymmetric auxiliary group of the compound [14] can be performed as in the reaction of removing the asymmetric auxiliary group of the compound [11] in Intermediate Production Method b-2 described above.

The reaction of converting the compound [15] into the compound [7] can be performed in an appropriate solvent in the presence of an acid. The solvent may be an alcohol such as methanol, for example. The acid may be hydrochloric acid, for example. This reaction can also be performed using a combination of an alcohol such as methanol and thionyl chloride.

Intermediate Production Method c

[Formula 20]

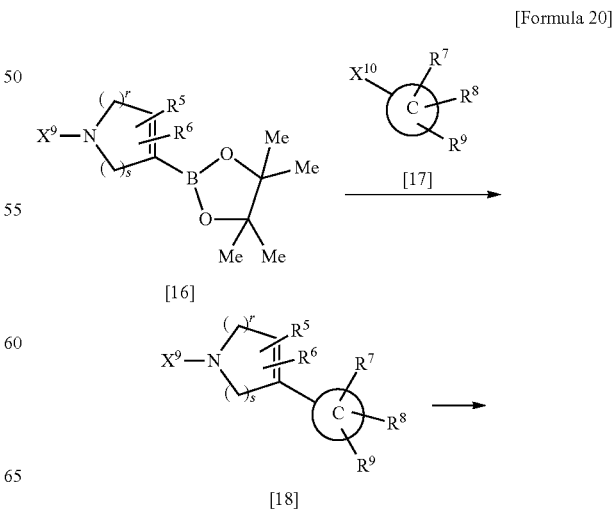

-continued

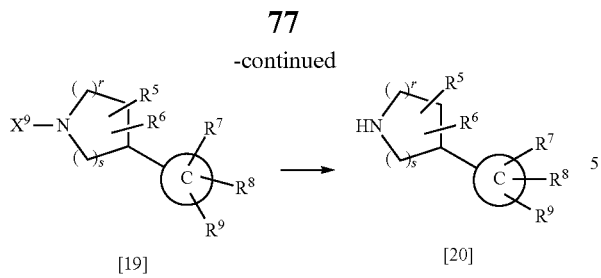

[19] → [20]

Among the compounds [j] used in Synthesis Method B described above, a compound wherein $R^3$ and $R^4$ are groups that are terminally attached to each other, and together with the nitrogen atom to which they are attached, form a nitrogen-containing aliphatic heterocyclic ring substituted with an aryl or heteroaryl group, which compound is represented by general formula [20] (wherein r and s each independently represent an integer of 1 or 2, the sum of r and s is 3, and the other symbols have the same meanings as those described above), can be produced as follows, for example.

A compound represented by general formula [16] (wherein $X^9$ represents an amino-protecting group, and the other symbols have the same meanings as those described above) is subjected to a coupling reaction with a compound represented by general formula [17] (wherein $X^{10}$ represents a leaving group, and the other symbols have the same meanings as those described above) to obtain a compound represented by general formula [18] (wherein the symbols have the same meanings as those described above).

The compound [18] is subjected to a catalytic hydrogenation reaction to obtain a compound represented by general formula [19] (wherein the symbols have the same meanings as those described above).

A compound [20] can be obtained by removing the amino-protecting group of the compound [19].

Examples of the amino-protecting group represented by $X^9$ include benzyl and t-butoxycarbonyl groups.

The leaving group represented by $X^{10}$ may be a halogen atom, for example.

The coupling reaction of the compound [16] with the compound [17] can be performed in accordance with a conventional method, in an appropriate solvent in the presence of a palladium catalyst and a base, for example. The solvent may be any that does not hinder the reaction, and examples of such solvents include an amide such as N,N-dimethylformamide, an ether such as dioxane, an aromatic hydrocarbon such as toluene, an alcohol such as t-butanol, and mixtures thereof. The palladium catalyst may be dichloro[1,1'-bis(diphenylphosphino) ferrocene]palladium (II) dichloromethane adduct, for example. The base may be sodium carbonate, for example.

The catalytic hydrogenation reaction of the compound [18] can be performed in accordance with a conventional method, in an appropriate solvent in the presence of hydrogen gas and a palladium catalyst, for example. The solvent may be any that does not hinder the reaction, and examples of such solvents include an alcohol such as ethanol, an ether such as tetrahydrofuran, an ester such as ethyl acetate, and mixtures thereof. The palladium catalyst may be a palladium catalyst supported on activated carbon, for example.

The reaction of removing the amino-protecting group of the compound [19] can be performed as in the reaction of removing the amino-protecting group of the compound [2] in Intermediate Production Method a described above.

Intermediate Production Method d

[Formula 21]

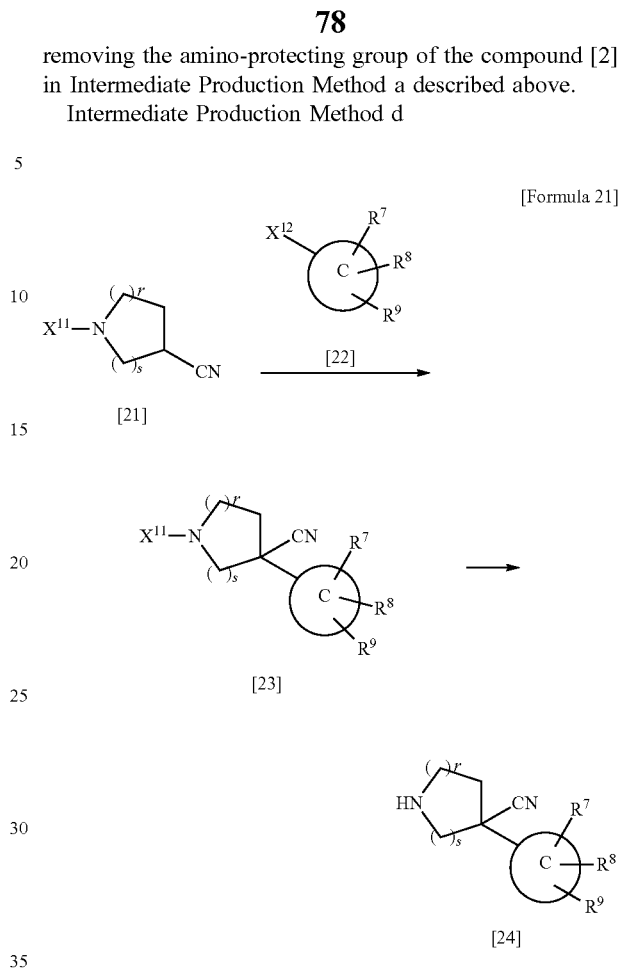

Among the compounds [j] used in Synthesis Method B described above, a compound represented by general formula [24] (wherein the symbols have the same meanings as those described above) can be produced as follows, for example.

A compound represented by general formula [23] (wherein the symbols have the same meanings as those described above) can be obtained by reacting a compound represented by general formula [21] (wherein $X^{11}$ represents an amino-protecting group, and the other symbols have the same meanings as those described above) with a compound represented by general formula [22] (wherein $X^{12}$ represents a leaving group, and the other symbols have the same meanings as those described above).

The compound [24] can be obtained by removing the amino-protecting group of the obtained compound [23].

The amino-protecting group represented by $X^{11}$ may be a t-butoxycarbonyl group, for example.

The leaving group represented by $X^{12}$ may be a halogen atom (e.g., a fluorine or chlorine atom), for example.

The reaction of the compound [21] with the compound [22] can be performed in an appropriate solvent in the presence of a base. The solvent may be any that does not hinder the reaction, and examples of such solvents include an aromatic hydrocarbon such as toluene, an ether such as tetrahydrofuran, and mixtures thereof. The base may be potassium bis(trimethylsilyl)amide, for example.

The reaction of removing the amino-protecting group of the compound [23] can be performed as in the reaction of removing the amino-protecting group of the compound [2] in Intermediate Production Method a described above.

Intermediate Production Method e-1

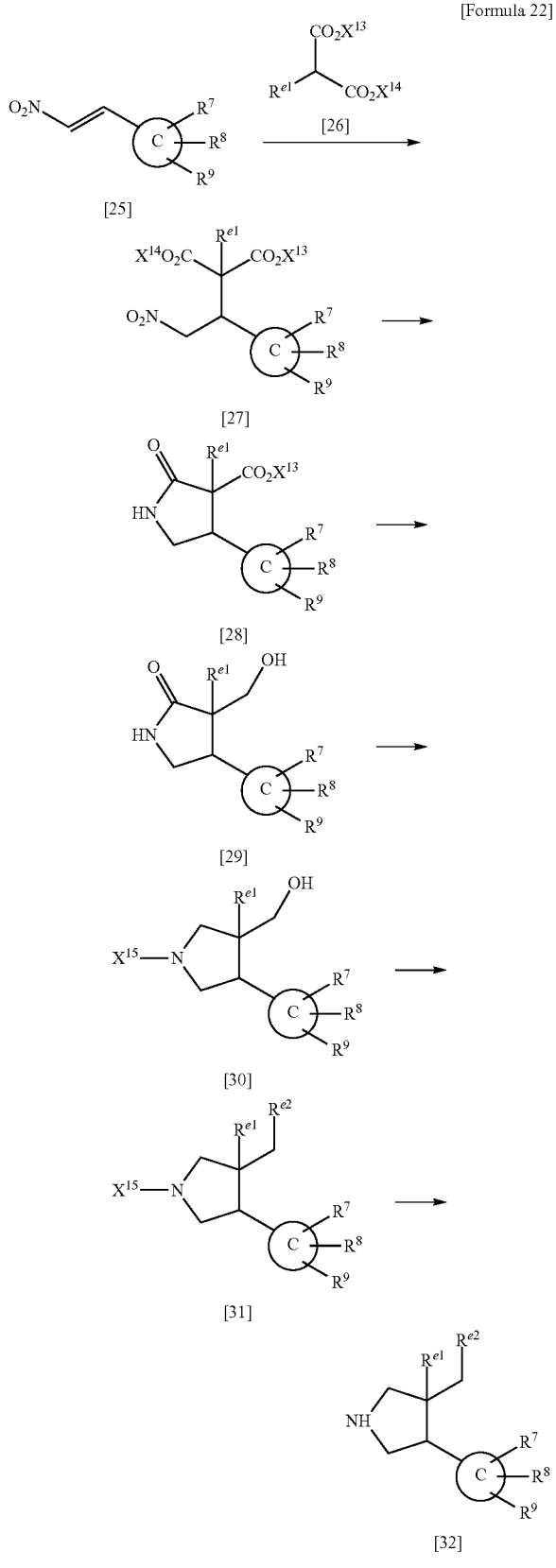

[Formula 22]

Among the compounds [j] used in Synthesis Method B described above, a compound represented by general formula [32] (wherein $R^{e1}$ represents a hydrogen atom, halogen atom, alkyl group, or alkoxy group, $R^{e2}$ represents an alkoxy group, and the other symbols have the same meanings as those described above) can be produced as follows, for example.

A compound represented by general formula [25] (wherein the symbols have the same meanings as those described above) is subjected to an addition reaction with a compound represented by general formula [26] (wherein $X^{13}$ and $X^{14}$ each independently represent a carboxyl-protecting group, and the other symbol has the same meaning as that described above) to produce a compound represented by general formula [27] (wherein the symbols have the same meanings as those described above).

Next, the compound [27] is subjected to a reduction reaction and a ring closure reaction to produce a compound represented by general formula [28] (wherein the symbols have the same meanings as those described above).

The obtained compound [28] is subjected to a reduction reaction to produce a compound represented by general formula [29] (wherein the symbols have the same meanings as those described above).

The obtained compound [29] is converted into a compound represented by general formula [30] (wherein $X^{15}$ represents an amino-protecting group, and the other symbols have the same meanings as those described above).

The hydroxy group of the obtained compound [30] is alkylated to produce a compound represented by general formula [31] (wherein the symbols have the same meanings as those described above).

A compound [32] can be obtained by removing the amino-protecting group of the compound [31].

The carboxyl-protecting groups represented by $X^{13}$ and $X^{14}$ may be alkyl groups, for example. Specific examples include methyl and ethyl groups.

The amino-protecting group represented by $X^{15}$ may be a t-butoxycarbonyl group, for example.

The addition reaction of the compound [25] with the compound [26] can be performed as in the reaction of the compound [3] with the compound [4] in Intermediate Production Method b-1 described above. Similarly, in this reaction, the addition reaction can be stereoselectively performed by adding a chiral catalyst into the reaction system. Examples of chiral catalysts include 1-[3,5-bis(trifluoromethyl)phenyl]-3-[(1R,2R)-(−)-2-(dimethylamino)cyclohexyl]thiourea; 1-[3,5-bis(trifluoromethyl)phenyl]-3-[(1S,2S)-(−)-2-(dimethylamino)cyclohexyl]thiourea; and 6'-hydroxycinchonine.

The reduction reaction and ring closure reaction of the compound [27] can be performed as in the reaction from the compound [5] into the compound [6] in Intermediate Production Method b-1 described above.

The reduction reaction of the compound [28] can be performed in accordance with a conventional method, in an appropriate solvent in the presence of a reducing agent. The solvent may be any that does not hinder the reaction, and examples of such solvents include an alcohol such as ethanol, an ether such as tetrahydrofuran, and mixtures thereof. The reducing agent may be sodium borohydride, for example.

The reaction of converting the compound [29] into the compound [30] can be performed in an appropriate solvent in the presence of an alkylating agent, a reducing agent, and a protecting group donor. The solvent may be any that does not hinder the reaction, and examples of such solvents include a halogenated aliphatic hydrocarbon such as methylene chloride, an alcohol such as methanol, an ether such as tetrahydrofuran, an aromatic hydrocarbon such as toluene, and mixtures thereof. Examples of alkylating agents include a trialkyloxonium tetrafluoroborate such as trimethyloxonium tetrafluoroborate and methyl trifluoromethanesulfonate. Examples of reducing agents include sodium borohydride and a borane-pyridine complex. The protecting group donor may be di-t-butyl dicarbonate, for example.

The alkylation reaction of the hydroxy group in the compound [30] can be performed in accordance with a conventional method, in an appropriate solvent in the presence of a base and an alkylating agent, for example. The solvent may be any that does not hinder the reaction, and examples of such solvents include an amide such as N,N-dimethylformamide, an ether such as tetrahydrofuran, and mixtures thereof. Examples of bases include sodium hydride, sodium hydroxide, and potassium carbonate. The alkylating agent may be an alkyl halide (e.g., methyl iodide or ethyl iodide), for example.

The reaction of removing the amino-protecting group of the compound [31] can be performed as in the reaction of removing the amino-protecting group of the compound [23] in Intermediate Production Method d described above.

Intermediate Production Method e-2a

Among the compounds [j] used in Synthesis Method B described above, compounds represented by general formulas [39a] and [39a'] (wherein $R^{e3}$ represents a hydrogen atom, cyano group, or alkoxy group, and the other symbols have the same meanings as those described above) can be produced as follows, for example.

By reacting a compound represented by general formula [33a] (wherein $X^{16}$ represents an asymmetric auxiliary group, and the other symbols have the same meanings as those described above) with a compound represented by general formula [34] (wherein $X^{17}$ is an amino-protecting group), a compound represented by general formula [35a] or [35a'] (wherein the symbols have the same meanings as those described above) can be obtained.

A compound represented by general formula [36a] or [36a'] (wherein $X^{18}$ represents an amino-protecting group different from $X^{17}$, and the other symbols have the same meanings as those described above) can be obtained by converting the amino-protecting group of the obtained compound [35a] or [35a'].

A compound represented by general formula [37a] or [37a'] (wherein the symbols have the same meanings as those described above) can be obtained by subjecting the obtained compound [36a] or [36a'] to a reduction reaction.

[Formula 23]

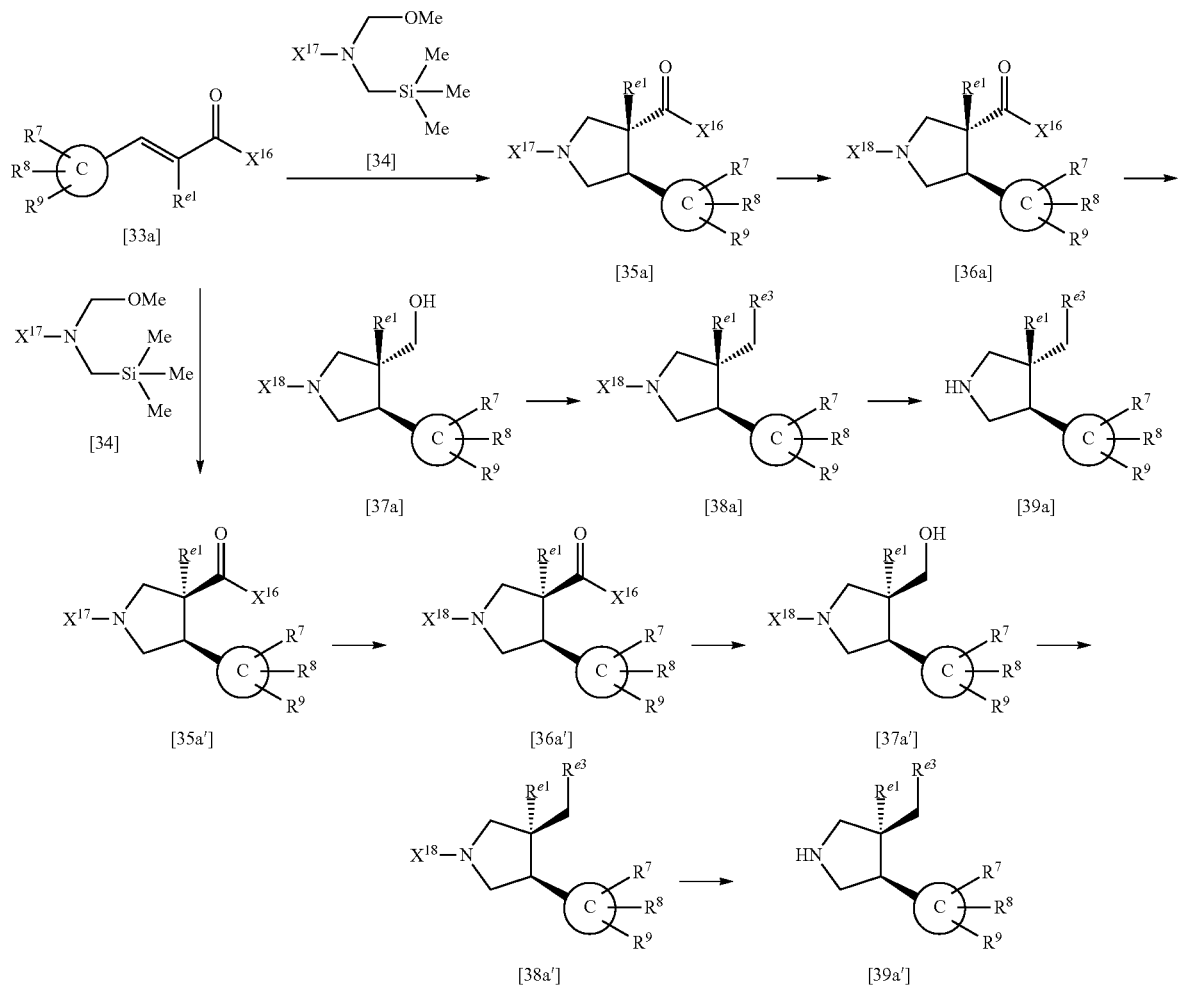

A compound represented by general formula [38a] or [38a'] (wherein the symbols have the same meanings as those described above) can be obtained by converting the obtained compound [37a] or [37a'].

The compound represented by formula [39a] or [39a'] can be produced by deprotecting the amino-protecting group of the obtained compound [38a] or [38a'].

Examples of the asymmetric auxiliary group represented by $X^{16}$ include chiral 4-benzyl-2-oxazolidinone, chiral 4-phenyl-2-oxazolidinone, and chiral 10,2-camphorsultam.

The amino-protecting group represented by $X^{17}$ may be a benzyl group, for example.

The amino-protecting group represented by $X^{18}$ may be an amino-protecting group different from $X^{17}$, and is preferably a t-butoxycarbonyl group, for example.

Each of the reactions in Intermediate Production Method e-2 can be performed as follows.

The reaction of the compound [33a] with the compound [34] can be performed as in the reaction of the compound [9] with the compound [12] in Intermediate Production Method b-3 described above.

The reaction of converting the compound [35a] into the compound [36a] or the compound [35a'] into the compound [36a'] can be performed as in the reaction of converting the compound [13] into the compound [14] in Intermediate Production Method b-3 described above.

The reduction reaction of the compound [36a] or [36a'] can be performed in accordance with a conventional method, in an appropriate solvent in the presence of a reducing agent. The solvent may be any that does not hinder the reaction, and examples of such solvents include an alcohol such as ethanol, an ether such as tetrahydrofuran, water, and mixtures thereof. The reducing agent may be sodium borohydride, for example.

Where $R^{e3}$ is an alkoxy group, the reaction of converting the compound [37a] into the compound [38a] or the compound [37a'] into the compound [38a'] can be performed as in the reaction of converting the compound [30] into the compound [31] in Intermediate Production Method e-1 described above.

Where $R^{e3}$ is a cyano group, the reaction of converting the compound [37a] into the compound [38a] or the compound [37a'] into the compound [38a'] can be performed in an appropriate solvent in the presence of an azodicarboxylic acid derivative, a phosphine derivative, and a cyano group donor. The solvent may be any that does not hinder the reaction, and examples of such solvents include an ether such as tetrahydrofuran, an aromatic hydrocarbon such as toluene, a halogenated aliphatic hydrocarbon such as methylene chloride, and mixtures thereof. The azodicarboxylic acid derivative may be diethyl azodicarboxylate, for example. The phosphine derivative may be triphenylphosphine, for example. The cyano group donor may be acetone cyanohydrin, for example.

Where $R^{e3}$ is a hydrogen atom, the reaction of converting the compound [37a] into the compound [38a] or the compound [37a'] into the compound [38a'] can be performed in an appropriate solvent in the presence of an azodicarboxylic acid derivative, a phosphine derivative, and deoxygenating agent. The solvent may be any that does not hinder the reaction, and examples of such solvents include an ether such as tetrahydrofuran, an aromatic hydrocarbon such as toluene, a halogenated aliphatic hydrocarbon such as methylene chloride, and mixtures thereof. The azodicarboxylic acid derivative may be diethyl azodicarboxylate, for example. The phosphine derivative may be triphenylphosphine, for example. The deoxygenating agent may be N'-isopropylidene-2-nitrobenzenesulfonohydrazide, for example.

The reaction of removing the amino-protecting group of the compound [38a] or [38a'] can be performed as in the reaction of removing the amino-protecting group of the compound [2] in Intermediate Production Method a described above.

Intermediate Production Method e-2b

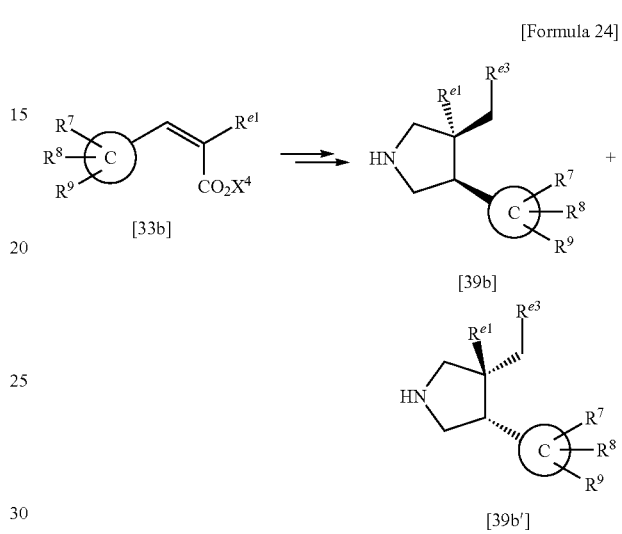

[Formula 24]

Among the compounds [j] used in Synthesis Method B described above, a compound represented by general formula [39b] (wherein the symbols have the same meanings as those described above) and a compound represented by general formula [39b'] (wherein the symbols have the same meanings as those described above) can be produced from a compound represented by general formula [33b] (wherein the symbols have the same meanings as those described above). Specifically, this can be performed by treating the compound [33b] as in the reaction of converting the compound [33a] into the compound [39a] or compound [39a'] in Intermediate Production Method e-2a described above. Where it is necessary to selectively produce the compound [39b] and compound [39b'], an appropriate asymmetric auxiliary group may be selected as $X^4$ of the compound [33b]. Alternatively, after the compound [39b] and compound [39b'] are obtained as a mixture, each of the diastereomers may be separated in any subsequent step. In this case, the separation can be performed using a common method, for example, silica gel column chromatography or liquid chromatography.

Intermediate Production Method e-3

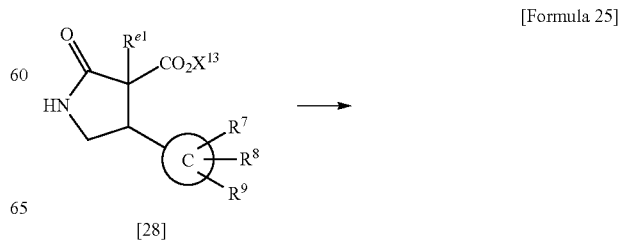

[Formula 25]

-continued

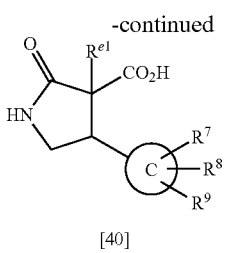

[40]

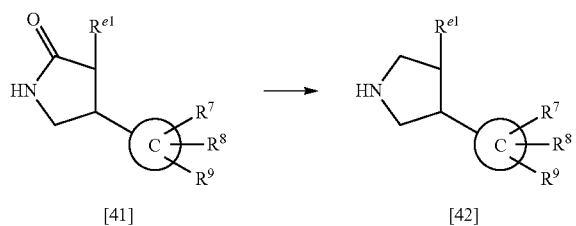

[41] [42]

Among the compounds [j] used in Synthesis Method B described above, a compound represented by general formula [42] (wherein the symbols have the same meanings as those described above) can be produced as follows, for example.

A compound represented by general formula [40] (wherein the symbols have the same meanings as those described above) can be obtained by removing the carboxyl-protecting group of the compound [28] (wherein the symbols have the same meanings as those described above).

A compound represented by general formula [41] (wherein the symbols have the same meanings as those described above) can be obtained by subjecting the compound [40] to a decarboxylation reaction.

The compound [42] can be obtained by reducing the compound [41].

The reaction of converting the compound [28] into the compound [40] can be performed as in the reaction of removing the carboxyl-protecting group of the compound [8] in Intermediate Production Method b-1.

The decarboxylation reaction of the compound [40] can be performed with heating in an appropriate solvent. The solvent may be any that does not hinder the reaction, and examples of such solvents include an aromatic hydrocarbon such as toluene, an amide such as N,N-dimethylformamide, dimethylsulfoxide, and mixtures thereof. In this reaction, a reaction adjuvant may be added to accelerate the reaction. The reaction adjuvant may be acetic acid, for example.

The reduction reaction of the compound [41] can be performed as in the reduction reaction of the compound [6] in Intermediate Production Method b-1.

Intermediate Production Method f

[Formula 26]

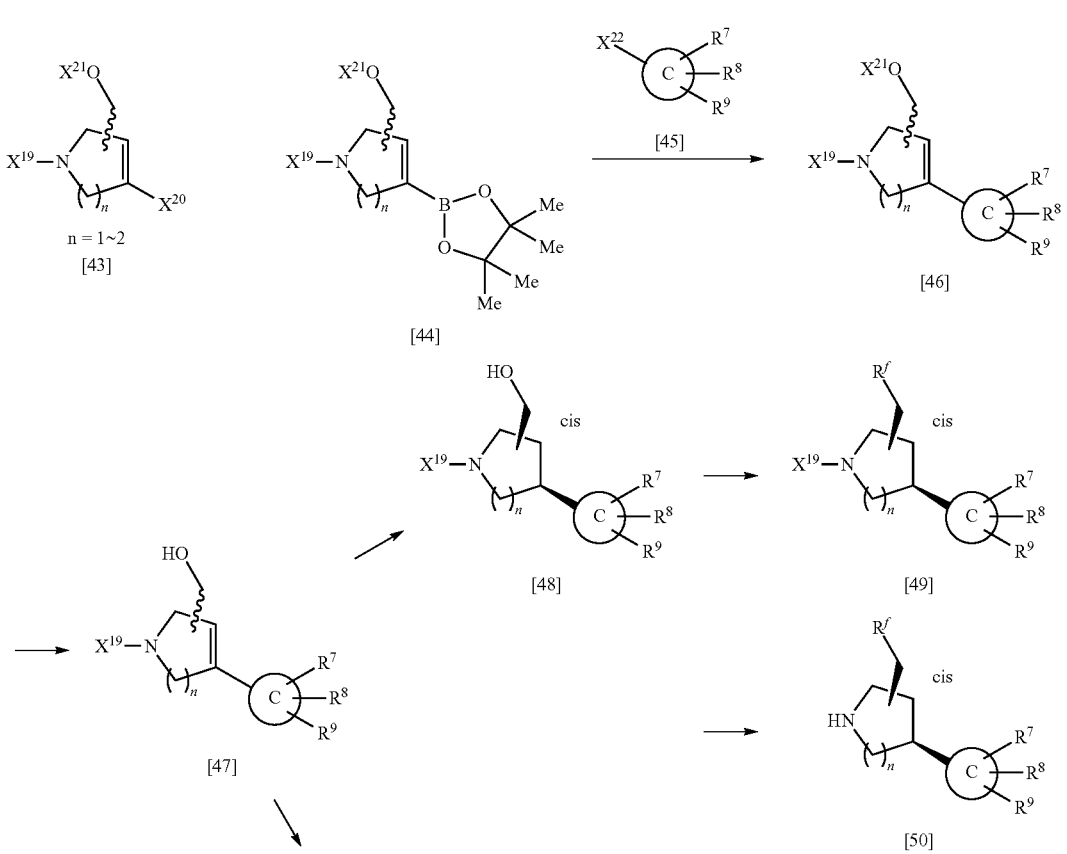

-continued

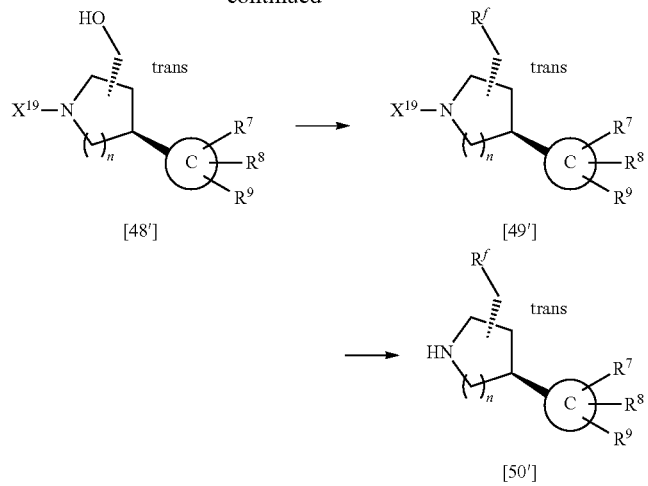

Among the compounds [j] used in Synthesis Method B described above, a compound represented by general formula [50] (wherein $R^f$ represents a halogen atom, cyano group, or alkoxy group, and the other symbols have the same meanings as those described above) or general formula [50'] (wherein the symbols have the same meanings as those described above) can be produced as follows, for example.

By treating a compound represented by general formula [43] (wherein $X^{19}$ represents an amino-protecting group, $X^{20}$ represents a leaving group, $X^{21}$ represents a hydroxy-protecting group, and n represents 1 or 2) with a boronic ester donor, a compound represented by general formula [44] (wherein the symbols have the same meanings as those described above) can be obtained.

A compound represented by general formula [46] (wherein the symbols have the same meanings as those described above) can be obtained by subjecting the obtained compound [44] to a coupling reaction with a compound represented by general formula [45] (wherein $X^{22}$ represents a leaving group, and the other symbols have the same meanings as those described above).

A compound represented by general formula [47] (wherein the symbols have the same meanings as those described above) can be obtained by removing the hydroxy-protecting group of the obtained compound [46].

A compound represented by general formula [48] (wherein the symbols have the same meanings as those described above) or a compound represented by general formula [48'] (wherein the symbols have the same meanings as those described above) can be obtained by stereoselectively reducing the obtained compound [47].

A compound represented by general formula [49] (wherein the symbols have the same meanings as those described above) or a compound represented by general formula [49'] (wherein the symbols have the same meanings as those described above) can be obtained by converting the hydroxy group of the obtained compound [48] or [48'] into any of the various substituents.

The compound [50] or [50'] can be obtained by removing the amino-protecting group of the obtained compound [49] or [49'].

The amino-protecting group represented by $X^{19}$ may be a t-butoxycarbonyl group, for example.

The leaving group represented by $X^{20}$ may be a trifluoromethylsulfonyloxy group, for example.

The hydroxy-protecting group represented by $X^{21}$ may be a trialkylsilyl group such as a t-butyldimethylsilyl group.

The leaving group represented by $X^{22}$ may be a halogen atom or trifluoromethylsulfonyloxy group, for example.

The reaction of converting the compound [43] into the compound [44] can be performed by reaction with a boronic ester donor in an appropriate solvent in the presence of a palladium catalyst, a base, and a ligand. The solvent may be any that does not hinder the reaction, and examples of such solvents include an ether such as 1,4-dioxane, an amide such as N,N-dimethylformamide, an aromatic hydrocarbon such as toluene, an alcohol such as t-butanol, and mixtures thereof. The palladium catalyst may be dichloro[1,1'-bis(diphenylphosphino)ferrocene]palladium (II) dichloromethane adduct, for example. The ligand may be 1,1'-bis(diphenylphosphino)ferrocene, for example. The base may be potassium acetate, for example. The boronic ester donor may be bis(pinacolato)diboran, for example.

The coupling reaction of the compound [44] with the compound [45] can be performed as in the coupling reaction of the compound [16] with the compound [17] in Intermediate Production Method c described above.

The hydroxy-protecting group of the compound [46] can be removed in accordance with a conventional method, in an appropriate solvent in the presence of a deprotecting agent, for example, depending on the type of the protecting group to be removed. The solvent may be any that does not hinder the reaction, and examples of such solvents include an ether such as tetrahydrofuran, a halogenated aliphatic hydrocarbon such as methylene chloride, an alcohol such as methanol, and mixtures thereof. The deprotecting agent may be tetra-n-butyl ammonium fluoride, for example.

The stereoselective reduction reaction of the compound [47] can be performed in accordance with a conventional method, in an appropriate solvent in the presence of hydrogen gas and a catalyst. The solvent may be any that does not hinder the reaction, and examples of such solvents include an aromatic hydrocarbon such as toluene, a halogenated aliphatic hydrocarbon such as methylene chloride, an alcohol such as methanol, an ether such as tetrahydrofuran, an ester such as ethyl acetate, and mixtures thereof. As the catalyst, a palladium catalyst supported on activated carbon, for example, can be used for obtaining a cis-form such as the compound [48] (e.g., (2R,4S)-form or (2S,4R)-form), and the Crabtree's catalyst, for example, can be used for obtaining a trans-form such as the compound [48'] (e.g., (2S,4S)-form or (2R,4R)-form).

Where $R^f$ is a cyano or alkoxy group, the reaction of converting the compound [48] into the compound [49] or the compound [48'] into the compound [49'] can be performed as in the reaction of converting the compound [37] into the compound [38] or the compound [37'] into the compound [38'] described in Intermediate Production Method e-2 above.

Where $R^f$ is a fluorine atom, the reaction of converting the compound [48] into the compound [49] or the compound [48'] into the compound [49'] can be performed by reaction with a fluorinating agent in an appropriate solvent. The solvent may be any that does not hinder the reaction, and may be a halogenated aliphatic hydrocarbon such as methylene chloride, for example. As the fluorinating agent, (diethylamino)sulfur trifluoride can be used, for example.

The reaction of removing the amino-protecting group of the compound [49] or [49'] can be performed as in the reaction of removing the amino-protecting group of the compound [2] in Intermediate Production Method a described above.

Note that where the compounds [48] and [48'] are obtained as a mixture, they may be separated from each other in or after this step. The separation can be performed using a common method, for example, silica gel column chromatography or liquid chromatography.

Intermediate Production Method g

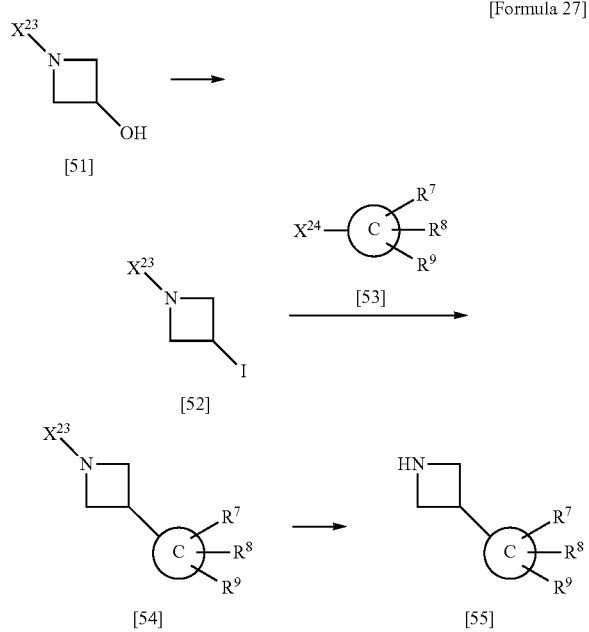

[Formula 27]

Among the compounds [j] used in Synthesis Method B described above, a compound represented by general formula [55] (wherein the symbols have the same meanings as those described above) can be produced as follows, for example.

By iodinating a compound represented by general formula [51] (wherein $X^{23}$ represents an amino-protecting group), a compound represented by general formula [52] (wherein the symbol has the same meaning as that described above) can be obtained.

A compound represented by general formula [54] (wherein the symbols have the same meanings as those described above) can be obtained by subjecting the obtained compound [52] to a coupling reaction with a compound represented by general formula [53] (wherein $X^{24}$ represents a leaving group, and the other symbols have the same meanings as those described above).

The compound [55] can be obtained by removing the amino-protecting group of the compound [54].

The amino-protecting group represented by $X^{23}$ may be a t-butoxycarbonyl group, for example.

The leaving group represented by $X^{24}$ may be a halogen atom (e.g., a bromine atom), for example.

The iodination reaction of the compound [51] into the compound [52] can be performed in an appropriate solvent in the presence of iodine. The solvent may be any that does not hinder the reaction, and examples of such solvents include an aromatic hydrocarbon such as toluene, an ether such as tetrahydrofuran, a halogenated aliphatic hydrocarbon such as methylene chloride, and mixtures thereof. In this reaction, a reaction adjuvant may be added to accelerate the reaction. Examples of reaction adjuvants include triphenylphosphine and imidazole.

The coupling reaction of the compound [52] with the compound [53] can be performed in accordance with a conventional method, in an appropriate solvent in the presence of a zinc reagent and a palladium catalyst, for example. The solvent may be any that does not hinder the reaction, and examples of such solvents include an amide such as dimethylacetamide, an aromatic hydrocarbon such as toluene, an ether such as tetrahydrofuran, and mixtures thereof. Examples of zinc reagents include zinc powder and zinc chloride (II). The palladium catalyst may be dichloro[1,1'-bis(diphenylphosphino)ferrocene]palladium (II) dichloromethane adduct, for example. In this reaction, a reaction adjuvant can be added to accelerate the reaction. The reaction adjuvant may be copper iodide, for example.

The reaction of removing the amino-protecting group of the compound [54] can be performed as in the reaction of removing the amino-protecting group of the compound [2] in Intermediate Production Method a described above.

Intermediate Production Method h

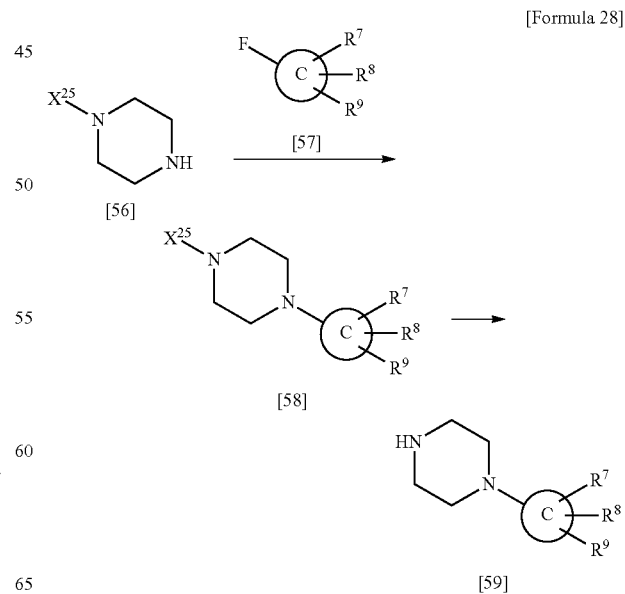

[Formula 28]

Among the compounds [j] used in Synthesis Method B described above, a compound represented by general formula [59] (wherein the symbols have the same meanings as those described above) can be produced as follows, for example.

By subjecting a compound represented by general formula [56] (wherein $X^{25}$ represents an amino-protecting group) to a substitution reaction with a compound represented by general formula [57] (wherein the symbols have the same meanings as those described above), a compound represented by general formula [58] (wherein the symbols have the same meanings as those described above) can be obtained.

The compound [59] can be obtained by removing the amino-protecting group of the compound [58].

The amino-protecting group represented by $X^{25}$ may be a t-butoxycarbonyl group, for example.

The substitution reaction of the compound [56] with the compound [57] can be performed in accordance with a conventional method, in an appropriate solvent in the presence of a base. The solvent may be any that does not hinder the reaction, and examples of such solvents include an amide such as N-methylpyrrolidone, a nitrile such as acetonitrile, an ether such as 1,4-dioxane, dimethylsulfoxide, and mixtures thereof. The base may be potassium carbonate, for example.

The reaction of removing the amino-protecting group of the compound [58] can be performed as in the reaction of removing the amino-protecting group of the compound [2] in Intermediate Production Method a described above.

Intermediate Production Method i formula [62] (wherein the symbols have the same meanings as those described above) can be obtained.

The compound [63] can be obtained by subsequently removing the amino-protecting group of the obtained compound [62], as required.

The amino-protecting group represented by $X^{26}$ may be a benzyl group, for example.

The reductive amination reaction of the compound [60] with the compound [61] can be performed as in the reductive amination reaction of the compound [a] with the compound [b] or [c] in Synthesis Method A-1 described above.

The reaction of removing the amino-protecting group of the compound [62] can be performed as in the reaction of removing the amino-protecting group of the compound [2] in Intermediate Production Method a described above.

Intermediate Production Method j

[Formula 30]

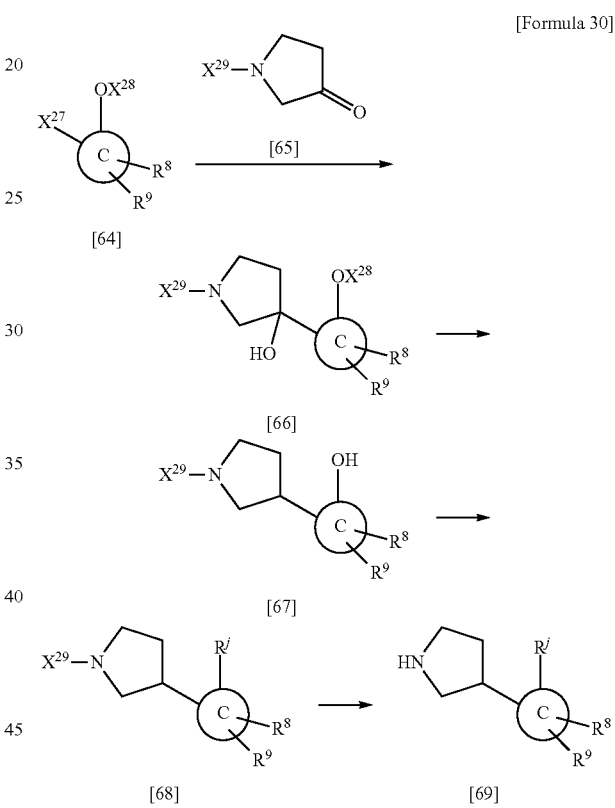

[Formula 29]

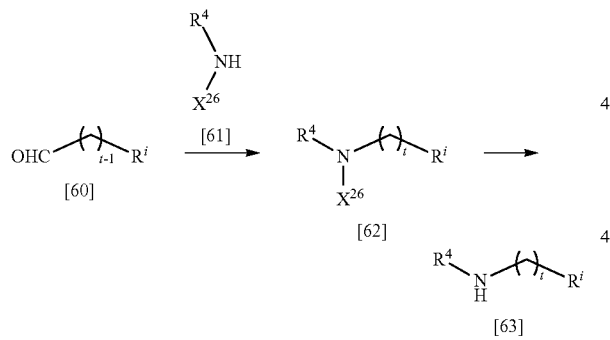

Among the compounds [j] used in Synthesis Method B described above, a compound wherein $R^3$ is an alkyl group substituted with an optionally substituted aryl group, or an alkyl group substituted with an optionally substituted heteroaryl group, and $R^4$ is a hydrogen atom or an alkyl group, which compound is represented by general formula [63] (wherein $R^i$ represents an optionally substituted aryl group or an optionally substituted heteroaryl group, and t represents an integer from 1 to 3), can be produced as follows, for example.

By subjecting a compound represented by general formula [60] (wherein the symbols have the same meanings as those described above) to a reductive amination reaction with a compound represented by general formula [61] (wherein $X^{26}$ represents an amino-protecting group or hydrogen, and the other symbol has the same meaning as that described above), a compound represented by general Among the compounds [j] used in Synthesis Method B described above, a compound represented by general formula [69] (wherein $R^j$ represents an optionally substituted alkoxy group, and the other symbols have the same meanings as those described above) can be produced as follows, for example.

A compound represented by general formula [64] (wherein $X^{27}$ represents a leaving group, $X^{28}$ represents a hydroxy-protecting group, and the other symbols have the same meanings as those described above) is reacted with a compound represented by general formula [65] (wherein $X^{29}$ represents an amino-protecting group) to obtain a compound represented by general formula [66] (wherein the symbols have the same meanings as those described above).

A compound represented by general formula [67] (wherein the symbols have the same meanings as those described above) can be obtained by converting the compound [66].

A compound represented by general formula [68] (wherein R$^j$ represents an optionally substituted alkoxy group, and the other symbols have the same meanings as those described above) can be obtained by alkylating the hydroxy group of the compound [67].

The compound [69] can be obtained by removing the amino-protecting group of the compound [68].

The leaving group represented by X$^{27}$ may be a halogen atom, for example.

The hydroxy-protecting group represented by X$^{28}$ is preferably a benzyl group.

The amino-protecting group represented by X$^{29}$ may be a t-butoxycarbonyl or benzyl group, for example.

The reaction of the compound [64] with the compound [65] can be performed in an appropriate solvent in the presence of a metallizing reagent. The solvent may be any that does not hinder the reaction, and examples of such solvents include an ether such as tetrahydrofuran, an aliphatic hydrocarbon such as hexane, and mixtures thereof. The metallizing reagent may be n-butyllithium, for example.

The reaction of converting the compound [66] into the compound [67] can be performed in an appropriate solvent in the presence of a trialkylsilane, an acid, hydrogen, and a palladium catalyst. The solvent may be any that does not hinder the reaction, and examples of such solvents include a halogenated aliphatic hydrocarbon such as methylene chloride, an aromatic hydrocarbon such as toluene, and mixtures thereof. The trialkylsilane may be triethylsilane, for example. The acid may be trifluoroacetic acid, for example. The palladium catalyst may be a palladium catalyst supported on activated carbon, for example.

The alkylation reaction of the hydroxy group of the compound [67] can be performed as in the alkylation reaction of the compound [30] in Intermediate Production Method e-1 described above.

The reaction of removing the amino-protecting group of the compound [68] can be performed as in the reaction of removing the amino-protecting group of the compound [2] in Intermediate Production Method a described above.

Intermediate Production Method k

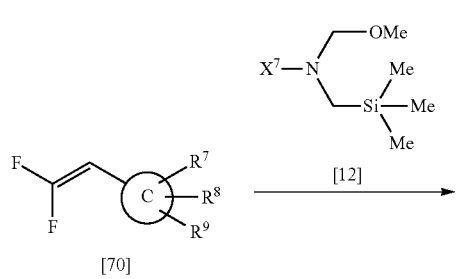

[Formula 31]

Among the compounds [j] used in Synthesis Method B described above, a compound represented by general formula [72] (wherein the symbols have the same meanings as those described above) can be produced as follows, for example.

A compound represented by general formula [71] (wherein the symbols have the same meanings as those described above) can be obtained by reacting a compound represented by general formula [70] (wherein the symbols have the same meanings as those described above) with the compound represented by general formula [12] (wherein the symbol has the same meaning as that described above).

The compound [72] can be obtained by removing the amino-protecting group of the compound [71].

The reaction of the compound [70] with the compound [12] can be performed in an appropriate solvent in the presence of an acid. The solvent may be any that does not hinder the reaction, and examples of such solvents include a halogenated aliphatic hydrocarbon such as methylene chloride, an aromatic hydrocarbon such as toluene, a nitrile such as acetonitrile, an ether such as tetrahydrofuran, and mixtures thereof. The acid may be trifluoroacetic acid, for example.

The reaction of removing the amino-protecting group of the compound [72] can be performed as in the reaction of removing the amino-protecting group of the compound [2] in Intermediate Production Method a described above.

Intermediate Production Method 1

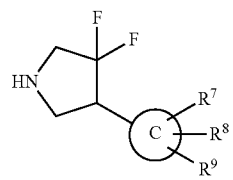

[72]

[Formula 32]

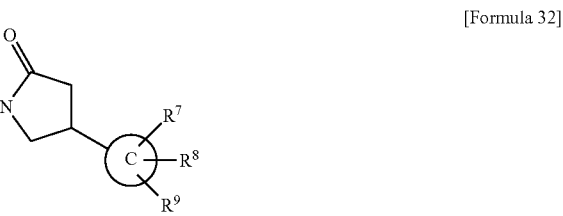

[73]

[74]

[75]

Intermediate Production Method m

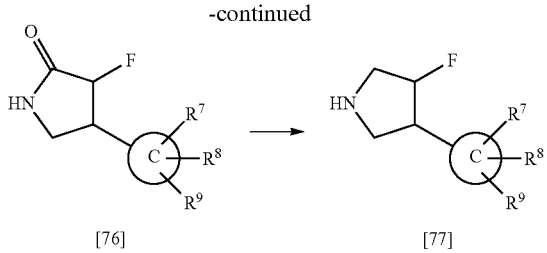

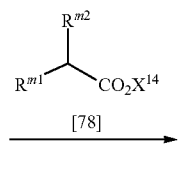

[Formula 33]

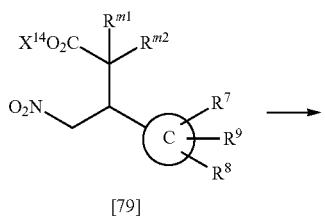

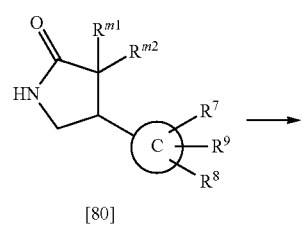

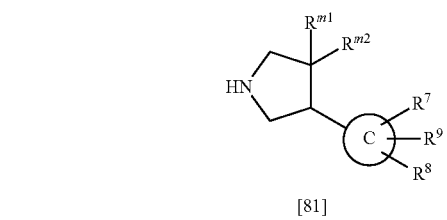

Among the compounds [j] used in Synthesis Method B described above, a compound represented by general formula [77] (wherein the symbols have the same meanings as those described above) can be produced as follows, for example.

By protecting a lactam group of a compound represented by general formula [73] (wherein the symbols have the same meanings as those described above), a compound represented by general formula [74] (wherein $X^{30}$ represents a lactam-protecting group, and the other symbols have the same meanings as those described above) can be obtained.

A compound represented by general formula [75] (wherein the symbols have the same meanings as those described above) can be obtained by fluorinating the compound [74].

A compound represented by general formula [76] (wherein the symbols have the same meanings as those described above) can be obtained by removing the lactam-protecting group of the obtained compound [75].

The compound [77] can be obtained by subjecting the compound [76] to a reductive reaction.

The lactam-protecting group represented by $X^{30}$ may be a t-butoxycarbonyl group, for example.

The reaction of introducing the lactam-protecting group into the compound [73] can be performed in accordance with a conventional method, in an appropriate solvent in the presence of a donor of the lactam-protecting group. The solvent may be any that does not hinder the reaction, and examples of such solvents include a nitrile such as acetonitrile, a halogenated aliphatic hydrocarbon such as methylene chloride, an aromatic hydrocarbon such as toluene, an ether such as tetrahydrofuran, and mixtures thereof. The protecting group donor may be di-t-butyl dicarbonate, for example. In this reaction, a reaction adjuvant may be added to accelerate the reaction. The reaction adjuvant may be 4-dimethylaminopyridine, for example.

The fluorination reaction of the compound [74] can be performed in accordance with a conventional method, in an appropriate solvent in the presence of a fluorinating agent and a base, for example. The solvent may be any that does not hinder the reaction, and examples of such solvents include an ether such as tetrahydrofuran, a halogenated aliphatic hydrocarbon such as methylene chloride, and mixtures thereof. The fluorinating agent may be N-fluorobenzenesulfonimide, for example. The base may be lithium bis(trimethylsilyl)amide, for example.

The reaction of removing the amino-protecting group of the compound [75] can be performed as in the reaction of removing the amino-protecting group of the compound [2] in Intermediate Production Method a described above.

The reduction reaction of the compound [76] can be performed as in the reduction reaction of the compound [6] in Intermediate Production Method b-1.

Among the compounds [j] used in Synthesis Method B described above, a compound represented by general formula [81] (wherein $R^{m1}$ and $R^{m2}$ each independently represent an alkyl or alkoxyalkyl group) can be produced as follows, for example.

A compound represented by general formula [79] (wherein the symbols have the same meanings as those described above) can be obtained by subjecting the compound represented by general formula [25] (wherein the symbols have the same meanings as those described above) to an addition reaction with a compound represented by general formula [78] (wherein the symbols have the same meanings as those described above).

A compound represented by general formula [80] (wherein the symbols have the same meanings as those described above) can be obtained by subjecting the compound [79] to a reduction reaction and a ring closure reaction.

The compound represented by general formula [81] (wherein the symbols have the same meanings as those described above) can be obtained by subjecting the obtained compound [80] to a reduction reaction.

The addition reaction of the compound [25] with the compound [78] can be performed in accordance with a conventional method, in an appropriate solvent in the presence of an alkylating agent and a base, for example. The solvent may be any that does not hinder the reaction, and examples of such solvents include an ether such as tetrahydrofuran, an aliphatic hydrocarbon such as hexane, and mixtures thereof. The alkylating agent may be ethyl isobutyrate, for example. The base may be lithium diisopropylamide, for example.

The reduction reaction and ring closure reaction of the compound [79] can be performed as in the ring closure reaction of the compound [5] in Intermediate Production Method b-1 described above.

The reduction reaction of the compound [80] can be performed as in the reduction reaction of the compound [6] in Intermediate Production Method b-1 described above.

Intermediate Production Method n

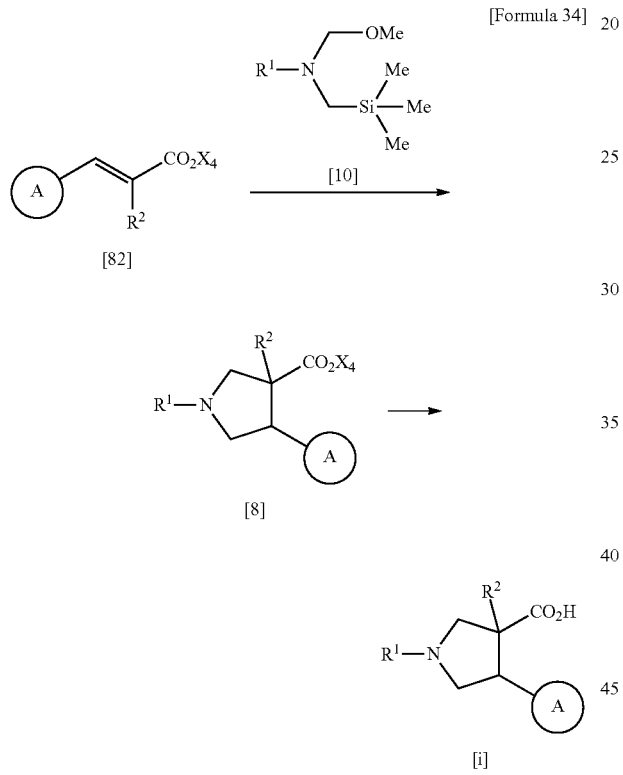

The compound [i] used in Synthesis Method B described above can also be produced as follows, for example.

The compound represented by general formula [8] (wherein the symbols have the same meanings as those described above) can be obtained by reacting a compound represented by general formula [82] (wherein the symbols have the same meanings as those described above) with the compound represented by general formula [10] (wherein the symbol has the same meaning as that described above).

The compound [i] can be obtained by removing the carboxyl-protecting group of the obtained compound [8].

The reaction of the compound [82] with the compound [10] can be performed as in the reaction of the compound [9] with the compound [10] in Intermediate Production Method b-2 described above.

The reaction of removing the carboxyl-protecting group from the compound [8] to form the compound [i] can be performed as in the reaction from the compound [8] into the compound [i] in Intermediate Production Method b-1 described above.

Intermediate Production Method o

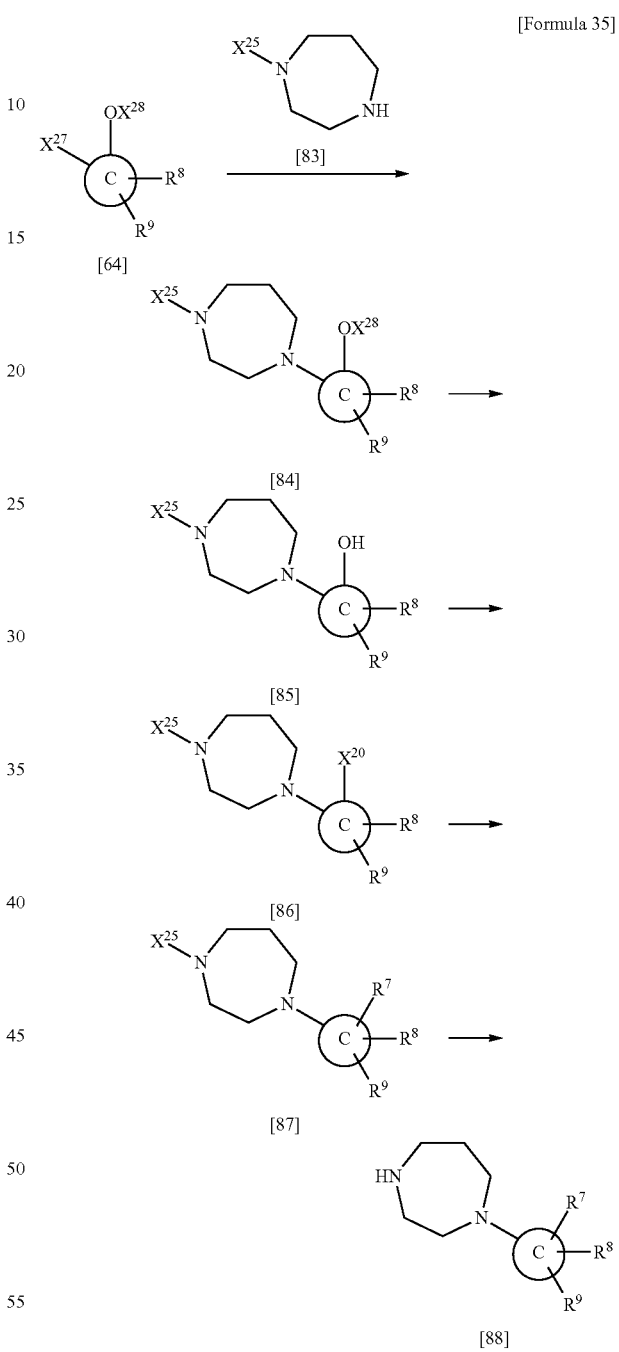

Among the compounds [j] used in Synthesis Method B described above, a compound represented by general formula [88] (wherein the symbols have the same meanings as those described above) can be produced as follows, for example.

A compound represented by general formula [84] (wherein the symbols have the same meanings as those described above) can be obtained by subjecting the compound represented by general formula [64] (wherein the symbols have the same meanings as those described above) to a coupling reaction with a compound represented by general formula [83] (wherein the symbol has the same meaning as that described above).

A compound represented by general formula [85] (wherein the symbols have the same meanings as those described above) can be obtained by removing the hydroxy-protecting group of the obtained compound [84].

A compound represented by general formula [86] (wherein the symbols have the same meanings as those described above) can be obtained by converting the hydroxy group of the obtained compound [85] into a leaving group (e.g., a trifluoromethanesulfonyloxy group).

A compound represented by general formula [87] (wherein the symbols have the same meanings as those described above) can be obtained by reacting the obtained compound [86] with a desired boronic acid compound or an ester thereof.

The compound represented by general formula [88] (wherein the symbols have the same meanings as those described above) can be obtained by removing the amino-protecting group of the obtained compound [87].

The coupling reaction of the compound [64] with the compound [83] can be performed as in the reaction from the compound [a] into the compound [Ic] in Synthesis Method A-3 described above.

The reaction of converting the compound [84] into the compound [85] can be performed in accordance with a conventional method, for example, in an appropriate solvent in the presence of hydrogen and a palladium catalyst. The solvent may be any that does not hinder the reaction, and examples of such solvents include an ether such as tetrahydrofuran, an alcohol such as methanol, an ester such as ethyl acetate, and mixtures thereof. The palladium catalyst may be a palladium catalyst supported on activated carbon, for example.

The reaction of converting the compound [85] into the compound [86] can be performed in accordance with a conventional method, for example, by reaction with an acid anhydride in an appropriate solvent in the presence of a base. The solvent may be any that does not hinder the reaction, and examples of such solvents include an ether such as tetrahydrofuran, a halogenated aliphatic hydrocarbon such as methylene chloride, a nitrile such as acetonitrile, an aromatic hydrocarbon such as toluene, and mixtures thereof. Examples of bases include an amine such as diisopropylethylamine and an alkali metal carbonate such as potassium carbonate. The acid anhydride may be trifluoromethanesulfonic anhydride.

The step of converting the compound [86] into the compound [87] can be performed in accordance with a conventional method, for example, by reaction with a desired boronic acid compound or an ester thereof in an appropriate solvent in the presence of a palladium catalyst and a base. The solvent may be any that does not hinder the reaction, and examples of such solvents include an ether such as 1,4-dioxane, an amide such as N,N-dimethylformamide, an aromatic hydrocarbon such as toluene, an alcohol such as t-butanol, and mixtures thereof. The palladium catalyst may be dichloro[1,1'-bis(diphenylphosphino)ferrocene]palladium (II) dichloromethane adduct, for example. The base may be sodium carbonate or potassium acetate, for example.

The reaction of removing the amino-protecting group of the compound [87] can be performed as in the reaction of removing the amino-protecting group of the compound [2] in Intermediate Production Method a described above.

Intermediate Production Method p

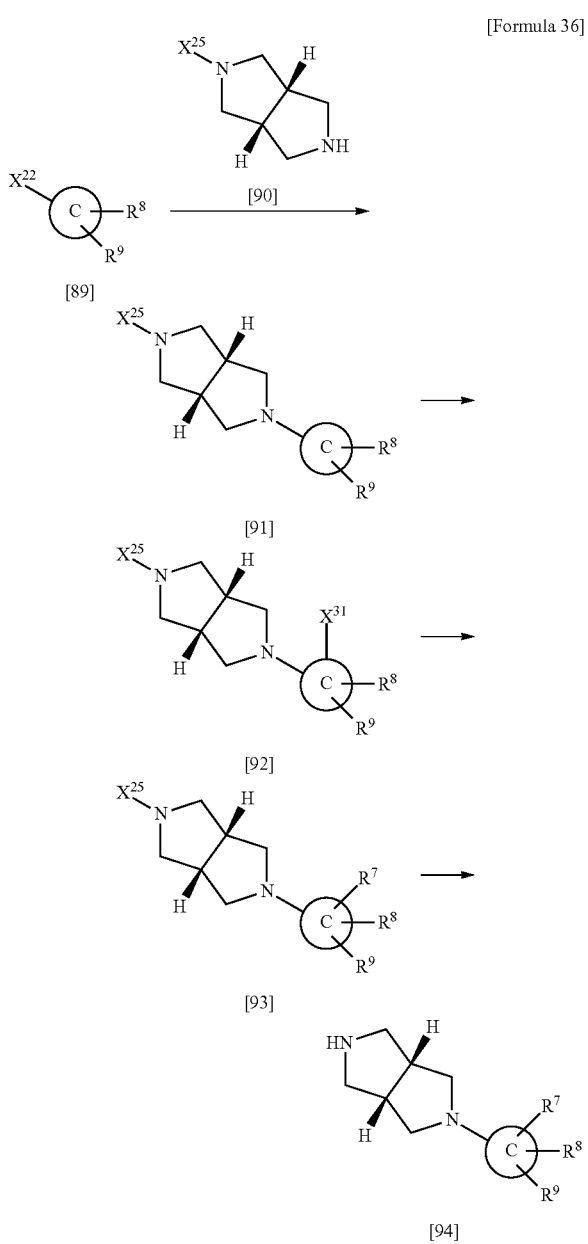

[Formula 36]

Among the compounds [j] used in Synthesis Method B described above, a compound represented by general formula [94] (wherein the symbols have the same meanings as those described above) can be produced as follows, for example.

A compound represented by general formula [91] (wherein the symbols have the same meanings as those described above) can be obtained by subjecting a compound represented by general formula [89] (wherein the symbols have the same meanings as those described above) to a coupling reaction with a compound represented by general formula [90] (wherein the symbol has the same meaning as that described above).

A compound represented by general formula [92] (wherein $X^{31}$ represents a halogen atom, and the other symbols have the same meanings as those described above) can be obtained by halogenating the obtained compound [91].

A compound represented by general formula [93] (wherein the symbols have the same meanings as those described above) can be obtained by reacting the obtained compound [92] with a desired boronic acid compound or an ester thereof.

The compound represented by general formula [94] (wherein the symbols have the same meanings as those described above) can be obtained by removing the amino-protecting group of the obtained compound [93].

The coupling reaction of the compound [89] with the compound [90] can be performed as in the reaction from the compound [a] into the compound [Ic] in Synthesis Method A-3 described above.

The halogenation reaction of the compound [91] into the compound [92] can be performed in accordance with a conventional method, by reaction with a halogenating agent in an appropriate solvent. The solvent may be any that does not hinder the reaction, and examples of such solvents include an ether such as tetrahydrofuran, an alcohol such as methanol, a halogenated aliphatic hydrocarbon such as chloroform, and mixtures thereof. The halogenating agent may be N-bromosuccinimide, for example.

The reaction of converting the compound [92] into the compound [93] by reaction with a desired boronic acid compound or an ester thereof can be performed as in the reaction from the compound [86] into the compound [87] in Intermediate Production Method o described above.

The reaction of removing the amino-protecting group of the compound [93] can be performed as in the reaction of removing the amino-protecting group of the compound [2] in Intermediate Production Method a described above.

Intermediate Production Method q

[Formula 37]

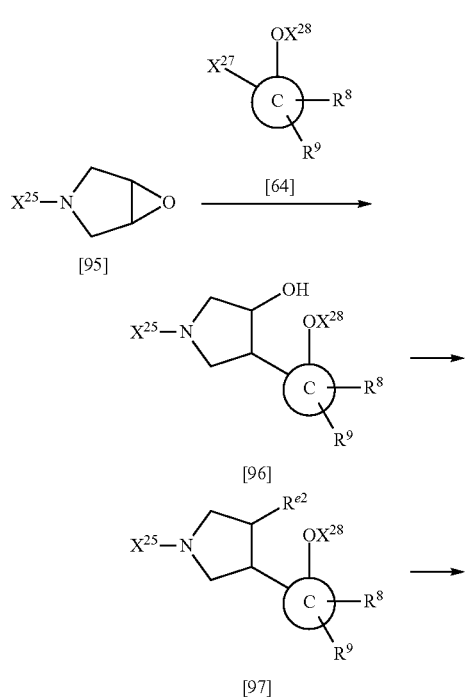

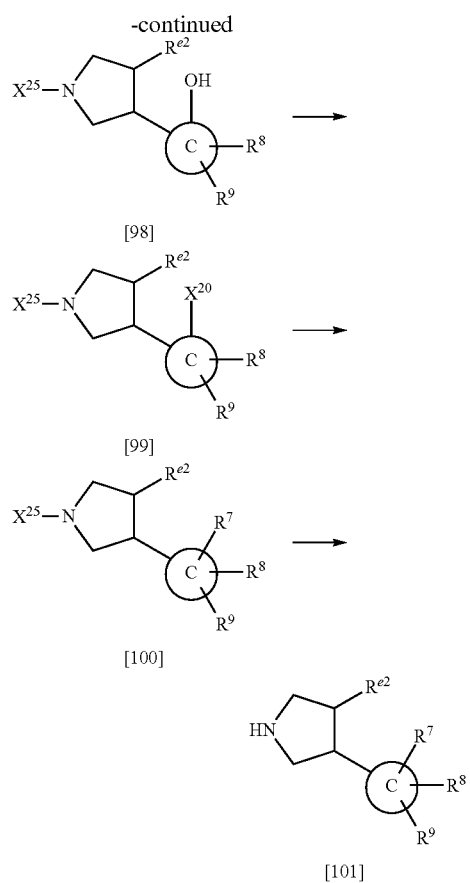

Among the compounds [j] used in Synthesis Method B described above, a compound represented by general formula [101] (wherein the symbols have the same meanings as those described above) can be produced as follows, for example.

A compound represented by general formula [96] (wherein the symbols have the same meanings as those described above) can be obtained by reacting a compound represented by general formula [95] (wherein the symbol has the same meaning as that described above) with the compound represented by general formula [64] (wherein the symbols have the same meanings as those described above).

A compound represented by general formula [97] (wherein the symbols have the same meanings as those described above) can be obtained by converting the hydroxy group of the obtained compound [96].

A compound represented by general formula [98] (wherein the symbols have the same meanings as those described above) can be obtained by removing the hydroxy-protecting group of the obtained compound [97].

A compound represented by general formula [99] (wherein the symbols have the same meanings as those described above) can be obtained by converting the hydroxy group of the obtained compound [98] into a leaving group.

A compound represented by general formula [100] (wherein the symbols have the same meanings as those described above) can be obtained by reacting the obtained compound [99] with a desired boronic acid compound or an ester thereof.

The compound represented by general formula [101] (wherein the symbols have the same meanings as those described above) can be obtained by removing the amino-protecting group of the obtained compound [100].

The reaction of the compound [95] with the compound [64] can be performed in an appropriate solvent in the presence of a metallizing reagent. The solvent may be any that does not hinder the reaction, and examples of such solvents include an ether such as tetrahydrofuran, an aliphatic hydrocarbon such as hexane, and mixtures thereof. The metallizing reagent may be isopropylmagnesium bromide, for example. In this reaction, a reaction adjuvant can be added to accelerate the reaction. The reaction adjuvant may be copper iodide, for example.

The reaction of converting the compound [96] into the compound [97] can be performed as in the reaction of converting the compound [30] into the compound [31] in Intermediate Production Method e-1 described above.

The reaction of converting the compound [97] into the compound [98] can be performed as in the reaction from the compound [84] into the compound [85] in Intermediate Production Method o described above.

The reaction of converting the compound [98] into the compound [99] can be performed as in the reaction from the compound [85] into the compound [86] in Intermediate Production Method o described above.

The reaction of converting the compound [99] into the compound [100] can be performed as in the reaction from the compound [86] into the compound [87] in Intermediate Production Method o described above.

The reaction of removing the amino-protecting group of the compound [100] can be performed as in the reaction of removing the amino-protecting group of the compound [2] in Intermediate Production Method a described above.

Intermediate Production Method r

[Formula 38]

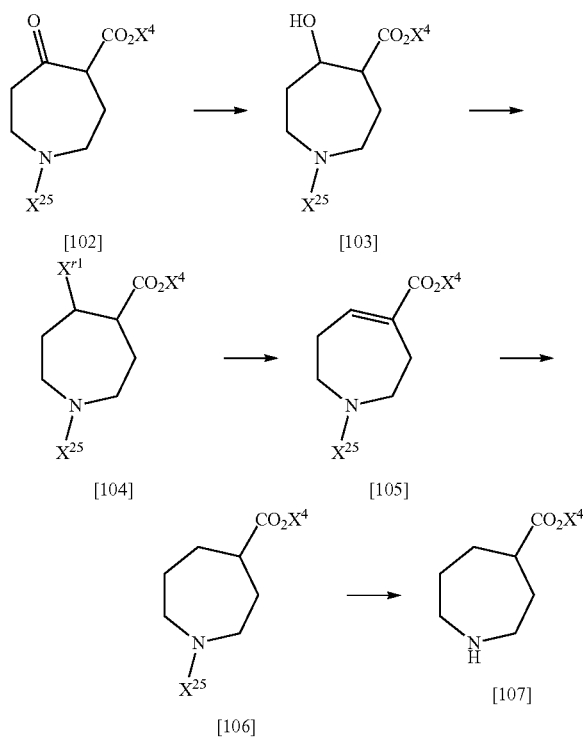

A raw material for Example 340 can be produced as follows in accordance with the scheme shown above, for example.

A compound represented by general formula [103] (wherein the symbols have the same meanings as those described above) can be obtained by subjecting a compound [102] (wherein the symbols have the same meanings as those described above) to a reduction reaction.

A compound represented by general formula [104] (wherein $X^{r1}$ represents a leaving group, and the other symbols have the same meanings as those described above) can be obtained by converting the obtained compound [103].

A compound represented by general formula [105] (wherein the symbols have the same meanings as those described above) can be obtained by converting the obtained compound [104].

A compound represented by general formula [106] (wherein the symbols have the same meanings as those described above) can be obtained by subjecting the obtained compound [105] to a reduction reaction.

A compound represented by general formula [107] (wherein the symbol has the same meaning as that described above) can be obtained by removing the amino-protecting group of the obtained compound [106].

The leaving group represented by $X^{r1}$ may be a methylsulfonyloxy group, for example.

The reduction reaction of the compound [102] can be performed in accordance with a conventional method, by reaction with a reducing agent in an appropriate solvent. The solvent may be any that does not hinder the reaction, and examples of such solvents include an ether such as tetrahydrofuran, an alcohol such as methanol, water, and mixtures thereof. The reducing agent may be sodium borohydride, for example.

The reaction of converting the compound [103] into the compound [104] can be performed in an appropriate solvent in the presence of a sulfonylating agent and a base. The solvent may be any that does not hinder the reaction, and examples of such solvents include an ether such as tetrahydrofuran, a nitrile such as acetonitrile, a halogenated aliphatic hydrocarbon such as methylene chloride, and mixtures thereof. The sulfonylating agent may be methanesulfonyl chloride, for example. The base may be diisopropylethylamine, for example.

The reaction of converting the compound [104] into the compound [105] can be performed by heating in an appropriate solvent in the presence of a base. The solvent may be any that does not hinder the reaction, and examples of such solvents include an ether such as tetrahydrofuran, a nitrile such as acetonitrile, a halogenated aliphatic hydrocarbon such as methylene chloride, an aromatic hydrocarbon such as toluene, and mixtures thereof. The base may be 1,8-diazabicyclo[5.4.0]-7-undecene, for example.

The catalytic hydrogenation reaction of the compound [105] can be performed as in the catalytic hydrogenation reaction of the compound [18] in Intermediate Production Method c described above.

The reaction of removing the amino-protecting group of the compound [106] can be performed as in the reaction of removing the amino-protecting group of the compound [2] in Intermediate Production Method a described above.

Intermediate Production Method s

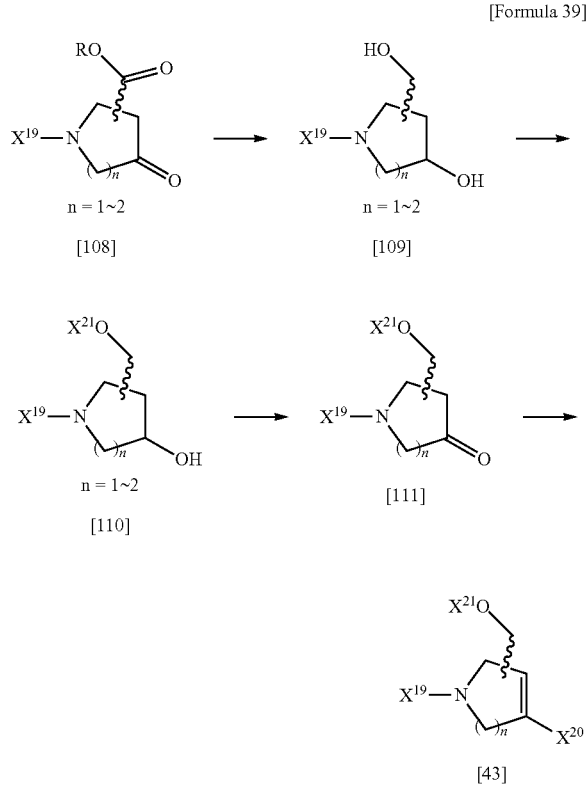

[Formula 39]

The compound represented by general formula [43] (wherein the symbols have the same meanings as those described above) in Intermediate Production Method f described above can be produced as follows, for example.

A compound represented by general formula [109] (wherein the symbols have the same meanings as those described above) can be obtained by subjecting a compound [108] (wherein the symbols have the same meanings as those described above) to a reduction reaction.

A compound represented by general formula [110] (wherein the symbols have the same meanings as those described above) can be obtained by converting the obtained compound [109].

A compound represented by general formula [111] (wherein the symbols have the same meanings as those described above) can be obtained by subjecting the obtained compound [110] to an oxidation reaction.

The compound represented by general formula [43] (wherein the symbols have the same meanings as those described above) can be obtained by converting the obtained compound [111].

The reduction reaction of the compound [108] can be performed in accordance with a conventional method, in an appropriate solvent in the presence of a reducing agent. The solvent may be any that does not hinder the reaction, and examples of such solvents include an ether such as tetrahydrofuran, an alcohol such as methanol, and mixtures thereof. The reducing agent may be sodium borohydride or lithium borohydride, for example.

The reaction of converting the compound [109] into the compound [110] can be performed in accordance with a conventional method, depending on the type of the protecting group. For example, the conversion into a compound having a trialkylsilyl group as $X^{21}$ can be performed in an appropriate solvent in the presence of a silylating agent and a base. The solvent may be any that does not hinder the reaction, and examples of such solvents include a halogenated aliphatic hydrocarbon such as methylene chloride, a nitrile such as acetonitrile, an amide such as N,N-dimethylformamide, an ether such as tetrahydrofuran, and mixtures thereof. The silylating agent may be t-butyldimethylsilyl chloride, for example.

The oxidation reaction of the compound [110] can be performed in accordance with a conventional method, in an appropriate solvent in the presence of a radical reaction agent and an oxidizing agent. The solvent may be any that does not hinder the reaction, and examples of such solvents include a halogenated aliphatic hydrocarbon such as methylene chloride, a nitrile such as acetonitrile, water, and mixtures thereof. The radical reaction agent may be 2,2,6,6-tetramethylpiperidin-1-oxyl, for example. The oxidizing agent may be trichloroisocyanuric acid or meta-chlorobenzoic acid, for example.

The reaction of converting the compound [111] into the compound [43] can be performed in an appropriate solvent in the presence of a sulfonylating agent and a base. The solvent may be any that does not hinder the reaction, and examples of such solvents include an ether such as tetrahydrofuran, an aromatic hydrocarbon such as toluene, and mixtures thereof. The sulfonylating agent may be N-phenylbis(trifluoromethanesulfonimide), for example. The base may be sodium bis(trimethylsilyl)amide, for example.

Intermediate Production Method t

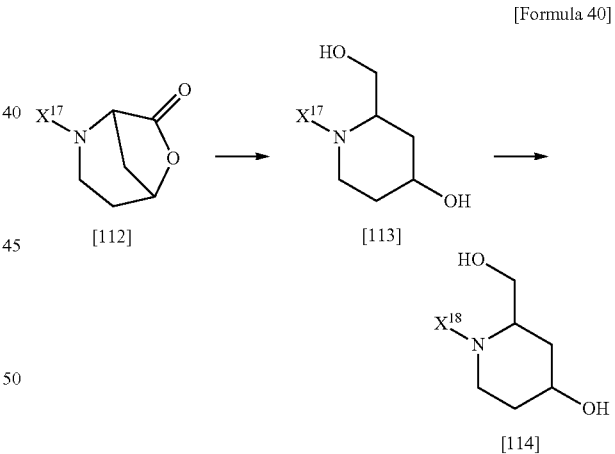

[Formula 40]

Among the compounds represented by general formula [109] in Intermediate Production Method s described above, a compound represented by general formula [114] (wherein the symbol has the same meaning as that described above) can be produced as follows, for example.

A compound represented by general formula [113] (wherein the symbol has the same meaning as that described above) can be obtained by subjecting a compound represented by general formula [112] (wherein the symbol has the same meaning as that described above) to a reduction reaction.

The compound represented by general formula [114] (wherein the symbol has the same meaning as that described above) can be obtained by converting the amino-protecting group of the obtained compound [113].

The reduction reaction of the compound [112] can be performed in accordance with a conventional method, in an appropriate solvent in the presence of a reducing agent. The solvent may be any that does not hinder the reaction, and examples of such solvents include an ether such as tetrahydrofuran, an alcohol such as methanol, and mixtures thereof. The reducing agent may be sodium borohydride or lithium borohydride, for example.

The reaction of converting the compound [113] into the compound [114] can be performed as in the reaction of converting the compound [13] into the compound [14] in Intermediate Production Method b-3 described above.

Intermediate Production Method u

[Formula 41]

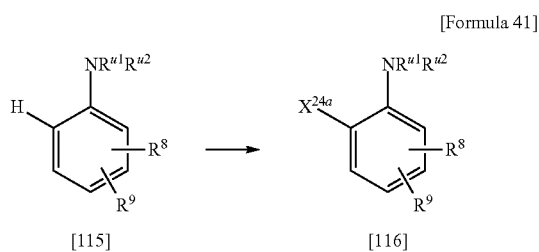

Among the compounds represented by [53] in Intermediate Production Method g described above, a compound represented by general formula [116] (wherein $X^{24a}$ represents a halogen atom; $R^{u1}$ is an optionally substituted alkyl group, and $R^{u2}$ is a hydrogen atom or an alkyl group, or $R^{u1}$ and $R^{u2}$ are terminally attached to each other, and together with the nitrogen atom to which they are attached, form an optionally substituted nitrogen-containing aliphatic heterocyclic ring; and the other symbols have the same meanings as those described above) can be produced as follows, for example.

The compound represented by general formula [116] (wherein the symbols have the same meanings as those described above) can be obtained by halogenating a compound represented by general formula [115] (wherein the symbols have the same meanings as those described above).

The halogenation reaction of the compound [115] can be performed in accordance with a conventional method, by reaction with a halogenating agent in an appropriate solvent. The solvent may be any that does not hinder the reaction, and examples of such solvents include an ether such as tetrahydrofuran, an alcohol such as methanol, a halogenated aliphatic hydrocarbon such as chloroform, and mixtures thereof. The halogenating agent may be N-bromosuccinimide, for example.

The raw material compounds for use in the above-described methods can be produced as in existing methods and/or methods described later in the Examples.

Note that the introduction of protective groups into functional groups and the removal of functional group-protecting groups can be performed with reference to existing methods (e.g., "PROTECTIVE GROUPS in ORGANIC SYNTHESIS" (by Theodora W. Greene and Peter G. M. Wuts)).

Moreover, the compounds of the present invention and intermediate compounds produced using the above-described methods can be further structurally converted into other target compounds or intermediates, using methods described later in the Examples and/or existing methods, or combinations thereof. Specific examples include the following methods.

(1) Conversion of an Alkoxycarbonyl Group or the Like into a Carboxyl Group

An alkoxycarbonyl group can be converted into a corresponding carboxyl group by hydrolysis with an alkali metal hydroxide base such as sodium hydroxide or potassium hydroxide; a benzyloxycarbonyl group can be converted into a corresponding carboxyl group by hydrogenolysis through treatment with palladium carbon in a hydrogen atmosphere; or a t-butoxycarbonyl group can be converted into a corresponding carboxyl group by treatment with an acid such as hydrochloric acid or trifluoroacetic acid.

(2) Conversion of a Carboxyl Group into a Carbamoyl Group

A carboxyl group can be converted into a corresponding carbamoyl group, for example, by reacting the carboxyl group or a salt thereof with an amine in the presence of a condensing agent, or by converting the carboxyl group or a salt thereof into an acyl halide, and then reacting the resulting product with an amine.

(3) Conversion of a Cyano Group into a Tetrazolyl Group

A cyano group can be converted into a corresponding tetrazolyl group by reacting the cyano group with tributyltin azide.

(4) Conversion of a Cyano Group into an Oxadiazolyl Group

A cyano group can be converted into a corresponding oxadiazolyl group by reacting the cyano group with hydroxylamine hydrochloride in the presence of a base, for example, and then reacting the reaction product with 1,1'-carbonyldiimidazole.

(5) Conversion of an Amino Group into a Carbamoylamino Group

An amino group can be converted into a corresponding carbamoylamino group by reacting the amino group with a desired isocyanate, or by reacting the amino group with a desired carbamoyl halide.

(6) Conversion of an Amino Group into a Sulfonylamino Group

An amino group can be converted into a corresponding sulfonylamino group by reacting the amino group with a desired sulfonyl halide.

(7) Conversion of an Amino Group into an Aminosulfonylamino Group

An amino group can be converted into a corresponding aminosulfonylamino group by reacting the amino group with a desired aminosulfonyl halide.

(8) Conversion of a Hydroxy Group into a Halogen Atom

A hydroxy group can be converted into a corresponding halogen atom by reacting the hydroxy group with a fluorinating agent such as (diethylamino)sulfur trifluoride or a chlorinating agent such as thionyl chloride, for example.

(9) Conversion of a Hydroxy Group into a Cyano Group

A hydroxy group can be converted into a corresponding cyano group by reacting the hydroxy group with acetone cyanohydrin, for example.

(10) Conversion of a Hydroxy Group into an Alkoxy Group

A hydroxy group can be converted into a corresponding alkoxy group by reacting the hydroxy group with a desired alkylating agent in the presence of a base. Alternatively, a hydroxy group can be converted into a corresponding alkoxy group by reacting the hydroxy group with a desired alcohol in the presence of diethyl azodicarboxylate.

(11) Conversion of a Hydroxy Group into an Aryl Group

A hydroxy group can be converted into a corresponding aryl group by converting the hydroxy group into a leaving group (e.g., a trifluoromethylsulfonyloxy group) in accordance with a conventional method, and then coupling the resulting product with a desired aryl halide or the like.

(12) Conversion of a Formyl Group into a Hydroxymethyl Group

A formyl group can be converted into a hydroxymethyl group by reducing the formyl group with sodium borohydride or the like.

(13) Conversion of a Halogen Atom into a Cycloalkyl Group

A halogen atom can be converted into a corresponding cycloalkyl group by coupling a compound having a halogen atom with a cycloalkylboronic acid or a cycloalkenyl boronic ester, for example, followed by reduction with hydrogen and palladium carbon, for example. Alternatively, a halogen atom can be converted into a corresponding cycloalkyl group by reacting a compound having a halogen atom with alkyl lithium or the like, and reacting the reaction product with a corresponding cycloalkanone or the like, and then reducing the produced hydroxy group with a trialkylsilane or the like in the presence of an acid.

(14) Conversion of a Carbonyl Group into an Amino Group

A carbonyl group can be converted into an amino group by reacting the carbonyl group with a desired amine in the presence of a reducing agent.

(15) Conversion of a Halogen Atom into an Alkyl Group

A halogen atom can be converted into a corresponding alkyl group by coupling a compound having a halogen atom with an alkylboronic acid derivative or an alkenyl boronic acid derivative, for example, followed by reduction with hydrogen and palladium carbon, for example. Alternatively, a halogen atom can be converted into a corresponding alkyl group by reacting a compound having a halogen atom with alkyl lithium or the like, and reacting the reaction product with a corresponding alkanone or the like, and then reducing the produced hydroxy group with a trialkylsilane or the like in the presence of an acid.

(16) Conversion of a Formyl Group into an Alkyl Dihalide Group

A formyl group can be converted into a corresponding alkyl dihalide group by reacting the formyl group with a fluorinating agent such as bis(2-methoxyethyl)aminosulfur trifluoride, for example.

(17) Conversion of a Sulfide Group into a Sulfonyl Group

A sulfide group can be converted into a corresponding sulfonyl group by reacting the sulfide group with an oxidizing agent such as Oxone, for example.

(18) Conversion of a Hydroxymethyl Group into a Carboxyl Group

A hydroxyalkyl group can be converted into a corresponding carboxyl group by reacting the hydroxyalkyl group with an oxidizing agent.

(19) Conversion of a Hydroxy Group into a Cycloalkyl Group

A hydroxy group can be converted into a corresponding cycloalkyl group by converting the hydroxy group into a leaving group (e.g., a trifluoromethylsulfonyloxy group), coupling the resulting product with a cycloalkenylboronic acid derivative or the like, and then reducing the alkenyl group with hydrogen and palladium carbon, for example.

(20) Conversion of a Carbamoyl Group into a Cyano Group

A carbamoyl group can be converted into a corresponding cyano group by reacting the carbamoyl group with a dehydrating agent such as cyanuric chloride, for example.

(21) Conversion of an Alkoxycarbonylalkynyl Group into a 3-Hydroxyisoxazolyl Group An alkoxycarbonylalkynyl group can be converted into a corresponding 3-hydroxyisoxazolyl group by reacting the alkoxycarbonylalkynyl group with hydroxylamine hydrochloride in the presence of a base.

(22) Conversion of a Carbonyl Group into a Hydroxy Group

A carbonyl group can be converted into a hydroxy group by reducing the carbonyl group with sodium borohydride or the like.

(23) Conversion of a Carboxyl Group into a Hydroxymethyl Group

A carboxyl group can be converted into a hydroxymethyl group by activating the carboxyl group with isobutyl chloroformate or the like, and then reducing the resulting product with sodium borohydride or the like. Alternatively, a carboxyl group can be converted into a hydroxymethyl group by reducing the carboxyl group with lithium aluminum hydride or the like.

(24) Conversion of an Alkenylene Group into an Alkylene Group

An alkenylene group can be converted into a corresponding alkylene group by reducing the alkenylene group with hydrogen and palladium carbon, for example.

(25) Conversion of a Cyano Group into a Formyl Group

A cyano group can be converted into a corresponding formyl group by reacting the cyano group with a reducing agent such as diisobutylaluminum hydride, for example.

(26) Conversion of Acetal into an Alkoxy Group

Acetal can be converted into a corresponding alkoxy group by reacting acetal with borane in the presence of trimethylsilyl trifluoromethanesulfonate, for example.

(27) Conversion of a Halogen Atom into an Alkenyl Group

A halogen atom can be converted into a corresponding alkenyl group by coupling a compound having a halogen atom with a compound having an alkenyl group such as an alkenyl carboxylic acid derivative or an alkenylboronic acid derivative, for example.

(28) Conversion of a Halogen Atom into an Aryl Group

A halogen atom can be converted into a corresponding aryl group by coupling a compound having a halogen atom with an arylboronic acid, for example.

(29) Conversion of a Formyl Group into an Alkoxycarbonylalkenyl Group

A formyl group can be converted into a corresponding alkoxycarbonylalkenyl group by reacting the formyl group with a desired (alkoxycarbonylmethylene)triphenylphosphorane or a desired trialkyl phosphonoacetate.

The compounds of the present invention produced as described above or raw material compounds thereof are isolated and purified either in their free form or in the form of their salts. Salts can be produced by subjecting the compounds to a salt-formation treatment that is commonly used. Isolation and purification can be performed through application of common chemical operations such as extraction, concentration, crystallization, filtration, recrystallization, and various types of chromatography.

Where any of the compounds of the present invention or a pharmaceutically acceptable salt thereof exists as an optical isomer based on asymmetric carbon, the compound can be separated into the individual optical isomers using a common means for optical resolution (e.g., a fractional crystallization method or a resolution method using a chiral column). Moreover, optical isomers can be synthesized using optically pure starting materials. Optical isomers can also be synthesized by stereoselectively performing each of the reactions using an asymmetric auxiliary group or an asymmetric catalyst.

EXAMPLES

Example 1

[Chemical Formula 42]

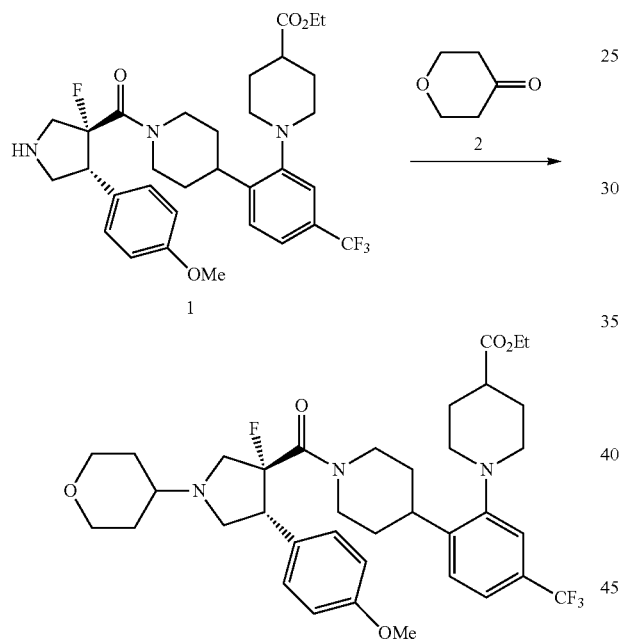

To a solution of Compound 1 (142 mg) and Compound 2 (26 µL) in dichloromethane (2 mL) was added acetic acid (20 µL), the mixture was stirred at room temperature for 10 minutes, sodium triacetoxyborohydride (74 mg) was added thereto, and stirred for 16 hours. To the mixture were added a saturated aqueous solution of sodium hydrogen carbonate and water, stirred, and then extracted with dichloromethane. The resultant organic layer was washed with saturated saline, dried, and concentrated under reduced pressure. The residue was purified with NH silica gel column chromatography (hexane:ethyl acetate=80:20-50:50) to give ethyl 1-[2-(1-{[(3R,4R)-3-fluoro-4-(4-methoxyphenyl)-1-(tetrahydro-2H-pyran-4-yl)pyrrolidin-3-yl]carbonyl}piperidin-4-yl)-5-(trifluoromethyl)phenyl]piperidine-4-carboxylate 3 (154 mg) as a colorless powder. MS (ESI): m/z 690 [M+H]+

Example 2

[Chemical Formula 43]

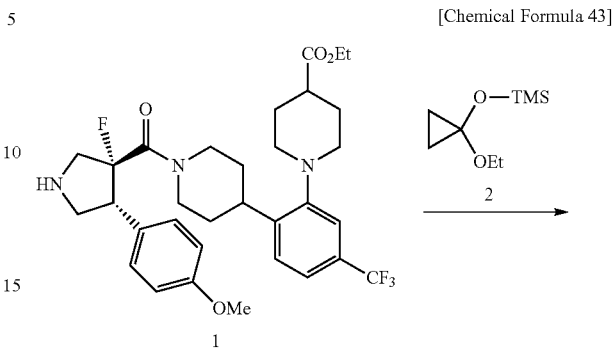

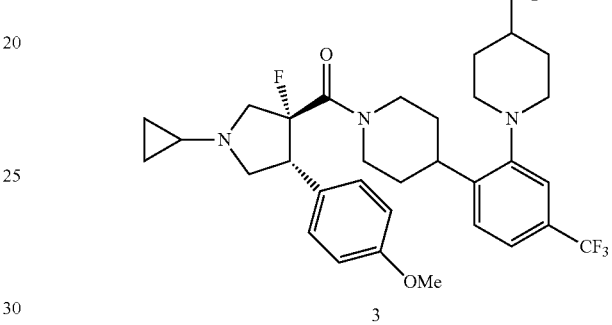

To a solution of Compound 1 (80 mg) and Compound 2 (528 µL) in dichloromethane (2 mL) were added acetic acid (76 µL) and sodium triacetoxyborohydride (336 mg), and stirred and heated under reflux for 16 hours. To the mixture were added a saturated aqueous solution of sodium hydrogen carbonate and water, stirred, and then extracted with dichloromethane. The resultant organic layer was washed with saturated saline, dried, and concentrated under reduced pressure. The residue was purified with NH silica gel column chromatography (hexane:ethyl acetate=95:5-70:30) to give ethyl 1-[2-(1-{[(3R,4R)-1-cyclopropyl-3-fluoro-4-(4-methoxyphenyl)pyrrolidin-3-yl]carbonyl}piperidin-4-yl)-5-(trifluoromethyl)phenyl]piperidine-4-carboxylate 3 (29 mg) as a colorless powder. MS (APCI): m/z 646 [M+H]+

Example 3

[Chemical Formula 44]

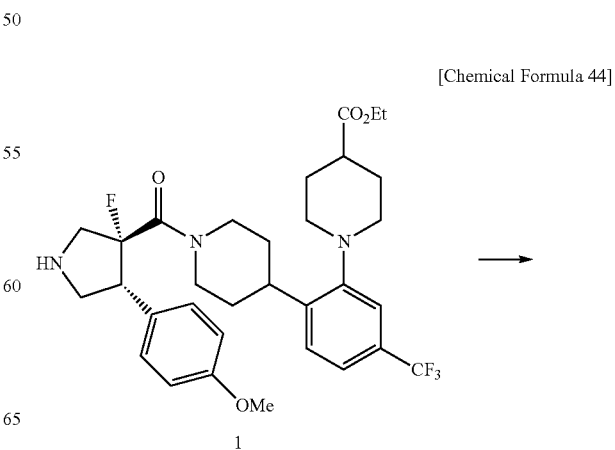

-continued

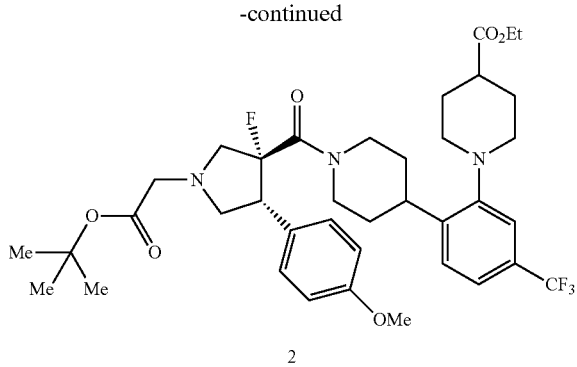

2

A suspension of Compound 1 (150 mg), t-butyl bromoacetate (44 μL), diisopropylethylamine (66 μL), and sodium iodide (19 mg) in acetonitrile (2 mL) was stirred under nitrogen atmosphere at 80° C. for 16 hours. The reaction mixture was cooled to room temperature, water was added thereto, stirred, and then extracted with dichloromethane. The resultant organic layer was washed with saturated saline, dried, and concentrated under reduced pressure. The residue was purified with NH silica gel column chromatography (hexane:ethyl acetate=85:25-60:40) to give ethyl 1-[2-(1-{[(3R,4R)-1-(2-tert-butoxy-2-oxoethyl)-3-fluoro-4-(4-methoxyphenyl)pyrrolidin-3-yl]carbonyl}piperidin-4-yl)-5-(trifluoromethyl)phenyl]piperidine-4-carboxylate 2 (159 mg) as a colorless powder. MS (ESI): m/z 720 [M+H]+

Example 4

[Chemical Formula 45]

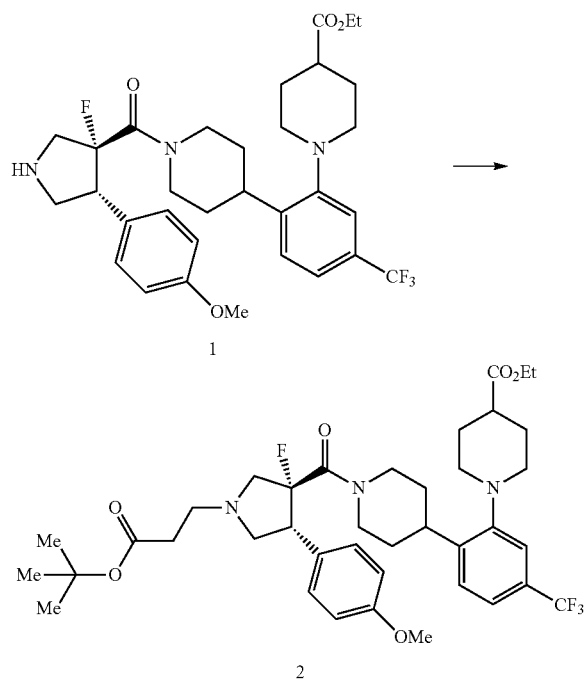

A mixed solution of Compound 1 (150 mg), t-butyl acrylate (44 μL), and triethylamine (53 μL) in ethanol (2 mL) was stirred at 80° C. for 16 hours. To the mixture were added t-butyl acrylate (88 μL) and triethylamine (106 μL), and stirred for additional for 4 hours. The reaction mixture was cooled to room temperature, water was added thereto, stirred, and then extracted with dichloromethane. The resultant organic layer was washed with saturated saline, dried, and concentrated under reduced pressure. The residue was purified with NH silica gel column chromatography (hexane:ethyl acetate=90:10-60:40) to give ethyl 1-[2-(1-{[(3R,4R)-1-(3-tert-butoxy-3-oxopropyl)-3-fluoro-4-(4-methoxyphenyl)pyrrolidin-3-yl]carbonyl}piperidin-4-yl)-5-(trifluoromethyl)phenyl]piperidine-4-carboxylate 2 (89 mg) as a colorless powder. MS (ESI): m/z 734 [M+H]+

Example 5

[Chemical Formula 46]

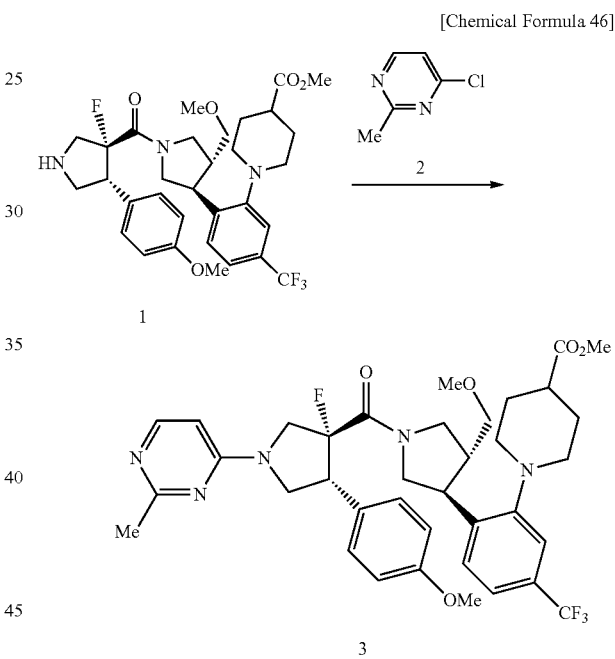

A mixed solution of Compound 1 (100 mg), Compound 2 (31 mg), tris(dibenzylideneacetone)dipalladium(0) (15 mg), (±)-2,2'-bis(diphenylphosphino)-1,1'-binaphthyl (20 mg), and t-butoxy sodium (46 mg) in toluene (2 mL) was stirred under nitrogen atmosphere at 110° C. for 21 hours. To the mixture was added Compound 2 (21 mg), and stirred for additional for 6 hours. The reaction mixture was cooled to room temperature, water was added thereto, stirred, and then extracted with ethyl acetate. The resultant organic layer was washed with saturated saline, dried, and concentrated under reduced pressure. The residue was purified with silica gel column chromatography (hexane:ethyl acetate=40:60-0:100) to give methyl 1-{2-[(3S,4R)-1-{[(3R,4R)-3-fluoro-4-(4-methoxyphenyl)-1-(2-methylpyrimidin-4-yl)pyrrolidin-3-yl]carbonyl}-4-(methoxymethyl)pyrrolidin-3-yl]-5-(trifluoromethyl)phenyl}piperidine-4-carboxylate 3 (36 mg) as a pale orange powder. MS (APCI): m/z 714 [M+H]+

Example 6

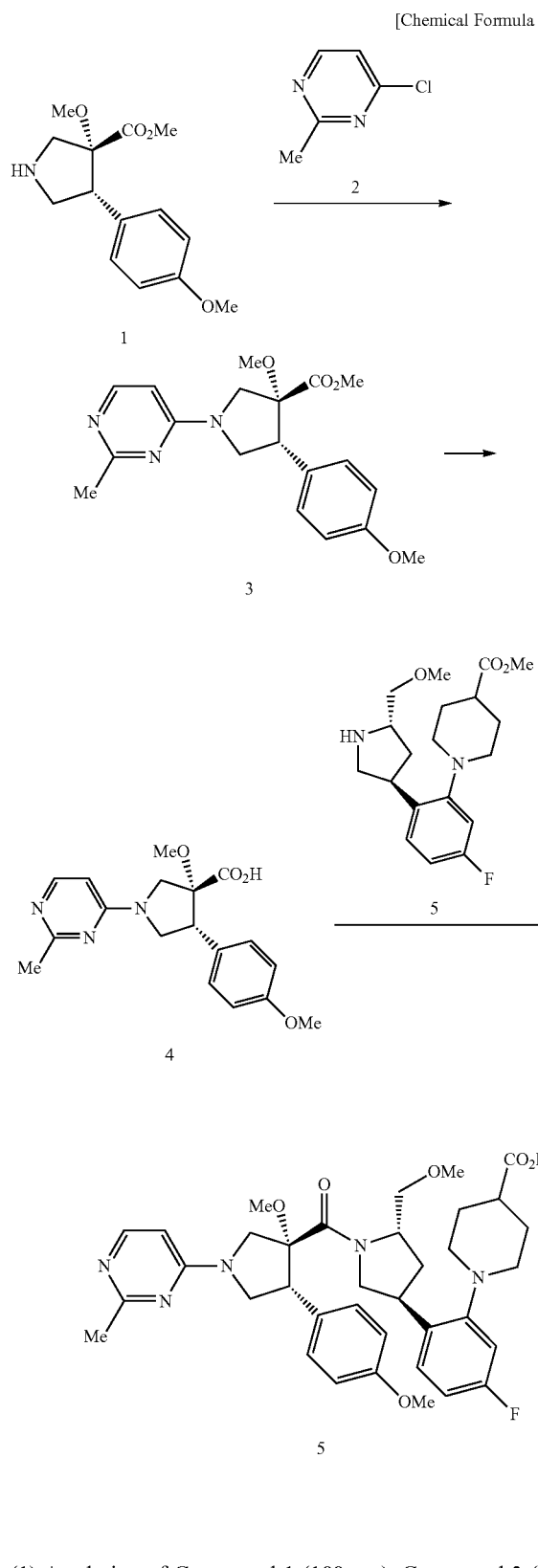

Example 7

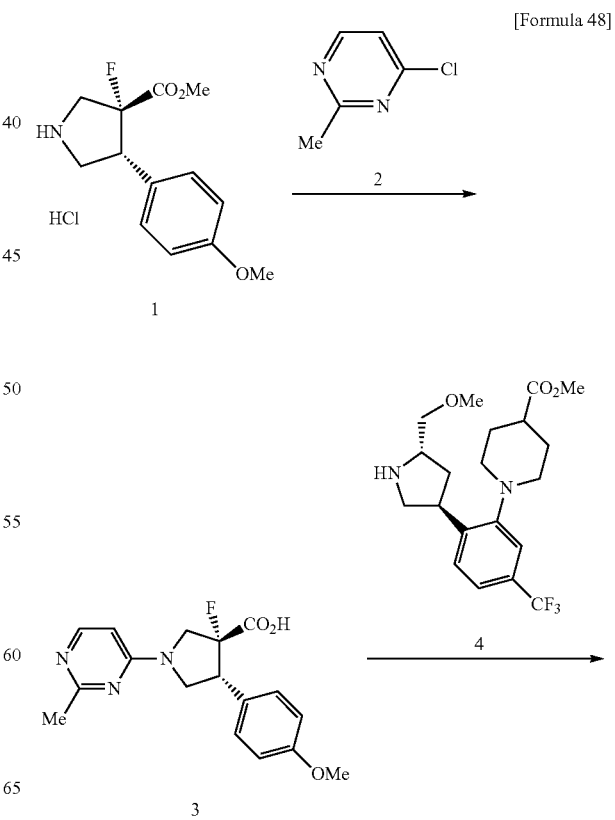

(1) A solution of Compound 1 (100 mg), Compound 2 (73 mg), and diisopropylethylamine (197 µL) in tetrahydrofuran (2 mL) was heated under reflux under nitrogen atmosphere for 4 hours. The reaction solution was concentrated under reduced pressure, and the residue was purified with NH silica gel column chromatography (hexane:ethyl acetate=80:20-50:50) to give Compound 3 (107 mg) as a colorless viscous material. MS (APCI): m/z 358 [M+H]+

(2) To a solution of Compound 3 (106 mg) in ethanol (2 mL) was added an aqueous solution of sodium hydroxide (2 mol/L, 297 µL) at room temperature, and the mixture was stirred at 70° C. for 6 hours. To the mixture was added an aqueous solution of hydrochloric acid (2 mol/L, 297 µL), and then the reaction solution was concentrated under reduced pressure to give Compound 4 as a colorless powder (138 mg) containing sodium chloride. MS (APCI): m/z 344 [M+H]+

(3) Compound 4 (65 mg), Compound 5 (50 mg), 1-ethyl-3-(3-dimethylaminopropyl)carbodiimide hydrochloride (55 mg), and 1-hydroxy-7-azabenzotriazole (39 mg) were added to N,N-dimethylformamide (2 mL), and the mixture was stirred at room temperature for 13 hours. To the mixture were added a saturated aqueous solution of sodium hydrogen carbonate and ethyl acetate, stirred, and then the organic layer was separated. The resultant organic layer was washed with saturated saline, dried, and concentrated under reduced pressure. The residue was purified with NH silica gel column chromatography (hexane:ethyl acetate=70:30-40:60) to give methyl 1-{5-fluoro-2-[(3S,5S)-1-{[(3R,4R)-3-methoxy-4-(4-methoxyphenyl)-1-(2-methylpyrimidin-4-yl)pyrrolidin-3-yl]carbonyl}-5-(methoxymethyl)pyrrolidin-3-yl]phenyl}piperidine-4-carboxylate 6 (64 mg) as a colorless powder. MS (APCI): m/z 676 [M+H]+

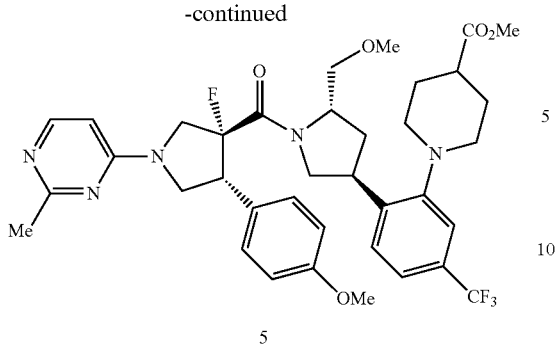

5

(1) To a mixture of Compound 1 (300 mg) in chloroform were added an aqueous solution of sodium hydroxide (1 mol/L, 1.03 mL) and water, stirred, and then extracted with chloroform. The resultant organic layer was dried, and concentrated under reduced pressure. A mixture of the residue, Compound 2 (333 mg), tris(dibenzylideneacetone) dipalladium(0) (95 mg), (±)-2,2'-bis(diphenylphosphino)-1, 1'-binaphthyl (129 mg), and t-butoxy sodium (299 mg) in toluene (4 mL) was stirred under nitrogen atmosphere at 100° C. for 15 hours. The reaction mixture was cooled to room temperature, diluted with water, an aqueous solution of hydrochloric acid (1 mol/L) was added thereto to neutralize the mixture, and filtrated. The filtrate was washed with chloroform, and the resultant aqueous layer was concentrated under reduced pressure to give Compound 3 as a crude material (344 mg) containing other materials such as sodium chloride.
(2) Compound 3 (68 mg), Compound 4 (68 mg), 1-ethyl-3-(3-dimethylaminopropyl)carbodiimide hydrochloride (49 mg), 1-hydroxy-7-azabenzotriazole (35 mg), and triethylamine (53 μL) were added to N,N-dimethylformamide (2 mL), and the mixture was stirred at room temperature for 2 hours. To the reaction mixture were added a saturated aqueous solution of sodium hydrogen carbonate and ethyl acetate, stirred, and then the organic layer was separated. The resultant organic layer was washed with water and saturated saline, dried, and concentrated under reduced pressure. The residue was purified with NH silica gel column chromatography (hexane:ethyl acetate=70:30-40:60) to give methyl 1-{2-[(3S,5S)-1-{[(3R,4R)-3-fluoro-4-(4-methoxyphenyl)-1-(2-methylpyrimidin-4-yl)pyrrolidin-3-yl]carbonyl}-5-(methoxymethyl)pyrrolidin-3-yl]-5-(trifluoromethyl)phenyl}piperidine-4-carboxylate 5 (28 mg) as a colorless powder. MS (APCI): m/z 714 [M+H]+

Example 8

[Chemical Formula 49]

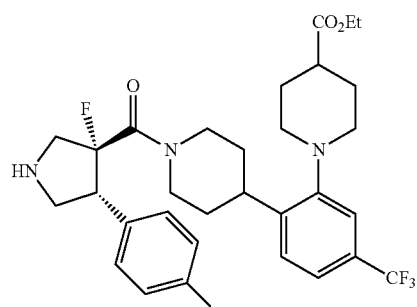

1

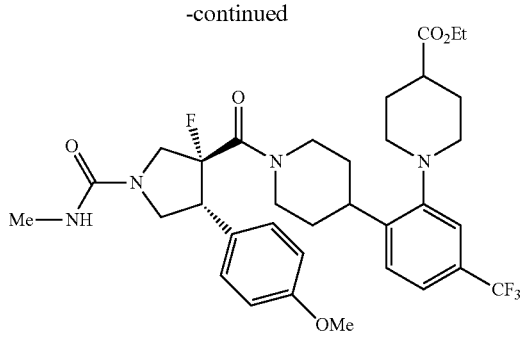

2

To a solution of Compound 1 (90 mg) and diisopropylethylamine (40 μL) in dichloromethane (2 mL) was added dropwise a suspension of methylaminoformylchloride (17 mg) in dichloromethane (1 mL) under ice-cooling, and then the mixture was stirred at room temperature for 1 hour. To the mixture were added tetrahydrofuran (1 mL), acetonitrile (1 mL), methylaminoformylchloride (51 mg), and diisopropylethylamine (120 μL), and stirred for additional 2 hours. To the reaction mixture was added water, stirred, and then extracted with ethyl acetate. The resultant organic layer was washed with saturated saline, dried, and concentrated under reduced pressure. The residue was purified with NH silica gel column chromatography (hexane:ethyl acetate=40:60-0:100) to give ethyl 1-[2-(1-{[(3R,4R)-1-carbamoyl-3-fluoro-4-(4-methoxyphenyl)pyrrolidin-3-yl]carbonyl}piperidin-4-yl)-5-(trifluoromethyl)phenyl]piperidine-4-carboxylate 2 (77 mg) as a colorless powder. MS (ESI): m/z 649 [M+H]+

Example 9

[Chemical Formula 50]

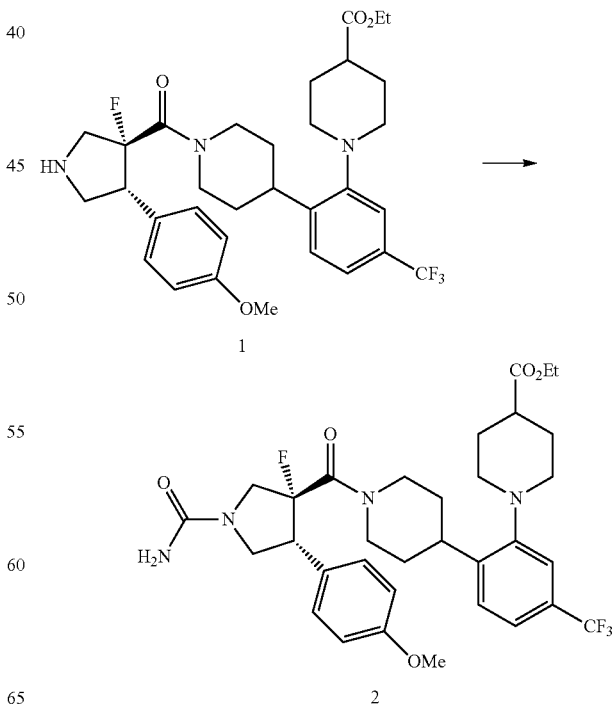

To a solution of Compound 1 (200 mg) and triethylamine (157 μL) in dichloromethane (8 mL) was added trimethylsilyl isocyanate (894 μL) under stirring, and then the mixture was stirred at room temperature for 17 hours. To the reaction mixture were added a saturated aqueous solution of sodium carbonate (5 mL) and water (80 mL), stirred, and then extracted with dichloromethane. The resultant organic layer was washed with saturated saline, dried, and concentrated under reduced pressure. The residue was purified with silica gel column chromatography (chloroform:methanol=99:1-90:10) to give ethyl 1-[2-(1-{[(3R,4R)-3-fluoro-4-(4-methoxyphenyl)-1-(methylcarbamoyl)pyrrolidin-3-yl]carbonyl}piperidin-4-yl)-5-(trifluoromethyl)phenyl]piperidine-4-carboxylate 2 (192 mg) as a colorless powder. MS (ESI): m/z 663 [M+H]+

Example 10

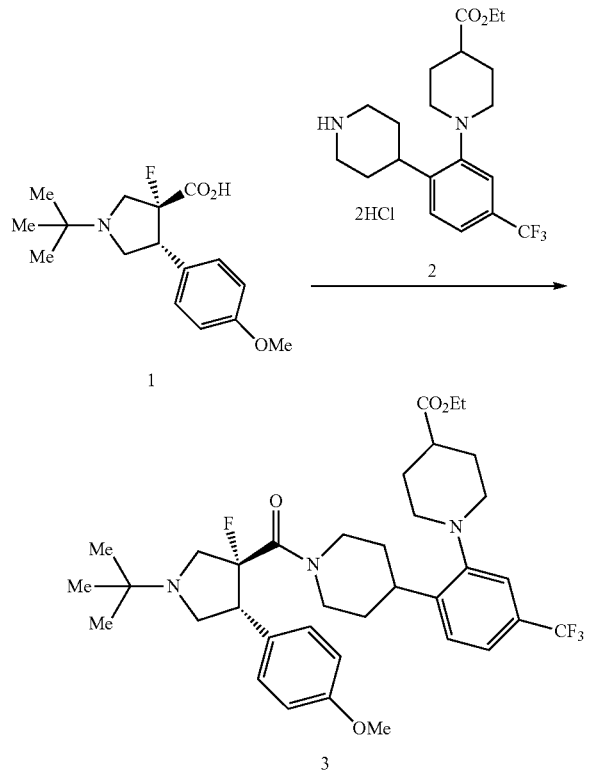

Compound 1 (116 mg), Compound 2 (120 mg), 1-ethyl-3-(3-dimethylaminopropyl)carbodiimide hydrochloride (85.5 mg), 1-hydroxy-7-azabenzotriazole (60.7 mg), and triethylamine (109.7 μL) were added to N,N-dimethylformamide (2.4 mL), and the mixture was stirred at room temperature for 5 hours. To the mixture were added a saturated aqueous solution of sodium hydrogen carbonate and ethyl acetate, stirred, and then the organic layer was separated. The resultant organic layer was washed with saturated saline, dried, and concentrated under reduced pressure. The residue was purified with silica gel column chromatography (chloroform:methanol=100:0-90:10) to give ethyl 1-[2-(1-{[(3R,4R)-1-tert-butyl-3-fluoro-4-(4-methoxyphenyl)pyrrolidin-3-yl]carbonyl}piperidin-4-yl)-5-(trifluoromethyl)phenyl]piperidine-4-carboxylate 3 (181 mg) as a colorless viscous material. MS (ESI): m/z 662 [M+H]+

Example 11

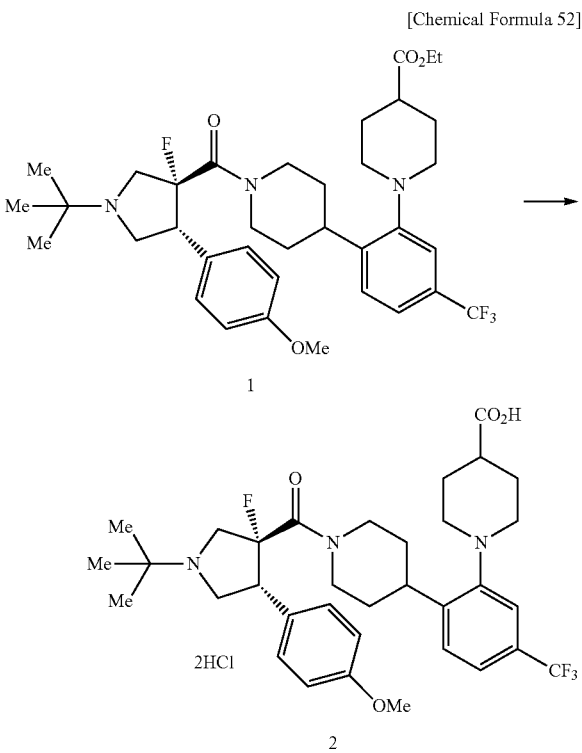

To a solution of Compound 1 (181 mg) in ethanol (2 mL) was added an aqueous solution of sodium hydroxide (2 mol/L, 1.09 mL) at room temperature, and the mixture was stirred for 12 hours. To the reaction mixture was added an aqueous solution of hydrochloric acid (2 mol/L, 1.09 mL), and concentrated under reduced pressure. The residue was purified with diol silica gel column chromatography (SHOKO SCIENTIFIC Purif-Pack (registered trademark) spherical silica gel 30 g) (chloroform:methanol=100:0-95:5). To a solution of the resultant compound in dichloromethane (1 mL) was added a solution of hydrochloric acid in 1,4-dioxane (4 mol/L, 254 μL), and the solvent was evaporated under reduced pressure. The residue was powdered with diisopropylether, collected by filtration, and dried under reduced pressure to give 1-[2-(1-{[(3R,4R)-1-tert-butyl-3-fluoro-4-(4-methoxyphenyl)pyrrolidin-3-yl]carbonyl}piperidin-4-yl)-5-(trifluoromethyl)phenyl]piperidine-4-carboxylic acid dihydrochloride 2 (134 mg) as a colorless powder. MS (APCI): m/z 634 [M+H]+

Examples 12-39

A corresponding starting compound was treated in a similar manner to the above Example 1 and subsequently Example 11 to give each compound in the following Table 1.

TABLE 1

| Example | Compound | Salt MS |
|---------|----------|---------|
| 12 | | 2 HCl (ESI): m/z 662 [M + H]+ |
| 13 | | 2 HCl (APCI): m/z 620 [M + H]+ |
| 14 | | 2 HCl (APCI): m/z 606 [M + H]+ |
| 15 | | 2 HCl (APCI): m/z 646 [M + H]+ |
| 16 | | 2 HCl (APCI): m/z 660 [M + H]+ |

TABLE 1-continued

| Example | Compound | Salt MS |
|---|---|---|
| 17 | | 2 HCl (ESI): m/z 648 [M + H]+ |
| 18 | | 2 HCl (ESI): m/z 632 [M + H]+ |
| 19 | | 2 HCl (ESI): m/z 676 [M + H]+ |
| 20 | | 2 HCl (ESI): m/z 646 [M + H]+ |
| 21 | | 2 HCl (ESI): m/z 626 [M + H]+ |

TABLE 1-continued

| Example | Compound | Salt MS |
|---------|----------|---------|
| 22 | | 2 HCl (ESI): m/z 660 [M + H]+ |
| 23 | | 2 HCl (ESI): m/z 676 [M + H]+ |
| 24 | | 2 HCl (ESI): m/z 690 [M + H]+ |
| 25 | | 2 HCl (ESI): m/z 694 [M + H]+ |
| 26 | | 2 HCl (ESI): m/z 650 [M + H]+ |

TABLE 1-continued

| Example | Compound | Salt MS |
|---|---|---|
| 27 | | 2 HCl (ESI): m/z 690 [M + H]+ |
| 28 | | 2 HCl (ESI): m/z 676 [M + H]+ |
| 29 | | 2 HCl (ESI): m/z 662 [M + H]+ |
| 30 | | 2 HCl (ESI): m/z 718 [M + H]+ |
| 31 | | 2 HCl (ESI): m/z 758 [M + H]+ |

TABLE 1-continued

| Example | Compound | Salt MS |
|---|---|---|
| 32 | (structure) | 2 HCl (ESI): m/z 758 [M + H]+ |
| 33 | (structure) | 2 HCl (APCI): m/z 592 [M + H]+ |
| 34 | (structure) | 2 HCl (ESI): m/z 634 [M + H]+ |
| 35 | (structure) | 2 HCl (ESI): m/z 621 [M + H]+ |

TABLE 1-continued
| Example | Compound | Salt MS |
|---|---|---|
| 36 | 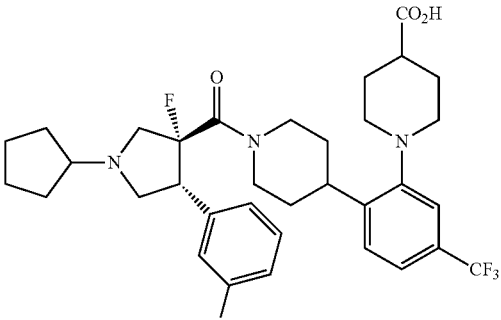 | 2 HCl (APCI): m/z 646 [M + H]+ |
| 37 | 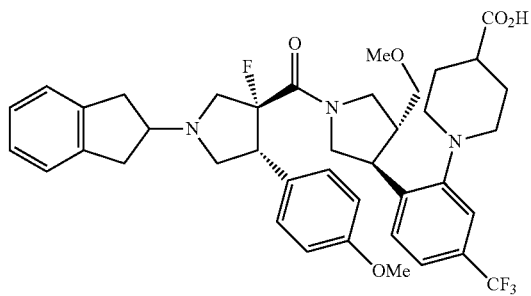 [SMILES: COC[C@H]1CN(C(=O)[C@]2(F)CN(C3Cc4ccccc4C3)C[C@H]2c2ccc(OC)cc2)C[C@@H]1c1ccc(C(F)(F)F)cc1N1CCC(C(=O)O)CC1] | 2 HCl (ESI): m/z 724 [M + H]+ |
| 38 | 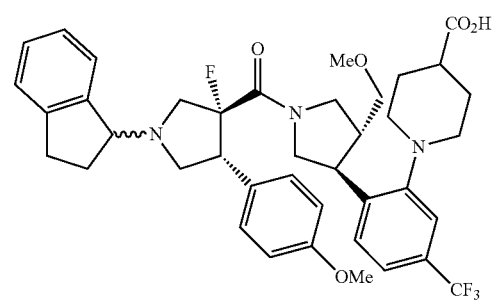<br>mixture of diastereomers | 2 HCl (ESI): m/z 724 [M + H]+ |
| 39 | 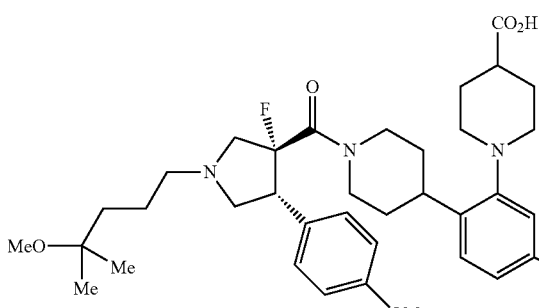 | 2 HCl (ESI): m/z 692 [M + H]+ |

Example 40

A corresponding starting compound was treated in a similar manner to the above Example 2 and subsequently Example 11 to give each compound in the following Table 2.

TABLE 2

| Example | Compound | Salt MS |
|---|---|---|
| 40 | 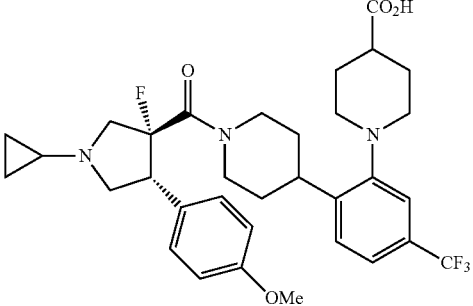 [SMILES: COc1ccc([C@@H]2CN(C3CC3)C[C@@]2(F)C(=O)N2CCC(c3ccc(C(F)(F)F)cc3N3CCC(C(=O)O)CC3)CC2)cc1] | 2 HCl (APCI): m/z 618 [M + H]+ |

Example 41

[Chemical Formula 53]

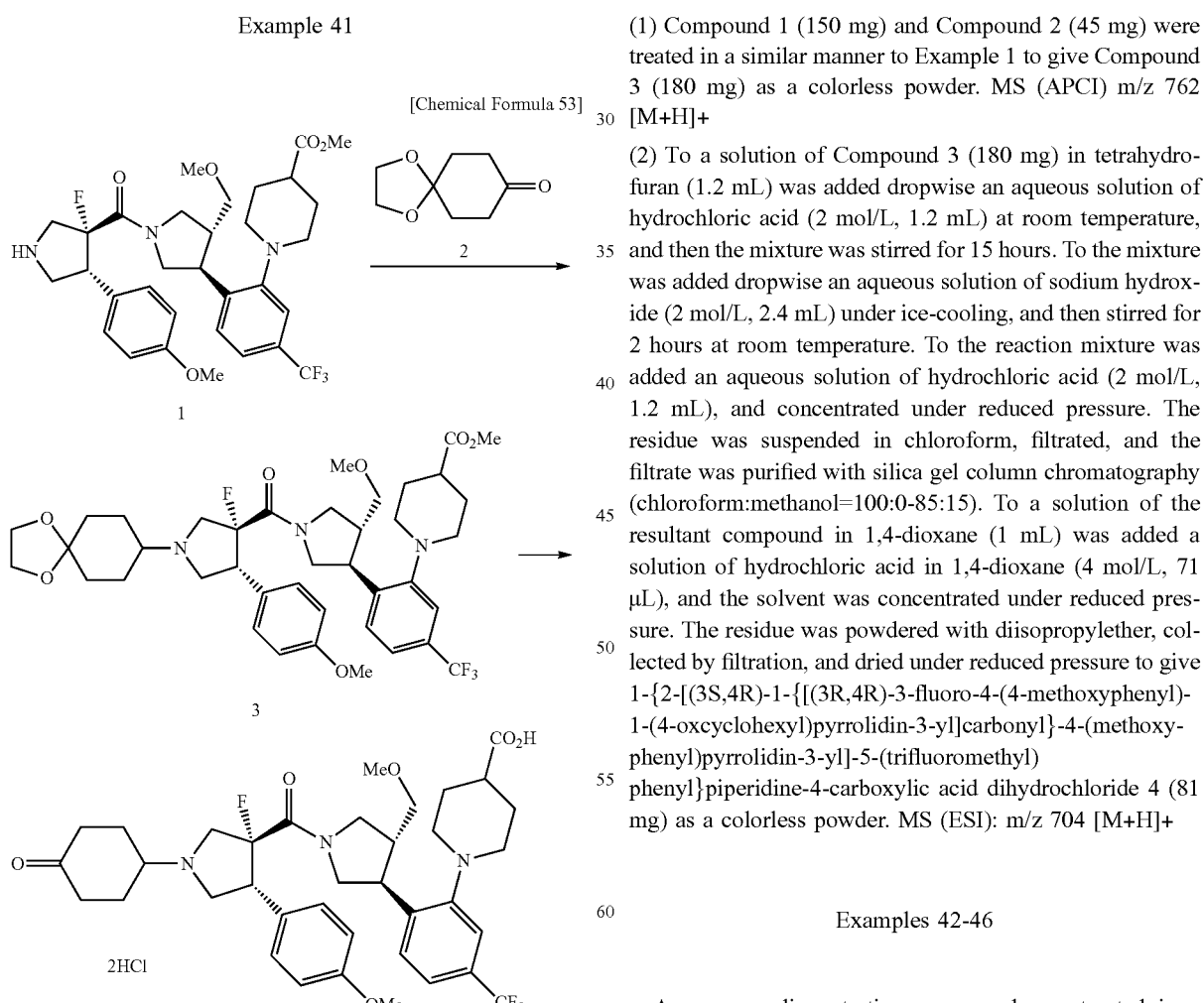

(1) Compound 1 (150 mg) and Compound 2 (45 mg) were treated in a similar manner to Example 1 to give Compound 3 (180 mg) as a colorless powder. MS (APCI) m/z 762 [M+H]+

(2) To a solution of Compound 3 (180 mg) in tetrahydrofuran (1.2 mL) was added dropwise an aqueous solution of hydrochloric acid (2 mol/L, 1.2 mL) at room temperature, and then the mixture was stirred for 15 hours. To the mixture was added dropwise an aqueous solution of sodium hydroxide (2 mol/L, 2.4 mL) under ice-cooling, and then stirred for 2 hours at room temperature. To the reaction mixture was added an aqueous solution of hydrochloric acid (2 mol/L, 1.2 mL), and concentrated under reduced pressure. The residue was suspended in chloroform, filtrated, and the filtrate was purified with silica gel column chromatography (chloroform:methanol=100:0-85:15). To a solution of the resultant compound in 1,4-dioxane (1 mL) was added a solution of hydrochloric acid in 1,4-dioxane (4 mol/L, 71 µL), and the solvent was concentrated under reduced pressure. The residue was powdered with diisopropylether, collected by filtration, and dried under reduced pressure to give 1-{2-[(3S,4R)-1-{[(3R,4R)-3-fluoro-4-(4-methoxyphenyl)-1-(4-oxcyclohexyl)pyrrolidin-3-yl]carbonyl}-4-(methoxyphenyl)pyrrolidin-3-yl]-5-(trifluoromethyl) phenyl}piperidine-4-carboxylic acid dihydrochloride 4 (81 mg) as a colorless powder. MS (ESI): m/z 704 [M+H]+

Examples 42-46

A corresponding starting compound was treated in a similar manner to the above Example 3 and subsequently Example 11 to give each compound in the following Table 3.

TABLE 3

| Example | Compound | Salt MS |
|---|---|---|
| 42 | | 2 HCl (ESI): m/z 676 [M + H]+ |
| 43 | | 2 HCl (ESI): m/z 632 [M + H]+ |
| 44 | | 2 HCl (APCI): m/z 622 [M + H]+ |
| 45 | | 2 HCl (ESI): m/z 753 [M + H]+ |
| 46 | | 2 HCl (ESI): m/z 678 [M + H]+ |

Examples 47-64

A corresponding starting compound was treated in a similar manner to the above Example 5 and subsequently Example 11 to give each compound in the following Table 4.

TABLE 4

| Example | Compound | Salt MS |
|---|---|---|
| 47 | | 2 HCl (APCI): m/z 700 [M + H]+ |
| 48 | | HCl (APCI): m/z 686 [M + H]+ |
| 49 | | HCl (APCI): m/z 710 [M + H]+ |
| 50 | | HCl (APCI): m/z 711 [M + H]+ |

TABLE 4-continued

| Example | Compound | Salt MS |
|---------|----------|---------|
| 51 | | HCl (APCI): m/z 729 [M + H]+ |
| 52 | | HCl (APCI): m/z 686 [M + H]+ |
| 53 | | 2 HCl (APCI): m/z 700 [M + H]+ |
| 54 | | HCl (APCI): m/z 686 [M + H]+ |
| 55 | | 2 HCl (APCI): m/z 685 [M + H]+ |

TABLE 4-continued

| Example | Compound | Salt MS |
|---|---|---|
| 56 | | 2 HCl (APCI): m/z 685 [M + H]+ |
| 57 | | 2 HCl (APCI): m/z 685 [M + H]+ |
| 58 | | HCl (APCI): m/z 700 [M + H]+ |
| 59 | | 2 HCl (APCI): m/z 699 [M + H]+ |
| 60 | | 2 HCl (APCI): m/z 713 [M + H]+ |

TABLE 4-continued

| Example | Compound | Salt MS |
|---|---|---|
| 61 | (structure) | 2 HCl (APCI): m/z 715 [M + H]+ |
| 62 | (structure) | 2 HCl (APCI): m/z 710 [M + H]+ |
| 63 | (structure) | HCl (APCI): m/z 700 [M + H]+ |
| 64 | (structure) | HCl (APCI): m/z 716 [M + H] |

Examples 65-66

A corresponding starting compound was treated in a similar manner to the above Example 6 and subsequently Example 11 to give each compound in the following Table 5.

TABLE 5

| Example | Compound | Salt MS |
|---|---|---|
| 65 | (structure with MeO-pyrrolidine bearing 2-methylpyrimidine, 4-methoxyphenyl, linked to pyrrolidine with CH2OMe, connected to piperidine-CO2H via fluoro-methoxyphenyl) | 2 HCl (APCI): m/z 662 [M + H] |
| 66 | (structure with MeO-pyrrolidine bearing 2-methylpyrimidine, 4-methoxyphenyl, linked to pyrrolidine with CH2OMe, connected to piperidine-CO2H via CF3-methoxyphenyl) | 2 HCl (APCI): m/z 712 [M + H] |

Examples 67-68

A corresponding starting compound was treated in a similar manner to the above Example 7 and subsequently Example 11 to give each compound in the following Table 6.

Example 69

A corresponding starting compound was treated in a similar manner to the above Example 8 and subsequently Example 11 to give each compound in the following Table 7.

TABLE 6

| Example | Compound | Salt MS |
|---|---|---|
| 67 | (structure with F-substituted pyrrolidine bearing 2-methylpyrimidine, 4-methoxyphenyl, linked to pyrrolidine with CH2OMe, connected to piperidine-CO2H via CF3-methoxyphenyl) | 2 HCl (APCI): m/z 700 [M + H] |
| 68 | (structure with F-substituted pyrrolidine bearing 2-methylpyridine, 4-methoxyphenyl, linked to pyrrolidine with CH2OMe, connected to piperidine-CO2H via CF3-methoxyphenyl) | 2 HCl (APCI): m/z 699 [M + H] |

TABLE 7

| Example | Compound | Salt MS |
|---|---|---|
| 69 | [structure: pyrrolidine with F, methylurea, linked via carbonyl to piperidine, connected to methoxyphenyl and phenyl-CF3-piperidine-CO2H] | HCl (APCI): m/z 635 [M + H]+ |

Example 70

A corresponding starting compound was treated in a similar manner to the above Example 9 and subsequently Example 11 to give each compound in the following Table 8.

TABLE 8

| Example | Compound | Salt MS |
|---|---|---|
| 70 | [structure: pyrrolidine with F, H2N-urea, linked via carbonyl to piperidine, connected to methoxyphenyl and phenyl-CF3-piperidine-CO2H] | HCl (ESI): m/z 621 [M + H]+ |

Examples 71-202

A corresponding starting compound was treated in a similar manner to the above Example 10 and subsequently Example 11 to give each compound in the following Table 9.

TABLE 9

| Example | Compound | Salt MS |
|---|---|---|
| 71 | [structure: cyclopentyl-pyrrolidine with F, linked via carbonyl to pyrrolidine with MeO-CH2, connected to methyl-methoxyphenyl and phenyl-CF3-piperidine-CO2H] | 2 HCl (APCI): m/z 690 [M + H]+ |

TABLE 9-continued

| Example | Compound | Salt MS |
|---|---|---|
| 72 | | 2 HCl (APCI): m/z 634 [M + H]+ |
| 73 | | 2 HCl (APCI): m/z 584 [M + H]+ |
| 74 | | 2 HCl (APCI): m/z 594 [M + H]+ |
| 75 | | 2 HCl (ESI): m/z 652 [M + H]+ |

TABLE 9-continued
| Example | Compound | Salt MS |
|---------|----------|---------|
| 76 | 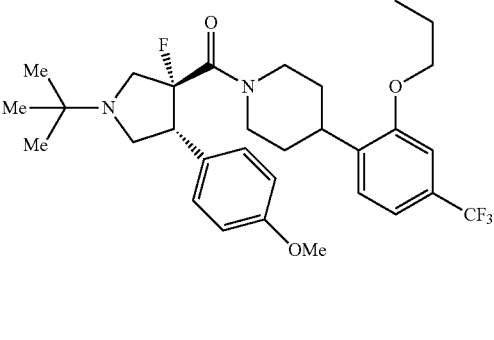 | HCl (ESI): m/z 609 [M + H]+ |
| 77 | 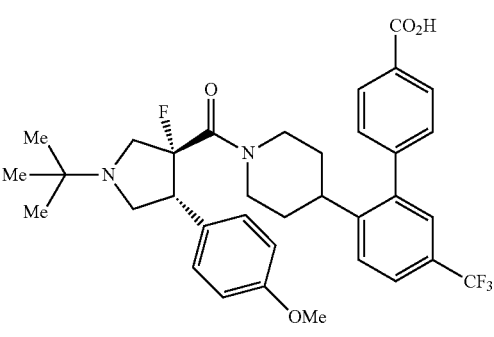 [SMILES: COc1ccc([C@@H]2CN(C(C)(C)C)C[C@@]2(F)C(=O)N2CCC(c3ccc(C(F)(F)F)cc3-c3ccc(C(=O)O)cc3)CC2)cc1] | HCl (APCI): m/z 627 [M + H]+ |
| 78 | 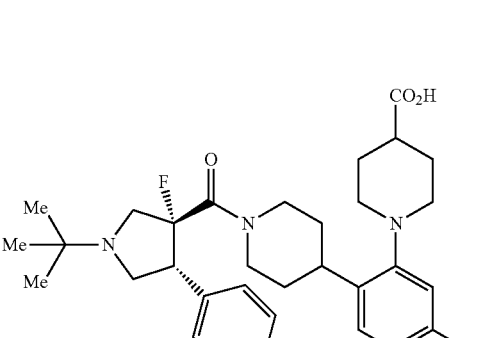 | 2 HCl (APCI): m/z 648 [M + H]+ |
| 79 | 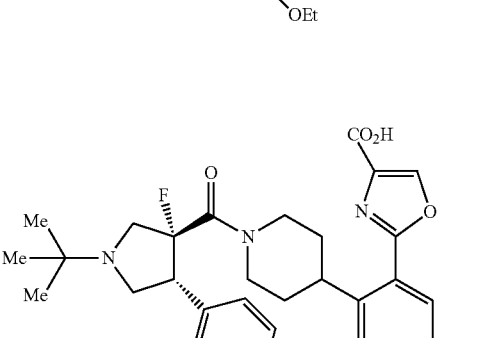 | HCl (APCI): m/z 618 [M + H]+ |

TABLE 9-continued

| Example | Compound | Salt MS |
|---|---|---|
| 80 | | 2 HCl (APCI): m/z 644 [M + H]+ |
| 81 | | 2 HCl (APCI): m/z 618 [M + H]+ |
| 82 | | 2 HCl (ESI): m/z 648 [M + H]+ |
| 83 | mixture of diastereomers | HCl (ESI): m/z 631 [M + H]+ |

TABLE 9-continued

| Example | Compound | Salt MS |
|---------|----------|---------|
| 84 | | 2 HCl (ESI): m/z 606 [M + H]+ |
| 85 | | HCl (ESI): m/z 633 [M + H]+ |
| 86 | | 2 HCl (APCI): m/z 664 [M + H]+ |
| 87 | | HCl (ESI): m/z 652 [M + H]+ |

TABLE 9-continued
| Example | Compound | Salt MS |
|---|---|---|
| 88 | 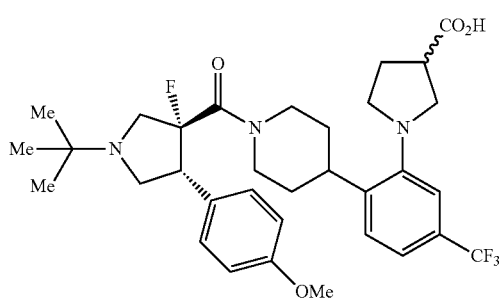 [SMILES: COc1ccc([C@@H]2CN(C(C)(C)C)C[C@@]2(F)C(=O)N2CCC(c3ccc(C(F)(F)F)cc3-c3nc(C(=O)O)co3)CC2)cc1] mixture of diastereomers | 2 HCl (ESI): m/z 620 [M + H]+ |
| 89 | 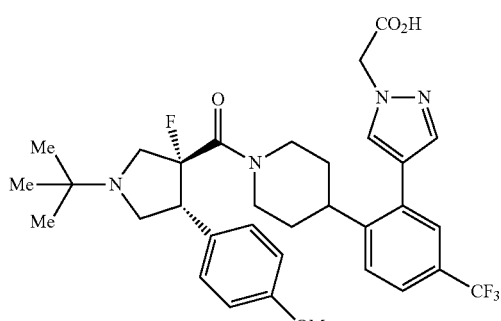 | HCl (APCI): m/z 631 [M + H]+ |
| 90 | 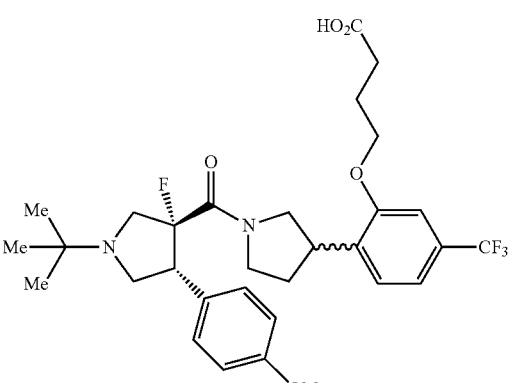 mixture of diastereomers | HCl (ESI): m/z 595 [M + H]+ |
| 91 | 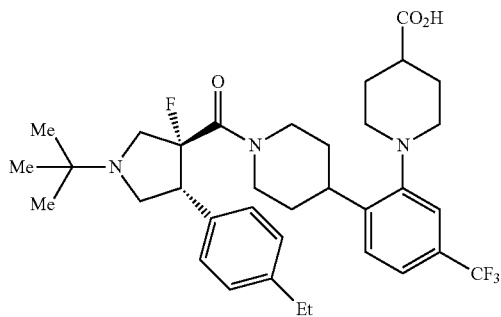 | 2 HCl (ESI): m/z 632 [M + H]+ |

TABLE 9-continued

| Example | Compound | Salt MS |
|---|---|---|
| 92 | | 2 HCl (ESI): m/z 646 [M + H]+ |
| 93 | | 2 HCl (ESI): m/z 652 [M + H]+ |
| 94 | | 2 HCl (ESI): m/z 632 [M + H]+ |
| 95 | | 2 HCl (ESI): m/z 692 [M + H]+ |

TABLE 9-continued

| Example | Compound | Salt MS |
|---|---|---|
| 96 | | 2 HCl (ESI): m/z 640 [M + H]+ |
| 97 | | 2 HCl (ESI): m/z 690 [M + H]+ |
| 98 | | 2 HCl (ESI): m/z 690 [M + H]+ |
| 99 | | 2 HCl (ESI): m/z 720 [M + H]+ |
| 100 | | 2 HCl (ESI): m/z 596 [M + H]+ |

TABLE 9-continued

| Example | Compound | Salt MS |
|---|---|---|
| 101 | | 2 HCl (APCI): m/z 690 [M + H]+ |
| 102 | | 2 HCl (APCI): m/z 676 [M + H]+ |
| 103 | | 2 HCl (APCI): m/z 734 [M + H]+ |
| 104 | | 2 HCl (ESI): m/z 598/600 [M + H]+ |
| 105 | | 2 HCl (ESI): m/z 671 [M + H]+ |

TABLE 9-continued

| Example | Compound | Salt MS |
|---|---|---|
| 106 | | 2 HCl (ESI): m/z 657 [M + H]+ |
| 107 | | 2 HCl (ESI): m/z 715 [M + H]+ |
| 108 | | 2 HCl (ESI): m/z 715 [M + H]+ |
| 109 | | 2 HCl (ESI): m/z 642/644 [M + H]+ |
| 110 | | 2 HCl (APCI): m/z 726 [M + H]+ |

TABLE 9-continued

| Example | Compound | Salt MS |
|---|---|---|
| 111 | | 2 HCl (ESI): m/z 686/688 [M + H]+ |
| 112 | | 2 HCl (APCI): m/z 690 [M + H]+ |
| 113 | | 2 HCl (ESI): m/z 670 [M + H]+ |
| 114 | | 2 HCl (ESI): m/z 664 [M + H]+ |
| 115 | | 2 HCl (ESI): m/z 708 [M + H]+ |

TABLE 9-continued

| Example | Compound | Salt MS |
|---|---|---|
| 116 | | 2 HCl (ESI): m/z 746 [M + H]+ |
| 117 | | 2 HCl (ESI): m/z 746 [M + H]+ |
| 118 | | 2 HCl (ESI): m/z 734 [M + H]+ |
| 119 | | 2 HCl (ESI): m/z 734 [M + H]+ |
| 120 | | 2 HCl (ESI): m/z 738 [M + H]+ |

TABLE 9-continued

| Example | Compound | Salt MS |
|---------|----------|---------|
| 121 | | 2 HCl (APCI): m/z 694 [M + H]+ |
| 122 | | 2 HCl (APCI): m/z 680 [M + H]+ |
| 123 | | 2 HCl (APCI): m/z 750 [M + H]+ |
| 124 | | 2 HCl (ESI): m/z 700/702 [M + H]+ |
| 125 | | 2 HCl (APCI): m/z 688 [M + H]+ |

TABLE 9-continued

| Example | Compound | Salt MS |
|---|---|---|
| 126 | | 2 HCl (ESI): m/z: 729 [M + H]+ |
| 127 | | 2 HCl (ESI): m/z 715 [M + H]+ |
| 128 | | 2 HCl (APCI): m/z 732 [M + H]+ |
| 129 | | 2 HCl (APCI): m/z 732 [M + H]+ |
| 130 | | 2 HCl (APCI): m/z 692 [M + H]+ |

TABLE 9-continued

| Example | Compound | Salt MS |
|---|---|---|
| 131 | | 2 HCl (APCI): m/z 736 [M + H]+ |
| 132 | | 2 HCl (ESI): m/z 676 [M + H]+ |
| 133 | | 2 HCl (ESI): m/z 676 [M + H]+ |
| 134 | | 2 HCl (ESI): m/z 676 [M + H]+ |
| 135 | | 2 HCl (ESI): m/z 720 [M + H]+ |

TABLE 9-continued

| Example | Compound | Salt MS |
|---|---|---|
| 136 | | 2 HCl (ESI): m/z 676 [M + H]+ |
| 137 | | 2 HCl (ESI): m/z 692 [M + H]+ |
| 138 | | 2 HCl (ESI): m/z 690 [M + H]+ |
| 139 | | 2 HCl (ESI): m/z 662 [M + H]+ |
| 140 | | 2 HCl (APCI): m/z 746 [M + H]+ |

TABLE 9-continued

| Example | Compound | Salt MS |
|---------|----------|---------|
| 141 | | 2 HCl (APCI): m/z 764 [M + H]+ |
| 142 | | 2 HCl (ESI): m/z 664 [M + H]+ |
| 143 | | 2 HCl (ESI): m/z 715 [M + H]+ |
| 144 | | 2 HCl (ESI): m/z 626 [M + H]+ |
| 145 | | 2 HCl (APCI): m/z 732 [M + H]+ |

TABLE 9-continued

| Example | Compound | Salt MS |
|---|---|---|
| 146 | | 2 HCl (APCI): m/z 746 [M + H]+ |
| 147 | | 2 HCl (ESI): m/z 670 [M + H]+ |
| 148 | | 2 HCl (APCI): m/z 694 [M + H]+ |
| 149 | | 2 HCl (APCI): m/z 650 [M + H]+ |
| 150 | | 2 HCl (APCI): m/z 688 [M + H]+ |

TABLE 9-continued

| Example | Compound | Salt MS |
|---|---|---|
| 151 | | 2 HCl (APCI): m/z 694 [M + H]+ |
| 152 | | 2 HCl (APCI): m/z 650 [M + H]+ |
| 153 | | 2 HCl (APCI): m/z 702 [M + H]+ |
| 154 | | 2 HCl (APCI): m/z 716 [M + H]+ |
| 155 | | 2 HCl (APCI): m/z 706 [M + H]+ |

TABLE 9-continued

| Example | Compound | Salt MS |
|---|---|---|
| 156 | | 2 HCl (APCI): m/z 750 [M + H]+ |
| 157 | | 2 HCl (ESI): m/z 734 [M + H]+ |
| 158 | | 2 HCl (ESI): m/z 690 [M + H]+ |
| 159 | | 2 HCl (APCI): m/z 760 [M + H]+ |
| 160 | | 2 HCl (APCI): m/z 760 [M + H]+ |

TABLE 9-continued

| Example | Compound | Salt MS |
|---------|----------|---------|
| 161 | | 2 HCl (APCI): m/z 710 [M + H]+ |
| 162 | | 2 HCl (APCI): m/z 738 [M + H]+ |
| 163 | | 2 HCl (ESI): m/z 644 [M + H]+ |
| 164 | | 2 HCl (ESI): m/z 634 [M + H]+ |
| 165 | | 2 HCl (APCI): m/z 623 [M + H]+ |

TABLE 9-continued

| Example | Compound | Salt MS |
|---|---|---|
| 166 | | 2 HCl (ESI): m/z 608 [M + H]+ |
| 167 | | 2 HCl (APCI): m/z 622 [M + H]+ |
| 168 | | 2 HCl (ESI): m/z 608 [M + H]+ |
| 169 | | 2 HCl (APCI): m/z 648 [M + H]+ |

TABLE 9-continued

| Example | Compound | Salt MS |
|---|---|---|
| 170 | | 2 HCl (ESI): m/z 634 [M + H]+ |
| 171 | | 2 HCl (ESI): m/z 634 [M + H]+ |
| 172 | | 2 HCl (ESI): m/z 632 [M + H]+ |
| 173 | | HCl (ESI): m/z 579 [M + H]+ |
| 174 | | HCl (ESI): m/z 605 [M + H]+ |

TABLE 9-continued
| Example | Compound | Salt MS |
|---|---|---|
| 175 | 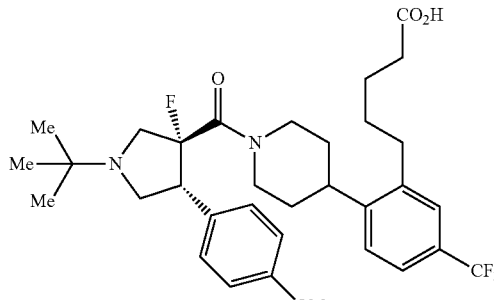 | HCl (ESI): m/z 607 [M + H]+ |
| 176 | 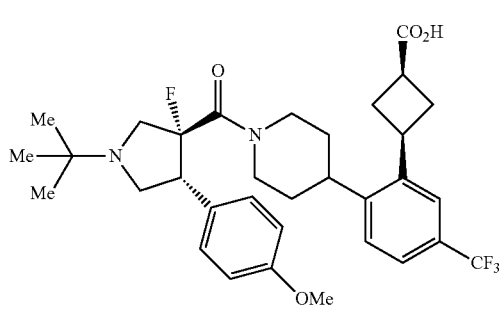 [SMILES: COc1ccc([C@@H]2CN(C(C)(C)C)C[C@@]2(F)C(=O)N2CCC(c3ccc(C(F)(F)F)cc3[C@H]3C[C@@H](C(=O)O)C3)CC2)cc1] | HCl (APCI): m/z 605 [M + H]+ |
| 177 | 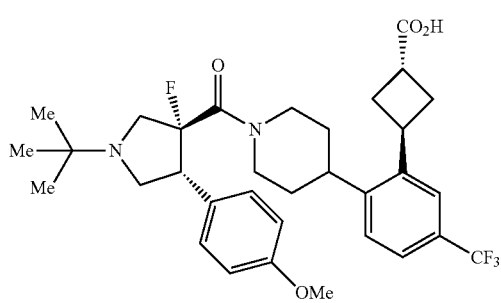 [SMILES: COc1ccc([C@@H]2CN(C(C)(C)C)C[C@@]2(F)C(=O)N2CCC(c3ccc(C(F)(F)F)cc3[C@H]3C[C@H](C(=O)O)C3)CC2)cc1] | HCl (APCI): m/z 605 [M + H]+ |
| 178 | 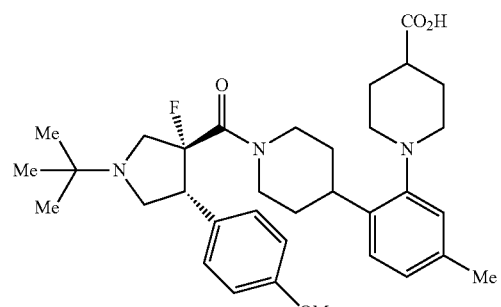 | 2 HCl (ESI): m/z 580 [M + H]+ |
| 179 | 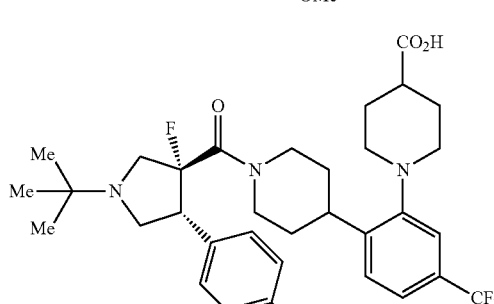 | 2 HCl (APCI): m/z 672 [M + H]+ |

TABLE 9-continued

| Example | Compound | Salt MS |
|---|---|---|
| 180 | | 2 HCl (ESI): m/z 688 [M + H]+ |
| 181 | | 2 HCl (ESI): m/z 646 [M + H]+ |
| 182 | | 2 HCl (ESI): m/z 640 [M + H]+ |
| 183 | | 2 HCl (ESI): m/z 676 [M + H]+ |
| 184 | | 2 HCl (APCI): m/z 746 [M + H]+ |

TABLE 9-continued

| Example | Compound | Salt MS |
|---|---|---|
| 185 | | 2 HCl (ESI): m/z 680/682 [M + H]+ |
| 186 | | 2 HCl (ESI): m/z 696/698 [M + H]+ |
| 187 | | 2 HCl (ESI): m/z 706 [M + H]+ |
| 188 | | 2 HCl (ESI): m/z 710 [M + H]+ |
| 189 | | 2 HCl (APCI): m/z 640 [M + H]+ |

TABLE 9-continued

| Example | Compound | Salt MS |
|---|---|---|
| 190 | | 2 HCl (APCI): m/z 584 [M + H]+ |
| 191 | | 2 HCl (ESI): m/z 622 [M + H]+ |
| 192 | | 2 HCl (APCI): m/z 591 [M + H]+ |
| 193 | | 3 HCl (ESI): m/z 739 [M + H]+ |
| 194 | | 3 HCl (APCI): m/z 769 [M + H]+ |

TABLE 9-continued

| Example | Compound | Salt MS |
|---|---|---|
| 195 | | 2 HCl (ESI): m/z 600/602 [M + H]+ |
| 196 | | 2 HCl (ESI): m/z 638/640 [M + H]+ |
| 197 | | 2 HCl (ESI): m/z 706 [M + H]+ |
| 198 | | 2 HCl (ESI): m/z 616 [M + H]+ |
| 199 | | HCl (ESI): m/z 713 [M + H]+ |

TABLE 9-continued

| Example | Compound | Salt MS |
|---|---|---|
| 200 | (structure) | HCl (ESI): m/z 606 [M + H]+ |
| 201 | (structure) | 2 HCl (ESI): m/z 644 [M + H]+ |
| 202 | (structure) | HCl (ESI): m/z 699 [M + H]+ |

Examples 203-211

A corresponding starting compound was treated in a similar manner to the above Example 10. To a solution of the resultant compound in dichloromethane were added 2 or 3 equivalents or more of a solution of hydrochloric acid in ethyl acetate (4 mol/L). The reaction mixture was concentrated under reduced pressure, and the residue was powdered with diisopropylether etc., collected by filtration, and dried under reduced pressure to give each compound in the following Table 10.

TABLE 10

| Example | Compound | Salt MS |
|---|---|---|
| 203 | (structure) | (ESI): m/z 590 [M + H]+ |

TABLE 10-continued

| Example | Compound | Salt MS |
|---------|----------|---------|
| 204 | | 2 HCl (ESI): m/z 640 [M + H]+ |
| 205 | | 3 HCl (ESI): m/z 633 [M + H]+ |
| 206 | | 2 HCl (ESI): m/z 661 [M + H]+ |
| 207 | | 2 HCl (ESI): m/z 697 [M + H]+ |

TABLE 10-continued

| Example | Compound | Salt MS |
|---|---|---|
| 208 | | 2 HCl (ESI): m/z 673 [M + H]+ |
| 209 | | 2 HCl (ESI): m/z 709 [M + H]+ |
| 210 | | 2 HCl (APCI): m/z 592 [M + H]+ |
| 211 | | 2 HCl (APCI): m/z 697 [M + H]+ |

Example 212a and Example 212b
[Chemical Formula 54]
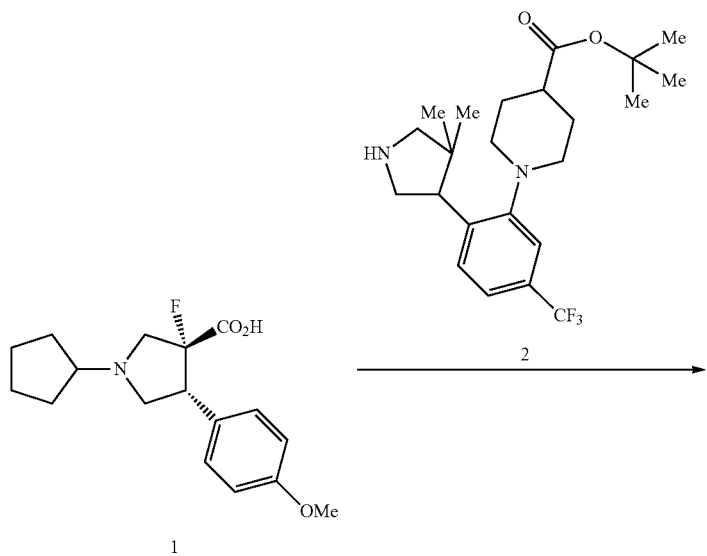
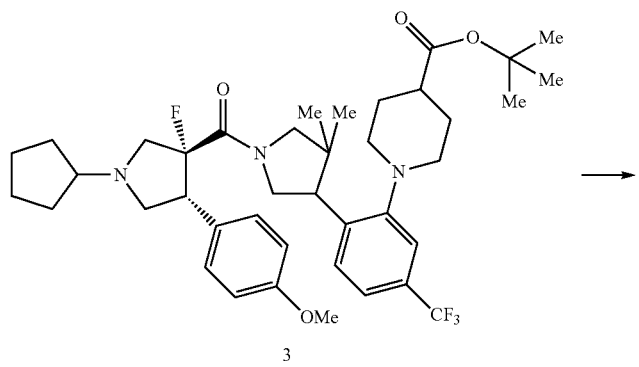
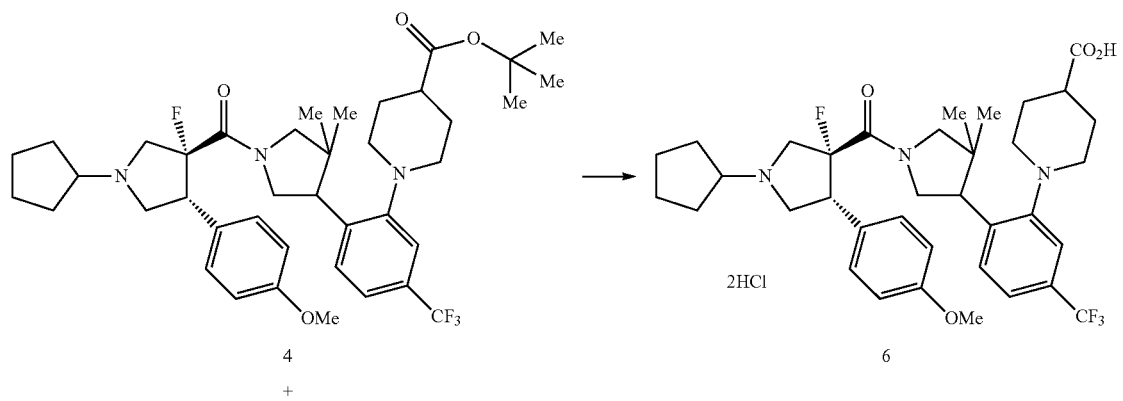

-continued

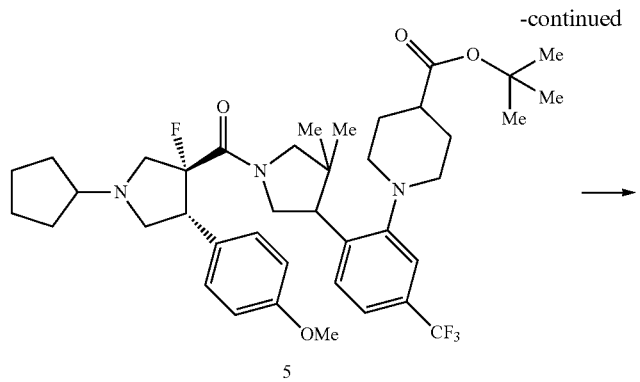

5

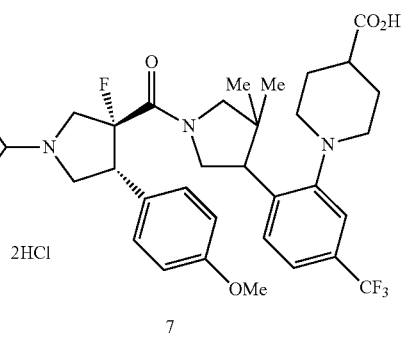

7

Compound 1 (90 mg) and Compound 2 (85 mg) were treated in a similar manner to Example 10 to give Compound 3 (106 mg). MS (ESI): m/z 716 [M+H]+

(2) Compound 3 (100 mg) was purified with CHIRAL HPLC (CHIRALPAK IE (20×250 mm) manufactured by DAICEL CORPORATION, Mobile phase: hexane/ethanol/diethylamine=75/25/0.1, Flow rate: 10 mL/min) to give optically active Compounds 4 (43 mg) and 5 (42 mg) as colorless powders. Compound 4: MS (ESI): m/z 716 [M+H]+(retention times of Compounds 4 and 5 on HPLC were 10.23 minutes and 11.64 minutes, respectively, with CHIRALPAK IE-3 (4.6×150 mm) manufactured by DAICEL CORPORATION, under the condition of Mobile phase: hexane/ethanol/diethylamine=75/25/0.1, Flow rate: 0.500 mL/min, Column temperature: 25° C.)

(3) To a solution of Compound 4 (43 mg) in chloroform (1 mL) was added trifluoroacetic acid (300 µL) under ice-cooling, and then the mixture was stirred for 2 hours at room temperature. The reaction mixture was diluted with chloroform, and then an aqueous solution of sodium hydroxide (1 mol/L) was added thereto to neutralize the mixture into pH=7. The organic layer was separated, washed with saturated saline, dried, and then concentrated under reduced pressure. The residue was purified with silica gel column chromatography (chloroform:methanol=100:0-85:15). To a solution of the resultant compound in dichloromethane (1 mL) was added a solution of hydrochloric acid in ethyl acetate (4 mol/L, 25 µL), and then the solvent was concentrated under reduced pressure. The residue was powdered with diisopropylether, collected by filtration, and dried under reduced pressure to give one stereoisomer 6 of 1-[2-(1-{[(3R,4R)-1-cyclopentyl-3-fluoro-4-(4-methoxyphenyl)pyrrolidin-3-yl]carbonyl}-4,4-dimethylpyrrolidin-3-yl)-5-(trifluoromethyl)phenyl]piperidine-4-carboxylic acid dihydrochloride (30 mg) as a colorless powder (Example 212a). MS (ESI): m/z 660 [M+H]+

(4) Compound 5 was treated in a similar manner to the above (3) to give the other stereoisomer 7 of 1-[2-(1-{[(3R,4R)-1-cyclopentyl-3-fluoro-4-(4-methoxyphenyl)pyrrolidin-3-yl]carbonyl}-4,4-dimethylpyrrolidin-3-yl)-5-(trifluoromethyl)phenyl]piperidine-4-carboxylic acid dihydrochloride (Example 212b). MS (ESI): m/z 660 [M+H]+

Examples 213-221

A corresponding starting compound was treated in a similar manner to the above Example 212a to give each compound in the following Table 11.

TABLE 11

| Example | Compound | Salt | MS |
|---------|----------|------|-----|
| 213 | | 2 HCl | (ESI): m/z 676 [M + H]+ |

TABLE 11-continued

| Example | Compound | Salt MS |
|---|---|---|
| 214 | | 2 HCl (APCI): m/z 632 [M + H]+ |
| 215 | | 2 HCl (APCI): m/z 648 [M + H]+ |
| 216 | | 2 HCl (APCI): m/z 582 [M + H]+ |
| 217 | | 2 HCl (ESI): m/z 620 [M + H]+ |

TABLE 11-continued

| Example | Compound | Salt MS |
|---|---|---|
| 218 | | 2 HCl (APCI): m/z 626 [M + H]+ |
| 219 | | 3 HCl (APCI): m/z 725 [M + H]+ |
| 220 | | 3 HCl (APCI): m/z 675 [M + H]+ |
| 221 | | 2 HCl (APCI): m/z 688 [M + H]+ |

Example 222

[Chemical Formula 55]

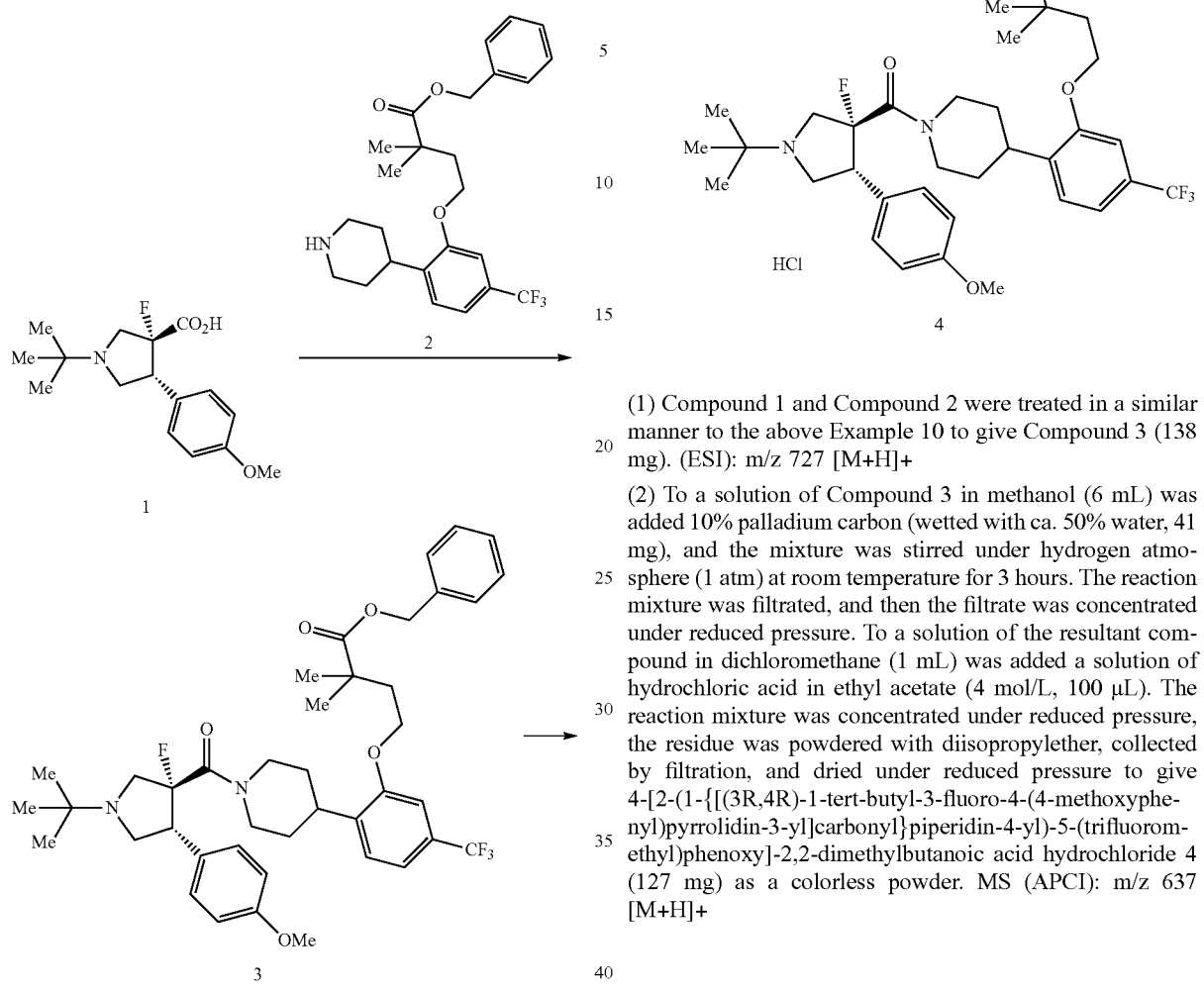

(1) Compound 1 and Compound 2 were treated in a similar manner to the above Example 10 to give Compound 3 (138 mg). (ESI): m/z 727 [M+H]+

(2) To a solution of Compound 3 in methanol (6 mL) was added 10% palladium carbon (wetted with ca. 50% water, 41 mg), and the mixture was stirred under hydrogen atmosphere (1 atm) at room temperature for 3 hours. The reaction mixture was filtrated, and then the filtrate was concentrated under reduced pressure. To a solution of the resultant compound in dichloromethane (1 mL) was added a solution of hydrochloric acid in ethyl acetate (4 mol/L, 100 μL). The reaction mixture was concentrated under reduced pressure, the residue was powdered with diisopropylether, collected by filtration, and dried under reduced pressure to give 4-[2-(1-{[(3R,4R)-1-tert-butyl-3-fluoro-4-(4-methoxyphenyl)pyrrolidin-3-yl]carbonyl}piperidin-4-yl)-5-(trifluoromethyl)phenoxy]-2,2-dimethylbutanoic acid hydrochloride 4 (127 mg) as a colorless powder. MS (APCI): m/z 637 [M+H]+

Example 223

[Chemical Formula 56]

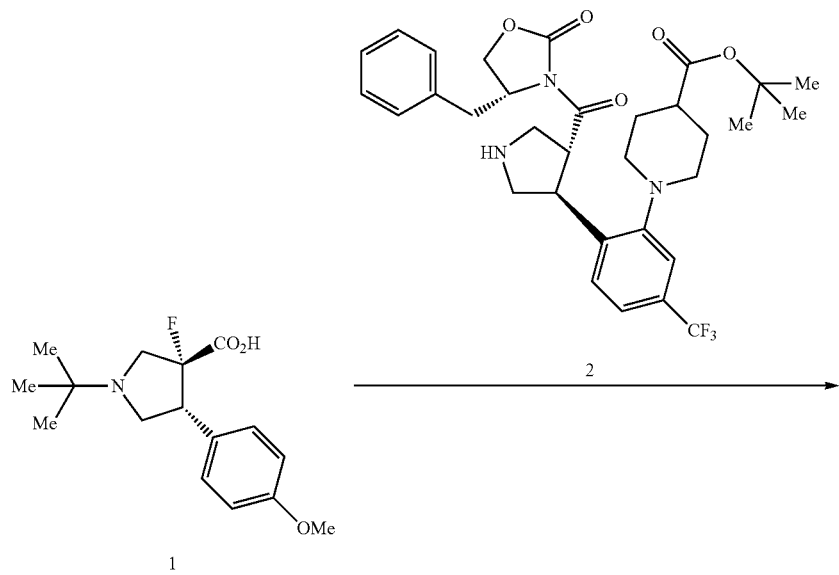

-continued

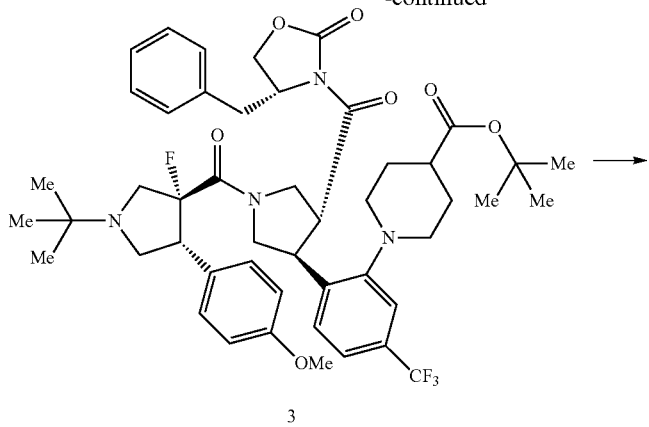

3

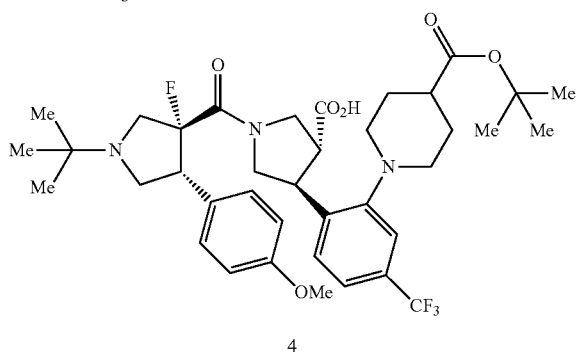

4

(1) Compound 1 and Compound 2 were treated in a similar manner to the above Example 10 to give Compound 3 (300 mg). MS (ESI): m/z 879 [M+H]+

(2) To a solution of Compound 3 in tetrahydrofuran (2 mL) was added an aqueous solution (1 mL) of lithium hydroxide (monohydrate) (17 mg) at room temperature, and the mixture was stirred for 20 hours. To the reaction mixture was added an aqueous solution of hydrochloric acid (1 mol/L, 410 μL), then water and dichloromethane were added thereto, and stirred. The organic layer was separated, washed with saturated saline, dried, and then concentrated under reduced pressure. The residue was purified with silica gel column chromatography (chloroform:methanol=98:2-80:20) to give (3R,4S)-4-{2-[4-(tert-butoxycarbonyl)piperidin-1-yl]-4-(trifluoromethyl)phenyl}-1-{[(3R,4R)-1-tert-butyl-3-fluoro-4-(4-methoxyphenyl)pyrrolidin-3-yl]carbonyl}pyrrolidin-3-carboxylic acid 4 (204 mg) as a colorless powder. MS (ESI): m/z 720 [M+H]+

Example 224

[Chemical Formula 57]

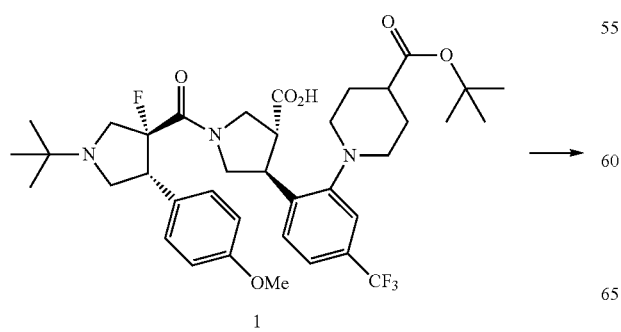

1

-continued

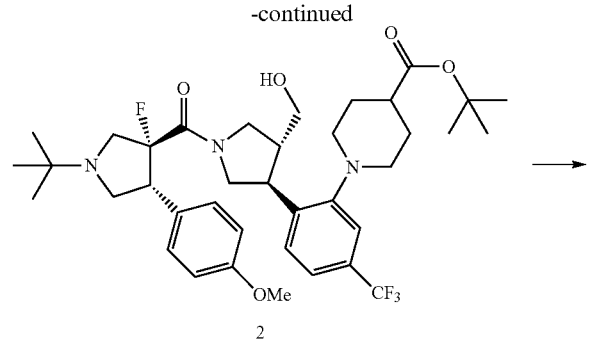

2

3

(1) To a solution of Compound 1 (116 mg) in 1,2-dimethoxyethane (2 mL) were added N-methylmorpholine (20 μL) and isobutyl chloroformate (23 μL) under nitrogen atmosphere and under ice-cooling, and the mixture was stirred at the same temperature for 1 hour. The precipitated insoluble matter was removed by filtration, and to the filtrate was added an aqueous solution (1 mL) of sodium borohydride (9 mg) under nitrogen atmosphere and under ice-cooling, and the mixture was stirred at the same temperature for 2 hours. To the reaction mixture were added water and ethyl acetate, stirred, then the organic layer was separated, washed with saturated saline, dried, and then concentrated under reduced pressure. The residue was purified with NH silica gel column chromatography (hexane:ethyl acetate=80: 20-30:70) to give Compound 2 (97 mg) as a colorless powder. MS (ESI): m/z 706 [M+H]+

(2) To a solution of Compound 2 (94 mg) in dichloromethane (1 mL) was added trifluoroacetic acid (500 μL) under ice-cooling, and then the mixture was stirred at room temperature for 3 hours. To the reaction mixture was added a saturated aqueous solution of sodium hydrogen carbonate to neutralize the mixture into pH=7, and extracted with dichloromethane. The resultant organic layer was washed with saturated saline, dried, and then concentrated under reduced pressure. The residue was purified with silica gel column chromatography (chloroform:methanol=98:2-75: 25). To a solution of the resultant compound in dichloromethane (1 mL) was added a solution of hydrochloric acid in ethyl acetate (4 mol/L, 67 μL), and then the solvent was evaporated under reduced pressure. The residue was powdered with diethylether, collected by filtration, and dried under reduced pressure to give 1-{2-[(3S,4R)-1-{[(3R,4R)-1-tert-butyl-3-fluoro-4-(4-methoxyphenyl)pyrrolidin-3-yl]carbonyl}-4-(hydroxymethyl)pyrrolidin-3-yl]-5-(trifluoromethyl)phenyl}piperidine-4-carboxylic acid dihydrochloride 3 (84 mg) as a colorless powder. MS (ESI): m/z 650 [M+H]+

Example 225

A corresponding starting compound was treated in a similar manner to the above Example 224 to give the compound in the following Table 12.

TABLE 12

| Example | Compound | Salt MS |
|---|---|---|
| 225 | ![structure] | 2 HCl (APCI): m/z 662 [M + H]+ |

Example 226

[Chemical Formula 58]

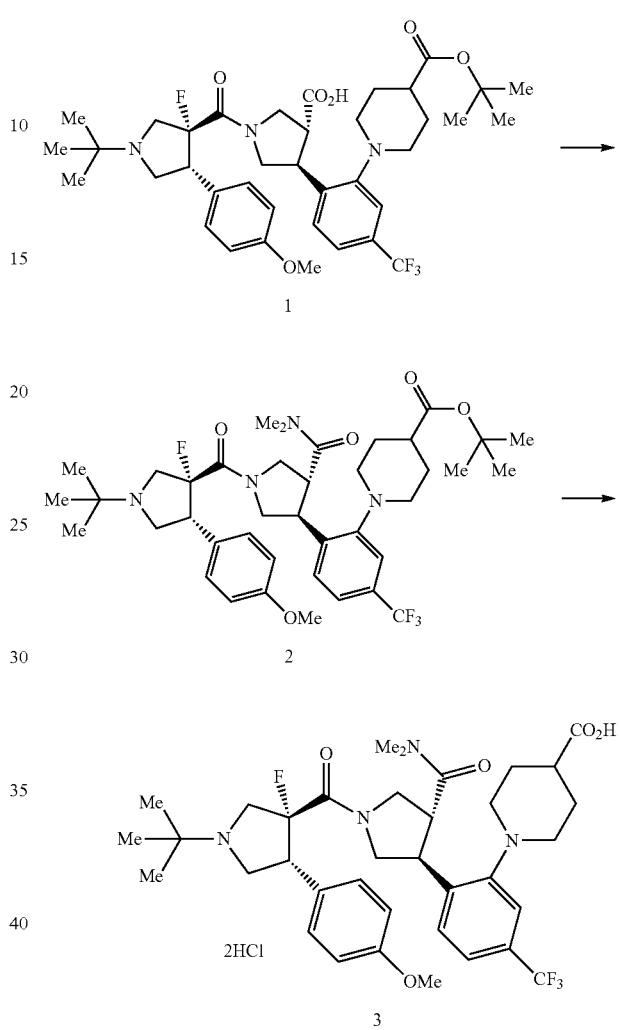

(1) To a solution of Compound 1 (80 mg) in N,N-dimethylformamide (2 mL) were added dimethylamine (2 mol/L solution in tetrahydrofuran, 220 μL), 1-ethyl-3-(3-dimethylaminopropyl)carbodiimide hydrochloride (84 mg), 1-hydroxy-7-azabenzotriazole (60 mg), and triethylamine (61 μL), and the mixture was stirred at room temperature for 6 hours. To the reaction mixture were added a saturated aqueous solution of sodium hydrogen carbonate and ethyl acetate, stirred, and then the organic layer was separated. The resultant organic layer was washed with saturated saline, dried, and concentrated under reduced pressure. The residue was purified with NH silica gel column chromatography (hexane:ethyl acetate=70:30-20:80) to give Compound 2 (55 mg) as a colorless powder. MS (ESI): m/z 747 [M+H]+

(2) To a solution of Compound 2 (53 mg) in dichloromethane (2 mL) was added a solution of hydrochloric acid in 1,4-dioxane (4 mol/L, 6 mL), and the mixture was stirred at room temperature for 4 hours. The reaction solution was concentrated under reduced pressure, and the residue was powdered with diethylether, collected by filtration, and dried under reduced pressure to give 1-{2-[(3S,4R)-1-{[(3R,4R)-1-tert-butyl-3-fluoro-4-(4-methoxyphenyl)pyrrolidin-3-yl]carbonyl}-4-(dimethylcarbamoyl)pyrrolidin-3-yl]-5-(trifluoromethyl)phenyl}piperidine-4-carboxylic acid dihydrochloride 3 (50 mg) as a colorless powder. MS (ESI): m/z 691 [M+H]+

Example 227

[Chemical Formula 59]

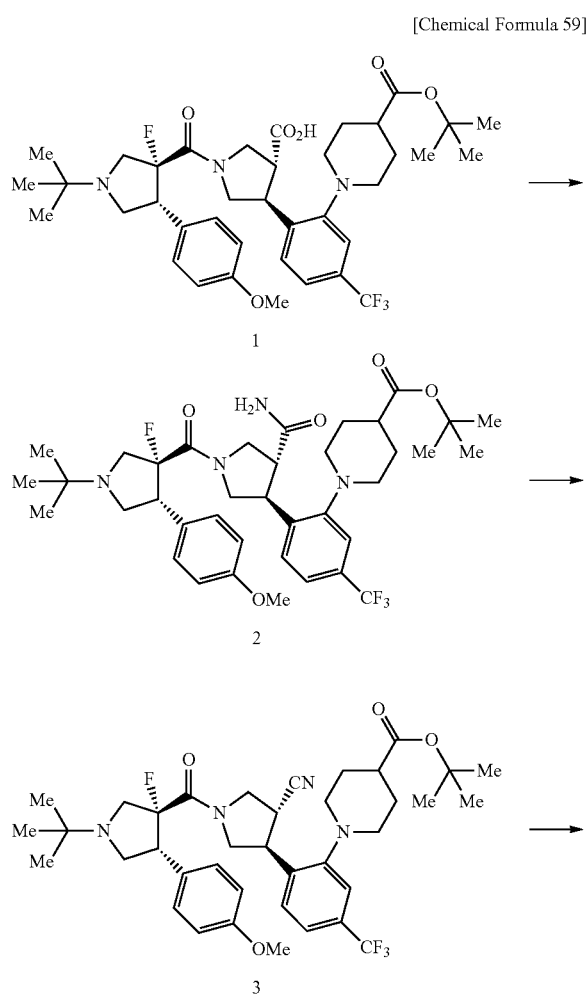

(1) To a solution of Compound 1 (140 mg) in N,N-dimethylformamide (2 mL) were added ammonium chloride (20 mg), 1-ethyl-3-(3-dimethylaminopropyl)carbodiimide hydrochloride (73 mg), 1-hydroxy-7-azabenzotriazole (52 mg), and triethylamine (106 μL), and the mixture was stirred at room temperature for 64 hours. To the reaction mixture were added a saturated aqueous solution of sodium hydrogen carbonate and ethyl acetate, stirred, and then the organic layer was separated. The resultant organic layer was washed with saturated saline, dried, and concentrated under reduced pressure. The residue was purified with silica gel column chromatography (chloroform:methanol=100:0-94:6) to give Compound 2 (129 mg) as a colorless powder. MS (ESI): m/z 719 [M+H]+

(2) To a solution of Compound 2 (128 mg) in N,N-dimethylformamide (2 mL) was added cyanuric chloride under ice-cooling (99 mg), and the mixture was stirred at the same temperature for 1 hour. To the reaction mixture were added iced water and ethyl acetate, stirred, and then the organic layer was separated. The resultant organic layer was washed with saturated saline, dried, and concentrated under reduced pressure. The residue was purified with silica gel column chromatography (chloroform:methanol=99:1-93:7) to give Compound 3 (118 mg) as a colorless powder. MS (ESI): m/z 701 [M+H]+

(3) To a solution of Compound 3 (117 mg) in dichloromethane (1 mL) was added trifluoroacetic acid (500 μL) under ice-cooling, and then the mixture was stirred at room temperature for 3 hours. To the reaction mixture was added a saturated aqueous solution of sodium hydrogen carbonate to neutralize the mixture into pH=7, and extracted with dichloromethane. The organic layer was separated, washed with saturated saline, dried, and then concentrated under reduced pressure. The residue was purified with silica gel column chromatography (chloroform:methanol=98:2-85:15). To a solution of the resultant compound in dichloromethane (1 mL) was added a solution of hydrochloric acid in ethyl acetate (4 mol/L, 84 μL), then the solvent was evaporated under reduced pressure, the residue was powdered with diisopropylether, collected by filtration, and dried under reduced pressure to give 1-{2-[(3S,4R)-1-{[(3R,4R)-1-tert-butyl-3-fluoro-4-(4-methoxyphenyl)pyrrolidin-3-yl]carbonyl}-4-cyanopyrrolidin-3-yl]-5-(trifluoromethyl)phenyl}piperidine-4-carboxylic acid dihydrochloride 4 (100 mg) as a colorless powder. MS (APCI): m/z 645 [M+H]+

Example 228

[Chemical Formula 60]

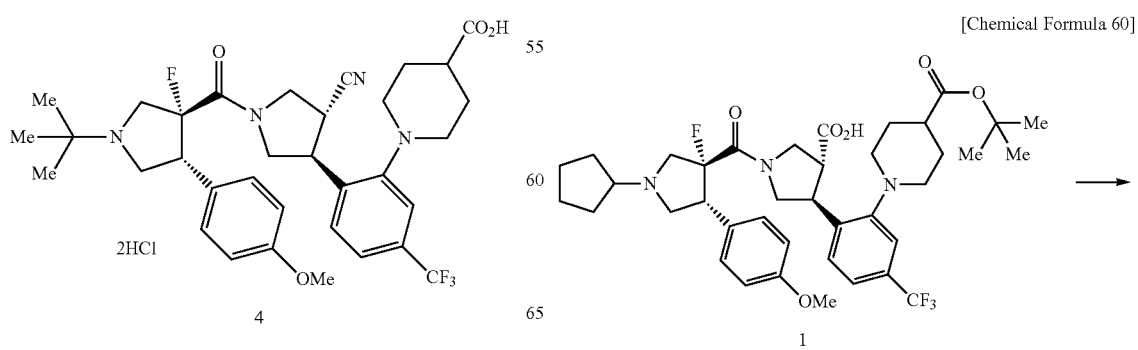

-continued

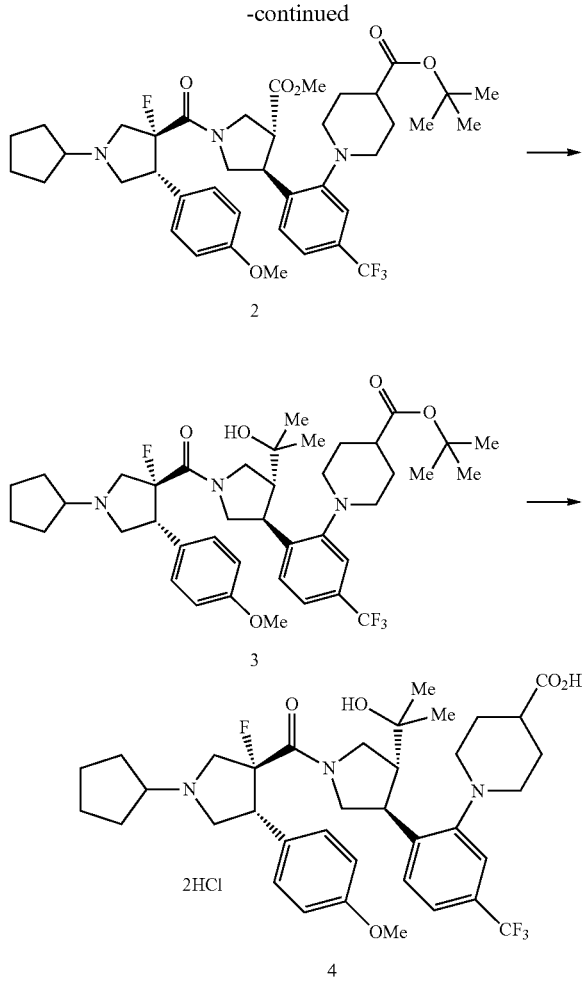

2

3

4 2HCl (1) To a solution of the compound 1 (150 mg), which was obtained by treating a corresponding starting compound in a similar manner to the above Example 223, in N,N-dimethylformamide (2 mL) were added methyl iodide (19 μL) and potassium carbonate (55 mg), and the mixture was stirred at room temperature for 2 hours. To the reaction mixture were added water and ethyl acetate, stirred, and then the organic layer was separated. The resultant organic layer was washed with water and saturated saline, dried, and concentrated under reduced pressure. The residue was purified with NH silica gel column chromatography (hexane:ethyl acetate=90:10-60:40) to give Compound 2 (111 mg) as a colorless powder. MS (ESI): m/z 746 [M+H]+

(2) To a solution of Compound 2 (110 mg) in tetrahydrofuran (2 mL) was added dropwise methylmagnesium bromide (3 mol/mL, 172 μL) under nitrogen atmosphere and under ice-cooling, and the mixture was stirred at room temperature for 4 hours. To the reaction mixture was added a saturated aqueous solution of ammonium chloride, stirred, and then ethyl acetate was added thereto. The organic layer was separated, washed with water and saturated saline, dried, and concentrated under reduced pressure. The residue was purified with NH silica gel column chromatography (hexane:ethyl acetate=80:20-50:50) to give Compound 3 (30 mg) as a colorless powder. MS (ESI): m/z 746 [M+H]+

(3) To a solution of Compound 3 (29 mg) in dichloromethane (1 mL) was added trifluoroacetic acid (500 μL) under ice-cooling, and then the mixture was stirred at room temperature for 17 hours. To the reaction mixture was added a saturated aqueous solution of sodium hydrogen carbonate to neutralize the mixture into pH=7, and extracted with dichloromethane. The organic layers were combined, washed with saturated saline, dried, and then concentrated under reduced pressure. The residue was purified with silica gel column chromatography (chloroform:methanol=99:1-85:15). To a solution of the resultant compound in dichloromethane (1 mL) was added a solution of hydrochloric acid in ethyl acetate (4 mol/L, 20 μL), then the solvent was evaporated under reduced pressure, the residue was powdered with diisopropylether, collected by filtration, and dried under reduced pressure to give 1-{2-[(3S,4R)-1-{[(3R,4R)-1-cyclopentyl-3-fluoro-4-(4-methoxyphenyl)pyrrolidin-3-yl]carbonyl}-4-(2-hydroxypropan-2-yl)pyrrolidin-3-yl]-5-(trifluoromethyl)phenyl}piperidine-4-carboxylic acid dihydrochloride 4 (18 mg) as a colorless powder. MS (ESI): m/z 690 [M+H]+

Example 229

[Chemical Formula 61]

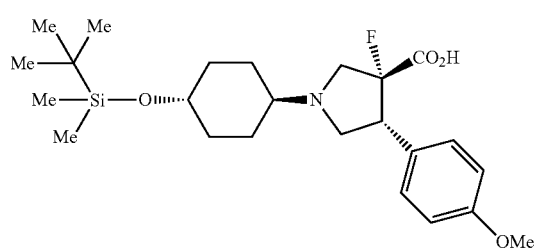

1

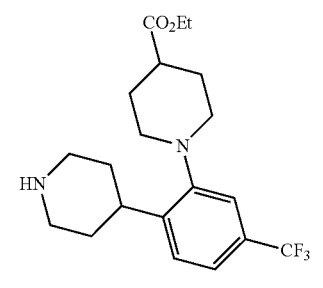

2

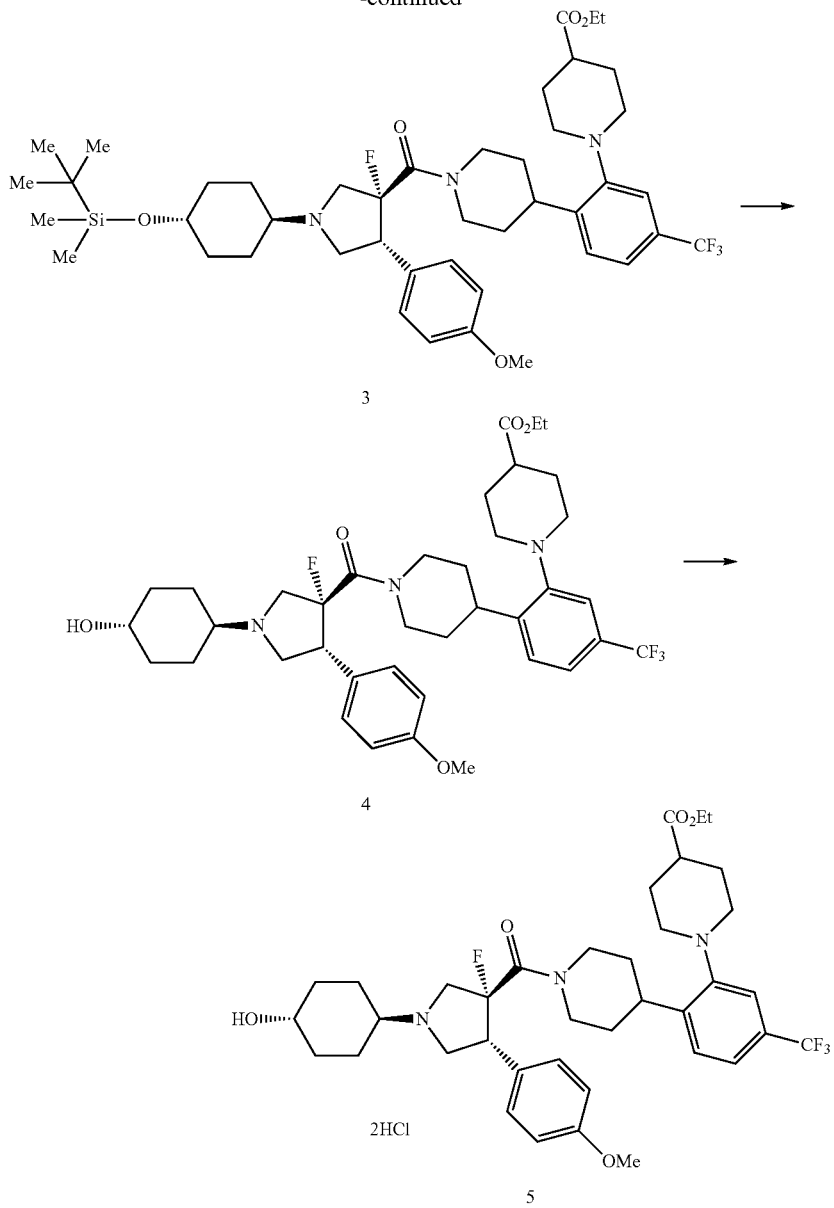

(1) Compound 1 and Compound 2 were treated in a similar manner to the above Example 10 to give Compound 3 (93 mg). MS (APCI) m/z 819 [M+H]+

(2) To a solution of Compound 3 in 1,4-dioxane (1 mL) was added a solution of hydrochloric acid in 1,4-dioxane (4 mol/L, 500 μL). The mixture was stirred at room temperature for 2 hours, and then the solvent was evaporated under reduced pressure. To the residue was added a saturated aqueous solution of sodium hydrogen carbonate to alkalify the mixture, and extracted with chloroform. The resultant organic layer was washed with saturated saline, dried, and then concentrated under reduced pressure. The residue was purified with silica gel column chromatography (chloroform:methanol=100:0-94:6) to give Compound 4. MS (ESI): m/z 704 [M+H]+

(3) To a solution of Compound 4 in ethanol (1 mL) was added an aqueous solution of sodium hydroxide (2 mol/L, 220 μL), and the mixture was stirred at room temperature for 2 hours. An aqueous solution of hydrochloric acid (2 mol/L, 220 μL) was added thereto, and then the reaction solution was concentrated under reduced pressure. To the residue were added chloroform and water, the mixture was stirred, then the organic layer was separated, dried, and concentrated under reduced pressure. To a solution of the resultant compound in dichloromethane (1 mL) was added a solution of hydrochloric acid in 1,4-dioxane (4 mol/L, 55 μL), then the solvent was evaporated under reduced pressure, the residue was powdered with diisopropylether, collected by filtration, and dried under reduced pressure to give 1-[2-(1-{[(3R,4R)-3-fluoro-1-(trans-4-hydroxycyclohexyl)-4-(4-methoxyphenyl)pyrrolidin-3-yl]carbonyl}piperidin-4-yl)-5-(trifluoromethyl)phenyl]piperidine-4-carboxylic acid dihydrochloride 5 (65 mg) as a colorless powder. MS (ESI): m/z 676 [M+H]+

Example 230

A corresponding starting compound was treated in a similar manner to the above Example 229 to give the compound in the following Table 13.

TABLE 13

| Example | Compound | Salt MS |
|---|---|---|
| 230 | | 2 HCl (ESI): m/z 676 [M + H]+ |

Example 231

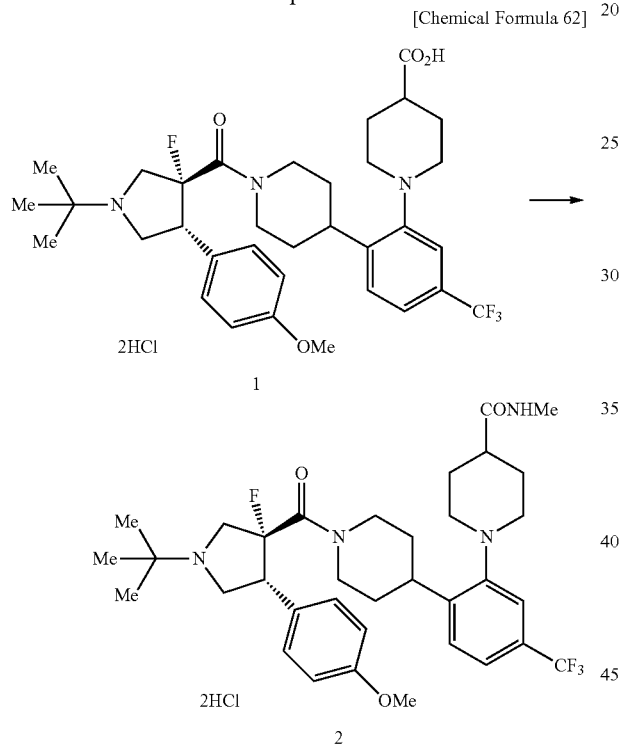

[Chemical Formula 62]

To a solution of Compound 1 (101 mg) in dichloromethane (2 mL) were added methylamine hydrochloride (21 mg), 1-ethyl-3-(3-dimethylaminopropyl) carbodiimide hydrochloride (61 mg), 1-hydroxy-7-azabenzotriazole (65 mg), and triethylamine (111 µL), and the mixture was stirred at room temperature for 4 hours. To the mixture were added methylamine hydrochloride (21 mg), 1-ethyl-3-(3-dimethylaminopropyl)carbodiimide hydrochloride (61 mg), 1-hydroxy-7-azabenzotriazole (44 mg), and triethylamine (111 µL), and stirred at room temperature for 15 hours. To the reaction mixture were added a saturated aqueous solution of sodium hydrogen carbonate and ethyl acetate, stirred, and then the organic layer was separated. The resultant organic layer was washed with saturated saline, dried, and concentrated under reduced pressure. The residue was purified with silica gel column chromatography (chloroform:methanol=100:0-90:10). To a solution of the resultant compound in chloroform (1 mL) was added a solution of hydrochloric acid in ethyl acetate (4 mol/L, 100 µL), then the solvent was evaporated under reduced pressure, the residue was powdered with diisopropylether, collected by filtration, and dried under reduced pressure to give 1-[2-(1-{[(3R,4R)-1-tert-butyl-3-fluoro-4-(4-methoxyphenyl)pyrrolidin-3-yl]carbonyl}piperidin-4-yl)-5-(trifluoromethyl)phenyl]-N-methylpiperidine-4-carboxamide dihydrochloride 2 (50 mg) as a colorless powder. MS (ESI): m/z 647 [M+H]+

Examples 232-267

A corresponding starting compound was treated in a similar manner to the above Example 231 to give each compound in the following Table 14.

TABLE 14

| Example | Compound | Salt MS |
|---|---|---|
| 232 | | 2 HCl (ESI): m/z 633 [M + H]+ |

TABLE 14-continued

| Example | Compound | Salt MS |
|---|---|---|
| 233 | | 2 HCl (ESI): m/z 649 [M + H]+ |
| 234 | | 2 HCl (ESI): m/z 661 [M + H]+ |
| 235 | | 2 HCl (ESI): m/z 687 [M + H]+ |
| 236 | mixture of diastereomers | 2 HCl (ESI): m/z 647 [M + H]+ |

TABLE 14-continued

| Example | Compound | Salt MS |
|---|---|---|
| 237 | | 2 HCl (ESI): m/z 639 [M + H]+ |
| 238 | | 2 HCl (APCI): m/z 625 [M + H]+ |
| 239 | | 2 HCl (APCI): m/z 639 [M + H]+ |
| 240 | | 2 HCl (APCI): m/z 669 [M + H]+ |

TABLE 14-continued

| Example | Compound | Salt MS |
|---|---|---|
| 241 | | 2 HCl (APCI): m/z 683 [M + H]+ |
| 242 | | 2 HCl (APCI): m/z 669 [M + H]+ |
| 243 | | 2 HCl (APCI): m/z 655 [M + H]+ |
| 244 | | 2 HCl (ESI): m/z 699 [M + H]+ |

TABLE 14-continued

| Example | Compound | Salt MS |
|---|---|---|
| 245 | | 2 HCl (APCI): m/z 675 [M + H]+ |
| 246 | | 2 HCl (ESI): m/z 611 [M + H]+ |
| 247 | | 2 HCl (ESI): m/z 719 [M + H]+ |
| 248 | | 2 HCl (ESI): m/z 703 [M + H]+ |

TABLE 14-continued

| Example | Compound | Salt MS |
|---|---|---|
| 249 | | 2 HCl (ESI): m/z 633 [M + H]+ |
| 250 | | 2 HCl (APCI): m/z 727 [M + H]+ |
| 251 | | 2 HCl (APCI): m/z 715 [M + H]+ |
| 252 | | 2 HCl (APCI): m/z 713/715 [M + H]+ |

TABLE 14-continued

| Example | Compound | Salt MS |
|---|---|---|
| 253 | | 2 HCl (APCI): m/z 699/701 [M + H]+ |
| 254 | | 2 HCl (APCI): m/z 713/715 [M + H]+ |
| 255 | | 2 HCl (APCI): m/z 685/687 [M + H]+ |
| 256 | | 2 HCl (ESI): m/z 747 [M + H]+ |
| 257 | | 2 HCl (ESI): m/z 719 [M + H]+ |

TABLE 14-continued

| Example | Compound | Salt MS |
|---|---|---|
| 258 | | 2 HCl (ESI): m/z 733 [M + H]+ |
| 259 | | 2 HCl (ESI): m/z 747 [M + H]+ |
| 260 | | 2 HCl (ESI): m/z 675 [M + H]+ |
| 261 | | 2 HCl (ESI): m/z 684 [M + H]+ |
| 262 | | 2 HCl (ESI): m/z 697 [M + H]+ |

TABLE 14-continued

| Example | Compound | Salt MS |
|---|---|---|
| 263 | | 2 HCl (ESI): m/z 669 [M + H]+ |
| 264 | | 2 HCl (ESI): m/z 683 [M + H]+ |
| 265 | | 2 HCl (ESI): m/zg 697 [M + H]+ |
| 266 | | 2 HCl (ESI): m/z 691 [M + H]+ |
| 267 | | Free form (ESI): m/z 550 [M + H]+ |

Example 268

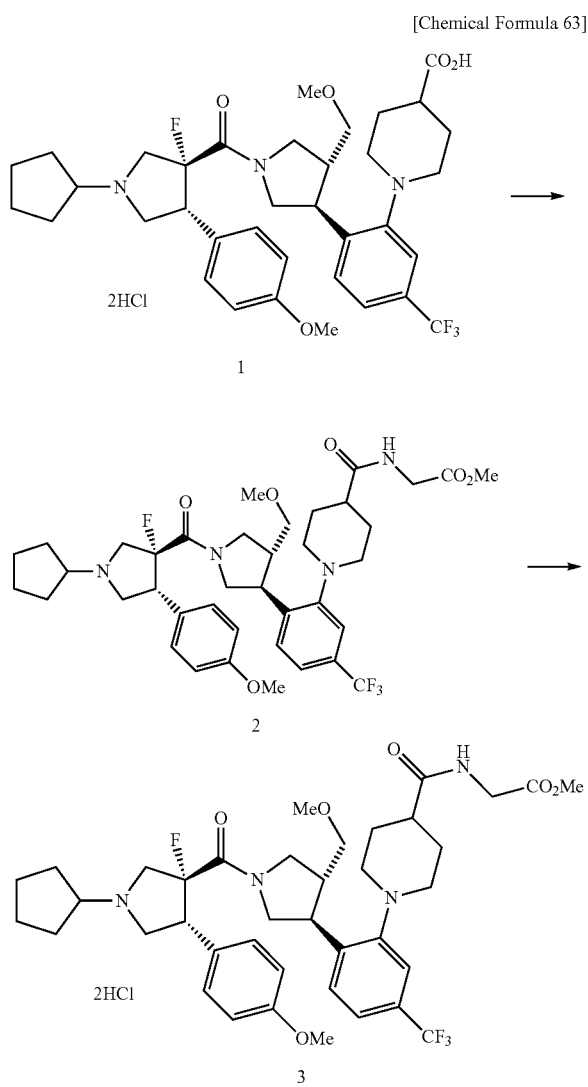

(1) Compound 1 (60 mg), glycine methyl ester hydrochloride (15 mg), 1-ethyl-3-(3-dimethylaminopropyl)carbodiimide hydrochloride (31 mg), 1-hydroxy-7-azabenzotriazole (22 mg), and triethylamine (45 μL) were added to N,N-dimethylformamide (1 mL), and the mixture was stirred at room temperature for 3 hours. To the reaction mixture were added a saturated aqueous solution of sodium hydrogen carbonate and ethyl acetate, stirred, and then the organic layer was separated. The resultant organic layer was washed with saturated saline, dried, and concentrated under reduced pressure. The residue was purified with NH silica gel column chromatography (hexane:ethyl acetate-60:40-30:70) to give Compound 2 (57 mg) as a colorless viscous material. MS (APCI): m/z 747 [M+H]+

(2) To a solution of Compound 2 (56 mg) in methanol (1 mL) was added an aqueous solution of sodium hydroxide (2 mol/L, 300 μL) at room temperature, and the mixture was stirred for 1 hour. To the reaction mixture was added an aqueous solution of hydrochloric acid (2 mol/L, 300 μL), and then concentrated under reduced pressure. The residue was suspended in ethyl acetate, filtered, and the filtrate was concentrated under reduced pressure. To a solution of the resultant compound in dichloromethane (1 mL) was added a solution of hydrochloric acid-1,4-ethyl acetate (4 mol/L, 94 μL), then the solvent was evaporated under reduced pressure, the residue was powdered with diisopropylether, collected by filtration, and dried under reduced pressure to give N-[(1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidin-4-yl)carbonyl]glycine dihydrochloride 3 (82 mg) as a colorless powder. MS (APCI): m/z 733 [M+H]+

Examples 269-271

A corresponding starting compound was treated in a similar manner to the above Example 268 to give each compound in the following Table 15.

TABLE 15

| Example | Compound | Salt | MS |
|---|---|---|---|
| 269 | | 2 HCl | (APCI): m/z 747 [M + H]+ |

TABLE 15-continued

| Example | Compound | Salt MS |
|---|---|---|
| 270 | | 2 HCl (APCI): m/z 773 [M + H]+ |
| 271 | | 2 HCl (APCI): m/z 773 [M + H]+ |

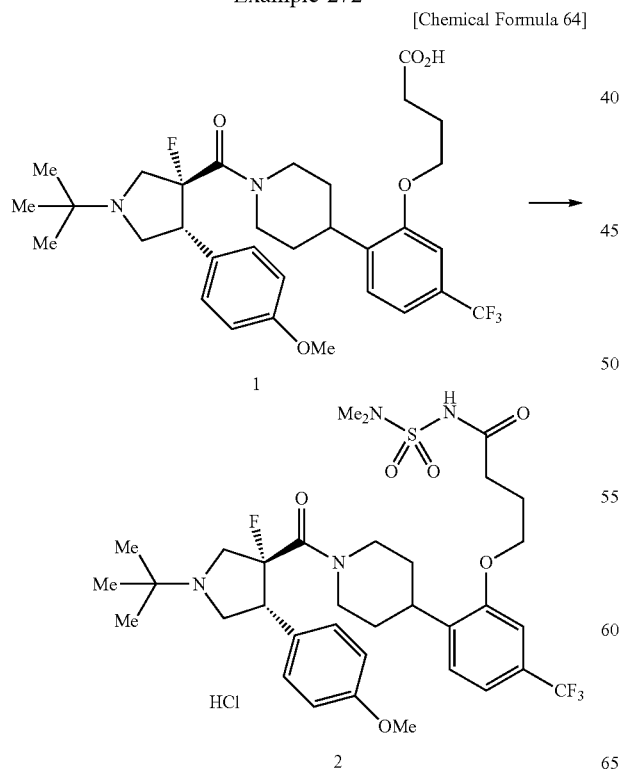

Example 272

To a solution of Compound 1 (150 mg) in chloroform (1 mL)/tetrahydrofuran (2 mL) were added N,N-dimethylsulfamide (62 mg), 1-ethyl-3-(3-dimethylaminopropyl)carbodiimide hydrochloride (96 mg), and 4-dimethylaminopyridine (16 mg), and the mixture was stirred at room temperature for 65 hours. The reaction solution was concentrated under reduced pressure, and the residue was purified with silica gel column chromatography (chloroform:methanol=98:2-91:9). To a solution of the resultant compound in dichloromethane (1 mL) was added a solution of hydrochloric acid in ethyl acetate (4 mol/L, 63 µL), then the solvent was evaporated under reduced pressure, the residue was powdered in a mixed solvent of diisopropylether and heptane, collected by filtration, and dried under reduced pressure to give 4-[2-(1-{[(3R,4R)-1-tert-butyl-3-fluoro-4-(4-methoxyphenyl)pyrrolidin-3-yl]carbonyl}piperidin-4-yl)-5-(trifluoromethyl)phenoxy]-N-(dimethylsulfamoyl)butanamide hydrochloride 2 (159 mg) as a colorless powder. MS (APCI): m/z 715 [M+H]+

Examples 273-276

A corresponding starting compound was treated in a similar manner to the above Example 272 to give each compound in the following Table 16.

TABLE 16

| Example | Compound | Salt MS |
|---|---|---|
| 273 | | HCl (APCI): m/z 686 [M + H]+ |
| 274 | | 2 HCl m/z 711 [M + H]+ |
| 275 | | 2 HCl (ESI): m/z 769 [M + H]+ |
| 276 | | 2 HCl (ESI): m/z 725 [M + H]+ |

Example 277

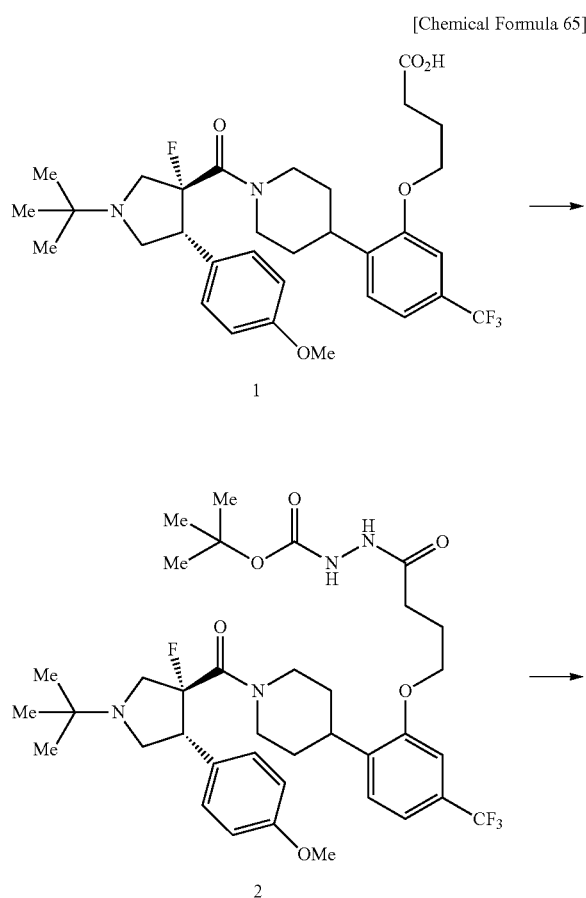

(1) A solution of Compound 1 (200 mg), t-butyl carbazate (66 mg), 1-ethyl-3-(3-dimethylaminopropyl)carbodiimide hydrochloride (127 mg), 1-hydroxy-7-azabenzotriazole (90 mg), and triethylamine (138 μL) in N,N-dimethylformamide (2 mL) was stirred at room temperature for 65 hours. To the reaction mixture were added a saturated aqueous solution of sodium hydrogen carbonate and ethyl acetate, stirred, then the organic layer was separated, washed with saturated saline, dried, and concentrated under reduced pressure. The residue was purified with silica gel column chromatography (chloroform:methanol=99:1-95:5) to give Compound 2 (188 mg) as a colorless powder. MS (ESI): m/z 723 [M+H]+

(2) To a solution of Compound 2 (180 mg) in dichloromethane (1 mL) was added trifluoroacetic acid (1 mL) under ice-cooling, and then the mixture was stirred at room temperature for 1 hour. To the reaction mixture was added a saturated aqueous solution of sodium hydrogen carbonate to alkalify the mixture, and extracted with dichloromethane. The resultant organic layer was washed with saturated saline, dried, and then concentrated under reduced pressure. The residue was dissolved in tetrahydrofuran, 1,1'-carbonyldiimidazole (203 mg) was added thereto, and the mixture was stirred at room temperature for 14 hours. The reaction solution was concentrated under reduced pressure, and then purified with silica gel column chromatography (chloroform:methanol=98:2-90:10). To a solution of the resultant compound in dichloromethane (1 mL) was added a solution of hydrochloric acid in ethyl acetate (4 mol/L, 63 μL), then the solvent was evaporated under reduced pressure, the residue was powdered with diethylether, collected by filtration, and dried under reduced pressure to give 5-{3-[2-(1-{[(3R,4R)-1-tert-butyl-3-fluoro-4-(4-methoxyphenyl)pyrrolidin-3-yl]carbonyl}piperidin-4-yl)-5-(trifluoromethyl)phenoxy]propyl}-1,3,4-oxadiazole-2(3H)-one hydrochloride 3 (93 mg) as a colorless powder. MS (APCI): m/z 649 [M+H]+

Example 278

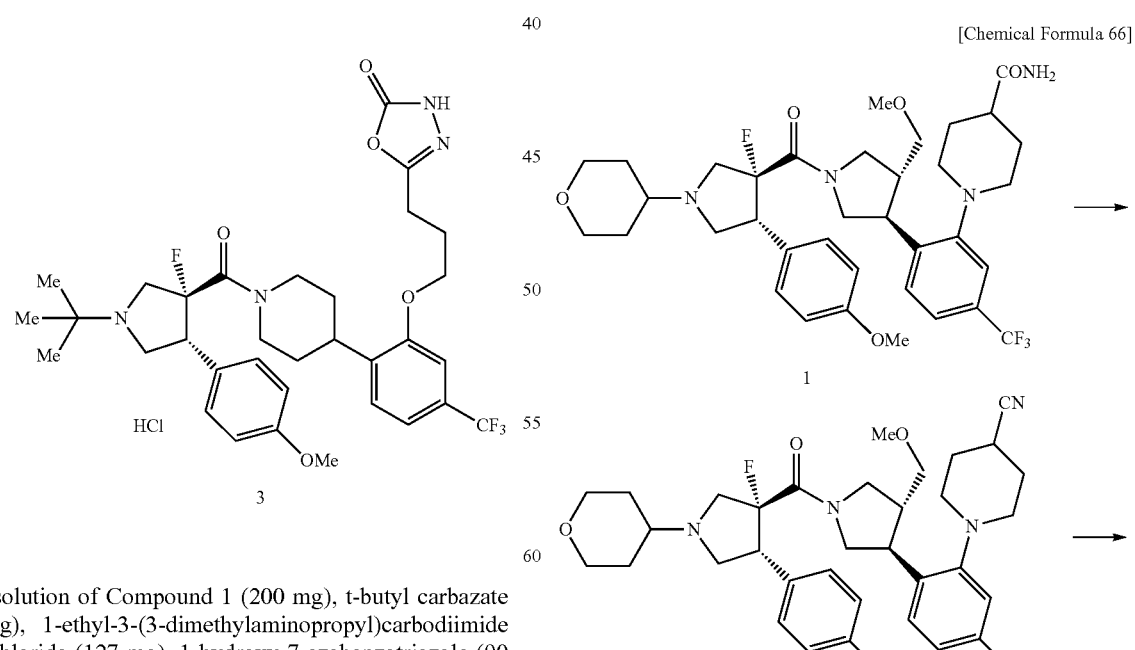

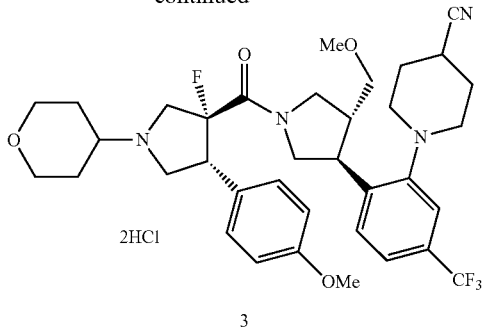

3

To a solution of Compound 1 (310 mg) in N,N-dimethylformamide (4.5 mL) was added cyanuric chloride (166 mg) under ice-cooling, and the mixture was stirred at the same temperature for 1.5 hours. To the reaction mixture were added iced water and ethyl acetate, stirred, and then the organic layer was separated. The resultant organic layer was washed with saturated saline, dried, and concentrated under reduced pressure. The residue was purified with NH silica gel column chromatography (hexane:ethyl acetate=60:40-30:70) and subsequently silica gel column chromatography (chloroform:methanol=100:0-94:6) to give Compound 2 (185 mg) as a colorless powder. To a solution of Compound 2 (35 mg) in dichloromethane (1 mL) was added a solution of hydrochloric acid in ethyl acetate (4 mol/L, 26 μL), then the solvent was evaporated under reduced pressure, the residue was powdered with diethylether, collected by filtration, and dried under reduced pressure to give 1-{2-[(3S,4R)-1-{[(3R,4R)-3-fluoro-4-(4-methoxyphenyl)-1-(tetrahydro-2H-pyran-4-yl)pyrrolidin-3-yl]carbonyl}-4-(methoxymethyl)pyrrolidin-3-yl]-5-(trifluoromethyl)phenyl}piperidine-4-carbonitrile dihydrochloride 3 (34 mg) as a colorless powder. MS (ESI): m/z 673 [M+H]+

Example 279

[Chemical Formula 67]

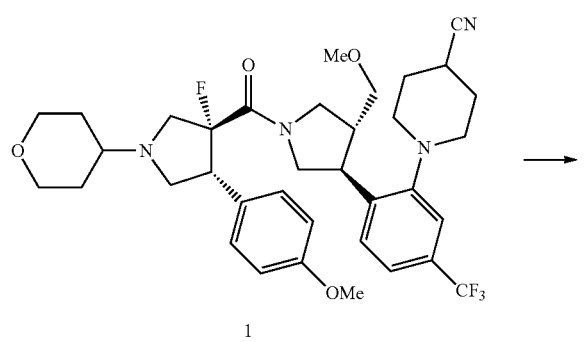

A solution of Compound 1 (80 mg) and tri-n-butyltin azide (331 μL) in toluene (2 mL) was heated under reflux for 17 hours, and then concentrated under reduced pressure. The residue was purified with silica gel column chromatography (chloroform:methanol=98:2-90:10). To a solution of the resultant compound in dichloromethane (2 mL) was added a solution of hydrochloric acid in ethyl acetate (4 mol/L, 60 μL), then the solvent was evaporated under reduced pressure, the residue was powdered with diethylether, collected by filtration, and dried under reduced pressure to give [(3R,4R)-3-fluoro-4-(4-methoxyphenyl)-1-(tetrahydro-2H-pyran-4-yl)pyrrolidin-3-yl][(3R,4S)-3-(methoxymethyl)-4-{2-[4-(1H-tetrazol-5-yl)piperidin-1-yl]-4-(trifluoromethyl)phenyl}pyrrolidin-1-yl]methanone dihydrochloride 2 (66 mg) as a colorless powder. MS (ESI): m/z 716 [M+H]+

Example 280

[Chemical Formula 68]

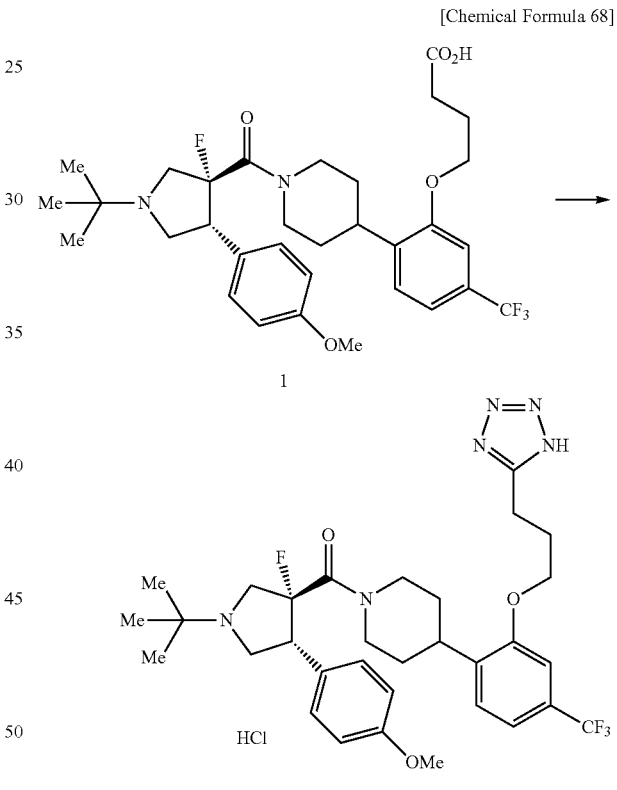

A solution of Compound 1 (193 mg) and tri-n-butyltin azide (901 μL) in toluene (6 mL) was heated under reflux for 14 hours, and then concentrated under reduced pressure. The residue was purified with silica gel column chromatography (chloroform:methanol=100:0-95:5-80:20). To a solution of the resultant compound in dichloromethane (1 mL) was added a solution of hydrochloric acid in ethyl acetate (4 mol/L, 100 μL), then the solvent was evaporated under reduced pressure, the residue was powdered with diethylether, collected by filtration, and dried under reduced pressure to give [(3R,4R)-1-tert-butyl-3-fluoro-4-(4-methoxyphenyl)pyrrolidin-3-yl](4-{2-[3-(1H-tetrazol-5-yl)propoxy]-4-(trifluoromethyl)phenyl}piperidin-1-yl)methanone hydrochloride 2 (66 mg) as a colorless powder. MS (ESI): m/z 633 [M+H]+

Example 281

[Chemical Formula 69]

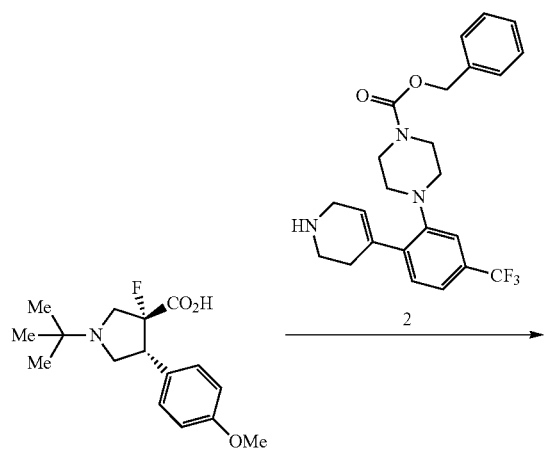

(1) Compound 1 and Compound 2 were treated in a similar manner to the above Example 10 to give Compound 3 (500 mg).

(2) To a solution of Compound 3 in methanol (10 mL)/tetrahydrofuran (10 mL) was added 10% palladium carbon (wetted with ca. 50% water, 250 mg), and the mixture was stirred under hydrogen atmosphere (1 atm) and at room temperature for 3 hours. To the reaction mixture were added acetic acid (10 mL) and 10% palladium carbon (wetted with ca. 50% water, 125 mg), and the mixture was stirred under hydrogen atmosphere (1 atm) and at room temperature for 1 hour. The insoluble matter was removed by filtration, and then the filtrate was concentrated under reduced pressure. To the residue were added dichloromethane and a saturated aqueous solution of sodium hydrogen carbonate, the mixture was stirred, and then the organic layer was separated. The resultant organic layer was dried, and then concentrated under reduced pressure to give [(3R,4R)-1-tert-butyl-3-fluoro-4-(4-methoxyphenyl)pyrrolidin-3-yl]{4-[2-(piperazin-1-yl)-4-(trifluoromethyl)phenyl]piperidin-1-yl}methanone 4 (379 mg) as a colorless powder. MS (ESI): m/z 591 [M+H]+

Example 282

[Chemical Formula 70]

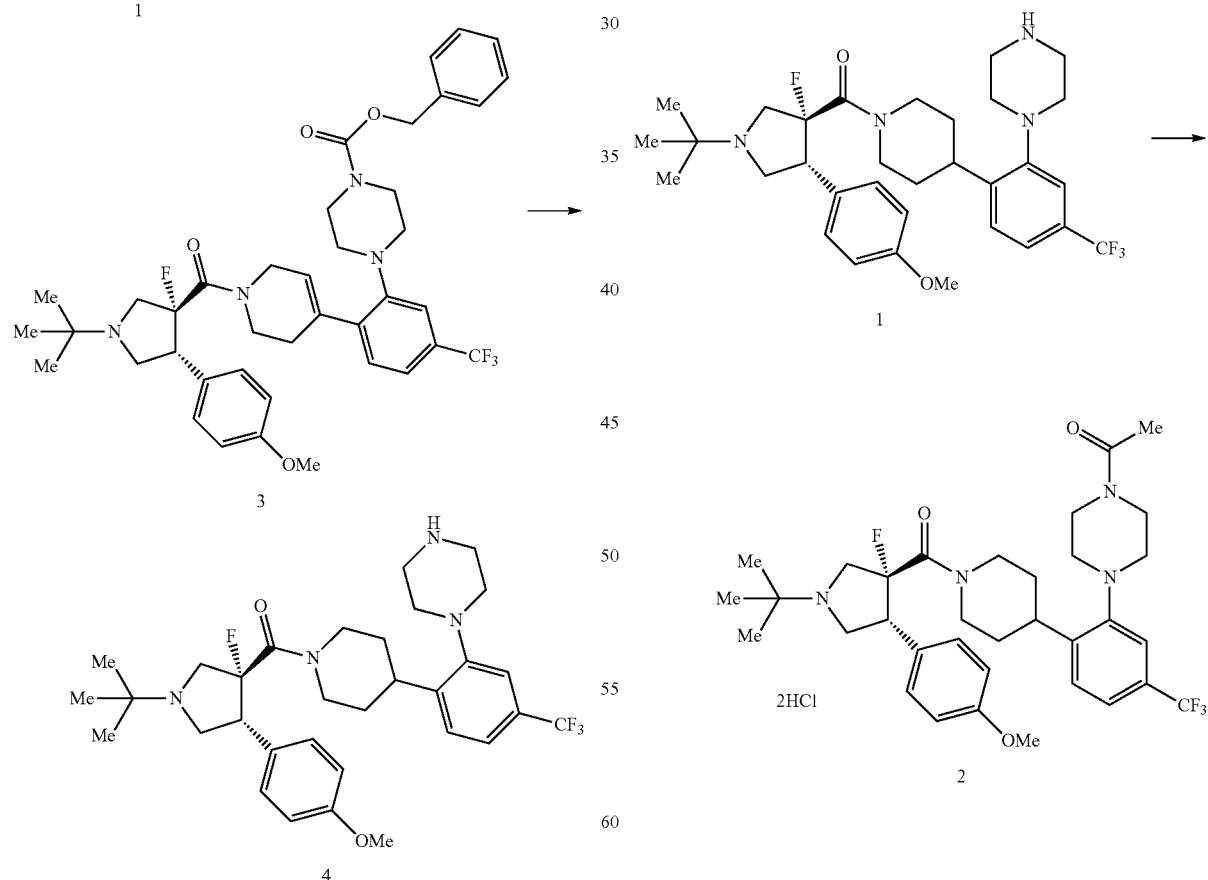

To a solution of Compound 1 (90 mg) and diisopropylethylamine (52 μL) in dichloromethane (2 mL) was added acetyl chloride (16 μL) under ice-cooling, and then the mixture was stirred at room temperature for 2 hours. To the reaction mixture were added water and dichloromethane, stirred, and then the organic layer was separated. The resultant organic layer was washed with saturated saline, dried, and then concentrated under reduced pressure. The residue was purified with NH silica gel column chromatography (hexane:ethyl acetate=75:25-25:75). To a solution of the resultant compound in dichloromethane (1 mL) was added a solution of hydrochloric acid in ethyl acetate (4 mol/L, 100 μL), then the solvent was evaporated under reduced pressure, the residue was powdered with diethylether, collected by filtration, and dried under reduced pressure to give 1-{4-[2-(1-{[(3R,4R)-1-tert-butyl-3-fluoro-4-(4-methoxyphenyl)pyrrolidin-3-yl]carbonyl}piperidin-4-yl)-5-(trifluoromethyl)phenyl]piperazin-1-yl}ethanone dihydrochloride 2 (86 mg) as a colorless powder. MS (ESI): m/z 633 [M+H]+

Example 283

[Chemical Formula 71]

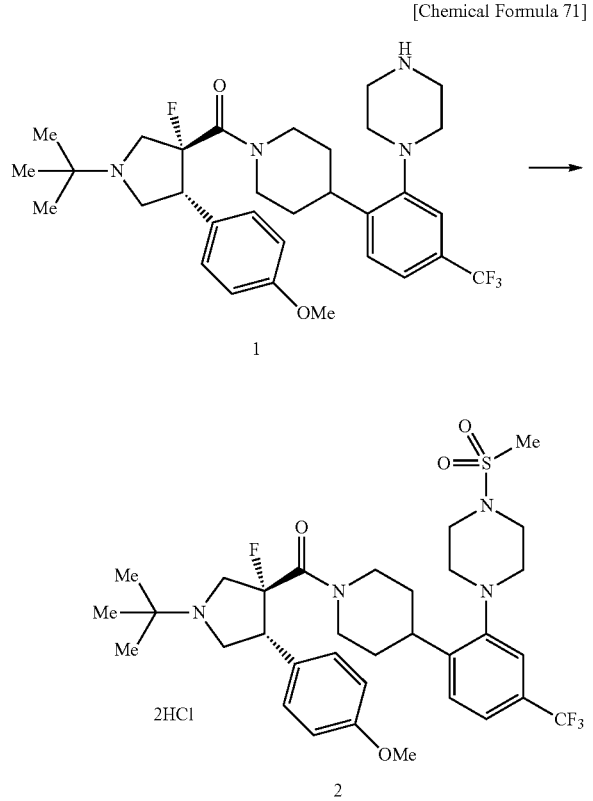 [SMILES: COc1ccc([C@@H]2CN(C(C)(C)C)C[C@@]2(F)C(=O)N2CCC(c3ccc(C(F)(F)F)cc3N3CCNCC3)CC2)cc1 ; COc1ccc([C@@H]2CN(C(C)(C)C)C[C@@]2(F)C(=O)N2CCC(c3ccc(C(F)(F)F)cc3N3CCN(C(N)=O)CC3)CC2)cc1 ; "2HCl"]

added a solution of hydrochloric acid in ethyl acetate (4 mol/L, 100 μL), then the solvent was evaporated under reduced pressure, the residue was powdered with diethylether, collected by filtration, and dried under reduced pressure to give [(3R,4R)-1-tert-butyl-3-fluoro-4-(4-methoxyphenyl)pyrrolidin-3-yl](4-{2-[4-(methylsulfonyl)piperazin-1-yl]-4-(trifluoromethyl)phenyl}piperidin-1-yl)methanone dihydrochloride 2 (93 mg) as a colorless powder. MS (ESI): m/z 669 [M+H]+

Example 284

[Chemical Formula 72]

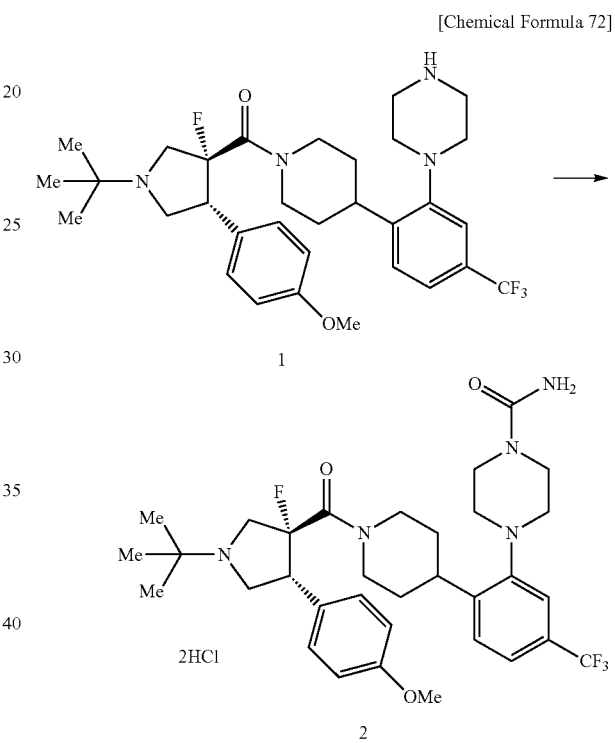

To a solution of Compound 1 (90 mg) and diisopropylethylamine (52 μL) in dichloromethane (2 mL) was added methanesulfonyl chloride (17 μL) under ice-cooling, and then the mixture was stirred at room temperature for 2 hours. To the reaction mixture were added water and dichloromethane, stirred, and then the organic layer was separated. The resultant organic layer was washed with saturated saline, dried, and then concentrated under reduced pressure. The residue was purified with NH silica gel column chromatography (hexane:ethyl acetate=90:10-40:60). To a solution of the resultant compound in dichloromethane (1 mL) was To a solution of Compound 1 (90 mg) and triethylamine (71 μL) in dichloromethane (3 mL) was added trimethylsilyl isocyanate (406 μL) under stirring, and then the mixture was stirred at room temperature for 2 hours. To the reaction mixture was added water, stirred, and then extracted with dichloromethane. The resultant organic layer was washed with saturated saline, dried, and concentrated under reduced pressure. The residue was purified with silica gel column chromatography (chloroform:methanol=98:2-88:12). To a solution of the resultant compound in dichloromethane (1 mL) was added a solution of hydrochloric acid in ethyl acetate (4 mol/L, 100 μL), then the solvent was evaporated under reduced pressure, the residue was powdered with diethylether, collected by filtration, and dried under reduced pressure to give 4-[2-(1-{[(3R,4R)-1-tert-butyl-3-fluoro-4-(4-methoxyphenyl)pyrrolidin-3-yl]carbonyl}piperidin-4-yl)-5-(trifluoromethyl)phenyl]piperazine-1-carboxamide dihydrochloride 2 (87 mg) as a colorless powder. MS (ESI): m/z 634 [M+H]+

Example 285

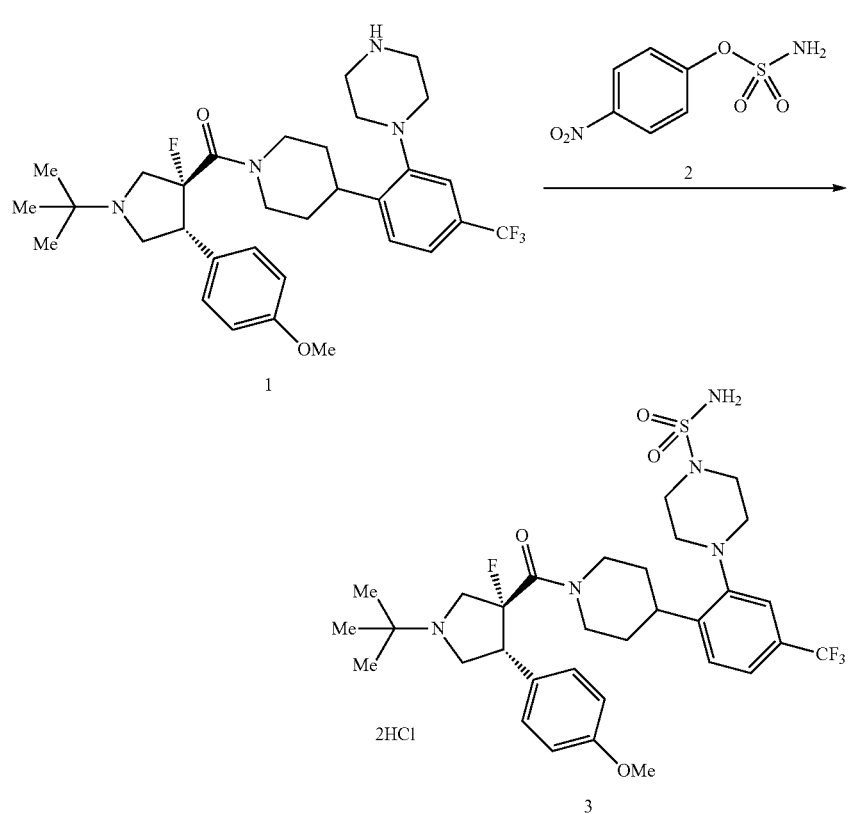

To a solution of Compound 1 (90 mg) and Compound 2 (39 mg) obtained by the method described in U.S. Pat. No. 5,192,785 in chloroform (1.5 mL)/acetonitrile (1.5 mL) was added triethylamine (105 μL) under stirring, and then the mixture was stirred at room temperature for 2 hours. To the reaction mixture was added a saturated aqueous solution of sodium hydrogen carbonate, stirred, and then extracted with dichloromethane. The resultant organic layer was washed with saturated saline, dried, and concentrated under reduced pressure. The residue was purified with silica gel column chromatography (chloroform:methanol=99:1-93:7). To a solution of the resultant compound in dichloromethane (1 mL) was added a solution of hydrochloric acid in ethyl acetate (4 mol/L, 75 μL), then the solvent was evaporated under reduced pressure, the residue was powdered with diethylether, collected by filtration, and dried under reduced pressure to give 4-[2-(1-{[(3R,4R)-1-tert-butyl-3-fluoro-4-(4-methoxyphenyl)pyrrolidin-3-yl]carbonyl}piperidin-4-yl)-5-(trifluoromethyl)phenyl]piperazine-1-sulfonamide dihydrochloride 3 (87 mg) as a colorless powder. MS (ESI): m/z 670 [M+H]+

Examples 286a, 286b

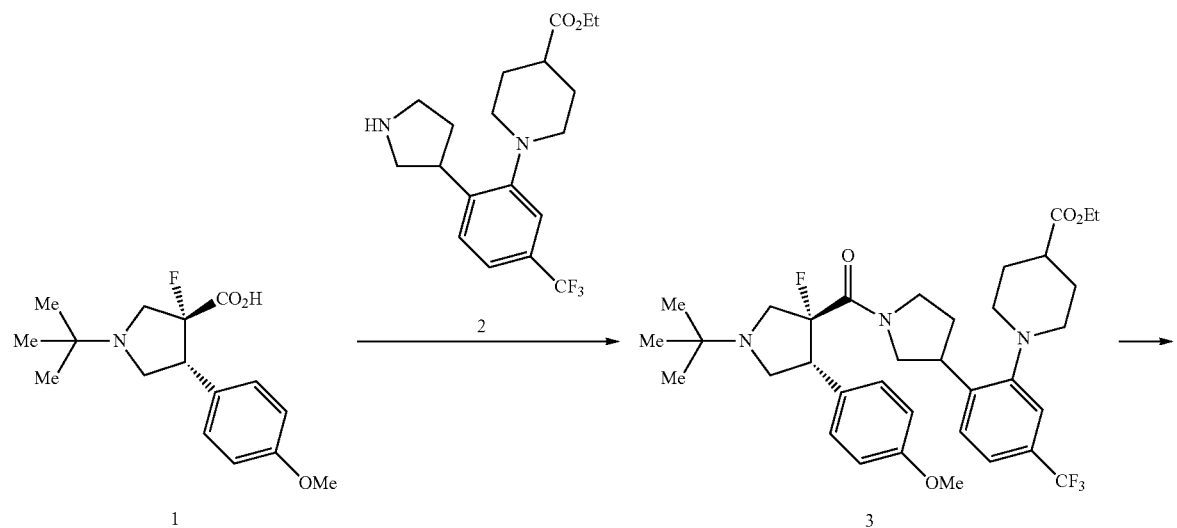

-continued

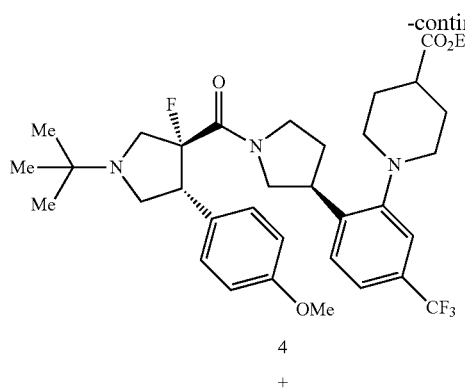

4

+

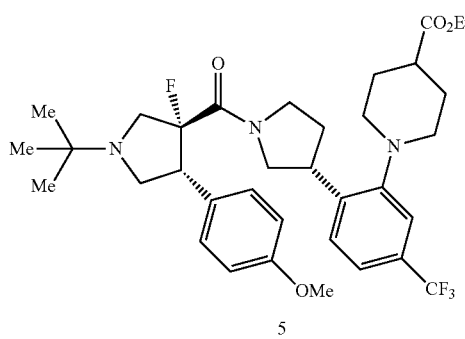

5

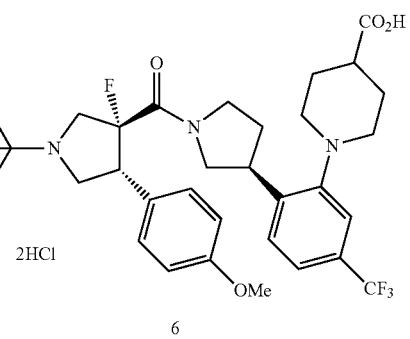

6

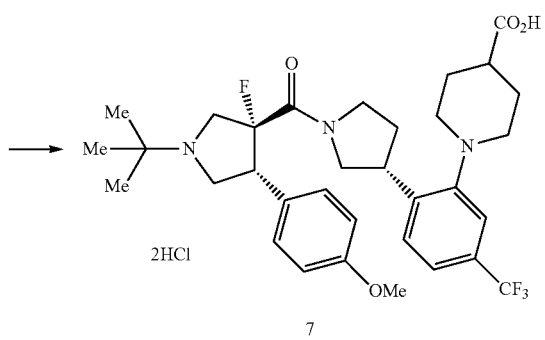

7

(1) Compound 1 (430 mg) and Compound 2 (343 mg) were treated in a similar manner to Example 10 to give Compound 3 (492 mg) as a mixture of diastereomers. MS (APCI): m/z 648 [M+H]+

(2) Compound 3 (420 mg) was separated and purified with CHIRAL HPLC (CHIRALPAK IA (20×250 mm) manufactured by DAICEL CORPORATION, Mobile phase: hexane/ethanol/diethylamine=60/40/0.1, Flow rate: 10 mL/min) to give optically active Compound 4 (184 mg) and optically active Compound 5 (169 mg) as colorless powders. Each MS (APCI): m/z 648 [M+H]+. (retention times of Compound 4 and Compound 5 on HPLC were 6.28 minutes and 7.52 minutes, respectively, with CHIRALPAK IA-3 (4.6× 150 mm) manufactured by DAICEL CORPORATION, under the conditions of Mobile phase: hexane/ethanol/diethylamine=60/40/0.1, Flow rate: 0.500 mL/min, Column temperature: 25° C.). The amide compound obtained by fusing the resultant optically active amine, which was obtained by the method in Reference Example 100, with Compound 1 was confirmed to be Compound 5, and Compounds 4 and Compounds 5 were confirmed to have the above configurations, respectively.

(3) Compound 4 and Compound 5 were treated in a similar manner to Example 11 to give 1-{2-[(3S)-1-{[(3R,4R)-1-tert-butyl-3-fluoro-4-(4-methoxyphenyl)pyrrolidin-3-yl]carbonyl}pyrrolidin-3-yl]-5-(trifluoromethyl)phenyl}piperidine-4-carboxylic acid dihydrochloride 6 (Example 286a) and 1-{2-[(3R)-1-{[(3R,4R)-1-tert-butyl-3-fluoro-4-(4-methoxyphenyl)pyrrolidin-3-yl]carbonyl}pyrrolidin-3-yl]-5-(trifluoromethyl)phenyl}piperidine-4-carboxylic acid dihydrochloride 7 (Example 286b) as colorless powders, respectively. Each MS (APCI): m/z 620 [M+H]+

Examples 287-294

A corresponding starting compound was treated in a similar manner to the above Example 286 to give an ester compound as an intermediate, and subsequently treated in a similar manner to Example 11 to give each compound in the following Table 17. The HPLC analysis of the ester intermediate was carried out with HPLC column (4.6×150 mm) manufactured by DAICEL CORPORATION, under Flow rate: 0.500 mL/min, Column temperature: 25° C., and the following conditions.

Analysis Conditions:
A: CHIRALPAK IA-3, Mobile phase: Hexane/Isopropanol/Tetrahydrofuran/Diethylamine=80/10/10/0.1
B: CHIRALPAK IC-3, Mobile phase: Ethanol/Diethylamine=100/0.1
C: CHIRALPAK IA-3, Mobile phase: Hexane/Ethanol/Diethylamine=80/20/0.1
D: CHIRALPAK IA-3, Mobile phase: Hexane/Isopropanol/Tetrahydrofuran/Diethylamine=80/10/10/0.1

TABLE 17

| Example | Structural form | Ester intermediate | R.T. 1) | A.C. 2) |
|---|---|---|---|---|
| 287 | (structure) 2HCl | (structure) | 10.48 min. | A |
| 288 | MS (ESI): m/z 676 [M + H]+ | MS (ESI): m/z 690 [M + H]+ | 13.77 min. | |
| 289 | (structure) 2HCl | (structure) | 13.45 min. | B |
| 290 | MS (APCI): m/z 648 [M + H]+ | MS (ESI): m/z 676 [M + H]+ | 16.70 min. | |
| 291 | (structure) 2HCl | (structure) | 8.27 min. | C |
| 292 | MS (ESI): m/z 646 [M + H]+ | MS (ESI): m/z 660 [M + H]+ | 9.51 min. | |
| 293 | (structure) 2HCl | (structure) | 8.25 min. | D |
| 294 | MS (ESI): m/z 668 [M + H]+ | MS (ESI): m/z 682 [M + H]+ | 9.71 min. | |

1) Retention time of ester intermediate
2) Analysis condition

Example 295

[Chemical Formula 75]

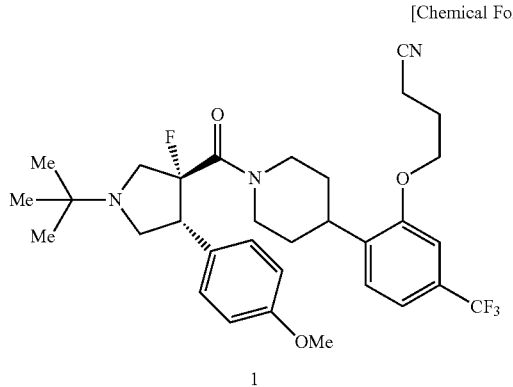

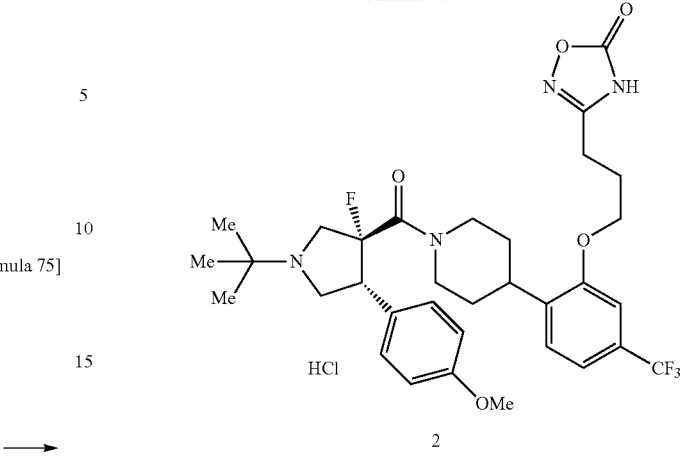

An ethanol solution (4 mL) of Compound 1 (300 mg), hydroxylamine hydrochloride (42 mg), and triethylamine (106 μL) was stirred at room temperature for 62 hours. To the reaction mixture were added water and ethyl acetate, stirred, and then extracted with ethyl acetate. The resultant organic layer was concentrated under reduced pressure, and the residue was purified with silica gel column chromatography (chloroform:methanol=99:1-90:10). A solution of the resultant mixture (165 mg) and 1,1'-carbonyldiimidazole (215 mg) in tetrahydrofuran (3 mL) was stirred at 70° C. for 6 hours. The reaction solution was concentrated under reduced pressure, to the residue were added water and chloroform, stirred, and then the organic layer was separated. The resultant organic layer was washed with saturated saline, dried, concentrated under reduced pressure, and the residue was purified with silica gel column chromatography (chloroform:methanol=99:1-93:7). To a solution of the resultant compound in dichloromethane (1 mL) was added a solution of hydrochloric acid in ethyl acetate (4 mol/L, 66 μL), then the solvent was evaporated under reduced pressure, the residue was powdered with diethylether, collected by filtration, and dried under reduced pressure to give 3-{3-[2-(1-{[(3R,4R)-1-tert-butyl-3-fluoro-4-(4-methoxyphenyl)pyrrolidin-3-yl]carbonyl}piperidin-4-yl)-5-(trifluoromethyl)phenoxy]propyl}-1,2,4-oxadiazole-5(4H)-one hydrochloride 2 (57 mg) as a colorless powder. MS (ESI): m/z 649 [M+H]+

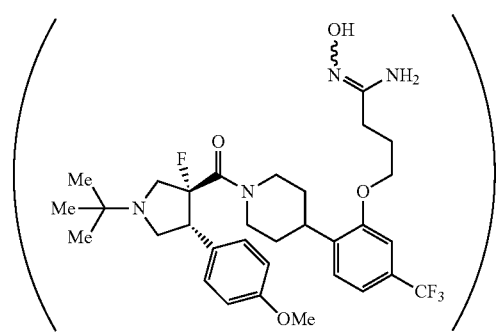

Examples 296a, 296b, 296c

[Chemical Formula 76]

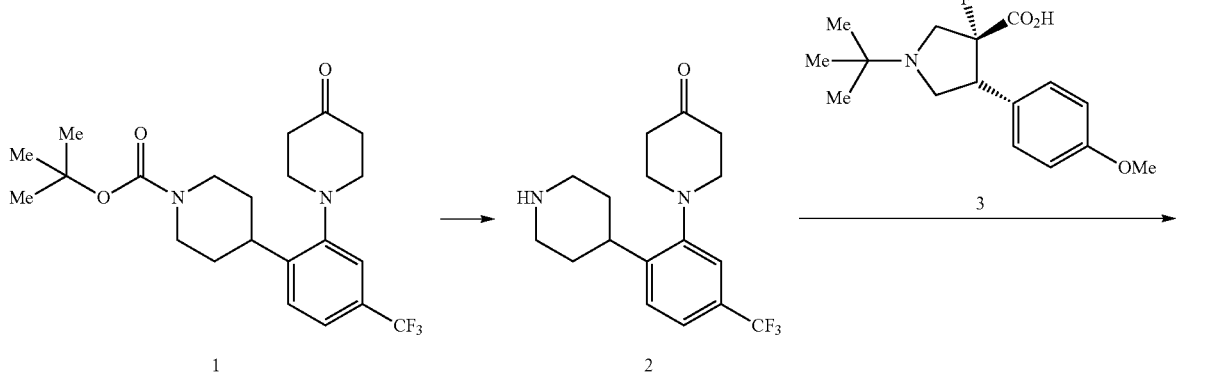

-continued

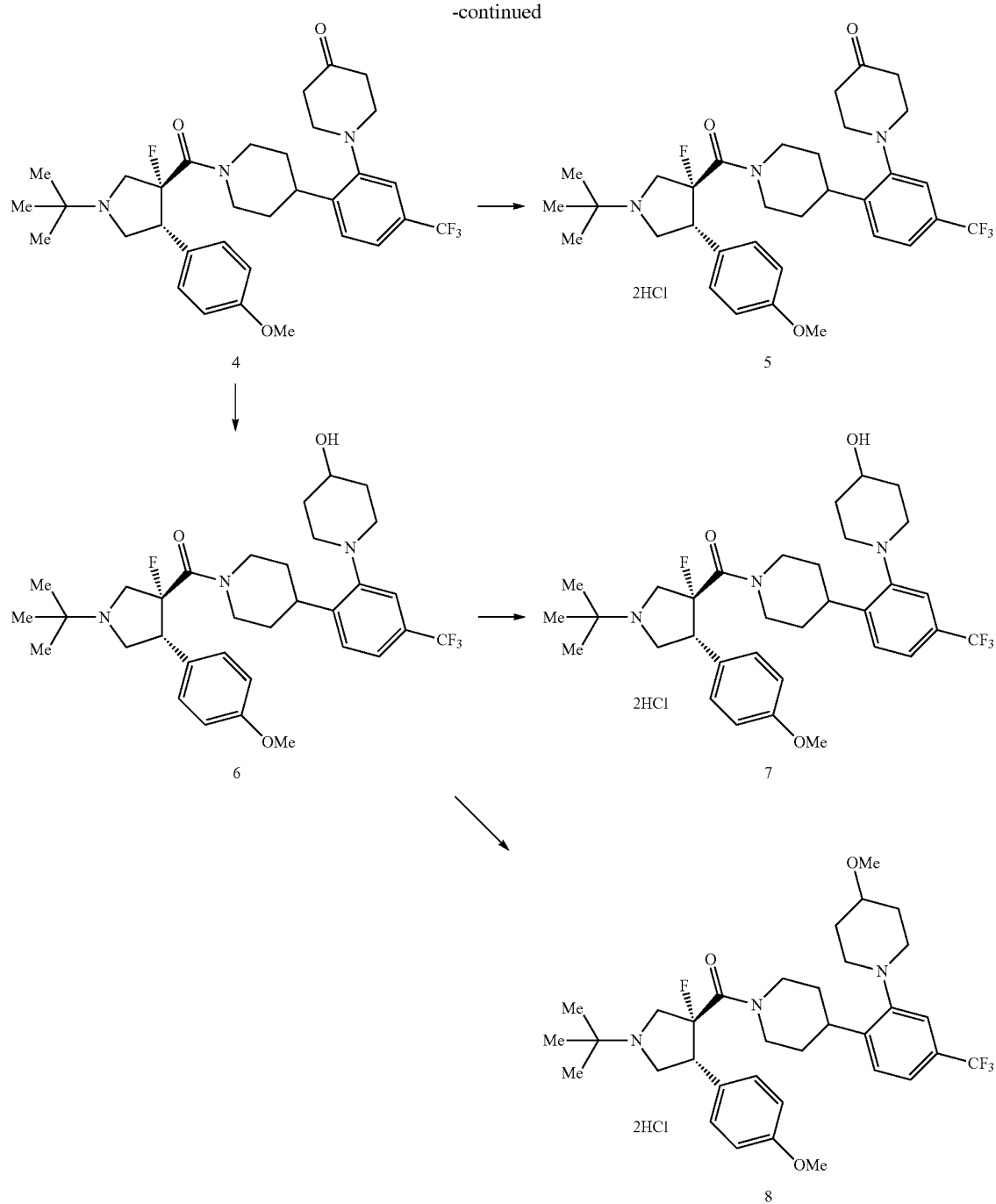

(1) To a solution of Compound 1 (302 mg) in chloroform (7 mL) was added trifluoroacetic acid (3.5 mL) under ice-cooling, and the mixture was stirred at room temperature for 1.5 hours. To the reaction mixture was added an aqueous solution of sodium hydroxide (2 mol/mL) under ice-cooling to adjust it into pH=8, and extracted with chloroform. The resultant organic layer was washed with saturated saline, then dried, and concentrated under reduced pressure. To a solution of the resultant compound (Compound 2) in N,N-dimethylformamide (7.1 mL) were added Compound 3 (314 mg), 1-ethyl-3-(3-dimethylaminopropyl)carbodiimide hydrochloride (272 mg), 1-hydroxy-7-azabenzotriazole (193 mg), and triethylamine (200 μL), and the mixture was stirred at room temperature for 16 hours. To the reaction mixture were added a saturated aqueous solution of sodium hydrogen carbonate and ethyl acetate, stirred, and then the organic layer was separated. The resultant organic layer was washed with saturated saline, dried, and concentrated under reduced pressure. The residue was purified with silica gel column chromatography (chloroform:methanol=100:0-90:10) to give Compound 4 (403 mg) as a pale yellow viscous material. MS (ESI): m/z 604 [M+H]+

(2) To a solution of Compound 4 (88 mg) in dichloromethane (1.5 mL) was added a solution of hydrochloric acid in ethyl acetate (4 mol/L, 70 μL), then the solvent was evaporated under reduced pressure, the residue was powdered with diisopropylether, collected by filtration, and dried under reduced pressure to give 1-[2-(1-{[(3R,4R)-1-tert-butyl-3-fluoro-4-(4-methoxyphenyl)pyrrolidin-3-yl]carbonyl}piperidin-4-yl)-5-(trifluoromethyl)phenyl]piperidine-4-one dihydrochloride 5 (Example 296a, 69 mg) as a colorless powder. MS (ESI): m/z 604 [M+H]+

(3) To a solution of Compound 4 (314 mg) in methanol (5 mL) was added sodium borohydride (24 mg) under ice-cooling, and the mixture was stirred at the same temperature for 1.5 hours. To the reaction mixture was added water, and then extracted with chloroform. The organic layer was washed with saturated saline, then dried, and concentrated under reduced pressure. The residue was purified with silica gel column chromatography (chloroform:methanol=100:0-90:10) to give Compound 6 (202 mg) as a colorless viscous material. MS (ESI): m/z 606 [M+H]+

(4) To a solution of Compound 6 (100 mg) in dichloromethane (1.7 mL) was added a solution of hydrochloric acid in 1,4-dioxane (4 mol/L, 83 μL), then the solvent was evaporated under reduced pressure, the residue was powdered with diisopropylether, collected by filtration, and dried under reduced pressure to give [(3R,4R)-1-tert-butyl-3-fluoro-4-(4-methoxyphenyl)pyrrolidin-3-yl]{4-[2-(4-hydroxypiperidin-1-yl)-4-(trifluoromethyl)phenyl]piperidin-1-yl}methanone dihydrochloride 7 (Example 296b, 105 mg) as a colorless powder. MS (ESI): m/z 606 [M+H]+

(5) To a solution of Compound 6 (150 mg) in N,N-dimethylformamide (1.2 mL) was added sodium hydride (60% in oil, 15 mg) under ice-cooling, the mixture was stirred for 10 minutes, then methyl iodide (31 μL) was added thereto, and stirred at room temperature for 24 hours. To the reaction mixture were added sodium hydride (60% in oil, 50 mg) and methyl iodide (160 μL), and stirred at 60° C. for 2 hours. The reaction mixture was cooled to room temperature, then water and ethyl acetate were added thereto, stirred, and the organic layer was separated. The resultant organic layer was washed with water and saturated saline, dried, concentrated under reduced pressure, and the residue was purified with silica gel column chromatography (chloroform:methanol=100:0-90:10). To a solution of the resultant compound in dichloromethane (1 mL) was added a solution of hydrochloric acid in ethyl acetate (4 mol/L, 50 μL), and then the solvent was evaporated under reduced pressure. The residue was powdered with diisopropylether, collected by filtration, and dried under reduced pressure to give [(3R,4R)-1-tert-butyl-3-fluoro-4-(4-methoxyphenyl)pyrrolidin-3-yl]{4-[2-(4-methoxypiperidin-1-yl)-4-(trifluoromethyl)phenyl]piperidin-1-yl}methanone dihydrochloride 8 (Example 296c, 62 mg) as a colorless powder. MS (ESI): m/z 620 [M+H]+

Examples 297a, 297b, 297c

[Chemical Formula 77]

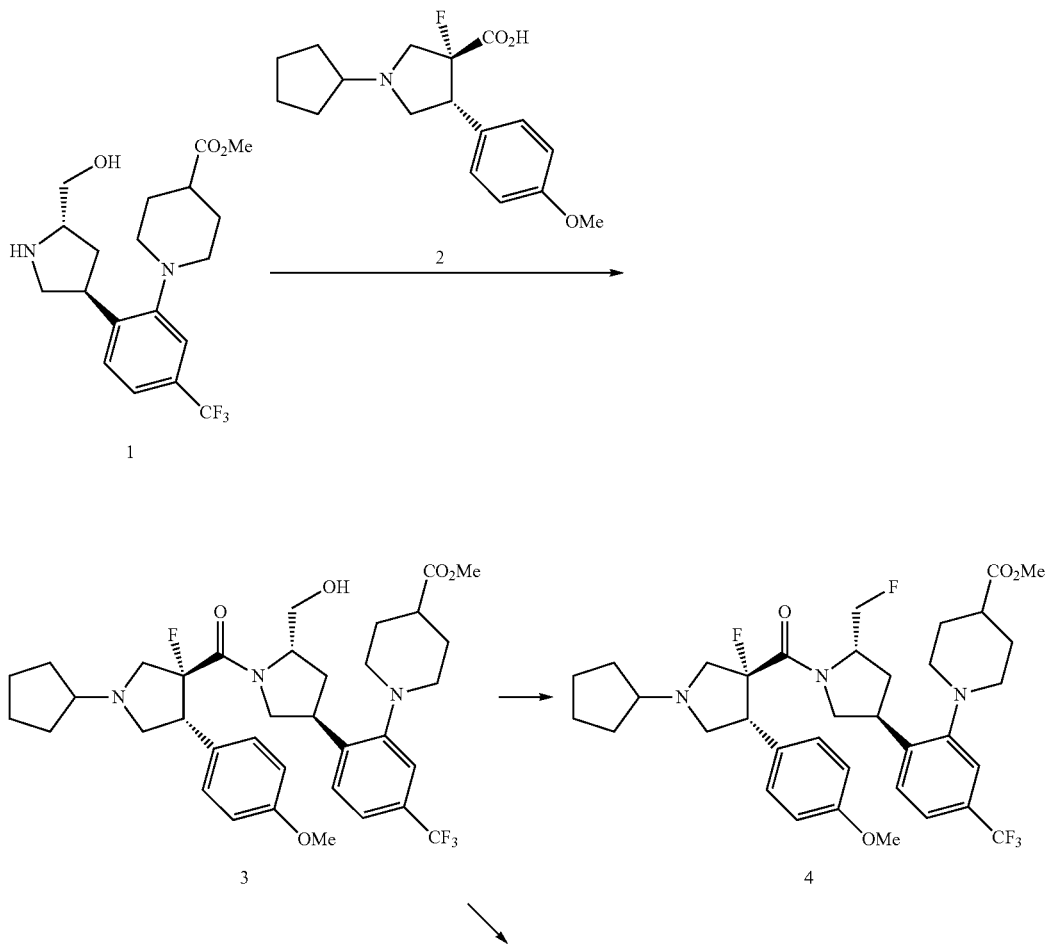

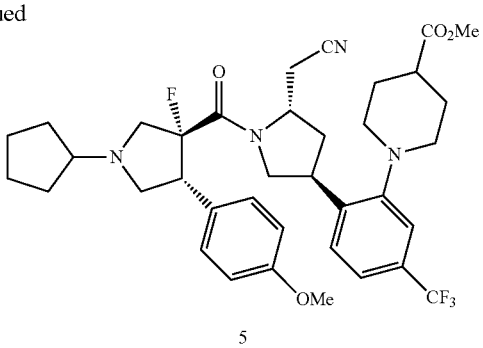

5

(1) To a solution of Compound 1 (348 mg) in N,N-dimethylformamide (15 mL) were added triethylamine (422 μL) and N,O-bis(trimethylsilyl)acetamide (204 μL) at room temperature, and the mixture was stirred for 30 minutes. To the mixture were added Compound 2 (349 mg), 1-ethyl-3-(3-dimethylaminopropyl)carbodiimide hydrochloride (290 mg), and 1-hydroxy-7-azabenzotriazole (206 mg), and stirred at room temperature for 15 hours. To the reaction mixture were added water and ethyl acetate, stirred, and then the organic layer was separated. The resultant organic layer was washed with water and saturated saline, dried, and concentrated under reduced pressure. The residue was purified with NH silica gel column chromatography (hexane:ethyl acetate=90:10-50:50) to give methyl 1-{2-[(3S,5S)-1-{[(3R,4R)-1-cyclopentyl-3-fluoro-4-(4-methoxyphenyl)pyrrolidin-3-yl]carbonyl}-5-(hydroxymethyl)pyrrolidin-3-yl]-5-(trifluoromethyl)phenyl}piperidine-4-carboxylate 3 (Example 297a, 406 mg). MS (ESI): m/z 676 [M+H]+

(2) Under nitrogen atmosphere, to a solution of Compound 3 (101 mg) in dichloromethane (3 mL) was added (diethylamino)sulfurtrifluoride (59 μL) under ice-cooling, and then the mixture was stirred at room temperature for 15 hours. To the reaction solution was added a saturated aqueous solution of sodium hydrogen carbonate, stirred, and then extracted with dichloromethane. The resultant organic layer was washed with saturated saline, dried, and concentrated under reduced pressure. The residue was purified with NH silica gel column chromatography (hexane:ethyl acetate=95:5-60:40) and subsequently silica gel column chromatography (hexane:ethyl acetate=80:20-30:70) to give 1-{2-[(3S,5S)-1-{[(3R,4R)-1-cyclopentyl-3-fluoro-4-(4-methoxyphenyl)pyrrolidin-3-yl]carbonyl}-5-(fluoromethyl)pyrrolidin-3-yl]-5-(trifluoromethyl)phenyl}piperidine-4-carboxylic acid dihydrochloride 4 (Example 297b, 45 mg). MS (ESI): m/z 678 [M+H]+

(3) To a solution of Compound 3 (119 mg) and triphenylphosphine (370 mg) in tetrahydrofuran (4 mL) were added acetone cyanohydrin (129 μL) and diethyl azodicarboxylate (2.2 mol/L toluene solution, 640 μL) at room temperature, and then the mixture was stirred for 14 hours. The reaction solution was concentrated under reduced pressure, and the residue was purified with silica gel column chromatography (hexane:ethyl acetate=80:20-30:70) to give methyl 1-{2-[(3S,5S)-5-(cyanomethyl)-1-{[(3R,4R)-1-cyclopentyl-3-fluoro-4-(4-methoxyphenyl)pyrrolidin-3-yl]carbonyl}pyrrolidin-3-yl]-5-(trifluoromethyl)phenyl}piperidine-4-carboxylate 5 (Example 297c, 90 mg). MS (ESI): m/z 685 [M+H]+

Examples 298-300

Each compound in the above Example 297a, Example 297b, and Example 297c was treated in a similar manner to the above Example 11 to give each compound in the following Table 18.

TABLE 18

| Example | Compound | Salt | MS |
|---|---|---|---|
| 298 | | 2 HCl | (ESI): m/z 662 [M + H]+ |
| 299 | | 2 HCl | (ESI): m/z 664 [M + H]+ |
| 300 | | 2 HCl | (ESI): m/z 671 [M + H]+ |

Example 301

[Chemical Formula 78]

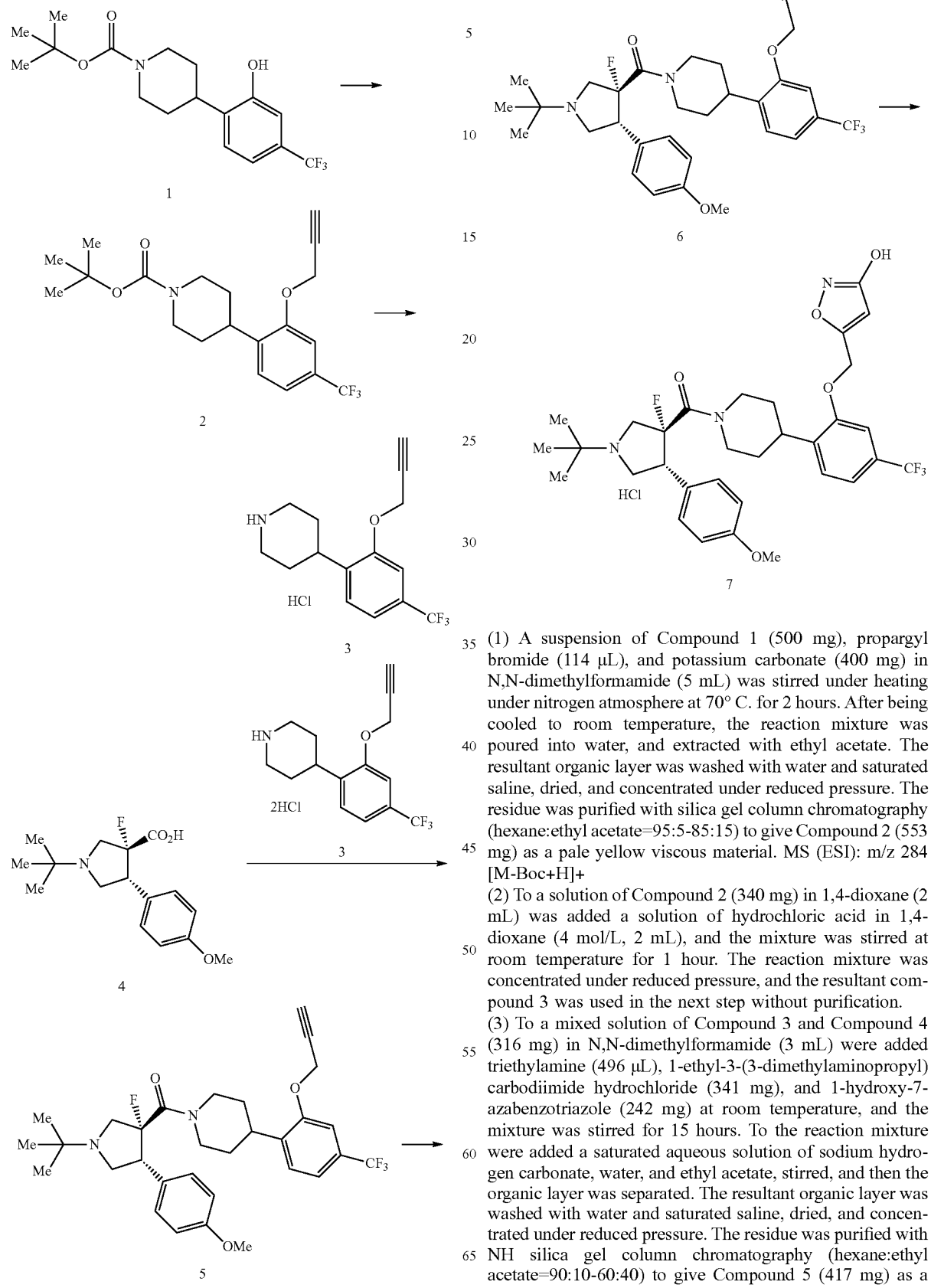

(1) A suspension of Compound 1 (500 mg), propargyl bromide (114 µL), and potassium carbonate (400 mg) in N,N-dimethylformamide (5 mL) was stirred under heating under nitrogen atmosphere at 70° C. for 2 hours. After being cooled to room temperature, the reaction mixture was poured into water, and extracted with ethyl acetate. The resultant organic layer was washed with water and saturated saline, dried, and concentrated under reduced pressure. The residue was purified with silica gel column chromatography (hexane:ethyl acetate=95:5-85:15) to give Compound 2 (553 mg) as a pale yellow viscous material. MS (ESI): m/z 284 [M-Boc+H]+

(2) To a solution of Compound 2 (340 mg) in 1,4-dioxane (2 mL) was added a solution of hydrochloric acid in 1,4-dioxane (4 mol/L, 2 mL), and the mixture was stirred at room temperature for 1 hour. The reaction mixture was concentrated under reduced pressure, and the resultant compound 3 was used in the next step without purification.

(3) To a mixed solution of Compound 3 and Compound 4 (316 mg) in N,N-dimethylformamide (3 mL) were added triethylamine (496 µL), 1-ethyl-3-(3-dimethylaminopropyl)carbodiimide hydrochloride (341 mg), and 1-hydroxy-7-azabenzotriazole (242 mg) at room temperature, and the mixture was stirred for 15 hours. To the reaction mixture were added a saturated aqueous solution of sodium hydrogen carbonate, water, and ethyl acetate, stirred, and then the organic layer was separated. The resultant organic layer was washed with water and saturated saline, dried, and concentrated under reduced pressure. The residue was purified with NH silica gel column chromatography (hexane:ethyl acetate=90:10-60:40) to give Compound 5 (417 mg) as a colorless powder. MS (ESI): m/z 561 [M+H]+

(4) To a solution of Compound 5 (410 mg) in diethylether (3 mL) was added dropwise a solution of methyllithium-diethylether (1.14 mol/mL, 772 μL) under nitrogen atmosphere at −78° C., the mixture was stirred for 1.5 hours, then a solution of methyl chloroformate (138 mg) in diethylether (1 mL) was added thereto, and stirred at the same temperature for 1 hour. After being stirred at room temperature for additional 3 hours, to the reaction mixture were added water and ethyl acetate, and stirred. The organic layer was separated, and the resultant organic layer was washed with water and saturated saline, dried, and concentrated under reduced pressure. The residue was purified with silica gel column chromatography (chloroform:methanol=100:0-95:5) to give Compound 6 (416 mg) as a colorless viscous material. MS (ESI): m/z 619 [M+H]+

(5) To a solution of hydroxylamine hydrochloride (410 mg) in methanol (4 mL) was added an aqueous solution of sodium hydroxide (2 mol/mL, 860 μL) under ice-cooling, then a solution of Compound 6 (410 mg) in methanol (2 mL) was added dropwise thereto, and the mixture was stirred at room temperature for 20 hours. The reaction mixture was neutralized with a solution of citric acid aqueous, then water and ethyl acetate were added thereto, and stirred. The organic layer was separated, and the resultant organic layer was washed with water and saturated saline, dried, and concentrated under reduced pressure. The residue was purified with silica gel column chromatography (chloroform:methanol=99:1-90:10). To a solution of the resultant compound in dichloromethane (1 mL) was added a solution of hydrochloric acid in ethyl acetate (4 mol/L, 165 μL), then the solvent was evaporated under reduced pressure, the residue was powdered with diethylether, collected by filtration, and dried under reduced pressure to give [(3R,4R)-1-tert-butyl-3-fluoro-4-(4-methoxyphenyl)pyrrolidin-3-yl](4-{2-[(3-hydroxyisoxazol-5-yl)methoxy]-4-(trifluoromethyl)phenyl}piperidin-1-yl)methanone hydrochloride 7 (140 mg) as a colorless powder. MS (APCI): m/z 620 [M+H]+

Example 302

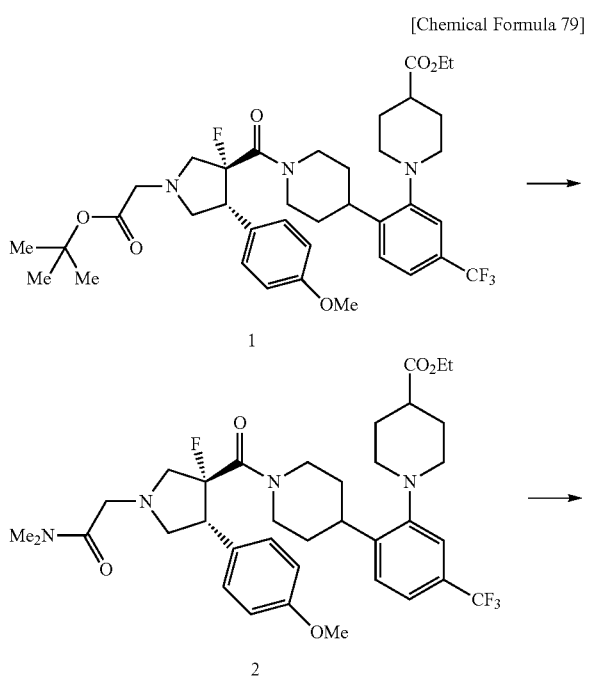

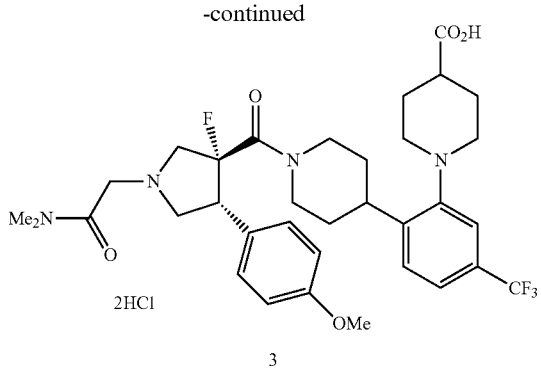

(1) To a solution of Compound 1 (152 mg) in 1,4-dioxane (1.5 mL) was added a solution of hydrochloric acid in 1,4-dioxane (4 mol/L, 1.5 mL), and then the mixture was stirred at room temperature for 22 hours. The reaction mixture was concentrated under reduced pressure, to the residue were added N,N-dimethylformamide (2 mL), an aqueous solution of dimethylamine (50%, 38 μL), 1-ethyl-3-(3-dimethylaminopropyl)carbodiimide hydrochloride (81 mg), 1-hydroxy-7-azabenzotriazole (57 mg), and triethylamine (117 μL), and the mixture was stirred at room temperature for 18 hours. To the reaction mixture were added a saturated aqueous solution of sodium hydrogen carbonate, water, and ethyl acetate, stirred, and then the organic layer was separated. The resultant organic layer was washed with water and saturated saline, dried, and concentrated under reduced pressure. The residue was purified with NH silica gel column chromatography (hexane:ethyl acetate=40:60-0:100).

(2) To a solution of Compound 2 (73 mg) in ethanol (2 mL) was added an aqueous solution of sodium hydroxide (2 mol/L, 636 μL) at room temperature, and the mixture was stirred for 1 hour. To the reaction mixture was added an aqueous solution of hydrochloric acid (2 mol/L, 650 μL), and concentrated under reduced pressure. To the residue were added water and dichloromethane, stirred, then the organic layer was separated, dried, and concentrated under reduced pressure. The residue was purified with silica gel column chromatography (chloroform:methanol=99:1-85:15). To a solution of the resultant compound in dichloromethane (1 mL) was added a solution of hydrochloric acid in ethyl acetate (4 mol/L, 60 μL), then the solvent was evaporated under reduced pressure, the residue was powdered with diethylether, collected by filtration, and dried under reduced pressure to give 1-[2-(1-{[(3R,4R)-1-[2-(dimethylamino)-2-oxoethyl]-3-fluoro-4-(4-methoxyphenyl)pyrrolidin-3-yl]carbonyl}piperidin-4-yl)-5-(trifluoromethyl)phenyl]piperidine-4-carboxylic acid dihydrochloride 3 (72-mg) as a colorless powder. MS (APCI): m/z 663 [M+H]+

Examples 303-318

A corresponding starting compound was treated in a similar manner to the above Example 302 to give each compound in the following Table 19.

TABLE 19

| Example | Compound | Salt MS |
|---|---|---|
| 303 | | 2 HCl (APCI): m/z 677 [M + H]+ |
| 304 | | 2 HCl (ESI): m/z 691 [M + H]+ |
| 305 | | 2 HCl (ESI): m/z 693 [M + H]+ |
| 306 | | 2 HCl (APCI): m/z 733 [M + H]+ |
| 307 | | 2 HCl (APCI): m/z 737 [M + H]+ |

TABLE 19-continued

| Example | Compound | Salt MS |
|---|---|---|
| 308 | | 2 HCl (APCI): m/z 737 [M + H]+ |
| 309 | | 2 HCl (APCI): m/z 719 [M + H]+ |
| 310 | | 2 HCl (APCI): m/z 733 [M + H]+ |
| 311 | | 2 HCl (APCI): m/z 733 [M + H]+ |
| 312 | | 2 HCl (APCI): m/z 763 [M + H]+ |

TABLE 19-continued

| Example | Compound | Salt MS |
|---|---|---|
| 313 | | 2 HCl (APCI): m/z 763 [M + H]+ |
| 314 | | 2 HCl (APCI): m/z 735 [M + H]+ |
| 315 | | 2 HCl (APCI): m/z 769 [M + H]+ |
| 316 | | 2 HCl (APCI): m/z 787 [M + H]+ |
| 317 | | 2 HCl (APCI): m/z 787 [M + H]+ |

TABLE 19-continued

| Example | Compound | Salt MS |
|---|---|---|
| 318 | 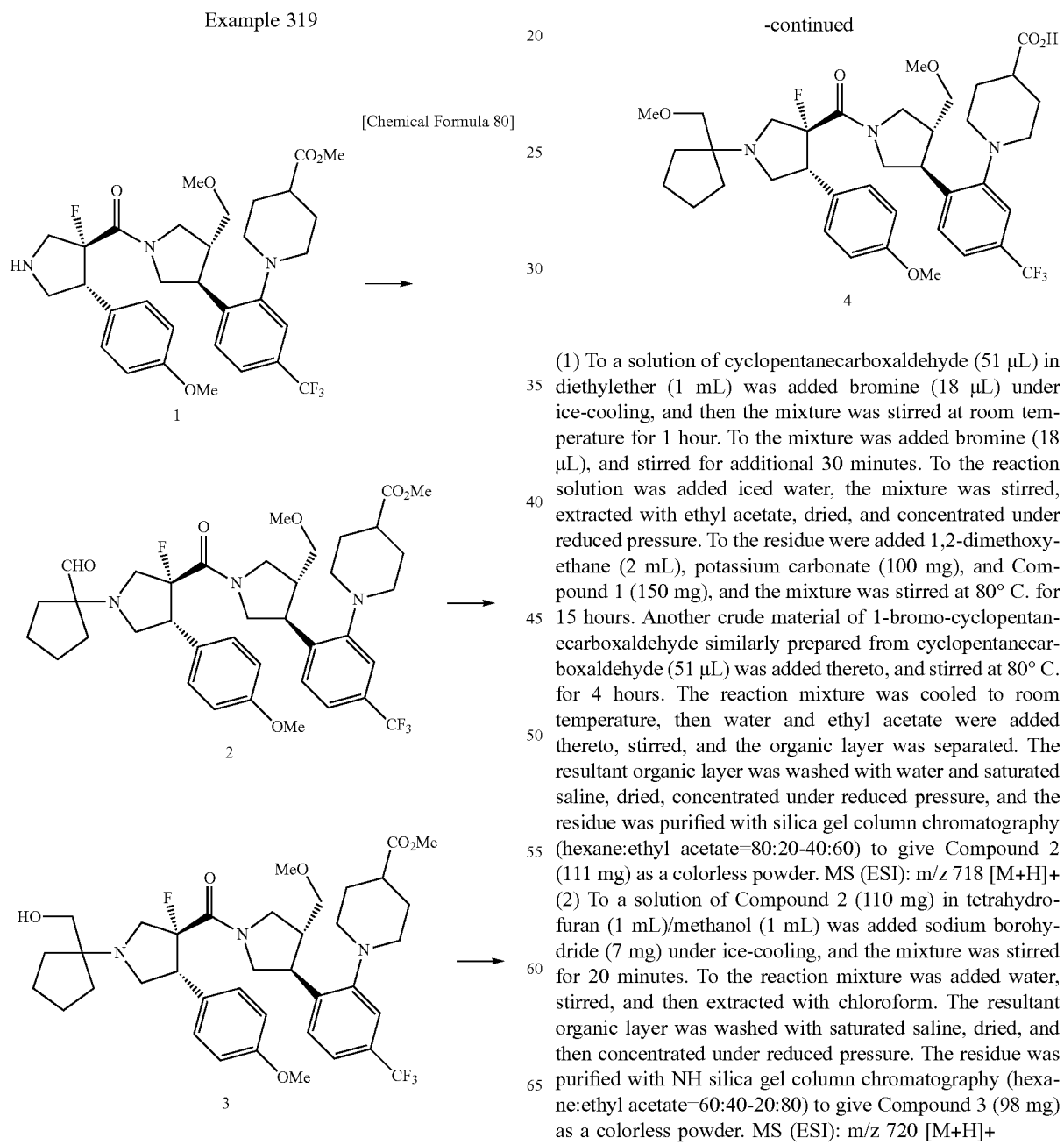 | 2 HCl (APCI): m/z 691 [M + H]+ |

Example 319

[Chemical Formula 80]

(1) To a solution of cyclopentanecarboxaldehyde (51 μL) in diethylether (1 mL) was added bromine (18 μL) under ice-cooling, and then the mixture was stirred at room temperature for 1 hour. To the mixture was added bromine (18 μL), and stirred for additional 30 minutes. To the reaction solution was added iced water, the mixture was stirred, extracted with ethyl acetate, dried, and concentrated under reduced pressure. To the residue were added 1,2-dimethoxyethane (2 mL), potassium carbonate (100 mg), and Compound 1 (150 mg), and the mixture was stirred at 80° C. for 15 hours. Another crude material of 1-bromo-cyclopentanecarboxaldehyde similarly prepared from cyclopentanecarboxaldehyde (51 μL) was added thereto, and stirred at 80° C. for 4 hours. The reaction mixture was cooled to room temperature, then water and ethyl acetate were added thereto, stirred, and the organic layer was separated. The resultant organic layer was washed with water and saturated saline, dried, concentrated under reduced pressure, and the residue was purified with silica gel column chromatography (hexane:ethyl acetate=80:20-40:60) to give Compound 2 (111 mg) as a colorless powder. MS (ESI): m/z 718 [M+H]+

(2) To a solution of Compound 2 (110 mg) in tetrahydrofuran (1 mL)/methanol (1 mL) was added sodium borohydride (7 mg) under ice-cooling, and the mixture was stirred for 20 minutes. To the reaction mixture was added water, stirred, and then extracted with chloroform. The resultant organic layer was washed with saturated saline, dried, and then concentrated under reduced pressure. The residue was purified with NH silica gel column chromatography (hexane:ethyl acetate=60:40-20:80) to give Compound 3 (98 mg) as a colorless powder. MS (ESI): m/z 720 [M+H]+

(3) To a solution of Compound 3 (96 mg) in N,N-dimethylformamide (1 mL) was added sodium hydride (60% in oil, 6.4 mg) under ice-cooling, the mixture was stirred for 5 minutes, then methyl iodide (12.5 µL) was added thereto, and stirred at room temperature for 1 hour. Sodium hydride (60% in oil, 6.4 mg) and methyl iodide (12.5 µL) were added thereto, and the mixture was stirred at room temperature for 1 hour. To the reaction solution were added water and 1N hydrochloric acid to adjust it into pH=7, and then extracted with ethyl acetate. The resultant organic layer was dried, and concentrated under reduced pressure. The residue was dissolved in methanol (1 mL), an aqueous solution of sodium hydroxide (2 mol/L, 266 µL) was added thereto at room temperature, and the mixture was stirred for 14 hours. To the reaction mixture was added an aqueous solution of hydrochloric acid (2 mol/L, 266 µL), stirred, and then concentrated under reduced pressure. The residue was suspended in chloroform, insoluble matter was removed by filtration, and then the filtrate was purified with silica gel column chromatography (chloroform:methanol=99:1-90:10). To a solution of the resultant compound in dichloromethane (1 mL) was added a solution of hydrochloric acid in ethyl acetate (4 mol/L, 50 µL), then the solvent was evaporated under reduced pressure, the residue was powdered with diisopropylether, collected by filtration, and dried under reduced pressure to give 1-{2-[(3S,4R)-1-{[(3R,4R)-3-fluoro-1-[1-(methoxymethyl)cyclopentyl]-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid dihydrochloride 4 (70 mg) as a colorless powder. MS (ESI): m/z 720 [M+H]+

Examples 320-322

A corresponding starting compound was treated in a similar manner to the above Example 319 to give each compound in the following Table 20.

TABLE 20

| Example MS | Compound | Salt |
|---|---|---|
| 320 | | 2 HCl (ESI): m/z 650 [M + H]+ |
| 321 | | 2 HCl (ESI): m/z 664 [M + H]+ |
| 322 | | 2 HCl (ESI): m/z 692 [M + H]+ |

Example 323

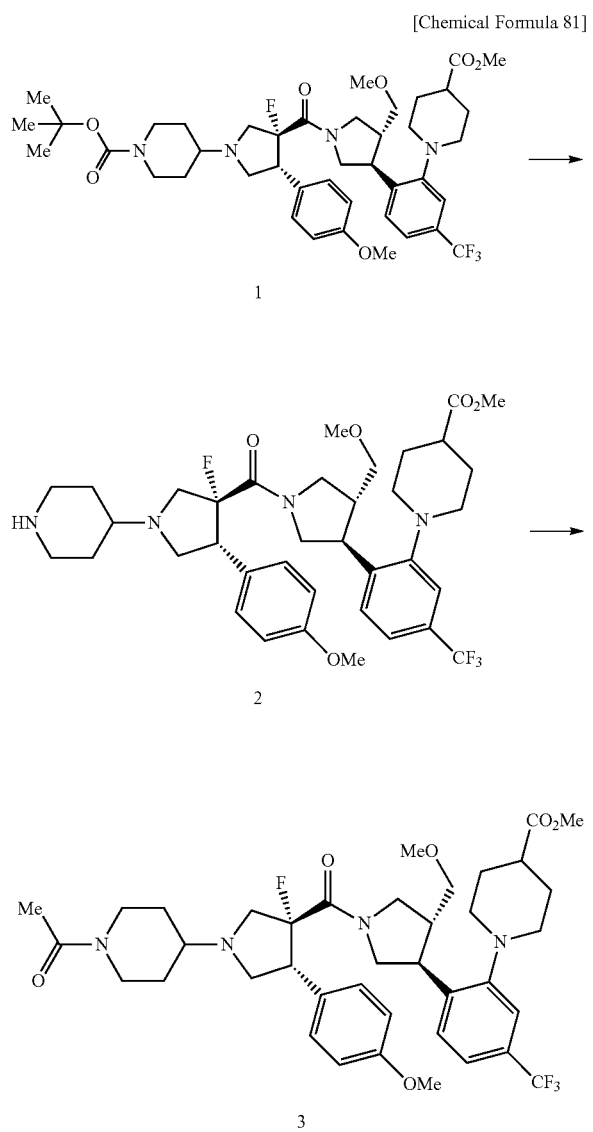

(1) To a solution of Compound 1 (312 mg) in chloroform (3.9 mL) was added trifluoroacetic acid (1.9 mL) under ice-cooling, and then the mixture was stirred at room temperature for 2 hours. To the reaction mixture was added chloroform to dilute it, then a saturated aqueous solution of sodium hydrogen carbonate was added thereto to alkalify the mixture, and the organic layer was separated. The aqueous layer was extracted with chloroform, the organic layers were combined, washed with a saturated aqueous solution of sodium hydrogen carbonate, dried, and concentrated under reduced pressure to give Compound 2 (280 mg) as a yellow viscous material. MS (ESI): m/z 705 [M+H]+

(2) To a solution of Compound 2 (100 mg) and triethylamine (60 μL) in dichloromethane was added acetylchloride (20 μL) under ice-cooling, and then the mixture was stirred at room temperature for 2 hours. The reaction mixture was diluted with chloroform, a saturated aqueous solution of sodium hydrogen carbonate was added thereto, stirred, and then the organic layer was separated. The resultant organic layer was washed with saturated saline, dried, and concentrated under reduced pressure. The residue was purified with NH silica gel column chromatography (hexane:ethyl acetate=50:50-100:0) to give methyl 1-{2-[(3S,4R)-1-{[(3R,4R)-1-(1-acetylpiperidin-4-yl)-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylate 3 (62 mg) as a pale yellow viscous material. MS (ESI): m/z 747 [M+H]+

Examples 324-325

A corresponding starting compound was treated in a similar manner to the above Example 323 to give each compound in the following Table 21.

TABLE 21

| Example | Compound | MS |
|---|---|---|
| 324 | 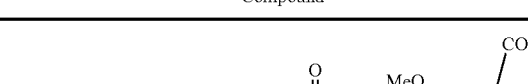 | (ESI): m/z 761 [M + H]+ |

TABLE 21-continued

| Example | Compound | MS |
|---------|----------|-----|
| 325 | | (ESI): m/z 797 [M + H]+ |

Examples 326-328

Each compound in the above Example 323, Example 324, and Example 325 was treated in a similar manner to the above Example 11 to give each compound in the following Table 22.

Examples 329-331

A corresponding starting compound was treated in a similar manner to the above Example 1 and subsequently Example 11 to give each compound in the following Table 23.

TABLE 22

| Example | Compound | Salt MS |
|---------|----------|---------|
| 326 | | 2 HCl (ESI): m/z 733 [M + H]+ |
| 327 | | 2 HCl (ESI): m/z 747 [M + H]+ |
| 328 | | 2 HCl (ESI): m/z 783 [M + H]+ |

TABLE 23

| Example | Compound | Salt MS |
|---|---|---|
| 329 | (structure) | 3 HCl (APCI): m/z 665 [M + H]+ |
| 330 | (structure) | 2 HCl (APCI): m/z 671 [M + H]+ |

TABLE 23-continued

| Example | Compound | Salt MS |
|---|---|---|
| 331 | (structure) | 2 HCl (ESI): m/z 672 [M + H]+ |

Examples 332-345

A corresponding starting compound was treated in a similar manner to the above Example 10 and subsequently Example 11 to give each compound in the following Table 24.

TABLE 24

| Example | Compound | Salt MS |
|---|---|---|
| 332 | (structure) | 2 HCl (ESI): m/z 654 [M + H]+ |
| 333 | (structure) | 2 HCl (APCI): m/z 666 [M + H]+ |
| 334 | (structure) | 2 HCl (APCI): m/z 710 [M + H]+ |

TABLE 24-continued

| Example | Compound | Salt MS |
|---------|----------|---------|
| 335 | | 2 HCl (APCI): m/z 702 [M + H]+ |
| 336 | | 2 HCl (ESI): m/z 760 [M + H]+ |
| 337 | | 2 HCl (ESI): m/z 746 [M + H]+ |
| 338 | | 2 HCl (ESI): m/z 677 [M + H]+ |

TABLE 24-continued

| Example | Compound | Salt MS |
|---|---|---|
| 339 | | 2 HCl (APCI): m/z 670 [M + H]+ |
| 340 | mixture of diastereomers | 2 HCl (APCI): m/z 690 [M + H]+ |
| 341 | | HCl (ESI): m/z 691 [M + H]+ |
| 342 | | 2 HCl (APCI): m/z 690 [M + H]+ |
| 343 | | 2 HCl (APCI): m/z 690 [M + H]+ |

TABLE 24-continued

| Example | Compound | Salt MS |
|---|---|---|
| 344 | 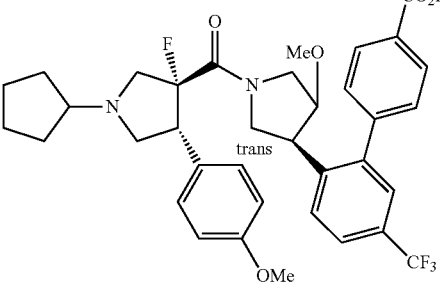<br>mixture of diastereomers | HCl (APCI): m/z 655 [M + H]+ |
| 345 | 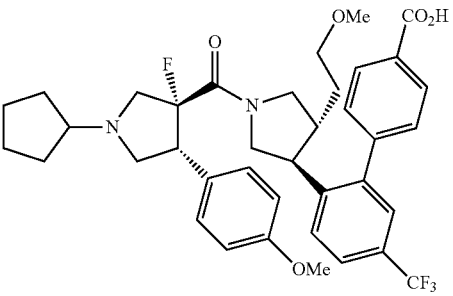 [SMILES: COCC[C@H]1CN(C(=O)[C@]2(F)CN(C3CCCC3)C[C@H]2c2ccc(OC)cc2)C[C@@H]1c1ccc(C(F)(F)F)cc1-c1ccc(C(=O)O)cc1] | HCl (APCI): m/z 683 [M + H]+ |

Examples 346, 347

A corresponding starting compound was treated in a similar manner to the above Example 286 to give an ester compound as an intermediate, and subsequently treated in a similar manner to Example 11 to give each compound in the following Table 25. HPLC column (CHIRALPAK IF (4.6× 150 mm)) manufactured by DAICEL CORPORATION was used in HPLC analysis of the ester intermediate, in the conditions of Flow rate: 0.500 mL/min, Column temperature: 25° C., Mobile phase: Hexane/Methanol/Tetrahydrofuran/Diethylamine=83/5/12/0.1.

TABLE 25

| Example | Structure | Ester intermediate | Retention time of ester intermediate |
|---|---|---|---|
| 346 | 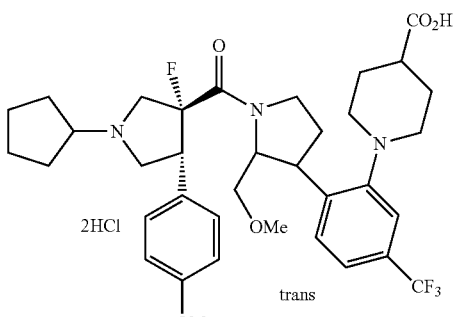 | 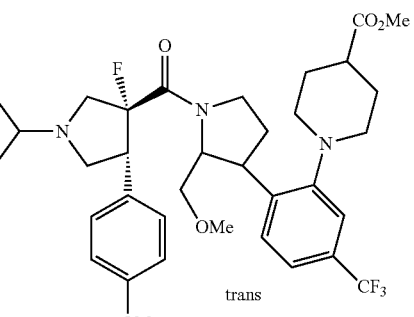 | 9.71 min |
| 347 | MS (APCI): m/z 676 [M + H]+ | MS (APCI): m/z 690 [M + H]+ | 12.88 min |

Example 348

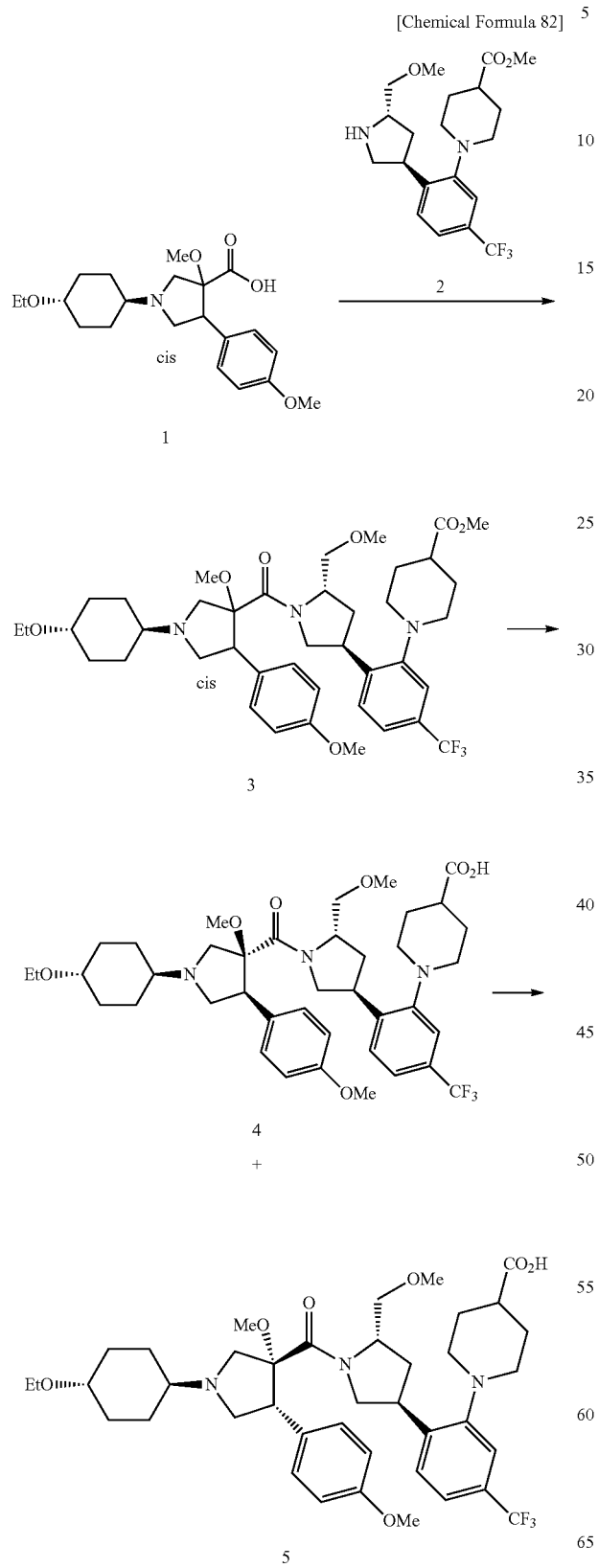
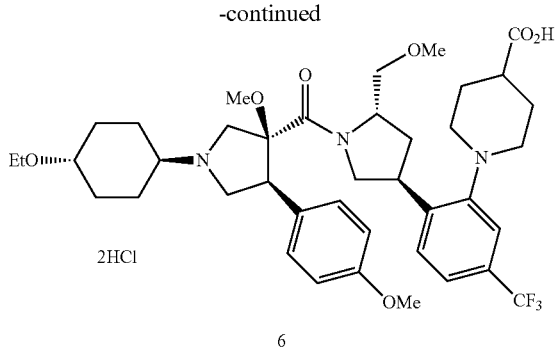

(1) To a mixed solution of Compound 1 (100 mg) and Compound 2 (124 mg) in N,N-dimethylformamide (3 mL) were added 1-ethyl-3-(3-dimethylaminopropyl)carbodiimide hydrochloride (96 mg) and 1-hydroxy-7-azabenzotriazole (68 mg), and the mixture was stirred at room temperature for 2 hours. To the reaction mixture were added a saturated aqueous solution of sodium hydrogen carbonate and ethyl acetate, stirred, and then the organic layer was separated. The resultant organic layer was washed with water and saturated saline, dried, and concentrated under reduced pressure. The residue was purified with NH silica gel column chromatography (hexane:ethyl acetate=85:15-65:35) to give a mixture of diastereomers of Compound 3 as a colorless powder (118 mg) of. MS (APCI): m/z 760 [M+H]+

(2) To a solution of Compound 3 (115 mg) in methanol (2 mL) was added an aqueous solution of sodium hydroxide (2 mol/L, 605 μL), and the mixture was stirred at room temperature for 4 hours. To the reaction mixture was added an aqueous solution of hydrochloric acid (2 mol/L, 605 μL), stirred, concentrated under reduced pressure, dichloromethane and water were added thereto, stirred, then the organic layer was separated, and concentrated under reduced pressure. The resultant residue was purified with silica gel column chromatography (chloroform:methanol=100:0-90:10) to give Compound 4 (58 mg) and Compound 5 (49 mg) as colorless powders respectively. Each MS (APCI): m/z 746 [M+H]+TLC (chloroform:methanol=95:5): Rf value of Compound 4≈0.30, Rfvalue of Compound 5≈0.15 (TLC plate: 1.05715.0001 TLC Silica gel 60 $F_{254}$ manufactured by Merck KGaA). 1H-NMR data of Example 146 and Compound 5 was the same with each other to confirm that Compound 4 had the above configuration.

(3) To a solution of Compound 4 (54 mg) in dichloromethane (1 mL) was added a solution of hydrochloric acid in ethyl acetate (4 mol/L, 90 μL), and the solvent was evaporated under reduced pressure. The residue was powdered with diethylether, collected by filtration, and dried under reduced pressure to give Compound 6 (45 mg) as a pale pink powder. MS (APCI): m/z 746 [M+H]+

Examples 349, 350

A corresponding starting compound was treated in a similar manner to the above Example 348 to give each compound in the following Table 26.

TABLE 26
| Example | Compound | Salt | MS |
|---------|----------|------|-----|
| 349 | (structure shown) | 2 HCl | (APCI): m/z 746 [M + H]+ |
| 350 | (structure shown) | 2 HCl | (APCI): m/z 746 [M + H]+ |
Reference Examples
Reference Example 1
[Chemical Formula 83]
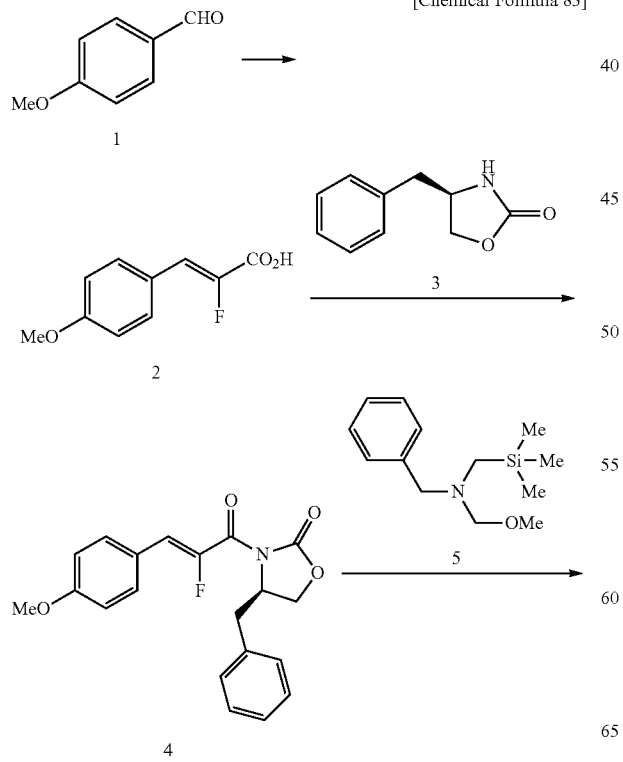
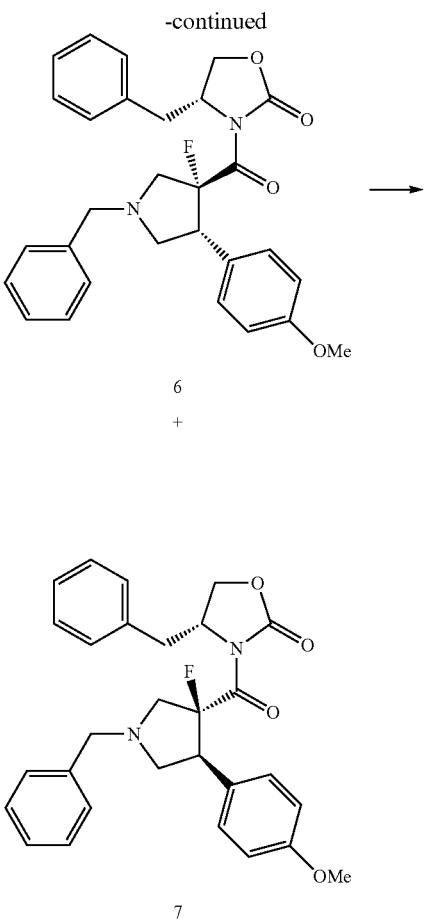

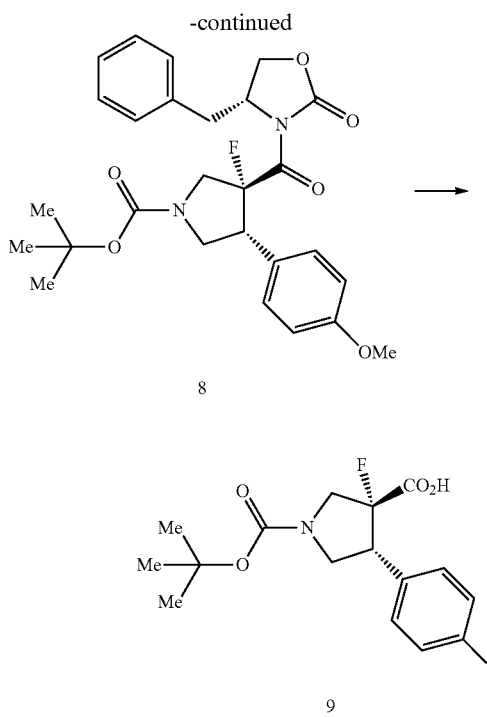

(1) Under nitrogen atmosphere, to a solution of triethyl 2-fluoro-2-phosphonoacetate (55.6 g) in tetrahydrofuran (100 mL) were added magnesium bromide-diethylether complex (71.3 g) and triethylamine (35.3 mL) under ice-cooling, and the mixture was stirred at room temperature for 1.5 hours. To the reaction mixture was added dropwise a solution of Compound 1 (25 g) in tetrahydrofuran (375 mL) under ice-cooling, and then the mixture was stirred at room temperature for 15 hours. The reaction mixture was concentrated until the volume became approximately half, water (400 mL) and ethyl acetate (500 mL) were added thereto, and stirred. The insoluble matter was removed by filtration, and the organic layer was separated. The resultant organic layer was washed with saturated saline, dried, and concentrated under reduced pressure. To a solution of the residue in tetrahydrofuran (210 mL)/ethanol (210 mL) was added an aqueous solution of sodium hydroxide (2 mol/L, 188 mL) at room temperature. To the reaction mixture were added ethanol (300 mL) and tetrahydrofuran (100 mL), stirred, an aqueous solution of hydrochloric acid (1 mol/L, 390 mL) was added after 1 hour, and then tetrahydrofuran was evaporated under reduced pressure. To a suspension of the resultant was added water (300 mL), the mixture was stirred at room temperature for 1 hour, and then the precipitate was collected by filtration. The precipitate was washed with water and subsequently diisopropylether, and draught dried at 60° C. for 12 hours to give Compound 2 (26.63 g) as a colorless powder. MS (APCI): m/z 197 [M+H]+

(2) To a suspension of Compound 2 (26.6 g) in dichloromethane (270 mL) were added thionyl chloride (29.7 mL) and N,N-dimethylformamide (1.04 mL), and the mixture was heated under reflux for 4 hours. The reaction solution was concentrated under reduced pressure, and then the residue was azeotropically concentrated with toluene twice. To a solution of the residue in dichloromethane (532 mL) were added Compound 3 (26.3 g) and lithium chloride (12.5 g), triethylamine (65.9 mL) was added dropwise thereto under nitrogen atmosphere under ice-cooling, and then stirred at room temperature for 15 hours. The reaction suspension was poured into an aqueous solution of citric acid (citric acid: 102 g+water: 950 mL) under ice-cooling, and extracted with chloroform (300 mL). The resultant organic layer was washed with saturated saline, dried, and concentrated under reduced pressure. The residue was powdered with diisopropylether, collected by filtration, and then dried to give Compound 4 (44.7 g) as a colorless powder. MS (APCI): m/z 356 [M+H]+

(3) To a suspension of Compound 4 (10 g) and Compound 5 (13.3 g) in dichloromethane (100 mL) was added trifluoroacetic acid (215 µL) at room temperature, and the mixture was heated under reflux under nitrogen atmosphere for 1 hour. To the reaction solution were added Compound 5 (3.34 g) and trifluoroacetic acid (54 µL) at room temperature, and the mixture was heated under reflux for additional 30 minutes. The reaction solution was poured into an aqueous solution of citric acid (citric acid: 35 g+water: 350 mL) under ice-cooling, and extracted with dichloromethane. The resultant organic layer was washed with a saturated aqueous solution of sodium hydrogen carbonate and saturated saline, then dried, and concentrated under reduced pressure. The residue was purified with silica gel column chromatography (hexane:ethyl acetate=80:20-40:60) and crystallized with diisopropylether to give Compound 6 (6.06 g) and Compound 7 (3.3 g) as colorless powders respectively. Each MS (APCI): m/z 489 [M+H]+TLC (hexane:ethyl acetate-80:20): Rf value of Compound 6 r 0.45, Rf value of Compound 7≈0.2 (TLC plate: 1.05715.0001 TLC Silica gel 60 F$_{254}$ manufactured by Merck KGaA). Compound 6 was dissolved in a small amount of a mixed solution of dichloromethane and ethyl acetate, and diethylether was added thereto to recrystallize it. The resultant crystal was subject to X-ray crystallography to confirm that Compound 6 and Compound 7 have the above configurations respectively.

(4) To a solution of Compound 6 (6.05 g) and di-t-butyl dicarbonate (2.84 g) in ethanol (85 mL)/tetrahydrofuran (150 mL) was added 10% palladium carbon (wetted with ca. 50% water, 1.8 g) under stirring, and the mixture was stirred under hydrogen atmosphere (1 atm) for 24 hours. The precipitate was dissolved in chloroform (100 mL) and methanol (20 mL), and palladium carbon was removed by filtration. The filtrate was concentrated, the residue was powdered with hexane, collected by filtration, and dried under reduced pressure to give Compound 8 (6.28 g) as a colorless powder. MS (APCI): m/z 399 [M-Boc+H]+

(5) To a suspension of Compound 8 (6.28 g) in tetrahydrofuran (45 mL) was added an aqueous solution of lithium hydroxide (lithium hydroxide (monohydrate): 635 mg+water: 20 mL) under ice-cooling, the mixture was stirred at room temperature for 1 hour, and then tetrahydrofuran was evaporated. To the residue was added water (20 mL), and then washed with a mixed solution (30 mL) of ethyl acetate and diethylether (1:1) four times. To the resultant aqueous layer was added an aqueous solution of hydrochloric acid (1 mol/L, 15.5 mL) to acidify it, and then extracted with chloroform twice. The resultant organic layers were combined, washed with saturated saline, dried, and the solvent was evaporated to give Compound 9 (4.11 g) as a colorless powder. MS (APCI): m/z 338 [M−H]−

Reference Example 2

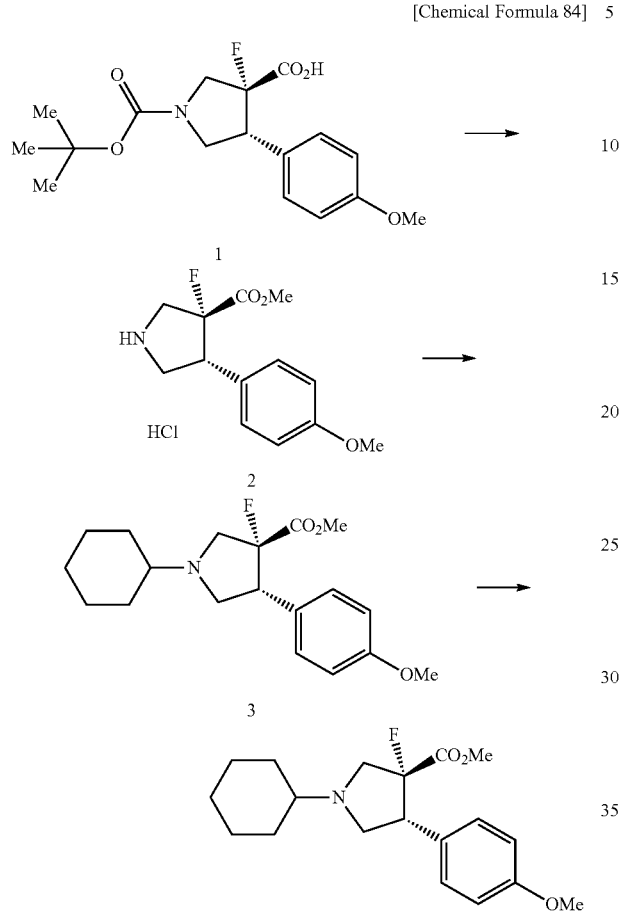

(1) To a solution of Compound 1 (6 g) in methanol (45 mL) was added dropwise thionyl chloride (5.16 mL) under ice-cooling. After stirred at room temperature for 3 hours, the reaction mixture was concentrated under reduced pressure. The residue was powdered with diethylether, collected by filtration, and dried under reduced pressure to give Compound 2 (4.906 g) as a colorless powder. MS (APCI): m/z 254 [M+H]+

(2) To a suspension of Compound 2 (579 mg) and cyclohexanone (248 μL) in dichloromethane (15 mL) was added sodium acetate (197 mg), the mixture was stirred at room temperature for 30 minutes, then sodium triacetoxyborohydride (509 mg) was added thereto, and the mixture was stirred for 15 hours. To the reaction mixture were added a saturated aqueous solution of sodium hydrogen carbonate and water, stirred, and then extracted with chloroform. The resultant organic layer was washed with saturated saline, dried, and concentrated under reduced pressure. The residue was purified with NH silica gel column chromatography (hexane:ethyl acetate=95:5-80:20) to give Compound 3 (678 mg) as a colorless viscous material. MS (ESI): m/z 336 [M+H]+

(3) To a solution of Compound 3 (655 mg) in methanol (6 mL) was added an aqueous solution of sodium hydroxide (2 mol/L, 1.27 mL) at room temperature, and the mixture was stirred for 2 hours. To the reaction mixture was added an aqueous solution of hydrochloric acid (2 mol/L, 1.27 mL), stirred, and then the reaction solution was concentrated under reduced pressure to give Compound 4 as a colorless powder (780 mg) containing sodium chloride.

MS (ESI): m/z 322 [M+H]+

Reference Examples 3-16

A corresponding starting compound was treated in a similar manner to the above Reference Example 2 to give each compound in the following Table 27.

TABLE 27

| Reference Example | Compound | MS |
|---|---|---|
| 3 | (structure: 4,4-difluorocyclohexyl-pyrrolidine with F, CO₂H, and 4-methoxyphenyl substituents) | (APCI): m/z 358 [M + H]+ |
| 4 | (structure: tetrahydropyran-4-yl-pyrrolidine with F, CO₂H, and 4-methoxyphenyl substituents) | (ESI): m/z 324 [M + H]+ |

TABLE 27-continued

| Reference Example | Compound | MS |
|---|---|---|
| 5 | cyclopentyl-N-pyrrolidine with F, CO2H, 4-methoxyphenyl | (APCI): m/z 308 [M + H]+ |
| 6 | trans-4-methoxycyclohexyl-N-pyrrolidine with F, CO2H, 4-methoxyphenyl | (ESI): m/z 352 [M + H]+ |
| 7 | cis-4-methoxycyclohexyl-N-pyrrolidine with F, CO2H, 4-methoxyphenyl | (ESI): m/z 352 [M + H]+ |
| 8 | trans-4-(TBSO)cyclohexyl-N-pyrrolidine with F, CO2H, 4-methoxyphenyl | (ESI): m/z 452 [M + H]+ |
| 9 | cis-4-(TBSO)cyclohexyl-N-pyrrolidine with F, CO2H, 4-methoxyphenyl | (ESI): m/z 452 [M + H]+ |
| 10 | cyclobutyl-N-pyrrolidine with F, CO2H, 4-methoxyphenyl | (APCI): m/z 294 [M + H]+ |
| 11 | 4-cyanocyclohexyl-N-pyrrolidine with F, CO2H, 4-methoxyphenyl | (ESI): m/z 347 [M + H]+ |

TABLE 27-continued
| Reference Example | Compound | MS |
|---|---|---|
| 12 | | (ESI): m/z 347 [M + H]+ |
| 13 | | (ESI): m/z 366 [M + H]+ |
| 14 | | (ESI): m/z 366 [M + H]+ |
| 15 | | (APCI): m/z 322 [M + H]+ |
| 16 | | (APCI): m/z 322 [M + H]+ |
Reference Example 17
[Chemical Formula 85]
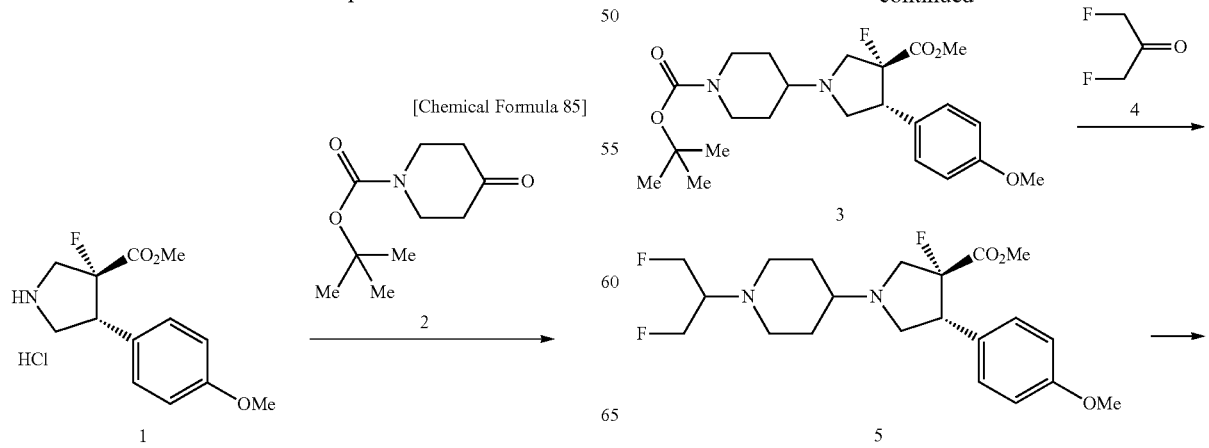

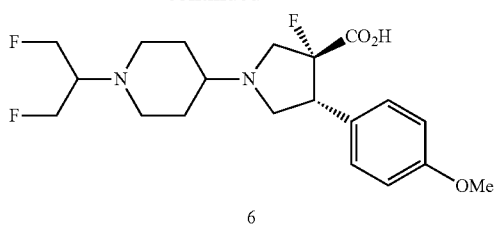

(1) To a suspension of Compound 1 (500 mg) and sodium acetate (142 mg) in dichloromethane (20 mL) were added Compound 2 (413 mg), acetic acid (99 μL), and sodium triacetoxyborohydride (585 mg) at room temperature, and the mixture was stirred for 15 hours. To the reaction mixture were added a saturated aqueous solution of sodium hydrogen carbonate and water, stirred, and then extracted with chloroform. The resultant organic layer was washed with saturated saline, dried, and concentrated under reduced pressure. The residue was purified with silica gel column chromatography (hexane:ethyl acetate=80:20-60:40) to give Compound 3 (720 mg) as a colorless viscous material. MS (APCI): m/z 437 [M+H]+

(2) To a solution of Compound 3 (719 mg) in dichloromethane (14 mL) was added trifluoroacetic acid (4 mL) under ice-cooling, and then the mixture was stirred at room temperature for 3 hours. To the reaction mixture was added dichloromethane to dilute it, then was added a saturated aqueous solution of sodium hydrogen carbonate under stirring to alkalify the mixture, and the organic layer was separated. The resultant organic layer was dried, and then concentrated under reduced pressure. To a solution of the residue in dichloromethane (24 mL) were added Compound 4 (741 mg), acetic acid (101 μL), and sodium triacetoxyborohydride (967 mg), and the mixture was stirred for 15 hours. To the reaction mixture were added a saturated aqueous solution of sodium hydrogen carbonate and water, stirred, and then extracted with dichloromethane. The resultant organic layer was washed with saturated saline, dried, and concentrated under reduced pressure. The residue was purified with NH silica gel column chromatography (hexane:ethyl acetate=85:15-65:35) to give Compound 5 (283 mg) as a colorless viscous material. MS (APCI): m/z 415 [M+H]+

(3) To a solution of Compound 5 (280 mg) in methanol (6 mL) was added an aqueous solution of sodium hydroxide (2 mol/L, 405 μL) at room temperature, and the mixture was stirred for 2 hours. To the reaction mixture was added an aqueous solution of hydrochloric acid (2 mol/L, 405 μL), stirred, and then the reaction solution was concentrated under reduced pressure to give Compound 6 as a colorless powder (320 mg) containing sodium chloride.

MS (APCI): m/z 401 [M+H]+

Reference Example 18a, Reference Example 18b

[Chemical Formula 86]

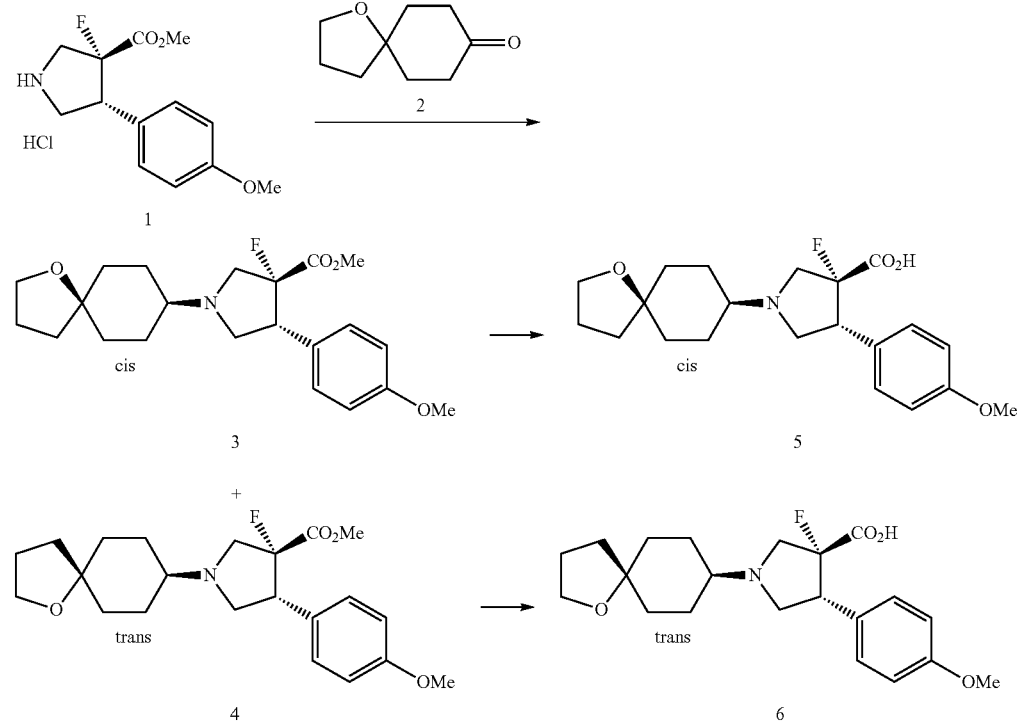

(1) To a solution of Compound 1 (200 mg) and Compound 2 (128 mg) in dichloromethane (7 mL) was added sodium triacetoxyborohydride (219 mg), and the mixture was stirred at room temperature for 16 hours. To the reaction mixture were added a saturated aqueous solution of sodium hydrogen carbonate and water, stirred, and then extracted with chloroform. The resultant organic layer was washed with saturated saline, dried, and concentrated under reduced pressure. The residue was purified with silica gel column chromatography (hexane:ethyl acetate=70:30-0:100) to give Compound 3 (cis) (81 mg) and Compound 4 (trans) (10 mg) as colorless powders. TLC (Eluent: ethyl acetate): Rf value of Compound 3-0.35, Rf value of Compound 4≈0.45 (TLC plate: 1.05715.0001 TLC Silica gel 60 $F_{254}$ manufactured by Merck KGaA). A crystal obtained from a solution of Compound 3 in diisopropylether was subjected to X-ray crystallography to confirm that Compound 3 and Compound 4 have the above configurations respectively. Each MS (ESI): m/z 392 [M+H]+

(2) To a solution of Compound 3 (40 mg) in methanol (1 mL) was added an aqueous solution of sodium hydroxide (2 mol/L, 220 μL) at room temperature, and the mixture was stirred for 2.5 hours. To the reaction mixture was added an aqueous solution of hydrochloric acid (2 mol/L, 220 μL), stirred, and then the reaction solution was concentrated under reduced pressure to give Compound 5 as a colorless powder (Reference Example 18a, 52 mg) containing sodium chloride. MS (ESI): m/z 378 [M+H]+

(3) Compound 4 (110 mg) was treated in a similar manner to the above step (2) to give Compound 6 as a colorless powder (Reference Example 18b, 125 mg) containing sodium chloride. MS (ESI): m/z 378 [M+H]+

Reference Example 19

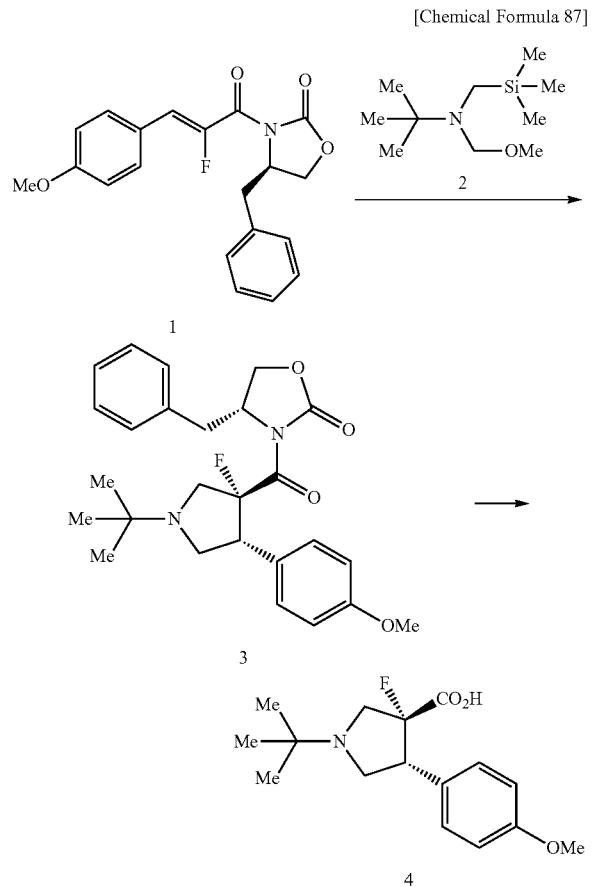

(1) Compound 1 (7.45 g) and Compound 2 (8.54 g) obtained by the method described in WO2004/089307 were treated in a similar manner to Reference Example 1 to give Compound 3 (3.58 g) as a pale yellow powder. MS (ESI): m/z 455 [M+H]+

(2) To a solution of Compound 3 (27.9 g) in tetrahydrofuran (140 mL) was added an aqueous solution of lithium hydroxide (lithium hydroxide (monohydrate): 3.09 g+water: 70 mL) under ice-cooling, and the mixture was stirred at room temperature for 2 hours. To the reaction mixture was added an aqueous solution of hydrochloric acid (1 mol/L, 73.7 mL), stirred, and tetrahydrofuran was evaporated under reduced pressure. The resultant aqueous solution was washed with ethyl acetate three times, and the aqueous layer was concentrated under reduced pressure. The residue was purified with column chromatography (chloroform:methanol=97:3-80:20) using diol silica gel (FUJI SILYSIA CHEMICAL LTD.), powdered with diisopropylether, collected by filtration, and dried under reduced pressure to give Compound 4 (18.04 g) as a colorless powder. MS (ESI): m/z 296 [M+H]+

Reference Examples 20-31

A corresponding starting compound was treated in a similar manner to the above Reference Example 19 to give each compound in the following Table 28.

TABLE 28

| Reference Example | Compound | MS |
|---|---|---|
| 20 | (structure with Br) | (ESI): m/z 344/346 [M + H]+ |
| 21 | (structure with Cl) | (ESI): m/z 300/302 [M + H]+ |
| 22 | (structure with F, OMe) | (APCI): m/z 314 [M + H]+ |
| 23 | (structure with OEt) | (ESI): m/z 310 [M + H]+ |
| 24 | (structure with Me) | (ESI): m/z 280 [M + H]+ |

TABLE 28-continued
| Reference Example | Compound | MS |
|---|---|---|
| 25 | | (ESI): m/z 294 [M + H]+ |
| 26 | | (ESI): m/z 308 [M + H]+ |
| 27 | | (ESI): m/z 324 [M + H]+ |
| 28 | | (ESI): m/z 350 [M + H]+ |
| 29 | | (ESI): m/z 308 [M + H]+ |
| 30 | | (APCI): m/z 302 [M + H]+ |
| 31 | | (ESI): m/z 284 [M + H]+ |
Reference Example 32
[Chemical Formula 88]
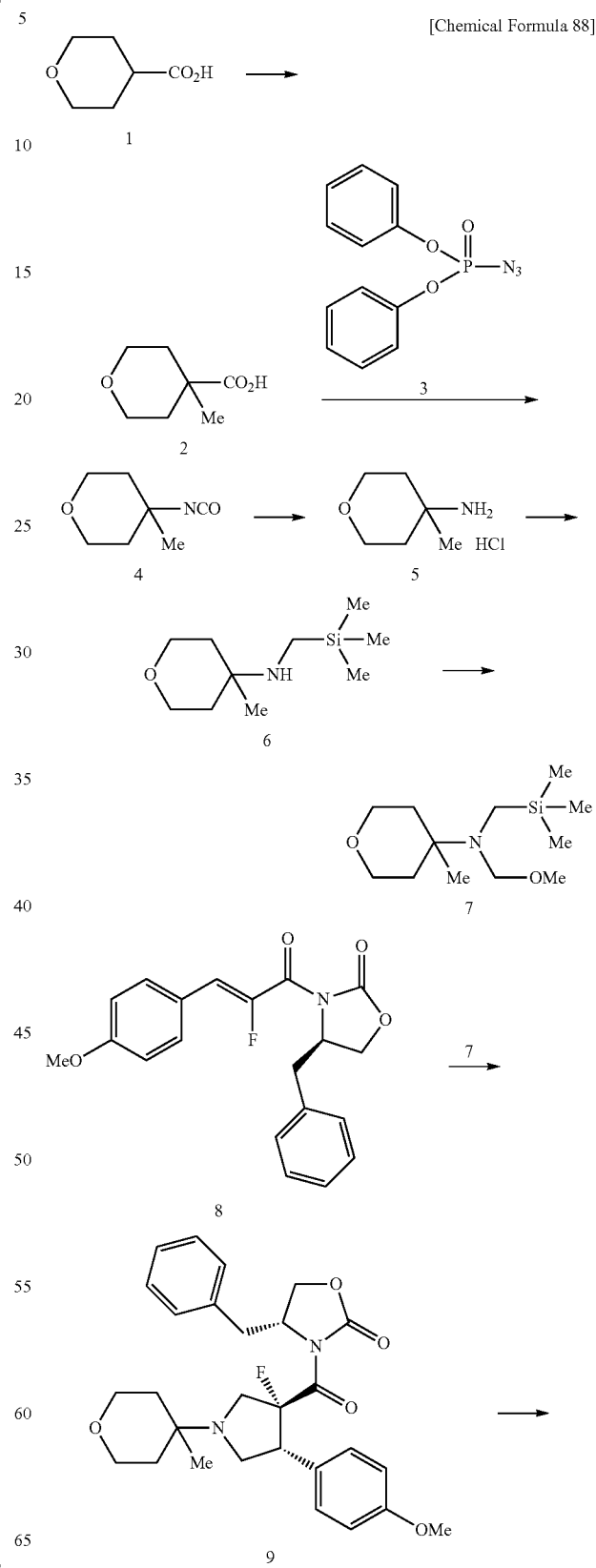

-continued

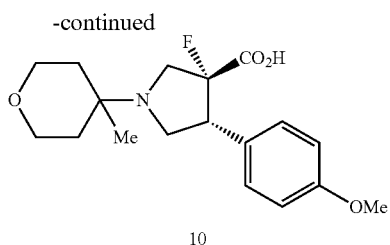

10

(1) To a solution of Compound 1 (1.3 g) in tetrahydrofuran (20 mL) was added dropwise a solution of lithiumdiisopropylamide-tetrahydrofuran (2 mol/mL, 14 mL) under nitrogen atmosphere under ice-cooling, and then the mixture was stirred at 50° C. for 3 hours. To the reaction mixture was added dropwise methyl iodide (1.87 mL) under ice-cooling, and the mixture was stirred at room temperature for 19 hours. To the reaction mixture was added a 10% aqueous solution of citric acid (20 mL), stirred, then tetrahydrofuran was evaporated under reduced pressure, and extracted with ethyl acetate. The organic layer was dried, and concentrated under reduced pressure. The residue was purified with silica gel column chromatography (hexane:ethyl acetate=80:20-50:50) to give Compound 2 (1.05 g) as a pale brown powder. To a solution of Compound 2 (896 mg) in toluene (37 mL) were added triethylamine (1.12 mL) and Compound 3 (1.39 mL), and the mixture was stirred under nitrogen atmosphere at 85° C. for 17 hours. To the reaction solution was added dropwise an aqueous solution of sodium hydroxide (1 mol/mL, 27 mL) under ice-cooling, ethyl acetate and water were added thereto, and then the organic layer was separated. The resultant organic layer was dried, and concentrated under reduced pressure to give a crude material of Compound 4 (671 mg) as a brown viscous material. To a solution of Compound 4 (665 mg) in tetrahydrofuran (55 mL) was added a mixed solution of concentrated hydrochloric acid (3.05 mL) and water (5.5 mL), and the mixture was stirred at room temperature for 48 hours. The reaction solution was concentrated under reduced pressure to give a crude material of Compound 5 (558 mg) as a pale brown powder. MS (ESI): m/z 116 [M+H]+

(2) A suspension of Compound 5 (630 mg), (chloromethyl) trimethylsilane (695 μL), sodium iodide (746 mg), and potassium carbonate (1.38 g) in acetonitrile (10 mL) was stirred under nitrogen atmosphere at 80° C. for 88 hours. After being cooled to room temperature, the insoluble matter was removed by filtration, and the filtrate was concentrated under reduced pressure. The residue was purified with NH silica gel column chromatography (hexane:ethyl acetate=98:2-90:10) to give Compound 6 (500 mg) as a pale yellow viscous material. MS (ESI): m/z 202 [M+H]+

(3) To Compound 6 (400 mg) was added a solution of formaldehyde (37%, 216 μL) under ice-cooling and subsequently methanol (488 μL), and the mixture was stirred at room temperature for 12 hours. To the reaction mixture was added potassium carbonate (720 mg), stirred at room temperature for 12 hours, then the insoluble matter was removed by filtration, and the filtrate was concentrated under reduced pressure to give a crude material containing Compound 7. The crude material was all used in the next step without purification. MS (ESI): m/z 202 [M+H]+

(4) Compound 8 (283 mg) and Compound 7 were treated in a similar manner to Reference Example 1 to give Compound 9 (59 mg) as a colorless powder. MS (ESI): m/z 497 [M+H]+

(5) To a solution of Compound 9 (59 mg) in tetrahydrofuran (1 mL) was added an aqueous solution of lithium hydroxide (lithium hydroxide (monohydrate): 7 mg+water: 500 μL) under ice-cooling, and the mixture was stirred at room temperature for 4 hours. To the reaction mixture was added an aqueous solution of hydrochloric acid (2 mol/L, 83.5 μL), stirred, then washed with a mixed solution of ethyl acetate and diethylether (1:2) three times, and the aqueous layer was concentrated under reduced pressure to give Compound 10 as a colorless crude material (48 mg) containing lithium chloride. MS (ESI): m/z 338 [M+H]+

Reference Example 33

[Chemical Formula 89]

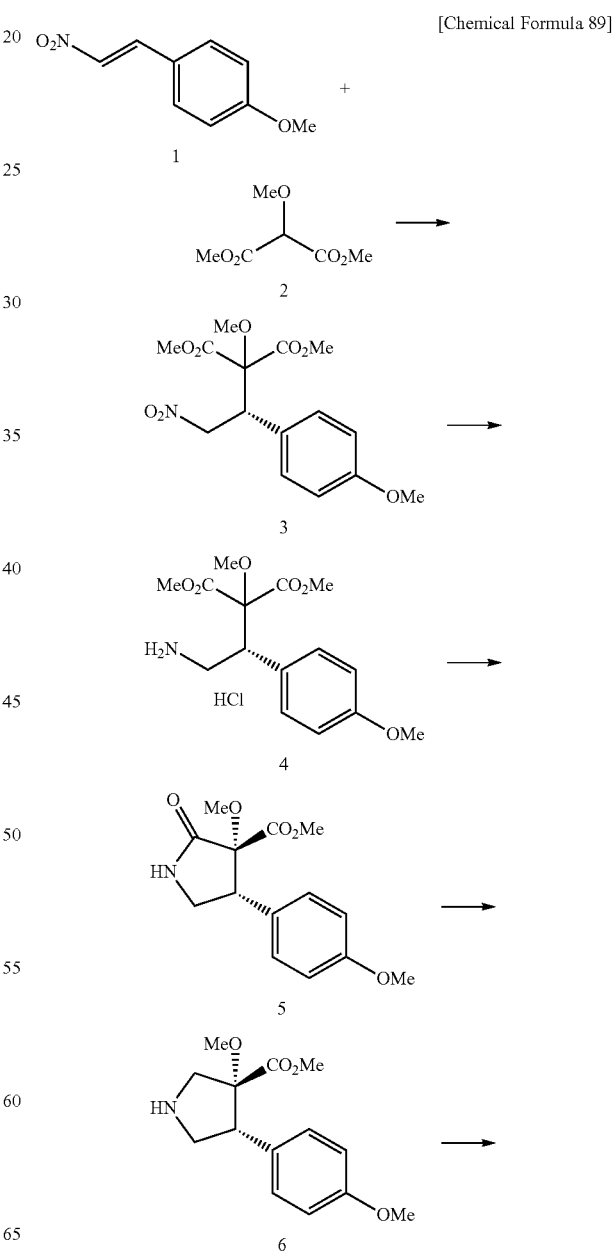

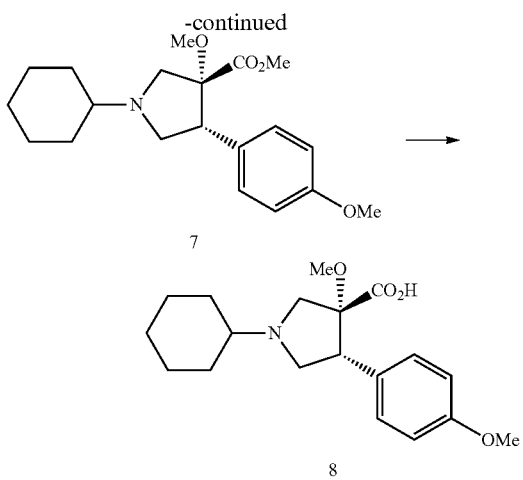

(1) Compound 5 was prepared according to the method described in a literature (J. Am. Chem. Soc. 2005, 127, 119-125). Namely, to a solution of Compound 1 (1 g) and Compound 2 (1534 µL) in toluene (10 mL) was added 1-[3,5-bis(trifluoromethyl)phenyl]-3-[(1R,2R)-(−)-2-(dimethylamino)cyclohexyl]thiourea (231 mg), and the mixture was stirred at room temperature for 24 hours. The reaction solution was concentrated under reduced pressure, the residue was purified with NH silica gel column chromatography (hexane:ethyl acetate=95:5-80:20), then powdered with diisopropylether, collected by filtration, and dried under reduced pressure to give Compound 3 (1294 mg) as a colorless powder. MS (APCI): m/z 342 [M+H]+Optical purity 92.18% e.e.

(2) To a solution of Compound 3 (1200 mg) in methanol (36 mL) was added an aqueous solution of hydrochloric acid (1 mol/L, 3867 µL) and 10% palladium carbon (wetted with ca. 50% water, 240 mg), and the mixture was stirred under hydrogen atmosphere (1 atm) at room temperature for 21 hour. Palladium carbon was removed by filtration, and then the filtrate was concentrated under reduced pressure. To the residue was added toluene, concentrated under reduced pressure again, the resultant residue was powdered with diethylether, collected by filtration, and dried under reduced pressure to give Compound 4 (1174 mg) as a colorless powder. MS (APCI): m/z 312 [M+H]+

(3) To a suspension of Compound 4 (1170 mg) in dichloromethane (23 mL) was added 1,8-diazabicyclo[5.4.0]-7-undecene (1258 µL) at −70° C., and the mixture was stirred at the same temperature for 4 hours. To the reaction mixture were added an aqueous solution of hydrochloric acid (1 mol/L, 10 mL) and water, stirred, and then extracted with dichloromethane. The resultant organic layer was washed with saturated saline, dried, and concentrated under reduced pressure. The residue was purified with silica gel column chromatography (hexane:ethyl acetate=70:30-40:60) to give Compound 5 (577 mg) as a colorless powder. MS (APCI): m/z 280 [M+H]+

(4) To a solution of Compound 5 (570 mg) in dichloromethane (11 mL) was added trimethyloxonium tetrafluoroborate (604 mg), and the mixture was stirred at room temperature for 6 hours. Trimethyloxonium tetrafluoroborate (604 mg) was added thereto, and the mixture was stirred at room temperature for additional 22 hours (reaction solution A). Separately, to a solution of sodium cyanoborohydride (1026 mg) in methanol (11 mL) was added acetic acid (1167 µL), and the mixture was cooled to 0° C. (reaction solution B). The reaction solution A was added dropwise to the reaction solution B at 0° C., and then the mixture was stirred at room temperature for 1 hour. To the reaction mixture were added a saturated aqueous solution of sodium hydrogen carbonate and water, stirred, and then extracted with chloroform. The resultant organic layer was washed with saturated saline, dried, and concentrated under reduced pressure. The residue was purified with silica gel column chromatography (chloroform:methanol=99:1-93:7) to give Compound 6 (367 mg) as a colorless viscous material. MS (APCI): m/z 266 [M+H]+

(5) To a suspension of Compound 6 (320 mg) and cyclohexanone (13 µL) in dichloromethane (6 mL) was added sodium triacetoxyborohydride (383 mg), and the mixture was stirred at room temperature for 7 hours. To the reaction mixture was added a saturated aqueous solution of sodium hydrogen carbonate and water, stirred, and then extracted with dichloromethane. The resultant organic layer was washed with saturated saline, dried, and concentrated under reduced pressure. The residue was purified with NH silica gel column chromatography (hexane:ethyl acetate=95:5-80:20) to give Compound 7 (345 mg) as a colorless viscous material. MS (APCI): m/z 348 [M+H]+

(6) To a solution of Compound 7 (343 mg) in ethanol (7 mL) was added an aqueous solution of sodium hydroxide (2 mol/L, 987 µL) at room temperature, and the mixture was stirred at 70° C. for 13 hours. After being cooled to room temperature, to the reaction mixture was added an aqueous solution of hydrochloric acid (2 mol/L, 987 µL), stirred, and concentrated under reduced pressure to give Compound 8 as a colorless powder (423 mg) containing sodium chloride. MS (APCI): m/z 334 [M+H]+

Reference Examples 34-40

A corresponding starting compound was treated in a similar manner to the above Reference Example 32 to give each compound in the following Table 29.

TABLE 29

| Reference Example | Compound | MS |
|---|---|---|
| 34 | ![structure] | (APCI): m/z 348 [M + H]+ |

TABLE 29-continued

| Reference Example | Compound | MS |
|---|---|---|
| 33 | | (APCI): m/z 320 [M + H]+ |
| 36 | | (APCI): m/z 370 [M + H]+ |
| 37 | | (ESI): m/z 364 [M + H]+ |
| 38 | | (APCI): m/z 364 [M + H]+ |
| 39 | | (ESI): m/z 378 [M + H]+ |
| 40 | | (ESI): m/z 392 [M + H]+ |

Reference Example 41

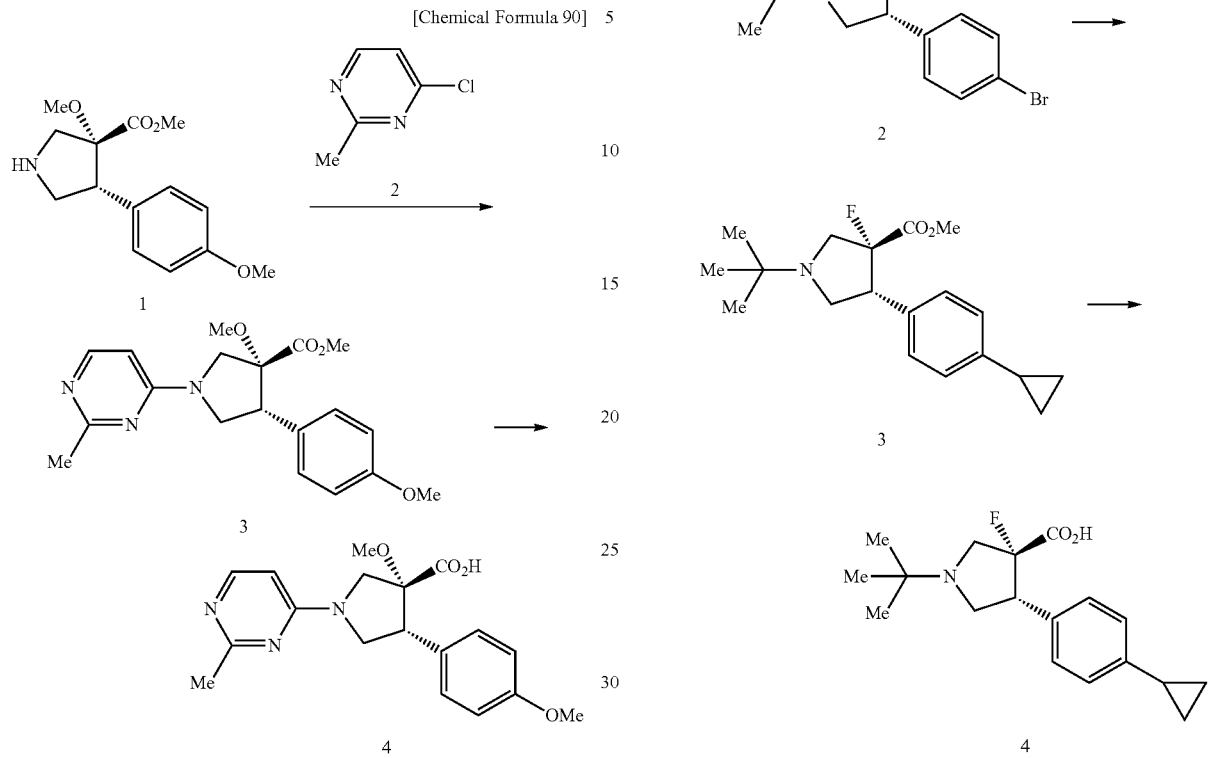

(1) A solution of Compound 1 (100 mg), Compound 2 (73 mg), and diisopropylethylamine (197 μL) in tetrahydrofuran (2 mL) was heated under reflux under nitrogen atmosphere for 3 hours. To the reaction solution were added Compound 2 (24 mg) and diisopropylethylamine (66 μL), and the mixture was heated under reflux for 1 hour. The reaction solution was concentrated under reduced pressure, and the residue was purified with NH silica gel column chromatography (hexane:ethyl acetate=80:20-50:50) to give Compound 3 (107 mg) as a colorless viscous material. MS (APCI): m/z 358 [M+H]+

(2) Compound 3 (106 mg) was treated in a similar manner to the step (6) of Reference Example 33 to give Compound 4 as a colorless powder (138 mg) containing sodium chloride. MS (APCI): m/z 344 [M+H]+

Reference Example 42

[Chemical Formula 91]

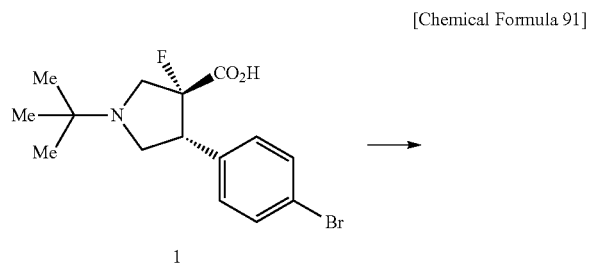

(1) To a solution of Compound 1 (265 mg) in methanol (2 mL) was added concentrated sulfuric acid (20 μL), and the mixture was stirred at 50° C. for 30 minutes. To the reaction mixture was added concentrated sulfuric acid (200 μL), and stirred at 70° C. for 3 hours. After being cooled to room temperature, to the reaction mixture was added a saturated aqueous solution of sodium hydrogen carbonate to alkalify it, and extracted with chloroform. The resultant organic layer was washed with saturated saline, dried, and concentrated under reduced pressure. The residue was purified with silica gel column chromatography (hexane:ethyl acetate=80:20-40:60) to give Compound 2 (217 mg) as a colorless viscous material. MS (ESI): m/z 358/360 [M+H]+

(2) A mixed solution of Compound 2 (105 mg), cyclopropylboronic acid (38 mg), tricyclohexylphosphine (8.1 mg), and potassium phosphate (123 mg) in toluene (2 mL)/water (100 μL) was degassed, then to the mixture was added palladium acetate (3.3 mg), and stirred under nitrogen atmosphere at 100° C. for 14 hours. The reaction mixture was cooled to room temperature, then insoluble matter was removed by filtration, and the filtrate was concentrated under reduced pressure. The residue was sequentially purified with silica gel column chromatography (hexane:ethyl acetate=80:20-50:50) and NH silica gel column chromatography (hexane:ethyl acetate=95:5-75:25) to give Compound 3 (78 mg) as a pale yellow viscous material. MS (ESI): m/z 320 [M+H]+

(3) To a solution of Compound 3 (77 mg) in methanol (2 mL) was added an aqueous solution of sodium hydroxide (2 mol/L, 480 μL) at room temperature, and the mixture was stirred for 15 hours. To the reaction mixture was added an aqueous solution of hydrochloric acid (2 mol/L, 480 μL), stirred, and then concentrated under reduced pressure to give Compound 4 as a colorless powder (130 mg) containing sodium chloride. MS (APCI): m/z 306 [M+H]+

Reference Example 43

[Chemical Formula 92]

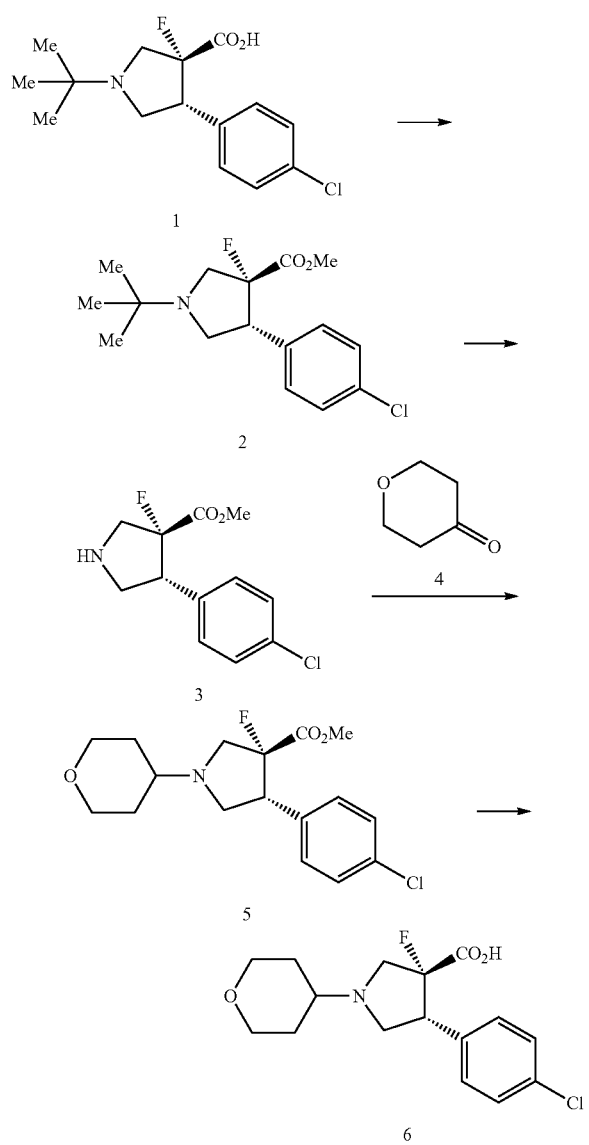

(1) To a solution of Compound 1 (700 mg) in methanol (5 mL) was added thionyl chloride (205 μL), and the mixture was stirred at room temperature for 6 hours. The reaction solution was concentrated under reduced pressure, a saturated aqueous solution of sodium hydrogen carbonate was added thereto to alkalify it, and extracted with dichloromethane. The resultant organic layer was washed with saturated saline, dried, and concentrated under reduced pressure to give Compound 2 (585 mg) as a pale yellow viscous material. MS (ESI): m/z 314/316 [M+H]+

(2) To a solution of Compound 2 (580 mg) in 1,2-dichloroethane (5 mL) was added 1-chloroethyl chloroformate (300 μL), and then the mixture was stirred at 70° C. To the reaction mixture was added dropwise a solution of diisopropylethylamine (484 μL) in 1,2-dichloroethane (5 mL), and stirred at the same temperature for 1 hour. To the reaction mixture was added dropwise a solution of 1-chloroethyl chloroformate (300 μL) in 1,2-dichloroethane (5 mL), then added dropwise a solution of diisopropylethylamine (484 μL) in 1,2-dichloroethane (5 mL), and the mixture was stirred at the same temperature for 19 hours. To the reaction mixture was added methanol (5 mL), stirred at 70° C. for 1 hour, and then the reaction solution was concentrated under reduced pressure. To the residue was added a saturated aqueous solution of sodium hydrogen carbonate to alkalify it, and extracted with chloroform. The resultant organic layer was washed with saturated saline, dried, and concentrated under reduced pressure. The residue was purified with silica gel column chromatography (chloroform:methanol=99:1-93:7) to give Compound 3 (165 mg) as a brown viscous material. MS (ESI): m/z 258/260 [M+H]+

(3) To a suspension of Compound 3 (80 mg) and Compound 4 (34 μL) in dichloromethane (2 mL) was added acetic acid (27 μL), the mixture was stirred at room temperature for 30 minutes, then sodium triacetoxyborohydride (100 mg) was added thereto, and stirred at room temperature for 17 hours. To the reaction mixture was added a saturated aqueous solution of sodium hydrogen carbonate, stirred, and then extracted with dichloromethane. The resultant organic layer was washed with saturated saline, dried, and concentrated under reduced pressure. The residue was purified with NH silica gel column chromatography (hexane:ethyl acetate=90:10-60:40) to give Compound 5 (93 mg) as a pale yellow viscous material. MS (ESI): m/z 342/344 [M+H]+

(4) To a solution of Compound 5 (93 mg) in methanol (2 mL) was added an aqueous solution of sodium hydroxide (2 mol/L, 540 μL), and the mixture was stirred at 40° C. for 1 hour. To the reaction mixture was added an aqueous solution of hydrochloric acid (2 mol/L, 540 μL), stirred, and then concentrated under reduced pressure to give Compound 6 as a colorless powder (151 mg) containing sodium chloride. MS (ESI): m/z 328/330 [M+H]+

Reference Example 44

A corresponding starting compound was treated in a similar manner to the above Reference Example 43 to give the compound in the following Table 30.

TABLE 30

| Reference Example | Compound | MS |
|---|---|---|
| 44 | ![structure] | (ESI): m/z 312/314 [M + H]+ |

Reference Example 45

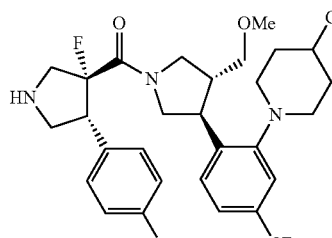

(1) To a mixed solution Compound 1 (167 mg) and Compound 2 (150 mg) in N,N-dimethylformamide (3 mL) were added 1-ethyl-3-(3-dimethylaminopropyl)carbodiimide hydrochloride (126 mg), 1-hydroxy-7-azabenzotriazole (89 mg), and triethylamine (183 μL), and the mixture was stirred at room temperature for 2.5 hours. To the reaction mixture were added a saturated aqueous solution of sodium hydrogen carbonate and ethyl acetate, stirred, and then the organic layer was separated. The resultant organic layer was washed with saturated saline, dried, and concentrated under reduced pressure. The residue was purified with silica gel column chromatography (hexane:ethyl acetate=85:15-70:30) to give Compound 3 (218 mg) as a colorless powder. MS (APCI): m/z 706 [M+H]+

(2) To a solution of Compound 3 (218 mg) in dichloromethane (4.4 mL) was added trifluoroacetic acid (1.1 mL) under ice-cooling, and then the mixture was stirred at room temperature for 4 hours. The reaction mixture was diluted with dichloromethane, then a saturated aqueous solution of sodium hydrogen carbonate was added thereto under stirring until the mixture became alkaline, and then the organic layer was separated. The resultant organic layer was dried, and then concentrated under reduced pressure to give Compound 4 (186 mg) as a colorless powder. MS (ESI): m/z 606 [M+H]+

Reference Examples 46-48

A corresponding starting compound was treated in a similar manner to the above Reference Example 45 to give each compound in the following Table 31.

TABLE 31

| Reference Example | Compound | MS |
|---|---|---|
| 46 | 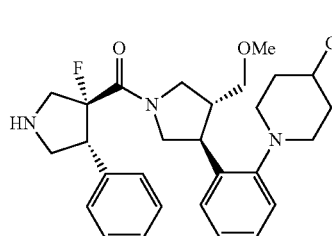 | (APCI) m/z 622 [M + H]+ |
| 47 | | (ESI) m/z 572 [M + H]+ |

TABLE 31-continued

| Reference Example | Compound | MS |
|---|---|---|
| 48 | 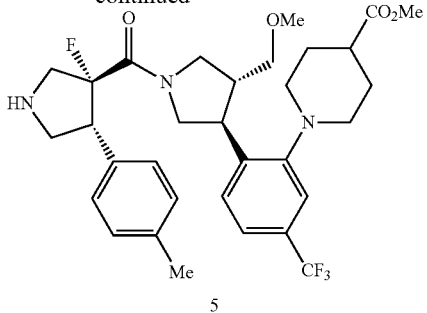 | (ESI) m/z 636 [M + H]+ |

Reference Example 49

[Chemical Formula 94]

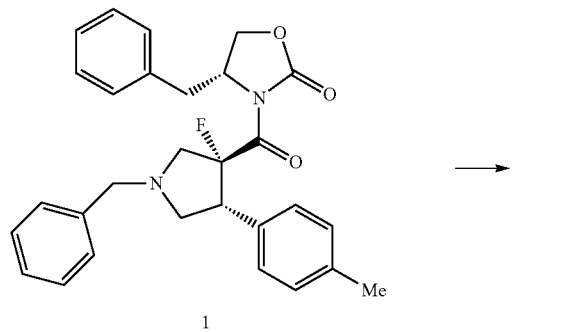

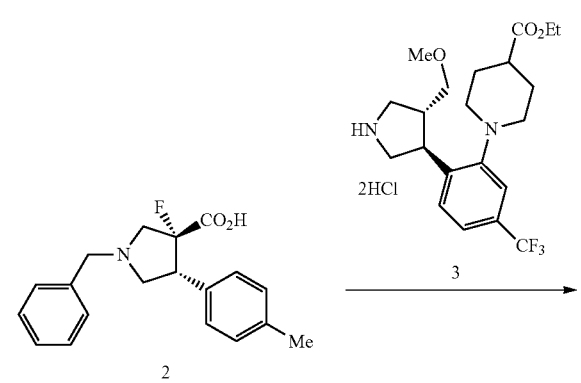

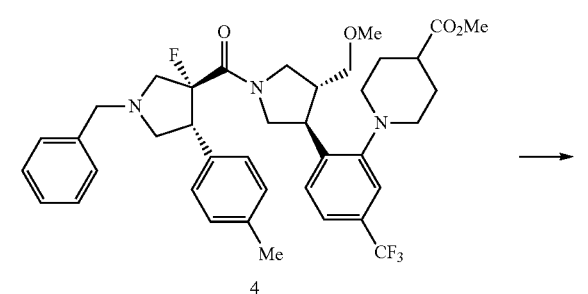

(1) To a solution of Compound 1 (735 mg) obtained by treating a corresponding starting compound in a similar manner to Reference Example 1 in tetrahydrofuran (8 mL) was added an aqueous solution of lithium hydroxide (lithium hydroxide (monohydrate): 78 mg+water: 4 mL) under ice-cooling, the mixture was stirred at room temperature for 2 hours, and then tetrahydrofuran was evaporated. To the residue was added water (20 mL), and then washed with a mixed solution (20 mL) of ethyl acetate and diethylether (1:3) three times. To the resultant aqueous layer was added an aqueous solution of hydrochloric acid (2 mol/L, 935 µL), and then concentrated under reduced pressure to give Compound 2 as a colorless powder (610 mg) containing lithium chloride. MS (ESI): m/z 314[M+H]+

(2) Compound 2 (200 mg), Compound 3 (303 mg), 1-ethyl-3-(3-dimethylaminopropyl)carbodiimide hydrochloride (184 mg), 1-hydroxy-7-azabenzotriazole (131 mg), and triethylamine (357 µL) were added to N,N-dimethylformamide (5 mL), and the mixture was stirred at room temperature for 17 hours. To the reaction mixture were added a saturated aqueous solution of sodium hydrogen carbonate and ethyl acetate, stirred, and then the organic layer was separated. The resultant organic layer was washed with saturated saline, dried, and concentrated under reduced pressure. The residue was purified with NH silica gel column chromatography (hexane:ethyl acetate=90:10-65:35) to give Compound 4 (280 mg) as a colorless viscous material.

MS (ESI): m/z 696[M+H]+

(3) To a solution of Compound 4 (280 mg) in methanol (5 mL) was added 10% palladium carbon (wetted with ca. 50% water, 80 mg), and the mixture was stirred under hydrogen atmosphere (1 atm) for 2 hours. Palladium carbon was removed by filtration, and the filtrate was concentrated under reduced pressure to give Compound 5 (240 mg) as a colorless viscous material. MS (ESI): m/z 606 [M+H]+

Reference Examples 50-51

A corresponding starting compound was treated in a similar manner to the above Reference Example 49 to give each compound in the following Table 32.

TABLE 32

| Reference Example | Compound | MS |
|---|---|---|
| 50 | 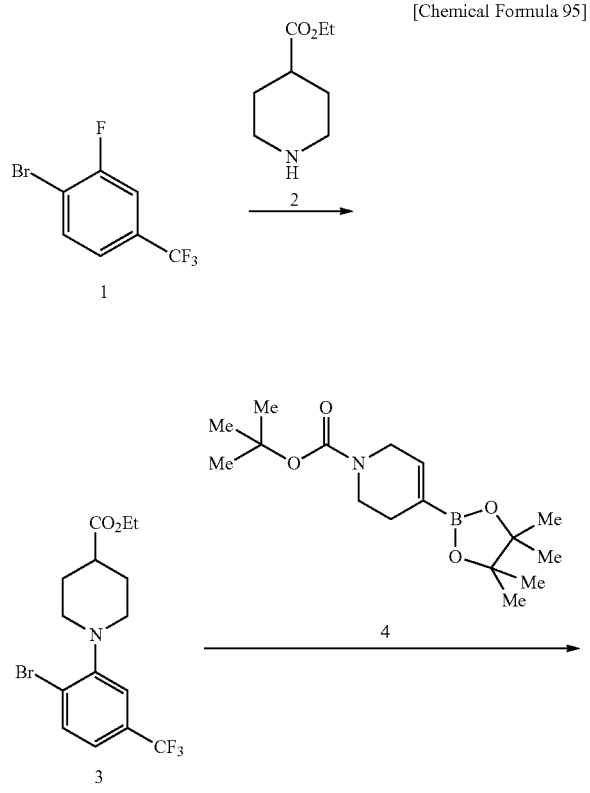 | (ESI) m/z 640 [M + H]+ |
| 51 |  | (APCI) m/z 606 [M + H]+ |

Reference Example 52

[Chemical Formula 95]

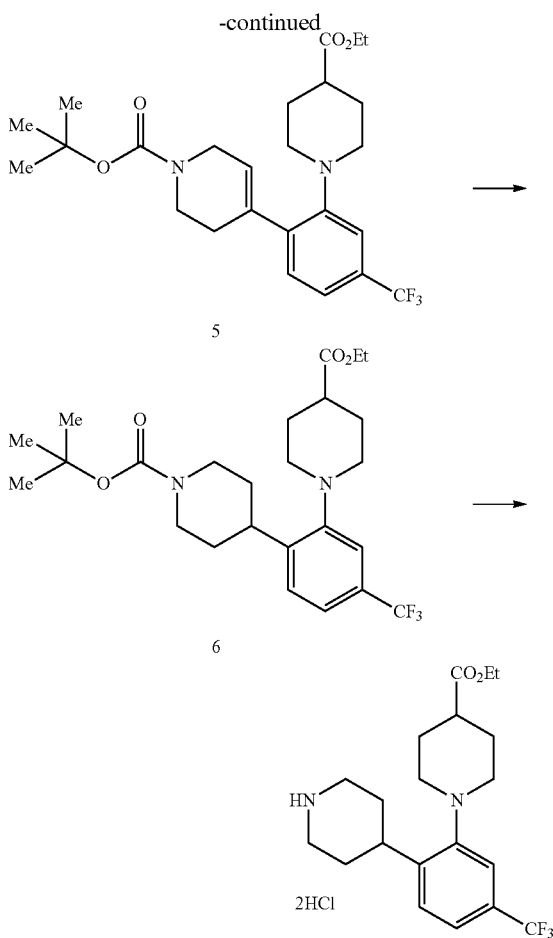

(1) A suspension of Compound 1 (590 µL), Compound 2 (3162 µL), and potassium carbonate (1191 mg) in N-methylpyrrolidone (3 mL) was heated under microwave radiation at 180° C. for 2 hours. The reaction solution was cooled to room temperature, poured into water, and then extracted with ethyl acetate. The resultant organic layer was washed with water and saturated saline, dried, and concentrated under reduced pressure. The residue was purified with silica gel column chromatography (hexane:ethyl acetate=99:1-90:10) to give Compound 3 (3.336 g) as a colorless viscous material. MS (ESI): m/z 380/382 [M+H]+

(2) To a solution of Compound 3 (3336 mg) and Compound 4 (3256 mg) in N,N-dimethylformamide (67 mL) were added an aqueous solution of sodium carbonate (2 mol/L, 3.16 mL) and dichloro[1, 1'-bis(diphenylphosphino) ferrocene]palladium(II) dichloromethane adduct (358 mg), and the mixture was stirred under heating under nitrogen atmosphere at 80° C. for 4 hours. After being cooled to room temperature, the reaction mixture was poured into water, and extracted with ethyl acetate. The organic layer was washed with water and saturated saline, dried, and concentrated under reduced pressure. The residue was purified with silica gel column chromatography (hexane:ethyl acetate=90:10-75:25) to give Compound 5 (3483 mg) as a pale yellow viscous material. MS (APCI): m/z 483 [M+H]+

(3) To a solution of Compound 5 (3000 mg) in ethanol (30 mL) was added 10% palladium carbon (wetted with ca. 50% water, 600 mg), and the mixture was stirred under hydrogen atmosphere (1 atm) at room temperature for 4.5 hours. Palladium carbon was removed by filtration, and then the filtrate was concentrated under reduced pressure. The residue was purified with silica gel column chromatography (hexane:ethyl acetate=90:10-70:30) to give Compound 6 (2880 mg) as a colorless viscous material. MS (APCI): m/z 485 [M+H]+

(4) To a solution of Compound 6 (2880 mg) in 1,4-dioxane (57.6 mL)/ethanol (10 mL) was added a solution of hydrochloric acid in 1,4-dioxane (4 mol/L, 14.86 mL), and the mixture was stirred at room temperature for 3 hours. The reaction mixture was concentrated under reduced pressure, the residue was powdered with diethylether, collected by filtration, and then dried under reduced pressure to give Compound 7 (2454 mg) as a pale yellow powder. MS (ESI): m/z 385 [M+H]+

Reference Examples 53-63

A corresponding starting compound was treated in a similar manner to the above Reference Example 52 to give each compound in the following Table 33.

TABLE 33

| Reference Example | Compound | MS |
|---|---|---|
| 53 | (structure with CO₂Et, piperidine, 2HCl, F) | MS (APCI): m/z 335 [M + H]+ |
| 54 | (structure with CO₂Et, piperidine, 2HCl, Me) | MS (ESI): m/z 331 [M + H]+ |
| 55 | (structure with CO₂Et, piperidine, 2HCl, CHF₂) | MS (ESI): m/z 367 [M + H]+ |

TABLE 33-continued

| Reference Example | Compound | MS |
|---|---|---|
| 56 | (structure with SO₂NMe₂, piperidine, 2HCl, CF₃) | MS (APCI): m/z 420 [M + H]+ |
| 57 | (structure with CO₂Et oxazole, HCl, CF₃) | MS (ESI): m/z 369 [M + H]+ |
| 58 | (structure with thiomorpholine dioxide, 2HCl, CF₃) | MS (ESI): m/z 363 [M + H]+ |
| 59 | (structure with CO₂Me cyclopropane-azabicyclic, 2HCl, CF₃) | MS (ESI): m/z 369 [M + H]+ |
| 60 | (structure with Me, Me, CO₂Me, ether, HCl, CF₃) | MS (ESI): m/z 360 [M + H]+ |

TABLE 33-continued

| Reference Example | Compound | MS |
|---|---|---|
| 61 | 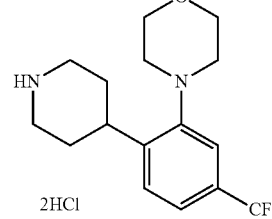 | MS (APCI): m/z 315 [M + H]+ |
| 62 | 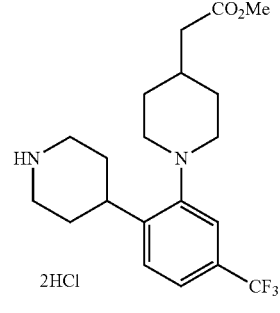 [SMILES: COC(=O)CC1CCN(c2cc(C(F)(F)F)ccc2C2CCNCC2)CC1 ; "2HCl"] | MS (APCI): m/z 385 [M + H]+ |
| 63 | 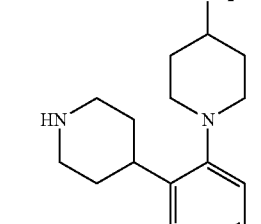 | MS (ESI): m/z 335 [M + H]+ |

Reference Example 64

A starting material of Reference Example 55 was prepared according to the following method.

[Chemical Formula 96]

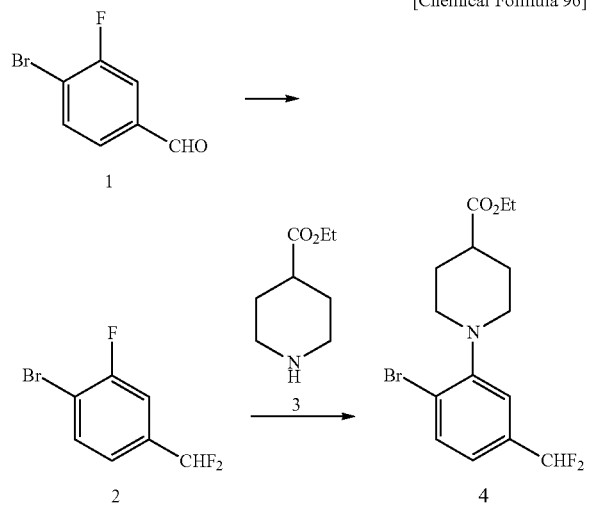

Reference Example 65

A starting material of Reference Example 56 was prepared according to the following method.

[Chemical Formula 97]

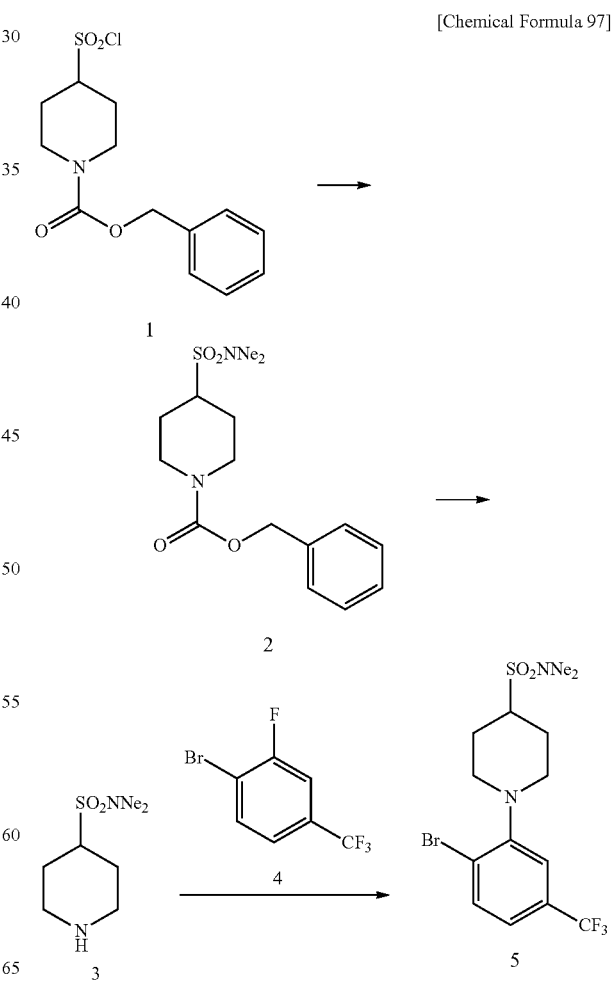

(1) To a solution of Compound 1 (1.296 mg) in dichloromethane (12 mL) was added dropwise bis(2-methoxyethyl)aminosulfurtrifluoride (1.294 mL) under cooling, the mixture was stirred at room temperature for 12 hours, and then the reaction solution was concentrated under reduced pressure. The residue was purified with silica gel column chromatography (hexane:ethyl acetate=100:0-92:8) to give Compound 2 (1.38 g) as a colorless liquid.

(2) A solution of Compound 2 (1.38 g), Compound 3 (1.6 mL), and potassium carbonate (1.61 g) in 1,3-dimethyl-2-imidazolidinone (6 mL) was heated under microwave radiation at 180° C. for 24 hours, then ethyl iodide (1.43 mL) and potassium carbonate (924 mg) were added thereto, and the mixture was stirred at 50° C. for 4 hours. The reaction solution was cooled to room temperature, poured into water, and extracted with ethyl acetate. The resultant organic layer was washed with water and saturated saline, dried, and concentrated under reduced pressure. The residue was purified with silica gel column chromatography (hexane:ethyl acetate=97:3-80:20) to give Compound 4 (1 g) as a pale yellow viscous material. MS (ESI): m/z 362/364 [M+H]+

(1) To a solution of Compound 1 (1574 mg) in dichloromethane (10 mL) was added an aqueous solution of dimethylamine (50% aqueous solution, 2 mL) under ice-cooling, and then the mixture was stirred at room temperature for 2 hours. To the reaction mixture were added an aqueous solution of hydrochloric acid (0.5 mol/L) and chloroform, stirred, then the organic layer was separated, washed with saturated saline, dried, and then concentrated under reduced pressure to give Compound 2 (1.609 g) as a colorless viscous material. MS (APCI): m/z 327 [M+H]+

(2) To a solution of Compound 2 (1.57 g) in methanol (5 mL)/tetrahydrofuran (20 mL) was added 10% palladium carbon (wetted with ca. 50% water, 300 mg), and the mixture was stirred under hydrogen atmosphere (1 atm) at room temperature for 2 hours. Palladium carbon was removed by filtration, and then the filtrate was concentrated under reduced pressure to give Compound 3 (906 mg) as a colorless powder. MS (APCI): m/z 193 [M+H]+

(3) A solution of Compound 3 (880 mg), Compound 4 (556 mg), and potassium carbonate (665 mg) in 1,3-dimethyl-2-imidazolidinone (5 mL) was heated under nitrogen atmosphere at 190° C. for 5 hours. The reaction mixture was cooled to room temperature, poured into water, and extracted with ethyl acetate. The resultant organic layer was washed with water and saturated saline, dried, and concentrated under reduced pressure. The residue was purified with silica gel column chromatography (hexane:ethyl acetate=95:5-60:40) to give Compound 5 (119 mg) as a colorless solid. MS (ESI): m/z 415/417 [M+H]+

Reference Example 66

A starting material of Reference Example 57 was prepared according to the following method.

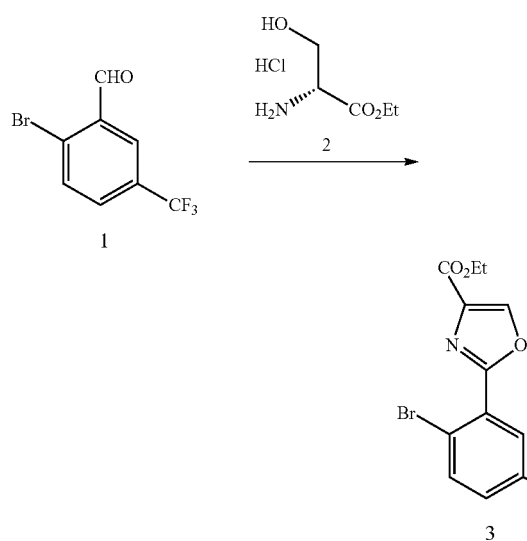

[Chemical Formula 98]

A solution of Compound 1 (2 g), Compound 2 (2.01 g), magnesium sulfate (950 mg), and triethylamine (2.75 mL) in tetrahydrofuran (40 mL) was stirred at room temperature for 15 hours. The insoluble matter was removed by filtration, and then the filtrate was concentrated under reduced pressure. To a solution of the residue in dichloromethane (40 mL) were added bromotrichloromethane (2.33 mL) and subsequently 1,8-diazabicyclo[5.4.0]-7-undecene (3.55 mL) under ice-cooling, and the mixture was stirred for 1 hour. The mixture was stirred at room temperature for 6 hours, and then the reaction solution was concentrated under reduced pressure. The residue was purified with silica gel column chromatography (hexane:ethyl acetate=90:10-60:40), powdered with hexane, collected by filtration, and then dried under reduced pressure to give Compound 3 (936 mg) as a colorless powder. MS (APCI): m/z 327 [M+H]+

Reference Example 67

A starting material of Reference Example 58 was prepared according to the following method.

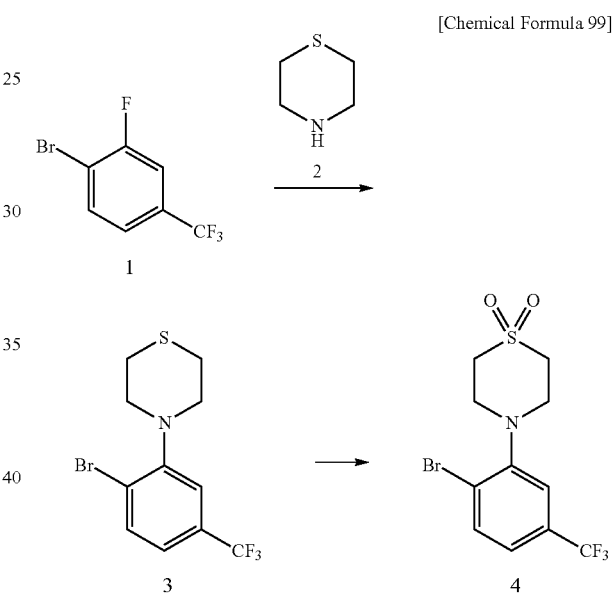

[Chemical Formula 99]

(1) Compound 1 (3 g) and Compound 2 (2.47 mL) were treated in a similar manner to Reference Example 52 to give Compound 3 (1.71 g) as a yellow viscous material.

(2) To a solution of Compound 3 (1.7 g) in N-methylpyrrolidone (30 mL) was added oxone (Sigma-Aldrich, 4.8 g), and the mixture was stirred at room temperature for 5 hours. To the reaction mixture were added water and ethyl acetate, stirred, and then the organic layer was separated. The resultant organic layer was washed with water and saturated saline, dried, and concentrated under reduced pressure. The residue was purified with silica gel column chromatography (hexane:ethyl acetate=95:5-80:20) to give Compound 4 (1055 mg) as a colorless powder. MS (ESI): m/z 358/360 [M+H]+

Reference Example 68

A starting material of Reference Example 60 was prepared according to the following method.

Reference Example 69

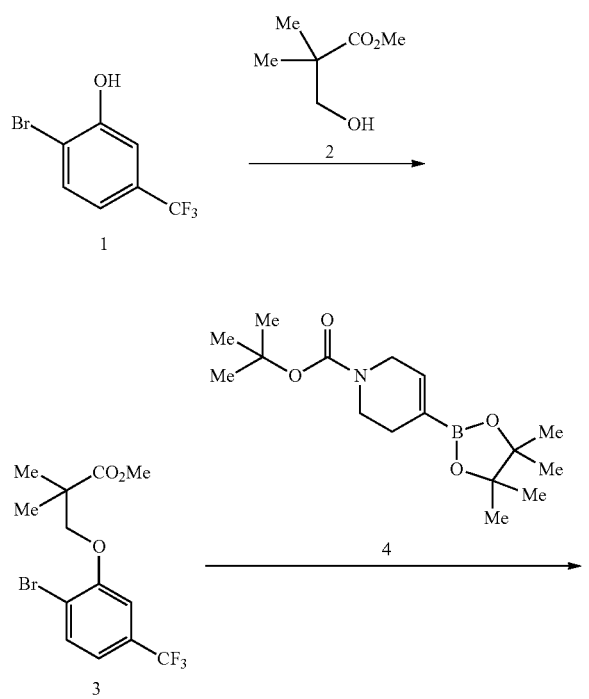

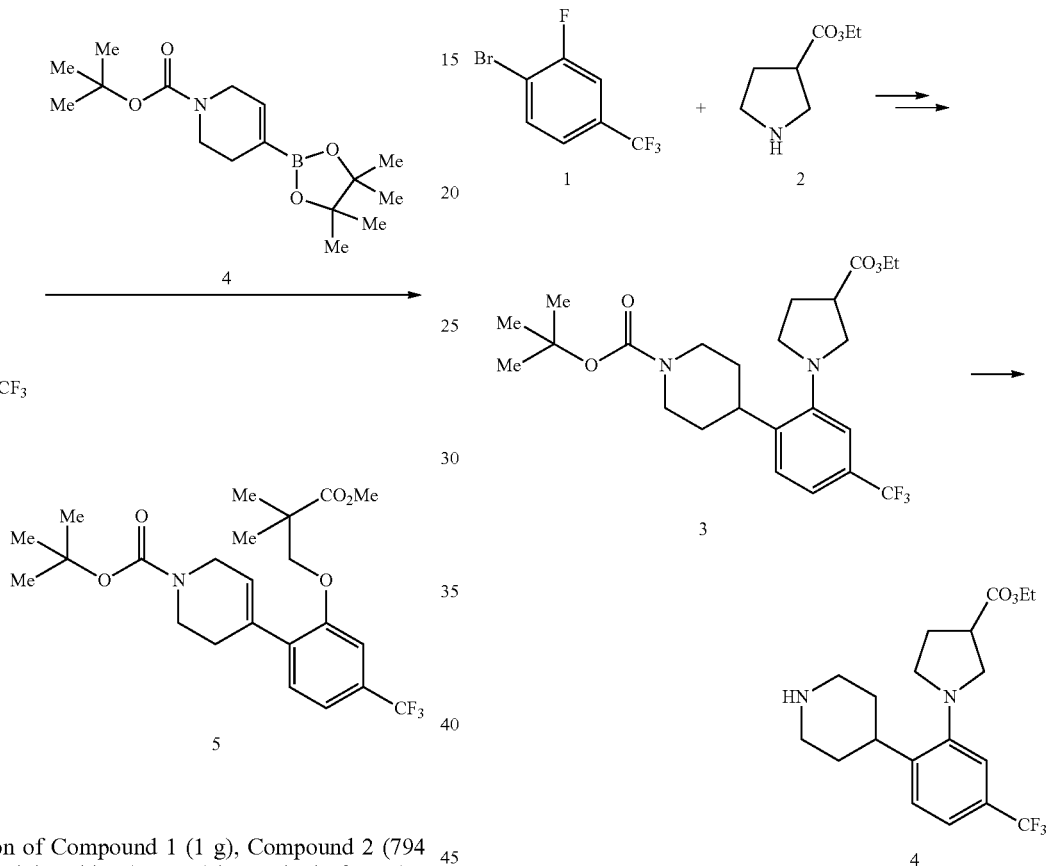

(1) To a solution of Compound 1 (1 g), Compound 2 (794 µL), and triphenylphosphine (2.177 g) in tetrahydrofuran (20 mL) was added dropwise diethyl azodicarboxylate (40 wt % toluene solution, 3.722 mL) under stirring. The mixture was heated at 70° C. for 4 hours, and then the solvent was evaporated under reduced pressure. To the residue was added diisopropylether, stirred, and then precipitated insoluble matter was removed by filtration. The filtrate was concentrated, and then the same process was repeated again. The filtrate was concentrated, and the residue was purified with silica gel column chromatography (hexane:ethyl acetate=100:0-90:10) to give Compound 3 (1319 mg) as a pale yellow viscous material.

(2) To a solution of Compound 3 (1310 mg) and Compound 4 (1369 mg) in N,N-dimethylformamide (26 mL) was added an aqueous solution of sodium carbonate (2 mol/L, 5.533 mL) and dichloro[1,1'-bis(diphenylphosphino)ferrocene]palladium(II) dichloromethane adduct (151 mg), and the mixture was heated under nitrogen atmosphere at 80° C. for 5 hours. The reaction mixture was cooled to room temperature, poured into water, and extracted with ethyl acetate. The resultant organic layer was washed with water and saturated saline, dried, and concentrated under reduced pressure. The residue was purified with silica gel column chromatography (hexane:ethyl acetate=95:5-85:15) to give Compound 5 (1423 mg) as a colorless viscous material. MS (APCI): m/z 458 [M+H]+

Reference Example 69

(1) Compound 1 and Compound 2 were treated in a similar manner to Reference Example 52 to give Compound 3 (305 mg).

(2) To a solution of Compound 3 in chloroform (6.5 mL) was added trifluoroacetic acid (3.2 mL) under ice-cooling, and then the mixture was stirred at room temperature for 1.5 hours. To the reaction mixture was added a saturated aqueous solution of sodium hydrogen carbonate to become it alkaline, and extracted with chloroform. The resultant organic layer was dried, and concentrated under reduced pressure to give racemic Compound 4 (235 mg) as a colorless viscous material. MS (ESI): m/z 371 [M+H]+

Reference Examples 70-73

A corresponding starting compound was treated in a similar manner to the above Reference Example 69 to give each compound in the following Table 34.

TABLE 34

| Reference Example | Compound | MS |
|---|---|---|
| 70 | [structure: piperidine with CO2Et and Me, connected via N to phenyl with CF3, and HN-piperidine] | MS (ESI): m/z 399 [M + H]+ |
| 71 | [structure: piperidine with CO2Et, connected via N to phenyl with CF3, and HN-piperidine] | MS (ESI): m/z 385 [M + H]+ |
| 72 | [structure: piperidine with CO2Et, connected via N to phenyl with CF3, and HN-piperidine] | MS (ESI): m/z 385 [M + H]+ |
| 73 | [structure: azetidine with CO2Me, connected via N to phenyl with CF3, and HN-piperidine] | MS (ESI): m/z 343 [M + H]+ |

Reference Example 74

A starting material of Reference Example 73 was prepared according to the following method.

[Chemical Formula 102]

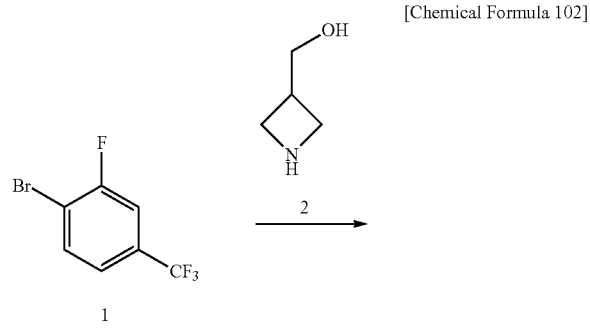

(1) Compound 1 (1385 mg) and Compound 2 (740 mg) were treated in a similar manner to Reference Example 52 to give Compound 3 (1104 mg) as a colorless powder. MS (ESI) m/z 310/312 [M+H]+

(2) To a solution of oxalyl chloride (525 μL) in dichloromethane (20 mL) was added dropwise a solution of dimethylsulfoxide (652 μL) in dichloromethane (15 mL) at −78° C., and then the mixture was stirred at the same temperature for 10 minutes. To the reaction mixture was added dropwise a solution of Compound 3 (950 mg) in dichloromethane (10 mL), and then stirred at the same temperature for 1 hour. To the reaction mixture was added dropwise triethylamine (2.56 mL), and then stirred at room temperature for 10 minutes. The reaction mixture was diluted with dichloromethane, then washed with a saturated aqueous solution of sodium hydrogen carbonate, dried, and then the solvent was evaporated under reduced pressure. To a solution of the residue in t-butanol (15 mL)/water (3 mL) was added sodium dihydrogen phosphate (807 mg) and 2-methyl-2-butene (6.5 mL). The reaction mixture was ice-cooled, sodium chlorite (609 mg) was added thereto, stirred at room temperature for 1 hour, then water and saturated saline were added thereto, and extracted with ethyl acetate. The resultant organic layer was washed sequentially with water and saturated saline, dried, and concentrated under reduced pressure. The residue was purified with silica gel column chromatography (chloroform:methanol=98:2-80:20) to give Compound 4 (788 mg) as a pale yellow viscous material. MS (ESI): m/z 324/326 [M+H]+

(3) To a solution of Compound 4 (780 mg) in N,N-dimethylformamide (15 mL) was added potassium carbonate (500 mg) and methyl iodide (180 μL), and the mixture was stirred at room temperature for 12 hours. The reaction mixture was diluted with ethyl acetate, then washed with water and saturated saline, dried, and then the solvent was evaporated under reduced pressure. The residue was purified with silica gel column chromatography (hexane:ethyl acetate=98:2-85:15) to give Compound 5 (766 mg) as a colorless viscous material. MS (ESI): m/z 338/340 [M+H]+

Reference Example 75

As a starting material of Reference Example 59, a corresponding starting compound was treated in a similar manner to the above Reference Example 74 to give the compound in the following Table 35.

TABLE 35

| Reference Example | Compound | MS |
|---|---|---|
| 75 | 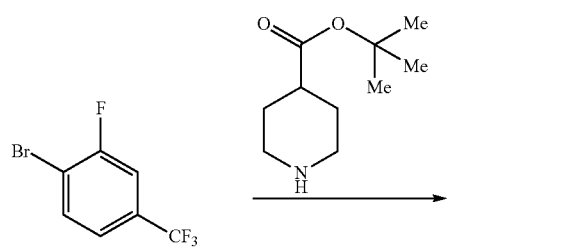 | MS (ESI): m/z 364/366 [M + H]+ |

Reference Example 76

[Chemical Formula 103]

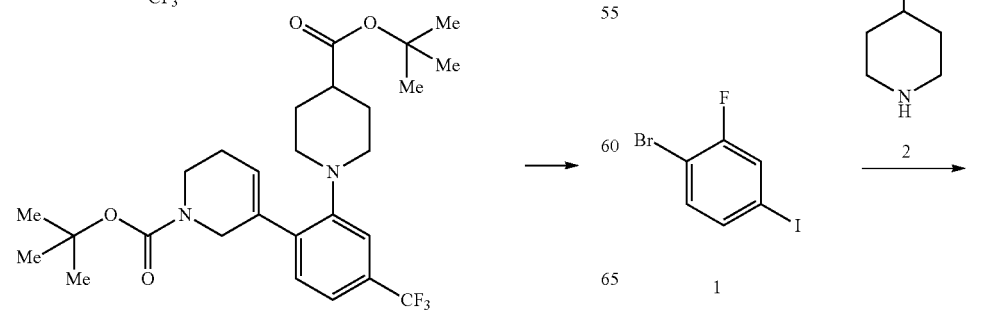

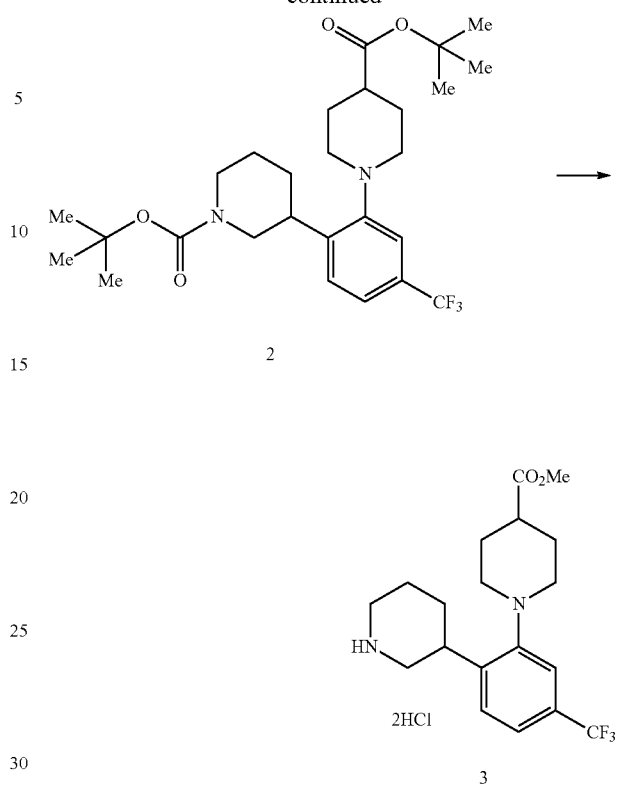

(1) Compound 1 obtained by the method described in WO2006/47277 was treated in a similar manner to Reference Example 52 to give Compound 2 (250 mg).

(2) Compound 2 (250 mg) was dissolved in a solution of hydrochloric acid in methanol (2 mol/L, 12 mL), and the mixture was stirred at 50° C. for 14 hours. The reaction mixture was concentrated under reduced pressure, to the residue was added toluene, and concentrate again to give racemic Compound 3 (193 mg) as a colorless powder. MS (ESI): m/z 371 [M+H]+

Reference Example 77

[Chemical Formula 104]

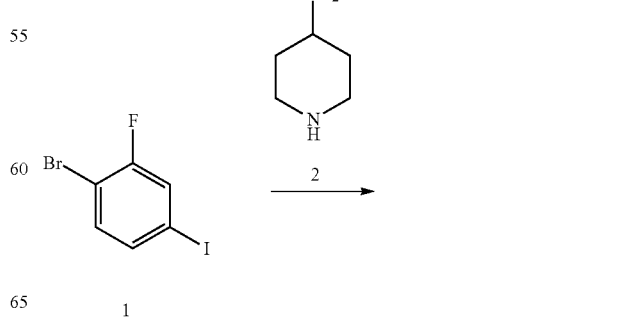

-continued

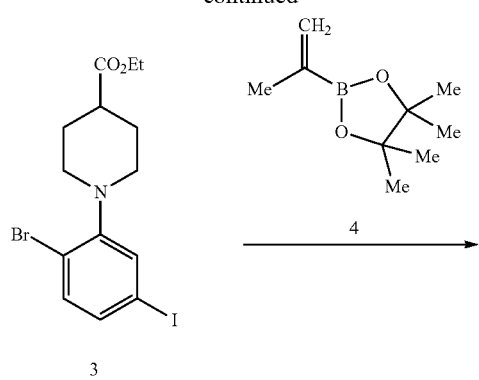

3

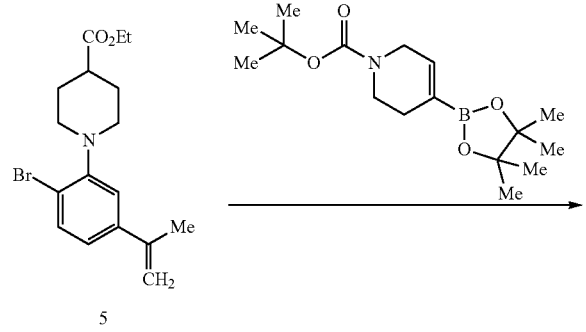

5

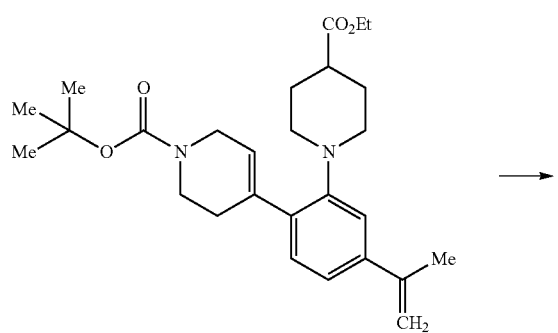

-continued

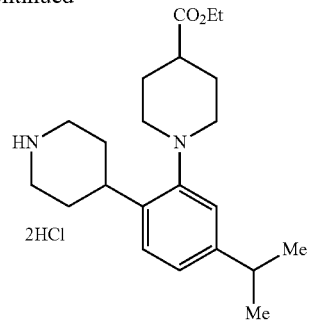

6

(1) A suspension of Compound 1 (3 g), Compound 2 (3.07 mL), and potassium carbonate (2.76 g) in N-methylpyrrolidone (3 mL) was heated under microwave radiation at 190° C. for 2 hours, then cooled to room temperature, and poured into water. The reaction mixture was extracted with ethyl acetate, the resultant organic layer was washed with water and saturated saline, dried, and concentrated under reduced pressure. The residue was purified with silica gel column chromatography (hexane:ethyl acetate=97:3-93:7) to give Compound 3 (2.449 g) as a colorless viscous material. MS (ESI): m/z 438/440 [M+H]+

(2) To a solution of Compound 3 (1 g) and Compound 4 (450 µL) in N,N-dimethylformamide (30 mL) were added an aqueous solution of sodium carbonate (2 mol/L, 3.42 mL) and dichloro[1,1'-bis(diphenylphosphino)ferrocene]palladium(II) dichloromethane adduct (93 mg), and the mixture was heated at 80° C. under nitrogen atmosphere for 3 hours. After being cooled to room temperature, the reaction mixture was poured into water, and extracted with ethyl acetate. The resultant organic layer was washed with water and saturated saline, dried, and concentrated under reduced pressure. The residue was purified with silica gel column chromatography (hexane:ethyl acetate=95:5-85:15) to give Compound 5 (768 mg) as a pale yellow viscous material. MS (ESI): m/z 353 [M+H]+

(3) Compound 5 was treated in a similar manner to the step (2) of Reference Example 52 to give Compound 6. MS (APCI) m/z 359 [M+H]+

Reference Example 78

[Chemical Formula 105]

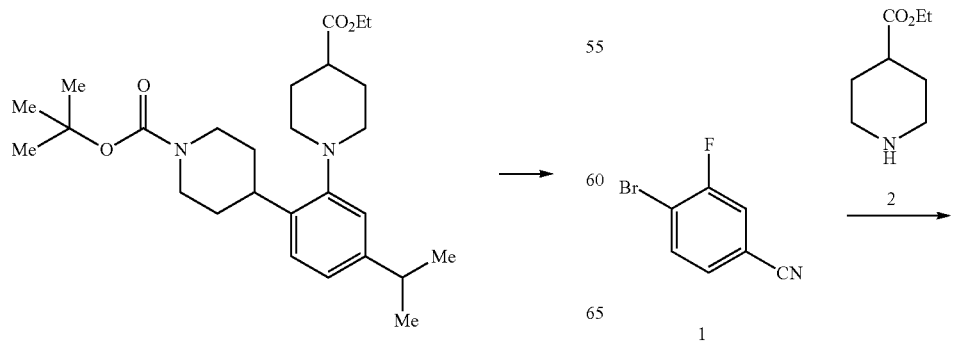

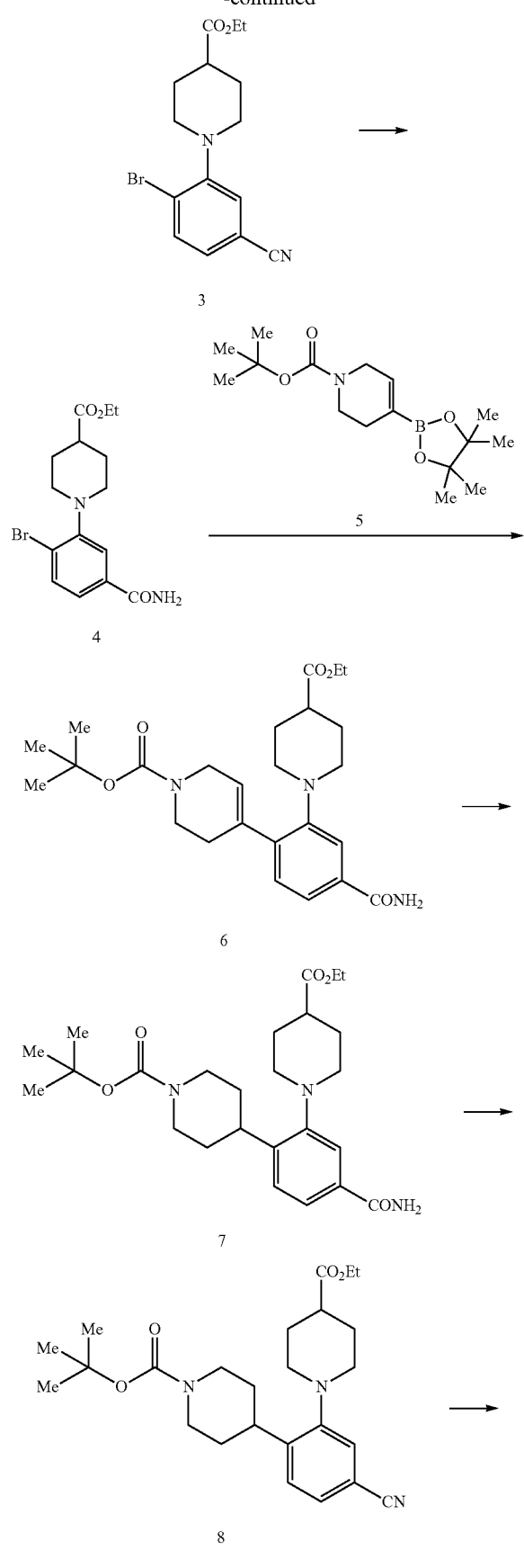

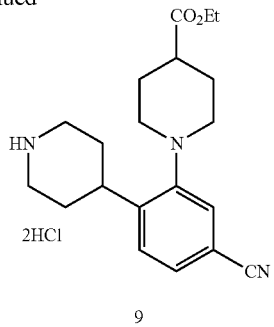

(1) A suspension of Compound 1 (1.5 g), Compound 2 (1618 μL), and potassium carbonate (2073 mg) in N-methylpyrrolidone (15 mL) was heated at 190° C. under microwave radiation for 1.5 hours, then cooled to room temperature, and poured into water. The reaction mixture was extracted with ethyl acetate, the resultant organic layer was washed with water and saturated saline, dried, and concentrated under reduced pressure. The residue was purified with silica gel column chromatography (hexane:ethyl acetate=98:2-85:15) to give Compound 3 (731 mg) as a colorless viscous material. MS (APCI): m/z 337/339 [M+H]+

(2) To a solution of Compound 3 (730 mg) in trifluoroacetic acid (4 mL) was added concentrated sulfuric acid (1 mL), and the mixture was stirred at room temperature for 7 days. The reaction solution was added dropwise to iced water, then 1N aqueous solution of sodium hydroxide was added thereto to neutralize it, and extracted with ethyl acetate. The organic layer was washed with saturated saline, dried, and concentrated under reduced pressure. The residue was powdered with diisopropylether, collected by filtration, and dried under reduced pressure to give Compound 4 (664 mg) as a colorless powder. MS (APCI): m/z 355/357 [M+H]+

(3) Compound 4 (640 mg) and Compound 5 (613 mg) were treated in a similar manner to the step (2) of Reference Example 52 to give Compound 6 (631 mg) as a colorless powder. MS (APCI) m/z 458 [M+H]+

(4) Compound 6 (620 mg) was treated in a similar manner to the step (3) of Reference Example 52 to give Compound 7 (621 mg) as a colorless powder. MS (APCI) m/z 460 [M+H]+

(5) To a solution of Compound 7 (500 mg) in N,N-dimethylformamide (10 mL) was added cyanuric chloride (590 mg) under ice-cooling, and the mixture was stirred for 1.5 hours. To the reaction solution was added iced water, and then extracted with ethyl acetate. The resultant organic layer was washed with a saturated aqueous solution of sodium hydrogen carbonate and saturated saline, dried, and concentrated under reduced pressure. The residue was purified with silica gel column chromatography (hexane:ethyl acetate=90:10-75:25) to give Compound 8 (459 mg) as a colorless viscous material. MS (ESI): m/z 442 [M+H]+

(6) Compound 8 (458 mg) was treated in a similar manner to the step (4) of Reference Example 52 to give Compound 9 (458 mg) as a colorless powder. MS (ESI) m/z 342 [M+H]+

Reference Example 79

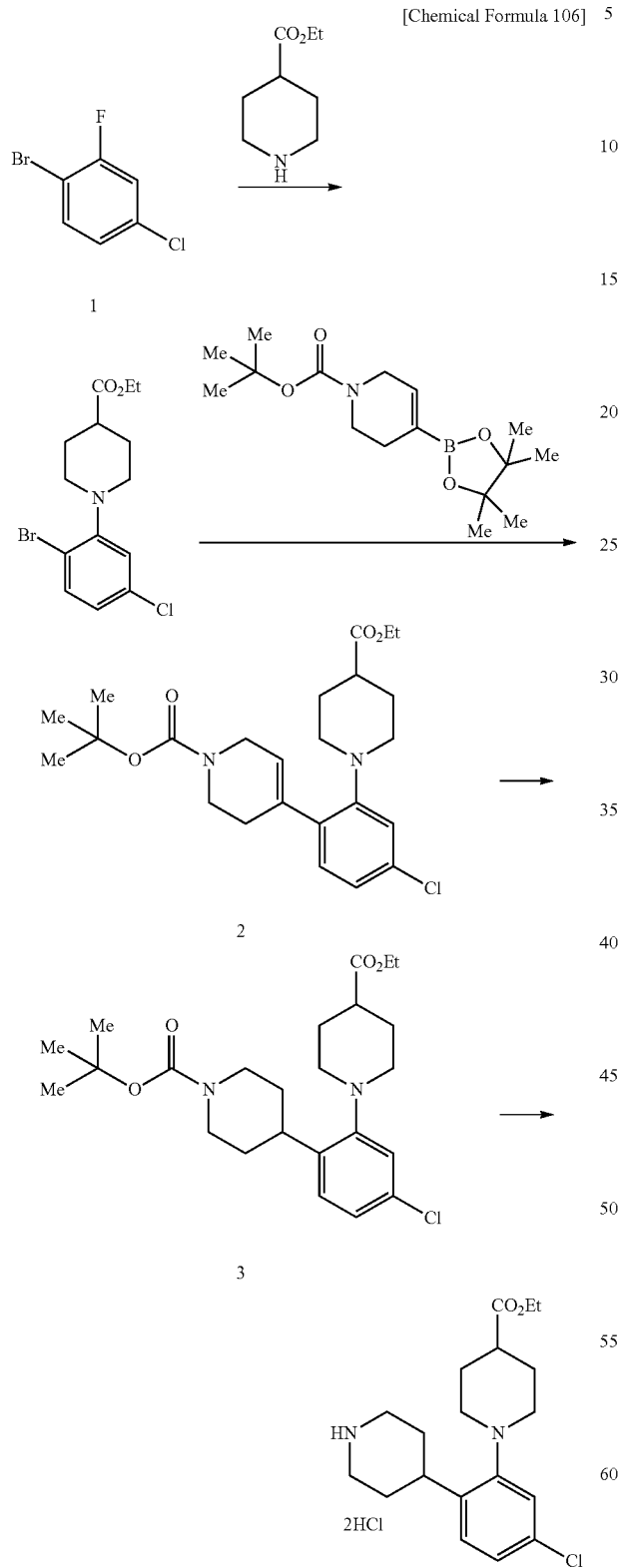

(1) Compound 1 was treated in a similar manner to the step (1) of Reference Example 52 to give Compound 2 (393 mg).
(2) To a solution of Compound 2 (393 mg) in ethanol (4 mL)/acetic acid (4 mL) was added platinum(IV) oxide (99 mg), and the mixture was stirred under hydrogen atmosphere (1 atm) at room temperature for 16 hours. The insoluble matter was removed by filtration, then to the filtrate were added water and ethyl acetate, subsequently added a saturated aqueous solution of sodium hydrogen carbonate to alkalify it, and the organic layer was separated. The resultant organic layer was washed with saturated saline, dried, and concentrated under reduced pressure. The residue was purified with silica gel column chromatography (hexane:ethyl acetate=90:10-80:20) to give Compound 3 (202 mg) as a colorless viscous material. MS (ESI): m/z 451/453 [M+H]+
(3) Compound 3 (200 mg) was treated in a similar manner to the step (4) of Reference Example 52 to give Compound 4 (181 mg) as a colorless powder. MS (ESI) m/z 351/353 [M+H]+

Reference Example 80

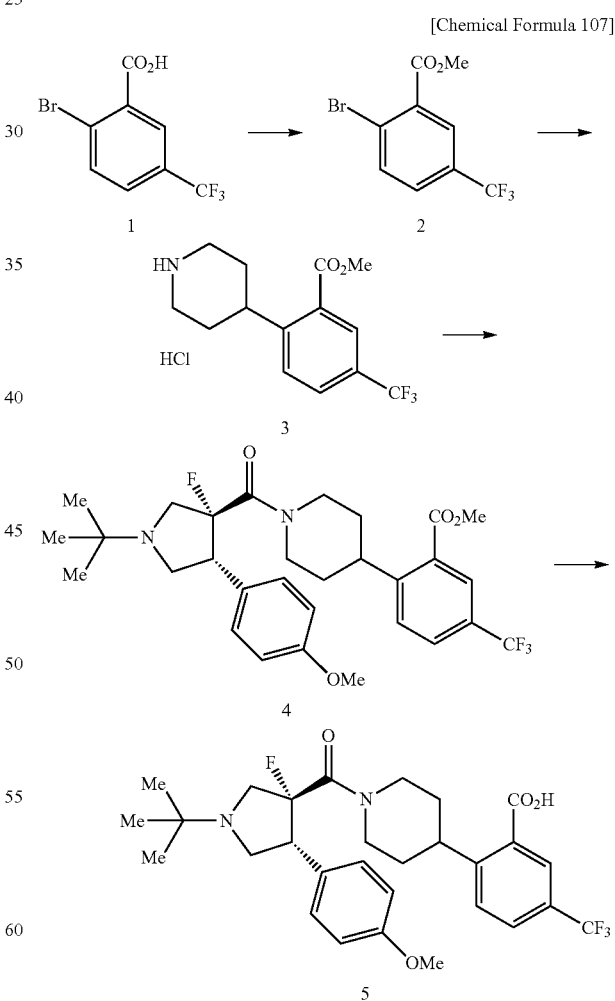

(1) To a solution of Compound 1 (4 g) in methanol (80 mL) was added concentrated sulfuric acid (1.94 mL) under ice-cooling, and the mixture was heated under reflux for 15 hours. Methanol was evaporated under reduced pressure, to the residue was added iced water, and then the mixture was extracted with ethyl acetate. The resultant organic layer was washed with a saturated aqueous solution of sodium hydrogen carbonate and saturated saline, dried, and concentrated under reduced pressure. The residue was purified with silica gel column chromatography (hexane:ethyl acetate=98:2-85:15) to give Compound 2 (3.68 g) as a colorless viscous material. MS (APCI): m/z 283/285 [M+H]+

(2) Compound 2 was treated in a similar manner to Reference Example 52 to give Compound 3 as a colorless powder. MS (ESI) m/z 288 [M+H]+

(3) Compound 3 was treated in a similar manner to Example 10 to give Compound 4 as a colorless powder. MS (ESI) m/z 565 [M+H]+

(4) Compound 4 was treated in a similar manner to Example 11 to give Compound 5 as a colorless powder. MS (ESI) m/z 551 [M+H]+

Reference Example 81

[Chemical Formula 108]

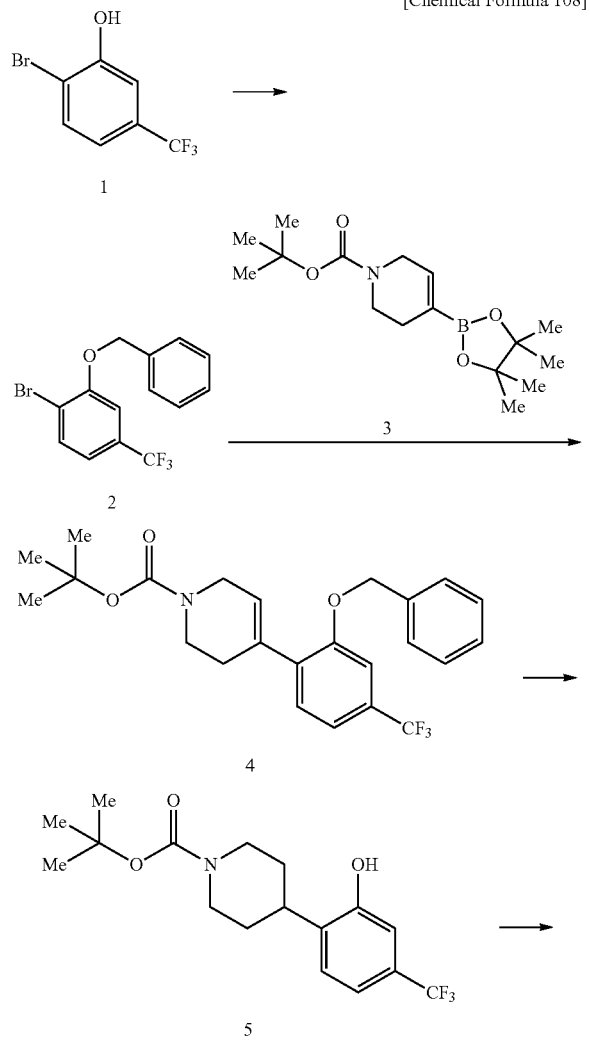

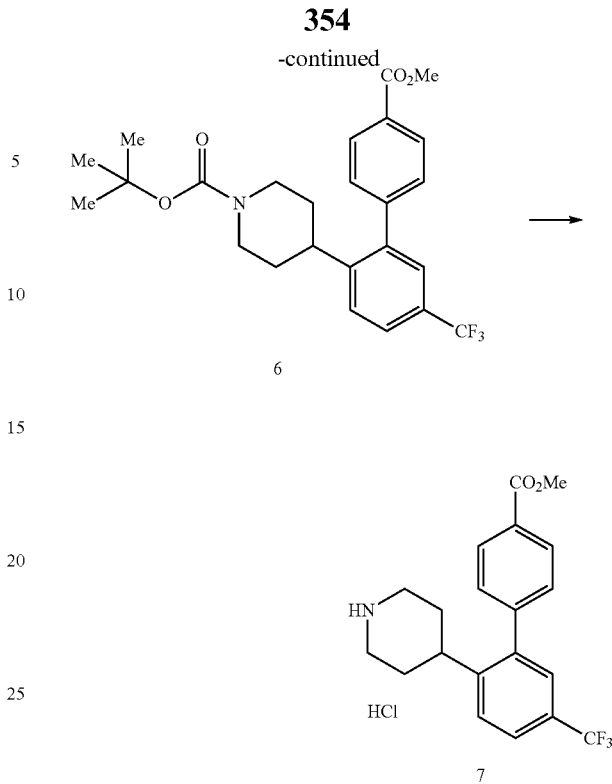

(1) To a solution of Compound 1 (2 g) and benzyl bromide (1086 µL) in N,N-dimethylformamide (40 mL) was added sodium hydride (60% in oil, 398 mg) under ice-cooling, and then the mixture was stirred at room temperature for 3 hours. The reaction mixture was poured into water, and extracted with ethyl acetate. The resultant organic layer was washed with water and saturated saline, dried, and concentrated under reduced pressure. The residue was purified with silica gel column chromatography (hexane:ethyl acetate=98:2-90:10) to give Compound 2 (2.7 g) as a colorless powder.

(2) To a solution of Compound 2 (1 g) and Compound 3 (1027 mg) in N,N-dimethylformamide (20 mL) was added an aqueous solution of sodium carbonate (2 mol/L, 4.53 mL) and dichloro[1,1'-bis(diphenylphosphino)ferrocene]palladium(II) dichloromethane adduct (123 mg), and the mixture was heated at 80° C. under nitrogen atmosphere for 4 hours. The reaction mixture was cooled to room temperature, poured into water, and extracted with ethyl acetate. The resultant organic layer was washed with water and saturated saline, dried, and concentrated under reduced pressure. The residue was purified with silica gel column chromatography (hexane:ethyl acetate=95:5-85:15) to give Compound 4 (935 mg) as a pale yellow viscous material. MS (APCI): m/z 334 [M-Boc+H]+

(3) To a solution of Compound 4 (930 mg) in methanol (19 mL) was added 10% palladium carbon (wetted with ca. 50% water, 186 mg), and the mixture was stirred under hydrogen atmosphere (1 atm) at room temperature for 4 hours. Palladium carbon was removed by filtration, and then the filtrate was concentrated to give Compound 5 (723 mg) as a colorless powder.

(4) To a solution of Compound 5 (300 mg) in dichloromethane (3.6 mL) were added trifluoromethanesulfonic anhydride (183 µL) and subsequently triethylamine (182 µL) under ice-cooling, the mixture was stirred for 10 minutes, then warmed to room temperature, and stirred for 1 hour. To the reaction mixture were added trifluoromethanesulfonic anhydride (43 μL) and subsequently triethylamine (43 μL) under ice-cooling, and stirred at room temperature for 14 hours. To the reaction mixture were added a saturated aqueous solution of sodium hydrogen carbonate and dichloromethane, stirred, and then extracted with dichloromethane. The resultant organic layer was dried, and concentrated under reduced pressure. To a solution of the residue in N,N-dimethylformamide (2 mL) were added 4-methoxycarbonylphenylboronic acid (45 mg), an aqueous solution of sodium carbonate (2 mol/L, 251 μL), and dichloro[1,1'-bis(diphenylphosphino)ferrocene]palladium(II) dichloromethane adduct (7 mg), and the mixture was stirred under nitrogen atmosphere at 80° C. for 2 hours. The reaction mixture was cooled to room temperature, poured into water, and extracted with ethyl acetate. The resultant organic layer was washed with water and saturated saline, dried, and concentrated under reduced pressure. The residue was purified with silica gel column chromatography (hexane:ethyl acetate=90:10-75:25) to give Compound 6 (62 mg) as a colorless powder. MS (APCI): m/z 464 [M+H]+

(5) To a solution of Compound 6 (60 mg) in 1,4-dioxane (1.2 mL) was added a solution of hydrochloric acid in 1,4-dioxane (4 mol/L, 324 μL), and the mixture was stirred at room temperature for 23 hours. The reaction mixture was concentrated under reduced pressure, the residue was powdered with diisopropylether, collected by filtration, and then dried to give Compound 7 (49 mg) as a colorless powder. MS (APCI): m/z 364 [M+H]+

Reference Example 82

[Chemical Formula 109]

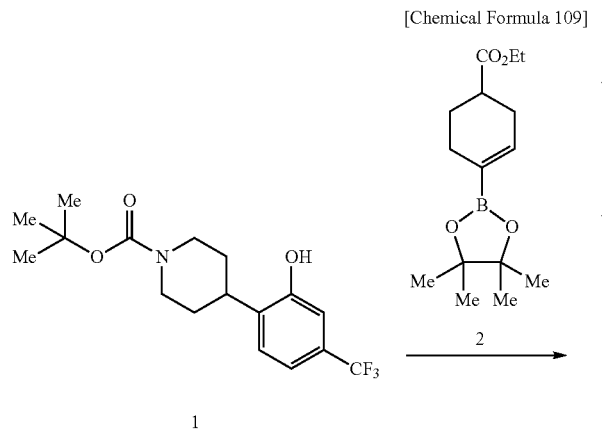

(1) To a solution of Compound 1 (800 mg) in dichloromethane (23 mL) were added trifluoromethanesulfonic anhydride (487 μL) and subsequently triethylamine (484 μL) under ice-cooling, the mixture was stirred for 10 minutes, then warmed to room temperature, and the stirred for 5 hours. To the reaction mixture was added iced water, and extracted with dichloromethane. The resultant organic layer was dried, and concentrated under reduced pressure. To a solution of the half amount of the residue and Compound 2 (361 mg) obtained by the method described in WO2013/187496 in N,N-dimethylformamide (8 mL) were added an aqueous solution of sodium carbonate (2 mol/L, 1759 μL) and dichloro[1,1'-bis(diphenylphosphino)ferrocene]palladium (II) dichloromethane adduct (48 mg), and the mixture was heated at 60° C. under nitrogen atmosphere for 2.5 hours. To the reaction mixture were added Compound 2 (164 mg) and dichloro[1,1'-bis(diphenylphosphino)ferrocene]palladium (II) dichloromethane adduct (48 mg), and stirred at 60° C. for 16 hours. The reaction mixture was cooled to room temperature, poured into water, and extracted with ethyl acetate. The resultant organic layer was washed with water and saturated saline, dried, and concentrated under reduced pressure. The residue was purified with silica gel column chromatography (hexane:ethyl acetate=95:5-80:20) to give racemic Compound 3 (502 mg) as a colorless viscous material. MS (ESI): m/z 482 [M+H]+

(2) To a solution of Compound 3 (100 mg) in 1,4-dioxane (2 mL) was added a solution of hydrochloric acid in 1,4-dioxane (4 mol/L, 519 μL), and the mixture was stirred at room temperature for 24 hours. The reaction mixture was concentrated under reduced pressure, the residue was powdered with diisopropylether, collected by filtration, and then dried to give Compound 4 (81 mg) as a colorless powder. MS (APCI): m/z 382 [M+H]+

Reference Example 83

[Chemical Formula 110]

-continued

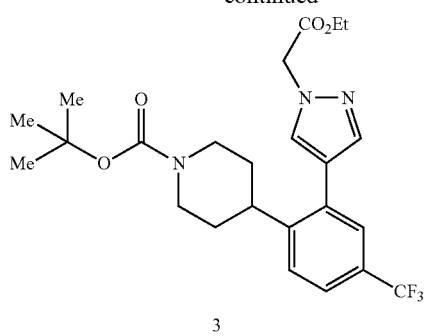

3

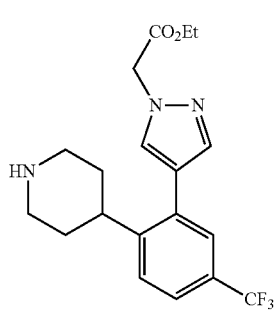

4

(1) Compound 1 (173 mg) and Compound 2 were treated in a similar manner to Reference Example 82 to give Compound 3 (102 mg) as a colorless viscous material. MS (ESI): m/z 482 [M+H]+

(2) To a solution of Compound 3 (95 mg) in dichloromethane (2 mL) was added trifluoroacetic acid (1 mL), and the mixture was stirred at room temperature for 2 hours. To the reaction mixture was added a saturated aqueous solution of sodium hydrogen carbonate to alkalify it, and extracted with dichloromethane. The resultant organic layer was dried, and concentrated under reduced pressure to give Compound 4 (72 mg) as a colorless viscous material. MS (ESI): m/z 382 [M+H]+

Reference Example 84

[Chemical Formula 111]

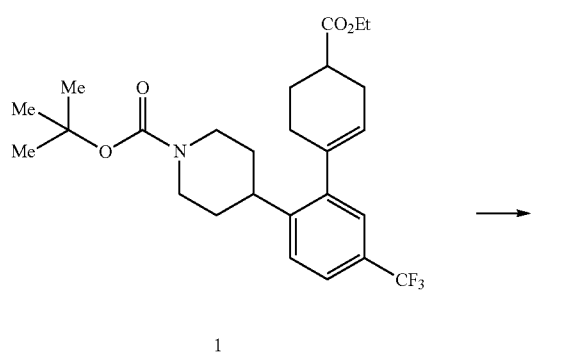

1

-continued

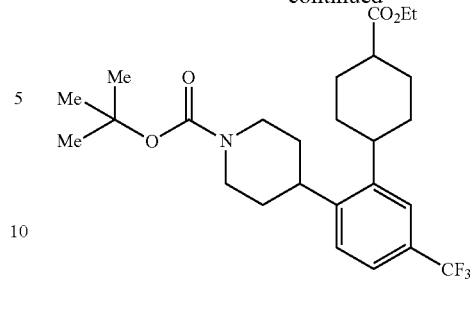

2

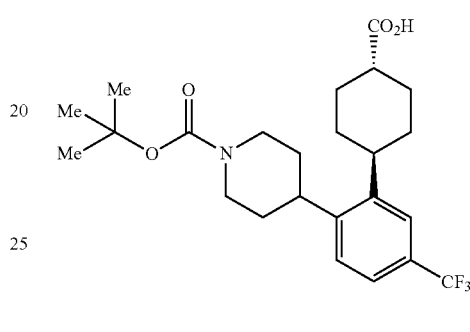

3

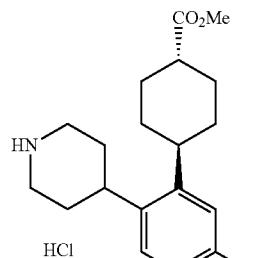

4

(1) To a solution of Compound 1 (400 mg) in ethanol (8 mL) was added 10% palladium carbon (wetted with ca. 50% water, 80 mg), and the mixture was stirred under hydrogen atmosphere (1 atm) at room temperature for 3.5 hours. Palladium carbon was removed by filtration, and then the filtrate was concentrated under reduced pressure to give Compound 2 (390 mg) as a colorless viscous material. MS (ESI): m/z 384 [M-Boc+H]+

(2) To a solution of Compound 2 (290 mg) in t-butanol (6 mL) was added potassium t-butoxy (74 mg), and then the mixture was heated at 40° C. for 4 hours. To the reaction mixture was added water (30 μL), stirred for 1.5 hours, then added additional water (50 μL), and stirred at the same temperature for 16 hours. To the reaction mixture was added an aqueous solution of sodium hydroxide (2 mol/L, 900 μL), stirred at 30° C. for 0.5 hours, and then left to stand at room temperature for 2 days. To the reaction mixture was added an aqueous solution of hydrochloric acid (2 mol/L, 1200 μL), then poured into water, and extracted with ethyl acetate. The resultant organic layer was washed with water and saturated saline, dried, and concentrated under reduced pressure. The residue was powdered with hexane, collected by filtration, and dried under reduced pressure to give Compound 3 (trans) (210 mg) as a colorless powder. MS (APCI): m/z 454 [M−H]−

(3) To a solution of Compound 3 (205 mg) in methanol (3 mL) was added thionyl chloride (174 μL) under ice-cooling, and then the mixture was warmed to room temperature for 16 hours. The reaction mixture was concentrated under reduced pressure, the residue was powdered with diisopropylether, collected by filtration, and dried under reduced pressure to give Compound 4 (180 mg) as a colorless powder. MS (APCI): m/z 370 [M+H]+

Reference Example 85

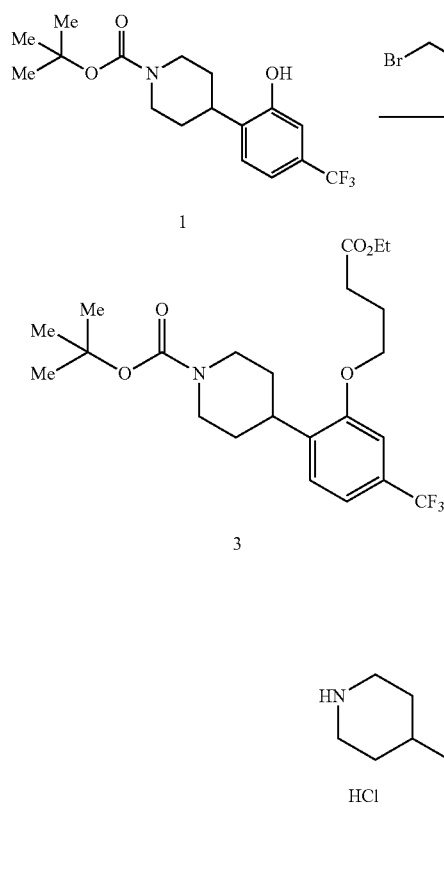

(1) A suspension of Compound 1 (200 mg), Compound 2 (100 μL), and potassium carbonate (160 mg) in N,N-dimethylformamide (4 mL) was heated at 70° C. under nitrogen atmosphere for 2.5 hours. The reaction mixture was cooled to room temperature, poured into water, and extracted with ethyl acetate. The resultant organic layer was washed with water and saturated saline, dried, and concentrated under reduced pressure. The residue was purified with silica gel column chromatography (hexane:ethyl acetate=97:3-80:20) to give Compound 3 (263 mg) as a colorless viscous material. MS (APCI): m/z 460 [M+H]+

(2) To a solution of Compound 3 (263 mg) in 1,4-dioxane (5 mL) was added a solution of hydrochloric acid in 1,4-dioxane (4 mol/L, 1431 μL), and the mixture was stirred at room temperature for 22 hours. The reaction mixture was concentrated under reduced pressure, the residue was powdered with diethylether, collected by filtration, and then dried to give Compound 4 (184 mg) as a colorless powder. MS (APCI): m/z 360 [M+H]+

Reference Example 86

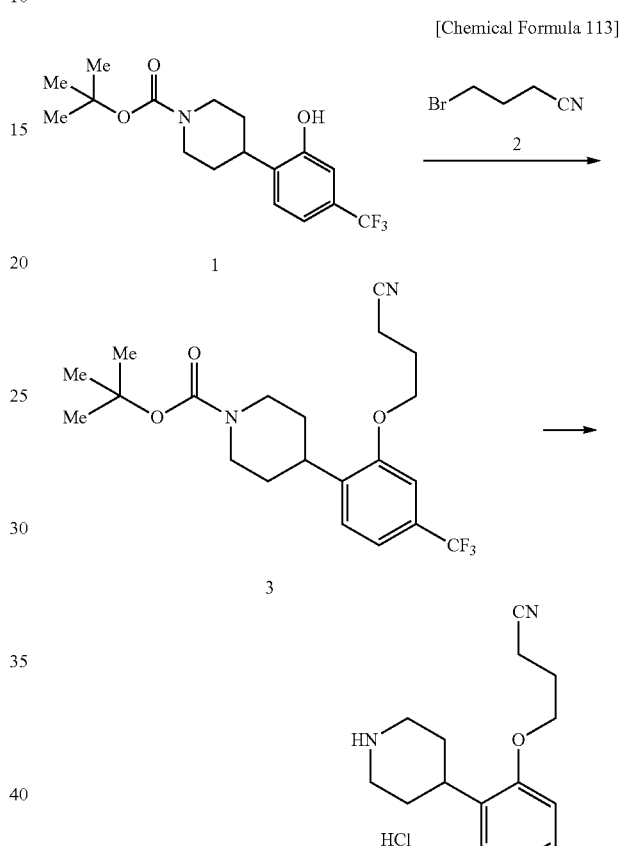

(1) A suspension of Compound 1 (200 mg), Compound 2 (70 μL), and potassium carbonate (160 mg) in N,N-dimethylformamide (4 mL) was heated at 70° C. under nitrogen atmosphere for 2 hours. The reaction mixture was cooled to room temperature, poured into water, and extracted with ethyl acetate. The organic layer was washed with water and saturated saline, dried, and concentrated under reduced pressure. The residue was purified with silica gel column chromatography (hexane:ethyl acetate=90:10-60:40) to give Compound 3 (245 mg) as a colorless viscous material. MS (ESI): m/z 413 [M+H]+

(2) To a solution of Compound 3 (240 mg) in dichloromethane (3 mL) was added trifluoroacetic acid (2 mL) under ice-cooling, and then the mixture was stirred at room temperature for 2 hours. To the reaction mixture was added a saturated aqueous solution of sodium hydrogen carbonate to alkalify it, and extracted with chloroform. The organic layer was dried, and concentrated under reduced pressure to give Compound 4 (175 mg) as a colorless viscous material. MS (ESI): m/z 313 [M+H]+

Reference Example 87

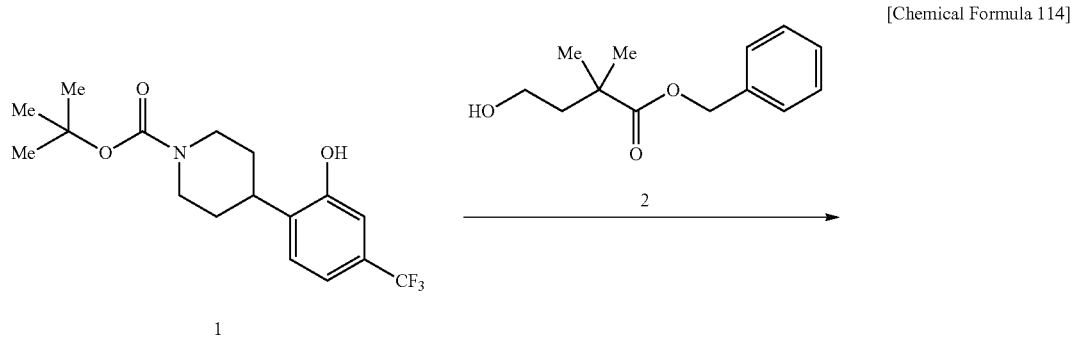

[Chemical Formula 114]

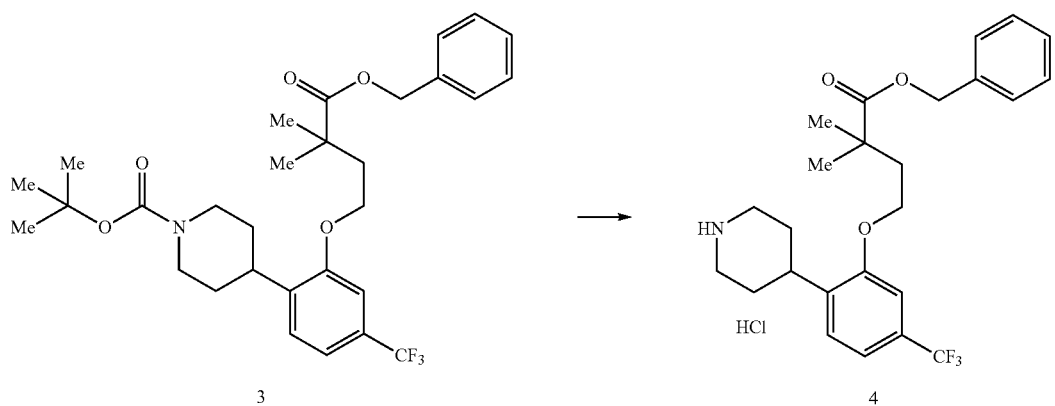

(1) To a solution of Compound 1 (200 mg), Compound 2 (193 mg), and triphenylphosphine (304 mg) in tetrahydrofuran (4 mL) was added diethyl azodicarboxylate (40 wt % toluene solution, 526 µL) at room temperature, and then heated at 70° C. for 2 hours. The reaction mixture was cooled to room temperature, concentrated under reduced pressure, diisopropylether was added thereto, stirred, the precipitated insoluble matter was removed by filtration, and then the filtrate was concentrated. The residue was purified with silica gel column chromatography (hexane:ethyl acetate-99:1-85:15) to give Compound 3 (124 mg) as a colorless viscous material. MS (ESI): m/z 550 [M+H]+

(2) To a solution of Compound 3 (123 mg) in 1,4-dioxane (2.5 mL) was added a solution of hydrochloric acid in 1,4-dioxane (4 mol/L, 1120 µL), and the mixture was stirred at room temperature for 14 hours. The reaction mixture was concentrated under reduced pressure, the residue was powdered with diisopropylether, collected by filtration, and then dried to give Compound 4 (103 mg) as a colorless powder. MS (APCI): m/z 450 [M+H]+

Reference Example 88

[Chemical Formula 115]

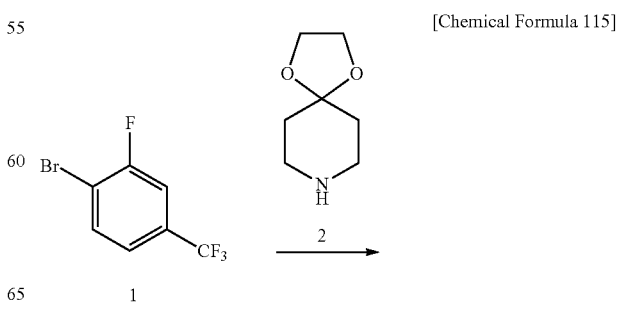

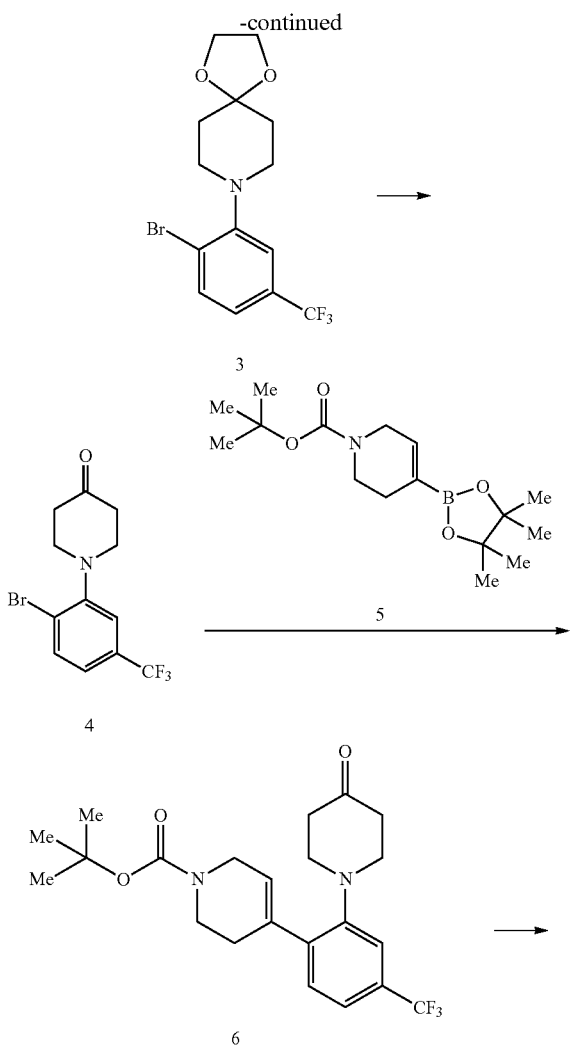

(1) A solution of Compound 1 (3 g), Compound 2 (3.54 g), and potassium carbonate (2.56 g) in 1,3-dimethyl-2-imidazolidinone (6 mL) was heated at 120° C. for 16 hours, then cooled to room temperature, and poured into water. The reaction mixture was extracted with ethyl acetate, the resultant organic layer was washed with water and saturated saline, dried, and concentrated under reduced pressure. The residue was purified with silica gel column chromatography (hexane:ethyl acetate=99:1-80:20) to give Compound 3 (1.14 g) as a colorless viscous material. MS (ESI): m/z 366/368 [M+H]+

(2) To a solution of Compound 3 (769 mg) in tetrahydrofuran (4 mL) was added dropwise an aqueous solution of hydrochloric acid (2 mol/mL, 1.05 mL), and then the mixture was stirred at room temperature for 5 hours. To the reaction mixture was added a saturated aqueous solution of sodium hydrogen carbonate to neutralized it, and then extracted with ethyl acetate. The resultant organic layer was washed with water and saturated saline, dried, and concentrated under reduced pressure. The residue was purified with silica gel column chromatography (hexane:ethyl acetate=99:1-80:30) to give Compound 4 (494 mg) as a colorless viscous material. MS (ESI): m/z 322/324 [M+H]+

(3) To a solution of Compound 4 (494 mg) and Compound 5 (570 mg) in N,N-dimethylformamide (12 mL) were added an aqueous solution of sodium carbonate (2 mol/L, 1.5 mL) and dichloro[1,1'-bis(diphenylphosphino)ferrocene]palladium(II) dichloromethane adduct (125 mg), and the mixture was heated at 80° C. under nitrogen atmosphere for 15 hours. The reaction mixture was cooled to room temperature, poured into water, and extracted with ethyl acetate. The resultant organic layer was washed with water and saturated saline, dried, and concentrated under reduced pressure. The residue was purified with silica gel column chromatography (hexane:ethyl acetate=95:5-60:40) to give Compound 6 (641 mg) as a pale yellow viscous material. MS (ESI): m/z 425 [M+H]+

(4) To a solution of Compound 6 (641 mg) in ethanol (15 mL) was added 10% palladium carbon (wetted with ca. 50% water, 213 mg), and the mixture was stirred under hydrogen atmosphere (I atm) at room temperature for 17 hours. Palladium carbon was removed by filtration, then the filtrate was concentrated under reduced pressure, and the residue was purified with silica gel column chromatography (hexane:ethyl acetate=70:30-30:70) to give Compound 7 (213 mg) as a colorless viscous material. MS (ESI): m/z 427 [M+H]+

Reference Example 89

[Chemical Formula 116]

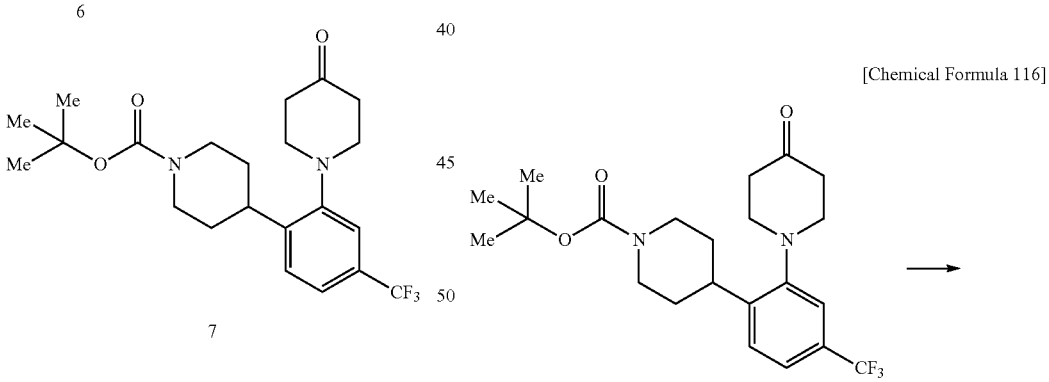

-continued

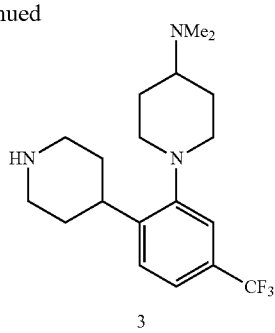
3

(1) To a solution of Compound 1 (150 mg) and a solution of dimethylamine-tetrahydrofuran (2 mol/mL, 210 μL) in 1,2-dichloroethane (2 mL) was added sodium triacetoxyborohydride (112 mg), and the mixture was stirred for 2 hours. To the reaction mixture were added a saturated aqueous solution of sodium hydrogen carbonate and water, stirred, and then extracted with chloroform. The resultant organic layer was washed with saturated saline, dried, and concentrated under reduced pressure. The residue was purified with NH silica gel column chromatography (hexane:ethyl acetate-80:20-0:100) to give Compound 2 (134 mg) as a colorless viscous material. MS (ESI): m/z 456 [M+H]+

(2) To a solution of Compound 2 (134 mg) in chloroform (3 mL) was added trifluoroacetic acid (1.5 mL), and the mixture was stirred at room temperature for 1.5 hours. To the reaction solution was added a saturated aqueous solution of sodium hydrogen carbonate to alkalify it, and extracted with chloroform. The organic layer was dried, and concentrated to give Compound 3 (102 mg) as a pale yellow viscous material. MS (ESI): m/z 356 [M+H]+

Reference Example 90

[Chemical Formula 117]

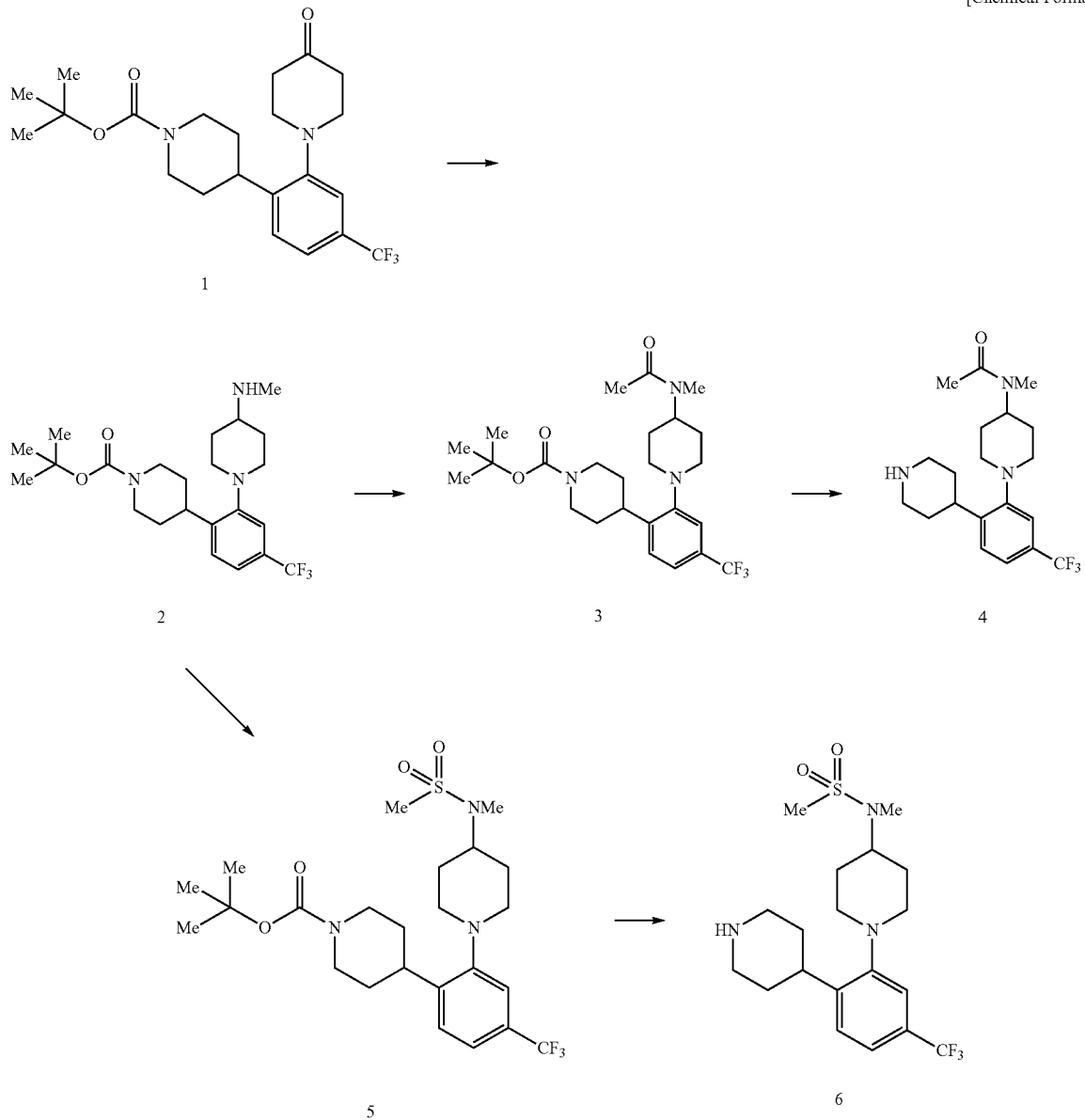

(1) To a solution of Compound 1 (300 mg) and a solution of methylamine-methanol (40%, 90 μL) in 1,2-dichloroethane (3.5 mL) was added sodium triacetoxyborohydride (224 mg), and the mixture was stirred for 2 hours. To the reaction mixture were added a saturated aqueous solution of sodium hydrogen carbonate and water, stirred, and then extracted with chloroform. The resultant organic layer was washed with saturated saline, dried, and concentrated under reduced pressure to give Compound 2 (307 mg) as a colorless viscous material. MS (ESI): m/z 442 [M+H]+

(2) To a solution of Compound 2 (100 mg) in chloroform (1 mL) were added triethylamine (40 μL) and acetyl chloride (20 μL) under ice-cooling, and then the mixture was stirred at room temperature for 1.5 hours. To the reaction mixture were added water and chloroform, stirred, then the organic layer was separated, washed with saturated saline, dried, and then concentrated under reduced pressure. The residue was purified with NH silica gel column chromatography (hexane:ethyl acetate=70:30-20:80) to give Compound 3 (86 mg) as a colorless viscous material. MS (ESI): m/z 484 [M+H]+

(3) To a solution of Compound 3 (85 mg) in chloroform (2 mL) was added trifluoroacetic acid (1.8 mL), and the mixture was stirred at room temperature for 1 hour. To the reaction solution was added a saturated aqueous solution of sodium hydrogen carbonate to alkalify it, and extracted with chloroform. The resultant organic layer was dried, and concentrated under reduced pressure to give Compound 4 (63 mg) as a colorless solid. MS (ESI): m/z 384 [M+H]+

(4) To a solution of Compound 2 (100 mg) and triethylamine (80 μL) in chloroform (2 mL) was added methanesulfonyl chloride (40 μL) under ice-cooling, and then the mixture was stirred at room temperature for 1 hour. To the reaction mixture were added water and dichloromethane, stirred, then the organic layer was separated, washed with saturated saline, dried, and concentrated under reduced pressure. The residue was purified with silica gel column chromatography (hexane:ethyl acetate=85:15-40:60) to give Compound 5 (64 mg) as a colorless viscous material. MS (ESI): m/z 520 [M+H]+

(5) To a solution of Compound 5 (64 mg) in chloroform (1.2 mL) was added trifluoroacetic acid (0.6 mL), and the mixture was stirred at room temperature for 1.5 hours. To the reaction solution was added a saturated aqueous solution of sodium hydrogen carbonate to alkalify it, and extracted with chloroform. The resultant organic layer was dried, and concentrated under reduced pressure to give Compound 6 (48 mg) as a colorless solid. MS (ESI): m/z 420 [M+H]+

Reference Example 91

[Chemical Formula 118]

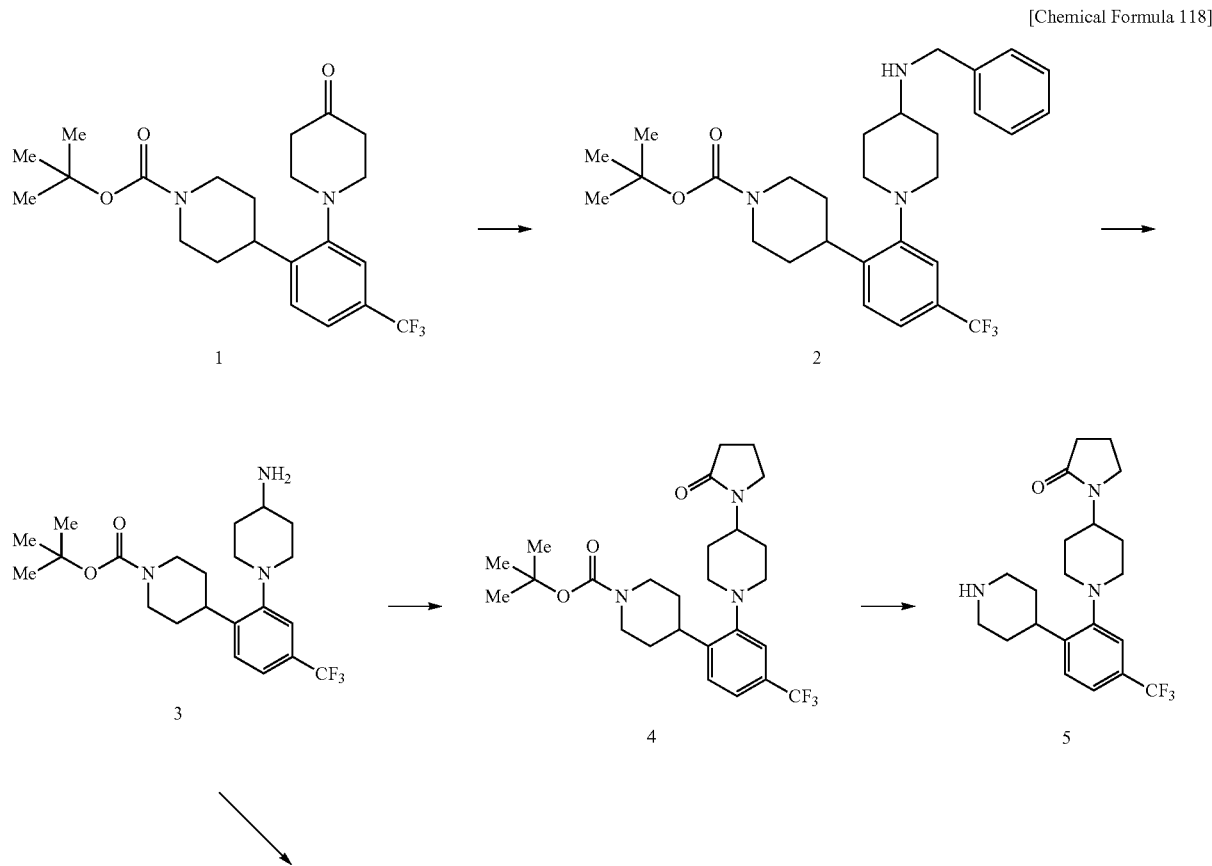

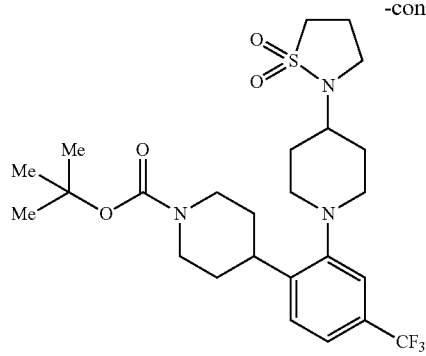

6

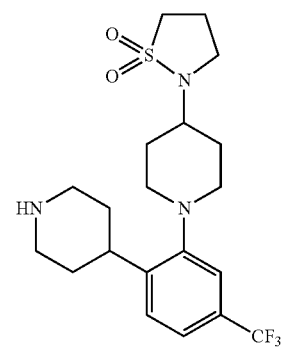

7

(1) To a solution of Compound 1 (400 mg) and benzylamine (120 μL) in 1,2-dichloroethane (5 mL) was added sodium triacetoxyborohydride (298 mg), and the mixture was stirred for 2 hours. To the reaction mixture were added a saturated aqueous solution of sodium hydrogen carbonate and water, stirred, and then extracted with chloroform. The resultant organic layer was washed with saturated saline, dried, and concentrated under reduced pressure to give Compound 2 (408 mg) as a colorless solid. MS (ESI): m/z 518 [M+H]+

(2) To a solution of Compound 2 (400 mg) in tetrahydrofuran (6 mL)/diisopropylether (2 mL) were added 10% palladium carbon (wetted with ca. 50% water, 80 mg) and 20% palladium hydroxide carbon (wetted with ca. 50% water, 80 mg), and the mixture was stirred under hydrogen atmosphere (1 atm) at room temperature for 5 hours. The insoluble matter was removed by filtration, and then the filtrate was concentrated. The residue was purified with NH silica gel column chromatography (hexane:ethyl acetate=50:50-0:100) to give Compound 3 (222 mg) as a colorless viscous material. MS (ESI): m/z 428 [M+H]+

(3) To a solution of Compound 3 (100 mg) in chloroform (2.3 mL) were added triethylamine (40 μL) and 4-chlorobutyryl chloride (30 μL) under ice-cooling, and then the mixture was stirred at room temperature for 2 hours. To the reaction mixture were added a saturated aqueous solution of sodium hydrogen carbonate and chloroform, stirred, then the organic layer was separated, washed with saturated saline, dried, and concentrated under reduced pressure. To a solution of the residue in N,N-dimethylformamide (2.3 mL) was added sodium hydride (60% in oil, 11 mg) under ice-cooling, the mixture was stirred for 2 hours, then additional sodium hydride (60% in oil, 11 mg) was added thereto under ice-cooling, and stirred at room temperature for additional 2 hours. To the reaction mixture were added a saturated aqueous solution of ammonium chloride and ethyl acetate, stirred, then the organic layer was separated, washed with saturated saline, dried, and concentrated under reduced pressure. The residue was purified with silica gel column chromatography (hexane:ethyl acetate=30:70-0:100) to give Compound 4 (87 mg) as a pale yellow viscous material. MS (ESI): m/z 496 [M+H]+

(4) To a solution of Compound 4 (87 mg) in chloroform (1.8 mL) was added trifluoroacetic acid (0.88 mL), and the mixture was stirred at room temperature for 4 hours. To the reaction solution was added a saturated aqueous solution of sodium hydrogen carbonate to alkalify it, and extracted with chloroform. The organic layer was dried, and concentrated to give Compound 5 (65 mg) as a colorless viscous material. MS (ESI): m/z 396 [M+H]+

(5) To a solution of Compound 3 (80 mg) in dichloromethane (1.9 mL) were added pyridine (100 μL) and 3-chloropropanesulfonyl chloride (60 μL) under ice-cooling, and then the mixture was stirred at room temperature for 15 hours. To the reaction mixture were added water and chloroform, stirred, then the organic layer was separated, washed with saturated saline, dried, and concentrated under reduced pressure. To a solution of the residue in N,N-dimethylformamide (1.9 mL) was added sodium hydride (60% in oil, 8.2 mg) at room temperature, the mixture was stirred for 2 hours, then heated at 60° C. for 1.5 hours, and stirred at room temperature for additional 2 hours. To the reaction mixture were added a saturated aqueous solution of ammonium chloride and ethyl acetate, stirred, then the organic layer was separated, washed with saturated saline, dried, and concentrated under reduced pressure. The residue was purified with silica gel column chromatography (chloroform:methanol=100:0-90:10) to give Compound 6 (25 mg) as a colorless viscous material. MS (ESI): m/z 532 [M+H]+

(6) To a solution of Compound 6 (25 mg) in chloroform (0.5 mL) was added trifluoroacetic acid (0.5 mL), and the mixture was stirred at room temperature for 3 hours. To the reaction solution was added a saturated aqueous solution of sodium hydrogen carbonate to alkalify it, and extracted with chloroform. The organic layer was dried, and concentrated under reduced pressure to give Compound 7 (18 mg) as a colorless viscous material. MS (ESI): m/z 432 [M+H]+

Reference Example 92

[Chemical Formula 119]

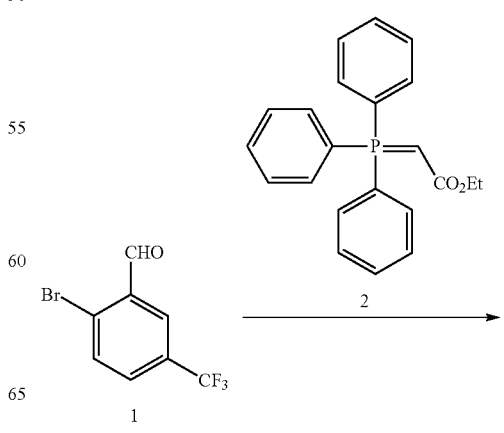

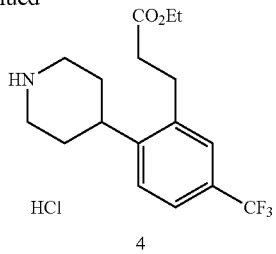

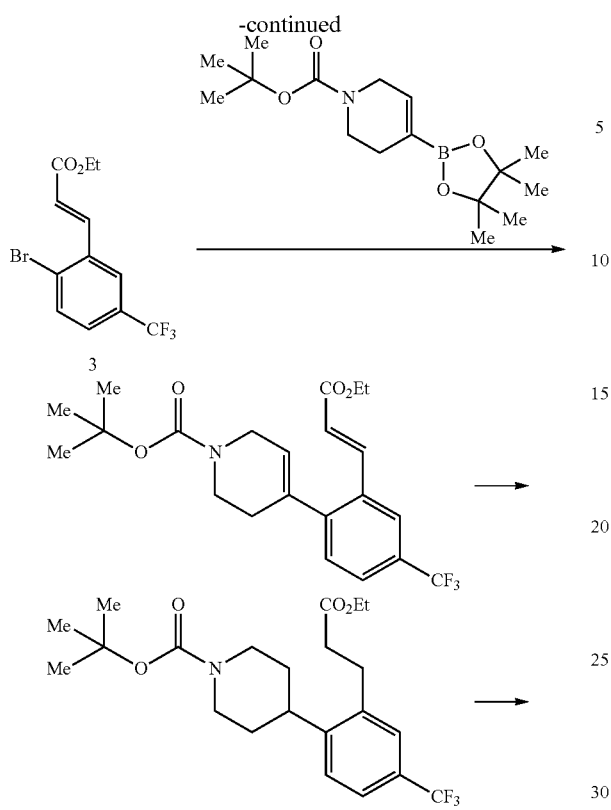

(1) To a solution of Compound 1 (4 g) in toluene (31 mL) was added Compound 2 (6.06 g), and then the mixture was heated under reflux for 1 hour. The reaction solution was concentrated, then to the residue was added diisopropyl-ether, and stirred. The insoluble matter was removed by filtration, then the filtrate was concentrated under reduced pressure, and the residue was purified with silica gel column chromatography (hexane:ethyl acetate=98:2-80:20) to give Compound 3 (4.7 g) as a pale yellow viscous material. MS (APCI): m/z 323/325 [M+H]+

(2) Compound 3 was treated in a similar manner to Reference Example 52 to give Compound 4 as a colorless powder. MS (APCI) m/z 330 [M+H]+

Reference Example 93

[Chemical Formula 120]

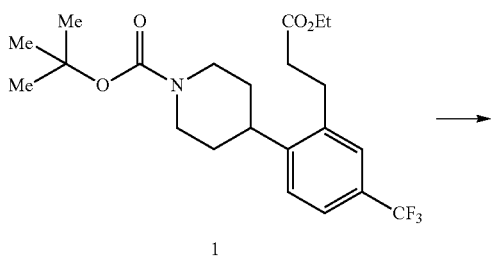

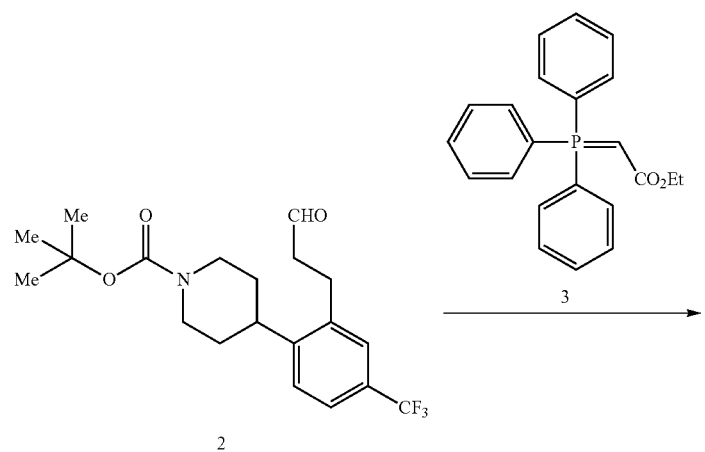

-continued

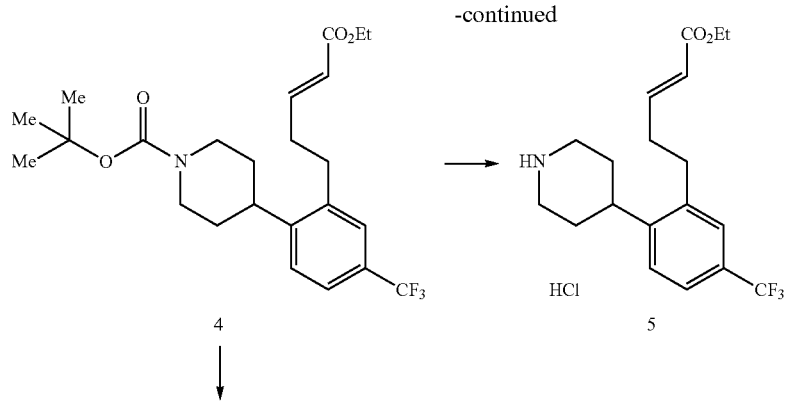

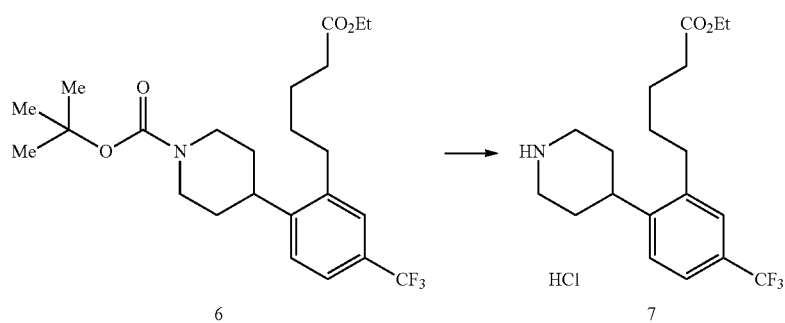

(1) To a solution of Compound 1 (1 g) in dichloromethane (10 mL) was added dropwise a solution of diisobutylaluminum hydride in toluene (1 mol/L, 9.6 mL) under nitrogen atmosphere at −78° C., and the mixture was stirred at 0° C. for 2 hours. To the reaction mixture was added iced water, then added potassium sodium tartrate tetrahydrate, added ethyl acetate, and stirred at room temperature for 15 hours. The insoluble matter was removed by filtration, and then the organic layer of the filtrate was separated. The resultant organic layer was washed with saturated saline, dried, and concentrated under reduced pressure. The residue was purified with silica gel column chromatography (hexane:ethyl acetate=67:33-40:60) to give an alcohol (252 mg) as a colorless viscous material.

(2) To a solution of oxalyl chloride (111 μL) in dichloromethane (5 mL) was added dropwise a solution of dimethylsulfoxide (137 μL) in dichloromethane (1 mL) at −78° C., and the mixture was stirred for 10 minutes. To the reaction mixture was added dropwise a solution of the alcohol (250 mg) obtained in the above (1) in dichloromethane (5 mL) at the same temperature, and stirred for 30 minutes. To the reaction mixture was added dropwise triethylamine (540 μL) at the same temperature, and then stirred at room temperature for 30 minutes. To the reaction mixture was added a saturated aqueous solution of sodium hydrogen carbonate, stirred, and extracted with dichloromethane. The resultant organic layer was washed with saturated saline, dried, and evaporated under reduced pressure to give Compound 2 (263 mg) as a pale yellow viscous material.

(3) To a solution of Compound 2 (262 mg) in toluene (1.4 mL) was added Compound 3 (262 mg), and then the mixture was heated under reflux at 70° C. for 2.5 hours. The reaction solution was concentrated under reduced pressure, then to the residue was added diisopropylether, and the mixture was stirred. The precipitated insoluble matter was removed by filtration, and then the resultant filtrate was concentrated under reduced pressure. The residue was purified with silica gel column chromatography (hexane:ethyl acetate=90:10-75:25) to give Compound 4 (208 mg) as a colorless viscous material. MS (ESI): m/z 456 [M+H]+

(4) Compound 4 (60 mg) was treated in a similar manner to Reference Example 52 to give Compound 5 (51 mg) as a colorless powder. MS (APCI) m/z 356 [M+H]+

(5) To a solution of Compound 4 (145 mg) in ethanol (3 mL) was added 10% palladium carbon (wetted with ca. 50% water, 29 mg), and the mixture was stirred under hydrogen atmosphere (1 atm) at room temperature for 18 hours. The reaction mixture was filtrated, and the filtrate was concentrated under reduced pressure to give Compound 6 (140 mg) as a pale yellow viscous material. MS (ESI): m/z 458 [M+H]+

(6) Compound 6 (139 mg) was treated in a similar manner to Reference Example 52 to give Compound 7 (118 mg) as a colorless powder. MS (APCI) m/z 358 [M+H]+

Reference Example 94
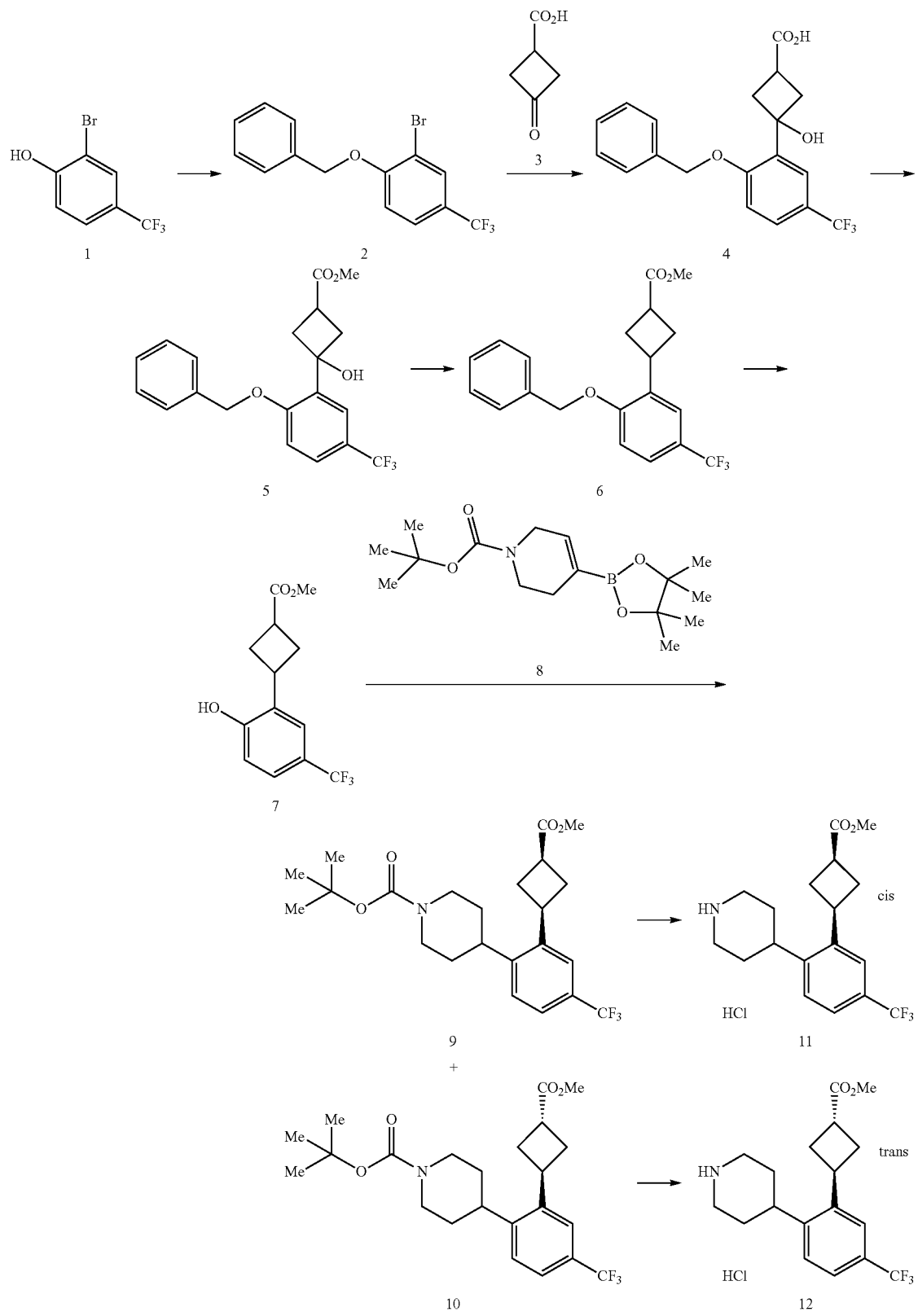

(1) To a solution of Compound 1 (15 g) and benzyl bromide (7 mL) in N,N-dimethylformamide (120 mL) was added potassium carbonate (12.9 g), and then the mixture was stirred at room temperature for 17 hours. The reaction mixture was poured into water, and extracted with ethyl acetate. The organic layer was washed with water and saturated saline, dried, and concentrated under reduced pressure. The residue was purified with NH silica gel column chromatography (hexane:ethyl acetate=100:0-90:10) to give Compound 2 (19.67 g) as a colorless viscous material.

(2) To a solution of Compound 2 (19.66 g) in tetrahydrofuran (60 mL) was added dropwise a solution of n-butyllithium in hexane (1.59 mol/L, 39.2 mL) under nitrogen atmosphere at −78° C., and the mixture was stirred for 1 hour. To the reaction mixture was added dropwise a solution of Compound 3 (3.39 g) in tetrahydrofuran (60 mL), and then stirred at room temperature for 17 hours. To the reaction mixture was added dropwise an aqueous solution of hydrochloric acid (1 mol/L, 80 mL), and then extracted with ethyl acetate. The organic layer was washed with water and saturated saline, dried, and concentrated under reduced pressure. The residue was purified with silica gel column chromatography (chloroform:methanol=100:0-90:10) to give Compound 4 (2.76 g) as an orange viscous material. MS (ESI): m/z 365 [M−H]−

(3) To a solution of Compound 4 (2.75 g) in methanol (25 mL) was added dropwise a solution of trimethylsilyldiazomethane in hexane (2 mol/L, 30 mL), and the mixture was stirred at room temperature for 17 hours. To the reaction mixture was added dropwise acetic acid until a gas bubble was not formed, and concentrated under reduced pressure. The residue was purified with silica gel column chromatography (hexane:ethyl acetate=95:5-75:25) to give Compound 5 (2.019 g) as a pale yellow viscous material. MS (ESI): m/z 379 [M−H]−

(4) A mixture of Compound 5 (2.01 g), triethylsilane (4.2 mL), and trifluoroacetic acid (3.9 mL) was stirred at room temperature for 5 hours. The reaction mixture was concentrated under reduced pressure, and the residue was purified with silica gel column chromatography (hexane:ethyl acetate=95:5-85:15) to give Compound 6 (1.31 g) as a pale yellow viscous material. MS (ESI): m/z 379 [M−H]−

(5) To a solution of Compound 6 (1.3 g) in methanol (20 mL) was added 10% palladium carbon (wetted with ca. 50% water, 650 mg), and the mixture was stirred under hydrogen atmosphere (1 atm) at room temperature for 2 hours. Palladium carbon was removed by filtration, and then the filtrate was concentrated under reduced pressure. The residue was purified with silica gel column chromatography (hexane:ethyl acetate=90:10-70:30) to give Compound 7 (865 mg) as a colorless powder. MS (APCI): m/z 275 [M+H]+

(6) A solution of Compound 7 (855 mg) in dichloromethane (15 mL) was ice-cooled, triethylamine (652 μL) and trifluoromethanesulfonic anhydride (629 μL) were added thereto under nitrogen atmosphere, and then stirred at the same temperature for 1 hour. To the reaction mixture was added a saturated aqueous solution of ammonium chloride and dichloromethane, stirred, and then extracted with dichloromethane. The organic layer was dried, and concentrated under reduced pressure. To a solution of the resultant residue in N,N-dimethylformamide (15 mL) were added Compound 8 (1.06 g), an aqueous solution of sodium carbonate (2 mol/L, 4.68 mL), and dichloro[1,1'-bis(diphenylphosphino)ferrocene]palladium(II) dichloromethane adduct (127 mg), and the mixture was stirred under heating at 80° C. under nitrogen atmosphere for 16 hours. The reaction mixture was cooled to room temperature, then poured into water, and extracted with ethyl acetate. The organic layer was washed with water and saturated saline, dried, and concentrated under reduced pressure. The residue was purified with silica gel column chromatography (hexane:ethyl acetate=95:5-80:20) to give Compound 9 (cis) (465 mg) and Compound 10 (trans) (164 mg) as colorless viscous materials. Each MS (APCI): m/z 440 [M+H]+

(7) To a solution of Compound 9 (460 mg) in methanol (3 mL)/acetic acid (3 mL) was added 10% palladium carbon (wetted with ca. 50% water, 230 mg), and the mixture was stirred under hydrogen atmosphere (1 atm) at room temperature for 2 hours. Palladium carbon was removed by Celite filtration, and then the resultant filtrate was concentrated. The residue was dissolved in dichloromethane, washed with a saturated aqueous solution of sodium hydrogen carbonate, dried, and concentrated under reduced pressure. The residue was purified with silica gel column chromatography (hexane:ethyl acetate-90:10-75:25). To a solution of the resultant compound (405 mg) in dichloromethane (2 mL) was added trifluoroacetic acid (1 mL), and the mixture was stirred at room temperature for 1 hour. To the reaction solution was added a saturated aqueous solution of sodium hydrogen carbonate to alkalify it, and extracted with dichloromethane. The organic layer was dried, and concentrated under reduced pressure to give Compound 11 (314 mg) as a colorless viscous material. MS (ESI): m/z 342 [M+H]+

(8) Compound 10 was treated in a similar manner to the step 7 to give Compound 12 as a colorless viscous material. MS (ESI): m/z 342 [M+H]+

Reference Example 95

[Chemical Formula 122]

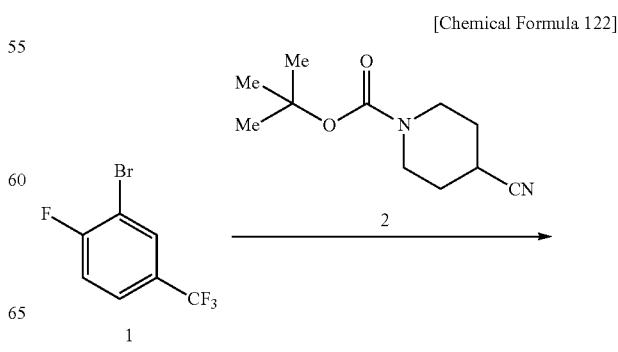

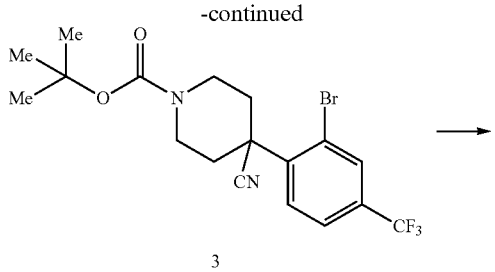

3

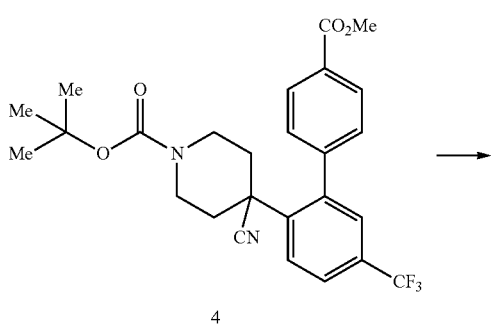

4

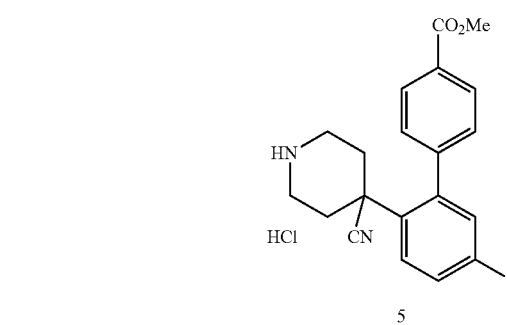

5

(1) To a solution of Compound 1 (1 g) and Compound 2 (870 mg) in toluene (2.5 mL) was added a solution of potassium bis(trimethylsilyl)amide in toluene (0.5 mol/L, 8.23 mL) under nitrogen atmosphere at room temperature, and then the mixture was heated under reflux for 15 minutes. To the reaction mixture was poured a saturated aqueous solution of ammonium chloride under ice-cooling, and extracted with ethyl acetate. The organic layer was washed with an aqueous solution of hydrochloric acid (1 mol/L), a saturated aqueous solution of sodium hydrogen carbonate, and saturated saline, dried, and concentrated under reduced pressure. The residue was purified with silica gel column chromatography (hexane:ethyl acetate=90:10-80:20) to give Compound 3 (1.08 g) as a pale yellow viscous material. MS (APCI): m/z 333/335 [M-Boc+H]+

(2) To a solution of Compound 3 (160 mg) in N,N-dimethylformamide (3 mL) was added 4-methoxycarbonylphenylboronic acid (93 mg), an aqueous solution of sodium carbonate (2 mol/L, 554 μL), and dichloro[1,1'-bis(diphenylphosphino)ferrocene]palladium(II) dichloromethane adduct (14 mg), and the mixture was heated at 80° C. under nitrogen atmosphere for 2 hours. The reaction mixture was cooled to room temperature, poured into water, and extracted with ethyl acetate. The organic layer was washed with water and saturated saline, dried, and concentrated under reduced pressure. The residue was purified with silica gel column chromatography (hexane:ethyl acetate=85:15-67:33) to give Compound 4 (164 mg) as a colorless powder.

(3) To a solution of Compound 4 (164 mg) in 1,4-dioxane (3 mL) was added a solution of hydrochloric acid in 1,4-dioxane (4 mol/L, 1680 μL), and the mixture was stirred at room temperature for 14 hours. The reaction mixture was concentrated under reduced pressure, the residue was powdered with diisopropylether, collected by filtration, and then dried to give Compound 5 (134 mg) as a colorless powder. MS (ESI): m/z 389 [M+H]+

Reference Example 96

[Chemical Formula 123]

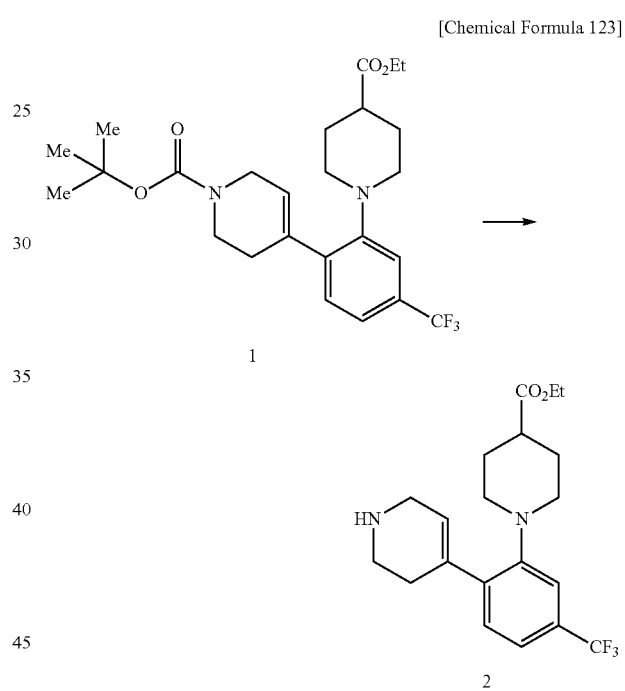

To a solution of Compound 1 (200 mg) in chloroform (4.1 mL) was added trifluoroacetic acid (2 mL) under ice-cooling, and then the mixture was stirred at room temperature for 1 hour. The reaction mixture was diluted with chloroform, then a saturated aqueous solution of sodium hydrogen carbonate was added thereto to alkalify it, and the organic layer was separated. The resultant organic layer was dried, and then concentrated under reduced pressure to give Compound 2 (186 mg) as a colorless powder. MS (ESI): m/z 383 [M+H]+

Reference Example 97

A corresponding starting compound was reacted and treated in a similar manner to the above Reference Example 52 and the above Reference Example 96 to give the compound in the following Table 36.

381

TABLE 36

| Reference Example | Compound | MS |
|---|---|---|
| 97 | 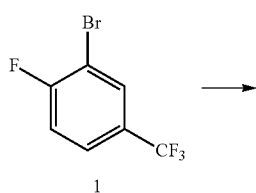 | MS (ESI): m/z 446 [M + H]+ |

Reference Example 98

[Chemical Formula 124]

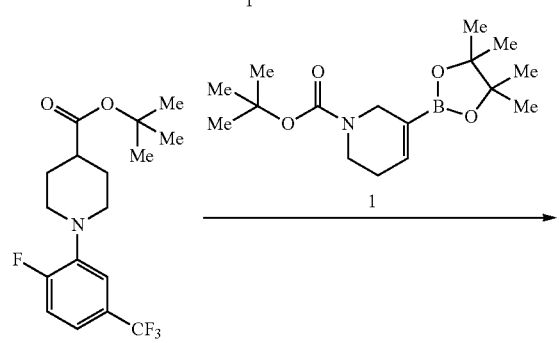

382

-continued

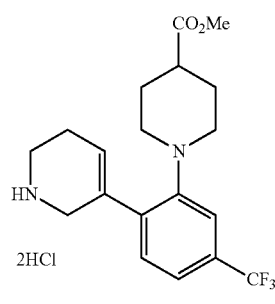

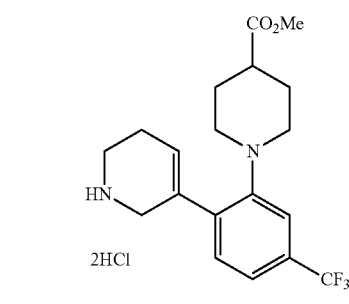

Compound 1 obtained by the method described in WO2006/47277 were treated in a similar manner to Reference Example 52 to give Compound 2 (106 mg). Compound 2 was dissolved in a solution of hydrochloric acid in methanol (2 mol/L, 5.2 mL), stirred at 50° C. for 18 hours, then the reaction solution was concentrated under reduced pressure, toluene was added thereto, and the mixture was again concentrated under reduced pressure to give Compound 3 (180 mg). MS (ESI): m/z 369 [M+H]+

Reference Example 99

[Chemical Formula 125]

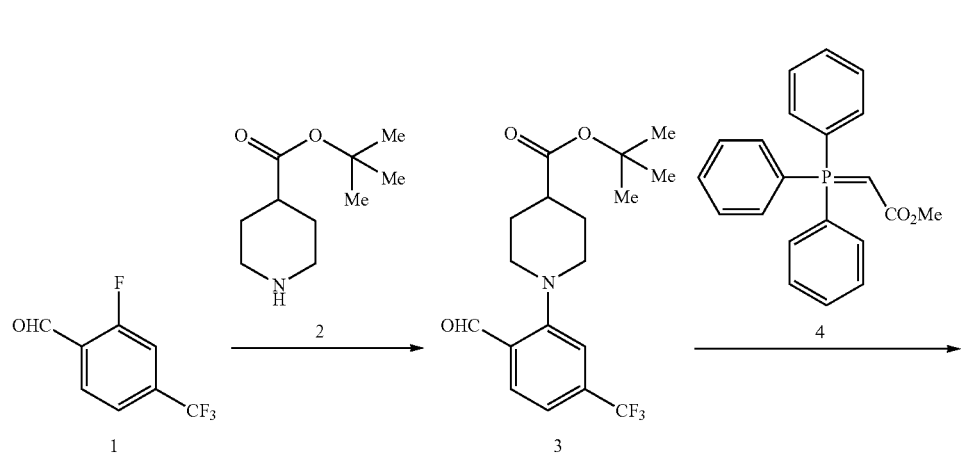

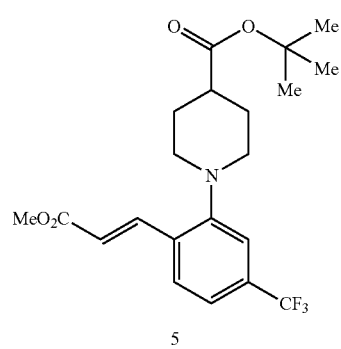
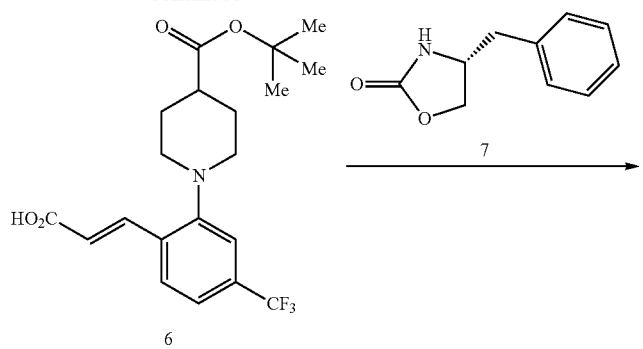
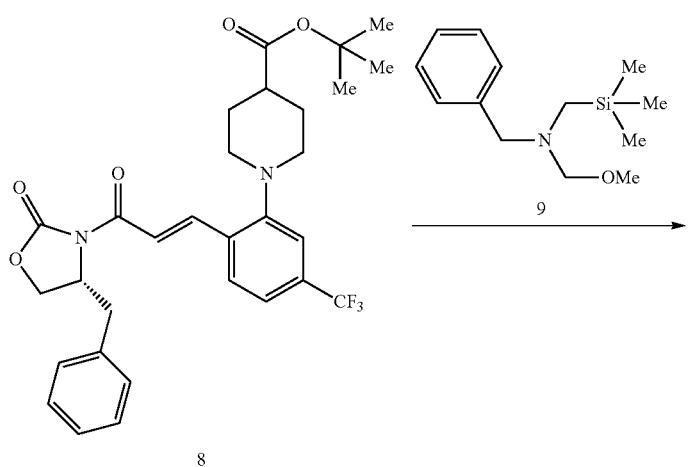
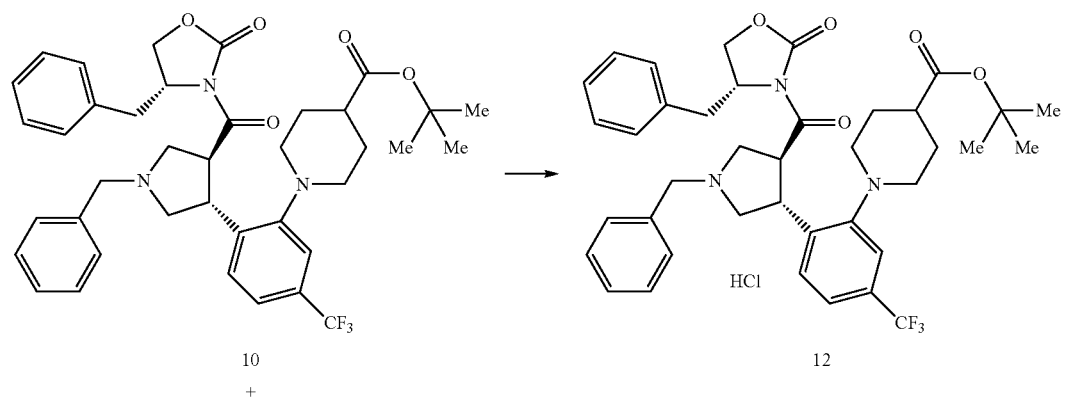
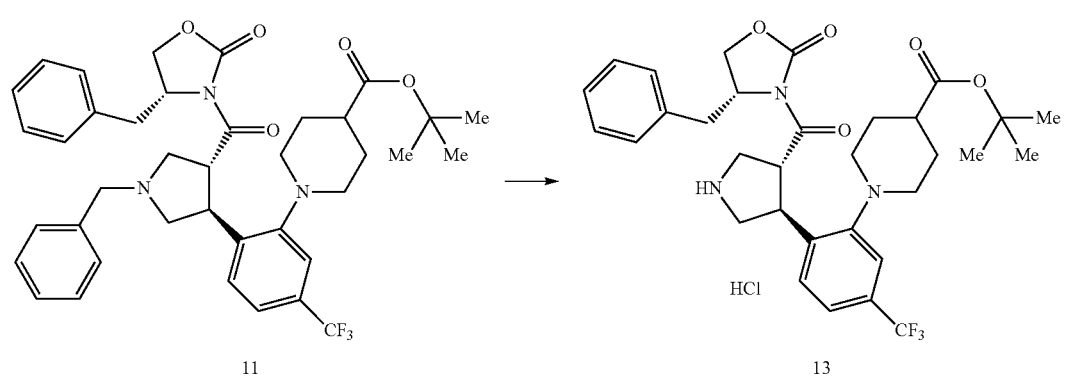 [SMILES: CC(C)(C)OC(=O)C1CCN(c2cc(C(F)(F)F)ccc2[C@H]2CN(Cc3ccccc3)C[C@@H]2C(=O)N2C(=O)OC[C@H]2Cc2ccccc2)CC1 ; CC(C)(C)OC(=O)C1CCN(c2cc(C(F)(F)F)ccc2[C@H]2CNC[C@@H]2C(=O)N2C(=O)OC[C@H]2Cc2ccccc2)CC1 ; Cl]

(1) A suspension of Compound 1 (3.05 g), Compound 2 (3.25 g), and potassium carbonate (3.3 g) in N-methylpyrrolidone (40 mL) was stirred at 80° C. for 19 hours. The reaction mixture was cooled to room temperature, water and ethyl acetate were added thereto, stirred, and then extracted with ethyl acetate. The resultant organic layer was washed with water and saturated saline, dried, and concentrated under reduced pressure. The residue was purified with silica gel column chromatography (hexane:ethyl acetate=98:2-88:12) to give Compound 3 (4.61 g) as a yellow viscous material. MS (ESI): m/z 358 [M+H]+

(2) To a solution of Compound 3 (4.61 g) in dichloromethane (16 mL) was added a solution of Compound 4 (4.43 g) in dichloro and ethane (16 mL), and the mixture was stirred at room temperature for 16 hours. The reaction solution was concentrated under reduced pressure, and the residue was purified with silica gel column chromatography (hexane:ethyl acetate=98:2-85:15) to give Compound 5 (5.16 g) as a pale yellow powder in the isomeric ratio of E:Z≈88:12. MS (ESI): m/z 414 [M+H]+

(3) To a solution of Compound 5 (3.8 g) in methanol (20 mL)/tetrahydrofuran (10 mL) was added an aqueous solution of sodium hydroxide (2 mol/L, 5.05 mL) under ice-cooling, and the mixture was stirred at room temperature for 16 hours. To the reaction mixture was added an aqueous solution of hydrochloric acid (2 mol/L, 5.05 mL), stirred, and then concentrated under reduced pressure. The residue was purified with silica gel column chromatography (chloroform:methanol=100:0-96:4) to give Compound 6 (2.07 g) as a pale yellow powder in the isomeric ratio of E:Z≈95:5. MS (ESI): m/z 398 [M−H]−

(4) To a solution of Compound 6 (2.06 g) and N,N-dimethylformamide (10 drops) in dichloromethane (30 mL) was added oxalyl chloride (873 µL) under ice-cooling, and the mixture was stirred at room temperature for 1 hour. The reaction solution was concentrated under reduced pressure, then the residue was dissolved in dichloromethane (30 mL), lithium chloride (437 mg), Compound 7 (1 g), and triethylamine (1.58 mL) were added thereto under ice-cooling, and the mixture was stirred at room temperature for 16 hours. The reaction solution was poured into an ice-cooled aqueous solution of citric acid (citric acid: 10 g and water: 100 mL), and extracted with dichloromethane. The resultant organic layer was dried, and concentrated under reduced pressure. The residue was purified with silica gel column chromatography (hexane:ethyl acetate=90:10-75:25) to give Compound 8 (2.21 g) as a yellow powder. MS (APCI): m/z 559 [M+H]+

(5) To a solution of Compound 8 (2.21 g) and Compound 9 (2.82 g) in dichloromethane (20 mL) was added trifluoroacetic acid (30 µL) under ice-cooling, and the mixture was stirred at 40° C. for 1 hour. To the reaction mixture were added water, a saturated aqueous solution of sodium hydrogen carbonate, and dichloromethane under ice-cooling, stirred, and the organic layer was separated. The resultant organic layer was washed with saturated saline, dried, and concentrated under reduced pressure. The residue was purified with silica gel column chromatography (hexane:ethyl acetate=95:5-60:40) to give Compound 10 (1.19 g) and Compound 11 (1.15 g) as colorless powders. Each MS (APCI): m/z 692 [M+H]+TLC (hexane:ethyl acetate=2:1): Rf value of Compound 10 z 0.8, Rf value of Compound 11≈0.4 (TLC plate: 1.05715.0001 TLC Silica gel 60 $F_{254}$ manufactured by Merck KGaA). To a solution of Compound 10 in ethyl acetate was added a solution of hydrochloric acid in ethyl acetate (4 mol/L) in 1.2 equivalent to give a hydrochloride crystal 12, and the crystal was subject to X-ray crystallography to confirm that Compound 10 and 11 have the above configurations respectively.

(6) To a solution of Compound 11 (288 mg) in methanol (6 mL)/tetrahydrofuran (6 mL) was added 10% palladium carbon (wetted with ca. 50% water, 150 mg), and the mixture was stirred at room temperature under hydrogen atmosphere (1 atm) for 2 hours. Palladium carbon was removed by Celite filtration, and the filtrate was concentrated under reduced pressure to give Compound 13 (261 mg) as a colorless powder. MS (ESI): m/z 602 [M+H]+

Reference Example 100

[Chemical Formula 126]

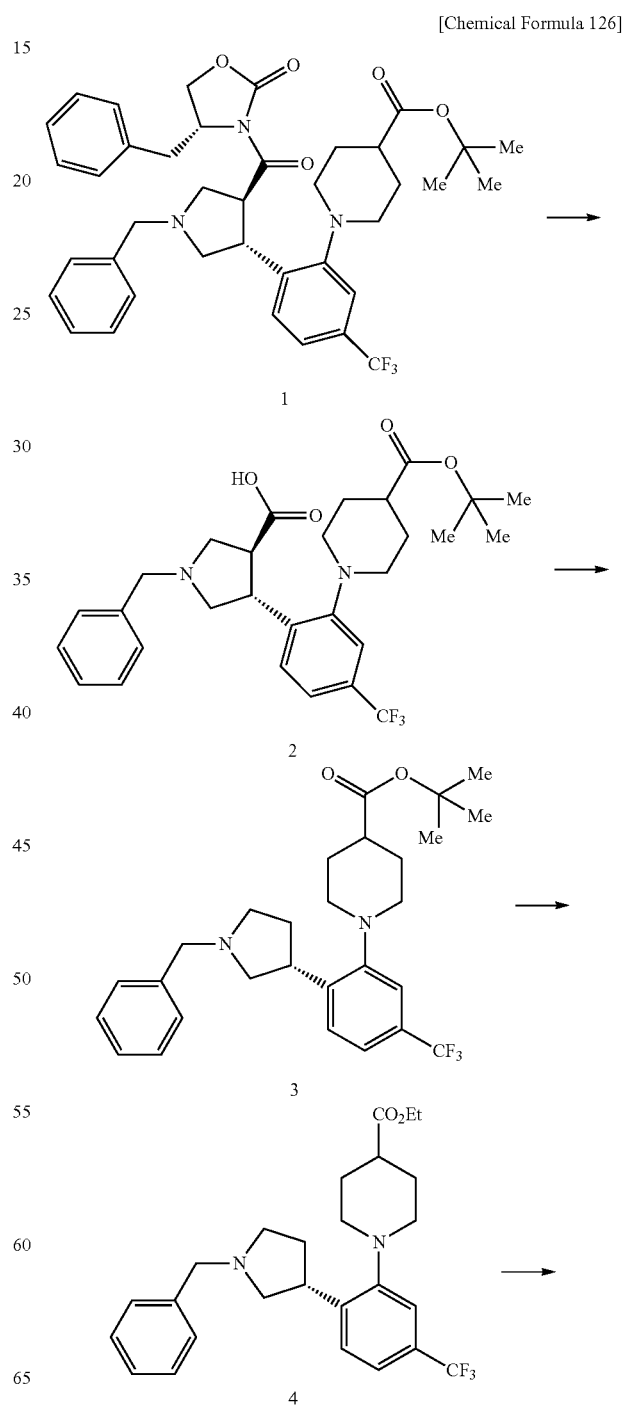

-continued

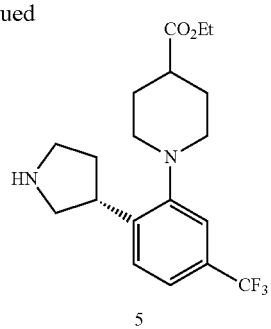

5

(1) To a solution of Compound 1 (500 mg) in tetrahydrofuran (7.2 mL) was added dropwise an aqueous solution of lithium hydroxide (monohydrate) (36 mg) (0.7 mL) under ice-cooling, and the mixture was stirred at room temperature for 3 hours. Tetrahydrofuran was evaporated under reduced pressure, to the residue were added chloroform and water, and then the organic layer was separated. The aqueous layer was extracted with chloroform twice, the resultant the organic layers were combined, washed with saturated saline, dried, and concentrated under reduced pressure. The residue was purified with silica gel column chromatography (chloroform:methanol=100:0-85:15) to give Compound 2 (328 mg) as a pale yellow viscous material. MS (ESI): m/z 533 [M+H]+

(2) To a solution of Compound 2 (260 mg) in dichloromethane (2.5 mL) was added N-hydroxypyridine-2-thione (75 mg) under light-shading, then the mixture was ice-cooled, N,N'-dicyclohexylcarbodiimide (102 mg) was added thereto, and stirred at the same temperature for 10 minutes and at room temperature for 3 hours. To the mixture were added 1,4-dioxane (5.0 mL), 2,2'-azobis(isobutyronitrile) (12 mg), and tributyltin hydride (0.40 mL), and stirred at 100° C. for 2 hours. The reaction solution was filtered, and the filtrate was concentrated under reduced pressure. The residue was purified with NH silica gel column chromatography (hexane:ethyl acetate=100:0-90:10) to give Compound 3 (125 mg) as a colorless viscous material. MS (ESI): m/z 489 [M+H]+

(3) To a solution of Compound 3 (120 mg) in chloroform (2.5 mL) was added trifluoroacetic acid (1.2 mL) under ice-cooling, and the mixture was stirred at room temperature for 2 hours. The reaction solution was ice-cooled, diluted with chloroform, and then a saturated aqueous solution of sodium hydrogen carbonate was added thereto to neutralize it. The organic layer was separated, washed with saturated saline, then dried, and concentrated under reduced pressure. To a solution of the residue in N,N-dimethylformamide (2.5 mL) were added N,N'-dicyclohexylcarbodiimide (61 mg) and ethanol (0.15 mL) under ice-cooling, and the mixture was stirred at room temperature for 16 hours. To the reaction mixture were added water and ethyl acetate, and the organic layer was separated. The resultant organic layer was washed with water and saturated saline, dried, and concentrated under reduced pressure. The residue was purified with silica gel column chromatography (chloroform:methanol=100:0-90:10) to give Compound 4 (70 mg) as a colorless powder. MS (ESI): m/z 461 [M+H]+

(4) To a solution of Compound 4 (70 mg) in ethanol (1.5 mL) was added acetic acid (0.6 mL) and 10% palladium carbon (wetted with ca. 50% water, 42 mg), and the mixture was stirred under hydrogen atmosphere (1 atm) at room temperature for 15 hours. Palladium carbon was removed by filtration, and the filtrate was concentrated under reduced pressure. The residue was diluted with ethyl acetate, then washed with saturated saline, dried, and concentrated under reduced pressure. The residue was purified with NH silica gel column chromatography (chloroform:methanol=100:0-90:10) to give Compound 5 (16 mg) as a colorless viscous material. MS (ESI): m/z 371 [M+H]+

Reference Example 101

[Chemical Formula 127]

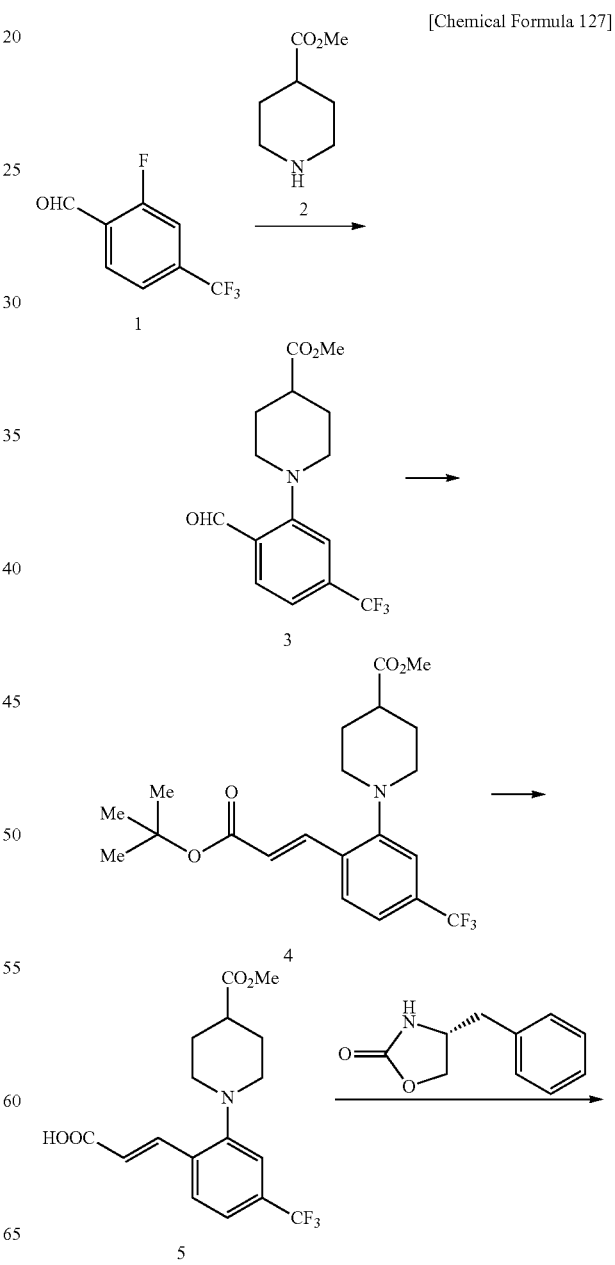

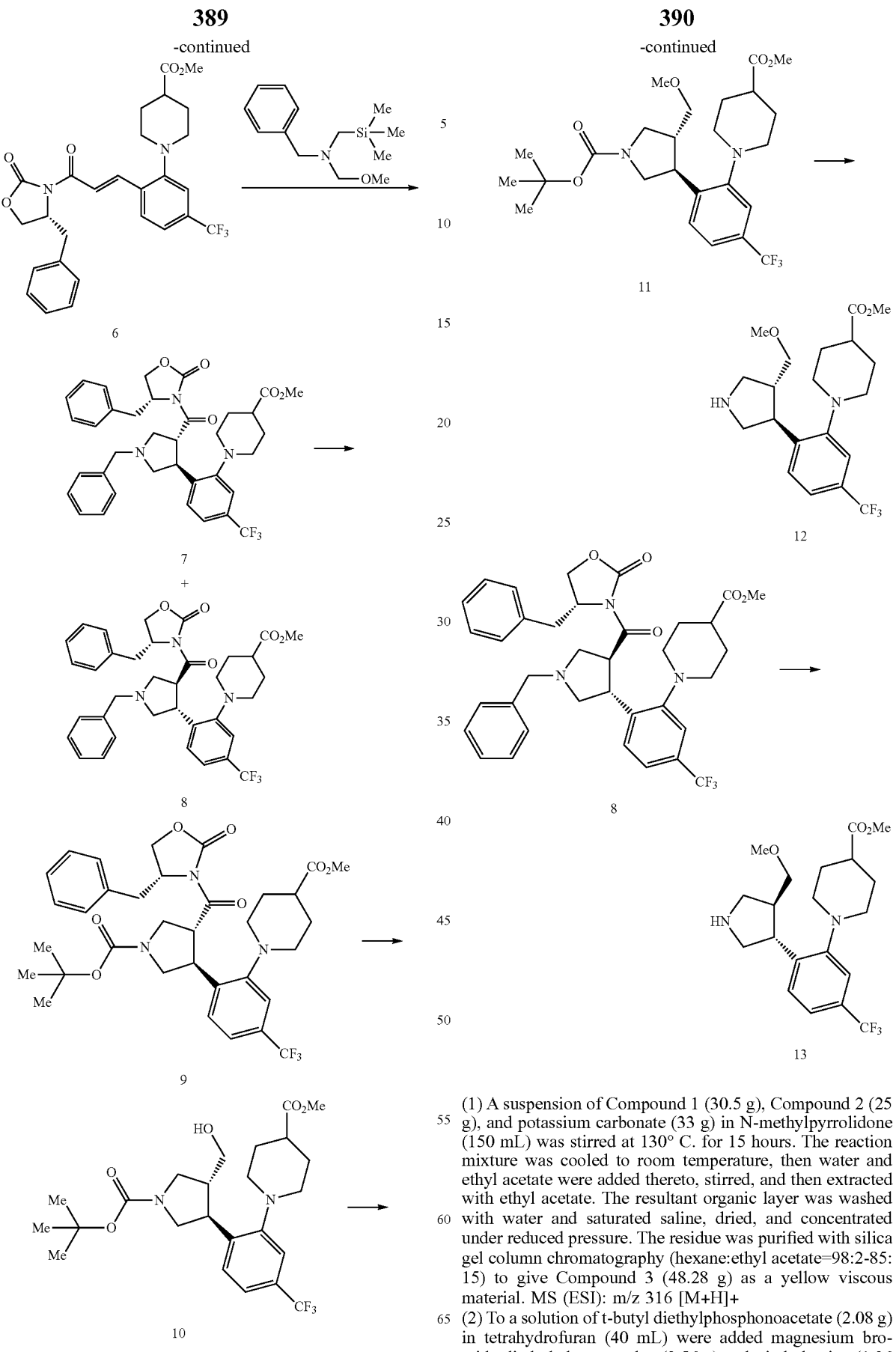

(1) A suspension of Compound 1 (30.5 g), Compound 2 (25 g), and potassium carbonate (33 g) in N-methylpyrrolidone (150 mL) was stirred at 130° C. for 15 hours. The reaction mixture was cooled to room temperature, then water and ethyl acetate were added thereto, stirred, and then extracted with ethyl acetate. The resultant organic layer was washed with water and saturated saline, dried, and concentrated under reduced pressure. The residue was purified with silica gel column chromatography (hexane:ethyl acetate=98:2-85:15) to give Compound 3 (48.28 g) as a yellow viscous material. MS (ESI): m/z 316 [M+H]+

(2) To a solution of t-butyl diethylphosphonoacetate (2.08 g) in tetrahydrofuran (40 mL) were added magnesium bromide-diethylether complex (2.56 g) and triethylamine (1.26 mL) under ice-cooling, the mixture was stirred at room temperature for 1 hour, then Compound 3 (2.00 g) was added thereto, and stirred at room temperature for 23 hours. To the reaction mixture was added sodium hydride (60% in oil, 507 mg), stirred at room temperature for 23 hours, then a saturated aqueous solution of ammonium chloride was added thereto, stirred, and extracted with ethyl acetate. The resultant organic layer was washed with saturated saline, dried, and concentrated under reduced pressure to give Compound 4 (3.17 g) as a yellow viscous material of a crude material. Said compound was used in the next step without purification. MS (APCI): m/z 414 [M+H]+

(3) To a solution of Compound 4 (53.0 g) in dichloromethane (500 mL) was added trifluoroacetic acid (160 mL), and the mixture was stirred at room temperature for 5 hours. To the reaction mixture was added water, stirred, and then extracted with dichloromethane. The resultant organic layer was dried, and concentrated under reduced pressure. To the residue was added diisopropylether, stirred, and then precipitate was collected by filtration to give Compound 5 (26.3 g) as a pale yellow powder. MS (ESI): m/z 358 [M+H]+

(4) Compound 5 (34 g) was treated in a similar manner to the above Reference Example 98 to give Compound 6 (45.6 g) as a yellow powder. MS (APCI): m/z 517 [M+H]+

(5) Compound 6 (45 g) was treated in a similar manner to the above Reference Example 98 to give Compound 7 (26.89 g) and Compound 8 (22.34 g) as pale yellow powders. Each MS (APCI): m/z 650 [M+H]+

(6) To a solution of Compound 7 (24 g) and di-t-butyl dicarbonate (8.45 g) in methanol (200 mL)/tetrahydrofuran (200 mL) was added 10% palladium carbon (wetted with ca. 50% water, 4.8 g), and the mixture was stirred under hydrogen atmosphere (1 atm) at room temperature for 17 hours. Palladium carbon was removed by filtration, and the filtrate was concentrated under reduced pressure. The residue was purified with silica gel column chromatography (hexane:ethyl acetate=85:15-60:40) to give Compound 9 (23.06 g) as a colorless powder. MS (ESI): m/z 660 [M+H]+

(7) To a solution of Compound 9 (10.0 g) in tetrahydrofuran (100 mL)/water (20 mL) was added sodium borohydride (1.15 g) under ice-cooling, and the mixture was stirred at the same temperature for 3.5 hours. To the reaction mixture was added a saturated aqueous solution of ammonium chloride, stirred, and then extracted with ethyl acetate. The resultant organic layer was dried, and concentrated under reduced pressure. The residue was purified with silica gel column chromatography (hexane:ethyl acetate=80:20-50:50) to give Compound 10 (6.93 g) as a colorless powder. MS (APCI): m/z 487 [M+H]+

(8) To a solution of Compound 10 (3.82 g) in N,N-dimethylformamide (80 mL) was added methyl iodide (4.9 mL), the mixture was cooled to −15° C., sodium hydride (60% in oil, 411 mg) was added thereto, and stirred at −10° C. for 1 hour and at 0° C. for 2 hours. To the reaction mixture was added a saturated aqueous solution of ammonium chloride, stirred, then water was added, and extracted with ethyl acetate. The resultant organic layer was washed with water and saturated saline, then dried, and concentrated under reduced pressure. The residue was purified with silica gel column chromatography (hexane:ethyl acetate=90:10-70:30) to give Compound 11 (3.19 g) as a colorless viscous material. MS (ESI): m/z 501 [M+H]+

(9) To a solution of Compound 11 (3.18 g) in dichloromethane (30 mL) was added trifluoroacetic acid (15 mL), and the mixture was stirred at room temperature for 19 hours. The reaction solution was concentrated under reduced pressure, then diluted with chloroform, then a saturated aqueous solution of sodium hydrogen carbonate was added thereto to alkalify it, and extracted with chloroform. The resultant organic layer was dried, and then concentrated under reduced pressure to give Compound 12 (3.16 g) as a pale yellow viscous material. MS (ESI): m/z 401 [M+H]+

(10) Compound 8 was treated in a similar manner to the above steps (6) to (9) to give Compound 13 as a pale yellow viscous material. MS (APCI): m/z 401 [M+H] MS (ESI): m/z 401 [M+H]+

Reference Examples 102-104

A corresponding starting compound was treated in a similar manner to the above Reference Example 101 to give each compound in the following Table 37.

TABLE 37

| Reference Example | Compound | MS |
|---|---|---|
| 102 | (structure with CO$_2$Me, MeO, HN, piperidine, fluorophenyl) | (ESI): m/z 351 [M + H]+ |
| 103 | (structure with CO$_2$Me, MeO, HN, piperidine, OCF$_3$ phenyl) | (ESI): m/z 417 [M + H]+ |
| 104 | (structure with CO$_2$Me, MeO, HN, piperidine, difluorophenyl) | (ESI): m/z 369 [M + H]+ |

Reference Example 105

The intermediate of Reference Example 104 was prepared according to the following method.

[Chemical Formula 128]

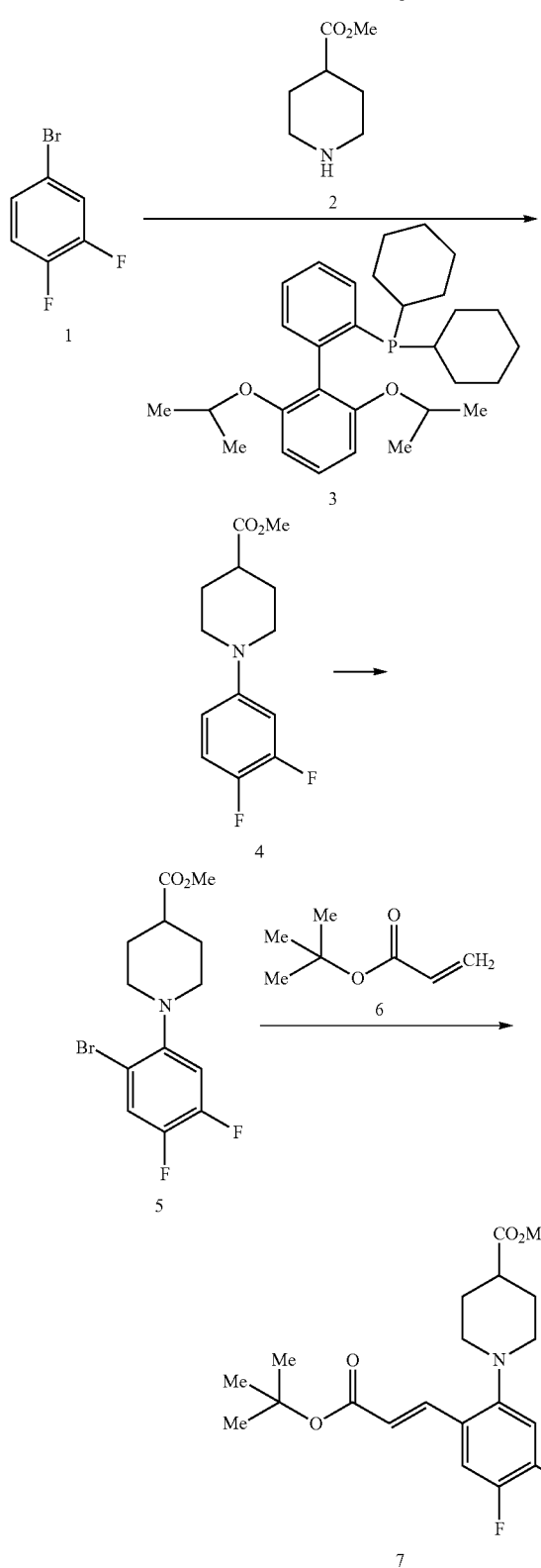

(1) A suspension of Compound 1 (2 g), Compound 2 (1.78 g), phosphine ligand 3 (483 mg), tris(dibenzylideneacetone)dipalladium(0) (474 mg), and cesium carbonate (10.1 g) in 1,4-dioxane (103 mL) was stirred under heating at 100° C. under nitrogen atmosphere for 16 hours. The insoluble matter was removed by filtration, the filtrate was concentrated under reduced pressure, and then the residue was purified with silica gel column chromatography (hexane:ethyl acetate=100:0-75:25) to give Compound 4 (1266 mg) as a yellow viscous material. MS (ESI): m/z 256 [M+H]+

(2) To a solution of Compound 4 (700 mg) in chloroform (27 mL)/methanol (13 mL) was added N-bromosuccinimide (488 mg) under ice-cooling, and then the mixture was stirred at room temperature for 5 hours. To the reaction mixture were added a saturated aqueous solution of sodium hydrogen carbonate and water, and then extracted with chloroform. The resultant organic layer was washed with water and saturated saline, and then concentrated under reduced pressure. The residue was purified with silica gel column chromatography (hexane:ethyl acetate=100:0-80:20) to give Compound 5 (747 mg) as a pale yellow powder. MS (ESI): m/z 334/336 [M+H]+

(3) A suspension of Compound 5 (1.5 g), Compound 6 (2.88 g), tri-o-tolylphosphine (273 mg), palladium acetate (100 mg), and diisopropylethylamine (1.53 mL) in N,N-dimethylformamide (15 mL) was heated at 140° C. by microwave radiation under nitrogen atmosphere for 2 hours. The reaction mixture was cooled to room temperature, then ethyl acetate and water were added thereto, and stirred. The organic layer was separated, washed with water and saturated saline, and then concentrated under reduced pressure. The residue was purified with silica gel column chromatography (hexane:ethyl acetate=100:0-80:20) to give Compound 7 (1.455 g) as a yellow viscous material. MS (ESI): m/z 382 [M+H]+

Reference Example 106

[Chemical Formula 129]

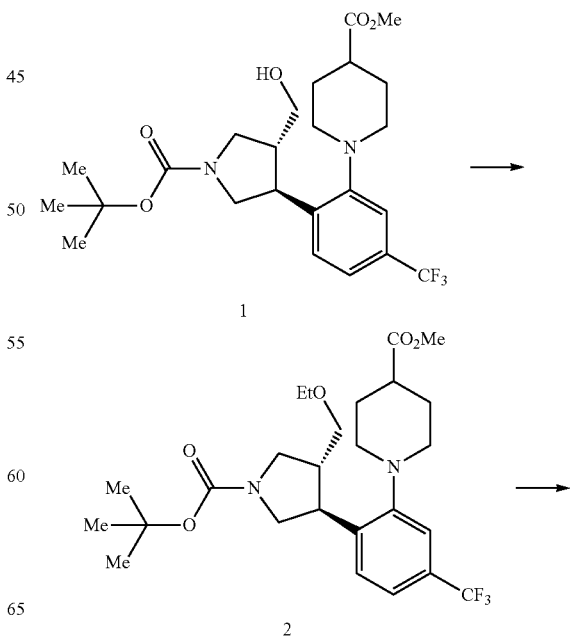

-continued

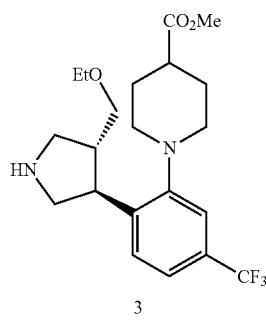

(1) A solution of Compound 1 (400 mg) and ethyl iodide (656 μL) in N,N-dimethylformamide (4 mL) was ice-cooled, sodium hydride (60% in oil, 39 mg) was added thereto, and the mixture was stirred at the same temperature for 2 hours. To the reaction mixture was added a saturated aqueous solution of ammonium chloride, stirred, and then extracted with ethyl acetate. The resultant organic layer was washed with water and saturated saline, and then concentrated under reduced pressure. The residue was purified with silica gel column chromatography (hexane:ethyl acetate=95:5-80:20) to give Compound 2 (148 mg) as a colorless viscous material. MS (ESI): m/z 515 [M+H]+

(2) To a solution of Compound 2 (140 mg) in dichloromethane (2 mL) was added trifluoroacetic acid (1 mL), and the mixture was stirred at room temperature for 1 hour. To the reaction mixture was added a saturated aqueous solution of sodium hydrogen carbonate to alkalify it, and extracted with dichloromethane. The organic layer was dried, and concentrated under reduced pressure to give Compound 3 (110 mg) as a colorless viscous material. MS (ESI): m/z 415 [M+H]+

Reference Example 107

A corresponding starting compound was treated in a similar manner to the above Reference Example 106 to give the compound in the following Table 38.

TABLE 38

| Reference Example | Compound | MS |
|---|---|---|
| 107 | 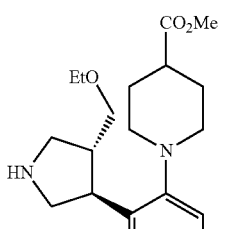 | (ESI): m/z 365 [M + H]+ |

Reference Example 108

[Chemical Formula 130]

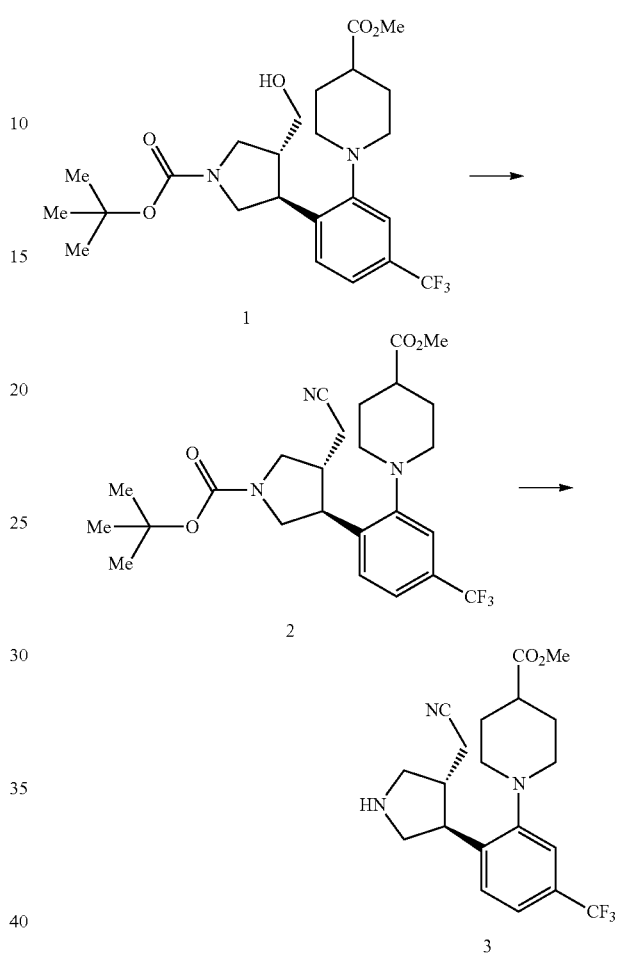

(1) To a solution of Compound 1 (600 mg), acetone cyanohydrin (228 μL), and triphenylphosphine (648 mg) in tetrahydrofuran (2 mL) was added diethyl azodicarboxylate (40 wt % toluene solution, 1.12 mL) under ice-cooling, the mixture was stirred at room temperature for 30 minutes, then acetone cyanohydrin (228 μL), triphenylphosphine (648 mg), and diethyl azodicarboxylate (40 wt % toluene solution, 1.12 mL) were added thereto, and stirred at room temperature for 14 hours. The reaction solution was concentrated under reduced pressure, diisopropylether was added thereto, and the mixture was stirred. The precipitate was removed by filtration, and then the filtrate was concentrated under reduced pressure. The residue was purified with NH silica gel column chromatography (hexane:ethyl acetate=84:16-70:30) to give Compound 2 (838 mg) as a colorless viscous material. MS (ESI): m/z 496 [M+H]+

(2) To a solution of Compound 2 (120 mg) in dichloromethane (2 mL) was added trifluoroacetic acid (0.5 mL), and the mixture was stirred at room temperature 30 minutes. The reaction solution was concentrated under reduced pressure, diluted with dichloromethane, then a saturated aqueous solution of sodium hydrogen carbonate was added thereto, the mixture was stirred, and the organic layer was extracted. The resultant organic layer was dried, and concentrated under reduced pressure. The residue was purified with NH silica gel column chromatography (ethyl acetate:methanol=100:0-90:10) to give Compound 3 (55 mg) as a colorless powder. MS (ESI): m/z 396 [M+H]+

Reference Example 109

[Chemical Formula 131]

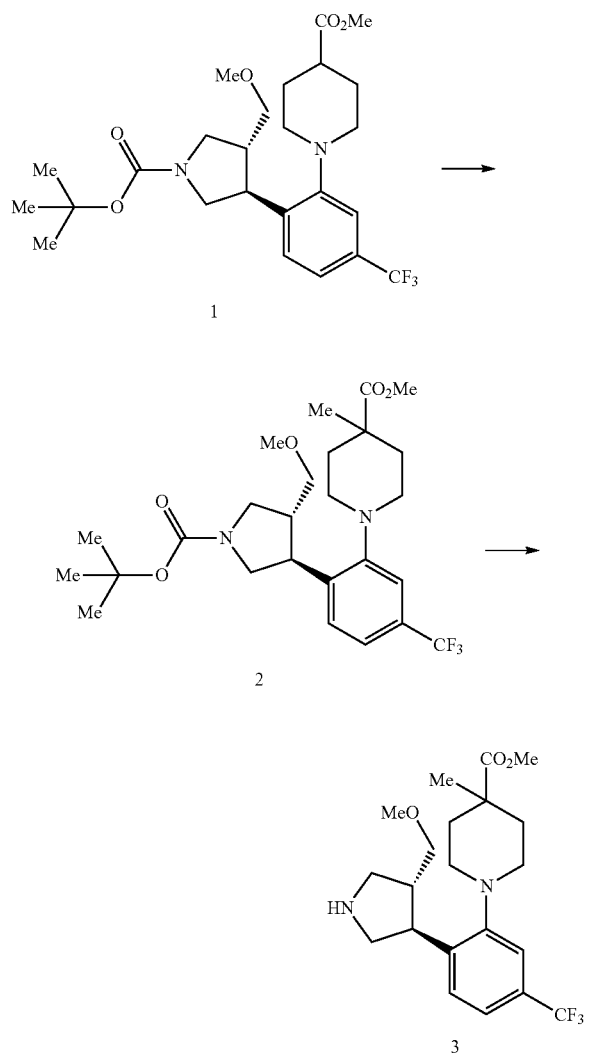

(1) Under nitrogen atmosphere, to a solution of Compound 1 (342 mg) in tetrahydrofuran (1.5 mL) was added a solution of lithium bis(trimethylsilyl)amide in tetrahydrofuran (1.09 mol/L, 1.26 mL) at −40° C., the mixture was stirred at the same temperature for 1 hour, then methyl iodide (85 μL) was added thereto, and stirred at room temperature for 15 hours. To the reaction mixture were added saturated saline and a saturated aqueous solution of sodium hydrogen carbonate, stirred, and then extracted with ethyl acetate. The resultant organic layer was washed with saturated saline, and then concentrated under reduced pressure. The residue was purified with silica gel column chromatography (hexane:ethyl acetate=93:7-80:20) to give Compound 2 (167 mg) as a colorless viscous material. MS (APCI): m/z 515 [M+H]+

(2) To a solution of Compound 2 (162 mg) in chloroform (4 mL) was added trifluoroacetic acid (4 mL), and the mixture was stirred at room temperature for 1 hour. To the reaction mixture was added a saturated aqueous solution of sodium hydrogen carbonate to alkalify it, and extracted with chloroform. The resultant organic layer was dried, and concentrated under reduced pressure to give Compound 3 (146 mg) as a pale yellow viscous material. MS (APCI): m/z 415 [M+H]+

Reference Example 110

[Chemical Formula 132]

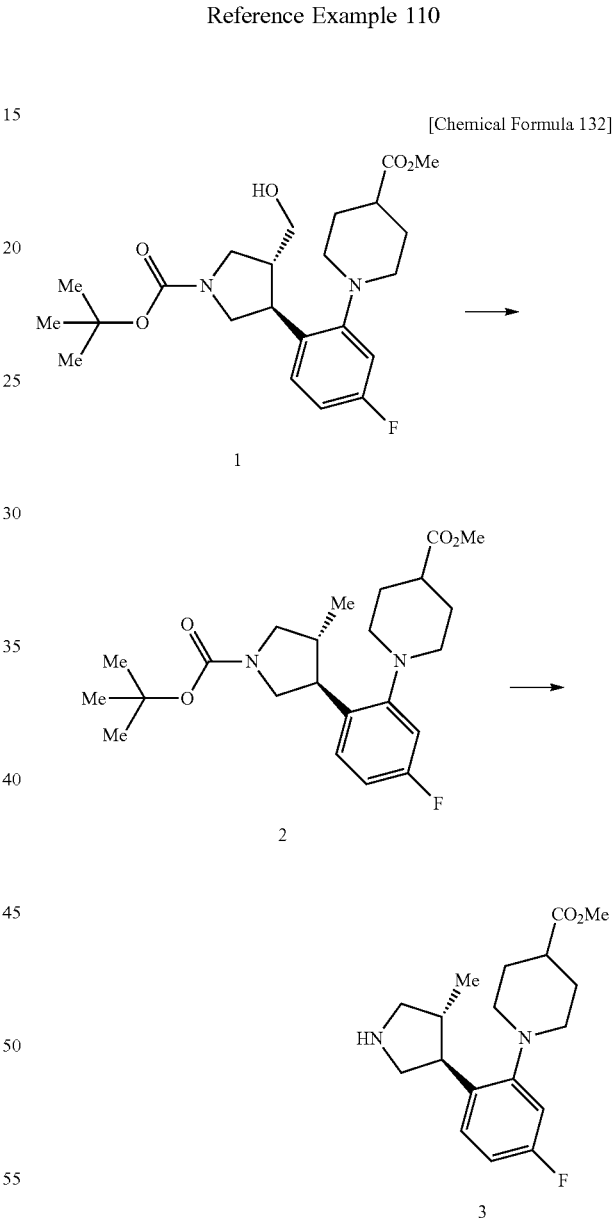

(1) To a solution of Compound 1 (500 mg) in tetrahydrofuran (10 mL) were added triphenylphosphine (484 mg), N'-isopropylidene-2-nitrobenzenesulfonohydrazide (474 mg), and diethyl azodicarboxylate (40 wt % toluene solution, 833 μL) under ice-cooling, and the mixture was stirred at room temperature for 3 hours. To the reaction solution was added phenylhydrazine (564 μL), and the mixture was stirred at room temperature for 15 hours. The reaction solution was concentrated under reduced pressure, ethyl acetate and a saturated aqueous solution of sodium hydrogen carbonate were added thereto, and extracted with ethyl acetate. The resultant organic layer was washed with a saturated aqueous solution of ammonium chloride, then dried, and concentrated under reduced pressure. The residue was purified with silica gel column chromatography (hexane:ethyl acetate=85:15-60:40) and NH silica gel column chromatography (hexane:ethyl acetate=90:10-65:35) to give Compound 2 (168 mg) as a pale yellow viscous material. MS (ESI): m/z 421 [M+H]+

(2) To a solution of Compound 2 (165 mg) in dichloromethane (1.6 mL) was added trifluoroacetic acid (0.8 mL), and the mixture was stirred at room temperature for 6 hours. The reaction solution was concentrated, then ethyl acetate and a saturated aqueous solution of sodium hydrogen carbonate were added thereto to alkalify it, and the organic layer was separated. The resultant organic layer was washed with saturated saline, dried, and concentrated under reduced pressure to give Compound 3 (149 mg) as a pale orange viscous material. MS (APCI): m/z 321 [M+H]+

Reference Example 111

[Chemical Formula 133]

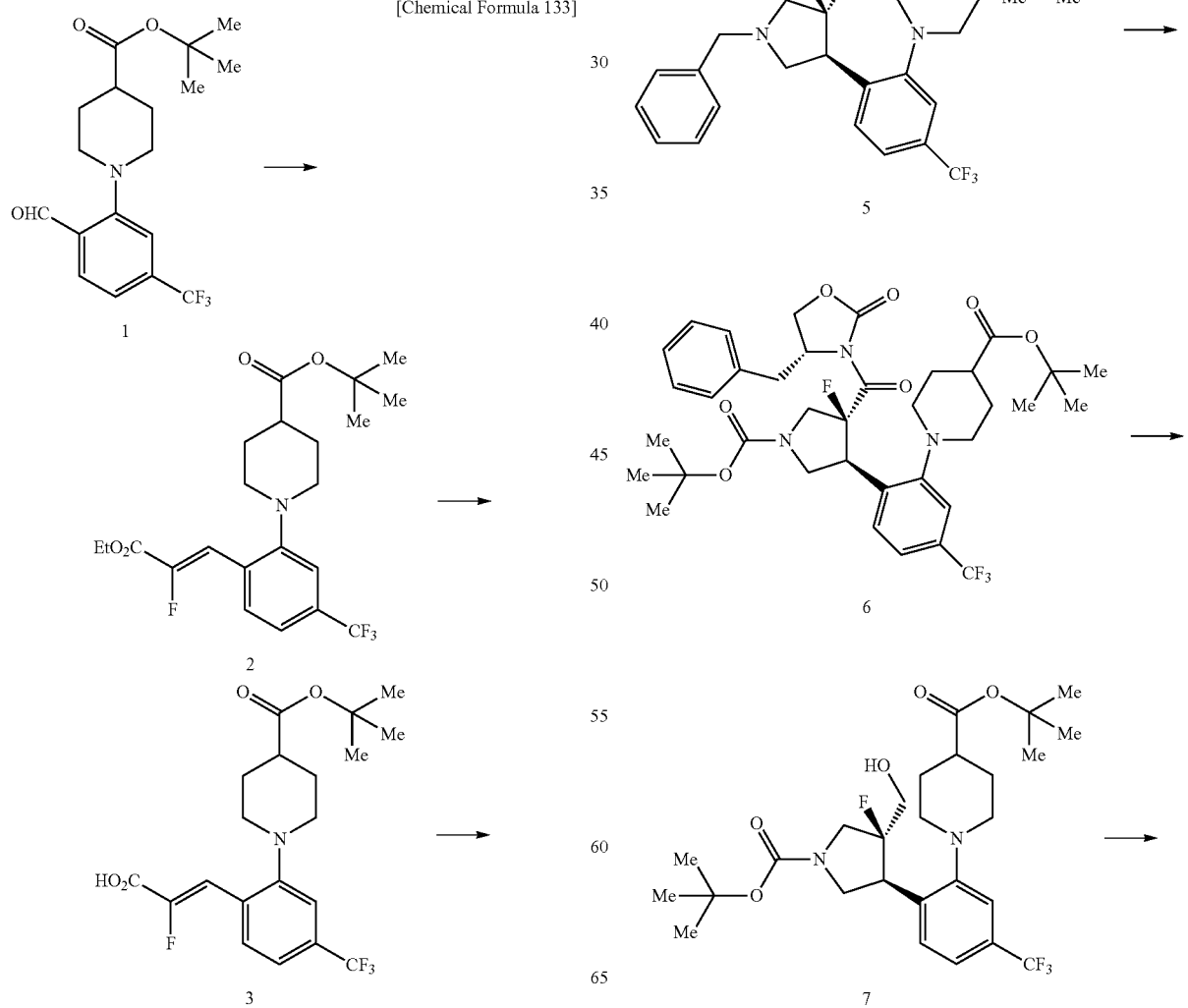

-continued

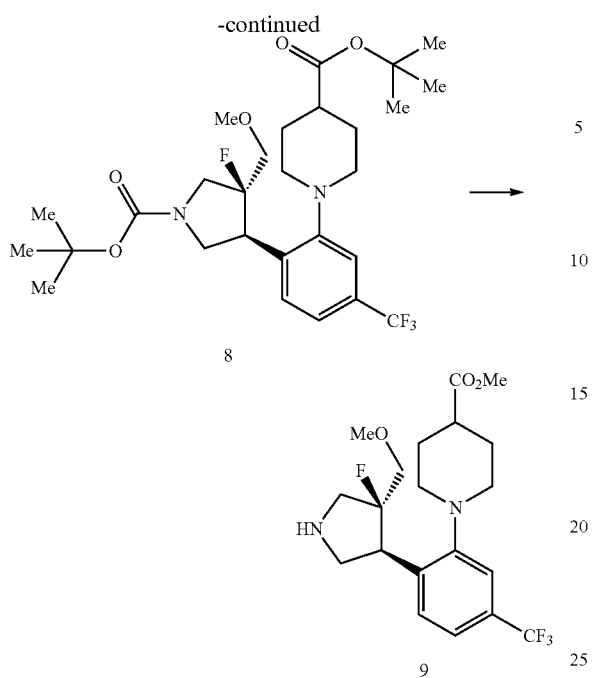

(1) To a solution of triethyl 2-fluoro-2-phosphonoacetate (1.01 g) in tetrahydrofuran (18 mL) were added magnesium bromide-diethylether complex (1.29 g) and triethylamine (638 μL) under ice-cooling, the mixture was stirred at room temperature for 1 hour, then a solution of Compound 1 (1.14 g) in tetrahydrofuran (5 mL) was added thereto, and stirred at room temperature for 6 hours. To the reaction mixture was added a saturated aqueous solution of ammonium chloride, stirred, and then extracted with ethyl acetate. The resultant organic layer was washed with saturated saline, dried, and concentrated under reduced pressure to give Compound 2 (1.41 g) as a yellow powder in the isomeric ratio of Z:E≈85:15. Said compound was used in the next step without purification. MS (APCI): m/z 446 [M+H]+

(2) To a solution of Compound 2 (2.65 g) in ethanol (13 mL)/tetrahydrofuran (13 mL) was added an aqueous solution of sodium hydroxide (2 mol/L, 5.95 mL), and the mixture was stirred at room temperature for 1 hour. To the reaction solution was added an aqueous solution of hydrochloric acid (1 mol/L, 10 mL), stirred, and then the organic solvent was evaporated under reduced pressure. The precipitate was collected by filtration, dissolved in a mixed solution of ethyl acetate and an aqueous solution of hydrochloric acid (0.1 mol/L), and the organic layer was separated. The resultant organic layer was washed with saturated saline, dried, and concentrated under reduced pressure. The residue was powdered with diisopropylether, collected by filtration, and then dried to give Compound 3 (1.79 g) as a colorless powder. MS (APCI): m/z 418 [M+H]+

(3) Compound 3 (500 mg) was treated in a similar manner to the above Reference Example 99 to give Compound 4 (123 mg) as a yellow viscous material. MS (APCI): m/z 577 [M+H]+

(4) Compound 4 (400 mg) was treated in a similar manner to the above Reference Example 99 to give Compound 5 (107 mg) as an orange viscous material. MS (APCI): m/z 710 [M+H]+

(5) Compound 5 (105 mg) was treated in a similar manner to Reference Example 101 to give Compound 6 (119 mg) as a yellow viscous material. MS (APCI): m/z 720 [M+H]+

(6) Compound 6 (100 mg) was treated in a similar manner to Reference Example 101 to give Compound 7 (57.9 mg) as a colorless viscous material. MS (APCI): m/z 547 [M+H]+

(7) Compound 7 (56 mg) was treated in a similar manner to Reference Example 101 to give Compound 8 (50.3 mg) as a colorless viscous material. MS (APCI): m/z 561 [M+H]+

(8) To a solution of Compound 8 (48 mg) in methanol (1.9 mL) was added a solution of hydrochloric acid in methanol (2 mol/L, 1.9 mL), and the mixture was stirred at 50° C. for 5 hours. The reaction mixture was cooled to room temperature, and then concentrated under reduced pressure. To the residue were added dichloromethane and a saturated aqueous solution of sodium hydrogen carbonate, stirred, and then extracted with dichloromethane. The resultant organic layer was dried, and then concentrated under reduced pressure to give Compound 9 (37.9 mg) as a pale yellow viscous material. MS (APCI): m/z 419 [M+H]+

Reference Example 112

[Chemical Formula 134]

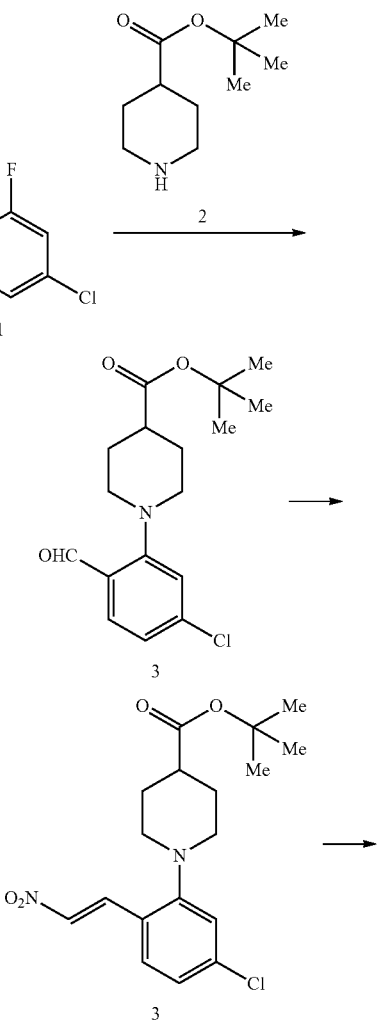

-continued

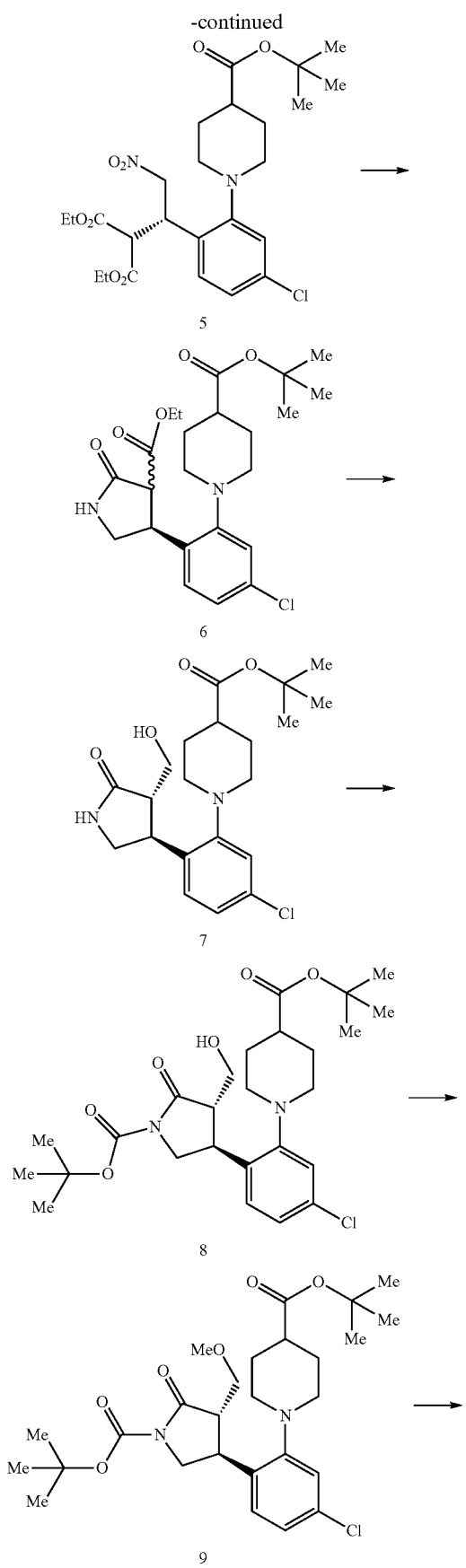

-continued

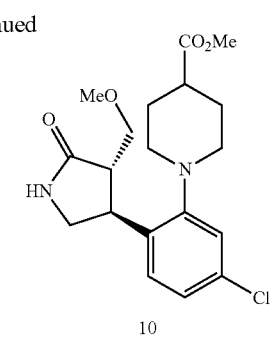

(1) A suspension of Compound 1 (10.0 g), Compound 2 (14.0 g), and potassium carbonate (13.1 g) in 1,3-dimethyl-2-imidazolidinone (80 mL) was stirred at 100° C. for 15 hours. The reaction mixture was cooled to room temperature, then water was added thereto, and extracted with ethyl acetate. The resultant organic layer was washed with water and saturated saline, dried, and concentrated under reduced pressure. The residue was purified with silica gel column chromatography (hexane:ethyl acetate=99:1-90:10) to give Compound 3 (19.0 g) as a yellow viscous material. MS (APCI): m/z 324/326 [M+H]+

(2) To a solution of Compound 3 (15.3 g) and nitromethane (12.8 mL) in methanol (76.5 mL) was added a solution of sodium methoxide in methanol (5 mol/L, 0.94 mL), the mixture was stirred at room temperature for 4 hours, then nitromethane (25.6 mL) was added thereto, and stirred at room temperature for 15 hours. To the reaction solution was added an aqueous solution of hydrochloric acid (1 mol/L, 4.7 mL) to neutralize it, and concentrated under reduced pressure. The residue was diluted with ethyl acetate and water, an aqueous solution of hydrochloric acid (1 mol/L) was added thereto to acidify it, and then the organic layer was separated. The resultant organic layer was washed with saturated saline, dried, and concentrated under reduced pressure. To a solution of the residue in tetrahydrofuran (76.5 mL) was added dropwise methanesulfonyl chloride (4.39 mL) and triethylamine (16.46 mL) under ice-cooling, and the mixture was stirred at the same temperature for 40 minutes. Tetrahydrofuran was evaporated under reduced pressure, then to the residue was added water (200 mL), and the mixture was stirred. The precipitate was collected by filtration, dissolved in ethyl acetate, then washed with saturated saline, dried, and concentrated under reduced pressure. The residue was purified with silica gel column chromatography (hexane:ethyl acetate=90:10-85:15), powdered with cooled hexane, collected by filtration, and dried under reduced pressure to give Compound 4 (11.12 g) as a yellow powder. MS (ESI): m/z 367/369 [M+H]+

As described in the following (3) and (4), Compound 4 was treated in a similar manner to a method described in a literature (J. Am. Chem. Soc. 2005, 127, 119-125) to prepare Compound 6.

(3) To a solution of Compound 4 (11.12 g) in toluene (55.6 mL) were added 1-[3,5-bis(trifluoromethyl)phenyl]-3-[(1S,2S)-(−)-2-(dimethylamino)cyclohexyl]thiourea (630 mg) and diethyl malonate (9.2 mL), and the mixture was stirred at room temperature for 62 hours. The reaction solution was concentrated under reduced pressure, and the residue was purified with silica gel column chromatography (hexane: ethyl acetate=100:0-90:10) to give Compound 5 (16.13 g) as a pale orange viscous material.

MS (ESI): m/z 527/529 [M+H]+

(4) To a solution of Compound 5 (16.13 g) and nickel chloride hexahydrate (7.27 g) in methanol (161.3 mL) was added sodium borohydride (6.95 g) under ice-cooling, and the mixture was stirred at room temperature for 2 hours. The reaction solution was ice-cooled, a saturated aqueous solution of ammonium chloride was added thereto, stirred, and then methanol was evaporated under reduced pressure. To the residue were added chloroform and water, stirred, and the organic layer was separated. The resultant organic layer was washed with water, dried, and concentrated under reduced pressure. The residue was purified with silica gel column chromatography (hexane:ethyl acetate=67:33-40:60) to give Compound 6 (3.52 g) as a pale orange powder. MS (ESI): m/z 451/453 [M+H]+

(5) To a solution of Compound 6 (2.31 g) in ethanol (45 mL) was added sodium borohydride (775 mg) under ice-cooling, and the mixture was stirred at room temperature for 10 minutes and at 40° C. for 4 hours. The reaction solution was ice-cooled, a saturated aqueous solution of ammonium chloride was added thereto, stirred, and then extracted with ethyl acetate. The resultant organic layer was washed with saturated saline, dried, and concentrated under reduced pressure. The residue was purified with silica gel column chromatography (chloroform:methanol=100:0-93:7), then powdered with diisopropylether, collected by filtration, and then dried to give Compound 7 (1.84 g) as a colorless powder. MS (APCI): m/z 409/411 [M+H]+

(6) To a solution of trimethyloxoniumtetrafluoroborate (1.32 g) in dichloromethane (36 mL) was added Compound 7 (1.82 g), the mixture was stirred at room temperature for 2 hours, then trimethyloxoniumtetrafluoroborate (330 mg) was added thereto, and stirred at room temperature for 1 hour. Dichloromethane was evaporated under reduced pressure until the volume of the reaction solution became about one third, then methanol (36 mL) and di-t-butyl dicarbonate (1.07 g) were added thereto, the mixture was ice-cooled, sodium borohydride (505 mg) was added thereto, and stirred at the same temperature for 30 minutes. To the reaction mixture was added an aqueous solution of ammonium chloride, stirred, and then extracted with ethyl acetate. The resultant organic layer was washed with saturated saline, dried, and concentrated under reduced pressure. The residue was purified with silica gel column chromatography (hexane:ethyl acetate=85:15-60:40) to give Compound 8 (1.18 g) as a colorless powder. MS (APCI): m/z 495/497 [M+H]+

(7) A solution of Compound 8 (1.16 g) and methyl iodide (1.46 mL) in N,N-dimethylformamide (23.2 mL) was cooled to −20° C., sodium hydride (60% in oil, 123 mg) was added thereto, and the mixture was stirred under nitrogen atmosphere at −15° C. for 1 hour and at −8° C. for 3 hours. To the reaction mixture was added a saturated aqueous solution of ammonium chloride, stirred, and then extracted with ethyl acetate. The resultant organic layer was washed with water and saturated saline, dried, and concentrated under reduced pressure. The residue was purified with silica gel column chromatography (hexane:ethyl acetate=90:10-60:40) to give Compound 9 (1.21 g) as a colorless powder. MS (APCI): m/z 509/511 [M+H]+

(8) To a solution of Compound 9 (1.16 g) in methanol (2 mL) was added a solution of hydrochloric acid in methanol (2 mol/L, 17.6 mL), and the mixture was stirred at 50° C. for 15 hours. The reaction mixture was cooled to room temperature, a saturated aqueous solution of sodium carbonate was added thereto to alkalify it, methanol was evaporated under reduced pressure, and the mixture was extracted with chloroform. The resultant organic layer was dried, and concentrated under reduced pressure to give Compound 10 (839 mg) as a colorless viscous material. MS (APCI): m/z 367/369 [M+H]+

Reference Examples 113-114

A corresponding starting compound was treated in a similar manner to the above Reference Example 112 to give each compound in the following Table 39.

TABLE 39

| Reference Example | Compound | MS |
|---|---|---|
| 113 | 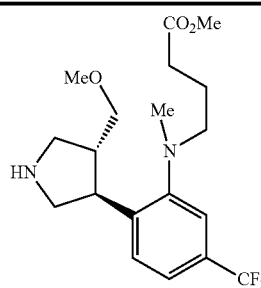 | (ESI): m/z 389 [M + H]+ |
| 114 | 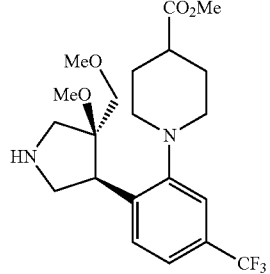 [SMILES: COC[C@@]1(OC)CNC[C@@H]1c1ccc(C(F)(F)F)cc1N1CCC(C(=O)OC)CC1] | (APCI): m/z 431 [M + H]+ |

Reference Example 115

[Chemical Formula 135]
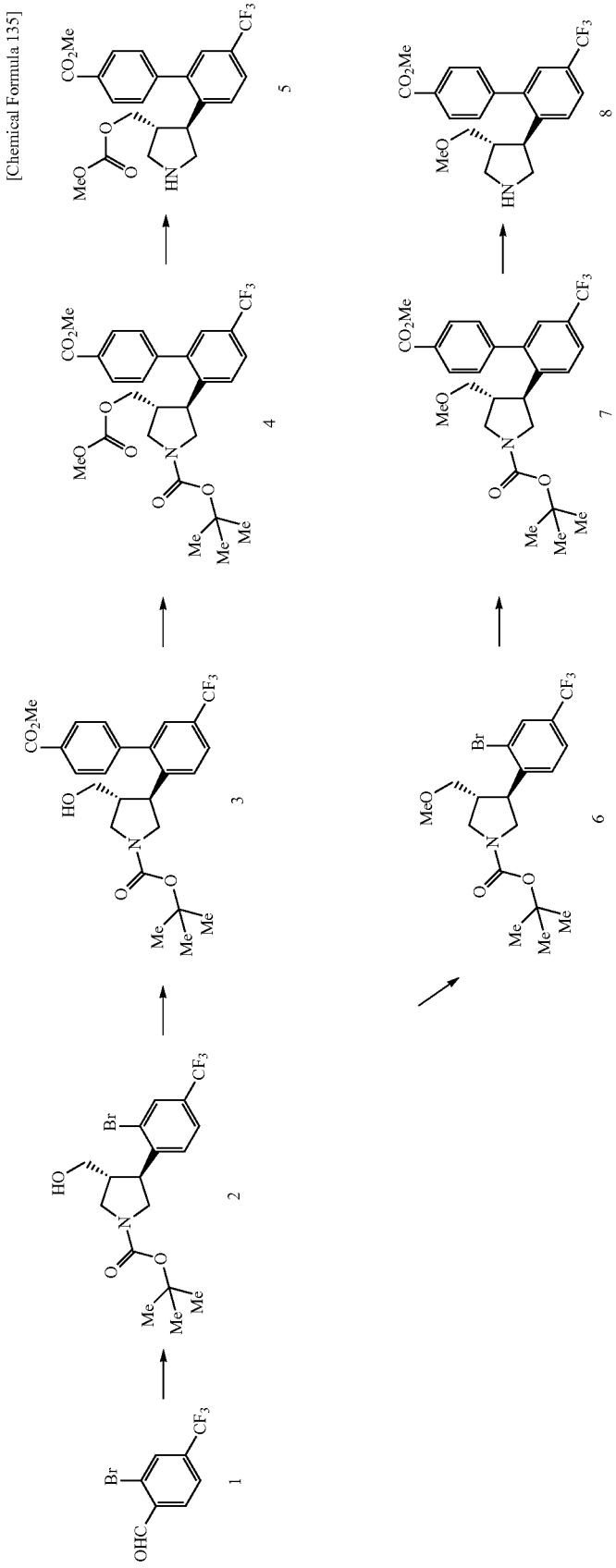

(1) A mixture of Compound 2 (100 mg) prepared according to the above Reference Example 112 from Compound 1, 4-methoxycarbonylphenylboronic acid (47 mg), dichloro[1,1'-bis(diphenylphosphino) ferrocene]palladium(II) dichloromethane adduct (20 mg), an aqueous solution of sodium carbonate (2 mol/L, 300 μL), and N,N-dimethylformamide (2 mL) was stirred under nitrogen atmosphere at 80° C. for 20 hours. The reaction mixture was cooled to room temperature, then ethyl acetate and water were added thereto, stirred, and extracted with ethyl acetate. The resultant organic layer was washed with water and saturated saline, and then concentrated under reduced pressure. The residue was purified with silica gel column chromatography (hexane:ethyl acetate=70:30-50:50) to give Compound 3 (52.7 mg) as a colorless powder. MS (ESI): m/z 480 [M+H]+

(2) A solution of Compound 3 (51 mg), acetic acid (18 μL), 1-ethyl-3-(3-dimethylaminopropyl)carbodiimide hydrochloride (30 mg), and 4-dimethylaminopyridine (6.5 mL) in N,N-dimethylformamide (2 mL) was stirred at room temperature for 3 hours. To the reaction mixture were added ethyl acetate and a saturated aqueous solution of sodium hydrogen carbonate, stirred, and extracted with ethyl acetate. The resultant organic layer was washed with water and saturated saline, and then concentrated under reduced pressure. The residue was purified with silica gel column chromatography (hexane:ethyl acetate=85:15-50:50) to give Compound 4 (47 mg) as a colorless powder. MS (ESI): m/z 422 [M-Boc+H]+

(3) To a solution of Compound 4 (45 mg) in dichloromethane (2 mL) was added trifluoroacetic acid (1 mL), and the mixture was stirred at room temperature for 17 hours. To the reaction mixture was added a saturated aqueous solution of sodium hydrogen carbonate to alkalify it, and extracted with dichloromethane. The organic layer was dried, and concentrated under reduced pressure to give Compound 5 (35 mg) as a colorless viscous material. MS (ESI): m/z 422 [M+H]+

(4) To a solution of Compound 2 (250 mg) and methyl iodide (110 μL) in N,N-dimethylformamide (2 mL) was added sodium hydride (60% in oil, 31 mg) under ice-cooling, and the mixture was stirred at the same temperature for 2 hours. To the reaction mixture was added water, stirred, and extracted with ethyl acetate. The resultant organic layer was washed with water and saturated saline, and then concentrated under reduced pressure. The residue was purified with silica gel column chromatography (hexane:ethyl acetate=90:10-70:30) to give Compound 6 (166 mg) as a colorless viscous material. MS (ESI): m/z 382/384 [M-tBu]+

(5) Compound 6 (160 mg) was treated in a similar manner to the reaction which gave Compound 3 from Compound 2 in the above step (1) to give Compound 7 (171 mg) as a colorless powder. MS (ESI): m/z 394 [M-Boc+H]+

(6) To a solution of Compound 7 (165 mg) in dichloromethane (2 mL) was added trifluoroacetic acid (1 mL), and the mixture was stirred at room temperature for 17 hours. To the reaction mixture was added a saturated aqueous solution of sodium hydrogen carbonate to alkalify it, and extracted with dichloromethane. The organic layer was dried, and concentrated under reduced pressure to give Compound 8 (130 mg) as a colorless viscous material. MS (ESI): m/z 394 [M+H]+

Reference Example 116

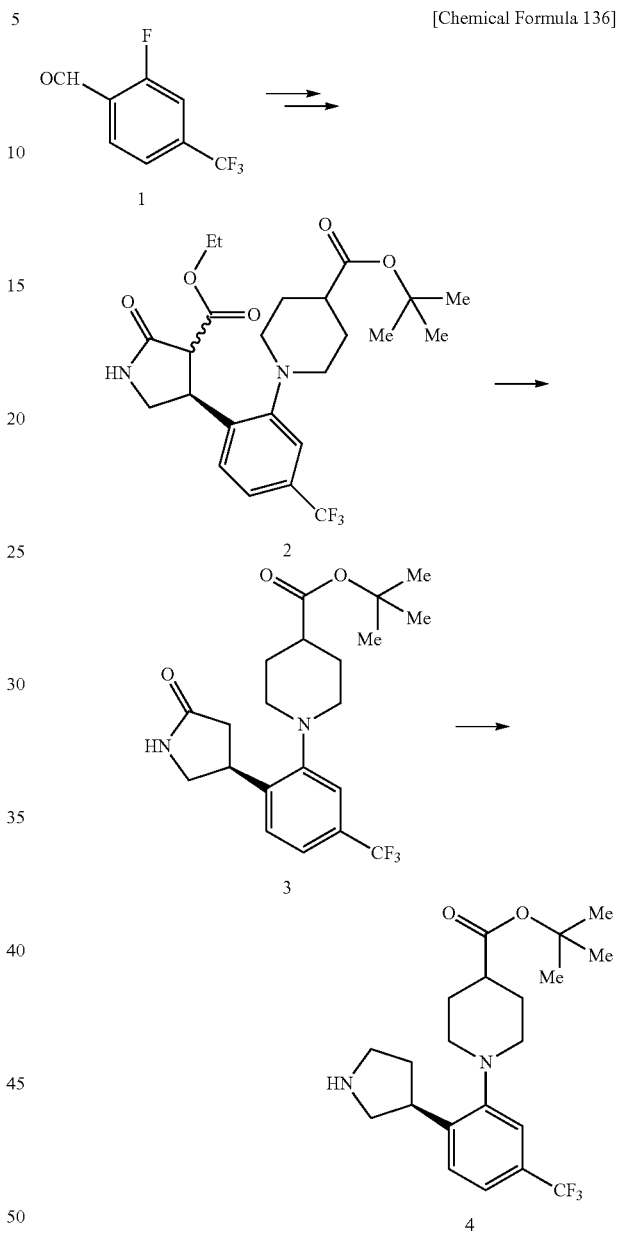

[Chemical Formula 136]

(1) Compound 1 was treated in a similar manner to Reference Example 112 to give Compound 2 (36.2 g).

(2) To a solution of Compound 2 in ethanol (360 mL) was added an aqueous solution of sodium hydroxide (1 mol/L, 82.2 mL), and the mixture was stirred at room temperature for 1 hour. Ethanol was evaporated under reduced pressure, the residue was diluted with water, then an aqueous solution of hydrochloric acid (1 mol/L) was added thereto until the mixture became pH=4 under ice-cooling, and the mixture was extracted with chloroform. The resultant organic layer was washed with saturated saline, dried, and concentrated under reduced pressure. To the residue was added toluene (180 mL), heated under reflux for 2 hours, then the reaction solution was concentrated under reduced pressure, the residue was purified with silica gel column chromatography (chloroform:methanol=100:0-95:5), then powdered with hexane, collected by filtration, and then dried to give Compound 3 (27.5 g) as a colorless solid. MS (ESI): m/z 413 [M+H]+

(3) To a solution of Compound 3 (4.12 g) in tetrahydrofuran (82 mL) was added trimethyloxoniumtetrafluoroborate (1.77 g), and the mixture was stirred at room temperature for 1.5 hours. The reaction mixture was concentrated under reduced pressure, and methanol (82 mL) was added to the residue, and acetic acid (4.46 mL) and sodium borohydride (3.04 g) were added thereto under ice-cooling, and the mixture was stirred at room temperature for 30 minutes. The solvent was evaporated under reduced pressure, to the residue was added a saturated aqueous solution of sodium hydrogen carbonate, and then extracted with chloroform. The resultant organic layer was dried, and concentrated under reduced pressure. The residue was purified with silica gel column chromatography (ethyl acetate:methanol=100:0-80:20) to give Compound 4 (2.95 g) as a pale yellow viscous material. MS (ESI): m/z 399 [M+H]+

Reference Example 117

A corresponding starting compound was treated in a similar manner to the above Reference Example 116 to give the compound in the following Table 40.

TABLE 40

| Reference Example | Compound | MS |
|---|---|---|
| 117 | 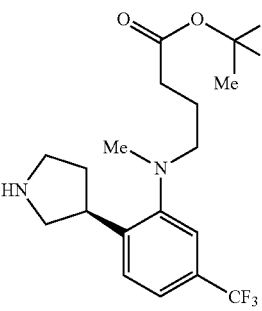 | (ESI): m/z 387 [M + H]+ |

Reference Example 118

[Chemical Formula 137]

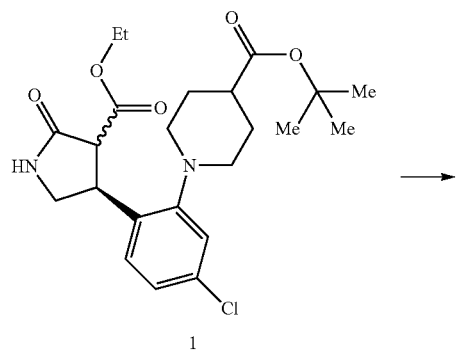

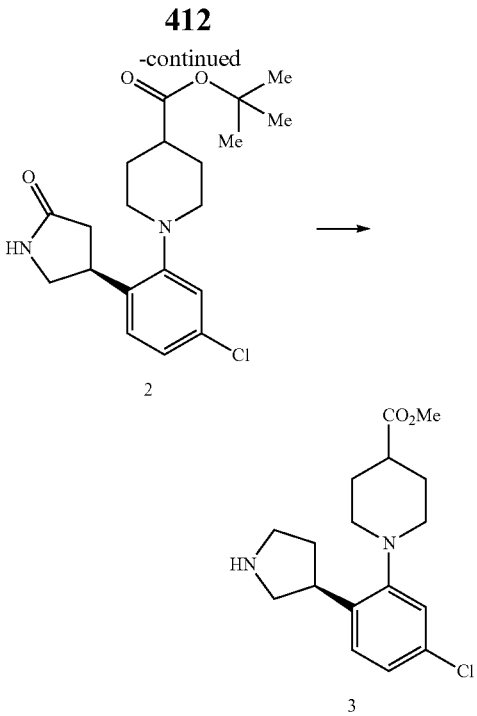

(1) Compound 1 (2 g) obtained in Reference Example 112 was treated in a similar manner to Reference Example 116 to give Compound 2 (829 mg). MS (ESI): m/z 379/381 [M+H]+

(2) To a solution of Compound 2 (300 mg) in 1,4-dioxane (6 mL) were added sodium borohydride (300 mg) and acetic acid (454 μL), and the mixture was stirred at 100° C. for 30 minutes. The reaction solution was ice-cooled, methanol (3 mL) was added thereto, the mixture was stirred, then a saturated aqueous solution of sodium hydrogen carbonate was added thereto to alkalify it, and extracted with chloroform. The resultant organic layer was washed with water, dried, and concentrated under reduced pressure. A solution of the residue in methanol (2 mL) was ice-cooled, a solution of hydrochloric acid in methanol (2 mol/L, 16 mL) was added thereto, and the mixture was heated under reflux for 18 hours. To the reaction mixture were added ethyl acetate and water at room temperature, stirred, then a saturated aqueous solution of sodium hydrogen carbonate was added thereto to alkalify it, and extracted with chloroform. The resultant organic layer was dried, and concentrated under reduced pressure. The residue was purified with NH silica gel column chromatography (ethyl acetate:methanol=100:0-90:10) to give Compound 3 (128 mg) as a pale yellow viscous material. MS (ESI): m/z 323/325 [M+H]+

Reference Example 119

[Chemical Formula 138]

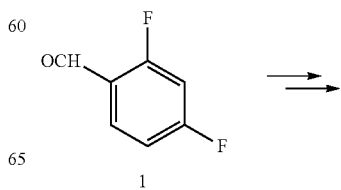

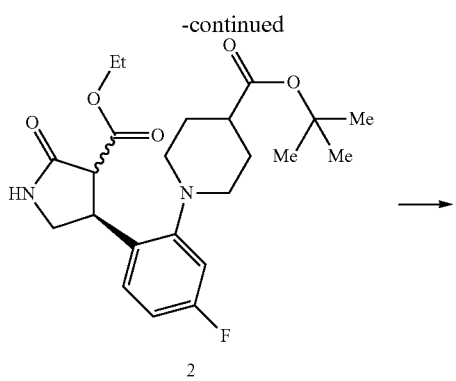

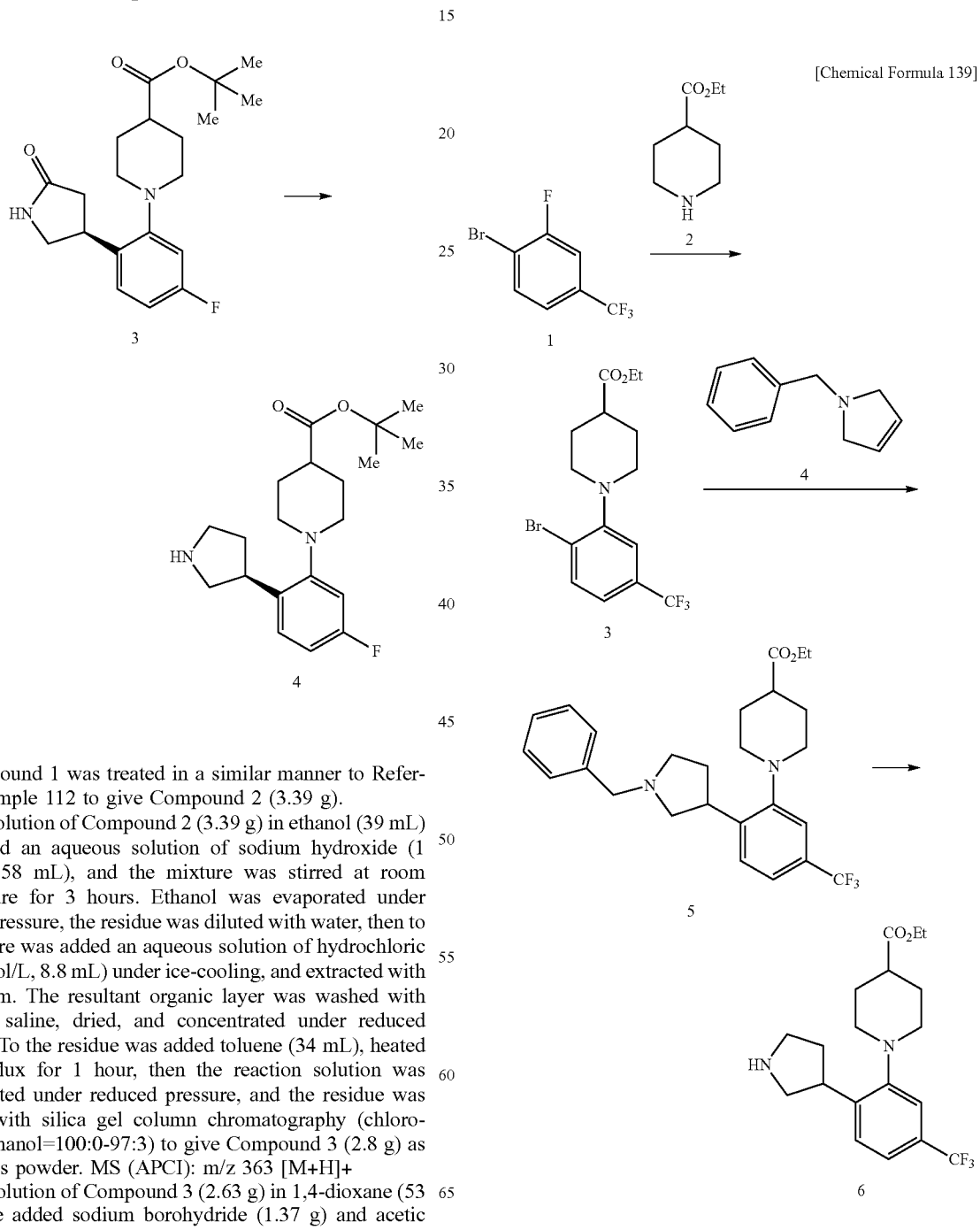

hours. The reaction solution was cooled to room temperature, water (5 drops) was added thereto, stirred, and then methanol (19 mL) was added thereto. To the mixture was added 10% palladium carbon (wetted with ca. 50% water, 530 mg), stirred at room temperature for 3 days, then palladium carbon was removed by filtration, and washed with methanol. The filtrate was concentrated, and then the residue was purified with NH silica gel column chromatography (ethyl acetate:methanol=100:0-98:2) to give Compound 4 (1.226 g) as a colorless powder. MS (APCI): m/z 349 [M+H]+

Reference Example 120

[Chemical Formula 139]

(1) Compound 1 was treated in a similar manner to Reference Example 112 to give Compound 2 (3.39 g).

(2) To a solution of Compound 2 (3.39 g) in ethanol (39 mL) was added an aqueous solution of sodium hydroxide (1 mol/L, 8.58 mL), and the mixture was stirred at room temperature for 3 hours. Ethanol was evaporated under reduced pressure, the residue was diluted with water, then to the mixture was added an aqueous solution of hydrochloric acid (1 mol/L, 8.8 mL) under ice-cooling, and extracted with chloroform. The resultant organic layer was washed with saturated saline, dried, and concentrated under reduced pressure. To the residue was added toluene (34 mL), heated under reflux for 1 hour, then the reaction solution was concentrated under reduced pressure, and the residue was purified with silica gel column chromatography (chloroform:methanol=100:0-97:3) to give Compound 3 (2.8 g) as a colorless powder. MS (APCI): m/z 363 [M+H]+

(3) To a solution of Compound 3 (2.63 g) in 1,4-dioxane (53 mL) were added sodium borohydride (1.37 g) and acetic acid (2.08 mL), and the mixture was stirred at 100° C. for 25

(1) A solution of Compound 1 (10.0 g), Compound 2 (30.5 g), and potassium carbonate (17.1 g) in 1,3-dimethyl-2-imidazolidinone (50 mL) was stirred at 155° C. for 5 hours. The reaction mixture was diluted with ethyl acetate at room temperature, the insoluble matter was removed by filtration, and the filtrate was concentrated under reduced pressure. The residue was purified with silica gel column chromatography (hexane:ethyl acetate=100:0-90:10) to give Compound 3 (8.70 g) as a colorless viscous material. MS (APCI): m/z 380/382 [M+H]+

(2) To a solution of triethylamine (4.18 mL) and formic acid (0.384 mL) in N,N-dimethylformamide (20 mL) were added dichloro[1,1'-bis(diphenylphosphino)ferrocene]palladium (II) dichloromethane adduct (205 mg), Compound 3 (1.90 g), Compound 4 (3.98 g), and N,N-dimethylformamide (10 mL), and the mixture was stirred at 95° C. for 2 hours. To the reaction mixture were added ethyl acetate and water at room temperature, stirred, and then extracted with ethyl acetate. The resultant organic layer was washed with water, dried, and concentrated under reduced pressure. The residue was purified with silica gel column chromatography (hexane:ethyl acetate=100:0-50:50) to give racemic Compound 5 (1.14 g) as a pale yellow viscous material. MS (APCI): m/z 461 [M+H]+

(3) To a solution of Compound 5 (611 mg) in ethanol (12 mL) was added 10% palladium carbon (wetted with ca. 50% water, 611 mg), and the mixture was stirred under hydrogen atmosphere (1 atm) at room temperature for 16 hours. Palladium carbon was removed by filtration, and then the filtrate was concentrated under reduced pressure to give racemic Compound 6 (447 mg) as a dark brown viscous material. MS (APCI): m/z 371 [M+H]+

Reference Example 121

[Chemical Formula 140]

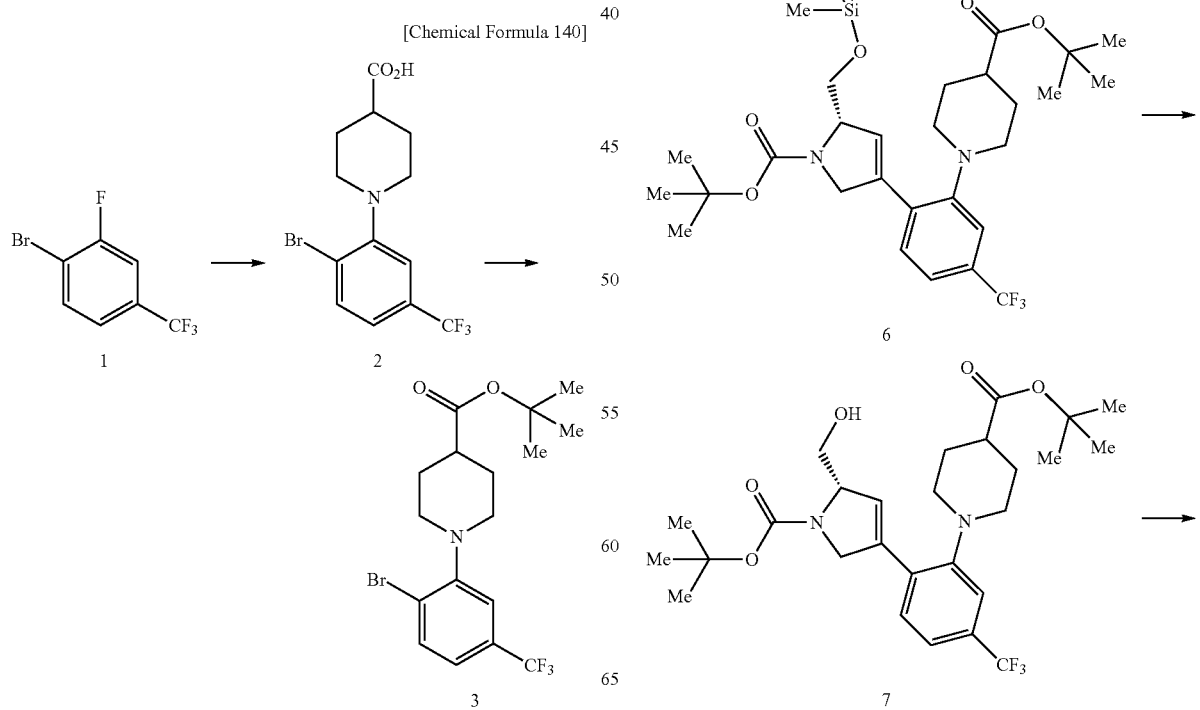
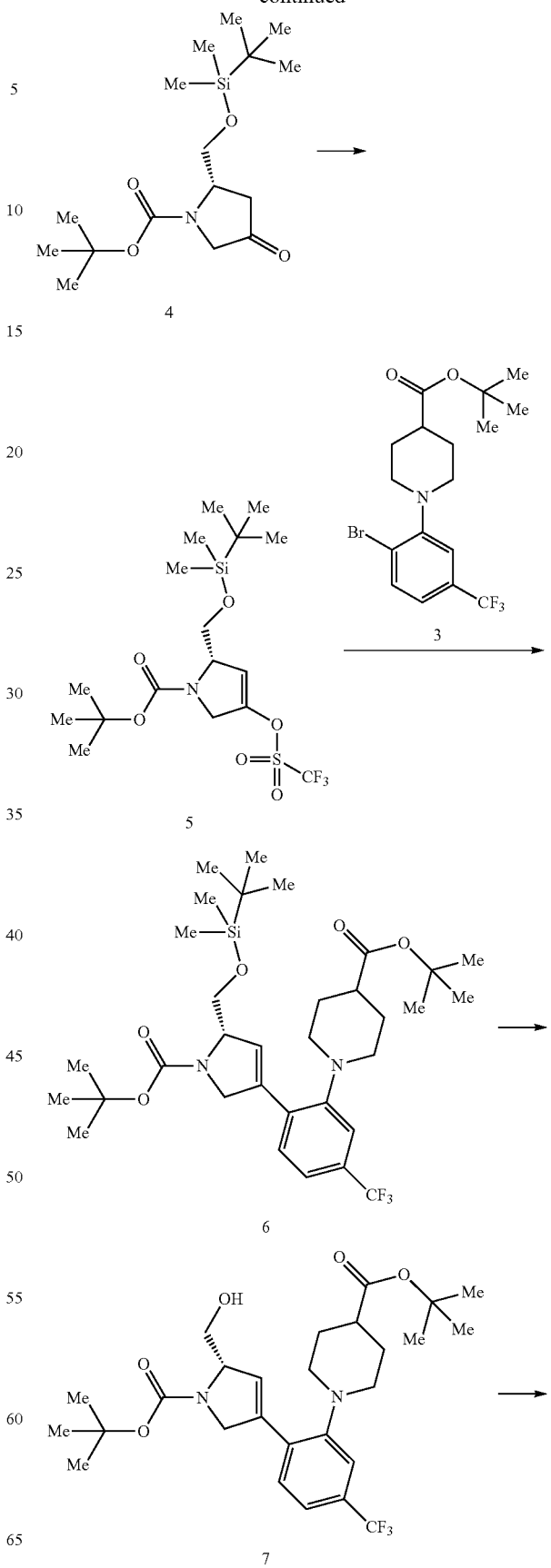

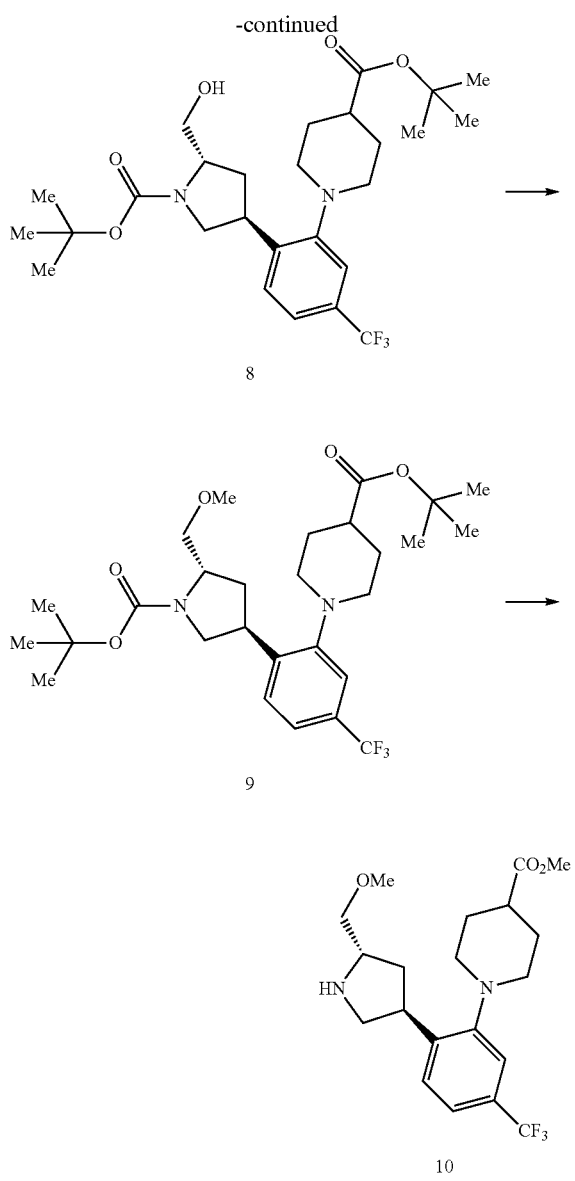

(1) A suspension of Compound 1 (20 g), piperidine-4-carboxylic acid (15.9 g), and potassium carbonate (34.12 g) in N-methylpyrrolidone (160 mL) was stirred under nitrogen atmosphere at 190° C. for 4 hours. The reaction mixture was poured into an ice-cooled aqueous solution of hydrochloric acid (1 mol/L, 480 mL), a saturated aqueous solution of sodium hydrogen carbonate was added thereto to neutralize it, then diluted with water, and extracted with ethyl acetate twice. The resultant organic layers were combined, washed with water and saturated saline, magnesium sulfate and active carbon were added thereto, the mixture was stirred, then filtrated, and the filtrate was concentrated under reduced pressure. The residue was powdered with isopropylether, collected by filtration, and then dried to give Compound 2 (14.1 g) as a colorless solid. MS (APCI): m/z 352/354 [M+H]+

(2) To a suspension of Compound 2 (21.3 g) and di-t-butyl dicarbonate (15.8 g) in acetonitrile (200 mL) was added 4-dimethylaminopyridine (1.48 g), the mixture was stirred at room temperature for 1 hour, then triethylamine (8.42 mL) was added thereto, and the mixture was stirred at room temperature for 15 hours. To the mixture were added triethylamine (4.21 mL) and di-t-butyl dicarbonate (2.60 g), and stirred at room temperature for 2 hours. The reaction mixture was concentrated, and then purified with silica gel column chromatography (hexane:ethyl acetate=99:1-96:4) to give Compound 3 (20.4 g) as a colorless solid. MS (APCI): m/z 408/410 [M+H]+

(3) Compound 4 was prepared according to a method described in a literature (J. Org. Chem. 2003, 68, 3923-3931).

(4) A solution of a solution of potassium bis(trimethylsilyl)amide in toluene (2 mol/L, 18.14 mL) in tetrahydrofuran (110 mL) was cooled to −78° C., a solution of Compound 4 (2.49 g) in tetrahydrofuran (20 mL) was added dropwise thereto, the mixture was stirred at the same temperature for 25 minutes, then a solution of N-phenylbis(trifluoromethane sulfonimide) (4.05 g) in tetrahydrofuran (20 mL) was added dropwise thereto, and the mixture was stirred at room temperature for 15 hours. To the reaction mixture was added a saturated aqueous solution of sodium hydrogen carbonate at 0° C., stirred, and then extracted with ethyl acetate. The resultant organic layer was dried, and then concentrated under reduced pressure. The residue was purified with silica gel column chromatography (hexane:ethyl acetate=95:5) to give Compound 5 (3.39 g) as a pale yellow viscous material.

(5) To a solution of Compound 5 (1.5 g) in 1,4-dioxane (11 mL) were added bis(pinacolato)diboron (991 mg), dichloro[1,1'-bis(diphenylphosphino)ferrocene]palladium(II) dichloromethane adduct (133 mg), 1,1'-bis(diphenylphosphino)ferrocene (90 mg), and potassium acetate (958 mg), and the mixture was stirred at 100° C. for 50 minutes. To the reaction mixture was added water at room temperature, stirred, and extracted with chloroform. The resultant organic layer was dried, and concentrated under reduced pressure. To the residue were added N,N-dimethylformamide (11 mL), water (3 mL), Compound 3 (1.33 g), dichloro[1,1'-bis(diphenylphosphino)ferrocene]palladium(II) dichloromethane adduct (133 mg), and sodium carbonate (1.03 g), and the mixture was stirred at 100° C. for 2.5 hours. To the reaction mixture was added water at room temperature, stirred, and extracted with ethyl acetate. The resultant organic layer was dried, and concentrated under reduced pressure. The residue was purified with silica gel column chromatography (hexane:ethyl acetate=95:5-80:20) to give Compound 6 (1.63 g) as a pale yellow viscous material.

(6) To a solution of Compound 6 (1.63 g) in tetrahydrofuran (6 mL) was added a solution of tetrabutylammonium fluoride in tetrahydrofuran (1 mol/L, 2.80 mL), and the mixture was stirred at room temperature for 3 hours. To the reaction mixture was added a saturated aqueous solution of sodium hydrogen carbonate, stirred, then extracted with chloroform, the resultant organic layer was dried, and concentrated under reduced pressure. The residue was purified with silica gel column chromatography (hexane:ethyl acetate=80:20-60:40) to give Compound 7 (1.16 g) as a colorless viscous material. MS (ESI): m/z 527 [M+H]+

(7) To a solution of Compound 7 (917 mg) in dichloromethane (34.8 mL) was added Crabtree's catalyst (14 mg), and the mixture was stirred under hydrogen atmosphere (1 atm) at room temperature for 19.5 hours. The reaction mixture was concentrated under reduced pressure, and then the residue was purified with silica gel column chromatography (hexane:ethyl acetate=80:20-60:40) to give Compound 8 (870 mg) as a colorless powder. MS (ESI): m/z 529 [M+H]+

(8) To a solution of Compound 8 (870 mg) in tetrahydrofuran (8 mL) were added methyl iodide (1.03 mL) and sodium hydride (60% in oil, 99 mg), and the mixture was stirred at room temperature for 2 hours and 15 minutes. To the reaction mixture was added water, stirred, and then extracted with ethyl acetate. The resultant organic layer was dried, and concentrated under reduced pressure. The residue was purified with silica gel column chromatography (hexane:ethyl acetate-95:5-80:20) to give Compound 9 (864 mg) as a colorless viscous material.

(9) To a solution of Compound 9 (31.4 g) in methanol (314 mL) was added a solution of hydrochloric acid in methanol (2 mol/L, 314 mL), and the mixture was stirred at 50° C. for 10 hours. The solvent was evaporated under reduced pressure, then to the residue was added a saturated aqueous solution of sodium hydrogen carbonate to alkalify the mixture, and extracted with chloroform. The resultant organic layer was dried, concentrated under reduced pressure to give Compound 10 (23.8 g) as a brown viscous material. MS (ESI): m/z 401 [M+H]+

Reference Examples 122-124

A corresponding starting compound was treated in a similar manner to Reference Example 121 to give each compound in the following Table 41.

TABLE 41

| Reference Example | Compound | MS |
|---|---|---|
| 122 | (structure with OMe, CO₂Me, F) | (ESI): m/z 351 [M + H]+ |
| 123 | (structure with OEt, CO₂Me, CF₃) | (ESI): m/z 415 [M + H]+ |
| 124 | (structure with OMe, CO₂Me, CF₃) | MS (ESI): m/z 401 [M + H]+ |

Reference Example 125

[Chemical Formula 141]

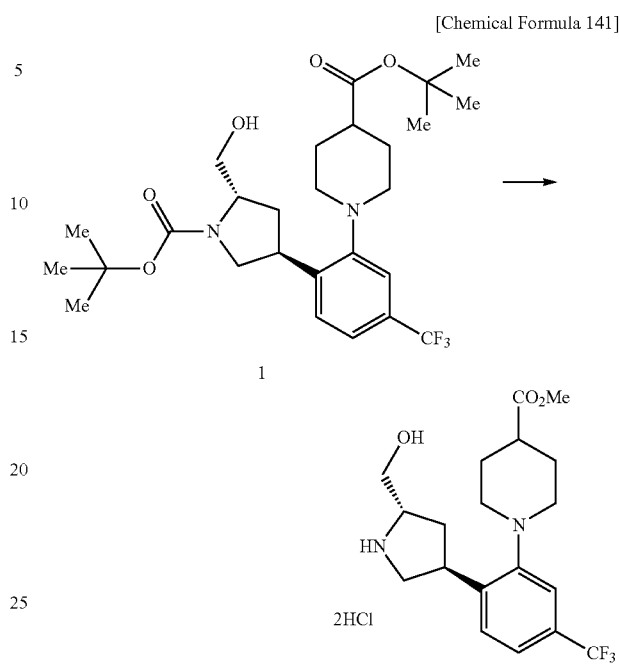

To Compound 1 (529 mg) was added a solution of hydrochloric acid in methanol (2 mol/L, 25 mL), and the mixture was stirred at 50° C. for 15 hours. The solvent was evaporated under reduced pressure, and then to the residue was added toluene, and the mixture was concentrated under reduced pressure to give Compound 2 (460 mg) as a pale brown powder. MS (ESI): m/z 387 [M+H]+

Reference Example 126

[Chemical Formula 142]

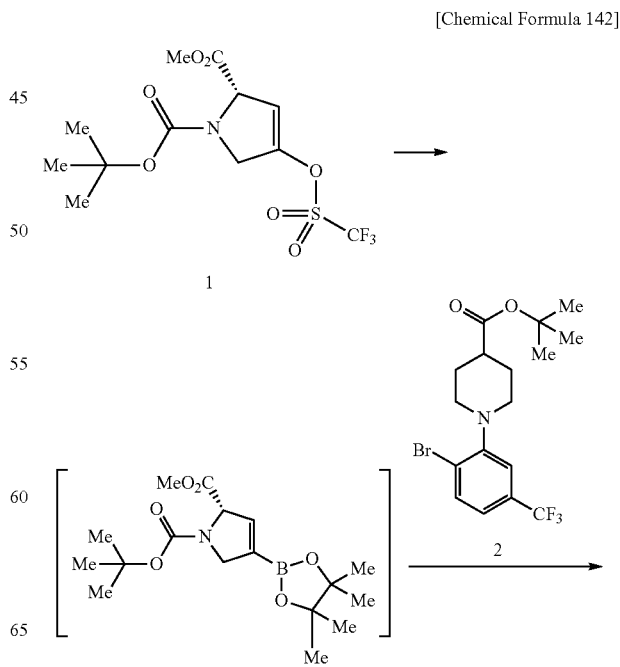

-continued

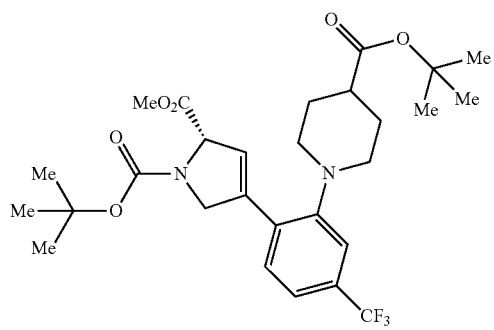

3

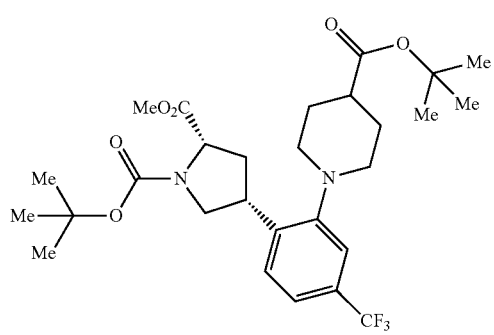

4

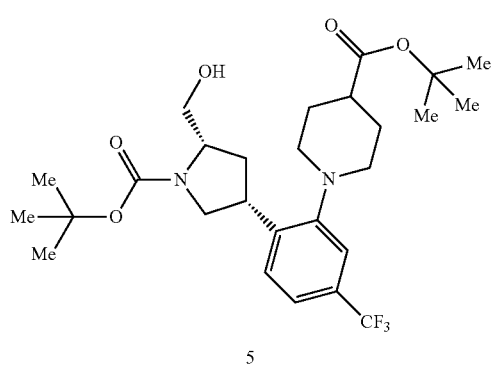

5

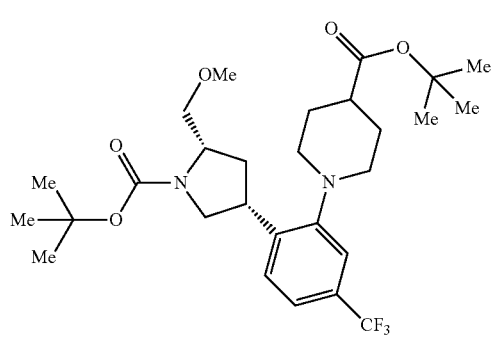

6

-continued

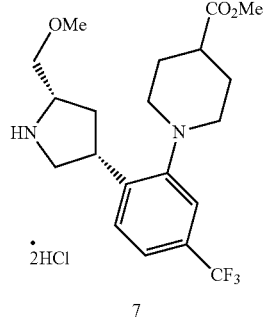

7

(1) A suspension of Compound 1 (2.25 g) prepared according to the method described in a literature (J. Org. Chem. 2012, 77, 5286-5296), bis(pinacolato)diboron (1.83 g), dichloro[1,1'-bis(diphenylphosphino)ferrocene]palladium (II) dichloromethane adduct (245 mg), 1,1'-bis(diphenylphosphino)ferrocene (166 mg), and potassium acetate (1.77 g) in 1,4-dioxane (60 mL) was stirred under nitrogen atmosphere at 80° C. for 1.5 hours. To the reaction mixture was added water at room temperature, stirred, and extracted with chloroform. The resultant organic layer was dried, and concentrated under reduced pressure. To the residue were added Compound 2 (2.45 g), dichloro[1,1'-bis(diphenylphosphino)ferrocene]palladium(II) dichloromethane adduct (490 mg), a 2M aqueous solution of sodium carbonate (9 mL), and N,N-dimethylformamide (60 mL), and the mixture was stirred under nitrogen atmosphere at 80° C. for 30 minutes. To the reaction mixture were added water and saturated saline at room temperature, stirred, and extracted with ethyl acetate. The resultant organic layer was dried, and concentrated under reduced pressure. The residue was purified with silica gel column chromatography (hexane:ethyl acetate=95:5-80:20) to give Compound 3 (1.23 g) as a pale yellow powder. MS (ESI): m/z 555 [M+H]+

(2) To a solution of Compound 3 (373 mg) in methanol (7 mL) was added 10% palladium carbon (wetted with ca. 50% water, 75 mg), and the mixture was stirred under hydrogen atmosphere (1 atm) at room temperature for 2 hours. To the mixture was added 10% palladium carbon (wetted with ca. 50% water, 150 mg), and stirred under hydrogen atmosphere (1 atm) at room temperature for additional 1 hour. Palladium carbon was removed by filtration, and then the filtrate was concentrated under reduced pressure. The residue was purified with silica gel column chromatography (hexane:ethyl acetate=95:5-80:20) to give Compound 4 (293 mg) as a colorless powder. MS (APCI): m/z 485 [M+H]+

(3) To a solution of Compound 4 (282 mg) in tetrahydrofuran (4 mL)/methanol (1 mL) were added sodium borohydride (77 mg) and lithium chloride (86 mg), and the mixture was stirred at room temperature for 30 minutes. To the reaction mixture was added water, stirred, and extracted with chloroform. The organic layer was dried, concentrated under reduced pressure, and then the residue was purified with silica gel column chromatography (hexane:ethyl acetate=95:5-70:30) to give Compound 5 (254 mg) as a colorless viscous material. MS (ESI): m/z 529 [M+H]+

(4) To a solution of Compound 5 (248 mg) in tetrahydrofuran (5 mL) were added methyl iodide (292 μL) and sodium hydride (60% in oil, 28 mg), and the mixture was stirred at room temperature for 5 minutes and then at 50° C. for 20 minutes. To the reaction mixture was added water at room temperature, stirred, and extracted with chloroform. The organic layer was dried, concentrated under reduced pressure, and then the residue was purified with silica gel column chromatography (hexane:ethyl acetate=95:5-75:25) to give Compound 6 (167 mg) as a pale yellow viscous material.

(5) A mixture of Compound 6 (160 mg) and a solution of hydrochloric acid in methanol (2 mol/L, 8 mL) was stirred at 60° C. for 6 hours. The reaction mixture was concentrated under reduced pressure to give Compound 7 (140 mg) as a brown powder. MS (ESI): m/z 401 [M+H]+

Reference Example 127

A corresponding starting compound was treated in a similar manner to Reference Example 126 to give the compound in the following Table 42.

TABLE 42

| Reference Example | Compound | MS |
|---|---|---|
| 127 | 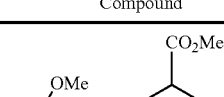 | (ESI): m/z 401 [M + H]+ |

Reference Example 128

[Chemical Formula 143]

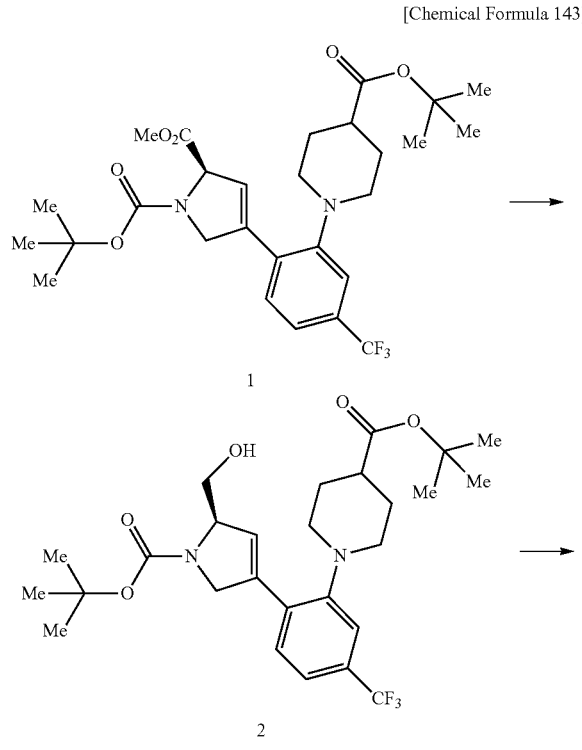

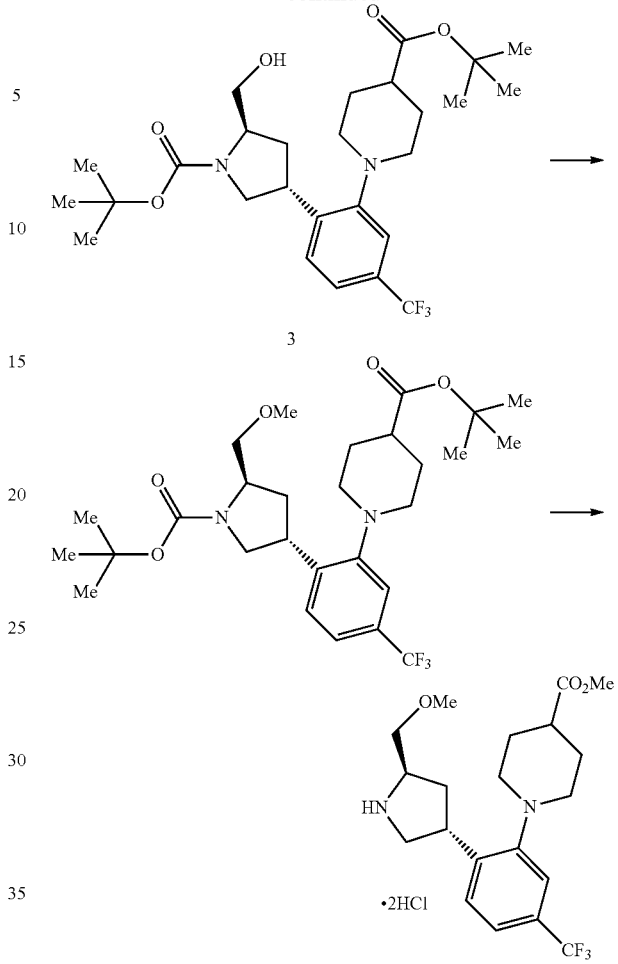

(1) A corresponding starting compound was treated in a similar manner to Reference Example 126 to give Compound 1 (260 mg).

(2) To a solution of Compound 1 (260 mg) in tetrahydrofuran (4 mL)/methanol (1 mL) were added sodium borohydride (71 mg) and lithium chloride (79 mg), and the mixture was stirred at room temperature for 10 minutes. To the reaction mixture was added water, stirred, and extracted with chloroform. The organic layer was washed with saturated saline, dried, and concentrated under reduced pressure. The residue was purified with silica gel column chromatography (hexane:ethyl acetate=95:5-70:30) to give Compound 2 (270 mg) as a colorless viscous material. MS (ESI): m/z 527 [M+H]+

(3) To a solution of Compound 2 (240 mg) in dichloromethane (10 mL) was added Crabtree's catalyst (7.3 mg), and the mixture was stirred under hydrogen atmosphere (1 atm) at room temperature for 15 hours. The reaction mixture was concentrated under reduced pressure, and then the residue was purified with silica gel column chromatography (hexane:ethyl acetate=95:5-70:30) to give Compound 3 (218 mg) as a colorless powder. MS (ESI): m/z 529 [M+H]+

(4) Compound 3 was treated in a similar manner to Reference Example 126 to give Compound 4. MS (ESI): m/z 401 [M+H]+

Reference Example 129

[Chemical Formula 144]

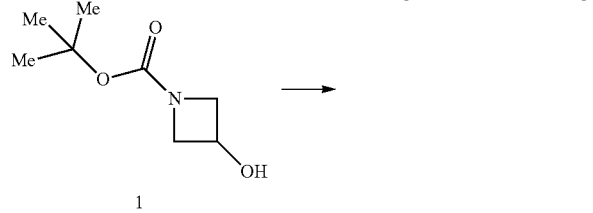

(1) To a solution of Compound 1 (2.0 g) in toluene (115 mL) was added imidazole (2.36 g), triphenylphosphine (6.06 g), and iodine (4.4 g), and the mixture was stirred at 100° C. for 1 hour and 45 minutes. The reaction mixture was cooled to room temperature, a saturated aqueous solution of sodium hydrogen carbonate was added thereto, stirred, then iodine was added thereto, stirred, and extracted with ethyl acetate. The resultant organic layer was dried, and concentrated under reduced pressure. The residue was purified with silica gel column chromatography (hexane:ethyl acetate=100:0-75:25) to give Compound 2 (3.23 g) as a colorless liquid.

(2) Under nitrogen atmosphere, to a suspension of zinc (292 mg) in N,N-dimethylacetamide (0.9 mL) was added 1,2-dibromoethane (0.04 mL), the mixture was stirred at 65° C. for 10 minutes, then trimethylsilyl chloride (0.09 mL) was added thereto, and stirred at room temperature 30 minutes. To the reaction mixture was added dropwise a solution of Compound 2 (1.04 g) in N,N-dimethylacetamide (1.8 mL), and stirred at room temperature for 1 hour. The insoluble matter was removed by filtration, and the filtrate was added dropwise to a suspension of Compound 3 (1 g), copper iodide (50 mg), and dichloro[1,1'-bis(diphenylphosphino)ferrocene]palladium(II) dichloromethane adduct (107 mg) in N,N-dimethylformacetamide (3.6 mL), and the mixture was stirred under nitrogen atmosphere at 85° C. for 15 hours. The insoluble matter was removed by filtration at room temperature, the filtrate was diluted with ethyl acetate, washed with water, an aqueous solution of sodium hydrogen carbonate, and saturated saline, then dried, and concentrated under reduced pressure. The residue was purified with silica gel column chromatography (hexane:ethyl acetate=100:0-50:50) to give Compound 4 (543 mg) as a yellow viscous material. MS (ESI): m/z 457 [M+H]+

(3) To a solution of Compound 4 (110 mg) in dichloromethane (2.4 mL) was added 2,6-dimethylpyridine (0.11 mL), the mixture was cooled to 0° C., trimethylsilyl triflate (0.13 mL) was added dropwise thereto, and stirred at the same temperature for 2 hours. The reaction mixture was diluted with dichloromethane, and then washed with a dilute aqueous solution of sodium hydrogen carbonate and saturated saline. The resultant organic layer was dried, and concentrated under reduced pressure to give a crude material of Compound 5 (96.9 mg) as a yellow viscous material. MS (ESI): m/z 357 [M+H]+

Reference Example 130

[Chemical Formula 145]

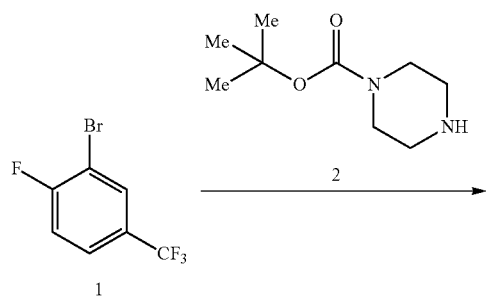

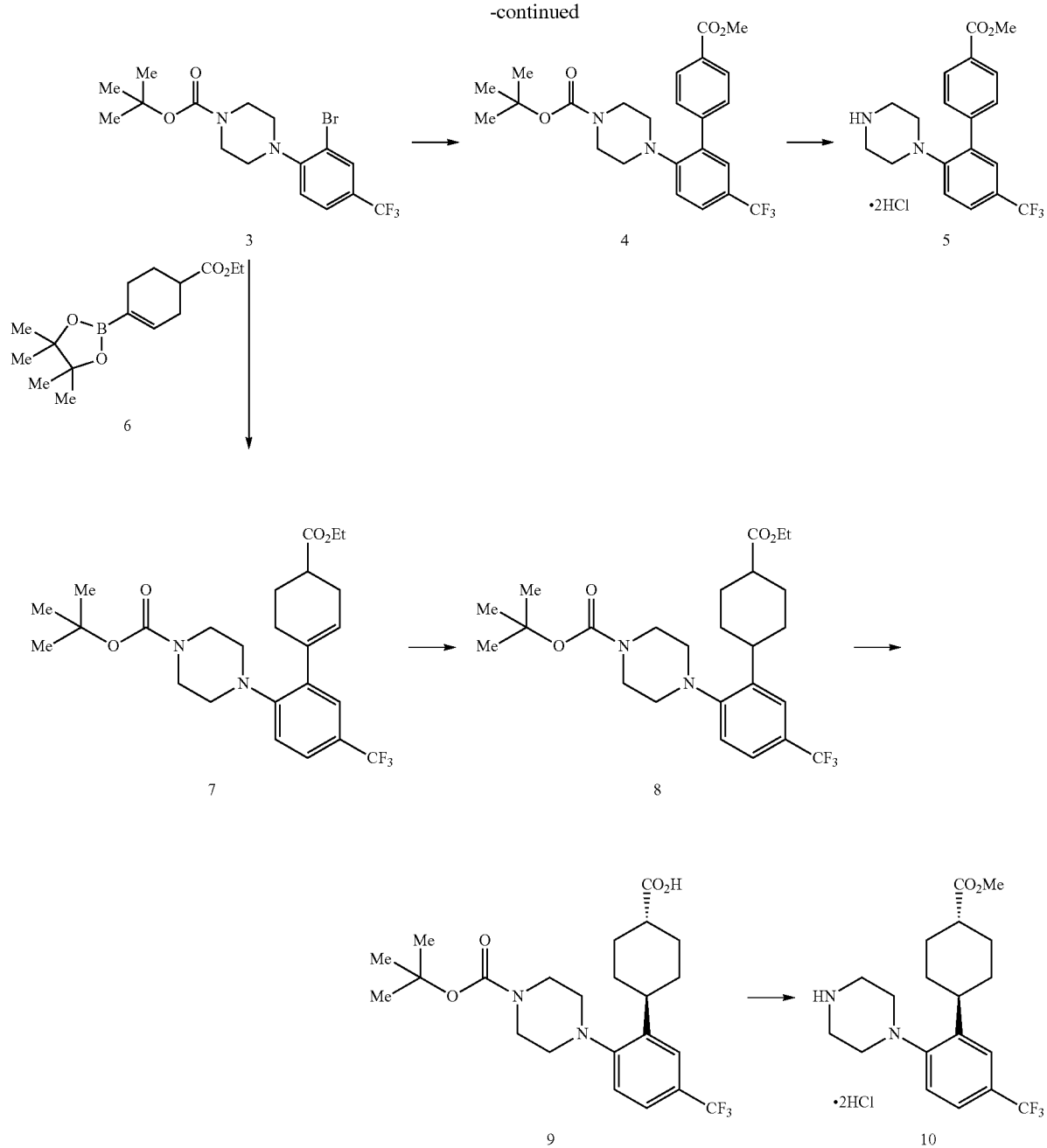

(1) A suspension of Compound 1 (5.52 g), potassium carbonate (6.28 g), and Compound 2 (4.65 g) in N-methylpyrrolidone (70 mL) was stirred at 190° C. for 3 hours, then di-t-butyl dicarbonate (4.96 g) was added thereto at room temperature, and stirred at the same temperature for 30 minutes. To the reaction mixture was added water, and then extracted with ethyl acetate. The resultant organic layer was washed with water and saturated saline, dried, and concentrated under reduced pressure. To the mixture was added hexane, stirred, the precipitate was removed by filtration, and then the filtrate was concentrated under reduced pressure. The residue was purified with silica gel column chromatography (hexane:ethyl acetate=100:0-90:10) to give Compound 3 (3.80 g) as a pale yellow viscous material.

MS (ESI): m/z 409/411 [M+H]+

(2) A suspension of Compound 3 (1.23 g), dichloro[1,1'-bis(diphenylphosphino)ferrocene]palladium(II) dichloromethane adduct (122 mg), an aqueous solution of sodium carbonate (2 mol/L, 4.5 mL), and 4-methoxycarbonylphenylboronic acid (649 mg) in N,N-dimethylformamide (30 mL) was stirred under nitrogen atmosphere at 80° C. for 1 hour. To the reaction mixture was added water at room temperature, and extracted with ethyl acetate. The resultant organic layer was washed with water, dried, and concentrated under reduced pressure. The residue was purified with silica gel column chromatography (hexane:ethyl acetate=100:0-80:20) to give Compound 4 (1.19 g) as a colorless powder. MS (ESI): m/z 465 [M+H]+

(3) To a solution of Compound 4 (1.16 g) in 1,4-dioxane (20 mL) was added a solution of hydrochloric acid in 1,4-dioxane (4 mol/L, 6.25 mL), and the mixture was stirred at room temperature for 15 hours. The reaction solution was concentrated under reduced pressure to give Compound 5 (1.09 g) as a colorless powder. MS (ESI): m/z 365 [M+H]+

(4) To a suspension of Compound 3 (1.5 g), Compound 6 (732 mg) obtained by the method described in WO2013/187496, and an aqueous solution of sodium carbonate (2 mol/L, 3.56 mL) in N,N-dimethylformamide (30 mL) was added dichloro[1,1'-bis(diphenylphosphino) ferrocene]palladium(II) dichloromethane adduct (122 mg) under nitrogen atmosphere, and the mixture was stirred at 80° C. for 3.5 hours. To the reaction mixture were added ethyl acetate and water at room temperature, stirred, and the insoluble matter was removed by filtration. The organic layer of the filtrate was separated, washed with saline, then dried, and concentrated under reduced pressure. The residue was purified with silica gel column chromatography (hexane:ethyl acetate=90:10-75:25) to give racemic Compound 7 (1.15 g) as a pale yellow viscous material.

MS (APCI): m/z 483 [M+H]+

(5) To a solution of Compound 7 (1.0 g) in ethanol (20 mL) was added 10% palladium carbon (wetted with ca. 50% water, 200 mg), and the mixture was stirred under hydrogen atmosphere (1 atm) at room temperature for 6 hours. Palladium carbon was removed by filtration, and then the filtrate was concentrated under reduced pressure to give Compound 8 (943 mg, cis:trans=2.1:1) as a colorless powder. MS (ESI): m/z 485 [M+H]+

(6) To a solution of Compound 8 (943 mg) in t-butanol (19 mL) was added potassium t-butoxy (240 mg), and the mixture was stirred at 35° C. for 2 hours. To the reaction mixture was added water (25 μL), stirred at the same temperature for 10 minutes, then water (25 μL) was added thereto, stirred for 5 hours, additional water (25 μL) was added thereto, and stirred at the same temperature for 1 hour. The reaction solution was concentrated under reduced pressure until the volume became half, then ethyl acetate and a saturated aqueous solution of ammonium chloride were added thereto, stirred, and then the organic layer was separated. The resultant organic layer was washed with saturated saline, dried, and concentrated under reduced pressure. The residue was powdered with hexane, collected by filtration, and then dried to give a trans compound, Compound 9 (747 mg) as a colorless powder. MS (APCI): m/z 457 [M+H]+

(7) A solution of Compound 9 (747 mg) in methanol (11 mL) was ice-cooled, thionyl chloride (597 mg) was added thereto, and the mixture was stirred at the same temperature for 1 hour and then at room temperature for 15 hours. The reaction solution was concentrated under reduced pressure, powdered with diisopropylether, collected by filtration, and then dried to give a trans compound, Compound 10 (702 mg) as a colorless powder. MS (APCI): m/z 371 [M+H]+

Reference Example 131

[Chemical Formula 146]

(1) To a solution of Compound 1 (3.0 g) in N-methylpyrrolidone (30 mL) were added Compound 2 (2.64 mL) and potassium carbonate (3.22 g), and the mixture was stirred at 130° C. for 2 hours. To the reaction mixture were added water and ethyl acetate at room temperature, stirred, and then extracted with ethyl acetate. The resultant organic layer was washed with saline, dried, and concentrated under reduced pressure. The residue was purified with silica gel column chromatography (hexane:ethyl acetate=95:5-85:15) to give Compound 3 (4.94 g) as a yellow viscous material. MS (ESI): m/z 330 [M+H]+

(2) To a solution of Compound 3 (600 mg) and a solution of methylamine in ethanol (33 wt %, 257 mg) in dichloromethane (10 mL) were added acetic acid (156 μL) and sodium triacetoxyborohydride (579 mg), and then the mixture was stirred at room temperature for 1 hour. To the reaction mixture was added an aqueous solution of sodium hydrogen carbonate, stirred, then extracted with dichloromethane, the organic layer was dried, and concentrated under reduced pressure. The residue was purified with NH silica gel column chromatography (hexane:ethyl acetate=80:20-50:50) to give Compound 4 (435 mg) as a pale pink viscous material. MS (ESI): m/z 345 [M+H]+

Reference Examples 132-133

A corresponding starting compound was treated in a similar manner to the above Reference Example 131 to give each compound in the following Table 43.

TABLE 43

| Reference Example | Compound | MS |
|---|---|---|
| 132 | 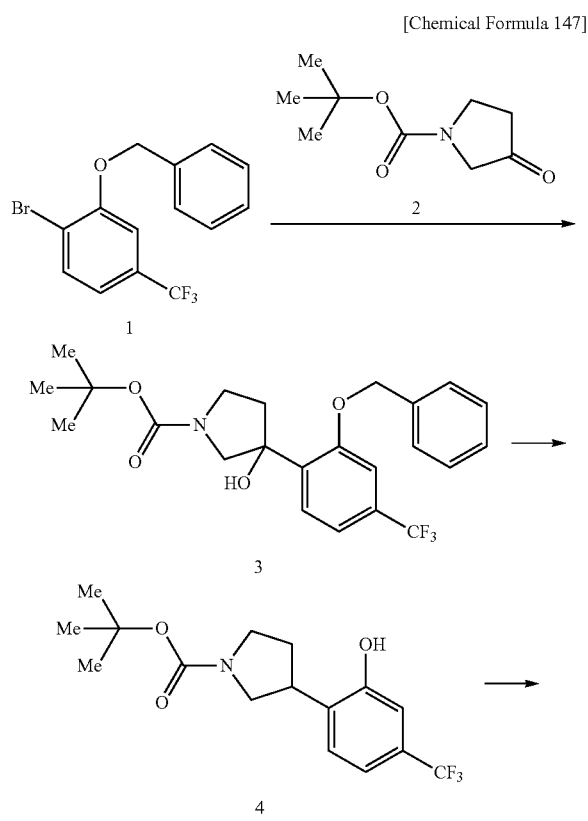 | (ESI): m/z 359 [M + H]+ |
| 133 | | (ESI): m/z 373 [M + H]+ |

Reference Example 134

[Chemical Formula 147]

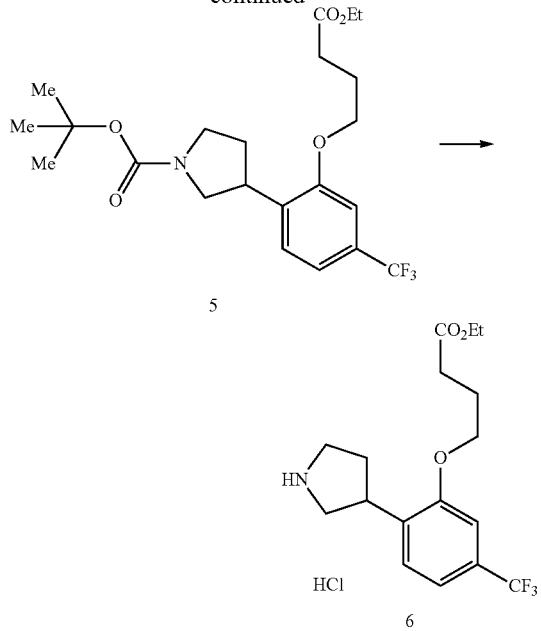

(1) A solution of Compound 1 (500 mg), which is an intermediate (Compound 2) of the above Reference Example 81, in tetrahydrofuran (10 mL) was cooled to −78° C., a solution of n-butyllithium in hexane (1.6 mol/L, 1.04 mL) was added dropwise thereto under nitrogen atmosphere, the mixture was stirred at the same temperature for 5 minutes, then Compound 2 (308 mg) was added thereto, stirred for 40 minutes, and stirred at room temperature for 15 hours. To the reaction mixture was added an aqueous solution of ammonium chloride, stirred, and extracted with ethyl acetate. The resultant organic layer was washed with saturated saline, dried, and concentrated under reduced pressure. The residue was purified with silica gel column chromatography (hexane:ethyl acetate=80:20-65:35) to give racemic Compound 3 (288 mg) as a pale yellow powder. MS (ESI): m/z 438 [M+H]+

(2) A solution of Compound 3 (100 mg) in dichloromethane (2 mL) was cooled to −30° C., triethylsilane (197 μL) and trifluoroacetic acid (289 μL) were added thereto, and stirred at the same temperature for 30 minutes and then at room temperature for 15 hours. To the reaction mixture was added a saturated aqueous solution of sodium hydrogen carbonate, stirred, then extracted with dichloromethane, the resultant organic layer was dried, and concentrated under reduced pressure. To the residue (73 mg) were added di-t-butyl dicarbonate (59 mg), triethylamine (63 μL), and tetrahydrofuran (1 mL), and the mixture was stirred at room temperature for 15 hours. The reaction solution was concentrated under reduced pressure, and the residue was purified with silica gel column chromatography (hexane:ethyl acetate=95: 5-82:18). To a solution of the resultant crude material (35 mg) in methanol (2.4 mL) was added 10% palladium carbon (wetted with ca. 50% water, 17.5 mg), and the mixture was stirred under hydrogen atmosphere (1 atm) at room temperature for 15 hours. Palladium carbon was removed by filtration, and the filtrate was concentrated under reduced pressure. The residue was powdered with hexane, collected by filtration, and then dried to give Compound 4 (21 mg) as a colorless powder.

(3) To a suspension of Compound 4 (21 mg) and potassium carbonate (17.5 mg) in N,N-dimethylformamide (0.80 mL) was added ethyl 4-bromobutyrate (10.9 μL), and the mixture was stirred at 70° C. for 15 hours. To the reaction mixture were added ethyl acetate and saline at room temperature, and the organic layer was separated. The resultant organic layer was washed with saline, dried, and the filtrate was concentrated under reduced pressure. The residue was purified with silica gel column chromatography (hexane:ethyl acetate=90: 10-75:25) to give Compound 5 (28 mg) as a colorless viscous material. MS (ESI): m/z 446 [M+H]+

(4) To a solution of Compound 5 (25 mg) in 1,4-dioxane (2 mL) was added a solution of hydrochloric acid in 1,4-dioxane (4 mol/L, 140 μL), and the mixture was stirred at room temperature for 15 hours. To the reaction mixture was added a solution of hydrochloric acid in 1,4-dioxane (4 mol/L, 840 μL), stirred at room temperature for 8 hours, and then concentrated under reduced pressure to give racemic Compound 6 (21 mg) as a purple viscous material. MS (ESI): m/z 346 [M+H]+

Reference Example 135

[Chemical Formula 148]

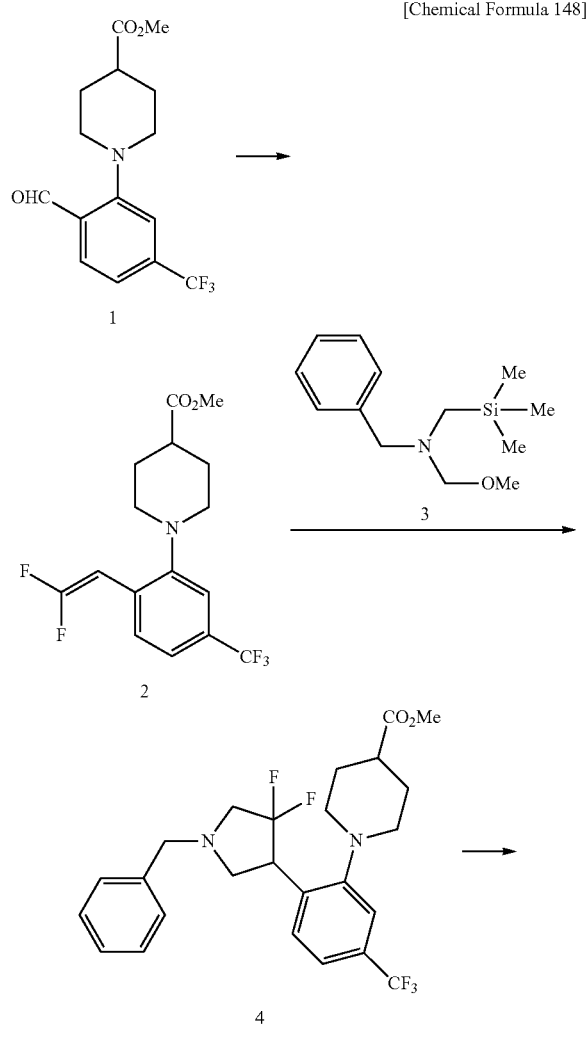

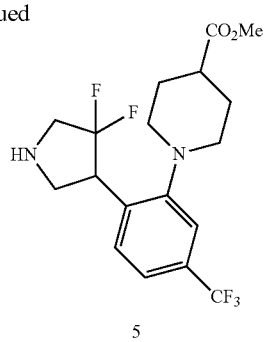

(1) To a solution of Compound 1 (315 mg), which is an intermediate (Compound 2) of Reference Example 101, in tetrahydrofuran (10 mL) were added dibromodifluoromethane (365 mg) and tris(dimethylamino)phosphine (727 μL) under ice-cooling, the mixture was stirred at the same temperature for 1 hour, then zinc (262 mg) was added thereto, and heated under reflux for 1 hours. To the reaction mixture was added water at room temperature, stirred, and extracted with ethyl acetate. The resultant organic layer was washed with water and saturated saline, dried, and concentrated under reduced pressure. The residue was purified with silica gel column chromatography (hexane:ethyl acetate=98: 2-85:15) to give Compound 2 (159 mg) as a pale yellow viscous material.

MS (ESI): m/z 350 [M+H]+

(2) To a solution of Compound 2 (105 mg) and Compound 3 (214 mg) in dichloromethane (2 mL) was added trifluoroacetic acid (4.5 μL), the mixture was heated under reflux for 16 hours, then Compound 3 (214 mg) and trifluoroacetic acid (4.5 μL) were added thereto, and heated under reflux for 2 hours. To the reaction mixture was added trifluoroacetic acid (9.0 μL), heated under reflux for 18 hours, then cooled to room temperature, and purified with silica gel column chromatography (hexane:ethyl acetate=98:2-88:12) to give racemic Compound 4 (86 mg) as a colorless viscous material. MS (ESI): m/z 483 [M+H]+

(3) To a solution of Compound 4 (266 mg) in methanol (4 mL) were added 10% palladium carbon (wetted with ca. 50% water, 80 mg) and acetic acid (5 mL), and the mixture was stirred under hydrogen atmosphere (1 atm) at room temperature for 2 hours. Palladium carbon was removed by filtration, and the filtrate was concentrated under reduced pressure. To the residue were added ethyl acetate and a saturated aqueous solution of sodium hydrogen carbonate, stirred, and then the mixture was extracted with ethyl acetate. The resultant organic layer was washed with saturated saline, dried, and concentrated under reduced pressure. The residue was purified with silica gel column chromatography (chloroform:methanol=100:0-93:7) to give racemic Compound 5 (184 mg) as a colorless viscous material. MS (ESI): m/z 393 [M+H]+

Reference Example 136

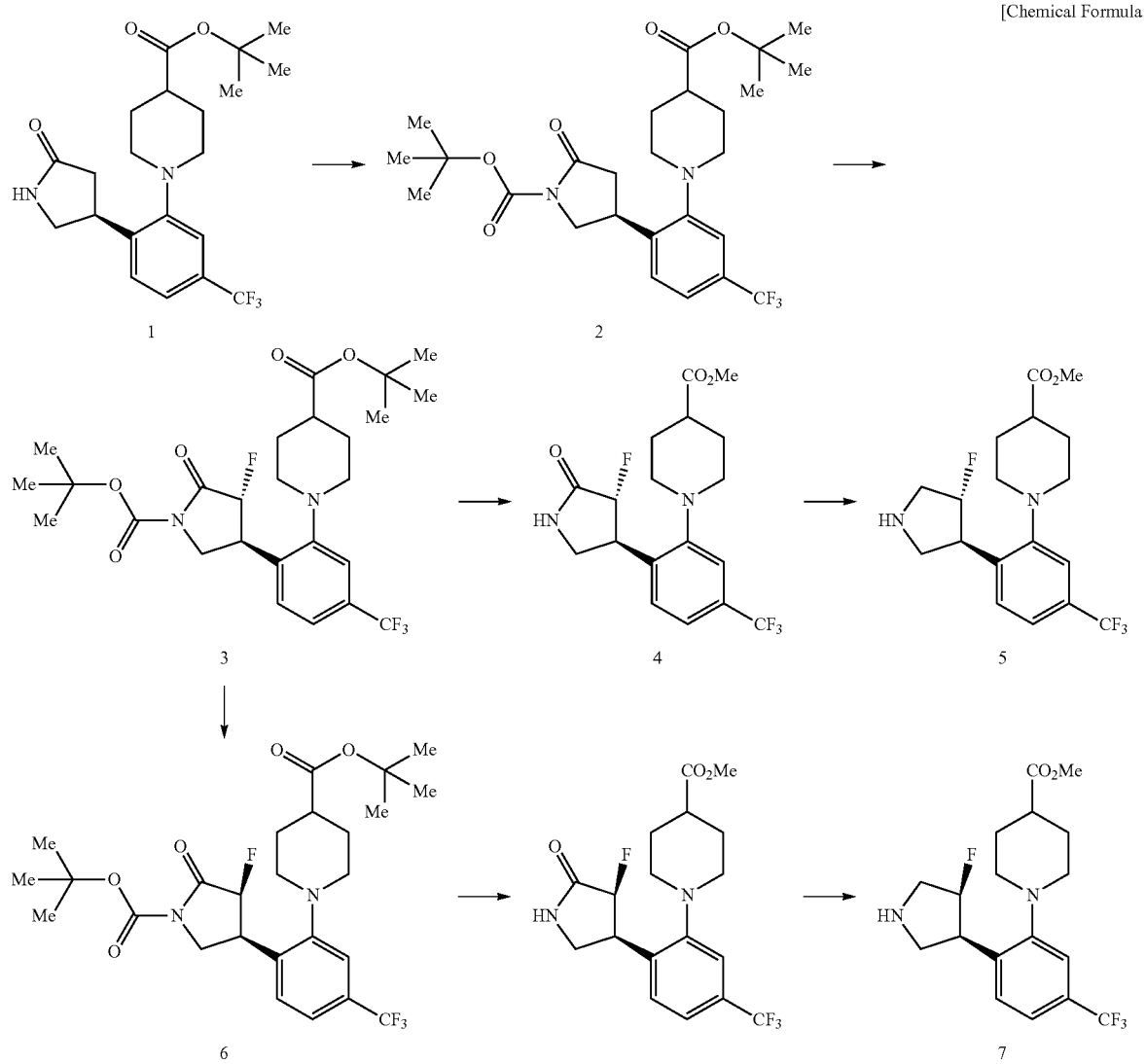

(1) A solution of Compound 1 (3.24 g), which is an intermediate (Compound 3) of Reference Example 116, di-t-butyl dicarbonate (2.06 g), and 4-dimethylaminopyridine (0.01 g) in acetonitrile (32.4 mL) was stirred at room temperature for 6 hours. To the reaction mixture was added water, and extracted with ethyl acetate. The resultant organic layer was washed with saturated saline, dried, and concentrated under reduced pressure. The residue was purified with silica gel column chromatography (hexane:ethyl acetate=95:5-80:20) to give Compound 2 (3.78 g) as a pale yellow powder. MS (APCI): m/z 530 [M+NH$_4$]+

(2) A solution of Compound 2 (3.34 g) in tetrahydrofuran (25 mL) was cooled to −78° C., then a solution of lithium bis(trimethylsilyl)amide in tetrahydrofuran (1.09 mol/L, 6.28 mL) was added dropwise thereto under nitrogen atmosphere, the mixture was stirred at the same temperature for 1 hour, then a solution of N-fluorobenzenesulfonimide (4.11 g) in tetrahydrofuran (8 mL) was added dropwise thereto, and stirred at the same temperature for 6 hours. To the reaction mixture was added an aqueous solution of ammonium chloride, stirred, and then extracted with ethyl acetate. The resultant organic layer was washed with saturated saline, dried, and concentrated under reduced pressure. To the residue was added ethyl acetate, the mixture was stirred, then the insoluble matter was removed by filtration, and the filtrate was concentrated under reduced pressure. The residue was purified with silica gel column chromatography (hexane:ethyl acetate=95:5-85:15) to give Compound 3 (2.08 g) as a colorless powder. MS (APCI): m/z 548 [M+NH4]+

(3) To a solution of Compound 3 (1.0 g) in methanol (10 mL) was added a solution of hydrochloric acid in methanol (2 mol/L, 10 mL), and the mixture was stirred at 50° C. for 16 hours. The reaction mixture was cooled to room temperature, then chloroform and a saturated aqueous solution of sodium hydrogen carbonate were added thereto, and the organic layer was separated. The resultant organic layer was washed with saturated saline, dried, and concentrated under reduced pressure to give Compound 4 (711 g) as a pale yellow powder. MS (APCI): m/z 389 [M+H]+

(4) To a solution of Compound 4 (350 mg) in dichloromethane (7 mL) was added trimethyloxonium tetrafluoroborate (1.11 g), and the mixture was stirred at room temperature for 1.5 hours. The reaction solution was added dropwise to a solution of sodium cyanoborohydride (630 mg), which was cooled to 0° C., and acetic acid (717 μl) in methanol (7 mL), and the mixture was stirred at room temperature for 1 hour. To the reaction mixture was added a saturated aqueous solution of sodium hydrogen carbonate, stirred, and then extracted with chloroform. The resultant organic layer was dried, and concentrated under reduced pressure. The residue was purified with silica gel column chromatography (chloroform:methanol=100:0-94:6) to give Compound 5 (244 mg) as a colorless viscous material. MS (APCI): m/z 375 [M+H]+

(5) To a solution of Compound 3 (710 mg) in tetrahydrofuran (10 mL) was added dropwise a solution of lithium bis(trimethylsilyl)amide in tetrahydrofuran (1.09 mol/L, 1.29 mL) under nitrogen atmosphere at −78° C., the mixture was stirred at the same temperature for 1 hour, then a solution of 2,6-di-t-butylphenol (331 mg) in tetrahydrofuran (4 mL) was added dropwise thereto, and stirred at the same temperature for 4 hours. To the reaction mixture was added an aqueous solution of ammonium chloride, stirred, and then extracted with ethyl acetate. The resultant organic layer was washed with saturated saline, dried, and concentrated under reduced pressure. The residue was purified with silica gel column chromatography (hexane:ethyl acetate=95:5-85:15) to give Compound 6 (308 mg) as a colorless powder. MS (APCI): m/z 548 [M+NH4]+

(6) Compound 6 was treated in a similar manner to the above step (3) and (4) to give Compound 7 as a colorless viscous material. MS (APCI): m/z 375 [M+H]+

Reference Example 137

[Chemical Formula 150]

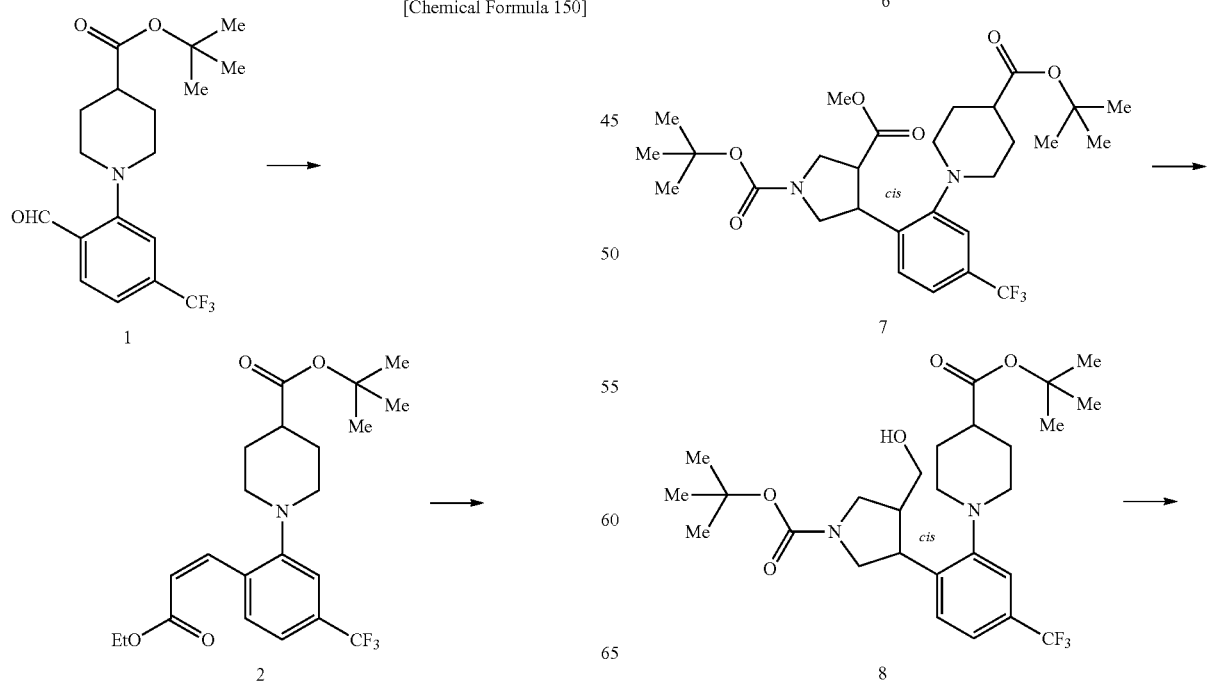

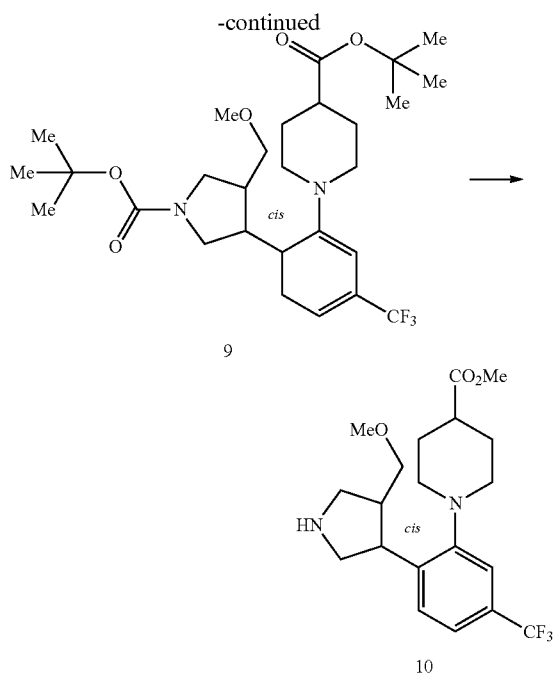

(1) To a solution of diphenylphosphonoacetic acid ethyl ester (3.05 g) in tetrahydrofuran (143 mL) was added sodium hydride (60% in oil, 381 mg) under ice-cooling, and the mixture was stirred under nitrogen atmosphere at the same temperature for 30 minutes. The reaction solution was cooled to −78° C., a solution of Compound 1 (3.40 g), which is an intermediate (Compound 2) of Reference Example 99, in tetrahydrofuran (48 mL) was added dropwise thereto, and the mixture was stirred at the same temperature for 3 hours. To the reaction mixture was added an aqueous solution of ammonium chloride, stirred at room temperature, and then extracted with ethyl acetate. The resultant organic layer was washed with water, a saturated aqueous solution of sodium hydrogen carbonate, and saturated saline, dried, and concentrated under reduced pressure. The residue was purified with NH silica gel column chromatography (hexane:ethyl acetate=98:2-90:10) to give Compound 2 (3.65 g) as a pale yellow powder. MS (ESI): m/z 428 [M+H]+

(2) To a solution of Compound 2 (3.64 g) in ethanol (30 mL) was added an aqueous solution of sodium hydroxide (2 mol/L, 4.69 mL), and the mixture was stirred at room temperature for 3 hours. The reaction solution was ice-cooled, an aqueous solution of hydrochloric acid (2 mol/L, 4.69 mL) was added thereto, the mixture was stirred, and then extracted with ethyl acetate. The resultant organic layer was washed with water and saturated saline, dried, and concentrated under reduced pressure. The residue was powdered with a mixed solvent of diisopropylether and hexane (mixture ratio=1:2), collected by filtration, and then dried to give Compound 3 (1.84 g) as a colorless powder. MS (ESI): m/z 400 [M+H]+

(3) To a solution of Compound 3 (300 mg) and potassium carbonate (207 mg) in N,N-dimethylformamide (2 mL) was added methyl iodide (70 μL) under ice-cooling, and then the mixture was stirred at room temperature for 2 hours. To the reaction mixture were added water and ethyl acetate, and the organic layer was separated. The resultant organic layer was washed with water and saturated saline, and concentrated under reduced pressure. The residue was purified with silica gel column chromatography (hexane:ethyl acetate=99:1-91:9) to give Compound 4 (294 mg) as a pale yellow viscous material.
MS (ESI): m/z 414 [M+H]+

(4) To a solution of Compound 4 (288 mg) and Compound 5 (499 mg) in dichloromethane (3 mL) was added trifluoroacetic acid (5.4 μL) under ice-cooling, the mixture was stirred at room temperature for 2 hours, then Compound 5 (499 mg) and trifluoroacetic acid (10.8 μL) was added thereto, and stirred at room temperature for additional 1 hour. To the reaction mixture was added a saturated aqueous solution of sodium hydrogen carbonate, stirred, and then extracted with chloroform. The organic layer was washed with saturated saline, dried, and concentrated under reduced pressure. The resultant residue was purified with silica gel column chromatography (hexane:ethyl acetate=95:5-75:25) to give cis compounds (racemates), Compound 6 (335 mg, 61%) as a colorless viscous material. MS (ESI): m/z 547 [M+H]+

(5) To a solution of Compound 6 (330 mg) and di-t-butyl dicarbonate (137 mg) in methanol (5 mL)/tetrahydrofuran (5 mL) was added 10% palladium carbon (wetted with ca. 50% water, 99 mg), and the mixture was stirred under hydrogen atmosphere (1 atm) at room temperature for 5 hours. Palladium carbon was removed by filtration, and then the filtrate was concentrated under reduced pressure. The residue was purified with silica gel column chromatography (hexane:ethyl acetate=95:5-70:30) to give Compound 7 (315 mg) as a colorless viscous material. MS (ESI): m/z 557 [M+H]+

(6) To a solution of Compound 7 (240 mg) in methanol (1 mL)/tetrahydrofuran (4 mL) was added lithium borohydride (37 mg) under ice-cooling, and the mixture was stirred at the same temperature for 2 hours. To the reaction mixture was added an aqueous solution of ammonium chloride, stirred, and then extracted with ethyl acetate. The resultant organic layer was dried, and concentrated under reduced pressure. The residue was purified with silica gel column chromatography (hexane:ethyl acetate=85:15-60:40) to give Compound 8 (187 mg) as a colorless viscous material. MS (ESI): m/z 529 [M+H]+

(7) To a solution of Compound 8 (210 mg) and methyl iodide (212 μL) in N,N-dimethylformamide (4 mL) was added sodium hydride (60% in oil, 19 mg) under ice-cooling, and the mixture was stirred at the same temperature for 3 hours. To the reaction mixture were added a saturated aqueous solution of ammonium chloride and water, stirred, and then extracted with ethyl acetate. The resultant organic layer was washed with water and saturated saline, and concentrated under reduced pressure. The residue was purified with silica gel column chromatography (hexane:ethyl acetate=95:5-80:20) to give Compound 9 (200 mg) as a colorless viscous material. MS (APCI): m/z 543 [M+H]+

(8) To a solution of Compound 9 (195 mg) in methanol (1 mL) was added a solution of hydrochloric acid in methanol (2 mol/L, 2.7 mL), and the mixture was stirred at 50° C. for 3 hours. To the reaction mixture was added a saturated aqueous solution of sodium hydrogen carbonate to alkalify it at room temperature, and extracted with chloroform. The resultant organic layer was dried, and concentrated under reduced pressure to give cis compounds (racemates), Compound 10 (133 mg) as a colorless viscous material. MS (ESI): m/z 401 [M+H]+

Reference Example 138

[Chemical Formula 151]

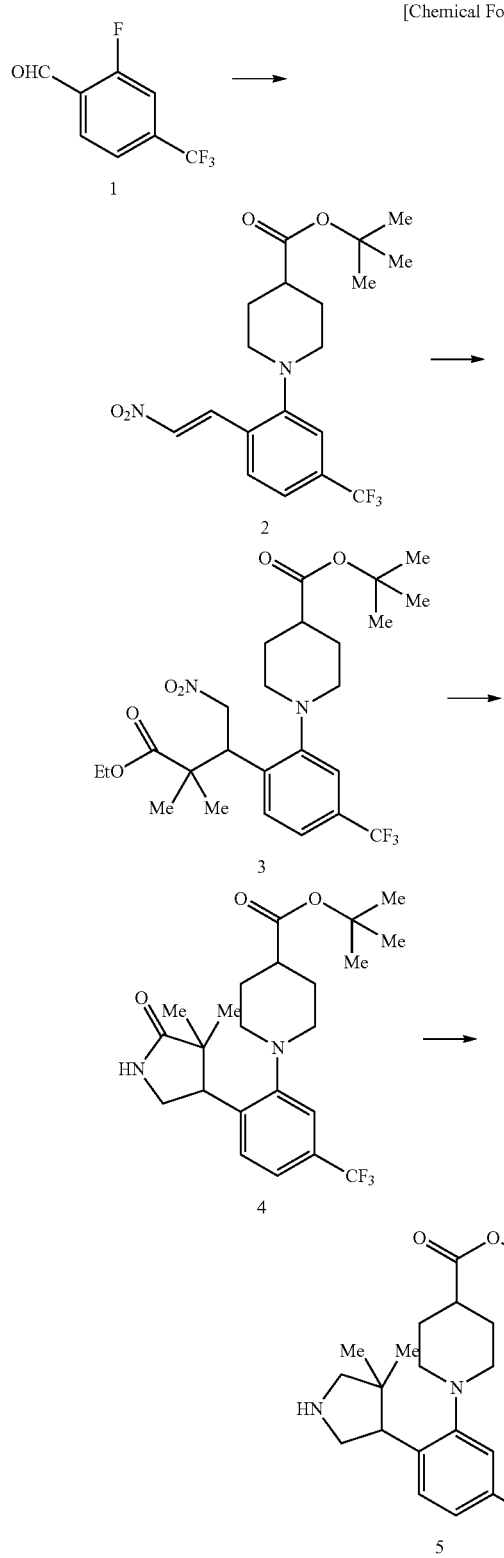

(1) Compound 1 was treated in a similar manner to Reference Example 112 to give Compound 2.

(2) Under nitrogen atmosphere, to tetrahydrofuran (1.1 mL) was added a solution of n-butyllithium in hexane (1.6 mol/L, 1.4 mL) at −78° C., then diisopropylamine (0.32 mL) was added dropwise thereto, and the mixture was stirred under ice-cooling for 10 minutes. To the reaction solution was added dropwise ethyl isobutyrate (0.28 mL) at −78° C., and the mixture was stirred at the same temperature for 30 minutes. To the reaction solution was added dropwise a solution of Compound 2 (750 mg) in tetrahydrofuran (2 mL), and the mixture was stirred at −78° C. to −40° C. for 1 hour. To the reaction mixture was added an aqueous solution of ammonium chloride under ice-cooling, stirred, and then extracted with ethyl acetate. The resultant organic layer was washed with saturated saline, dried, and concentrated under reduced pressure. The residue was purified with silica gel column chromatography (hexane:ethyl acetate=100:0-75:25) to give Compound 3 (816 mg) as a yellow viscous material. MS (ESI): m/z 517 [M+H]+

(3) A suspension of Compound 3 (1.23 g), ammonium formate (1.31 g), and 10% palladium carbon (wetted with ca. 50% water, 410 mg) in methanol (24 mL) was heated under microwave radiation at 120° C. for 15 minutes. The reaction mixture was cooled to room temperature, palladium carbon was removed by filtration, and then the filtrate was concentrated under reduced pressure. To the residue was added ethyl acetate, the insoluble matter was removed by filtration, and then the filtrate was concentrated under reduced pressure. The residue was purified with NH silica gel column chromatography (hexane:ethyl acetate=80:20-0:100) to give Compound 4 (428 mg) as a colorless powder (racemates). MS (ESI): m/z 441 [M+H]+

(4) A solution of Compound 4 (220 mg) and trimethyloxoniumtetrafluoroborate (148 mg) in dichloromethane (5 mL) was stirred at room temperature for 1.5 hours. The reaction solution was added dropwise to a solution, which was cooled to 0° C., of sodium cyanoborohydride (314 mg) and acetic acid (0.29 mL) in methanol (5 mL), and the mixture was stirred at the same temperature for 30 minutes and then at room temperature for 5 hours. The reaction solution was ice-cooled, a saturated aqueous solution of sodium hydrogen carbonate was added thereto, the mixture was stirred, and then extracted with chloroform. The resultant organic layer was washed with saturated saline, dried, and concentrated under reduced pressure. The residue was purified with NH silica gel column chromatography (chloroform:methanol=100:0-90:10) to give Compound 5 (85 mg) as a racemic colorless viscous material. MS (ESI): m/z 427 [M+H]+

Reference Example 139

[Chemical Formula 152]

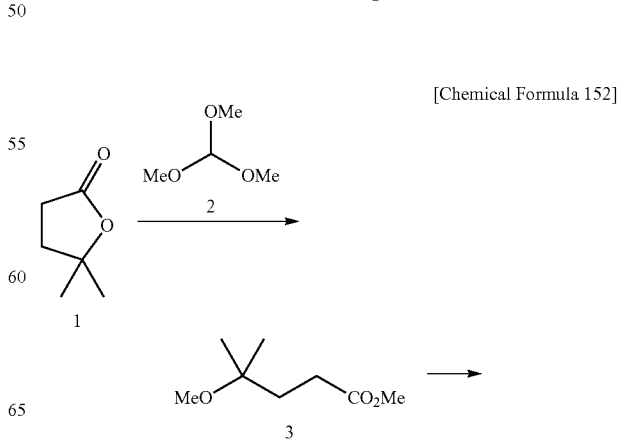

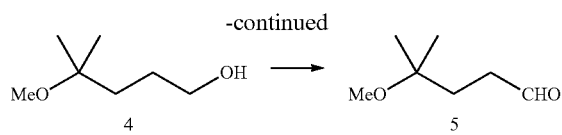

-continued (1) To a solution of Compound 1 (5.13 g) and Compound 2 (1.3 mL) in methanol (45 mL) was added dropwise concentrated sulfuric acid (350 μL), and the mixture was stirred at 50° C. for 2 hours. To the reaction mixture was added a saturated aqueous solution of sodium hydrogen carbonate to alkalify it at room temperature, chloroform was added thereto, and stirred. The organic layer was separated, then washed with saturated saline, dried, and concentrated under reduced pressure. The residue was purified with silica gel column chromatography (hexane:ethyl acetate=97:3-85:15) to give Compound 3 (6.2 g) as a pale yellow liquid.

(2) To a solution of Compound 3 (6.2 g) in methanol (60 mL) was added sodium borohydride (4.4 g) under ice-cooling, and then the mixture was stirred at room temperature for 5 hours. To the reaction mixture was added water, stirred, and then methanol was evaporated under reduced pressure at room temperature. To the resultant aqueous solution was added chloroform, the mixture was stirred, and then the organic layer was separated. The resultant organic layer was washed with saturated saline, dried, and evaporated under reduced pressure at room temperature. The residue was purified with silica gel column chromatography (chloroform:methanol=100:0-94:6) to give Compound 4 (3.65 g) as a colorless liquid. $^1$H-NMR (CDCl$_3$) δ 1.18 (s, 6H), 1.55-1.68 (m, 4H), 2.28 (t, J=5.4 Hz, 1H), 3.20 (s, 3H), 3.64 (td, J=5.7, 5.7 Hz, 2H)

(3) To a solution of dimethylsulfoxide (4.81 mL) in dichloromethane (40 mL) was added dropwise a solution of oxalyl chloride (2.91 mL) in dichloromethane (60 mL) at −78° C., the mixture was stirred for 2 minutes, then a solution of Compound 4 (3.64 g) and pyridine (4.97 mL) in dichloromethane (30 mL) was added dropwise thereto at the same temperature, and stirred for 15 minutes. To the reaction mixture was added dropwise a solution of triethylamine (21.5 mL) in dichloromethane (15 mL) at the same temperature, and then stirred under ice-cooling for 1 hour. To the reaction mixture was added an aqueous solution of hydrochloric acid (1 mol/L, 240 mL), stirred, and extracted with dichloromethane. The resultant organic layer was washed with saturated saline, dried, and evaporated under reduced pressure at room temperature. The residue was purified with silica gel column chromatography (hexane:ethyl acetate=95:5-75:25) to give Compound 5 (3.29 g) as a pale yellow liquid. $^1$H-NMR (CDCl$_3$) δ 1.16 (s, 6H), 1.82 (t, J=7.5 Hz, 2H), 2.49 (td, J=7.5, 1.5 Hz, 2H), 3.15 (s, 3H), 9.78 (t, J=1.8 Hz, 1H)

Reference Example 140

To a solution of Compound 1 (3.54 g) in tetrahydrofuran (50 mL) were added dropwise a solution of pyrrolidin (2.13 g) and triethylamine (1.9 mL) in tetrahydrofuran (20 mL) under ice-cooling under nitrogen atmosphere, and then the mixture was stirred at room temperature for 1 hour. The insoluble matter was removed by filtration, and then the filtrate was concentrated. The residue was purified with silica gel column chromatography (hexane:ethyl acetate=95:5-70:30) to give Compound 2 (3.99 g). MS (APCI): m/z 212/214 [M+H]+

Reference Example 141

[Chemical Formula 154]

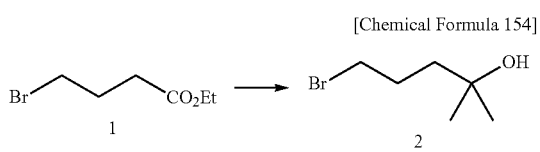

To a solution of Compound 1 (1 mL) in diethylether (60 mL) was added dropwise methylmagnesium bromide (0.99 mol/L, 15.6 mL) under nitrogen atmosphere at −15° C., then the mixture was warmed to room temperature, and stirred for 18 hours. To the reaction mixture were added sequentially a saturated aqueous solution of ammonium chloride and an aqueous solution of hydrochloric acid (1 mol/L, 10 mL), stirred, and then extracted with ethyl acetate. The resultant organic layer was washed with saturated saline, dried, and evaporated under reduced pressure at room temperature. The residue was partially purified with silica gel column chromatography (hexane:ethyl acetate=95:5-75:25) and the resultant compound 2 (853 mg) was used in the next step without purification.

Reference Example 142

A corresponding starting compound was treated in a similar manner to the above Reference Example 1 to give the compound in the following Table 44.

TABLE 44

| Reference Example | Compound | MS |
|---|---|---|
| 142 | ![structure] | (ESI): m/z 334 [M − H]− |

Reference Example 143

[Chemical Formula 153]

[Chemical Formula 155]

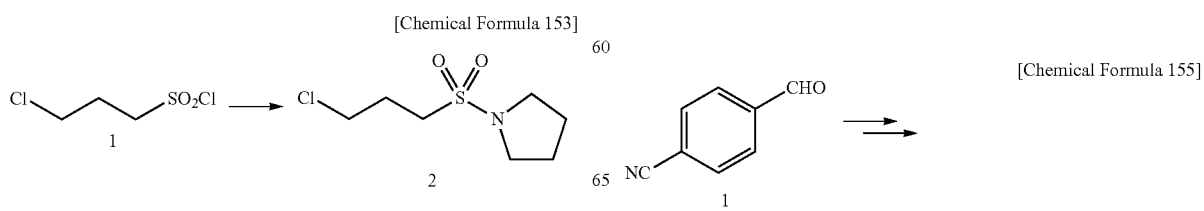

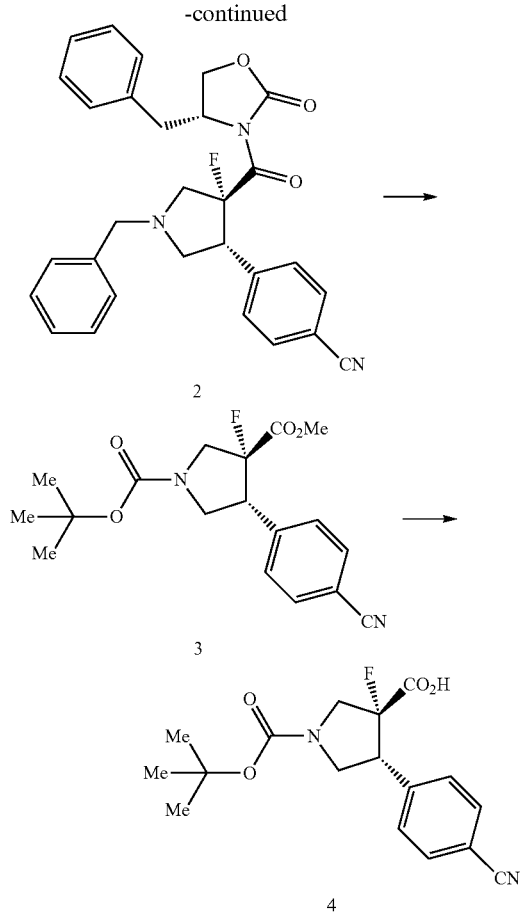

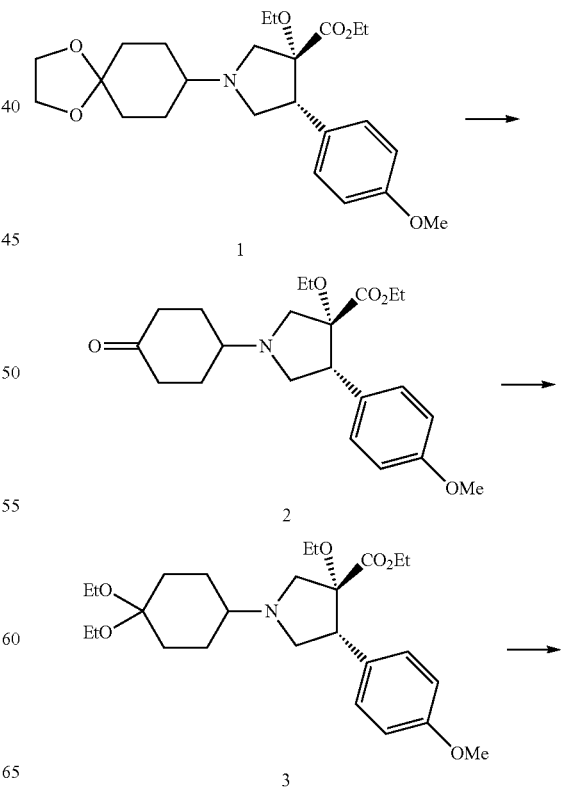

(1) Compound 1 was treated in a similar manner to Reference Example 1 to give Compound 2 (1240 mg) as a pale yellow powder. MS (APCI): m/z 484 [M+H]+

(2) To a solution of Compound 2 (620 mg) in dichloromethane (6.2 mL) was added 1-chloroethyl chloroformate (550 mg), the mixture was stirred under heat reflux for 2 hours, then diisopropylethylamine (998 µL) was added thereto, and stirred under heat reflux for additional 1 hour. The reaction mixture was allowed to cool to room temperature, then concentrated under reduced pressure, to the resultant residue was added methanol (6.2 mL), and stirred under heat reflux for 30 minutes. The reaction mixture was allowed to cool to room temperature, then di-t-butyl dicarbonate (336 mg) was added thereto, and stirred at room temperature for 1 hour. To the mixture were added di-t-butyl dicarbonate (672 mg) and diisopropylethylamine (998 µL), and stirred at room temperature for 15 hours. To the reaction mixture was added water, stirred, and then extracted with ethyl acetate. The resultant organic layer was washed with saturated saline, then dried, and concentrated under reduced pressure. The residue was purified with silica gel column chromatography (hexane:ethyl acetate-85:15-70:30) to give Compound 3 (374 mg) as an orange viscous material. MS (APCI): m/z 249 [M-Boc+H]+

(3) To a solution of Compound 3 (365 mg) in methanol (3.7 mL) was added an aqueous solution of sodium hydroxide (1.0 mol/L, 1.3 mL), and the mixture was stirred at room temperature for 30 minutes. The reaction mixture was ice-cooled, an aqueous solution of hydrochloric acid (1.0 mol/L, 1.3 mL) was added thereto, then ethyl acetate and water were added thereto, stirred, and extracted with ethyl acetate. The resultant organic layer was washed with saturated saline, dried, and concentrated under reduced pressure to give Compound 4 (331 mg) as a pale yellow powder. MS (APCI): m/z 333 [M−H]−

Reference Example 144

A corresponding starting compound was treated in a similar manner to the above Reference Example 33 to give the compound in the following Table 45.

TABLE 45

| Reference Example | Compound | MS |
|---|---|---|
| 144 | (structure with cyclopentyl-N-pyrrolidine bearing EtO, CO$_2$H, and 4-OMe-phenyl) | (APCI): m/z 334 [M + H]+ |

Reference Example 145

[Chemical Formula 156]

-continued

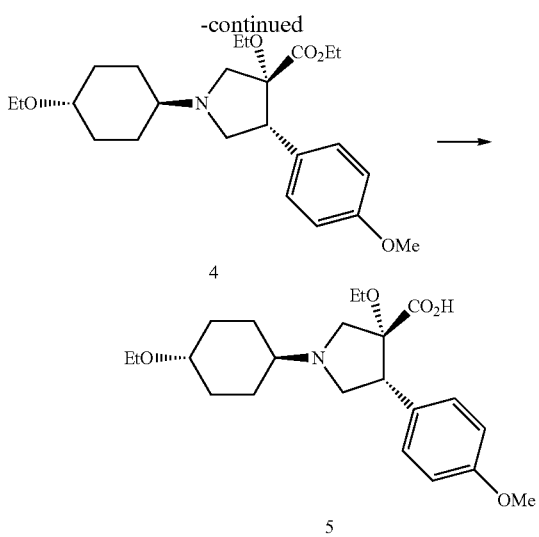

4

5

(1) To a solution of compound 1 (1.19 g), which was obtained by treating a corresponding starting compound in a similar manner to the above Reference Example 33, in tetrahydrofuran (11.9 mL) was added an aqueous solution of hydrochloric acid (1.0 mol/L, 11.9 mL), and the mixture was stirred at room temperature for 16 hours and 15 minutes and then at 40° C. for 3 hours and 45 minutes. The mixture was allowed to cool to room temperature, then to the reaction mixture was added an aqueous solution of sodium hydroxide (1.0 mol/L) to make it alkaline (pH 8), and extracted with ethyl acetate. The resultant organic layer was dried, and concentrated under reduced pressure. The residue was purified with silica gel column chromatography (chloroform:methanol=99:1-95:5) to give Compound 2 (757 mg) as a colorless liquid. MS (ESI): m/z 390 [M+H]+

(2) To a solution of Compound 2 (376 mg) in ethanol (3.76 mL) were added triethyl orthoformate (715 mg) and lithium borofluoride (109 mg), and the mixture was stirred at room temperature for 1.5 hours and then at 80° C. for 43 hours and 30 minutes. The reaction mixture was allowed to cool to room temperature, then a saturated aqueous solution of sodium hydrogen carbonate was added thereto, stirred, and extracted with ethyl acetate. The resultant organic layer was washed with saturated saline, dried, and concentrated under reduced pressure. The residue was purified with NH silica gel column chromatography (hexane:ethyl acetate=90:10-80:20) to give Compound 3 (430 mg) as a colorless liquid. MS (APCI): m/z 464 [M+H]+

(3) To a solution of Compound 3 (425 mg) in dichloromethane (4.3 mL) was added a solution of borane-tetrahydrofuran complex in tetrahydrofuran (1 mol/L, 1.0 mL) at −63° C., then trimethylsilyl trifluoromethanesulfonate (414 µL) was added thereto, and the mixture was stirred at the same temperature for 1.5 hours. To the reaction mixture was added ethanol (1 mL), then was added a saturated aqueous solution of sodium hydrogen carbonate under ice-cooling, stirred, and extracted with dichloromethane. The resultant organic layer was dried, and concentrated under reduced pressure. The residue was dissolved in methanol (8.5 mL), 10% palladium carbon (wetted with ca. 50% water, 98 mg) was added thereto, the mixture was stirred, then filtrated through Celite, and concentrated under reduced pressure. The residue was purified with silica gel column chromatography (hexane:ethyl acetate=85:15-60:40) to give Compound 4 (159 mg) as a colorless liquid. MS (ESI): m/z 420 [M+H]+

(4) To a solution of Compound 4 (425 mg) in ethanol (1.5 mL) was added an aqueous solution of sodium hydroxide (2.0 mol/L, 906 µL), and the mixture was stirred at room temperature for 30 minutes and at 60° C. for 1 hour. To the reaction mixture was added an aqueous solution of hydrochloric acid (1.0 mol/L) to neutralize it, and then concentrated under reduced pressure to give Compound 5 (246 mg) as a colorless solid containing sodium chloride. MS (ESI): m/z 392 [M+H]+

Reference Example 146

A corresponding starting compound was treated in a similar manner to the above Reference Example 145 to give the compound in the following Table 46.

TABLE 46

| Reference Example | Compound | MS |
| --- | --- | --- |
| 146 | ![structure] | (ESI): m/z 378 [M + H]+ |

Reference Example 147

[Chemical Formula 157]

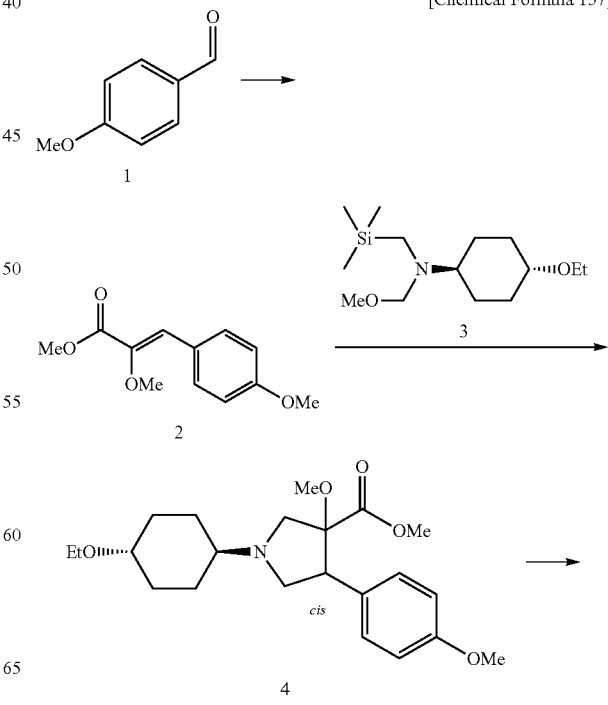

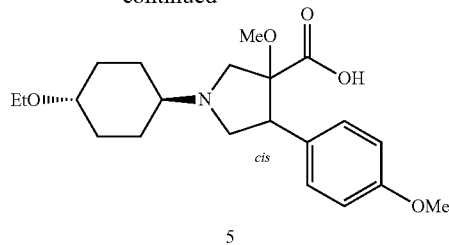

(1) Compound 1 was treated in a similar manner to a method described in a literature (Tetrahedron 1994, 50, 7543-7556) to give Compound 2 (47.6 g) as a colorless liquid. MS (APCI): m/z 223 [M+H]+

(2) A solution of Compound 3 (984 mg), which was prepared in a similar manner to a method described in a literature (J. Med. Chem. 1996, 39, 314-322, WO2007/006760, J. Med. Chem. 2013, 56, 10003-10015, WO2004/089307), in dichloromethane (6 mL) was added dropwise to a solution, which was heated to 45° C., of Compound 2 (400 mg) and trifluoroacetic acid (42 μL) in dichloromethane (6 mL), and the mixture was stirred at the same temperature for 3 hours. To an ice-cooled aqueous solution of citric acid (citric acid: 10 g+water: 100 mL) was poured the reaction solution, which was allowed to cool to room temperature, and extracted with dichloromethane. The resultant organic layer was washed with saturated sodium hydrogen carbonate, then dried, and concentrated under reduced pressure. The residue was purified with silica gel column chromatography (hexane:ethyl acetate=50:50-0:100) to give racemates (cis) of Compound 4 as a pale yellow liquid (522 mg). MS (APCI): m/z 392 [M+H]+

(3) To a solution of Compound 4 (520 mg) in ethanol (10 mL) was added an aqueous solution of sodium hydroxide (2 mol/L, 1328 μL), and the mixture was stirred at 70° C. for 20 hours. After being cooled to room temperature, to the reaction mixture was added an aqueous solution of hydrochloric acid (2 mol/L, 1328 μL), stirred, and concentrated under reduced pressure to give racemates (cis) of Compound 5 as a colorless powder (656 mg) containing sodium chloride. MS (APCI): m/z 378 [M+H]+

Reference Example 148

[Chemical Formula 158]

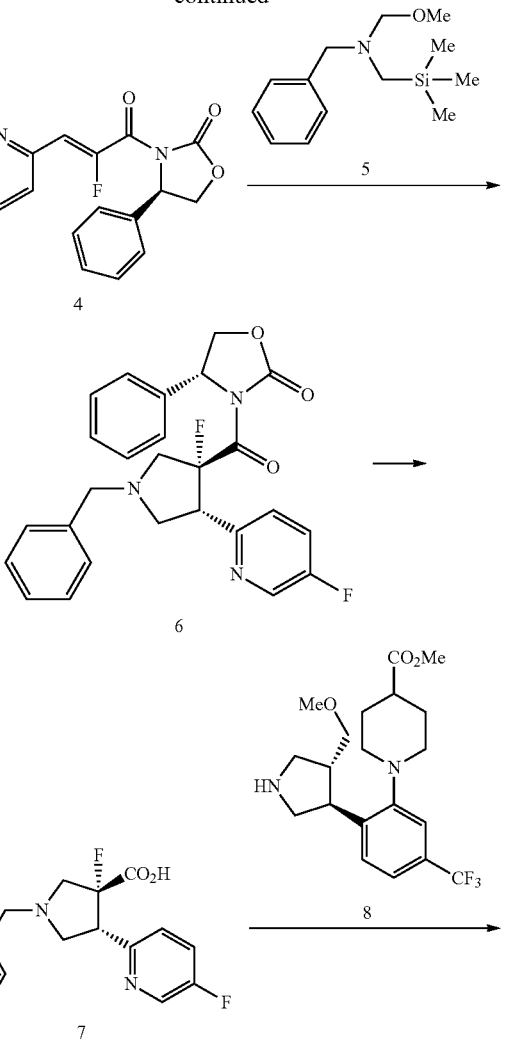

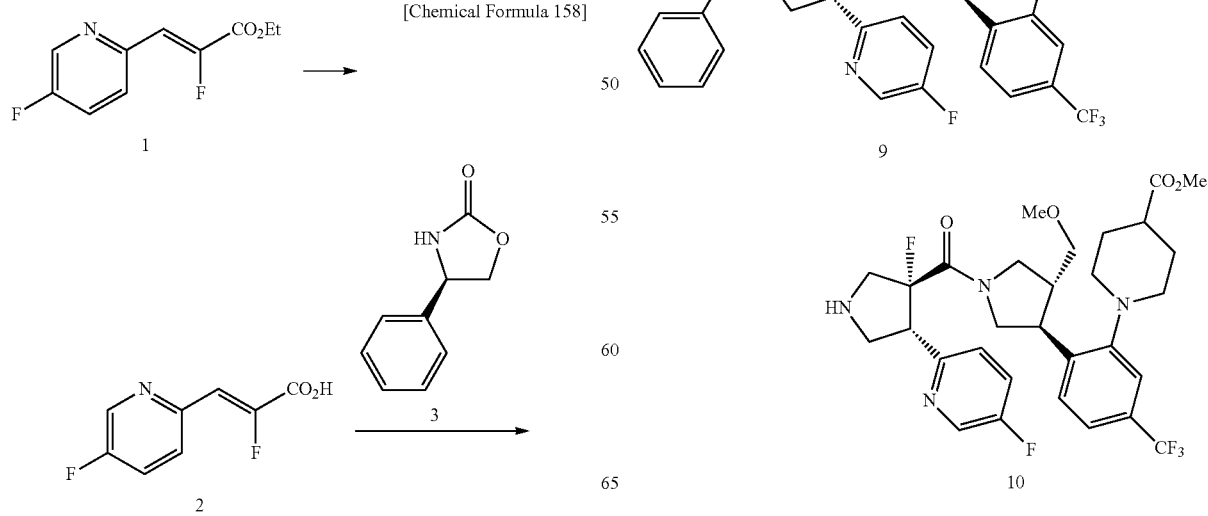

(1) Compound 1 (565 mg), which was prepared in a similar manner to a method described in a literature (Chemistry Letters 2008, 37, 809-810), was treated in a similar manner to Reference Example 1 to give Compound 2 (341 mg) as a colorless powder. MS (APCI): m/z 186 [M+H]+
(2) Compound 2 (320 mg) and Compound 3 (310 mg) were treated in a similar manner to Reference Example 1 to give Compound 4 (529 mg) as a gray powder. MS (APCI): m/z 331 [M+H]+
(3) Compound 4 (520 mg) and Compound 5 (1121 mg) were treated in a similar manner to Reference Example 1 to give Compound 6 (439 mg) as a pale yellow liquid. MS (APCI): m/z 464 [M+H]+
(4) Compound 6 (435 mg) was treated in a similar manner to Reference Example 49 to give Compound 7 as a colorless powder (307 mg) containing lithium chloride. MS (APCI): m/z 319 [M+H]+
(5) Compound 7 (75 mg) and Compound 8 (80 mg) were treated in a similar manner to Reference Example 49 to give Compound 9 (116 mg) as a colorless liquid. MS (APCI): m/z 701 [M+H]+
(6) Compound 9 (113 mg) was treated in a similar manner to Reference Example 49 to give Compound 10 (85 mg) as a colorless liquid. MS (APCI): m/z 611 [M+H]+

Reference Example 149

A corresponding starting compound was treated in a similar manner to the above Reference Example 45 to give the compound in the following Table 47.

TABLE 47

| Reference Example | Compound | MS |
|---|---|---|
| 149 | 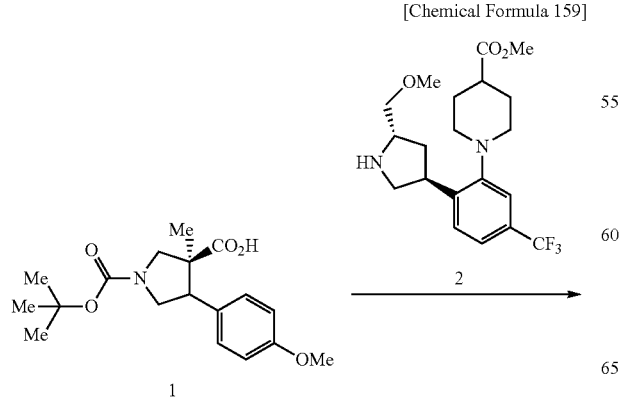 | (APCI): m/z 617 [M + H]+ |

Reference Example 150

[Chemical Formula 159]

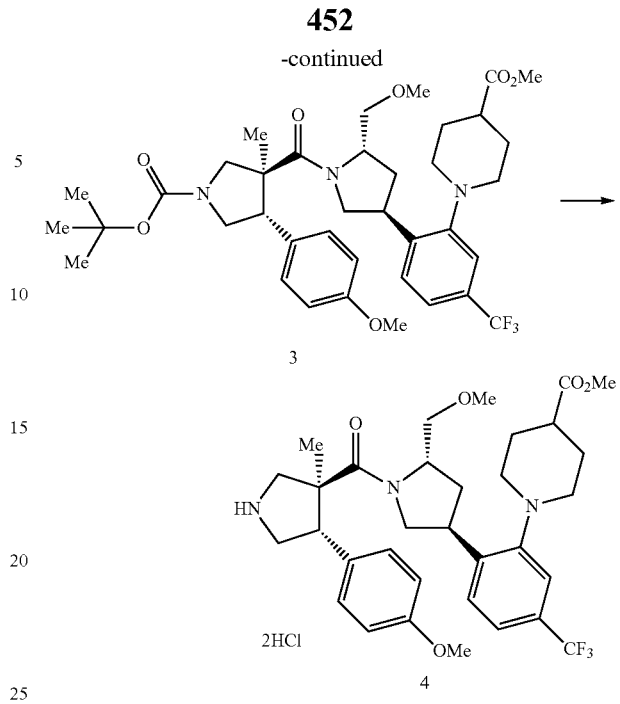

(1) Compound 1 (108 mg) and Compound 2 (142 mg) were treated in a similar manner to the above Reference Example 45 to give Compound 3 (129 mg) as a pale yellow viscous material. MS (ESI): m/z 718 [M+H]+
(2) A mixture of Compound 3 (129 mg) and a solution of hydrochloric acid in methanol (2 mol/L, 449 μL) was stirred at room temperature for 17 hours. The reaction mixture was concentrated under reduced pressure to give Compound 4 (117 mg) as a pale yellow powder. MS (ESI): m/z 0.618 [M+H]+

Reference Example 151

[Chemical Formula 160]

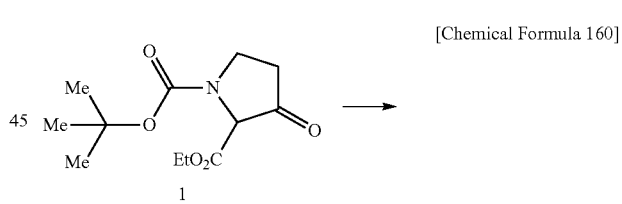

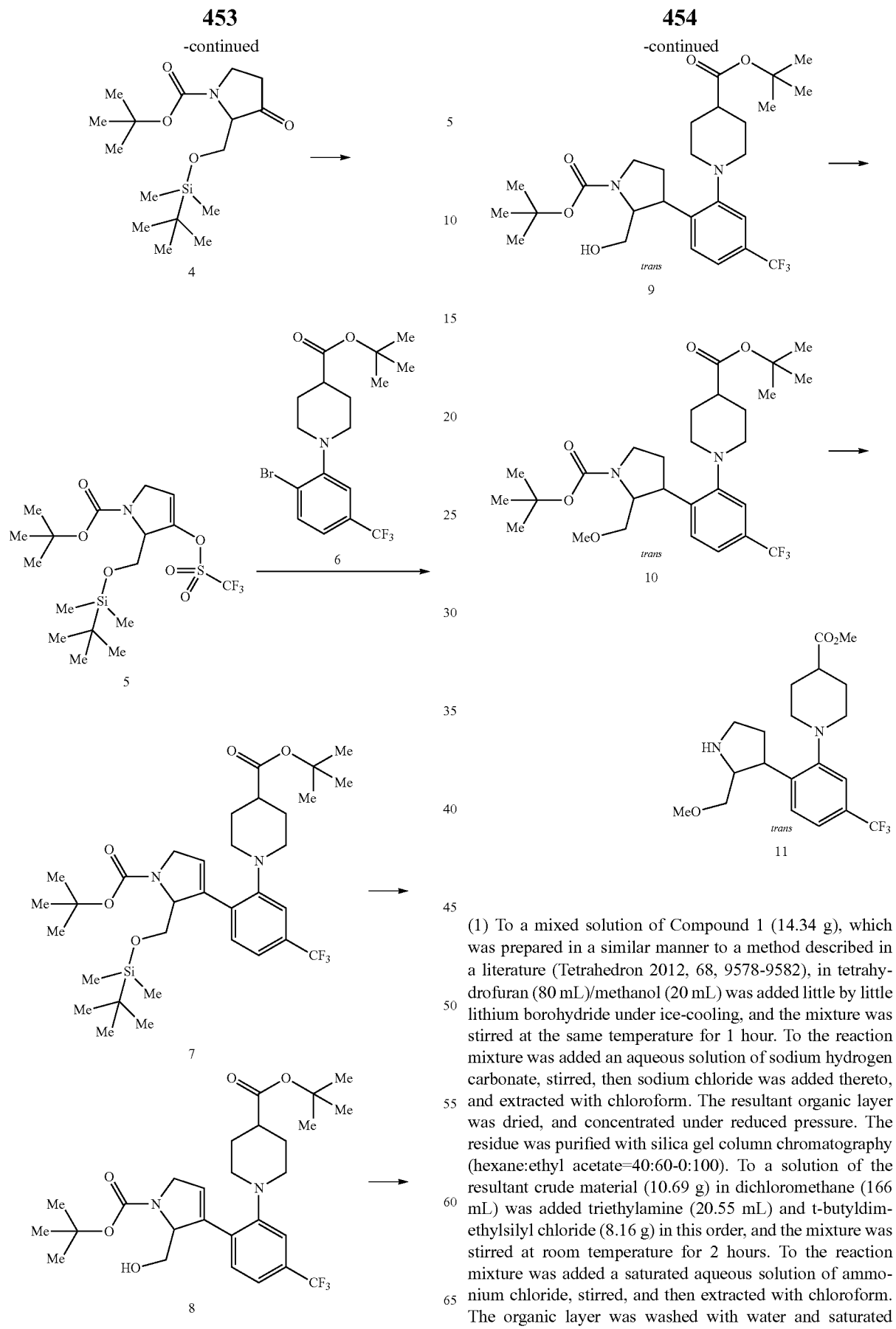

(1) To a mixed solution of Compound 1 (14.34 g), which was prepared in a similar manner to a method described in a literature (Tetrahedron 2012, 68, 9578-9582), in tetrahydrofuran (80 mL)/methanol (20 mL) was added little by little lithium borohydride under ice-cooling, and the mixture was stirred at the same temperature for 1 hour. To the reaction mixture was added an aqueous solution of sodium hydrogen carbonate, stirred, then sodium chloride was added thereto, and extracted with chloroform. The resultant organic layer was dried, and concentrated under reduced pressure. The residue was purified with silica gel column chromatography (hexane:ethyl acetate=40:60-0:100). To a solution of the resultant crude material (10.69 g) in dichloromethane (166 mL) was added triethylamine (20.55 mL) and t-butyldimethylsilyl chloride (8.16 g) in this order, and the mixture was stirred at room temperature for 2 hours. To the reaction mixture was added a saturated aqueous solution of ammonium chloride, stirred, and then extracted with chloroform. The organic layer was washed with water and saturated saline, dried, and concentrated under reduced pressure. The residue was purified with silica gel column chromatography (hexane:ethyl acetate=90:10-60:40) to give Compound 3 (13.24 g) as a colorless viscous material. MS (APCI): m/z 232 [M-Boc+H]+

(2) A solution of Compound 3 (13.24 g) in dichloromethane (201 mL) was ice-cooled, then trichloroisocyanuric acid (9.23 g) and 2,2,6,6-tetramethylpiperidine-1-oxyl (624 mg) were added thereto, and the mixture was stirred at the same temperature for 1 hour. To the reaction mixture was added a saturated aqueous solution of sodium hydrogen carbonate, stirred, and then extracted with chloroform. The resultant organic layer was washed with an aqueous solution of hydrochloric acid (0.5 mol/L), dried, and concentrated under reduced pressure. The residue was purified with silica gel column chromatography (hexane:ethyl acetate=97:3-85:15) to give Compound 4 as a racemic colorless liquid (13.22 g). MS (APCI): m/z 330 [M+H]+

(3) A solution of a solution of sodium bis(trimethylsilyl) amide in toluene (1.0 mol/L, 10 mL) in tetrahydrofuran (30 mL) was cooled to −78° C., a solution of Compound 4 (3.0 g) in tetrahydrofuran (6 mL) was added dropwise thereto, the mixture was stirred at the same temperature for 1 hour, then a solution of N-phenylbis(trifluoromethanesulfonimide) (4.89 g) in tetrahydrofuran (12 mL) was added dropwise thereto, and stirred at room temperature for 18 hours. To the reaction mixture was added a saturated aqueous solution of sodium hydrogen carbonate, stirred, and then extracted with ethyl acetate. The resultant organic layer was washed with saturated saline, dried, and then concentrated under reduced pressure. The residue was purified with silica gel column chromatography (hexane:ethyl acetate 100:0-95/5) and NH silica gel column chromatography (hexane:ethyl acetate 98:2-90/10) to give Compound 5 (3.57 g) as a colorless viscous material. MS (APCI): m/z 462 [M+H]+

(4) To a solution of Compound 5 (3.57 g) in 1,4-dioxane (36 mL) were added bis(pinacolato)diboron (2.36 g), dichloro[1,1'-bis(diphenylphosphino)ferrocene]palladium(II) dichloromethane adduct (318 mg), 1,1'-bis(diphenylphosphino)ferrocene (216 mg), and potassium acetate (2.28 g), and the mixture was stirred at 100° C. for 1 hour. The reaction mixture was allowed to cool to room temperature, Compound 6 (3.16 g) and an aqueous solution of sodium carbonate (2 mol/L, 11.6 mL) were added thereto, and stirred at 100° C. for 1.5 hours. The reaction mixture was allowed to cool to room temperature, water was added thereto, stirred, and then extracted with ethyl acetate. The resultant organic layer was washed with saturated saline, then dried, and concentrated under reduced pressure. The residue was purified with silica gel column chromatography (hexane:ethyl acetate=95:5-80:20) and NH silica gel column chromatography (hexane:ethyl acetate=95:5-80:20) to give Compound 7 (2.55 g) as a colorless powder. MS (APCI): m/z 641 [M+H]+

(5) To a solution of Compound 7 (2.54 g) in tetrahydrofuran (10 mL) was added a solution of tetrabutylammonium fluoride in tetrahydrofuran (1 mol/L, 4.36 mL), and the mixture was stirred at room temperature for 15 hours. To the reaction mixture was added a saturated aqueous solution of sodium hydrogen carbonate, stirred, and then extracted with ethyl acetate. The resultant organic layer was washed with saturated saline, then dried, and concentrated under reduced pressure. The residue was purified with silica gel column chromatography (hexane:ethyl acetate=80:20-60:40) and NH silica gel column chromatography (hexane:ethyl acetate=80:20-50:50) to give Compound 8 (2.01 g) as a colorless powder. MS (APCI): m/z 527 [M+H]+

(6) To a solution of Compound 8 (1.0 g) in dichloromethane (35 mL) was added Crabtree's catalyst (31 mg), and the mixture was stirred under hydrogen atmosphere (1 atm) at room temperature for 16 hours. The reaction mixture was concentrated under reduced pressure, and then the residue was purified with silica gel column chromatography (hexane:ethyl acetate=85:15-65:35) to give trans compounds (racemates), Compound 9 (518 mg) as a pale yellow powder. MS (APCI): m/z 529 [M+H]+

(7) To a solution of Compound 9 (511 mg) in tetrahydrofuran (5.1 mL) were added methyl iodide (604 µL) and sodium hydride (60% in oil, 46 mg) under ice-cooling, and the mixture was stirred at room temperature for 4 hours. To the reaction mixture was added water, stirred, and then extracted with ethyl acetate. The resultant organic layer was washed with saturated saline, then dried, and concentrated under reduced pressure. The residue was purified with silica gel column chromatography (hexane:ethyl acetate=95:5-80:20) to give trans compounds (racemates), Compound 10 (433 mg) as a pale yellow viscous material. MS (APCI): m/z 543 [M+H]+

(8) To Compound 10 (427 mg) was added a solution of hydrochloric acid in methanol (2 mol/L, 8.5 mL), and the mixture was stirred at 50° C. for 3 hours. The solvent was evaporated under reduced pressure, then the residue was diluted with chloroform, a saturated aqueous solution of sodium hydrogen carbonate was added thereto to alkalify the mixture, and extracted with chloroform. The resultant organic layer was dried, and concentrated under reduced pressure to give trans compounds (racemates), Compound 11 (329 mg) as a pale yellow viscous material.
MS (APCI): m/z 401 [M+H]+

Reference Example 152

A corresponding starting compound was treated in a similar manner to the above Reference Example 101 to give the compound in the following Table 48.

TABLE 48

| Reference Example | Compound | MS |
|---|---|---|
| 152 | 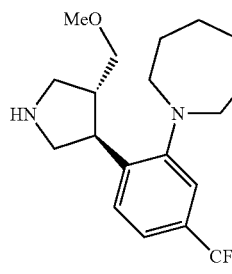<br>mixture of diastereomers | (APCI): m/z 429 [M + H]+ |

Reference Example 153

An intermediate of Reference Example 152 was prepared according to the following method.

[Chemical Formula 161]

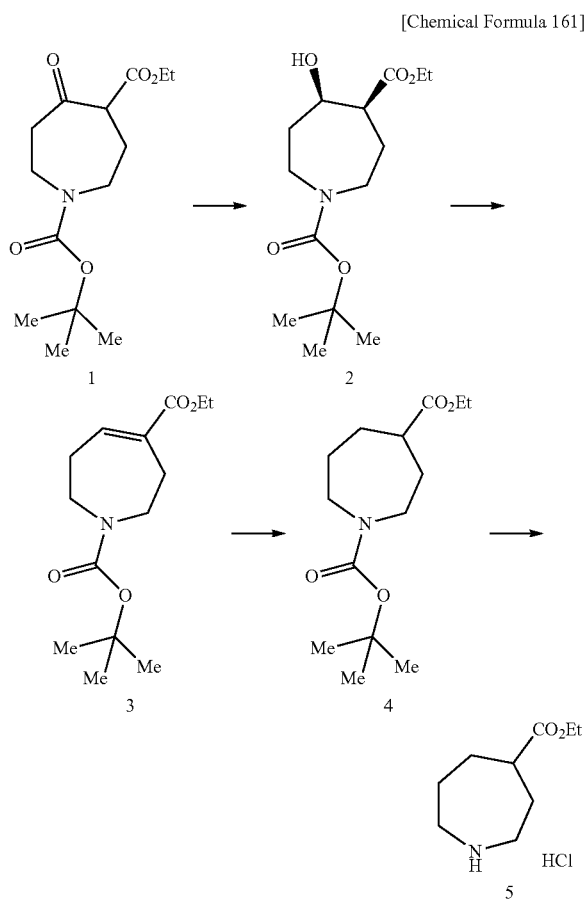

(1) A solution of Compound 1 (15 g) in ethanol (150 mL) was ice-cooled, sodium borohydride (2.0 g) was added thereto, and the mixture was stirred at the same temperature for 10 minutes and then at room temperature for 30 minutes. The reaction mixture was ice-cooled, an aqueous solution of hydrochloric acid (1.0 mol/L) was added thereto, stirred, and then concentrated under reduced pressure. The mixture was extracted with chloroform, dried, and concentrated under reduced pressure. The residue was purified with silica gel column chromatography (hexane:ethyl acetate=80:20-50:50) to give cis compounds (racemates), Compound 2 (6.44 g) as a colorless powder. MS (APCI): m/z 288 [M+H]+

(2) To a solution of Compound 2 (6.43 g) in tetrahydrofuran (130 mL) was added diisopropylethylamine, then added dropwise methanesulfonyl chloride (3.84 g) under ice-cooling, and the mixture was stirred at room temperature for 30 minutes. To the reaction mixture was added a saturated aqueous solution of sodium hydrogen carbonate, stirred, then extracted with ethyl acetate, dried, and concentrated under reduced pressure. To a solution of the residue in tetrahydrofuran (130 mL) was added 1,8-diazabicyclo[5.4.0]-7-undecene (5.0 mL), and the mixture was stirred at 70° C. for 30 minutes. The reaction mixture was concentrated under reduced pressure, then ethyl acetate and a saturated aqueous solution of sodium hydrogen carbonate were added thereto, stirred, and extracted with ethyl acetate. The resultant organic layer was washed with saturated saline, dried, and concentrated under reduced pressure. The residue was purified with silica gel column chromatography (hexane:ethyl acetate=95:5-80:20) to give Compound 3 (5.59 g) as a colorless liquid. MS (APCI): m/z 287 [M+NH4]+

(3) To a solution of Compound 3 (5.58 g) in ethanol (112 mL) was added 10% palladium carbon (wetted with ca. 50% water, 560 mg), and the mixture was stirred under hydrogen atmosphere (1 atm) at room temperature for 5 hours. Palladium carbon was removed by filtration, and then the filtrate was concentrated under reduced pressure to give racemic Compound 4 (5.37 g) as a colorless liquid. MS (APCI): m/z 272 [M+H]+

(4) To a solution of Compound 4 (5.36 g) in 1,4-dioxane (15 mL) was added a solution of hydrochloric acid in 1,4-dioxane (4 mol/L, 15 mL), and the mixture was stirred at room temperature for 23 hours. The reaction mixture was concentrated under reduced pressure, powdered with diethylether, collected by filtration, and dried under reduced pressure to give Compound 5 as a colorless powder. MS (APCI): m/z 172 [M+H]+

Reference Example 154

A corresponding starting compound was treated in a similar manner to the above Reference Example 115 to give the compound in the following Table 49.

TABLE 49

| Reference Example | Compound | MS |
|---|---|---|
| 154 | ![structure] | (APCI): m/z 395 [M + H]+ |

Reference Example 155

[Chemical Formula 162]

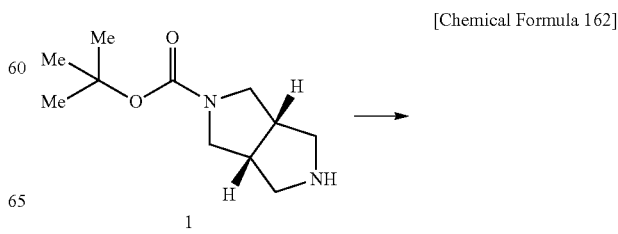

-continued

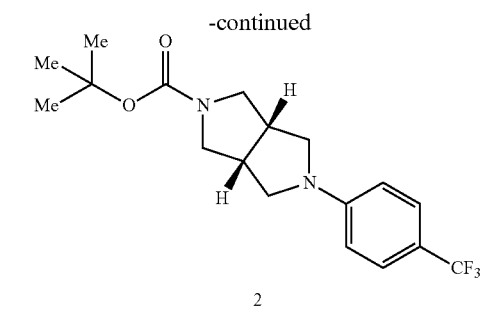

2

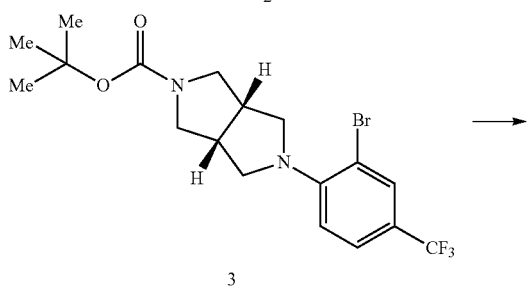

3

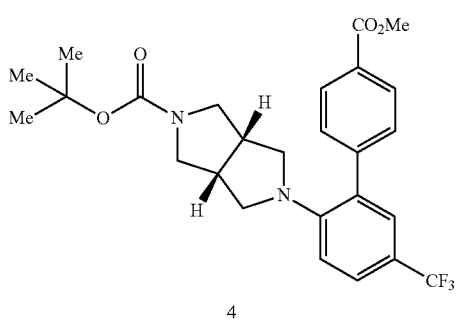

4

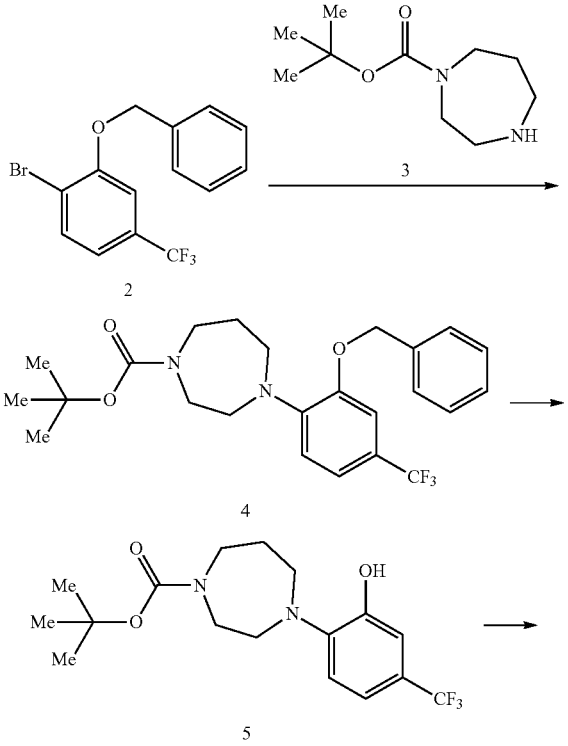

(2) To a solution of Compound 2 (376 mg) in chloroform (5 mL) was added N-bromosuccinimide (320 mg) under ice-cooling, and the mixture was stirred at room temperature for 14 hours. To the reaction mixture was added a saturated aqueous solution of sodium hydrogen carbonate, stirred, and then extracted with dichloromethane. The resultant organic layer was washed with saturated saline, dried, and concentrated under reduced pressure. The residue was purified with silica gel column chromatography (hexane:ethyl acetate=90:10-75:25) to give Compound 3 (663 mg) as a pale yellow liquid. MS (APCI): m/z 435/437 [M+H]+

(3) Compound 3 (660 mg) was treated in a similar manner to the above Reference Example 115 to give Compound 4 (602 mg) as a colorless powder. MS (APCI): m/z 491 [M+H]+

(4) Compound 4 (590 mg) was treated in a similar manner to the above Reference Example 115 to give Compound 5 (500 mg) as a pale yellow liquid. MS (APCI): m/z 391 [M+H]+

Reference Example 156

[Chemical Formula 163]

(1) To a suspension of 4-iodobenzotrifluoride (1015 mg), palladium(II) dibenzylideneacetone (67 mg), (±)-2,2'-bis(diphenylphosphino)-1,1'-binaphthyl (92 mg), and t-butoxy sodium (565 mg) in toluene (20 mL) was added Compound 1 (1000 mg), and the mixture was stirred at 85° C. for 6 hours. After being allowed to cool to room temperature, to the reaction mixture was added water, stirred, and extracted with ethyl acetate. The resultant organic layer was washed with saturated saline, then dried, and concentrated under reduced pressure. The residue was purified with silica gel column chromatography (hexane:ethyl acetate=90:10-70:30) to give Compound 2 (644 mg) as an orange liquid. MS (APCI): m/z 357 [M+H]+

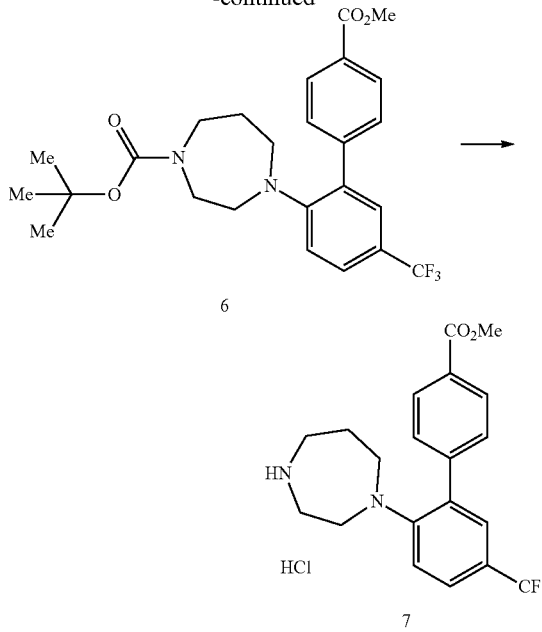

(1) A suspension of Compound 1 (5.0 g), benzyl bromide (2.96 (L), and potassium carbonate (4.3 g) in N,N-dimethylformamide (20.7 mL) was stirred at 80° C. for 90 minutes. The reaction mixture was allowed to cool to room temperature, and then a saturated aqueous solution of ammonium chloride was added thereto, stirred, and extracted with ethyl acetate. The resultant organic layer was washed with saturated saline, then dried, and concentrated under reduced pressure. The residue was purified with silica gel column chromatography (hexane:ethyl acetate=98:2) to give Compound 2 (6.34 g) as a colorless powder. MS (ESI): m/z 329/331 [M−H]−

(2) A solution of Compound 2 (1000 mg), Compound 3 (714 μL), tris(dibenzylideneacetone)dipalladium(0) (138 mg), (±)-2,2'-bis(diphenylphosphino)-1,1'-binaphthyl (188 mg), and t-butoxy sodium (581 mg) in toluene (10 mL) was stirred under nitrogen atmosphere at 100° C. for 15 hours. The reaction mixture was allowed to cool to room temperature, then filtrated by Celite, to the resultant filtrate was added a saturated aqueous solution of sodium hydrogen carbonate, stirred, and extracted with ethyl acetate. The resultant organic layer was washed with saturated saline, then dried, and concentrated under reduced pressure. The residue was purified with silica gel column chromatography (hexane:ethyl acetate=90:10-70:30) to give Compound-4 (1070 mg) as a colorless liquid. MS (ESI): m/z 451 [M+H]+

(3) To a solution of Compound 4 (1070 mg) in ethanol (7.9 mL) was added 10% palladium carbon (wetted with ca. 50% water, 214 mg), and the mixture was stirred under hydrogen atmosphere (1 atm) for 6.5 hours. Palladium carbon was removed by filtration, and then the filtrate was concentrated to give Compound 5 (798 mg) as a yellow viscous material. MS (ESI): m/z 361 [M+H]+

(4) A solution of Compound 5 (400 mg) and pyridine (449 μL) in dichloromethane (5.5 mL) was ice-cooled, trifluoromethanesulfonic anhydride (280 μL) was added thereto, and then the mixture was stirred at the same temperature for 1 hour. To the reaction mixture was added a saturated aqueous solution of sodium hydrogen carbonate, stirred, and then extracted with ethyl acetate. The organic layer was washed with a saturated aqueous solution of ammonium chloride and saturated saline, then dried, and concentrated under reduced pressure. The residue was purified with silica gel column chromatography (hexane:ethyl acetate=90:10-70:30). To a solution of the resultant compound (537 mg) in 1,4-dioxane (3.6 mL)/water (364 μL) was added 4-methoxycarbonylphenylboronic acid (294 mg), sodium carbonate (347 mg), and dichloro[1,1'-bis(diphenylphosphino)ferrocene]palladium(II) dichloromethane adduct (45 mg), and the mixture was stirred at 100° C. for 19.5 hours. The reaction mixture was allowed to cool to room temperature, ethyl acetate and a saturated aqueous solution of sodium hydrogen carbonate were added thereto, stirred, and then extracted with ethyl acetate. The resultant organic layer was washed with saturated saline, dried, and concentrated under reduced pressure. The residue was purified with silica gel column chromatography (hexane:ethyl acetate=90:10-70:30) to give Compound 6 (410 mg) as a colorless liquid. MS (ESI): m/z 479 [M+H]+

(5) A mixture of Compound 6 (101 mg) and a solution of hydrochloric acid in methanol (2 mol/L, 1.01 mL) was stirred at room temperature for 13.5 hours. The reaction mixture was concentrated under reduced pressure to give Compound 7 (88 mg) as a colorless powder. MS (ESI): m/z 379 [M+H]+

Reference Example 157

[Chemical Formula 164]

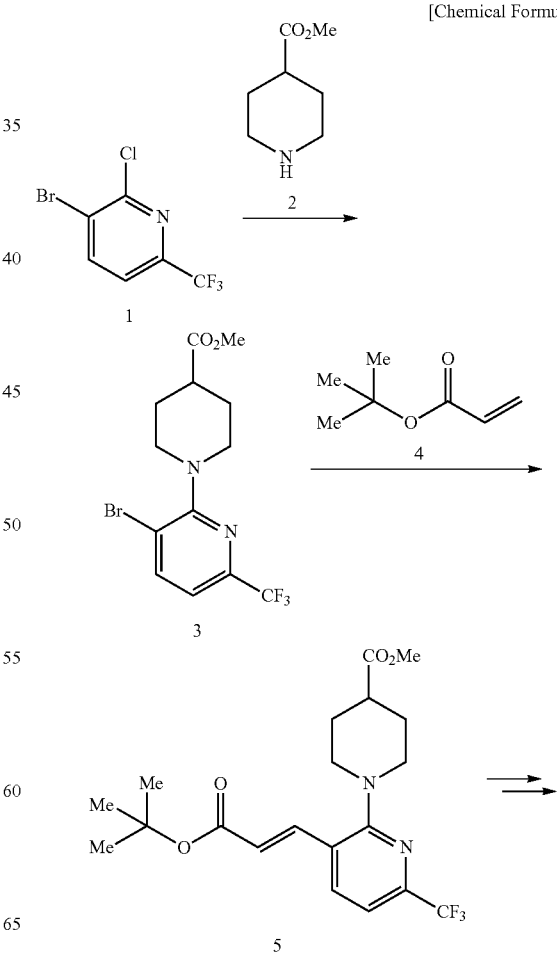

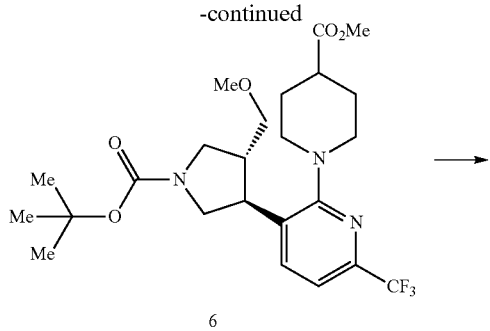

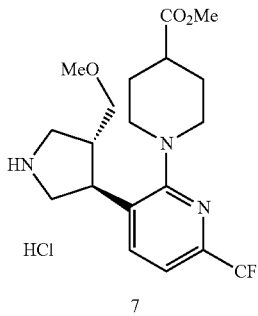

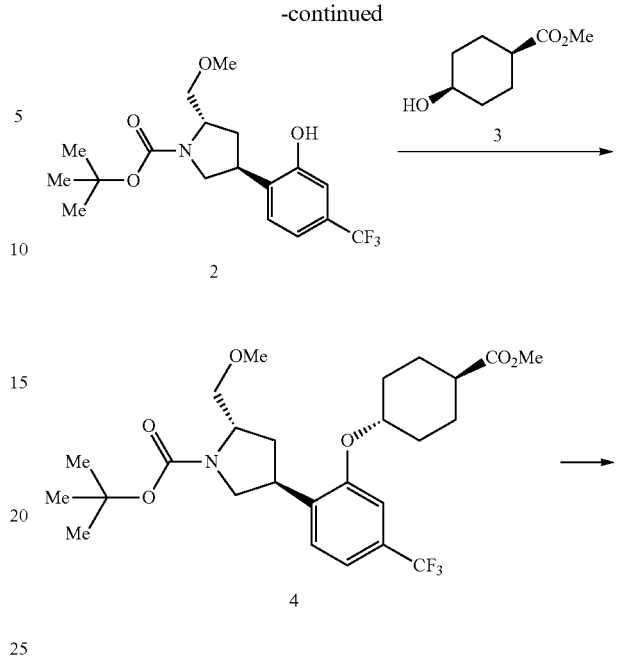

(1) A suspension of Compound 1 (2.0 g), Compound 2 (1.8 mL), and potassium carbonate (2.1 g) in acetonitrile (26 mL) was stirred at 60° C. for 17 hours. The reaction mixture was allowed to cool to room temperature, then water was added thereto, stirred, and extracted with ethyl acetate. The resultant organic layer was washed with saturated saline, then dried, and concentrated under reduced pressure. The residue was purified with silica gel column chromatography (hexane:ethyl acetate=90:10-70:30) to give Compound 3 (2.9 g) as a colorless liquid. MS (APCI): m/z 381/383 [M+H]+

(2) Compound 3 (2.9 g) and Compound 4 (3.3 mL) was treated in a similar manner to the above Reference Example 105 to give Compound 5 (2.8 g) as a yellow viscous material. MS (ESI): m/z 429 [M+H]+

(3) Compound 5 was treated in a similar manner to the above Reference Example 101 to give Compound 6 (48 mg) as a colorless viscous material. MS (ESI): m/z 502 [M+H]+

(4) A mixture of Compound 6 (48 mg) and a solution of hydrochloric acid in methanol (2 mol/L, 479 µL) was stirred at room temperature for 18 hours. The reaction mixture was concentrated under reduced pressure to give Compound 7 (45 mg) as a colorless viscous material. MS (ESI): m/z 402 [M+H]+

Reference Example 158

[Chemical Formula 165]

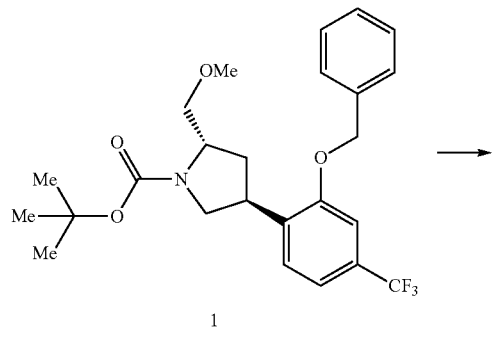

(1) A corresponding starting compound was treated in a similar manner to Reference Example 121 to give Compound 1 (1108 mg) as a colorless viscous material. MS (ESI): m/z 466 [M+H]+

(2) To a solution of Compound 1 (1070 mg) in ethanol (7.9 mL) was added 10% palladium carbon (wetted with ca. 50% water, 222 mg), and the mixture was stirred under hydrogen atmosphere (1 atm) for 3 hours. Palladium carbon was removed by filtration, and then the filtrate was concentrated to give Compound 2 (496 mg) as a colorless viscous material. MS (ESI): m/z 374 [M−H]−

(3) A solution of Compound 2 (200 mg), Compound 3 (126 mg), diisopropyl azodicarboxylate (309 µL), and triphenylphosphine (419 mg) in tetrahydrofuran (2.7 mL) was stirred at room temperature for 24 hours. The reaction mixture was diluted with ethyl acetate, washed with a saturated aqueous solution of sodium hydrogen carbonate and a saturated aqueous solution of ammonium chloride, then dried, and concentrated under reduced pressure. The residue was purified with silica gel column chromatography (hexane:ethyl acetate=90:10-70:30) to give Compound 4 (183 mg) as a colorless viscous material. MS (ESI): m/z 516 [M+H]+

(4) A mixture of Compound 4 (180 mg) and a solution of hydrochloric acid in methanol (2 mol/L, 873 µL) was stirred at room temperature for 6.5 hours. The reaction mixture was concentrated under reduced pressure to give Compound 5 (157 mg) as a colorless powder. MS (ESI): m/z 416 [M+H]+

Reference Example 159
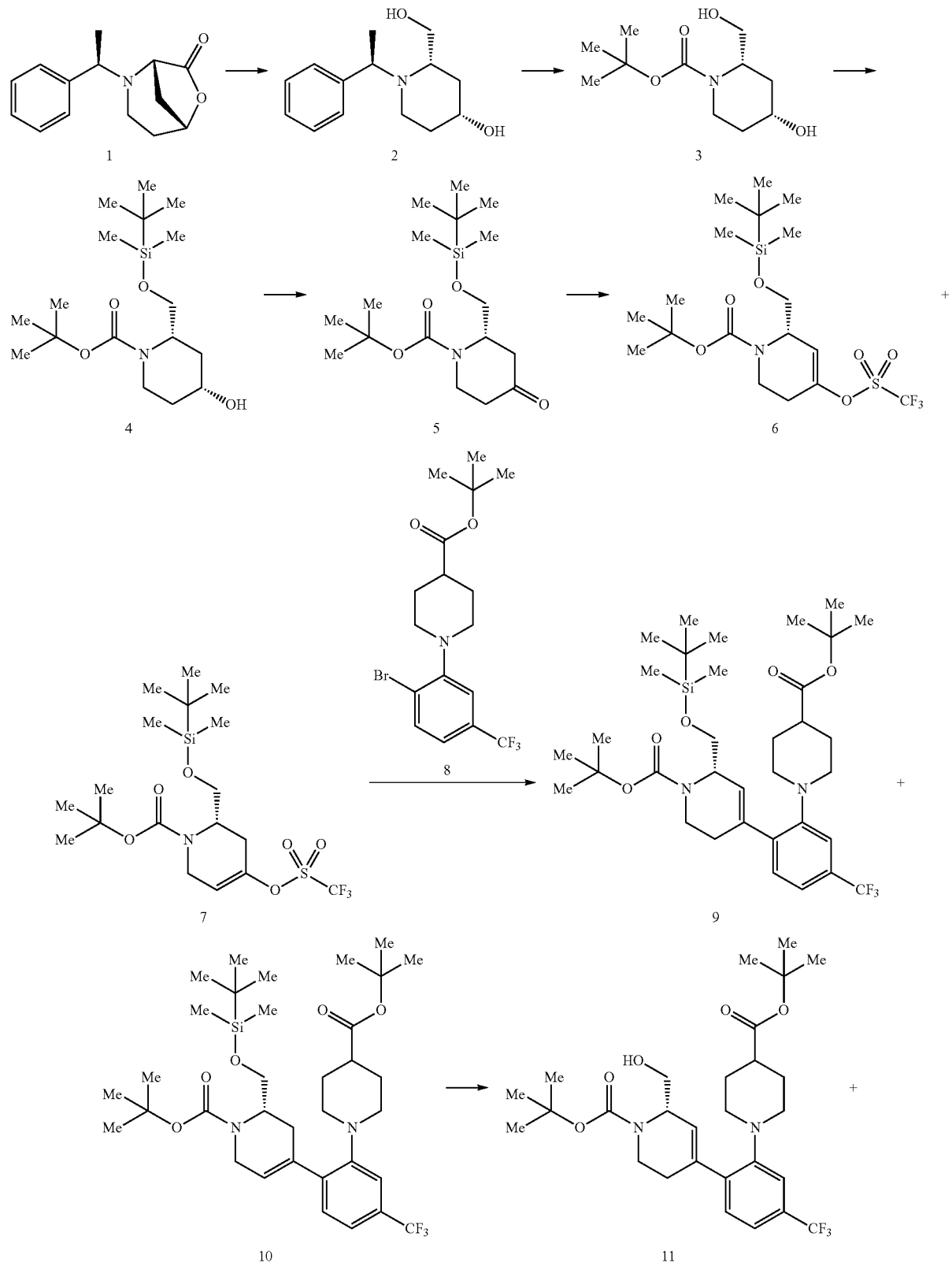

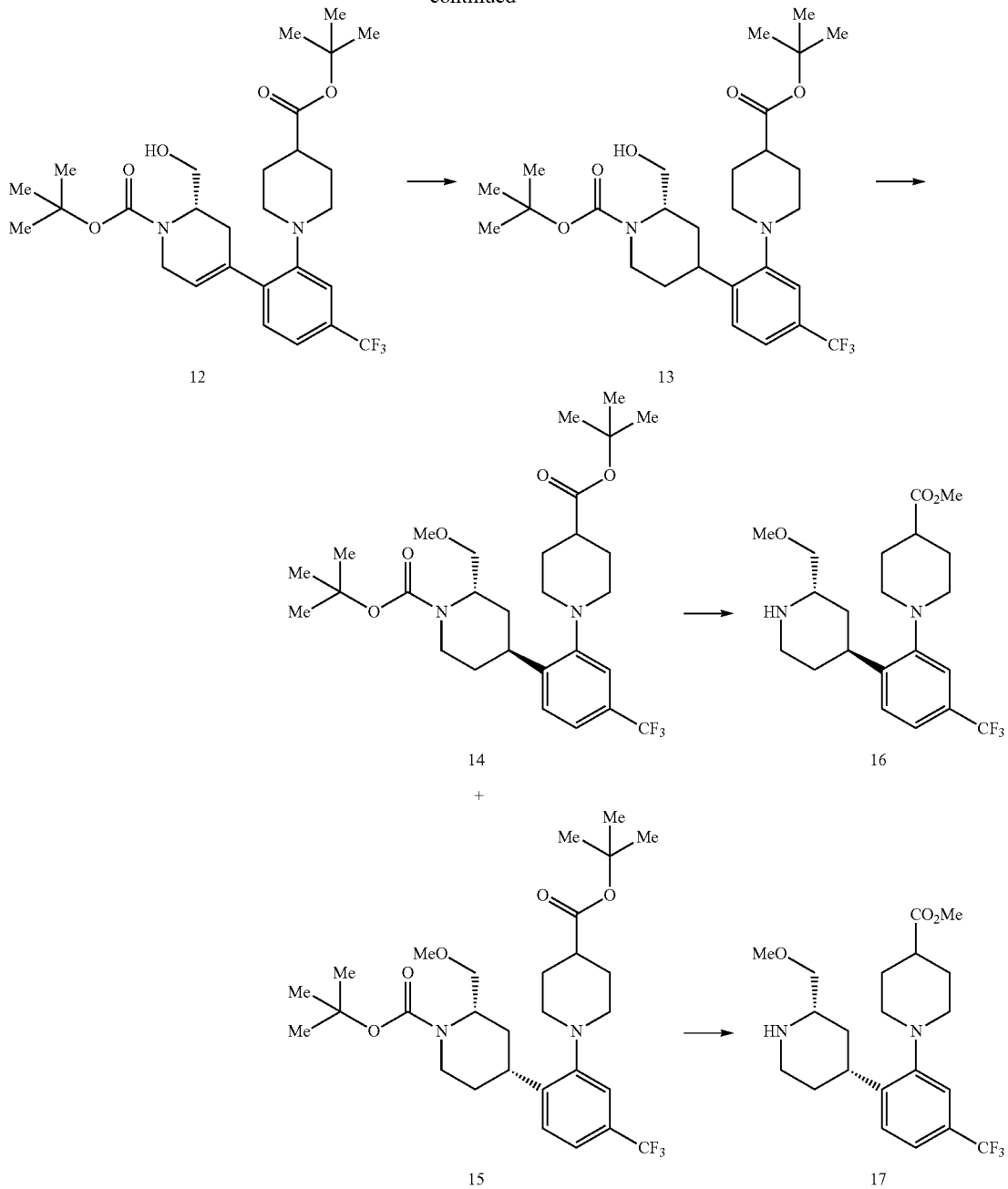

(1) To a suspension of lithium borohydride (622 mg) in tetrahydrofuran (25 mL) was added a solution of Compound 1 (2.0 g), which was prepared in a similar manner to a method described in a literature (Bioorganic & Medicinal Chemistry Letters 1996, 6, 963-966), in tetrahydrofuran (15 mL), the mixture was stirred at room temperature for 1 hour, then methanol (5 mL) was added thereto, and stirred at room temperature for 2 hours. To the reaction mixture was added water, stirred, and then extracted with ethyl acetate. The resultant organic layer was dried, and concentrated under reduced pressure to give Compound 2 (2.09 g) as a colorless viscous material. MS (APCI): m/z 236 [M+H]+

(2) To a solution of Compound 2 (2.09 g) and di-t-butyl dicarbonate (2.03 g) in methanol (42 mL) was added 10% palladium carbon (wetted with ca. 50% water, 625 mg) under stirring, and the mixture was stirred under hydrogen atmosphere (1 atm) at room temperature for 1.5 hours. Palladium carbon was removed by filtration, and then the filtrate was concentrated to give Compound 3 (2.33 g) as a pale yellow viscous material. MS (APCI): m/z 232 [M+H]+

(3) To a solution of Compound 3 (2.33 g) and t-butyldimethylsilyl chloride (1.67 g) in N,N-dimethylformamide (47 mL) was added triethylamine (2.10 mL) under ice-cooling, and the mixture was stirred at room temperature for 72 hours. To the reaction mixture were added water and ethyl acetate, stirred, and then extracted with ethyl acetate. The resultant organic layer was washed with water and saturated saline, then dried, and concentrated under reduced pressure.

The residue was purified with silica gel column chromatography (hexane:ethyl acetate=90:10-70:30) to give Compound 4 (1.99 g) as a colorless viscous material. MS (APCI): m/z 346 [M+H]+

(4) A solution of Compound 4 (1.99 g) in dichloromethane (30 mL) was ice-cooled, then trichloroisocyanuric acid (1.34 g) and 2,2,6,6-tetramethylpiperidine-1-oxyl (90 mg) were added thereto, and the mixture was stirred at the same temperature for 30 minutes. To the reaction mixture was added a saturated aqueous solution of sodium hydrogen carbonate, stirred, and then extracted with dichloromethane. The resultant organic layer was dried, and then concentrated under reduced pressure. The residue was purified with silica gel column chromatography (hexane:ethyl acetate=95:5-80:20) to give Compound 5 (1.67 g) as a colorless viscous material. MS (APCI): m/z 344 [M+H]+

(5) A solution of a solution of sodium bis(trimethylsilyl) amide in toluene (1 mol/L, 5.3 mL) in tetrahydrofuran (50 mL) was cooled to −78° C., a solution of Compound 5 (1.67 g) in tetrahydrofuran (10 mL) was added dropwise thereto, the mixture was stirred at the same temperature for 40 minutes, then a solution of N-phenylbis(trifluoromethanesulfonimide) (2.60 g) in tetrahydrofuran (7 mL) was added thereto, and the mixture was stirred at room temperature for 2 hours. To the reaction mixture was added a saturated aqueous solution of sodium hydrogen carbonate under ice-cooling, stirred, and then extracted with ethyl acetate. The resultant organic layer was washed with saturated saline, dried, and then concentrated under reduced pressure. The residue was purified with silica gel column chromatography (hexane:ethyl acetate 98:2-93/7) to give a mixture of Compound 6 and Compound 7 as a colorless viscous material (2.43 g). MS (APCI): m/z 476 [M+H]+

(6) To a solution of a mixture (2.43 g) of Compound 6 and Compound 7 in 1,4-dioxane (24 mL) were added bis(pinacolato)diboron (1.55 g), dichloro[1,1'-bis(diphenylphosphino) ferrocene]palladium(II) dichloromethane adduct (416 mg), 1,1'-bis(diphenylphosphino)ferrocene (282 mg), and potassium acetate (1.50 g), and the mixture was stirred at 100° C. for 1 hour. The reaction mixture was allowed to cool to room temperature, Compound 8 (2.08 g) and an aqueous solution of sodium carbonate (2 mol/L, 7.63 mL) were added thereto, and stirred at 85° C. for 17 hours. The reaction mixture was allowed to cool to room temperature, water was added thereto, stirred, and then extracted with ethyl acetate. The resultant organic layer was washed with saturated saline, then dried, and concentrated under reduced pressure. The residue was purified with silica gel column chromatography (hexane:ethyl acetate=98:2-92:8) to give a mixture of Compound 9 and Compound 10 as a colorless powder (1.50 g). MS (APCI): m/z 655 [M+H]+

(7) To a solution of a mixture (1.49 g) of Compound 9 and Compound 10 in tetrahydrofuran (7.5 mL) was added a solution of tetrabutylammonium fluoride in tetrahydrofuran (1 mol/L, 3.4 mL), and the mixture was stirred at room temperature for 1.5 hours. To the reaction mixture was added a saturated aqueous solution of sodium hydrogen carbonate, stirred, and then extracted with ethyl acetate. The resultant organic layer was washed with saturated saline, then dried, and concentrated under reduced pressure. The residue was purified with silica gel column chromatography (hexane:ethyl acetate=80:20-60:40) and NH silica gel column chromatography (hexane:ethyl acetate=80:20-60:40) to give a mixture of Compound 11 and Compound 12 as a colorless powder (1.53 g). MS (APCI): m/z 541 [M+H]+

(8) To a solution of a mixture (1.17 g) of Compound 11 and Compound 12 in methanol (23 mL) was added 10% palladium carbon (wetted with ca. 50% water, 350 mg) under stirring, and the mixture was stirred under hydrogen atmosphere (1 atm) at room temperature for 89 hours. Palladium carbon was removed by filtration, and then the filtrate was concentrated to give Compound 13, which was a mixture of diastereomers, as a colorless powder (1.15 g). MS (APCI): m/z 543 [M+H]+

(9) To a solution of Compound 13 (1.23 g) in N,N-dimethylformamide (25 mL) was added methyl iodide (1.41 mL), then added sodium hydride (60% in oil, 109 mg) under ice-cooling, and the mixture was stirred at room temperature for 21 hours. To the reaction mixture was added water, stirred, and then extracted with ethyl acetate. The resultant organic layer was washed with water and saturated saline, then dried, and concentrated under reduced pressure. The residue was purified with silica gel column chromatography (hexane:ethyl acetate=95:5-80:20) to give Compound 14 (683 mg) as a colorless powder and Compound 15 (164 mg) as a colorless viscous material. Each MS (APCI): m/z 557 [M+H]+TLC (hexane:ethyl acetate-80:20): Rf value of Compound 14≈0.55, Rf value of Compound 15≈0.50 (TLC plate: 1.05715.0001 TLC Silica gel 60 $F_{254}$ manufactured by Merck KGaA). The configuration of Compound 1 and 1D NOESY spectrum confirmed that Compound 14 had the above configuration.

(10) To Compound 14 (500 mg) was added a solution of hydrochloric acid in methanol (2 mol/L, 5 mL), and the mixture was stirred at 50° C. for 4 hours. To the mixture was added a solution of hydrochloric acid in methanol (2 mol/L, 2 mL), and stirred at 60° C. for 2 hours. The solvent was evaporated under reduced pressure, then the residue was diluted with chloroform, a saturated aqueous solution of sodium hydrogen carbonate was added thereto to alkalify the mixture, and extracted with chloroform. The resultant organic layer was dried, and concentrated under reduced pressure to give Compound 16 (367 mg) as a colorless viscous material. MS (APCI): m/z 415 [M+H]+

(11) To Compound 15 (149 mg) was added a solution of hydrochloric acid in methanol (2 mol/L, 4 mL), and the mixture was stirred at 60° C. for 5 hours. To the mixture was added sulfuric acid (0.15 mL), and stirred at 60° C. for 2 hours. The solvent was evaporated under reduced pressure, then the residue was diluted with dichloromethane, a saturated aqueous solution of sodium hydrogen carbonate was added thereto to alkalify the mixture, and extracted with dichloromethane. The resultant organic layer was dried, and concentrated under reduced pressure. The residue was purified with silica gel column chromatography (chloroform:methanol=100:0-90:10) to give Compound 17 (80.4 mg) as a colorless viscous material. MS (APCI): m/z 415 [M+H]+

Reference Example 160

[Chemical Formula 167]

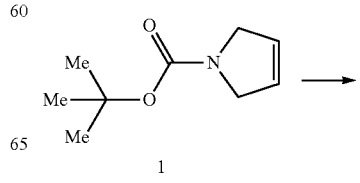

1

-continued

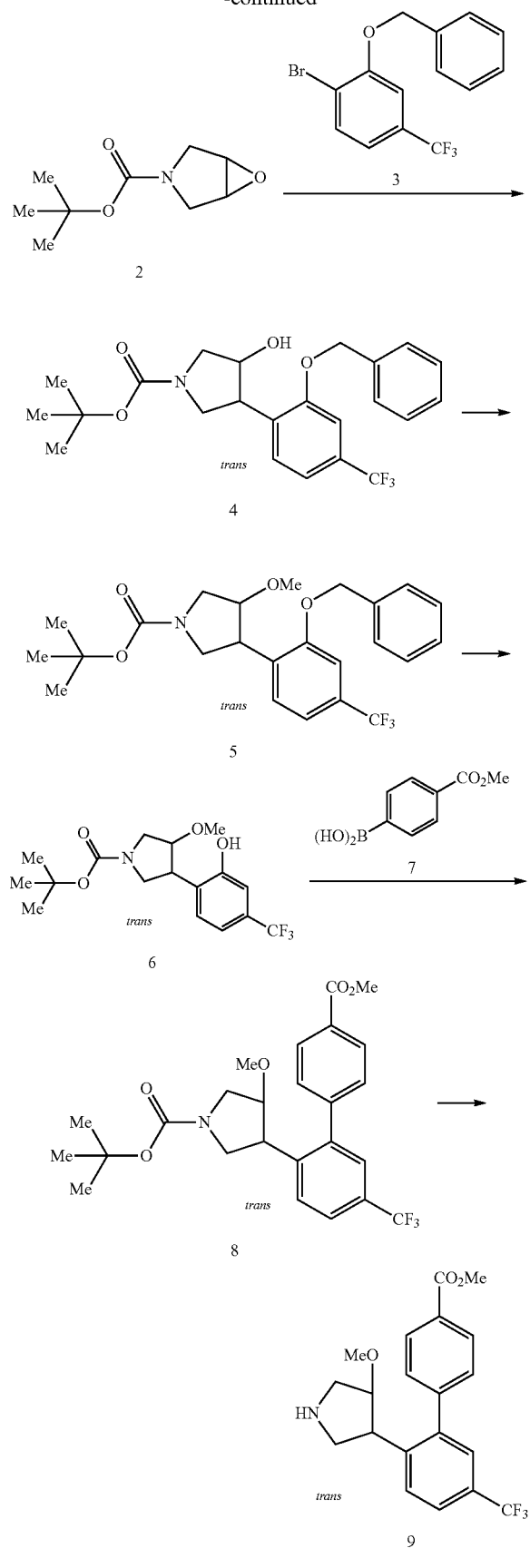

(1) To a solution of Compound 1 (3.0 g) in dichloromethane (30 mL) was added 3-chloroperoxybenzoic acid (8.74 g), and the mixture was stirred at room temperature for 22 hours. To the reaction mixture was added an aqueous solution of sodium hydroxide (1.0 mol/L), stirred, and then extracted with dichloromethane. The resultant organic layer was washed with an aqueous solution of sodium hydroxide (1.0 mol/L), dried, and then concentrated under reduced pressure. The residue was purified with silica gel column chromatography (hexane:ethyl acetate=85:15-60:40) to give Compound 2 (2.52 g) as a colorless liquid. MS (APCI): m/z 130 [M-tBu+2H]+

(2) To a solution of Compound 3 (1.29 g) in tetrahydrofuran (9 mL) was added a solution of isopropylmagnesium bromide in tetrahydrofuran (2 mol/L, 2.1 mL) under ice-cooling, and the mixture was stirred at room temperature for 2 hours. The reaction mixture was ice-cooled again, copper iodide (62 mg) and a solution of Compound 2 (600 mg) in tetrahydrofuran (4 mL) were added thereto, and the mixture was stirred at room temperature for 17 hours. The reaction mixture was ice-cooled, an aqueous solution of hydrochloric acid (1.0 mol/L) was added thereto, stirred, and then extracted with ethyl acetate. The resultant organic layer was washed with a saturated aqueous solution of sodium hydrogen carbonate, then dried, and concentrated under reduced pressure. The residue was purified with NH silica gel column chromatography (hexane:ethyl acetate=70:30-40:60) to give trans compounds (racemates), Compound 4 (2.52 g) as a pale yellow powder. MS (APCI): m/z 338 [M-Boc+H]+

(3) To a solution of Compound 4 (460 mg) in N,N-dimethylformamide (4.6 mL) were added methyl iodide (262 μL) and sodium hydride (60% in oil, 50 mg) under ice-cooling, and the mixture was stirred at room temperature for 2 hours. To the reaction mixture was added water, stirred, and then extracted with ethyl acetate. The resultant organic layer was washed with water and saturated saline, dried, and then concentrated under reduced pressure. The residue was purified with silica gel column chromatography (hexane:ethyl acetate=95:5-80:20) to give trans compounds (racemates), Compound 5 (362 mg) as a colorless viscous material. MS (APCI): m/z 352 [M-Boc+H]+

(4) To a solution of Compound 5 (355 mg) in methanol (4 mL)/tetrahydrofuran (2 mL) was added 10% palladium carbon (wetted with ca. 50% water, 106 mg) under stirring, and the mixture was stirred under hydrogen atmosphere (1 atm) at room temperature for 15 hours. Palladium carbon was removed by filtration, and then the filtrate was concentrated to give trans compounds (racemates), Compound 6 (280 mg) as a colorless powder. MS (APCI): m/z 262 [M-Boc+H]+

(5) Compound 6 (275 mg) and Compound 7 were treated in a similar manner to Reference Example 82 to give trans compounds (racemates), Compound 8 (293 mg) as a colorless powder. MS (APCI): m/z 380 [M-Boc+H]+

(6) Compound 8 (287 mg) was treated in a similar manner to the above Reference Example 115 to give trans compounds (racemates), Compound 9 (215 mg) as a pale yellow liquid. MS (APCI): m/z 380 [M+H]+

Reference Example 161

[Chemical Formula 168]

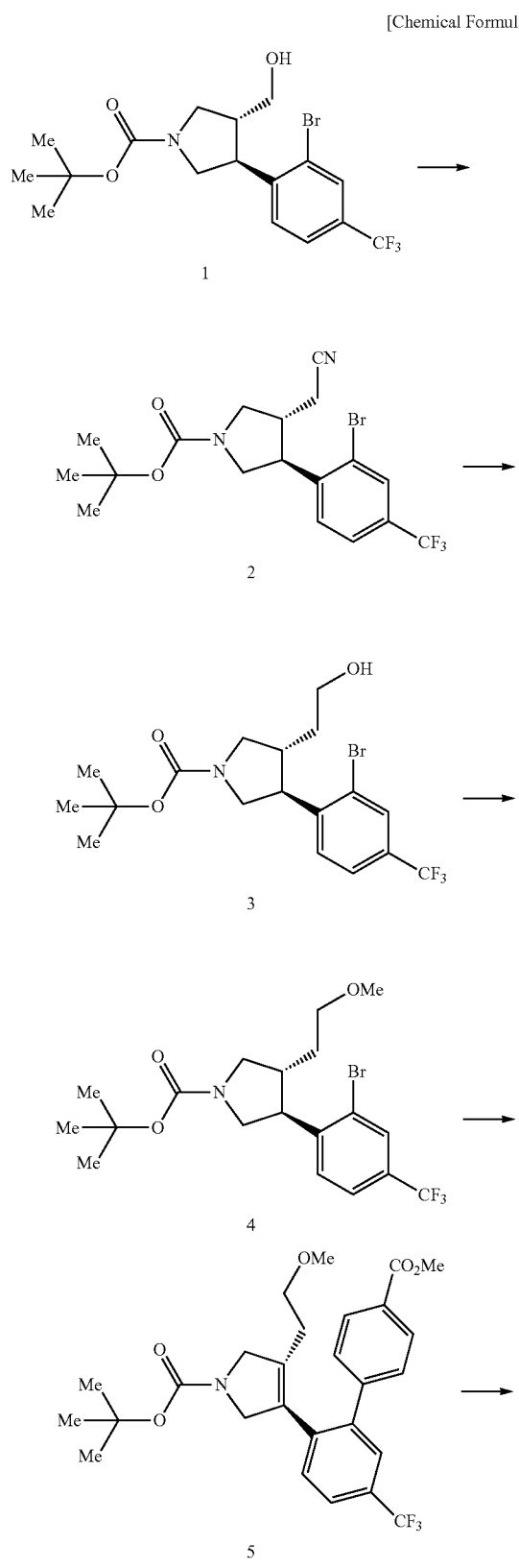

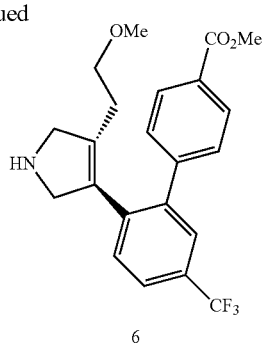

(1) To a solution of Compound 1 (150 mg) and triphenylphosphine (186 mg) in tetrahydrofuran (3 mL) was added carbon tetrachloride (68 μL), and the mixture was stirred at 60° C. for 17 hours. The reaction mixture was allowed to cool to room temperature, and the unnecessary materials were removed by filtration. The filtrate was concentrated under reduced pressure, then acetonitrile (3 mL), trimethylsilyl cyanide (133 μL), and a solution of tetrafluoroammonium fluoride in tetrahydrofuran (1 mol/L, 1.06 mL) were added thereto, and the mixture was stirred at 80° C. for 3 hours. To the mixture were added trimethylsilyl cyanide (44 μL) and a solution of tetrafluoroammonium fluoride in tetrahydrofuran (1 mol/L, 354 μL), and stirred at 80° C. for additional 2 hours. The reaction mixture was allowed to cool to room temperature, water was added thereto, stirred, and then extracted with ethyl acetate. The resultant organic layer was washed with saturated saline, dried, and concentrated under reduced pressure. The residue was purified with silica gel column chromatography (hexane:ethyl acetate=80:20-60:40) to give Compound 2 (120 mg) as a colorless viscous material. MS (APCI): m/z 333/335 [M-Boc+H]+

(2) A solution of Compound 2 (118 mg) in toluene (3 mL) was cooled to −78° C., a solution of diisobutylaluminum hydride in toluene (1.01 mol/L, 674 μL) was added thereto, and the mixture was stirred at the same temperature for 1 hour and then at room temperature for 2 hours. The reaction mixture was ice-cooled, 1 N of an aqueous solution of hydrochloric acid was added thereto, stirred, and then extracted with ethyl acetate. The resultant organic layer was dried, and then concentrated under reduced pressure. To a solution of the resultant crude material in tetrahydrofuran (4 mL)/water (1 mL) was added sodium borohydride (12 mg) under ice-cooling, and the mixture was stirred at the same temperature for 10 minutes. To the reaction mixture was added an aqueous solution of ammonium chloride, stirred, and then extracted with ethyl acetate. The resultant organic layer was dried, and then concentrated under reduced pressure. The residue was purified with silica gel column chromatography (hexane:ethyl acetate=70:30-40:60) to give Compound 3 (59 mg) as a colorless powder. MS (APCI): m/z 338/340 [M-Boc+H]+

(3) Compound 3 (87 mg) was treated in a similar manner to the above Reference Example 115 to give Compound 4 (71 mg) as a pale yellow viscous material. MS (APCI): m/z 352/354 [M-Boc+H]+

(4) Compound 4 (69 mg) was treated in a similar manner to the above Reference Example 115 to give Compound 5 (79 mg) as a pale yellow viscous material. MS (APCI): m/z 408 [M-Boc+H]+

(5) Compound 5 (78 mg) was treated in a similar manner to the above Reference Example 115 to give Compound 6 (77 mg) as a pale yellow viscous material. MS (APCI): m/z 408 [M+H]+

Experimental Example

Experimental Example 1 MCR Agonist Measurement (cAMP Measurement)

(1) Method for Culturing Cells

Human MC1R agonist activity measurement was carried out by using human melanoma cell line HBL. Culture of HBL: F-10 Nutrient Mixture containing 10% FCS and Penicillin-streptomycin was used in the culture.

(2) cAMP Assay and Data Calculation

Each compound solution having each concentration was mixed with cAMP assay buffer (HBSS (Hank's Balanced Salt Solution) containing 10 mM HEPES and 0.1% BSA), and dispensed into 96 well plate. HBL was suspended in cAMP assay buffer containing 0.5 mM IBMX so that the concentrate became $5 \times 10^4$/mL, dispensed into the above 96 well plate, then mixed, left to stand at 37° C. for 30 minutes, and then the intracellular AMP concentration was measured by fluorescence method using Envision (ex. 320 nm, em. 590 nm and 665 nm). Ratio value (665 nm measurement value/590 nm measurement value×10000) was calculated from the resultant data, then the quantitative value of cAMP concentration was calculated by using Prism 5.02, induction % value (% of each sample when the average concentration of cAMP of vehicle is 0% and the average concentration of cAMP of αMSH at $10^{-6}$ M is 100%) was calculated, and $EC_{50}$ value and Intrinsic Activity (IA) % value were calculated.

TABLE 50

| Example No. | Human MC1R (cAMP $EC_{50}$) nM | Human MC1R IA % |
| --- | --- | --- |
| 011 | 18 | 93 |
| 019 | 4.7 | 88 |
| 022 | 17 | 74 |
| 027 | 6.5 | 78 |
| 045 | 23 | 105 |
| 059 | 1.2 | 98 |
| 061 | 30 | 69 |
| 063 | 24 | 92 |
| 064 | 19 | 53 |
| 067 | 2.0 | 78 |
| 068 | 0.94 | 111 |
| 075 | 57 | 111 |
| 077 | 69 | 83 |
| 079 | 67 | 103 |
| 081 | 69 | 96 |
| 084 | 40 | 119 |
| 085 | 60 | 75 |
| 087 | 56 | 90 |
| 091 | 44 | 74 |
| 094 | 49 | 83 |
| 095 | 12 | 72 |
| 098 | 15 | 89 |
| 099 | 4.7 | 117 |
| 100 | 9.7 | 90 |
| 103 | 14 | 102 |
| 105 | 5.1 | 86 |
| 111 | 5.9 | 83 |
| 115 | 11 | 85 |
| 119 | 15 | 53 |
| 120 | 8.8 | 109 |
| 125 | 24 | 74 |
| 130 | 11 | 76 |
| 134 | 0.45 | 96 |

TABLE 50-continued

| Example No. | Human MC1R (cAMP $EC_{50}$) nM | Human MC1R IA % |
| --- | --- | --- |
| 135 | 0.47 | 96 |
| 137 | 7.3 | 106 |
| 138 | 0.98 | 111 |
| 139 | 0.80 | 80 |
| 140 | 4.1 | 98 |
| 141 | 3.6 | 105 |
| 143 | 0.76 | 96 |
| 146 | 0.75 | 118 |
| 147 | 1.7 | 102 |
| 148 | 3.6 | 93 |
| 154 | 1.1 | 85 |
| 156 | 29 | 83 |
| 159 | 0.75 | 103 |
| 160 | 0.67 | 106 |
| 163 | 20 | 36 |
| 177 | 7.4 | 80 |
| 193 | 17 | 103 |
| 194 | 5.6 | 83 |
| 195 | 40 | 87 |
| 198 | 45 | 66 |
| 201 | 31 | 107 |
| 205 | 38 | 67 |
| 213 | 0.89 | 88 |
| 215 | 14 | 59 |
| 218 | 4.3 | 110 |
| 219 | 6.7 | 104 |
| 220 | 2.8 | 75 |
| 223 | 90 | 71 |
| 224 | 11 | 109 |
| 225 | 5.3 | 84 |
| 226 | 47 | 132 |
| 227 | 85 | 114 |
| 228 | 11 | 77 |
| 231 | 11 | 82 |
| 232 | 10 | 95 |
| 234 | 7.3 | 105 |
| 235 | 79 | 124 |
| 248 | 5.1 | 92 |
| 249 | 37 | 149 |
| 256 | 3.0 | 115 |
| 267 | 80 | 112 |
| 269 | 6.7 | 73 |
| 270 | 5.6 | 82 |
| 272 | 18 | 91 |
| 273 | 13 | 79 |
| 274 | 7.5 | 89 |
| 278 | 39 | 46 |
| 279 | 59 | 90 |
| 280 | 42 | 86 |
| 281 | 19 | 72 |
| 282 | 27 | 79 |
| 284 | 14 | 81 |
| 286a | 4.4 | 105 |
| 286b | 189 | 71 |
| 289 | 124 | 55 |
| 290 | 115 | 69 |
| 291 | 734 | 67 |
| 292 | 217 | 25 |
| 293 | 20 | 99 |
| 294 | 804 | 81 |
| 295 | 31 | 91 |
| 299 | 0.70 | 83 |
| 300 | 1.2 | 93 |
| 304 | 8.7 | 89 |
| 306 | 6.8 | 96 |
| 320 | 30 | 79 |
| 327 | 23 | 67 |

INDUSTRIAL APPLICABILITY

The target compound [I] of the present invention or a pharmaceutically acceptable salt thereof has excellent MCR agonist activity, in particular, MC1R agonist activity, and thus, can be used as an agent for preventing or treating, or for improving the prognosis of, various diseases and/or symptoms of which pathological conditions are expected to be improved through activation of MC1R, for example, rheumatoid arthritis, gouty arthritis, osteoarthrosis, inflammatory bowel disease, systemic sclerosis, psoriasis, fibrosis, protoporphyria, systemic lupus erythematosus, melanoma, skin cancer, vitiligo, hair loss, pain, ischemia/reperfusion damage, cerebral inflammatory disease, hepatitis, septicemia/septic shock, nephritis, transplantation, HIV disease exacerbation, vasculitis, uveitis, retinitis pigmentosa, age-related macular degeneration, microbial infection, celiac disease, nephrotic syndrome, and melanoma invasion.

The invention claimed is:

1. A pyrrolidine derivative represented by formula [I]:

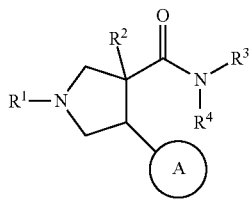

[I]

wherein ring A represents an optionally substituted aryl group or an optionally substituted heteroaryl group;

$R^1$ represents an optionally substituted alkyl group, an optionally substituted cycloalkyl group, an optionally substituted aliphatic heterocyclic group, an optionally substituted aryl group that may be partially hydrogenated, an optionally substituted heteroaryl group, or an optionally substituted carbamoyl group;

$R^2$ represents a halogen atom, an alkyl group, or an optionally substituted alkoxy group;

$R^3$ is an alkyl group substituted with an optionally substituted aryl group, or an alkyl group substituted with an optionally substituted heteroaryl group; and $R^4$ is a hydrogen atom or an alkyl group; or $R^3$ and $R^4$ are terminally attached to each other, and together with the nitrogen atom to which they are attached, form a group represented by formula [II]:

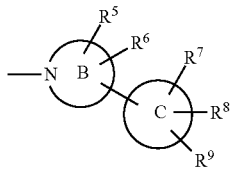

[II]

wherein ring B represents a nitrogen-containing aliphatic heterocyclic group that may partially contain a double bond;

ring C represents an aryl group or a heteroaryl group;

$R^5$ and $R^6$ each independently represent a group selected from the group consisting of a hydrogen atom, a halogen atom, a cyano group, an alkyl group, a haloalkyl group, a cyanoalkyl group, a hydroxyalkyl group, an alkoxyalkyl group, a carboxyl group, a carbamoyl group optionally substituted with one or two alkyl group(s), and an alkoxy group;

$R^7$ represents an optionally substituted alkyl group, an optionally substituted alkenyl group, an optionally substituted cycloalkyl group, an optionally substituted cycloalkenyl group, an optionally substituted aryl group, an optionally substituted heteroaryl group, an optionally substituted aliphatic heterocyclic group, an optionally substituted alkoxy group, an amino group optionally substituted with one or two alkyl group(s) optionally substituted with a carboxyl group, or a carbamoyl group optionally substituted with one or two alkyl group(s) optionally substituted with a carboxyl group, $R^8$ and $R^9$ each independently represent a group selected from the group consisting of a hydrogen atom, a halogen atom, a cyano group, an alkyl group, a haloalkyl group, and a haloalkoxy group, or a pharmaceutically acceptable salt thereof.

2. The compound or pharmaceutically acceptable salt thereof according to claim 1, wherein ring A is an optionally substituted aryl group or an optionally substituted heteroaryl group, wherein substituent(s) on each of the optionally substituted aryl group and the optionally substituted heteroaryl group is/are one to three group(s) independently selected from the group consisting of a halogen atom, an alkyl group, a haloalkyl group, a cycloalkyl group, an alkoxy group, a haloalkoxy group, and an alkyleneoxy group;

$R^1$ is an optionally substituted alkyl group, an optionally substituted cycloalkyl group, an optionally substituted aliphatic heterocyclic group, an optionally substituted aryl group that may be partially hydrogenated, an optionally substituted heteroaryl group, or a carbamoyl group optionally substituted with one or two alkyl group(s), wherein substituent(s) on the optionally substituted alkyl group is/are one to three group(s) independently selected from the group consisting of a halogen atom; a hydroxy group; an oxo group; a cyano group; a cycloalkyl group; an alkoxy group; an alkanoyl group; a carbamoyl group optionally substituted with one or two alkyl group(s); an aliphatic heterocyclic group; an aliphatic heterocyclic carbonyl group optionally substituted with one or two group(s) independently selected from the group consisting of a halogen atom, an alkyl group, a haloalkyl group, and an alkoxyalkyl group; an alkylsulfonyl group; an aliphatic heterocyclic sulfonyl group; and an alkyleneoxy group, and substituent(s) on each of the optionally substituted cycloalkyl group, the optionally substituted aliphatic heterocyclic group, the optionally substituted aryl group that may be partially hydrogenated, and the optionally substituted heteroaryl group is/are one to three group(s) independently selected from the group consisting of a halogen atom; a hydroxy group; an oxo group; a cyano group; an alkyl group; a haloalkyl group; a cycloalkyl group; an alkoxy group; a hydroxyalkyl group; an alkoxyalkyl group; an alkanoyl group; a carbamoyl group optionally substituted with one or two alkyl group(s); an aliphatic heterocyclic group; an aliphatic heterocyclic carbonyl group optionally substituted with one or two group(s) independently selected from the group consisting of a halogen atom, an alkyl group, a haloalkyl group, and an alkoxyalkyl group; an alkylsulfonyl group; an aliphatic heterocyclic sulfonyl group; and an alkyleneoxy group;

$R^2$ is a halogen atom, an alkyl group, or an alkoxy group;

$R^3$ is an alkyl group substituted with a substituted aryl group, or an alkyl group substituted with a substituted heteroaryl group, wherein a substituent on each of the substituted aryl group and the substituted heteroaryl group is an aliphatic heterocyclic group optionally substituted with a carboxyl group, and the aryl group and the heteroaryl group are each optionally further substituted with a haloalkyl group; and $R^4$ is a hydrogen atom or an alkyl group; or $R^3$ and $R^4$ are terminally attached to each other, and together with the nitrogen atom to which they are attached, form a group represented by formula [II]:

[Formula 3]

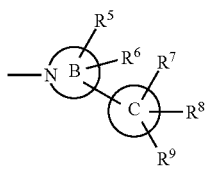

[II]

wherein ring B represents a nitrogen-containing aliphatic heterocyclic group that may partially contain a double bond;

ring C represents an aryl group or a heteroaryl group;

$R^5$ and $R^6$ each independently represent a group selected from the group consisting of a hydrogen atom, a halogen atom, a cyano group, an alkyl group, a haloalkyl group, a cyanoalkyl group, a hydroxyalkyl group, an alkoxyalkyl group, a carboxyl group, a carbamoyl group optionally substituted with one or two alkyl group(s), and an alkoxy group;

$R^7$ represents an optionally substituted alkyl group, an optionally substituted alkenyl group, an optionally substituted cycloalkyl group, an optionally substituted cycloalkenyl group, an optionally substituted aryl group, an optionally substituted heteroaryl group, an optionally substituted aliphatic heterocyclic group, an optionally substituted alkoxy group, an amino group optionally substituted with one or two alkyl group(s) optionally substituted with a carboxyl group, or a carbamoyl group optionally substituted with one or two alkyl group(s) optionally substituted with a carboxyl group, wherein substituent(s) on the optionally substituted alkyl group is/are one or two group(s) independently selected from the group consisting of a hydroxy group; an oxo group; a cyano group; an alkoxy group; an alkanoyl group; a carboxyl group; an alkoxycarbonyl group; an aliphatic heterocyclic carbonyl group optionally substituted with a carboxyl group; a heteroaryl group optionally substituted with a hydroxy or an oxo group; an aliphatic heterocyclic group optionally substituted with one or two oxo group(s); a carbamoyl group optionally substituted with one or two group(s) independently selected from the group consisting of an alkyl group (the alkyl moiety is optionally substituted with a hydroxyl group, an alkoxy group, or a carboxyl group) and a hydroxy group; an alkylsulfonyl group; an aminosulfonyl group optionally substituted with one or two alkyl group(s); an aminosulfonylaminocarbonyl group optionally substituted with one or two alkyl group(s); an alkylsulfonylaminocarbonyl group; and an amino group optionally substituted with one or two group(s) independently selected from the group consisting of an alkyl group, an alkanoyl group, and an alkylsulfonyl group, and substituent(s) on each of the optionally substituted alkenyl group, the optionally substituted cycloalkyl group, the optionally substituted cycloalkenyl group, the optionally substituted aryl group, the optionally substituted heteroaryl group, the optionally substituted aliphatic heterocyclic group, and the optionally substituted alkoxy group is/are one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; an aliphatic heterocyclic carbonyl group optionally substituted with a carboxyl group; a heteroaryl group optionally substituted with a hydroxy or an oxo group; an aliphatic heterocyclic group optionally substituted with one or two oxo group(s); a carbamoyl group optionally substituted with one or two group(s) independently selected from the group consisting of an alkyl group (the alkyl moiety is optionally substituted with a hydroxy group, an alkoxy group, or a carboxyl group) and a hydroxy group; an alkylsulfonyl group; an aminosulfonyl group optionally substituted with one or two alkyl group(s); an aminosulfonylaminocarbonyl group optionally substituted with one or two alkyl group(s); an alkylsulfonylaminocarbonyl group; and an amino group optionally substituted with one or two group(s) independently selected from the group consisting of an alkyl group, an alkanoyl group, and an alkylsulfonyl group; and $R^8$ and $R^9$ each independently represent a group selected from the group consisting of a hydrogen atom, a halogen atom, a cyano group, an alkyl group, a haloalkyl group, and a haloalkoxy group.

3. The compound or pharmaceutically acceptable salt thereof according to claim 1, wherein ring A is an optionally substituted aryl group or an optionally substituted heteroaryl group, wherein substituent(s) on each of the optionally substituted aryl group and the optionally substituted heteroaryl group is/are one to three group(s) independently selected from the group consisting of a halogen atom, an alkyl group, a haloalkyl group, a cycloalkyl group, an alkoxy group, a haloalkoxy group, and an alkyleneoxy group;

the aryl moiety of the optionally substituted aryl group represented by ring A is a monocyclic or bicyclic aryl group, the heteroaryl moiety of the optionally substituted heteroaryl group represented by ring A is a 5- to 10-membered monocyclic or bicyclic heteroaryl group containing one to four heteroatom(s) independently selected from the group consisting of an oxygen atom, a sulfur atom, and a nitrogen atom;

$R^1$ is an optionally substituted alkyl group, an optionally substituted cycloalkyl group, an optionally substituted aliphatic heterocyclic group, an optionally substituted aryl group that may be partially hydrogenated, an optionally substituted heteroaryl group, or a carbamoyl group optionally substituted with one or two alkyl group(s), wherein substituent(s) on the optionally substituted alkyl group is/are one to three group(s) independently selected from the group consisting of a halogen atom; a hydroxy group; an oxo group; a cyano group; a cycloalkyl group; an alkoxy group; an alkanoyl group; a carbamoyl group optionally substituted with one or two alkyl group(s); a 4- to 7-membered monocyclic aliphatic heterocyclic group containing one or two heteroatom(s) independently selected from the group consisting of an oxygen atom, a sulfur atom, and a nitrogen atom; an aliphatic heterocyclic carbonyl group optionally substituted with one or two group(s) independently selected from the group consisting of a halogen atom, an alkyl group, a haloalkyl group, and an alkoxyalkyl group; an alkylsulfonyl group; an aliphatic heterocyclic sulfonyl group; and an alkyleneoxy group, substituent(s) on each of the optionally substituted cycloalkyl group, the optionally substituted aliphatic heterocyclic group, the optionally substituted aryl group that may be partially hydrogenated, and the optionally substituted heteroaryl group is/are one to three group(s) independently selected from the group consisting of a halogen atom; a hydroxy group; an oxo group; a cyano group; an alkyl group; a haloalkyl group; a cycloalkyl group; an alkoxy group; a hydroxyalkyl group; an alkoxyalkyl group; an alkanoyl group; a carbamoyl group optionally substituted with one or two alkyl group(s); a 4- to 7-membered monocyclic aliphatic heterocyclic group containing one or two heteroatom(s) independently selected from the group consisting of an oxygen atom, a sulfur atom, and a nitrogen atom; an aliphatic heterocyclic carbonyl group optionally substituted with one or two group(s) independently selected from the group consisting of a halogen atom, an alkyl group, a haloalkyl group, and an alkoxyalkyl group; an alkylsulfonyl group; an aliphatic heterocyclic sulfonyl group; and an alkyleneoxy group, the aliphatic heterocyclic moiety of each of the aliphatic heterocyclic carbonyl group and the aliphatic heterocyclic sulfonyl group with which $R^1$ is substituted is a 4- to 7-membered monocyclic aliphatic heterocyclic ring containing at least one nitrogen atom, and an optionally further containing one heteroatom selected from the group consisting of an oxygen atom, a sulfur atom, and a nitrogen atom, the aliphatic heterocyclic moiety of the optionally substituted aliphatic heterocyclic group represented by $R^1$ is a 4- to 7-membered monocyclic aliphatic heterocyclic ring containing one or two heteroatom(s) independently selected from the group consisting of an oxygen atom, a sulfur atom, and a nitrogen atom, and the heteroaryl moiety of the optionally substituted heteroaryl group represented by $R^1$ is a 5- or 6-membered monocyclic heteroaryl containing one to four heteroatom(s) independently selected from the group consisting of an oxygen atom, a sulfur atom, and a nitrogen atom;

$R^2$ is a halogen atom, an alkyl group, or an alkoxy group;

$R^3$ is an alkyl group substituted with a substituted aryl group, wherein substituent(s) on the substituted aryl group is/are an aliphatic heterocyclic group optionally substituted with a carboxyl group (wherein the aliphatic heterocyclic group is a 4- to 8-membered monocyclic or bicyclic aliphatic heterocyclic group containing one or two heteroatom(s) independently selected from the group consisting of an oxygen atom, a sulfur atom, and a nitrogen atom) and a haloalkyl group; and $R^4$ is a hydrogen atom or an alkyl group; or $R^3$ and $R^4$ are terminally attached to each other, and together with the nitrogen atom to which they are attached, form a group represented by formula [II], wherein ring B is a 4- to 8-membered monocyclic or bicyclic aliphatic heterocyclic group that may further contain, in addition to the nitrogen atom shown in formula [II], one heteroatom selected from the group consisting of an oxygen atom, a sulfur atom, and a nitrogen atom, and may partially contain a double bond;

ring C is a monocyclic aryl group, or a 5- or 6-membered monocyclic heteroaryl group containing one to four heteroatom(s) independently selected from the group consisting of an oxygen atom, a sulfur atom, and a nitrogen atom;

$R^5$ and $R^6$ are each independently a group selected from the group consisting of a hydrogen atom, a halogen atom, a cyano group, an alkyl group, a haloalkyl group, a cyanoalkyl group, a hydroxyalkyl group, an alkoxyalkyl group, a carboxyl group, a carbamoyl group optionally substituted with one or two alkyl group(s), and an alkoxy group;

$R^7$ is an optionally substituted alkyl group, an optionally substituted alkenyl group, an optionally substituted cycloalkyl group, an optionally substituted cycloalkenyl group, an optionally substituted aryl group, an optionally substituted heteroaryl group, an optionally substituted aliphatic heterocyclic group, an optionally substituted alkoxy group, an amino group optionally substituted with one or two alkyl group(s) optionally substituted with a carboxyl group, or a carbamoyl group optionally substituted with one or two alkyl group(s) optionally substituted with a carboxyl group, wherein substituent(s) on the optionally substituted alkyl group is/are one or two group(s) independently selected from the group consisting of a hydroxy group; an oxo group; a cyano group; an alkoxy group; an alkanoyl group; a carboxyl group; an alkoxycarbonyl group; an aliphatic heterocyclic carbonyl group optionally substituted with a carboxyl group; a heteroaryl group optionally substituted with a hydroxy or an oxo group; a 4- to 7-membered monocyclic aliphatic heterocyclic group optionally substituted with one or two oxo group (s), and containing one or two heteroatom(s) independently selected from the group consisting of an oxygen atom, a sulfur atom, and a nitrogen atom; a carbamoyl group optionally substituted with one or two group(s) independently selected from the group consisting of an alkyl group (the alkyl group is optionally substituted with a hydroxy, an alkoxy, or a carboxyl group) and a hydroxy group; an alkylsulfonyl group; an aminosulfonyl group optionally substituted with one or two alkyl group(s); an aminosulfonylaminocarbonyl group optionally substituted with one or two alkyl group(s); an alkylsulfonylaminocarbonyl group; and an amino group optionally substituted with one or two group(s) independently selected from the group consisting of an alkyl group, an alkanoyl group, and an alkylsulfonyl group, substituent(s) on each of the optionally substituted alkenyl group, the optionally substituted cycloalkyl group, the optionally substituted cycloalkenyl group, the optionally substituted aryl group, the optionally substituted heteroaryl group, the optionally substituted aliphatic heterocyclic group, and the optionally substituted alkoxy group is/are one or two group(s) independently selected from the group consisting of a hydroxy group;

an oxo group; a cyano group; an alkyl group optionally substituted with a carboxyl group; an alkoxy group; an alkanoyl group; a carboxyl group; an alkoxycarbonyl group; an aliphatic heterocyclic carbonyl group optionally substituted with a carboxyl group; a heteroaryl group optionally substituted with a hydroxy or an oxo group; a 4- to 7-membered monocyclic aliphatic heterocyclic group optionally substituted with one or two oxo group(s), and containing one or two heteroatom(s) independently selected from the group consisting of an oxygen atom, a sulfur atom, and a nitrogen atom; a carbamoyl group optionally substituted with one or two group(s) independently selected from the group consisting of an alkyl group (the alkyl group is optionally substituted with a hydroxy group, an alkoxy group, or a carboxyl group) and a hydroxy group; an alkylsulfonyl group; an aminosulfonyl group optionally substituted with one or two alkyl group(s); an aminosulfonylaminocarbonyl group optionally substituted with one or two alkyl group(s); an alkylsulfonylaminocarbonyl group; and an amino group optionally substituted with one or two group(s) independently selected from the group consisting of an alkyl group, an alkanoyl group, and an alkylsulfonyl group, the aliphatic heterocyclic moiety of the aliphatic heterocyclic carbonyl group with which $R^7$ is substituted is a 4- to 7-membered monocyclic aliphatic heterocyclic ring containing at least one nitrogen atom, and optionally further containing one heteroatom selected from the group consisting of an oxygen atom, a sulfur atom, and a nitrogen atom, the heteroaryl group with which $R^7$ is substituted is a 5- or 6-membered monocyclic heteroaryl group containing one to four heteroatom(s) independently selected from the group consisting of an oxygen atom, a sulfur atom, and a nitrogen atom, the heteroaryl moiety of the optionally substituted heteroaryl group represented by $R^7$ is a 5- or 6-membered monocyclic heteroaryl containing one to four heteroatom(s) independently selected from the group consisting of an oxygen atom, a sulfur atom, and a nitrogen atom, and the aliphatic heterocyclic moiety of the optionally substituted aliphatic heterocyclic group represented by $R^7$ is a 4- to 8-membered monocyclic or bicyclic aliphatic heterocyclic ring containing one or two heteroatom(s) independently selected from the group consisting of an oxygen atom, a sulfur atom, and a nitrogen atom; and $R^8$ and $R^9$ are each independently a group selected from the group consisting of a hydrogen atom, a halogen atom, a cyano group, an alkyl group, a haloalkyl group, and a haloalkoxy group.

4. The compound or pharmaceutically acceptable salt thereof according to claim 1, wherein ring A is an optionally substituted aryl group or an optionally substituted heteroaryl group, wherein substituent(s) on each of the optionally substituted aryl group and the optionally substituted heteroaryl group is/are one or two group(s) independently selected from the group consisting of a halogen atom, an alkyl group, a haloalkyl group, a cycloalkyl group, an alkoxy group, a haloalkoxy group, and an alkyleneoxy group, the aryl moiety of the optionally substituted aryl group represented by ring A is a group selected from the group consisting of a phenyl group and a naphthyl group, and the heteroaryl moiety of the optionally substituted heteroaryl group represented by ring A is a group selected from the group consisting of a pyrrolyl group, a furanyl group, a thienyl group, an imidazolyl group, a pyrazolyl group, an oxazolyl group, an isoxazolyl group, a thiazolyl group, a tetrazolyl group, an oxadiazolyl group, a pyridinyl group, a pyrazinyl group, a pyrimidinyl group, a pyridazinyl group, a thiazinyl group, a triazinyl group, an indolyl group, an isoindolyl group, and a benzoimidazolyl group;

$R^1$ is an optionally substituted alkyl group, an optionally substituted cycloalkyl group, an optionally substituted aliphatic heterocyclic group, an optionally substituted aryl group that may be partially hydrogenated, an optionally substituted heteroaryl group, or a carbamoyl group optionally substituted with one or two alkyl group(s), wherein substituent(s) on the optionally substituted alkyl group is/are one or two group(s) independently selected from the group consisting of a halogen atom; a hydroxy group; an oxo group; a cyano group; a cycloalkyl group; an alkoxy group; an alkanoyl group; a carbamoyl group optionally substituted with one or two alkyl group(s); an aliphatic heterocyclic group; an aliphatic heterocyclic carbonyl group optionally substituted with one or two group(s) independently selected from the group consisting of a halogen atom, an alkyl group, a haloalkyl group, and an alkoxyalkyl group; an alkylsulfonyl group; an aliphatic heterocyclic sulfonyl group; and an alkyleneoxy group, substituent(s) on each of the optionally substituted cycloalkyl group, the optionally substituted aliphatic heterocyclic group, the optionally substituted aryl group that may be partially hydrogenated, and the optionally substituted heteroaryl group is/are one or two group(s) independently selected from the group consisting of a halogen atom; a hydroxy group; an oxo group; a cyano group; an alkyl group; a haloalkyl group; a cycloalkyl group; an alkoxy group; a hydroxyalkyl group; an alkoxyalkyl group; an alkanoyl group; a carbamoyl group optionally substituted with one or two alkyl group(s); an aliphatic heterocyclic group; an aliphatic heterocyclic carbonyl group optionally substituted with one or two group(s) independently selected from the group consisting of a halogen atom, an alkyl group, a haloalkyl group, and an alkoxyalkyl group; an alkylsulfonyl group; an aliphatic heterocyclic sulfonyl group; and an alkyleneoxy group, the aliphatic heterocyclic group with which $R^1$ is substituted is a group selected from the group consisting of an azetidinyl group, a pyrrolidinyl group, a tetrahydrofuranyl group, an imidazolinyl group, a thiazolidinyl group, an isothiazolidinyl group, a piperidinyl group, a piperazinyl group, a morpholinyl group, a thiomorpholinyl group, a tetrahydropyranyl group, a homopiperazinyl group, and an homomorpholinyl group, the aliphatic heterocyclic moiety of each of the aliphatic heterocyclic carbonyl group and the aliphatic heterocyclic sulfonyl group with which $R^1$ is substituted is a group selected from the group consisting of an azetidinyl group, a pyrrolidinyl group, an imidazolinyl group, a thiazolidinyl group, an isothiazolidinyl group, a piperidinyl group, a piperazinyl group, a morpholinyl group, a thiomorpholinyl group, a homopiperazinyl group, and a homomorpholinyl group, the aryl moiety of the optionally substituted aryl group that may be partially hydrogenated represented by $R^1$ is a group selected from the group consisting of a phenyl group, a naphthyl group, a dihydrophenyl group, an indanyl group, and a tetrahydronaphthyl group, the aliphatic heterocyclic moiety of the optionally substituted aliphatic heterocyclic group represented by $R^1$ is a group selected from the group consisting of an azetidinyl group, a pyrrolidinyl group, a tetrahydrofuranyl group, an imidazolinyl group, a thiazolidinyl group, an isothiazolidinyl group, a piperidinyl group, a piperazinyl group, a morpholinyl group, a thiomorpholinyl group, a tetrahydropyranyl group, a homopiperazinyl group, and a homomorpholinyl group, and the heteroaryl moiety of the optionally substituted heteroaryl group represented by $R^1$ is a group selected from the group consisting of a pyrrolyl group, a furanyl group, a thienyl group, an imidazolyl group, a pyrazolyl group, an oxazolyl group, an isoxazolyl group, a thiazolyl, tetrazolyl, oxadiazolyl, pyridinyl, pyrazinyl group, a pyrimidinyl group, a pyridazinyl group, a thiazinyl group, and a triazinyl group;

$R^2$ is a halogen atom, an alkyl group, or an alkoxy group;

$R^3$ is an alkyl group substituted with a substituted aryl group, wherein substituent(s) on the substituted aryl group is/are an aliphatic heterocyclic group optionally substituted with a carboxyl group (wherein the aliphatic heterocyclic group is a group selected from the group consisting of an azetidinyl group, a pyrrolidinyl group, a tetrahydrofuranyl group, an imidazolinyl group, a thiazolidinyl group, an isothiazolidinyl group, a piperidinyl group, a piperazinyl group, a morpholinyl group, a thiomorpholinyl group, a tetrahydropyranyl group, a homopiperazinyl group, a homomorpholinyl group, a 3-azabicyclo[3.1.0]hexyl group, and an octahydropyrrolo[3,4-c]pyrrolyl group) and a haloalkyl group; and $R^4$ is a hydrogen atom or an alkyl group; or $R^3$ and $R^4$ are terminally attached to each other, and together with the nitrogen atom to which they are attached, form a group represented by formula [II], wherein ring B is a group selected from the group consisting of an azetidinyl group, a pyrrolidinyl group, an imidazolinyl group, a thiazolidinyl group, an isothiazolidinyl group, a piperidinyl group, a piperazinyl group, a morpholinyl group, a thiomorpholinyl group, a tetrahydropyridinyl group, a homopiperazinyl group, a homomorpholinyl group, a 3-azabicyclo[3.1.0]hexyl group, and an octahydropyrrolo[3,4-c]pyrrolyl group;

ring C is a group selected from the group consisting of a phenyl group, a pyrrolyl group, a furanyl group, a thienyl group, an imidazolyl group, a pyrazolyl group, an oxazolyl group, an isoxazolyl group, a thiazolyl group, a tetrazolyl group, an oxadiazolyl group, a pyridinyl group, a pyrazinyl group, a pyrimidinyl group, a pyridazinyl group, a thiazinyl group, and a triazinyl group;

$R^5$ and $R^6$ are each independently a group selected from the group consisting of a hydrogen atom, a halogen atom, a cyano group, an alkyl group, a haloalkyl group, a cyanoalkyl group, a hydroxyalkyl group, an alkoxyalkyl group, a carboxyl group, a carbamoyl group optionally substituted with one or two alkyl group(s), and an alkoxy group;

$R^7$ is an optionally substituted alkyl group, an optionally substituted alkenyl group, an optionally substituted cycloalkyl group, an optionally substituted cycloalkenyl group, an optionally substituted aryl group, an optionally substituted heteroaryl group, an optionally substituted aliphatic heterocyclic group, an optionally substituted alkoxy group, an amino group optionally substituted with one or two alkyl group(s) optionally substituted with a carboxyl group, or a carbamoyl group optionally substituted with one or two alkyl group(s) optionally substituted with a carboxyl group, wherein substituent(s) on the optionally substituted alkyl group is/are one or two group(s) independently selected from the group consisting of a hydroxy group; an oxo group; a cyano group; an alkoxy group; an alkanoyl group; a carboxyl group; an alkoxycarbonyl group; an aliphatic heterocyclic carbonyl group optionally substituted with a carboxyl group; a heteroaryl group optionally substituted with a hydroxy group or an oxo group; an aliphatic heterocyclic group optionally substituted with one or two oxo group(s); a carbamoyl group optionally substituted with one or two group(s) independently selected from the group consisting of an alkyl group (the alkyl group is optionally substituted with a hydroxy group, an alkoxy group, or a carboxyl group) and a hydroxy group; an alkylsulfonyl group; an aminosulfonyl group optionally substituted with one or two alkyl group(s); an aminosulfonylaminocarbonyl group optionally substituted with one or two alkyl group(s); an alkylsulfonylaminocarbonyl group; and an amino group optionally substituted with one or two group(s) independently selected from the group consisting of an alkyl group, an alkanoyl group, and an alkylsulfonyl group, substituent(s) on each of the optionally substituted alkenyl group, the optionally substituted cycloalkyl group, the optionally substituted cycloalkenyl group, the optionally substituted aryl group, the optionally substituted heteroaryl group, the optionally substituted aliphatic heterocyclic group, and the optionally substituted alkoxy group is/are one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; an aliphatic heterocyclic carbonyl group optionally substituted with a carboxyl group; a heteroaryl group optionally substituted with a hydroxy group or an oxo group; an aliphatic heterocyclic group optionally substituted with one or two oxo group(s); a carbamoyl group optionally substituted with one or two group(s) independently selected from the group consisting of an alkyl group (the alkyl group is optionally substituted with a hydroxy group, an alkoxy group, or a carboxyl group) and a hydroxy group; an alkylsulfonyl group; an aminosulfonyl group optionally substituted with one or two alkyl group(s); an aminosulfonylaminocarbonyl group optionally substituted with one or two alkyl group(s); an alkylsulfonylaminocarbonyl group; and an amino group optionally substituted with one or two group(s) independently selected from the group consisting of an alkyl group, an alkanoyl group, and an alkylsulfonyl group, the aliphatic heterocyclic moiety of the aliphatic heterocyclic carbonyl group with which $R^7$ is substituted is a group selected from the group consisting of an azetidinyl group, a pyrrolidinyl group, an imidazolinyl group, a thiazolidinyl group, an isothiazolidinyl group, a piperidinyl group, a piperazinyl group, a morpholinyl group, a thiomorpholinyl group, a homopiperazinyl group, and a homomorpholinyl group, the heteroaryl group with which $R^7$ is substituted is a group selected from the group consisting of a pyrrolyl group, a furanyl group, a thienyl group, an imidazolyl group, a pyrazolyl group, an oxazolyl group, an isoxazolyl group, a thiazolyl group, a tetrazolyl group, an oxadiazolyl group, a pyridinyl group, a pyrazinyl group, a pyrimidinyl group, a pyridazinyl group, a thiazinyl group, and a triazinyl group, the aliphatic heterocyclic group with which $R^7$ is substituted is a group selected from the group consisting of an azetidinyl group, a pyrrolidinyl group, a tetrahydrofuranyl group, an imidazolinyl group, a thiazolidinyl group, an isothiazolidinyl group, a piperidinyl group, a piperazinyl group, a morpholinyl group, a thiomorpholinyl group, a tetrahydropyranyl group, a homopiperazinyl group, and a homomorpholinyl group, the heteroaryl moiety of the optionally substituted heteroaryl group represented by $R^7$ is a group selected from the group consisting of a pyrrolyl group, a furanyl group, a thienyl group, an imidazolyl group, a pyrazolyl group, an oxazolyl group, an isoxazolyl group, a thiazolyl group, a tetrazolyl group, an oxadiazolyl group, a pyridinyl group, a pyrazinyl group, a pyrimidinyl group, a pyridazinyl group, a thiazinyl group, and a triazinyl group, and the aliphatic heterocyclic moiety of the optionally substituted aliphatic heterocyclic group represented by $R^7$ is a group selected from the group consisting of an azetidinyl group, a pyrrolidinyl group, a tetrahydrofuranyl group, an imidazolinyl group, a thiazolidinyl group, an isothiazolidinyl group, a piperidinyl group, a piperazinyl group, a morpholinyl group, a thiomorpholinyl group, a tetrahydropyranyl group, a homopiperazinyl group, a homomorpholinyl group, a 3-azabicyclo[3.1.0]hexyl group, and an octahydropyrrolo[3,4-c]pyrrolyl group; and $R^8$ and $R^9$ are each independently a group selected from the group consisting of a hydrogen atom, a halogen atom, a cyano group, an alkyl group, a haloalkyl group, and a haloalkoxy group.

5. The compound or pharmaceutically acceptable salt thereof according to claim 1, wherein ring A is a phenyl group or a naphthyl group each optionally substituted with one or two group(s) independently selected from the group consisting of a halogen atom, an alkyl group, a haloalkyl group, a cycloalkyl group, an alkoxy group, a haloalkoxy group, and an alkyleneoxy group; or a heteroaryl group optionally substituted with one or two group(s) independently selected from the group consisting of a halogen atom and an alkoxy group, wherein the heteroaryl group is a group selected from the group consisting of a pyrrolyl group, a furanyl group, a thienyl group, an imidazolyl group, a pyrazolyl group, an oxazolyl group, an isoxazolyl group, a thiazolyl group, a tetrazolyl group, an oxadiazolyl group, a pyridinyl group, a pyrazinyl group, a pyrimidinyl group, a pyridazinyl group, a thiazinyl group, a triazinyl group, an indolyl group, an isoindolyl group, and a benzoimidazolyl group;

$R^1$ is (1) an alkyl group optionally substituted with one or two group(s) independently selected from the group consisting of a halogen atom; a hydroxy group; a cycloalkyl group; an alkoxy group; an aliphatic heterocyclic group; an aliphatic heterocyclic carbonyl group optionally substituted with one or two group(s) independently selected from the group consisting of a halogen atom, an alkyl group, a haloalkyl group, and an alkoxyalkyl group; an aliphatic heterocyclic sulfonyl group; and a carbamoyl group optionally substituted with one or two alkyl group(s)

(wherein the aliphatic heterocyclic group is a group selected from the group consisting of an azetidinyl group, a pyrrolidinyl group, a tetrahydrofuranyl group, an imidazolinyl group, a thiazolidinyl group, an isothiazolidinyl group, a piperidinyl group, a piperazinyl group, a morpholinyl group, a thiomorpholinyl group, a tetrahydropyranyl group, a homopiperazinyl group, and a homomorpholinyl group, and the aliphatic heterocyclic moiety of each of the aliphatic heterocyclic carbonyl group and the aliphatic heterocyclic sulfonyl group is a group selected from the group consisting of an azetidinyl group, a pyrrolidinyl group, an imidazolinyl group, a thiazolidinyl group, an isothiazolidinyl group, a piperidinyl group, a piperazinyl group, a morpholinyl group, a thiomorpholinyl group, a homopiperazinyl group, and a homomorpholinyl group), (2) a monocyclic cycloalkyl group optionally substituted with one or two group(s) independently selected from the group consisting of a halogen atom, a hydroxy group, an oxo group, a cyano group, an alkyl group, an alkoxy group, an alkoxyalkyl group, and an alkyleneoxy group, (3) an adamantyl group optionally substituted with a hydroxy group, (4) an aliphatic heterocyclic group optionally substituted with a group selected from the group consisting of an alkyl group, a hydroxyalkyl group, a haloalkyl group, an alkanoyl group, and an alkylsulfonyl group (wherein the aliphatic heterocyclic group is a group selected from the group consisting of an azetidinyl group, a pyrrolidinyl group, a tetrahydrofuranyl group, an imidazolinyl group, a thiazolidinyl group, an isothiazolidinyl group, a piperidinyl group, a piperazinyl group, a morpholinyl group, a thiomorpholinyl group, a tetrahydropyranyl group, a homopiperazinyl group, and a homomorpholinyl group), (5) a group selected from the group consisting of a phenyl group, a naphthyl group, a dihydrophenyl group, an indanyl group, and a tetrahydronaphthyl group, (6) a heteroaryl group which is optionally substituted with a group selected from the group consisting of a cyano group, an alkyl group, an alkoxy group, and a carbamoyl group (wherein the heteroaryl group is a group selected from the group consisting of a pyrrolyl group, a furanyl group, a thienyl group, an imidazolyl group, a pyrazolyl group, an oxazolyl group, an isoxazolyl group, a thiazolyl group, a tetrazolyl group, an oxadiazolyl group, a pyridinyl group, a pyrazinyl group, a pyrimidinyl group, a pyridazinyl group, a thiazinyl group, and a triazinyl group), (7) a carbamoyl group, or (8) a mono-alkylcarbamoyl group;

$R^2$ is a halogen atom, an alkyl group, or an alkoxy group;

$R^3$ is an alkyl group substituted with a substituted phenyl group, wherein substituent(s) on the substituted phenyl group is/are an aliphatic heterocyclic group substituted with a carboxyl group (wherein the aliphatic heterocyclic group is a group selected from the group consisting of an azetidinyl group, a pyrrolidinyl group, a tetrahydrofuranyl group, an imidazolinyl group, a thiazolidinyl group, an isothiazolidinyl group, a piperidinyl group, a piperazinyl group, a morpholinyl group, a thiomorpholinyl group, a tetrahydropyranyl group, a homopiperazinyl group, a homomorpholinyl group, a 3-azabicyclo[3.1.0]hexyl group, and an octahydropyrrolo[3,4-c]pyrrolyl group) and a haloalkyl group; and $R^4$ is an alkyl group; or $R^3$ and $R^4$ are terminally attached to each other, and together with the nitrogen atom to which they are attached, form a group represented by formula [II], wherein ring B is a group selected from the group consisting of an azetidinyl group, an imidazolinyl group, a thiazolidinyl group, an isothiazolidinyl group, a piperazinyl group, a morpholinyl group, a thiomorpholinyl group, a tetrahydropyridinyl group, a homopiperazinyl group, a homomorpholinyl group, a 3-azabicyclo[3.1.0]hexyl group, and an octahydropyrrolo[3,4-c]pyrrolyl group, and both $R^5$ and $R^6$ represent hydrogen atoms, or ring B is a piperidinyl group, and $R^5$ and $R^6$ are each a group independently selected from the group consisting of a hydrogen atom, a cyano group, and an alkoxyalkyl group, or ring B is a pyrrolidinyl group, and $R^5$ and $R^6$ are each a group independently selected from the group consisting of a hydrogen atom, a halogen atom, a cyano group, an alkyl group, a haloalkyl group, a cyanoalkyl group, a hydroxyalkyl group, an alkoxyalkyl group, a carboxyl group, a carbamoyl group optionally substituted with one or two alkyl group(s), and an alkoxy group;

ring C is a group selected from the group consisting of a phenyl group, a pyrrolyl group, a furanyl group, a thienyl group, an imidazolyl group, a pyrazolyl group, an oxazolyl group, an isoxazolyl group, a thiazolyl group, a tetrazolyl group, an oxadiazolyl group, a pyridinyl group, a pyrazinyl group, a pyrimidinyl group, a pyridazinyl group, a thiazinyl group, and a triazinyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group (wherein the heteroaryl group is a group selected from the group consisting of a pyrrolyl group, a furanyl group, a thienyl group, an imidazolyl group, a pyrazolyl group, an oxazolyl group, an isoxazolyl group, a thiazolyl group, a tetrazolyl group, an oxadiazolyl group, a pyridinyl group, a pyrazinyl group, a pyrimidinyl group, a pyridazinyl group, a thiazinyl group, and a triazinyl group), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy group, an alkoxy group, or a carboxyl group) and a hydroxy group; an alkylsulfonylaminocarbonyl group; an aliphatic heterocyclic carbonyl group optionally substituted with a carboxyl group (wherein the aliphatic heterocyclic ring is a group selected from the group consisting of an azetidinyl group, a pyrrolidinyl group, an imidazolinyl group, a thiazolidinyl group, an isothiazolidinyl group, a piperidinyl group, a piperazinyl group, a morpholinyl group, a thiomorpholinyl group, a homopiperazinyl group, and a homomorpholinyl group); an amino group optionally substituted with one or two group(s) independently selected from the group consisting of an alkyl group, an alkanoyl group, and an alkylsulfonyl group; an aliphatic heterocyclic group optionally substituted with one or two oxo group(s) (wherein the aliphatic heterocyclic group is a group selected from the group consisting of an azetidinyl group, a pyrrolidinyl group, a tetrahydrofuranyl group, an imidazolinyl group, a thiazolidinyl group, an isothiazolidinyl group, a piperidinyl group, a piperazinyl group, a morpholinyl group, a thiomorpholinyl group, a tetrahydropyranyl group, a homopiperazinyl group, and a homomorpholinyl group); an alkylsulfonyl group; a heteroaryl group (wherein the heteroaryl group is a group selected from the group consisting of a pyrrolyl group, a furanyl group, a thienyl group, an imidazolyl group, a pyrazolyl group, an oxazolyl group, an isoxazolyl group, a thiazolyl group, a tetrazolyl group, an oxadiazolyl group, a pyridinyl group, a pyrazinyl group, a pyrimidinyl group, a pyridazinyl group, a thiazinyl group, and a triazinyl group); and an aminosulfonyl group optionally substituted with one or two alkyl group(s)

(wherein the aliphatic heterocyclic group is a group selected from the group consisting of an azetidinyl group, a pyrrolidinyl group, a tetrahydrofuranyl group, an imidazolinyl group, a thiazolidinyl group, an isothiazolidinyl group, a piperidinyl group, a piperazinyl group, a morpholinyl group, a thiomorpholinyl group, a tetrahydropyranyl group, a homopiperazinyl group, a homomorpholinyl group, a 3-azabicyclo[3.1.0]hexyl group, and an octahydropyrrolo[3,4-c]pyrrolyl group), (8) an alkoxy group optionally substituted with a group selected from the group consisting of a cyano group; a carboxyl group; a heteroaryl group optionally substituted with a hydroxy group or an oxo group (wherein the heteroaryl group is a group selected from the group consisting of a pyrrolyl group, a furanyl group, a thienyl group, an imidazolyl group, a pyrazolyl group, an oxazolyl group, an isoxazolyl group, a thiazolyl group, a tetrazolyl group, an oxadiazolyl group, a pyridinyl group, a pyrazinyl group, a pyrimidinyl group, a pyridazinyl group, a thiazinyl group, and a triazinyl group); an aminosulfonylaminocarbonyl group optionally substituted with one or two alkyl group(s); and an alkylsulfonylaminocarbonyl group, (9) an amino group which is optionally substituted with one or two alkyl group(s) optionally substituted with a carboxyl group, or

(10) a carbamoyl group; and $R^8$ and $R^9$ are each independently a group selected from the group consisting of a hydrogen atom, a halogen atom, a cyano group, an alkyl group, a haloalkyl group, and a haloalkoxy group.

6. The compound or pharmaceutically acceptable salt thereof according to claim 1, wherein ring A is a phenyl group optionally substituted with one or two groups independently selected from the group consisting of a halogen atom, an alkyl group, a haloalkyl group, a cycloalkyl group, an alkoxy group, a haloalkoxy group, and an alkyleneoxy group, or a pyridinyl group optionally substituted with a group selected from the group consisting of a halogen atom and an alkoxy group;

$R^1$ is (1) an alkyl group optionally substituted with one or two group(s) independently selected from the group consisting of a halogen atom; a hydroxy group; a 3- to 7-membered monocyclic cycloalkyl group; an alkoxy group; a tetrahydropyranyl group; an aliphatic heterocyclic carbonyl group optionally substituted with one or two group(s) independently selected from the group consisting of a halogen atom, an alkyl group, a haloalkyl group, and an alkoxyalkyl group (wherein the aliphatic heterocyclic ring is a group selected from the group consisting of a pyrrolidinyl group, a piperidinyl group, and a morpholinyl group); a pyrrolidinylsulfonyl group; and a carbamoyl group optionally substituted with one or two alkyl group(s), (2) a 3- to 7-membered monocyclic cycloalkyl group optionally substituted with one or two group(s) independently selected from the group consisting of a halogen atom, a hydroxy group, an oxo group, a cyano group, an alkyl group, an alkoxy group, an alkoxyalkyl group, and an alkyleneoxy group, (3) an adamantyl group optionally substituted with a hydroxy group, (4) an aliphatic heterocyclic group optionally substituted with a group selected from the group consisting of an alkyl group, a hydroxyalkyl group, a haloalkyl group, an alkanoyl group, and an alkylsulfonyl group (wherein the aliphatic heterocyclic group is a group selected from the group consisting of a tetrahydrofuranyl group, a tetrahydropyranyl group, and a piperidinyl group), (5) an indanyl group, (6) a heteroaryl group which is optionally substituted with a group selected from the group consisting of a cyano group, an alkyl group, an alkoxy group, and a carbamoyl group (wherein the heteroaryl group is a group selected from the group consisting of a pyridazinyl group, a pyridinyl group, and a pyrimidinyl group), (7) a carbamoyl group, or (8) a mono-alkylcarbamoyl group;

$R^2$ is a halogen atom, a $C_{1-3}$ alkyl group, or an alkoxy group;

$R^3$ is an alkyl group substituted with a substituted phenyl group, wherein substituent(s) on the substituted phenyl group is/are a piperidinyl group substituted with a carboxyl group, and a haloalkyl group; and $R^4$ is an alkyl group; or $R^3$ and $R^4$ are terminally attached to each other, and together with the nitrogen atom to which they are attached, form a group represented by formula [II], wherein ring B is a group selected from the group consisting of an azetidinyl group, a tetrahydropyridinyl group, a piperazinyl group, a homopiperazinyl group, and an octahydropyrrolo[3,4-c]pyrrolyl group, and both $R^5$ and $R^6$ represent hydrogen atoms, or ring B is a piperidinyl group, and $R^5$ and $R^6$ are each a group independently selected from the group consisting of a hydrogen atom, a cyano group, and an alkoxyalkyl group, or ring B is a pyrrolidinyl group, and $R^5$ and $R^6$ are each a group independently selected from the group consisting of a hydrogen atom, a halogen atom, a cyano group, an alkyl group, a haloalkyl group, a cyanoalkyl group, a hydroxyalkyl group, an alkoxyalkyl group, a carboxyl group, carbamoyl group optionally substituted with one or two alkyl group(s), and an alkoxy group;

ring C is a phenyl group or a pyridinyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group (wherein the heteroaryl group is a group selected from the group consisting of an oxazolyl group and a pyrazolyl group), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy group, an alkoxy group, or a carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of an alkyl group, an alkanoyl group, and an alkylsulfonyl group; an aliphatic heterocyclic group optionally substituted with one or two oxo group(s) (wherein the aliphatic heterocyclic group is a group selected from the group consisting of a pyrrolidinyl group and an isothiazolidinyl group); an alkylsulfonyl group; a tetrazolyl group; and an aminosulfonyl group optionally substituted with one or two alkyl group(s) (wherein the aliphatic heterocyclic group is a group selected from the group consisting of an azetidinyl group, a pyrrolidinyl group, a piperidinyl group, a morpholinyl group, a thiomorpholinyl group, a piperazinyl group, and a 3-azabicyclo[3.1.0]hexyl group), (8) an alkoxy group optionally substituted with a group selected from the group consisting of a cyano group; a carboxyl group; a heteroaryl group optionally substituted with a hydroxy group or an oxo group (wherein the heteroaryl group is a group selected from the group consisting of an isoxazolyl group, an oxadiazolyl group, and a tetrazolyl group); an aminosulfonylaminocarbonyl group optionally substituted with one or two alkyl group(s); and an alkylsulfonylaminocarbonyl group, (9) an amino group which is optionally substituted with one or two alkyl group(s) optionally substituted with a carboxyl group, or

(10) a carbamoyl group; and $R^8$ and $R^9$ are each independently a group selected from the group consisting of a hydrogen atom, a halogen atom, a cyano group, an alkyl group, a haloalkyl group, and a haloalkoxy group.

7. The compound or pharmaceutically acceptable salt thereof according to claim 1, wherein $R^3$ and $R^4$ are terminally attached to each other, and together with the nitrogen atom to which they are attached, form a group represented by formula [II]:

[Formula 4]

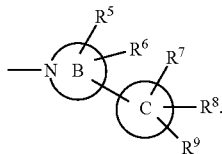

[II]

8. The compound or pharmaceutically acceptable salt thereof according to claim 1, wherein $R^1$ is (1) a 3- to 7-membered monocyclic cycloalkyl group optionally substituted with one or two group(s) independently selected from the group consisting of a halogen atom, a hydroxy group, an oxo group, a cyano group, an alkyl group, an alkoxy group, an alkoxyalkyl group, and an alkyleneoxy group;

(2) an adamantyl group optionally substituted with a hydroxy group; or (3) an aliphatic heterocyclic group optionally substituted with a group selected from the group consisting of an alkyl group, a hydroxyalkyl group, a haloalkyl group, an alkanoyl group, and an alkylsulfonyl group (wherein the aliphatic heterocyclic group is a group selected from the group consisting of a tetrahydrofuranyl group, a tetrahydropyranyl group, and a piperidinyl group).

9. The compound or pharmaceutically acceptable salt thereof according to claim 1, wherein $R^3$ and $R^4$ are terminally attached to each other, and together with the nitrogen atom to which they are attached, form a group represented by formula [II]:

[Formula 5]

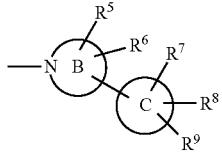

[II]

wherein ring B is a pyrrolidinyl group.

10. The compound or pharmaceutically acceptable salt thereof according to claim 1, wherein $R^1$ is a 3- to 7-membered monocyclic cycloalkyl group optionally substituted with one or two group(s) independently selected from the group consisting of a halogen atom, a hydroxy group, an oxo group, a cyano group, an alkyl group, an alkoxy group, an alkoxyalkyl group, and an alkyleneoxy group.

11. The compound or pharmaceutically acceptable salt thereof according to claim 1, wherein ring A is a phenyl group optionally substituted with one or two group(s) independently selected from the group consisting of a halogen atom, an alkyl group, a haloalkyl group, a cycloalkyl group, an alkoxy group, a haloalkoxy group, and an alkyleneoxy group;

$R^1$ is a 3- to 7-membered monocyclic cycloalkyl group optionally substituted with one or two group(s) independently selected from the group consisting of a halogen atom, a hydroxy group, an oxo group, a cyano group, an alkyl group, an alkoxy group, an alkoxyalkyl group, and an alkyleneoxy group;

$R^2$ is a halogen atom or an alkoxy group;

$R^3$ and $R^4$ are terminally attached to each other, and together with the nitrogen atom to which they are attached, form a group represented by formula [II], wherein ring B is a pyrrolidinyl group, and $R^5$ and $R^6$ are each a group independently selected from the group consisting of a hydrogen atom, a halogen atom, a cyano group, an alkyl group, a haloalkyl group, a cyanoalkyl group, a hydroxyalkyl group, an alkoxyalkyl group, a carboxyl group, a carbamoyl group optionally substituted with one or two alkyl group(s), and an alkoxy group;

ring C is a phenyl group;

$R^7$ is (1) an alkyl group optionally substituted with a carboxyl group, (2) an alkenyl group optionally substituted with a carboxyl group, (3) a 3- to 7-membered monocyclic cycloalkyl group optionally substituted with a carboxyl group, (4) a 3- to 7-membered monocyclic cycloalkenyl group optionally substituted with a carboxyl group, (5) a phenyl group optionally substituted with a carboxyl group, (6) a heteroaryl group which is optionally substituted with a carboxyl group or an alkyl group optionally substituted with a carboxyl group (wherein the heteroaryl group is a group selected from the group consisting of an oxazolyl group and a pyrazolyl group), (7) an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy group, an alkoxy group, or a carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of an alkyl group, an alkanoyl group, and an alkylsulfonyl group; an aliphatic heterocyclic group optionally substituted with one or two oxo group(s) (wherein the aliphatic heterocyclic group is a group selected from the group consisting of a pyrrolidinyl group and an isothiazolidinyl group); an alkylsulfonyl group; a tetrazolyl group; and an aminosulfonyl group optionally substituted with one or two alkyl group(s)
(wherein the aliphatic heterocyclic group is a group selected from the group consisting of an azetidinyl group, a pyrrolidinyl group, a piperidinyl group, a morpholinyl group, a thiomorpholinyl group, a piperazinyl group, and a 3-azabicyclo[3.1.0]hexyl group),
(8) an alkoxy group optionally substituted with a group selected from the group consisting of a cyano group; a carboxyl group; a heteroaryl group optionally substituted with a hydroxy group or an oxo group (wherein the heteroaryl group is a group selected from the group consisting of an isoxazolyl group, an oxadiazolyl group, and a tetrazolyl group); an aminosulfonylaminocarbonyl group optionally substituted with one or two alkyl group(s); and an alkylsulfonylaminocarbonyl group,
(9) an amino group which is optionally substituted with one or two alkyl group(s) optionally substituted with a carboxyl group, or
(10) a carbamoyl group; and
$R^8$ and $R^9$ are each independently a group selected from the group consisting of a hydrogen atom, a halogen atom, a cyano group, an alkyl group, a haloalkyl group, and a haloalkoxy group.

12. The compound or pharmaceutically acceptable salt thereof according to claim 11, wherein
ring A is a phenyl group optionally substituted with one or two group(s) independently selected from the group consisting of a halogen atom, an alkyl group, a haloalkyl group, a cycloalkyl group, an alkoxy group, a haloalkoxy group, and an alkyleneoxy group;
$R^1$ is a 3- to 7-membered monocyclic cycloalkyl group optionally substituted with one or two group(s) independently selected from the group consisting of a halogen atom, a hydroxy group, an oxo group, a cyano group, an alkyl group, an alkoxy group, an alkoxyalkyl group, and an alkyleneoxy group;
$R^2$ is a halogen atom or an alkoxy group;
$R^3$ and $R^4$ are terminally attached to each other, and together with the nitrogen atom to which they are attached, form a group represented by formula [II],
wherein ring B is a pyrrolidinyl group, and $R^5$ and $R^6$ are each a group independently selected from the group consisting of a hydrogen atom, a halogen atom, a cyano group, an alkyl group, a haloalkyl group, a cyanoalkyl group, a hydroxyalkyl group, an alkoxyalkyl group, a carboxyl group, a carbamoyl group optionally substituted with one or two alkyl group(s), and an alkoxy group;
ring C is a phenyl group;
$R^7$ is an aliphatic heterocyclic group optionally substituted with one or two group(s) independently selected from the group consisting of a hydroxy group; an oxo group; a cyano group; an alkyl group optionally substituted with a carboxyl group; an alkoxy group; an alkanoyl group; a carboxyl group; an alkoxycarbonyl group; a carbamoyl group optionally substituted with one or two group(s) independently selected from the group consisting of an alkyl group (the alkyl group is optionally substituted with a hydroxy group, an alkoxy group, or a carboxyl group) and a hydroxy group; an alkylsulfonylaminocarbonyl group; a pyrrolidinylcarbonyl group optionally substituted with a carboxyl group; an amino group optionally substituted with one or two group(s) independently selected from the group consisting of an alkyl group, an alkanoyl group, and an alkylsulfonyl group; an aliphatic heterocyclic group optionally substituted with one or two oxo group(s) (wherein the aliphatic heterocyclic group is a group selected from the group consisting of a pyrrolidinyl group and an isothiazolidinyl group); an alkylsulfonyl group; a tetrazolyl group; and an aminosulfonyl group optionally substituted with one or two alkyl group(s)
(wherein the aliphatic heterocyclic group is a group selected from the group consisting of an azetidinyl group, a pyrrolidinyl group, a piperidinyl group, a morpholinyl group, a thiomorpholinyl group, a piperazinyl group, and a 3-azabicyclo[3.1.0]hexyl group); and
$R^8$ and $R^9$ are each independently a group selected from the group consisting of a hydrogen atom, a halogen atom, a cyano group, an alkyl group, a haloalkyl group, and a haloalkoxy group.

13. The compound or pharmaceutically acceptable salt thereof according to claim 1, wherein
ring A is a phenyl group optionally substituted with an alkoxy group;
$R^1$ is an alkyl group; an aliphatic heterocyclic group (wherein the aliphatic heterocyclic group is a group selected from the group consisting of a tetrahydrofuranyl group, a tetrahydropyranyl group, and a piperidinyl group); a 3- to 7-membered monocyclic cycloalkyl group optionally substituted with a group selected from the group consisting of an alkoxy group and a cyano group; or a heteroaryl group optionally substituted with an alkyl group (wherein the heteroaryl group is a group selected from the group consisting of a pyridazinyl group, a pyridinyl group, and a pyrimidinyl group);
$R^2$ is a halogen atom or an alkoxy group;
$R^3$ and $R^4$ are terminally attached to each other, and together with the nitrogen atom to which they are attached, form a group represented by formula [II]:

[Formula 6]

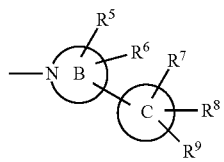

[II]

wherein ring B is selected from the group consisting of an azetidinyl group, a pyrrolidinyl group, a piperidinyl group, a tetrahydropyridinyl group, and a piperazinyl group, and $R^5$ and $R^6$ are hydrogen atoms, or
ring B is a pyrrolidinyl group, $R^5$ is an alkoxyalkyl group, and $R^6$ is a hydrogen atom or a halogen atom;
ring C is a phenyl group;
$R^7$ is an aliphatic heterocyclic group substituted with a carboxyl group (wherein the aliphatic heterocyclic group is a group selected from the group consisting of an azetidinyl group, a pyrrolidinyl group, a piperidinyl group, a morpholinyl group, a thiomorpholinyl group, a piperazinyl group, and a 3-azabicyclo[3.1.0]hexyl group);
$R^8$ is a halogen atom or a haloalkyl group; and
$R^9$ is a hydrogen atom.

14. The compound or pharmaceutically acceptable salt thereof according to claim 13, wherein ring A is a phenyl group optionally substituted with an alkoxy group;
$R^1$ is a tetrahydropyranyl group; or a 5- or 6-membered monocyclic cycloalkyl group optionally substituted with a group selected from the group consisting of an alkoxy group and a cyano group;
$R^2$ is a halogen atom or an alkoxy group;
$R^3$ and $R^4$ are terminally attached to each other, and together with the nitrogen atom to which they are attached, form a group represented by formula [II]:

[Formula 7]

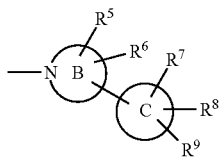

[II]

wherein ring B is a pyrrolidinyl group, $R^5$ is an alkoxyalkyl group, and $R^6$ is a hydrogen atom or a halogen atom;
ring C is a phenyl group;
$R^7$ is a piperidinyl group substituted with a carboxyl group;
$R^8$ is a halogen atom or a haloalkyl group; and
$R^9$ is a hydrogen atom.

15. The compound or pharmaceutically acceptable salt thereof according to claim 14, wherein
ring A is a phenyl group optionally substituted with an alkoxy group;
$R^1$ is a 5- or 6-membered monocyclic cycloalkyl group optionally substituted with a group selected from the group consisting of an alkoxy group and a cyano group;
$R^2$ is a halogen atom or an alkoxy group;
$R^3$ and $R^4$ are terminally attached to each other, and together with the nitrogen atom to which they are attached, form a group represented by formula [II]:

[Formula 8]

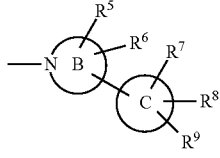

[II]

wherein ring B is a pyrrolidinyl group, $R^5$ is an alkoxyalkyl group, and $R^6$ is a hydrogen atom or a halogen atom;
ring C is a phenyl group;
$R^7$ is a piperidinyl group substituted with a carboxyl group;
$R^8$ is a halogen atom or a haloalkyl group; and
$R^9$ is a hydrogen atom.

16. A compound selected from the group consisting of:
1-{2-[(3S,5S)-1-{[(3R,4R)-1-(trans-4-ethoxycyclohexyl)-3-methoxy-4-(4-methoxyphenyl)pyrrolidin-3-yl]carbonyl}-5-(ethoxymethyl)pyrrolidin-3-yl]-5-(trifluoromethyl)phenyl}piperidine-4-carboxylic acid;

1-{2-[(3S,5S)-1-{[(3R,4R)-3-fluoro-4-(4-methoxyphenyl)-1-(2-methylpyridin-4-yl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,5S)-1-{[(3R,4R)-3-fluoro-4-(4-methoxyphenyl)-1-(2-methylpyrimidin-4-yl)pyrrolidin-3-yl]carbonyl}-5-(methoxymethyl)pyrrolidin-3-yl]-5-(trifluoromethyl)phenyl}piperidine-4-carboxylic acid;
1-{5-fluoro-2-[(3S,5S)-1-{[(3R,4R)-3-fluoro-1-(trans-4-methoxycyclohexyl)-4-(4-methoxyphenyl)pyrrolidin-3-yl]carbonyl}-5-(methoxymethyl)pyrrolidin-3-yl]phenyl}piperidine-4-carboxylic acid;
1-{2-[(3S,5S)-1-{[(3R,4R)-1-(trans-4-ethoxycyclohexyl)-3-methoxy-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,5S)-1-{[(3R,4R)-1-(trans-4-cyanocyclohexyl)-3-fluoro-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,4S)-1-{[(3R,4R)-1-(trans-4-ethoxycyclohexyl)-3-methoxy-4-(4-methoxyphenyl)pyrrolidin-3-yl]carbonyl}-4-fluoro-4-(methoxymethyl)pyrrolidin-3-yl]-5-(trifluoromethyl)phenyl}piperidine-4-carboxylic acid;
1-{2-[(3S,4R)-1-{[(3R,4R)-1-(trans-4-ethoxycyclohexyl)-3-methoxy-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid;
1-{2-[(3S,5S)-1-{[(3R,4R)-1-cyclohexyl-3-fluoro-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,5S)-1-{[(3R,4R)-3-fluoro-4-(4-methoxyphenyl)-1-(tetrahydro-2H-pyran-4-yl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,5S)-1-{[(3R,4R)-3-fluoro-1-(trans-4-methoxycyclohexyl)-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,5S)-1-{[(3R,4R)-1-cyclopentyl-3-fluoro-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,4R)-1-{[(3R,4R)-3-fluoro-4-(4-methoxyphenyl)-1-(2-methylpyridin-4-yl)pyrrolidin-3-yl]carbonyl}-4-(methoxymethyl)pyrrolidin-3-yl]-5-(trifluoromethyl)phenyl}piperidine-4-carboxylic acid;
1-{2-[(3S,4S)-4-fluoro-1-{[(3R,4R)-3-fluoro-1-(trans-4-methoxycyclohexyl)-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid;
1-{5-chloro-2-[(3S,4R)-1-{[(3R,4R)-3-fluoro-1-(trans-4-methoxycyclohexyl)-4-(4-methoxyphenyl)pyrrolidin-3-yl]carbonyl}-4-(methoxymethyl)pyrrolidin-3-yl]phenyl}piperidine-4-carboxylic acid;
1-{2-[(3S,4R)-4-(cyanomethyl)-1-{[(3R,4R)-1-cyclopentyl-3-fluoro-4-(4-methoxyphenyl)pyrrolidin-3-yl]carbonyl}pyrrolidin-3-yl]-5-(trifluoromethyl)phenyl}piperidine-4-carboxylic acid;
1-{2-[(3S,4R)-1-{[(3R,4R)-3-fluoro-1-(trans-4-methoxycyclohexyl)-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid;

1-[2-(1-{[(3R,4R)-3-fluoro-1-(trans-4-methoxycyclohexyl)-4-(4-methoxyphenyl)pyrrolidin-3-yl]carbonyl}piperidin-4-yl)-5-(trifluoromethyl)phenyl]piperidine-4-carboxylic acid;
1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid; and
1-{2-[(3S)-1-{[(3R,4R)-3-fluoro-1-(trans-4-methoxycyclohexyl)-4-(4-methoxyphenyl)pyrrolidin-3-yl]carbonyl}pyrrolidin-3-yl]-5-(trifluoromethyl)phenyl}piperidine-4-carboxylic acid;
or a pharmaceutically acceptable salt thereof.

17. A compound selected from the group consisting of:
1-{2-[(3S,5S)-1-{[(3R,4R)-1-(trans-4-ethoxycyclohexyl)-3-methoxy-4-(4-methoxyphenyl)pyrrolidin-3-yl]carbonyl}-5-(ethoxymethyl)pyrrolidin-3-yl]-5-(trifluoromethyl)phenyl}piperidine-4-carboxylic acid;
1-{5-fluoro-2-[(3S,5S)-1-{[(3R,4R)-3-fluoro-1-(trans-4-methoxycyclohexyl)-4-(4-methoxyphenyl)pyrrolidin-3-yl]carbonyl}-5-(methoxymethyl)pyrrolidin-3-yl]phenyl}piperidine-4-carboxylic acid;
1-{2-[(3S,5S)-1-{[(3R,4R)-1-(trans-4-ethoxycyclohexyl)-3-methoxy-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,5S)-1-{[(3R,4R)-1-(trans-4-cyanocyclohexyl)-3-fluoro-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,4S)-1-{[(3R,4R)-1-(trans-4-ethoxycyclohexyl)-3-methoxy-4-(4-methoxyphenyl)pyrrolidin-3-yl]carbonyl}-4-fluoro-4-(methoxymethyl)pyrrolidin-3-yl]-5-(trifluoromethyl)phenyl}piperidine-4-carboxylic acid;
1-{2-[(3S,4R)-1-{[(3R,4R)-1-(trans-4-ethoxycyclohexyl)-3-methoxy-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid;
1-{2-[(3S,5S)-1-{[(3R,4R)-1-cyclohexyl-3-fluoro-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,5S)-1-{[(3R,4R)-3-fluoro-1-(trans-4-methoxycyclohexyl)-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,5S)-1-{[(3R,4R)-1-cyclopentyl-3-fluoro-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,4S)-4-fluoro-1-{[(3R,4R)-3-fluoro-1-(trans-4-methoxycyclohexyl)-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid;
1-{5-chloro-2-[(3S,4R)-1-{[(3R,4R)-3-fluoro-1-(trans-4-methoxycyclohexyl)-4-(4-methoxyphenyl)pyrrolidin-3-yl]carbonyl}-4-(methoxymethyl)pyrrolidin-3-yl]phenyl}piperidine-4-carboxylic acid;
1-{2-[(3S,4R)-4-(cyanomethyl)-1-{[(3R,4R)-1-cyclopentyl-3-fluoro-4-(4-methoxyphenyl)pyrrolidin-3-yl]carbonyl}pyrrolidin-3-yl]-5-(trifluoromethyl)phenyl}piperidine-4-carboxylic acid;
1-{2-[(3S,4R)-1-{[(3R,4R)-3-fluoro-1-(trans-4-methoxycyclohexyl)-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid;
1-[2-(1-{[(3R,4R)-3-fluoro-1-(trans-4-methoxycyclohexyl)-4-(4-methoxyphenyl)pyrrolidin-3-yl]carbonyl}piperidin-4-yl)-5-(trifluoromethyl)phenyl]piperidine-4-carboxylic acid;
1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid; and
1-{2-[(3S)-1-{[(3R,4R)-3-fluoro-1-(trans-4-methoxycyclohexyl)-4-(4-methoxyphenyl)pyrrolidin-3-yl]carbonyl}pyrrolidin-3-yl]-5-(trifluoromethyl)phenyl}piperidine-4-carboxylic acid;
or a pharmaceutically acceptable salt thereof.

18. A compound selected from the group consisting of:
1-{5-fluoro-2-[(3S,5S)-1-{[(3R,4R)-3-fluoro-1-(trans-4-methoxycyclohexyl)-4-(4-methoxyphenyl)pyrrolidin-3-yl]carbonyl}-5-(methoxymethyl)pyrrolidin-3-yl]phenyl}piperidine-4-carboxylic acid;
1-{2-[(3S,5S)-1-{[(3R,4R)-1-(trans-4-ethoxycyclohexyl)-3-methoxy-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,5S)-1-{[(3R,4R)-3-fluoro-1-(trans-4-methoxycyclohexyl)-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,5S)-1-{[(3R,4R)-1-cyclopentyl-3-fluoro-4-(4-methoxyphenyl)pyrrolidin-3-yl]carbonyl}-5-(methoxymethyl)pyrrolidin-3-yl]-5-(trifluoromethyl)phenyl}piperidine-4-carboxylic acid;
1-{2-[(3S,4S)-4-fluoro-1-{[(3R,4R)-3-fluoro-1-(trans-4-methoxycyclohexyl)-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid;
1-{5-chloro-2-[(3S,4R)-1-{[(3R,4R)-3-fluoro-1-(trans-4-methoxycyclohexyl)-4-(4-methoxyphenyl)pyrrolidin-3-yl]carbonyl}-4-(methoxymethyl)pyrrolidin-3-yl]phenyl}piperidine-4-carboxylic acid;
1-{2-[(3S,4R)-1-{[(3R,4R)-3-fluoro-1-(trans-4-methoxycyclohexyl)-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid; and
1-{2-[(3S,4R)-1-{[(3R,4R)-1-cyclopentyl-3-fluoro-4-(4-methoxyphenyl)pyrrolidin-3-yl]carbonyl}-4-(methoxymethyl)pyrrolidin-3-yl]-5-(trifluoromethyl)phenyl}piperidine-4-carboxylic acid;
or a pharmaceutically acceptable salt thereof.

19. A pharmaceutical composition comprising, as an active ingredient, the compound according to claim 1 or a pharmaceutically acceptable salt thereof.

20. The pharmaceutical composition according to claim 19, which is used for activation of melanocortin 1 receptor.

21. The pharmaceutical composition according to claim 19, which is an agent for treating rheumatoid arthritis, gouty arthritis, osteoarthrosis, inflammatory bowel disease, systemic sclerosis, psoriasis, fibrosis, protoporphyria, systemic lupus erythematosus, melanoma, skin cancer, vitiligo, hair loss, pain, ischemia/reperfusion damage, cerebral inflammatory disease, hepatitis, septicemia/septic shock, nephritis, transplantation, HIV disease exacerbation, vasculitis, uveitis, retinitis pigmentosa, age-related macular degeneration, celiac disease, nephrotic syndrome, or melanoma invasion.

22. The pharmaceutical composition according to claim 19, which is an agent for treating systemic sclerosis, psoriasis, protoporphyria, melanoma, skin cancer, vitiligo, hair loss, nephrotic syndrome, retinitis pigmentosa, or age-related macular degeneration.

23. The pharmaceutical composition according to claim 19, which is an agent for treating systemic sclerosis, protoporphyria, melanoma, vitiligo, nephrotic syndrome, retinitis pigmentosa, or age-related macular degeneration.

24. The pharmaceutical composition according to claim 21, wherein the protoporphyria is erythropoietic protoporphyria.

25. A method for treating diseases and/or symptoms in which activation of melanocortin 1 receptor is involved, the method comprising administering to a patient an effective amount of the compound according to claim 1 or a pharmaceutically acceptable salt thereof,
wherein the diseases and/or symptoms is rheumatoid arthritis, gouty arthritis, osteoarthrosis, inflammatory bowel disease, systemic sclerosis, psoriasis, fibrosis, protoporphyria, systemic lupus erythematosus, melanoma, skin cancer, vitiligo, hair loss, pain, ischemia/reperfusion damage, cerebral inflammatory disease, hepatitis, septicemia/septic shock, nephritis, transplantation, HIV disease exacerbation, vasculitis, uveitis, retinitis pigmentosa, age-related macular degeneration, celiac disease, nephrotic syndrome, or melanoma invasion.

26. A pharmaceutical composition comprising, as an active ingredient, the compound according to claim 16 or a pharmaceutically acceptable salt thereof.

27. A pharmaceutical composition comprising, as an active ingredient, the compound according to claim 17 or a pharmaceutically acceptable salt thereof.

28. A pharmaceutical composition comprising, as an active ingredient, the compound according to claim 18 or a pharmaceutically acceptable salt thereof.

29. A method for activation of melanocortin 1 receptor, the method comprising administering to a patient an effective amount of the compound according to claim 16 or a pharmaceutically acceptable salt thereof.

30. A method for activation of melanocortin 1 receptor, the method comprising administering to a patient an effective amount of the compound according to claim 17 or a pharmaceutically acceptable salt thereof.

31. A method for activation of melanocortin 1 receptor, the method comprising administering to a patient an effective amount of the compound according to claim 18 or a pharmaceutically acceptable salt thereof.

32. The pharmaceutical composition according to claim 21, which is an agent for treating rheumatoid arthritis, gouty arthritis, osteoarthrosis, inflammatory bowel disease, systemic sclerosis, psoriasis, fibrosis, protoporphyria, systemic lupus erythematosus, melanoma, skin cancer, vitiligo, hair loss, pain, ischemia/reperfusion damage, cerebral inflammatory disease, hepatitis, septicemia/septic shock, nephritis, transplantation, vasculitis, uveitis, retinitis pigmentosa, age-related macular degeneration, celiac disease, nephrotic syndrome, or melanoma invasion.

33. The method according to claim 25, wherein the diseases and/or symptoms is rheumatoid arthritis, gouty arthritis, osteoarthrosis, inflammatory bowel disease, systemic sclerosis, psoriasis, fibrosis, protoporphyria, systemic lupus erythematosus, melanoma, skin cancer, vitiligo, hair loss, pain, ischemia/reperfusion damage, cerebral inflammatory disease, hepatitis, septicemia/septic shock, nephritis, transplantation, vasculitis, uveitis, retinitis pigmentosa, age-related macular degeneration, celiac disease, nephrotic syndrome, or melanoma invasion.

\* \* \* \* \*